US011903985B2

(12) United States Patent
Abeliovich et al.

(10) Patent No.: US 11,903,985 B2
(45) **Date of Patent: *Feb. 20, 2024**

(54) GENE THERAPIES FOR LYSOSOMAL DISORDERS

(71) Applicant: Prevail Therapeutics, Inc., New York, NY (US)

(72) Inventors: Asa Abeliovich, New York, NY (US); Laura Heckman, New York, NY (US); Herve Rhinn, New York, NY (US); Franz Hefti, New York, NY (US)

(73) Assignee: Prevail Therapeutics, Inc., New York, NY (US)

( * ) Notice: Subject to any disclaimer, the term of this patent is extended or adjusted under 35 U.S.C. 154(b) by 620 days.

This patent is subject to a terminal disclaimer.

(21) Appl. No.: 16/846,210

(22) Filed: Apr. 10, 2020

(65) Prior Publication Data

US 2020/0338148 A1 Oct. 29, 2020

Related U.S. Application Data

(60) Provisional application No. 62/990,246, filed on Mar. 16, 2020, provisional application No. 62/831,840, filed on Apr. 10, 2019.

(51) Int. Cl.
*A61P 25/28* (2006.01)
*A61K 35/761* (2015.01)
(Continued)

(52) U.S. Cl.
CPC .......... *A61K 35/761* (2013.01); *A61K 9/0085* (2013.01); *A61K 38/162* (2013.01);
(Continued)

(58) Field of Classification Search
None
See application file for complete search history.

(56) References Cited

U.S. PATENT DOCUMENTS 5,879,680 A 3/1999 Ginns et al.
6,521,225 B1 2/2003 Srivastava et al.
(Continued)

FOREIGN PATENT DOCUMENTS

EP 3091087 A1 11/2016
WO WO-0183692 A2 11/2001
(Continued)

OTHER PUBLICATIONS

Francois et al., The Cellular TATA Binding Protein Is Required for Rep-Dependent Replication of a Minimal Adeno-Associated Virus Type 2 p5 Element. Journal of Virology, Sep. 2005, p. 11082-11094 (Year: 2005).*
(Continued)

*Primary Examiner* — Aurora M Fontainhas
(74) *Attorney, Agent, or Firm* — COOLEY LLP; Ivor Elrifi

(57) ABSTRACT

The disclosure relates to compositions and methods for treatment of diseases associated with aberrant lysosomal function, such as Parkinson's disease and Gaucher disease. The disclosure provides expression constructs comprising a transgene encoding beta-glucocerebrosidase, an inhibitory RNA targeting alpha-Synuclein, or a combination of the foregoing. The disclosure further provides methods of treating Gaucher disease, Parkinson's disease or other synucleinopathies by administering such expression constructs to a subject in need thereof.

24 Claims, 70 Drawing Sheets

Specification includes a Sequence Listing.

(51) Int. Cl.

| | |
|---|---|
| ***A61K 38/16*** | (2006.01) |
| ***A61P 43/00*** | (2006.01) |
| ***C12N 15/86*** | (2006.01) |
| ***A61K 9/00*** | (2006.01) |

(52) U.S. Cl.

CPC ............... *A61P 25/28* (2018.01); *A61P 43/00* (2018.01); *C12N 15/86* (2013.01); *A61K 9/0019* (2013.01); *C12Y 302/01045* (2013.01)

(56) References Cited

U.S. PATENT DOCUMENTS

| | | | |
|---|---|---|---|
| 6,696,272 | B1 | 2/2004 | Mahuran et al. |
| 7,172,893 | B2 | 2/2007 | Rabinowitz |
| 7,452,716 | B2 | 11/2008 | Yew |
| 8,389,487 | B2 | 3/2013 | Bohn et al. |
| 8,454,954 | B2 | 6/2013 | Schlossmacher et al. |
| 8,962,273 | B2 | 2/2015 | Reczek |
| 9,290,759 | B2 | 3/2016 | Abeliovich et al. |
| 9,347,107 | B2 | 5/2016 | Lai et al. |
| 9,427,438 | B2 | 8/2016 | Alam et al. |
| 9,708,611 | B2 | 7/2017 | Mouradian et al. |
| 10,213,494 | B2 | 2/2019 | Schlossmacher et al. |
| 10,837,028 | B2 | 11/2020 | Abeliovich et al. |
| 11,060,113 | B2 | 7/2021 | Abeliovich et al. |
| 2003/0100115 | A1 | 5/2003 | Raj et al. |
| 2003/0133924 | A1 | 7/2003 | Canfield |
| 2006/0292117 | A1 | 12/2006 | Loiler et al. |
| 2008/0003204 | A1 | 1/2008 | Flotte et al. |
| 2009/0176729 | A1 | 7/2009 | Tan |
| 2013/0224836 | A1 | 8/2013 | Muramatsu |
| 2015/0284472 | A1 | 8/2015 | Sardi et al. |
| 2016/0243260 | A1 | 8/2016 | Blits |
| 2016/0264965 | A1 | 9/2016 | Mouradian et al. |
| 2017/0035860 | A1 | 2/2017 | Flynn |
| 2018/0071373 | A1 | 3/2018 | Melvor et al. |
| 2018/0147300 | A1 | 5/2018 | Park et al. |
| 2019/0038773 | A1 | 2/2019 | Esteves et al. |
| 2019/0055578 | A1 | 2/2019 | Sah et al. |
| 2019/0282662 | A1 | 9/2019 | Kay et al. |
| 2019/0328906 | A1 | 10/2019 | Chen Plotkin et al. |
| 2020/0071726 | A1 | 3/2020 | Abeliovich et al. |
| 2020/0231954 | A1 | 7/2020 | Abeliovich et al. |
| 2020/0231970 | A1 | 7/2020 | Abeliovich et al. |
| 2020/0318115 | A1 | 10/2020 | Abeliovich et al. |
| 2021/0010032 | A1 | 1/2021 | Abeliovich et al. |
| 2021/0332385 | A1 | 10/2021 | Abeliovich et al. |
| 2022/0211871 | A1 | 7/2022 | Abeliovich et al. |

FOREIGN PATENT DOCUMENTS

| | | | |
|---|---|---|---|
| WO | WO-0224932 | A2 | 3/2002 |
| WO | WO 2004/098648 | A1 | 11/2004 |
| WO | WO-03029403 | A3 | 8/2007 |
| WO | WO-2009079399 | A2 | 6/2009 |
| WO | WO-2011133890 | A1 | 10/2011 |
| WO | WO 2012/027558 | A2 | 3/2012 |
| WO | WO 2012/027713 | A2 | 3/2012 |
| WO | WO-2012057363 | A1 | 5/2012 |
| WO | WO 2014/071282 | A1 | 5/2014 |
| WO | WO 2014/186579 | A1 | 11/2014 |
| WO | WO 2016/081927 | A2 | 3/2016 |
| WO | WO 2016/179497 | A1 | 11/2016 |
| WO | WO-2017077451 | A1 | 5/2017 |
| WO | WO 2017/136202 | A1 | 8/2017 |
| WO | WO 2019/070891 | A1 | 4/2019 |
| WO | WO 2019/070893 | A1 | 4/2019 |
| WO | WO 2019/070894 | A1 | 4/2019 |
| WO | WO-2019084068 | A1 | 5/2019 |
| WO | WO-2020210615 | A1 | 10/2020 |

OTHER PUBLICATIONS

Bosch. "Novel therapeutic approaches for Juvenile Neuronal Ceroid Lipofuscinosis (CLN3)" (2017). Theses & Dissertations. 227. https://digitalcommons.unmc.edu/etd/227 (165 pages).

Ciesielska, et al. "Cerebral infusion of AAV9 vector-encoding non-self proteins can elicit cell-mediated immune responses." Mol Ther. Jan. 2013;21(1):158-66. doi: 10.1038/mt.2012.167.

GenBank Accession No. NP_000148.2 "lysosomal acid glucosylceramidase isoform 1 precursor [*Homo sapiens*]" Jan. 8, 2020 [online].

GenBank Accession No. NP_005497.1 "lysosome membrane protein 2 isoform 1 precursor [*Homo sapiens*]" Jan. 1, 2020 [online].

GenBank Accession No. NP_002769.1 "prosaposin isoform a preproprotein [*Homo sapiens*]" Sep. 27, 2019 [online].

GenBank Accession No. NP_001191184.1 "lysosome membrane protein 2 isoform 2 precursor [*Homo sapiens*]" Jan. 4, 2020 [online].

GenBank Accession No. AAH01503.1 "Prosaposin [*Homo sapiens*]" Aug. 4, 2008 [online].

GenBank Accession No. AAH07612.1 "Prosaposin [*Homo sapiens*]" Aug. 4, 2008 [online].

GenBank Accession No. AAH04275.1 "Prosaposin [*Homo sapiens*]" Aug. 4, 2008 [online].

GenBank Accession No. AAA60303.1 "Prosaposin [*Homo sapiens*]" Jan. 9, 1995 [online].

GenBank Accession No. AAP36904.1 "*Homo sapiens* glucosidase, beta; acid (includes glucosylceramidase), partial [synthetic construct]" Jul. 25, 2016 [online].

GenBank Accession No. BT008212.1 "Synthetic construct Homo sapiens glucosidase, beta; acid (includes glucosylceramidase) mRNA, partial cds" Jul. 25, 2016 [online].

GenBank Accession No. NP_001005742.1 "lysosomal acid glucosylceramidase isoform 1 precursor [*Homo sapiens*]" Nov. 11, 2019 [online].

GenBank Accession No. NP_001165282.1 "lysosomal acid glucosylceramidase isoform 2 [*Homo sapiens*]" Nov. 11, 2019 [online].

GenBank Accession No. NP_001165283.1 "lysosomal acid glucosylceramidase isoform 3 [*Homo sapiens*]" Nov. 11, 2019 [online].

GenBank Accession No. NP_065995.1 "non-lysosomal glucosylceramidase isoform 1 [*Homo sapiens*]" Aug. 22, 2019 [online].

GenBank Accession No. NP_000144.2 "galactocerebrosidase isoform a precursor [*Homo sapiens*]" Sep. 26, 2019 [online].

GenBank Accession No. NP_001899.1 "cathepsin B isoform 1 preproprotein [*Homo sapiens*]" Jan. 27, 2020 [online].

GenBank Accession No. NP_000534.3 "sphingomyelin phosphodiesterase isoform 1 precursor [*Homo sapiens*]" Jan. 13, 2020 [online].

GenBank Accession No. NP_003920.1 "ras-related protein Rab-7L1 isoform 1 [*Homo sapiens*]" Dec. 31, 2019 [online].

GenBank Accession No. NP_060676.2 "vacuolar protein sorting-associated protein 35 [*Homo sapiens*]" Oct. 11, 2019 [online].

GenBank Accession No. NP_689669.2 "interleukin-34 isoform 1 precursor [*Homo sapiens*]" Dec. 25, 2019 [online].

GenBank Accession No. NP_061838.1 "triggering receptor expressed on myeloid cells 2 precursor isoform 1 precursor [*Homo sapiens*]" Feb. 2, 2020 [online].

GenBank Accession No. NP_060844.2 "transmembrane protein 106B [*Homo sapiens*]" Jul. 28, 2019 [online].

GenBank Accession No. NP_002078.1 "progranulin precursor [*Homo sapiens*]" Jan. 21, 2020 [online].

GenBank Accession No. NP_001317589.1 "non-lysosomal glucosylceramidase isoform 2 [*Homo sapiens*]" Aug. 7, 2019 [online].

GenBank Accession No. EAW81359.1 "galactosylceramidase, isoform CRA_a [*Homo sapiens*]" Mar. 23, 2015 [online].

GenBank Accession No. EAW81360.1 "galactosylceramidase, isoform CRA_b [*Homo sapiens*]" Mar. 23, 2015 [online].

GenBank Accession No. EAW81362.1 "galactosylceramidase, isoform CRA_c [*Homo sapiens*]" Mar. 23, 2015 [online].

GenBank Accession No. EAW68726.1 "sphingomyelin phosphodiesterase 1, acid lysosomal (acid sphingomyelinase), isoform CRA_a [*Homo sapiens*]" Mar. 23, 2015 [online].

(56) References Cited

OTHER PUBLICATIONS

GenBank Accession No. EAW68727.1 "sphingomyelin phosphodiesterase 1, acid lysosomal (acid sphingomyelinase), isoform CRA_b [*Homo sapiens*]" Mar. 23, 2015 [online].
GenBank Accession No. EAW68728.1 "sphingomyelin phosphodiesterase 1, acid lysosomal (acid sphingomyelinase), isoform CRA_c [*Homo sapiens*]" Mar. 23, 2015 [online].
GenBank Accession No. EAW68729.1 "sphingomyelin phosphodiesterase 1, acid lysosomal (acid sphingomyelinase), isoform CRA_d [*Homo sapiens*]" Mar. 23, 2015 [online].
GenBank Accession No. AAC37547.1 "cathepsin B [*Homo sapiens*]" Apr. 7, 1994 [online].
GenBank Accession No. AAH95408.1 "Cathepsin B [*Homo sapiens*]" Jul. 17, 2006 [online].
GenBank Accession No. AAH10240.1 "Cathepsin B [*Homo sapiens*]" Jul. 15, 2006 [online].
GenBank Accession No. AAH02585.1 "RAB7, member RAS oncogene family-like 1 [*Homo sapiens*]" Jul. 15, 2006 [online].
GenBank Accession No. AAH25415.1 "GTP cyclohydrolase 1 [*Homo sapiens*]" Aug. 7, 2008 [online].
GenBank Accession No. AAH29804.1 "Interleukin 34 [*Homo sapiens*]" Jun. 9, 2008 [online].
GenBank Accession No. AAF69824.1 "triggering receptor expressed on myeloid cells 2 [*Homo sapiens*]" May 23, 2000 [online].
GenBank Accession No. NP_002087.1 "general transcription factor IIF, polypeptide 1, 74kDa [*Homo sapiens*]" Jun. 3, 2007 [online].
GenBank Accession No. NP_000152.1 "GTP cyclohydrolase 1 isoform 1 [*Homo sapiens*]" Dec. 30, 2019 [online].
Samaranch, et al. "AAV9-mediated expression of a non-self protein in nonhuman primate central nervous system triggers widespread neuroinflammation driven by antigen-presenting cell transduction." Mol Ther. Feb. 2014;22(2):329-337. doi: 10.1038/mt.2013.266.
Fumoto, et al. "Targeted Gene Delivery: Importance of Administration Routes." Chapter 1, Intech, 2013, pp. 3-31.
Hudry and Vandenberghe. "Therapeutic AAV Gene Transfer to the Nervous System: A Clinical Reality." Neuron 101, Mar. 6, 2019, 839-862.
Lazic and Barker. "Cell-based therapies for disorders of the CNS." Expert Opin. Ther. Patents (2005) 15(10): 1361-1376.
Ling, et al. "The Adeno-Associated Virus Genome Packaging Puzzle." J Mol Genet Med 2015, 9: 175, 4 pages.
Manno, et al. "Successful transduction of liver in hemophilia by AAV-Factor IX and limitations imposed by the host immune response." Nature Medicine, 2006, 12(3):342-349; 12(5):592.
Molnar and Nemeth. "Gene therapy in neurology: review of ongoing clinical trials." Clin. Invest. (2012) 2(6), 639-652.
Niederkofler, et al. "Characterization of relevant mouse models for new biomarkers." Poster #141, 2019, Society for Neuroscience Meeting, Chicago, IL, USA.
Salmon, et al. "Safety profile of recombinant adeno-associated viral vectors: focus on alipogene tiparvovec (Glybera)." Expert Rev. V Clin. Pharmacol., 2014,7(1), 53-65.
Shanks, et al. "Are animal models predictive for humans?" Philosophy, Ethics, and Humanities in Medicine, 2009, 4(2), 20 pages.
Wong, et al. "Lysosomal Trafficking Defects Link Parkinson's Disease With Gaucher's Disease." Movement Disorders, 2013, 31(11):1610-1618.
Khodr, et al. "Targeting alpha-synuclein with a microRNA-embedded silencing vector in the rat substantia nigra: Positive and negative effects," Brain Research, Mar. 6, 2014, 1550:47-60 (23 pages total).
Naso, et al. "Adeno-Associated Virus (AAV) as a Vector for Gene Therapy," BioDrugs, 2017, 31:317- 334.
Sinclair, et al. "Synonymous codon usage bias and the expression of human glucocerebrosidase in the methylotrophic yeast, *Pichia pastoris*", Protein Expression and Purification, 2002, 26(1):96-105.
Supplemental European Search Report issued in EP Application No. 18865080.8, dated Jan. 10, 2022, 1-19.
Supplementary Partial European Search Report issued in EP application No. 18865080.8, dated Aug. 16, 2021, 1-18.
Wang, et al. "Adeno-associated virus type 2 DNA replication in vivo: mutational analyses of the D sequence in viral inverted repeats", Journal of Virology, Apr. 1997, 71(4):3077-3082.
Xu, et al. "Tau Silencing by siRNA in the P301S Mouse Model of Tauopathy" Current Gene Therapy, 2014, 14:343-351 (numbered 1-9).
Fischell and Fishman, "A Multifaceted Approach to Optimizing AAV Delivery to the Brain for the Treatment of Neurodegenerative Diseases," Frontiers in Neuroscience, Sep. 24, 2021, 15: 747726, pp. 1-20.
Franco et al., "Glucocerebrosidase Mutations and Synucleinopathies. Potential Role of Sterylglucosides and Relevance of Studying Both GBA1 and GBA2 Genes." Front Neuroanat. Jun. 28, 2018; 12: 52.
Garcia-Gomez, M. et al. "Modelling gaucher disease through interference RNA technology." Human Gene Therapy, Sep. 1, 2015, 26(9): A22-A23.
Genbank Accession No. AA476718 "zw92f11.s1 Soares_total_fetus_Nb2H F8_9w *Homo sapiens* cDNA clone" Nov. 5, 2022 [online], 2 pages.
Gorski, "One reason mouse studies often don't translate to humans very well". Science-Based Medicine.org. Aug. 26, 2019. pp. 1-1. Retrieved from https://sciencebasedmedicine.org/one-reason-mouse-studies-often-dont-translate-to-humans-very-well/, Feb. 10, 2023, 11 pages.
International Patent Application No. PCT/US2018/054223, International Preliminary Report on Patentability dated Apr. 7, 2020, 8 pages.
Lonser et al., "Convection-enhanced delivery to the central nervous system" J Neurosurg. Mar. 2015; 122(3): 697-706. Epub Nov. 14, 2014.
Marchi et al., "Delivery of therapeutic AAV9 vector via cisterna magna to treat neurological disorders", Trends Mol Med. Jan. 2022; 28(1):79-80. Epub Oct. 28, 2021.
Orme et al. "The Genetics of Dementia with Lewy Bodies: Current Understanding and Future Directions," Curr Neurol Neurosci Rep. Aug. 10, 2018; 18(10): 67, 13 pages.
Siman, et al., "A Rapid Gene Delivery-Based Mouse Model for Early-Stage Alzheimer Disease-Type Tauopathy", J Neuropathol Exp Neurol. Nov. 2013; 72(11): 1062-71.
Xhima, et al., "Noninvasive delivery of an α-synuclein gene silencing vector with magnetic resonance-guided focused ultrasound". Mov Disord. Oct. 2018; 33(10): 1567-1579. Epub Sep. 28, 2018.
Zhang et al., "Disease-modifying therapeutics for Lewy-Body dementias," Front. Neurosci., 2015, 9 pages: 293. Published online Aug. 20, 2015.

* cited by examiner

PrevailVector_FP1_JetLong_GBA1_bGH_JetLong_SCARB2_SV40L_4464nt
11,420 bp

| PR001 dose | Total vg | vg/g brain |
|---|---|---|
| Low | 2.0 x 10^9 | 1.3 x 10^10 |
| Middle | 6.2 x 10^9 | 4.2 x 10^10 |
| High | 2.0 x 10^10 | 1.3 x 10^11 |

| PR001 dose | Total vg | vg/g brain |
|---|---|---|
| single | 2.0 x 1010 | 1.3 x 1011 |

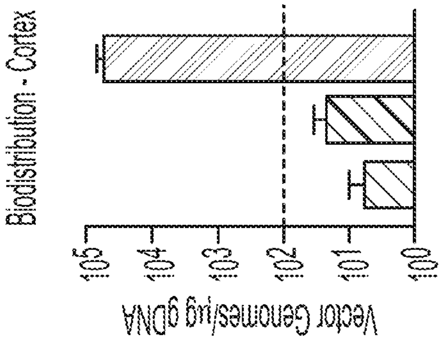
FIG. 37A
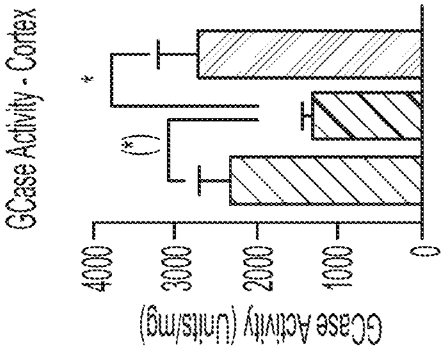
FIG. 37B
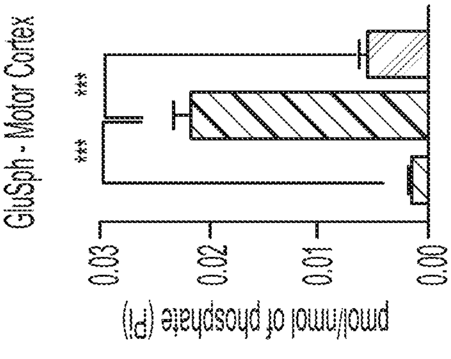
FIG. 37C
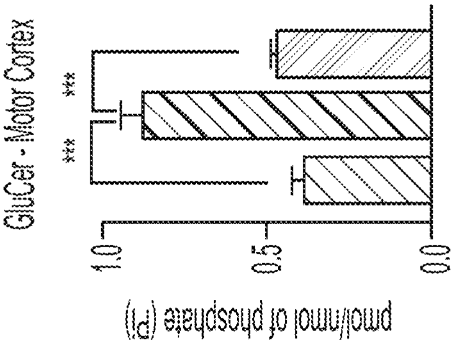
FIG. 37D
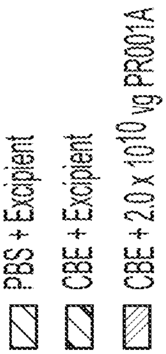

| PR001 dose | Total vg | vg/g brain |
|---|---|---|
| Single | $1.5 \times 10^{10}$ | $3.7 \times 10^{10}$ |

| PR001A dose | Total vg | vg/g brain |
|---|---|---|
| 1 | $2.9 \times 10^9$ | $7.4 \times 10^9$ |
| 2 | $2.9 \times 10^{10}$ | $7.4 \times 10^{10}$ |
| 3 | $9.3 \times 10^{10}$ | $2.3 \times 10^{11}$ |
| 4 | $2.9 \times 10^{11}$ | $7.4 \times 10^{11}$ |

GENE THERAPIES FOR LYSOSOMAL DISORDERS

CROSS-REFERENCE TO RELATED APPLICATIONS

This application claims priority to U.S. Provisional Patent Application No. 62/990,246, filed on Mar. 16, 2020 and U.S. Provisional Patent Application No. 62/831,840, filed on Apr. 10, 2019. The disclosure of each of these applications is incorporated herein by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PRVL_009_02US_SeqList.txt, date recorded: Apr. 10, 2020, file size ~361,154 bytes).

BACKGROUND

Aberrant expression of proteins such as lysosomal acid β-glucocerebrosidase (Gcase) and α-Synuclein is involved in many central nervous system disorders. Gaucher disease is a rare inborn error of glycosphingolipid metabolism due to deficiency of Gcase. Patients suffer from non-CNS symptoms and findings including hepatosplenomegaly, bone marrow insufficiency leading to pancytopenia, lung disorders and fibrosis, and bone defects. In addition, a significant number of patients suffer from neurological manifestations, including defective saccadic eye movements and gaze, seizures, cognitive deficits, developmental delay, and movement disorders including Parkinson's disease.

Several therapeutics exist that address the peripheral disease and the principal clinical manifestations in hematopoietic bone marrow and viscera, including enzyme replacement therapies, chaperone-like small molecule drugs that bind to defective Gcase and improve stability, and substrate reduction therapy that block the production of substrates that accumulate in Gaucher disease, leading to symptoms and pathology. However, other aspects of Gaucher disease appear refractory to treatment.

In addition to Gaucher disease patients (who possess mutations in both chromosomal alleles of GBA1 gene), patients with mutations in only one allele of GBA1 are at highly increased risk of Parkinson's disease (PD). Elevated α-Synuclein levels also underlie synucleinopathies such as PD. The severity of PD symptoms—which include gait difficulty, a tremor at rest, rigidity, and often depression, sleep difficulties, and cognitive decline—correlate with the degree of enzyme activity reduction. Thus, Gaucher disease patients have the most severe course, whereas patients with a single mild mutation in GBA1 typically have a more benign course. Mutation carriers are also at high risk of other PD-related disorders, including Lewy Body Dementia, characterized by executive dysfunction, psychosis, and a PD-like movement disorder, and multi-system atrophy, with characteristic motor and cognitive impairments. No therapies exist that alter the inexorable course of these disorders and other synucleinopathies.

FIELD

The disclosure relates to the field of gene therapy and methods of using same.

SUMMARY

Provided herein is a method for treating a subject having Type 2 Gaucher disease or Type 3 Gaucher disease, the method comprising administering to the subject a recombinant adeno-associated virus (rAAV) comprising: (i) a rAAV vector comprising a nucleic acid comprising an expression construct comprising a promoter operably linked to a transgene insert encoding a glucocerebrosidase (Gcase) protein, wherein the transgene insert comprises the nucleotide sequence of SEQ ID NO: 15; and (ii) an AAV9 capsid protein. In some embodiments, the rAAV is administered to the subject at a dose ranging from about $5\times10^{10}$ vg/g brain to about $5\times10^{11}$ vg/g brain. In some embodiments, the rAAV is administered to the subject at a dose of about $1.3\times10^{11}$ vg/g brain.

Provided herein is a method for treating a subject having Parkinson's disease with a glucocerebrosidase-1 (GBA1) mutation, the method comprising administering to the subject a recombinant adeno-associated virus (rAAV) comprising: (i) a rAAV vector comprising a nucleic acid comprising an expression construct comprising a promoter operably linked to a transgene insert encoding a Gcase protein, wherein the transgene insert comprises the nucleotide sequence of SEQ ID NO: 15; and (ii) an AAV9 capsid protein. In some embodiments, the rAAV is administered to the subject at a dose ranging from about $5\times10^{13}$ vg to about $5\times10^{14}$ vg. In some embodiments, the rAAV is administered to the subject at a dose of about $1\times10^{14}$ vg or about $2\times10^{14}$ vg.

In some embodiments, the rAAV is administered via a suboccipital injection into the cisterna *magna*.

Provided herein is a method for treating a subject having Type 1 Gaucher disease, the method comprising administering to the subject a recombinant adeno-associated virus (rAAV) comprising: (i) a rAAV vector comprising a nucleic acid comprising an expression construct comprising a promoter operably linked to a transgene insert encoding a Gcase protein, wherein the transgene insert comprises the nucleotide sequence of SEQ ID NO: 15; and (ii) an AAV9 capsid protein. In some embodiments, the rAAV is administered to the subject at a dose ranging from about $5\times10^{13}$ vg to about $5\times10^{14}$ vg. In some embodiments, the rAAV is administered intravenously.

Provided herein is a method for treating a subject having a synucleinopathy or parkinsonism, the method comprising administering to the subject a recombinant adeno-associated virus (rAAV) comprising: (i) a rAAV vector comprising a nucleic acid comprising an expression construct comprising a transgene comprising (a) a Gcase protein coding sequence comprising the nucleotide sequence of SEQ ID NO: 15; and (b) an inhibitory nucleic acid coding sequence comprising the nucleotide sequence of SEQ ID NO: 20; and (ii) an AAV9 capsid protein.

Provided herein is a method for treating a subject having a synucleinopathy or parkinsonism, the method comprising administering to the subject a recombinant adeno-associated virus (rAAV) comprising: (i) a rAAV vector comprising a nucleic acid comprising an expression construct comprising a transgene comprising an inhibitory nucleic acid coding sequence comprising the nucleotide sequence of SEQ ID NO: 20; and an AAV9 capsid protein.

In some embodiments, the synucleinopathy or parkinsonism is multiple system atrophy, Parkinson's disease, Parkinson's disease with GBA1 mutation, Lewy body disease, dementia with Lewy bodies, dementia with Lewy bodies with GBA1 mutation, progressive supranuclear palsy, or corticobasal syndrome.

In some embodiments, the promoter is a chicken beta actin (CBA) promoter. In some embodiments, the rAAV vector further comprises a cytomegalovirus (CMV)

enhancer. In some embodiments, the rAAV vector further comprises a Woodchuck Hepatitis Virus Posttranscriptional Regulatory Element (WPRE). In some embodiments, the rAAV vector further comprises a Bovine Growth Hormone polyA signal tail. In some embodiments, the nucleic acid comprises two adeno-associated virus inverted terminal repeats (ITR) sequences flanking the expression construct. In some embodiments, each ITR sequence is a wild-type AAV2 ITR sequence. In some embodiments, the rAAV vector further comprises a TRY region between the 5' ITR and the expression construct, wherein the TRY region comprises SEQ ID NO: 28.

Provided herein is a method for treating a subject having Type 2 Gaucher disease or Type 3 Gaucher disease, the method comprising administering to the subject a rAAV comprising:

- (i) a rAAV vector comprising a nucleic acid comprising, in 5' to 3' order:
  - (a) an AAV2 ITR;
  - (b) a CMV enhancer;
  - (c) a CBA promoter;
  - (d) a transgene insert encoding a Gcase protein, wherein the transgene insert comprises the nucleotide sequence of SEQ ID NO: 15;
  - (e) a WPRE;
  - (f) a Bovine Growth Hormone polyA signal tail; and
  - (g) an AAV2 ITR; and
- (ii) an AAV9 capsid protein;

wherein the rAAV is administered to the subject at a dose ranging from about $5\times10^{10}$ vg/g brain to about $5\times10^{11}$ vg/g brain.

Provided herein is a method for treating a subject having Parkinson's disease with a GBA1 mutation, the method comprising administering to the subject a rAAV comprising:

- (i) a rAAV vector comprising a nucleic acid comprising, in 5' to 3' order:
  - (a) an AAV2 ITR;
  - (b) a CMV enhancer;
  - (c) a CBA promoter;
  - (d) a transgene insert encoding a Gcase protein, wherein the transgene insert comprises the nucleotide sequence of SEQ ID NO: 15;
  - (e) a WPRE;
  - (f) a Bovine Growth Hormone polyA signal tail; and
  - (g) an AAV2 ITR; and
- (ii) an AAV9 capsid protein;

wherein the rAAV is administered to the subject at a dose ranging from about $5\times10^{13}$ vg to about $5\times10^{14}$ vg.

In some embodiments, the rAAV is administered via a suboccipital injection into the cisterna *magna*. In some embodiments, the rAAV is administered in a formulation comprising about 20 mM Tris, pH 8.0, about 1 mM $MgCl_2$, about 200 mM NaCl, and about 0.001% w/v poloxamer 188.

Provided herein is a pharmaceutical composition comprising

- (i) a rAAV comprising:
  - (a) a rAAV vector comprising a nucleic acid comprising an expression construct comprising a promoter operably linked to a transgene insert a Gcase protein, wherein the transgene insert comprises the nucleotide sequence of SEQ ID NO: 15; and
  - (b) an AAV9 capsid protein; and
- (ii) about 20 mM Tris, pH 8.0,
- (iii) about 1 mM $MgCl_2$,
- (iv) about 200 mM NaCl, and
- (v) about 0.001% w/v poloxamer 188.

Provided herein is a rAAV comprising:

- (a) a rAAV vector comprising a nucleic acid comprising an expression construct comprising a promoter operably linked to a transgene insert encoding a Gcase protein, wherein the transgene insert comprises the nucleotide sequence of SEQ ID NO: 15; and
- (b) an AAV9 capsid protein, for use in a method of treating Type 1 Gaucher disease, Type 2 Gaucher disease, Type 3 Gaucher disease or Parkinson's disease with a GBA1 mutation in a subject.

Provided herein is a rAAV comprising:

- (i) a rAAV vector comprising a nucleic acid comprising an expression construct comprising a promoter operably linked to a transgene insert comprising:
  - (a) a Gcase protein coding sequence comprising the nucleotide sequence of SEQ ID NO: 15; and
  - (b) an inhibitory nucleic acid coding sequence comprising the nucleotide sequence of SEQ ID NO: 20; and
- (ii) an AAV9 capsid protein, for use in a method of treating a synucleinopathy or parkinsonism in a subject.

Provided herein is a rAAV comprising:

- (i) a rAAV vector comprising a nucleic acid comprising an expression construct comprising a promoter operably linked to a transgene insert comprising an inhibitory nucleic acid coding sequence comprising the nucleotide sequence of SEQ ID NO: 20; and
- (ii) an AAV9 capsid protein, for use in a method of treating a synucleinopathy or parkinsonism in a subject.

(5M/5F) per group. All mice were sacrificed 1 day after their final CBE dose (P38-P40). All treatment groups were weighed daily (FIG. 15B), and their weight was analyzed at P37 (FIG. 15C). Motor performance was assessed by latency to fall on rotarod at P24 (FIG. 15D) and latency to traverse the tapered beam at P30 (FIG. 15E). Due to early lethality, the number of mice participating in the behavioral assays was: excipient+PBS (left-most bar) n=10; excipient+CBE (bar second from left) n=9; low dose PR001A+CBE (middle bar) n=6; medium dose PR001A+CBE (bar second from right) n=10; high dose PR001A+CBE (right-most bar) n=7. Means are presented. Error bars are SEM. *P<0.05; **P<0.01 for nominal P values in the CBE-treated groups, with gender corrected for as a covariate.

Figure 16A:
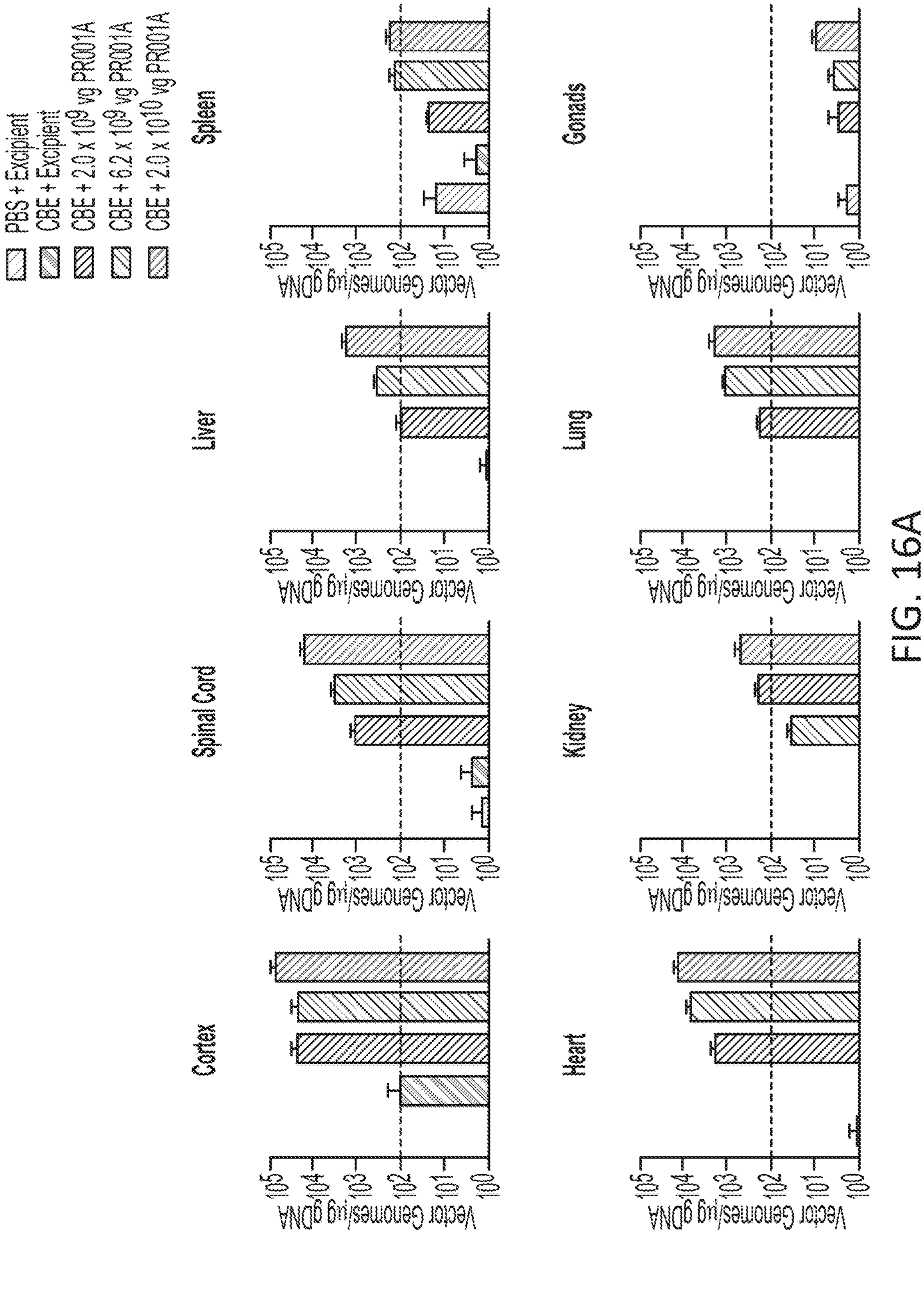

FIG. 16A shows representative data for biodistribution in a dose-ranging CBE model study of PR001A. Mice received excipient or 1 of 3 different doses of PR001A by ICV delivery at P3: low dose (middle bar), medium dose (bar second from right), or high dose (right-most bar). At P8, daily IP treatment of 25 mg/kg CBE was initiated. Mice that received excipient and CBE (bar second from left) or excipient and PBS (left-most bar) served as controls. All mice were sacrificed at P38-P40, 1 day after their final CBE dose. Presence of vector genomes was assessed in each tissue and all treatment groups, shown as number of vector copies per 1 μg of genomic DNA. Vector genome presence was quantified by qPCR using a vector reference standard curve; N=10, 9, 6, 10, 7 per group, respectively. Dashed lines represent the detection threshold for positive vector presence. Means are presented. Error bars are SEM.

Figure 16B:
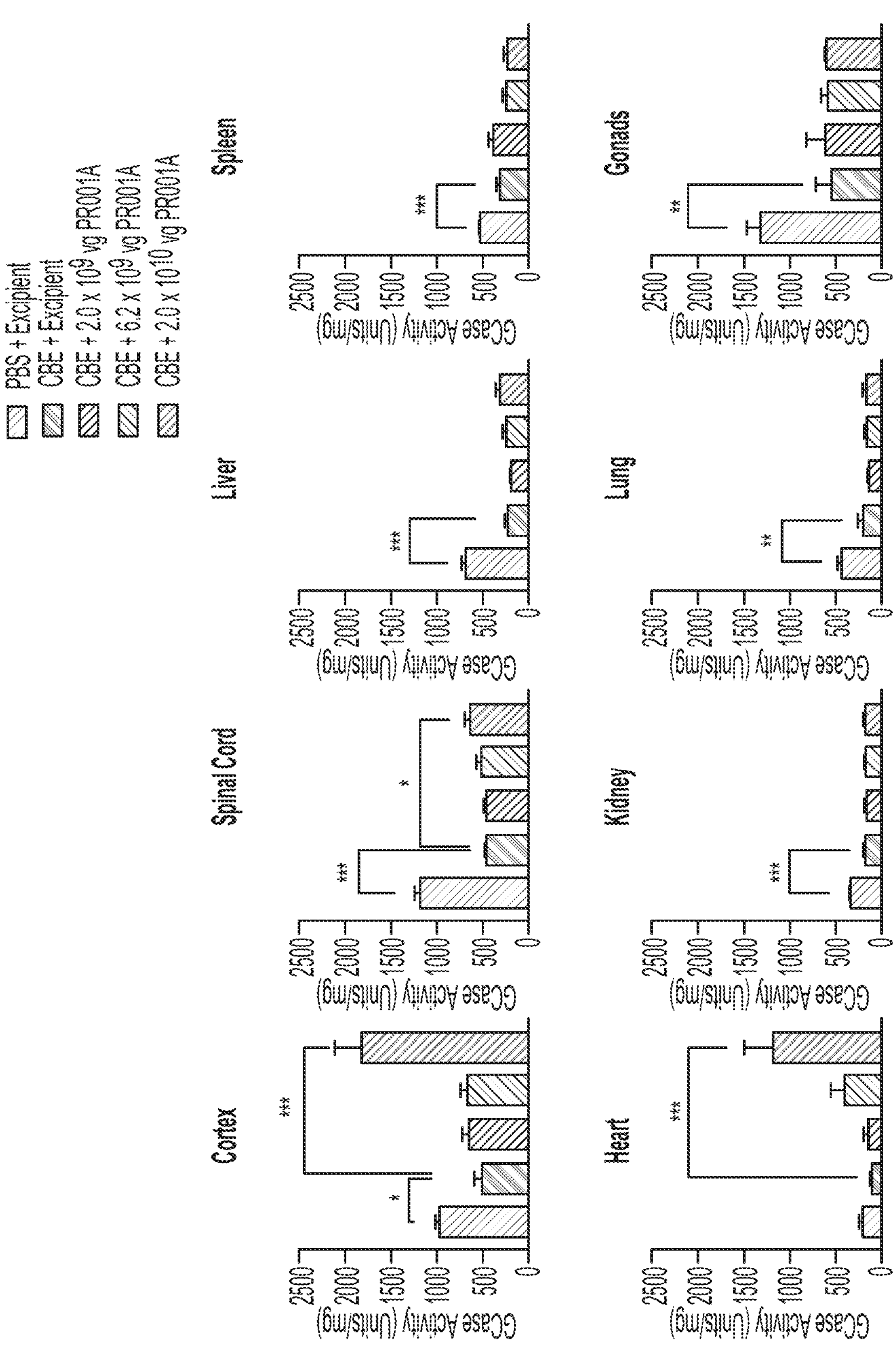

FIG. 16B shows representative data for GCase enzymatic activity in a dose-ranging CBE model study of PR001A. Effective enzymatic GCase activity is shown for each tissue and all treatment groups. Activity is shown as units per mg of total protein with one unit defined as the activity of 1 ng/mL of recombinant purified GCase. Means are presented. Error bars are SEM. Statistical results are presented for comparisons against the excipient+CBE groups (bar second from left). N=10, 9, 6, 10, 7 per group, respectively. *P<0.05; P<0.01; *P<0.001 by ANOVA followed by Tukey's HSD multiple tests correction.

Figures 16C, 16D, 16E, 16F:
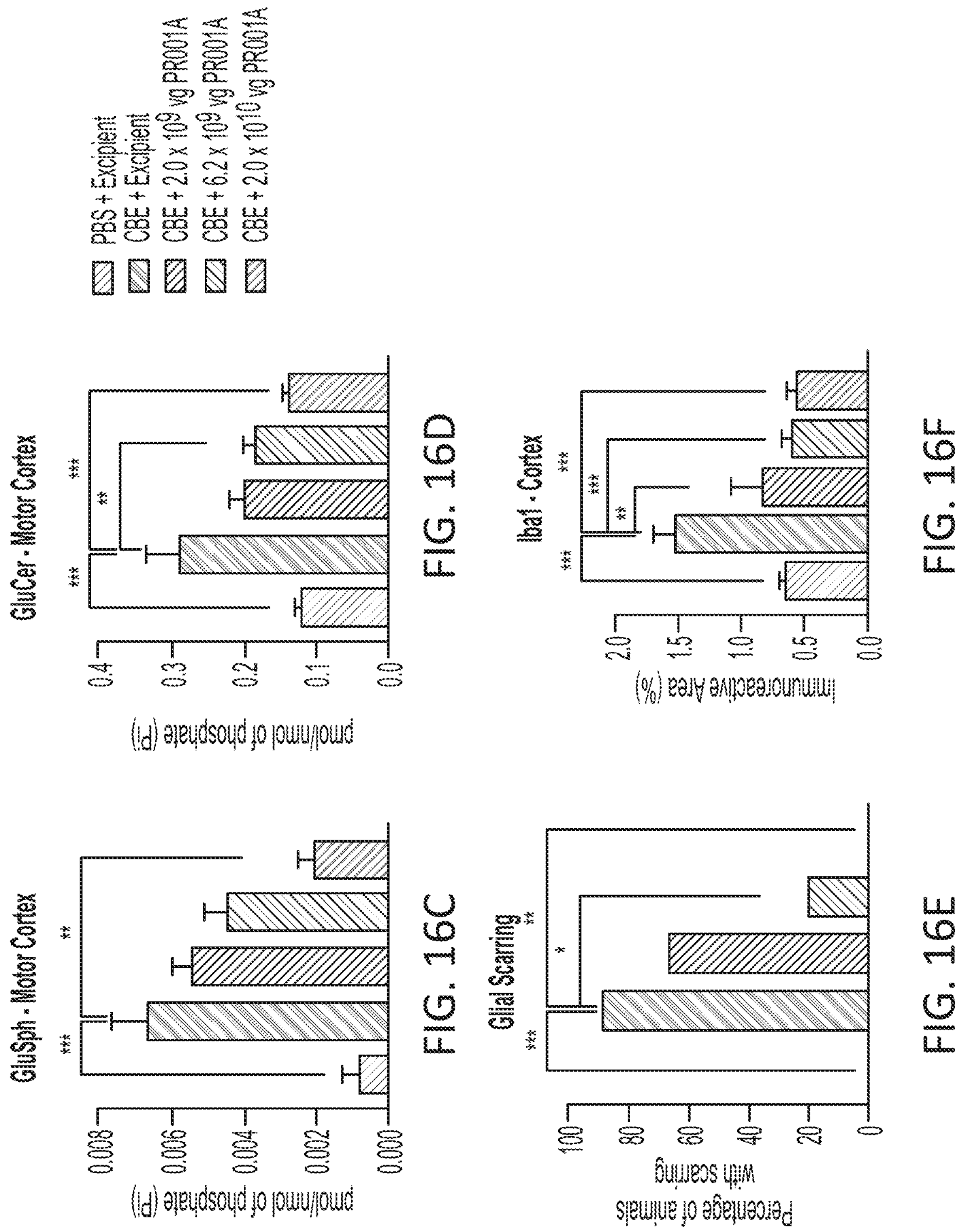

FIG. 16C-FIG. 16D show representative data for glycolipid analysis in a dose-ranging CBE model study of PR001A. GluSph (FIG. 16C) and GluCer (FIG. 16D) levels are shown as pmol per nmol of phosphate. Means are presented. Error bars are SEM. P<0.01; *P<0.001 by ANOVA followed by Tukey's HSD multiple tests correction.

FIG. 16E shows representative data for hematoxylin and eosin staining analysis in a dose-ranging CBE model study of PR001A. Brain tissue was processed for staining with hematoxylin and eosin (H&E) and tissue sections were evaluated for pathological changes. The percentage of animals positive for cerebrocortical glial scars, a sign of neuroinflammation, is shown. CBE treatment led to a significant increase in glial scars compared to excipient-treated controls. PR001A significantly reduced CBE-induced glial scarring in a dose-dependent manner. Statistical results are presented for comparisons against the CBE+excipient groups (left bar). N=10, 9, 6, 10, 7 per group, respectively. *: P<0.05; : P<0.01; *: P<0.001 for Fischer's exact test.

FIG. 16F shows representative data for cerebrocortical immunohistochemistry analysis in a dose-ranging CBE model study of PR001A. Graph presents the means of immunoreactive area measured within the cerebral cortex (11=5-10 per group). Iba1 (ionizing calcium-binding adaptor molecule 1) immunoreactive area was significantly higher in CBE+excipient-treated animals (bar second from left) than in mice of all other groups investigated. Means are presented and error bars are SEM. Data were analyzed by one-way ANOVA and Sidak's post hoc test for multiple comparisons. : P<0.01; *: P<0.001.

Figure 17:
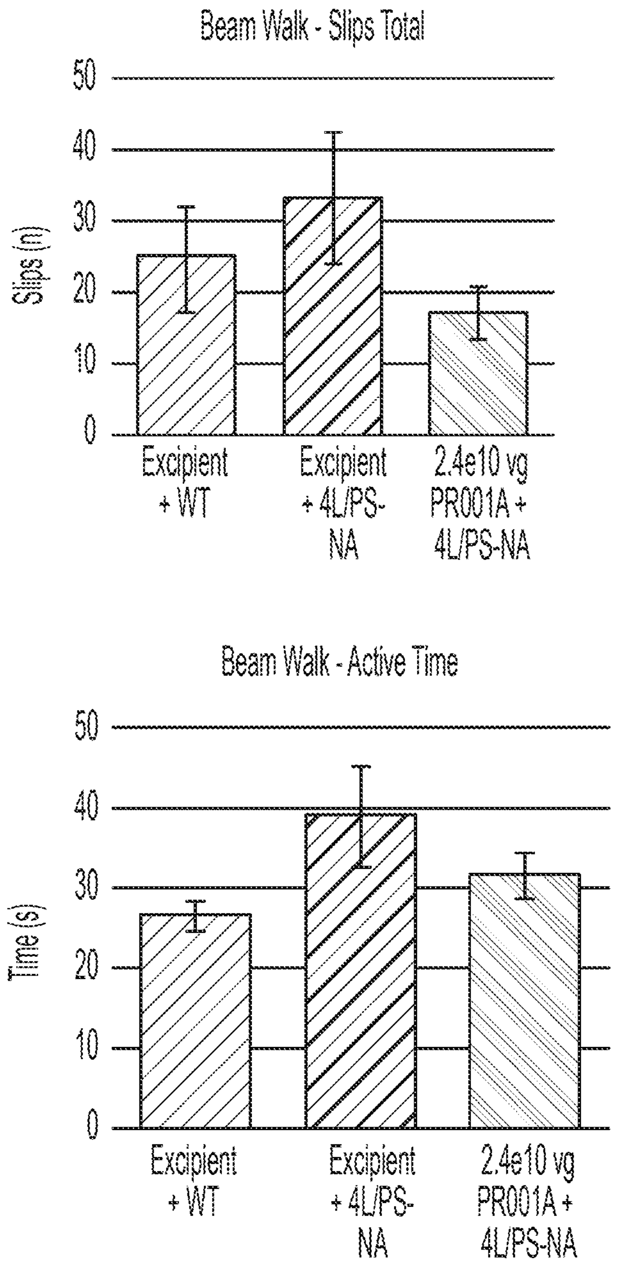
Figure 17:
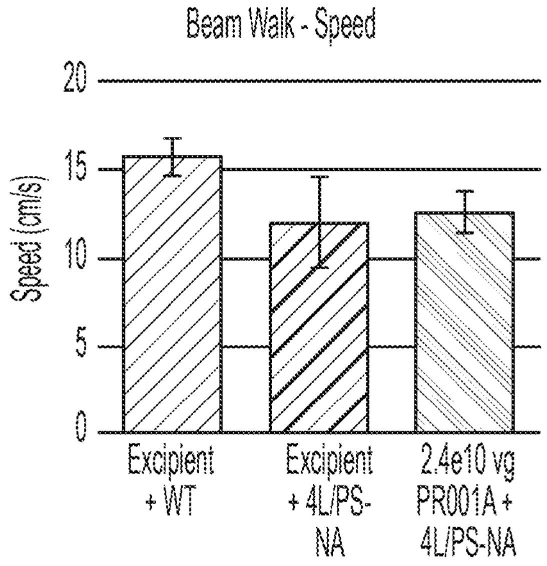
Figure 17:
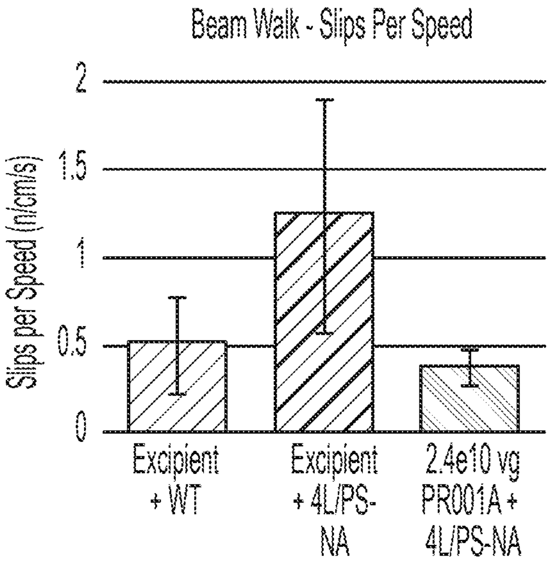

FIG. 17 shows representative data for tapered beam analysis in maximal dose GBA1 rAAV in a genetic mouse model. Motor performance of the treatment groups (WT+excipient, n=5), 4L/PS-NA+excipient (n=6), and 4L/PS-NA+rAAV (n=5)) was assayed by Beam Walk 4 weeks post rAAV administration. The total slips and active time are shown as total over 5 trials on different beams. Speed and slips per speed are shown as the average over 5 trials on different beams. Means are presented. Error bars are SEM.

Figure 18:
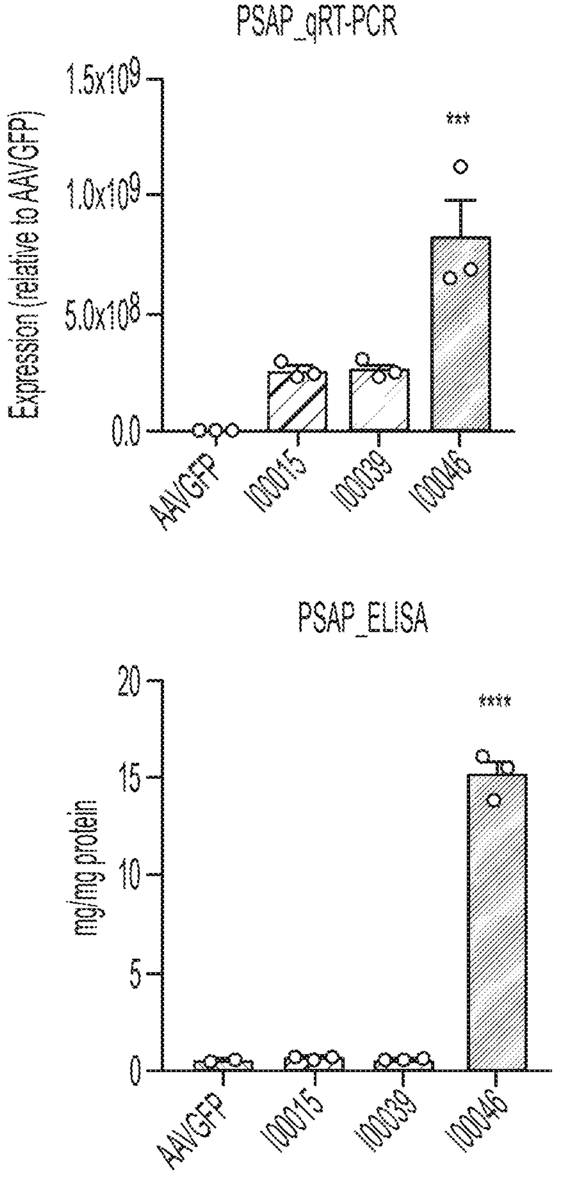
Figure 18:
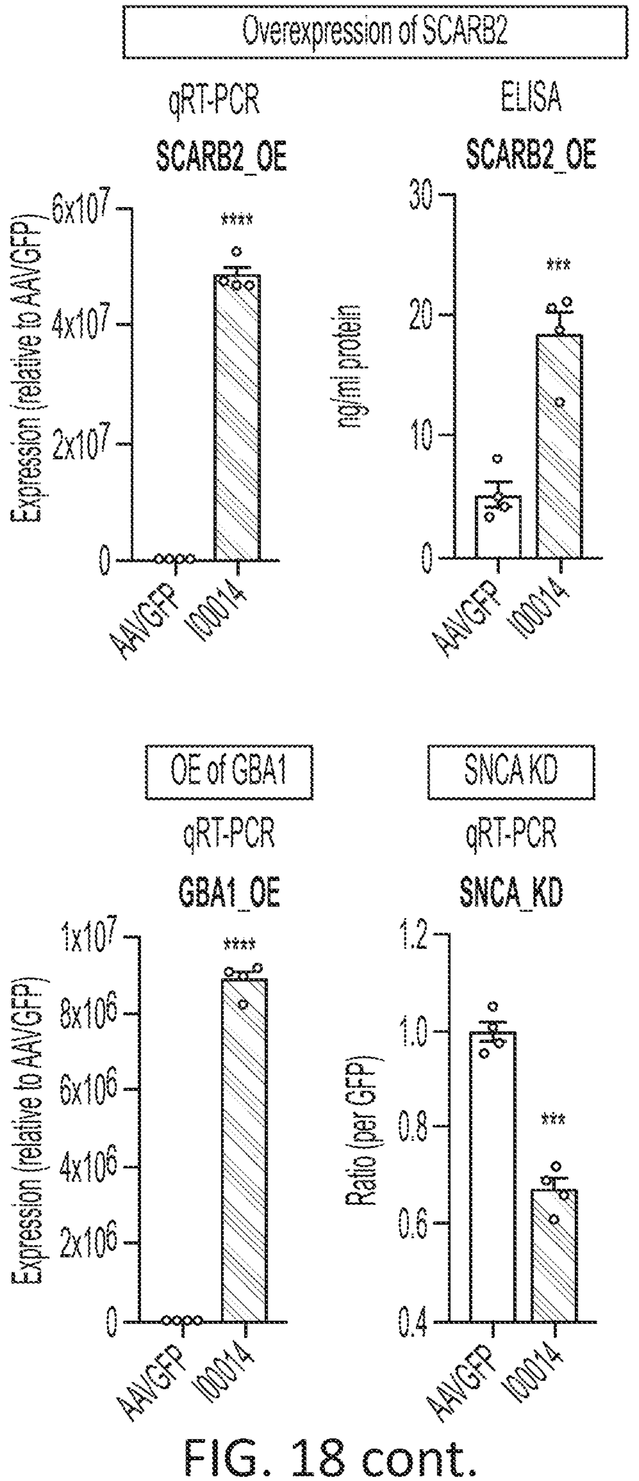

FIG. 18 shows representative data for in vitro expression of rAAV constructs encoding GBA1 in combination with Prosaposin (PSAP), SCARB2, and/or one or more inhibitory nucleic acids. Data indicate transfection of HEK293 cells with each construct resulted in overexpression of the transgenes of interest relative to GFP-transfected cells.

Figure 19:
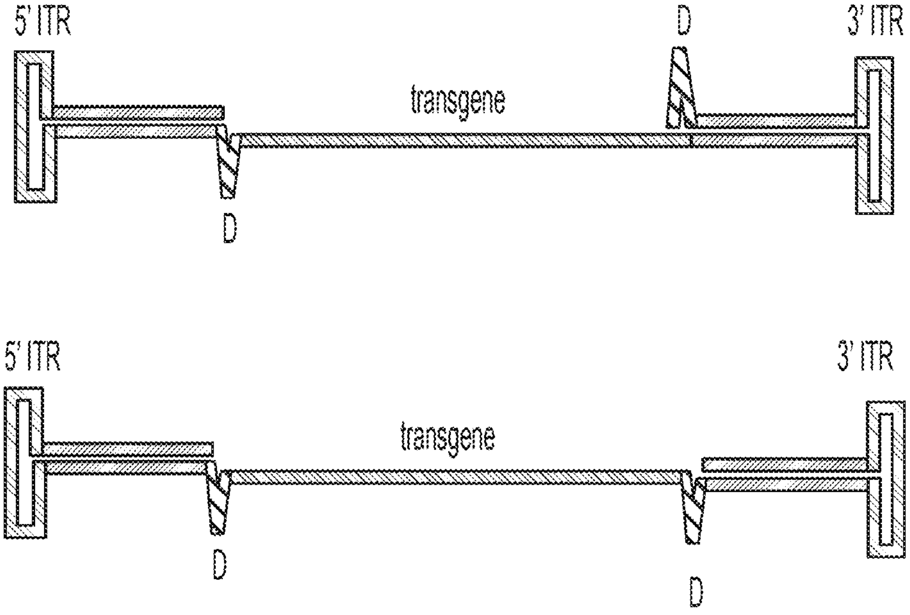

FIG. 19 is a schematic depicting an rAAV vectors comprising a "D" region located on the "outside" of the ITR (e.g., proximal to the terminus of the ITR relative to the transgene insert or expression construct) (top) and a wild-type rAAV vectors having ITRs on the "inside" of the vector (e.g., proximal to the transgene insert of the vector).

Figure 20:
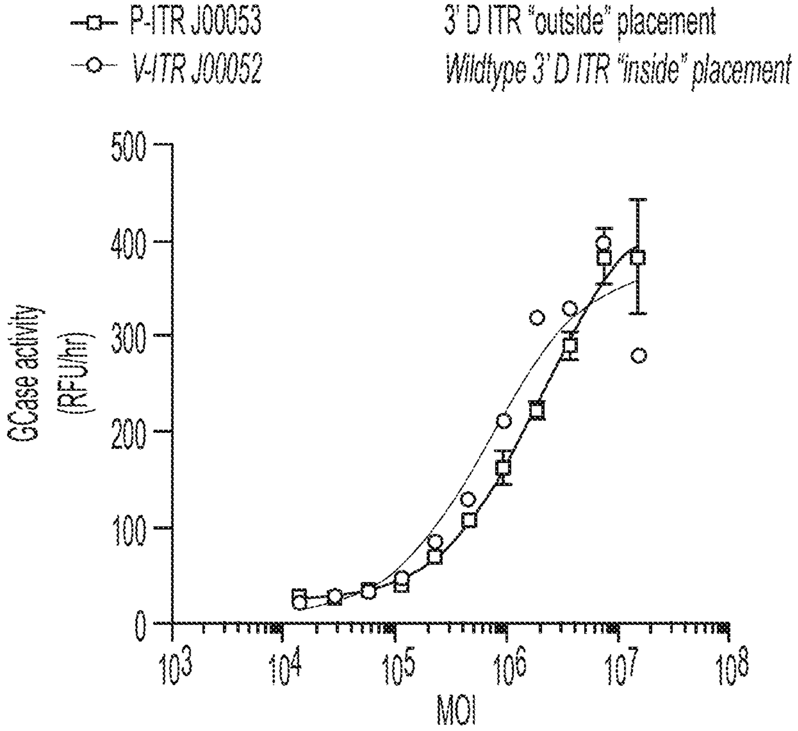

FIG. 20 shows data for transduction of HEK293 cells using rAAVs having ITRs with wild-type (circles) or alternative (e.g., "outside"; squares) placement of the "D" sequence. The rAAVs having ITRs placed on the "outside" were able to transduce cells as efficiently as rAAVs having wild-type ITRs.

Figure 21:
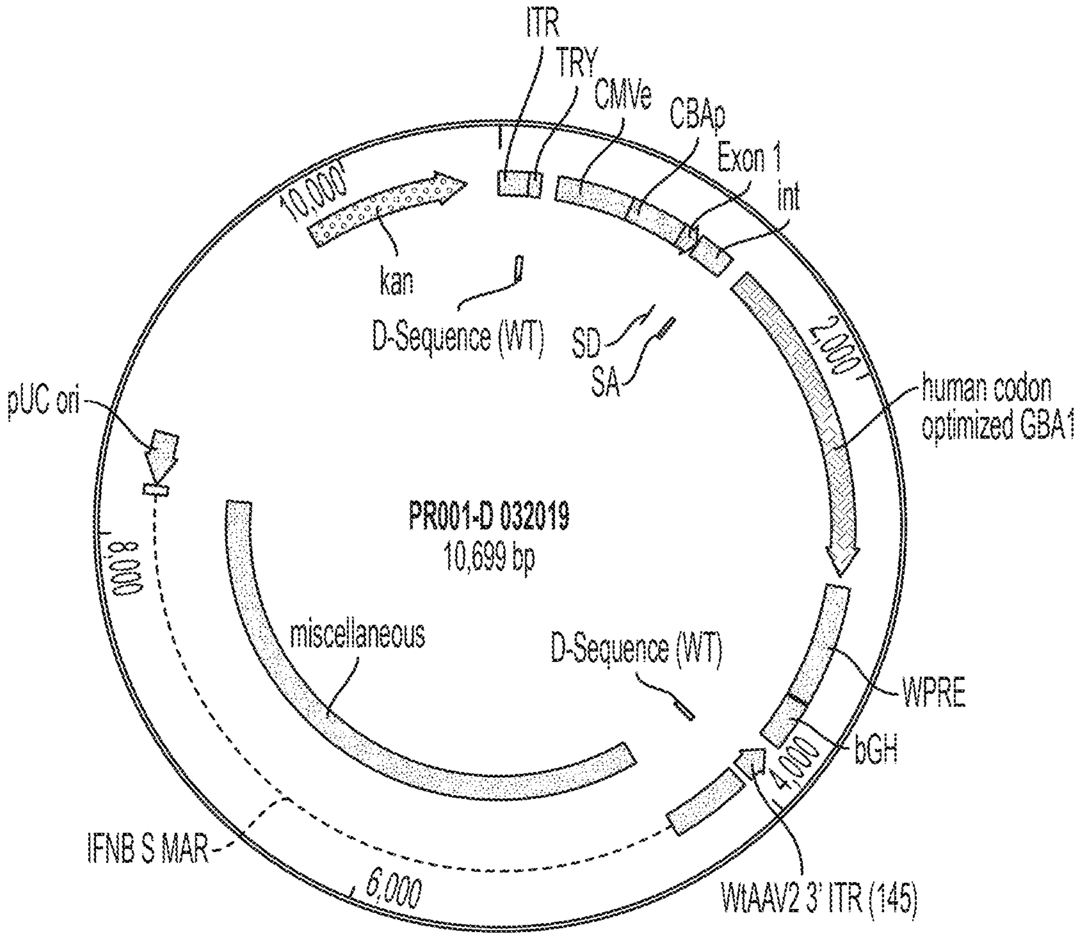

FIG. 21 is a schematic depicting one embodiment of a plasmid comprising an rAAV vector that includes an expression construct encoding Gcase (e.g., GBA1 or a portion thereof).

Figure 22:
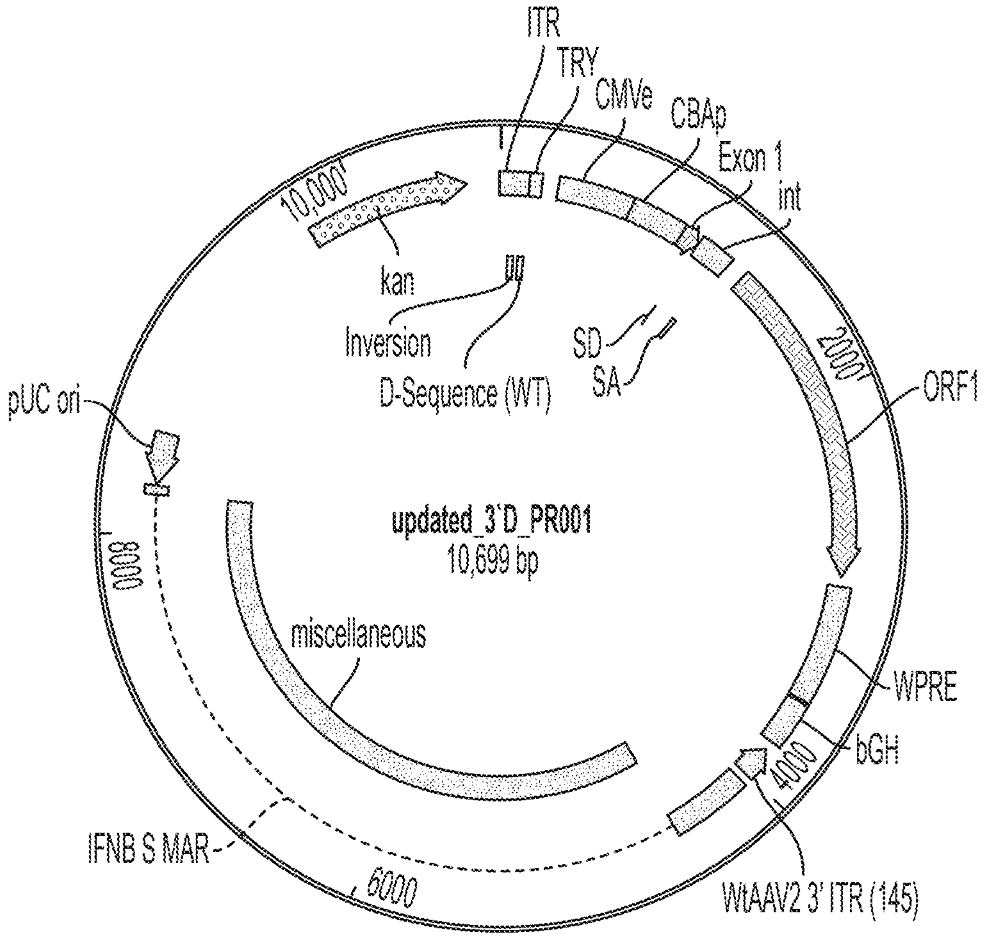

FIG. 22 is a schematic depicting one embodiment of a plasmid comprising an rAAV vector that includes an expression construct encoding Gcase (e.g., GBA1 or a portion thereof).

Figure 23:
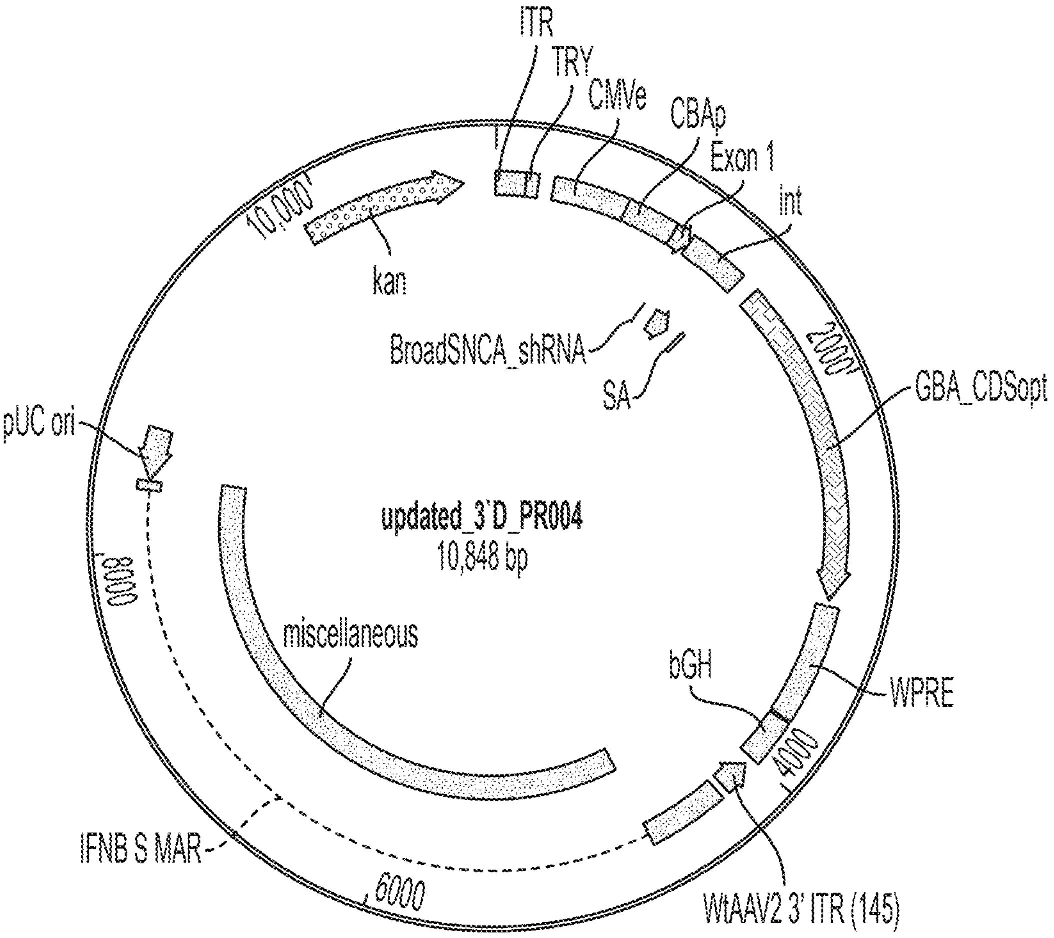

FIG. 23 is a schematic depicting one embodiment of a plasmid comprising an rAAV vector that includes an expression construct encoding Gcase (e.g., GBA1 or a portion thereof) and an interfering RNA for α-Syn.

Figure 24:
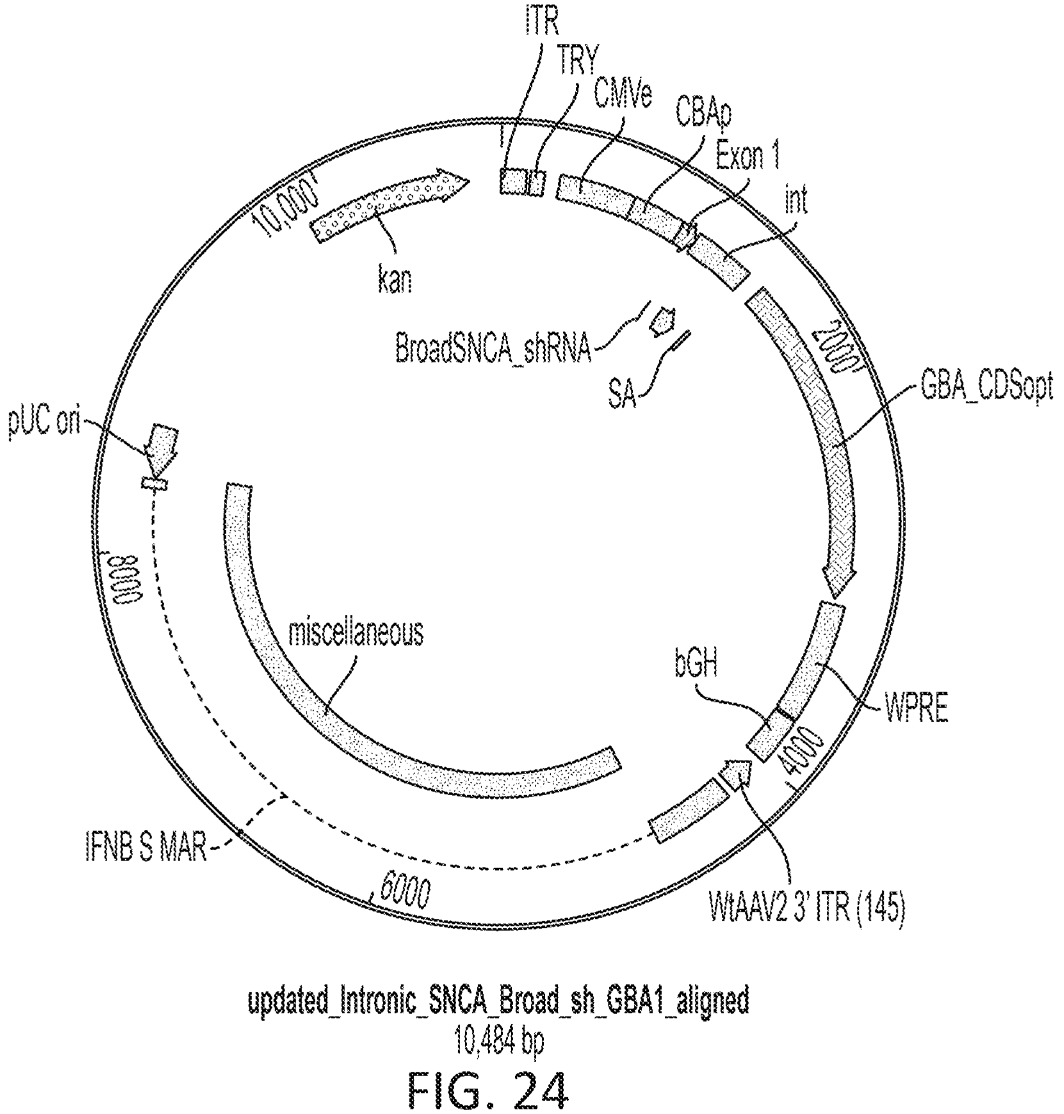

FIG. 24 is a schematic depicting one embodiment of a plasmid comprising an rAAV vector that includes an expression construct encoding Gcase (e.g., GBA1 or a portion thereof) and an interfering RNA for α-Syn.

Figure 25:
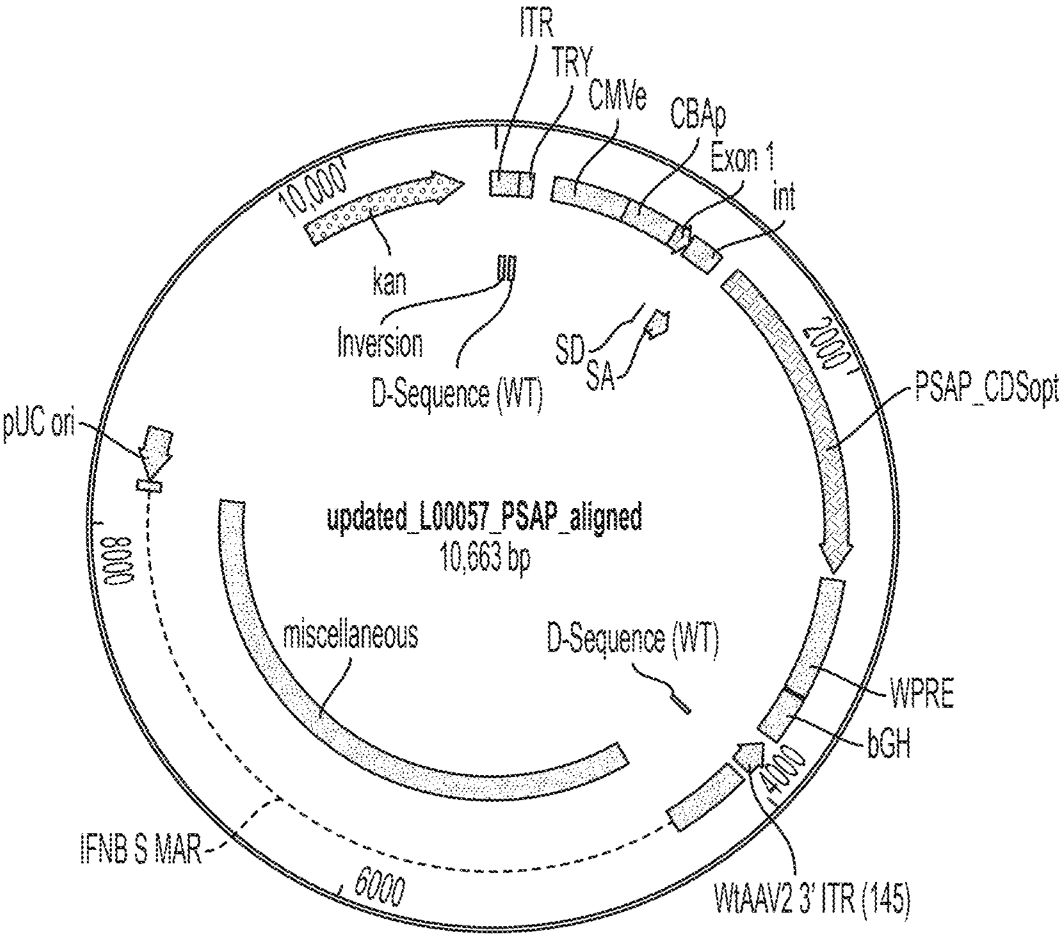

FIG. 25 is a schematic depicting one embodiment of a plasmid comprising an rAAV vector that includes an expression construct encoding Prosaposin (e.g., PSAP or a portion thereof).

Figure 26:
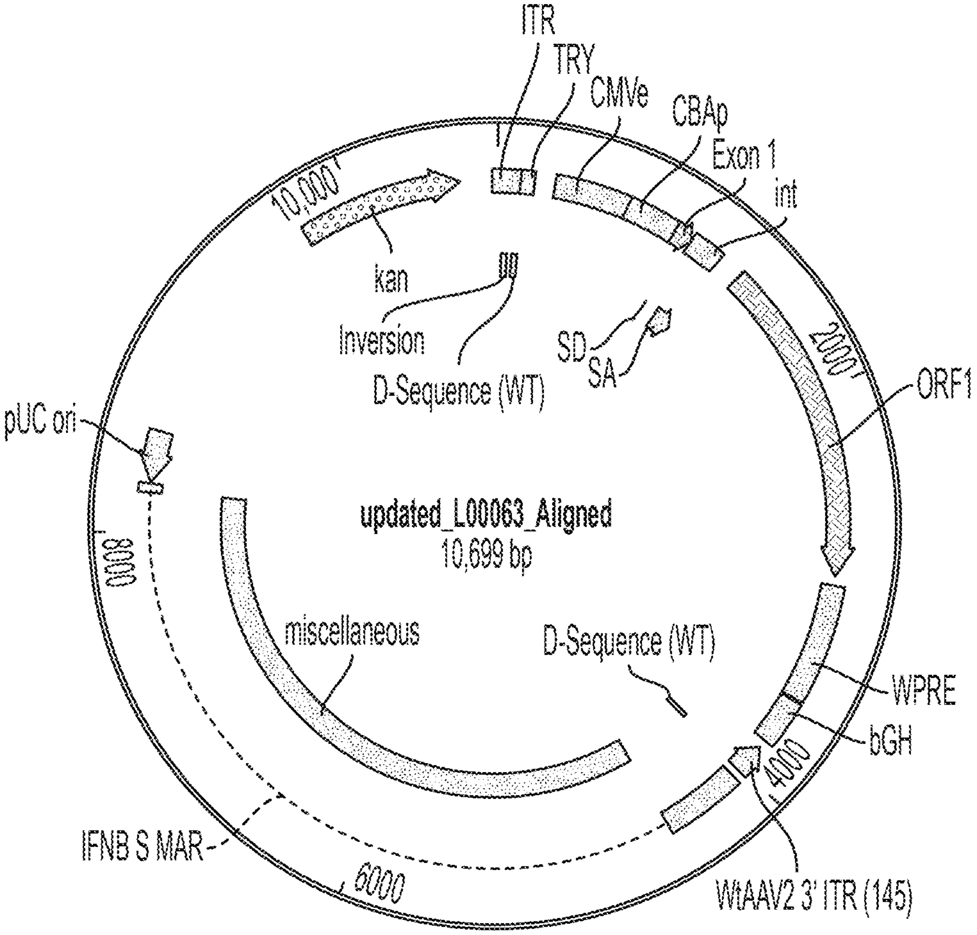

FIG. 26 is a schematic depicting one embodiment of a plasmid comprising an rAAV vector that includes an expression construct encoding Gcase (e.g., GBA1 or a portion thereof).

Figure 27:
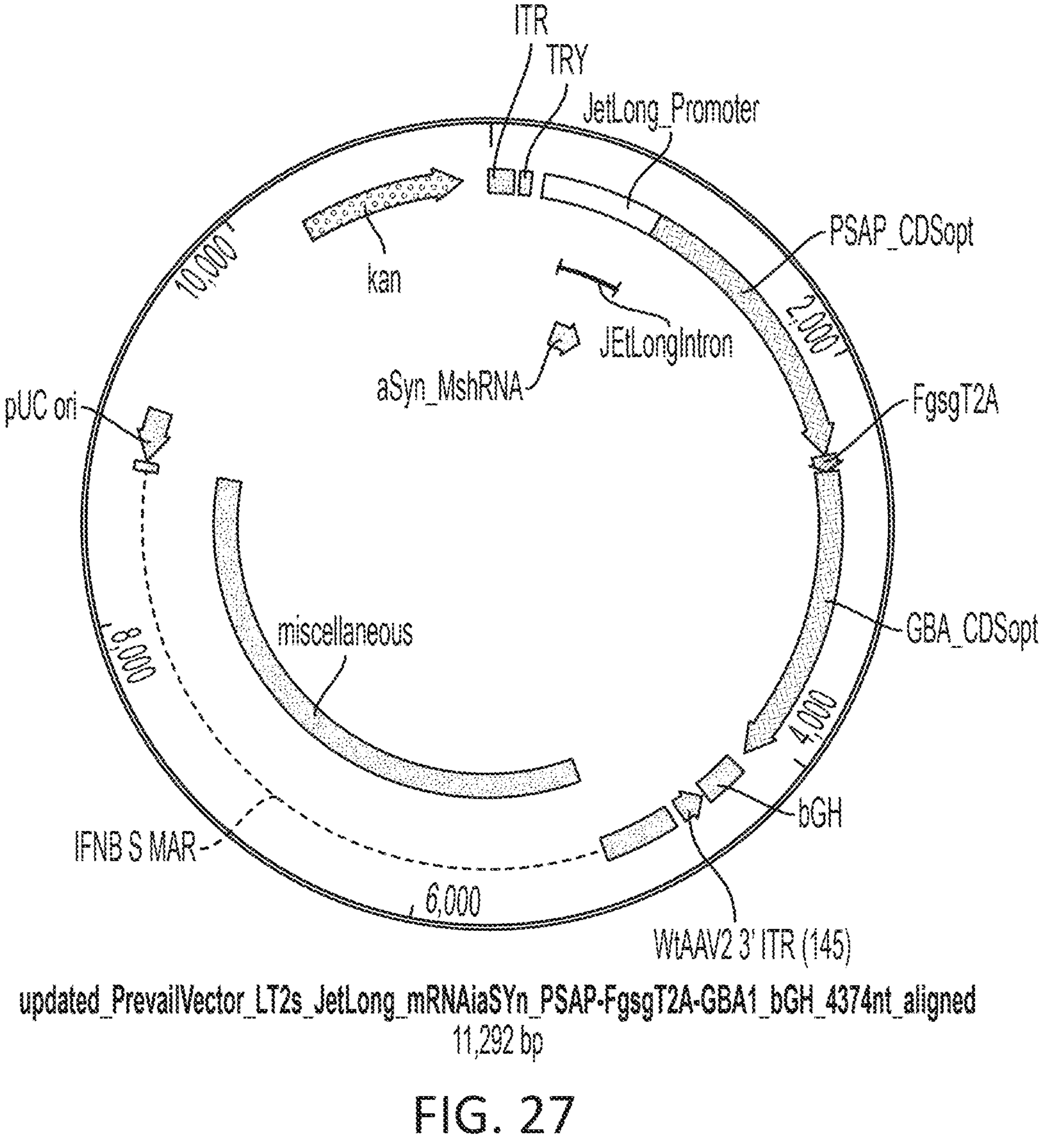

FIG. 27 is a schematic depicting one embodiment of a plasmid comprising an rAAV vector that includes an expression construct encoding Gcase (e.g., GBA1 or a portion thereof), Prosaposin (e.g., PSAP or a portion thereof), and an interfering RNA for α-Syn.

Figure 28:
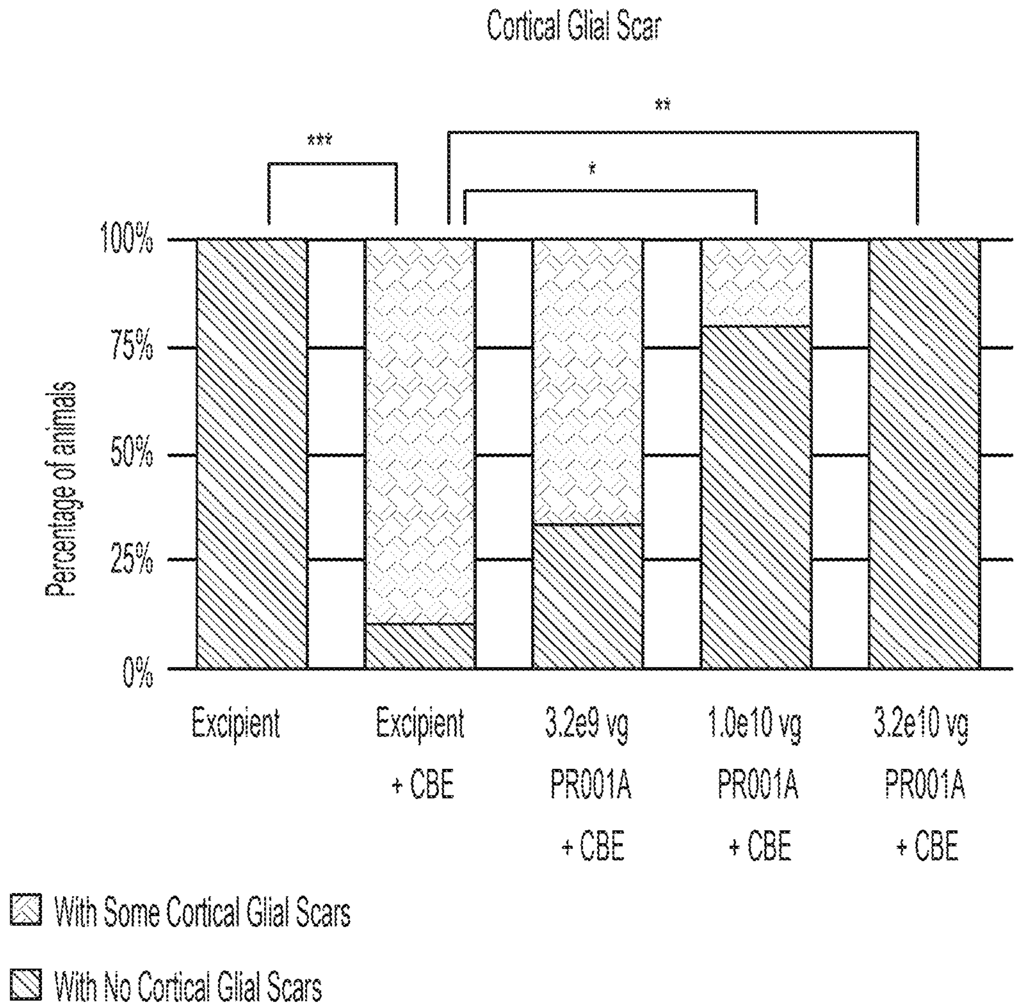

FIG. 28 shows representative data indicating administration of an rAAV vector encoding Gcase reduces glial scarring in vivo. Tissues were processed for staining with hematoxylin and eosin (H&E) and slides were evaluated for pathological changes. The percentage of animals positive for glial scars, a reflection of reactive astrogliosis, in each group is shown in light shading, while those negative for glial scars are in black. CBE treatment led to a significant increase in glial scars compared to excipient-treated controls. rAAV-GBA1 significantly reduced CBE-induced glial scarring in a dose-dependent manner. Statistical results are presented for comparisons against the Excipient+CBE groups (red). N=10,9,6,10,7 per group, respectively. *: $p<0.05$; : $p<0.01$; *: $p<0.001$ for Fischer's exact test.

Figure 29A:
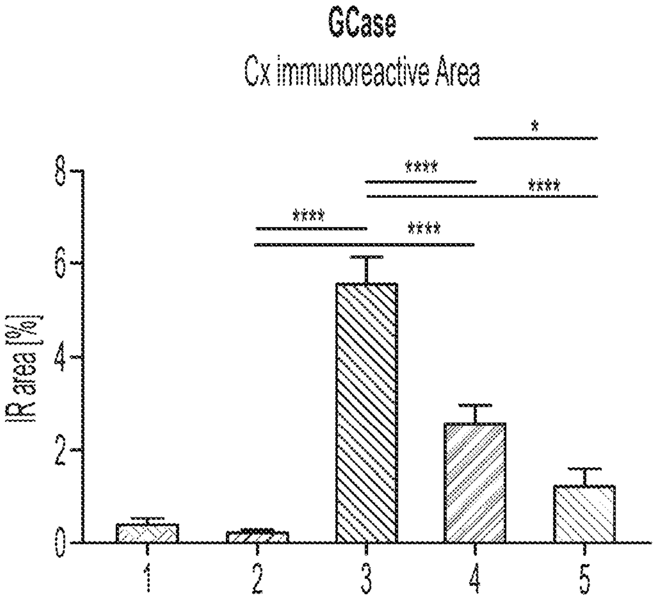
Figure 29B:
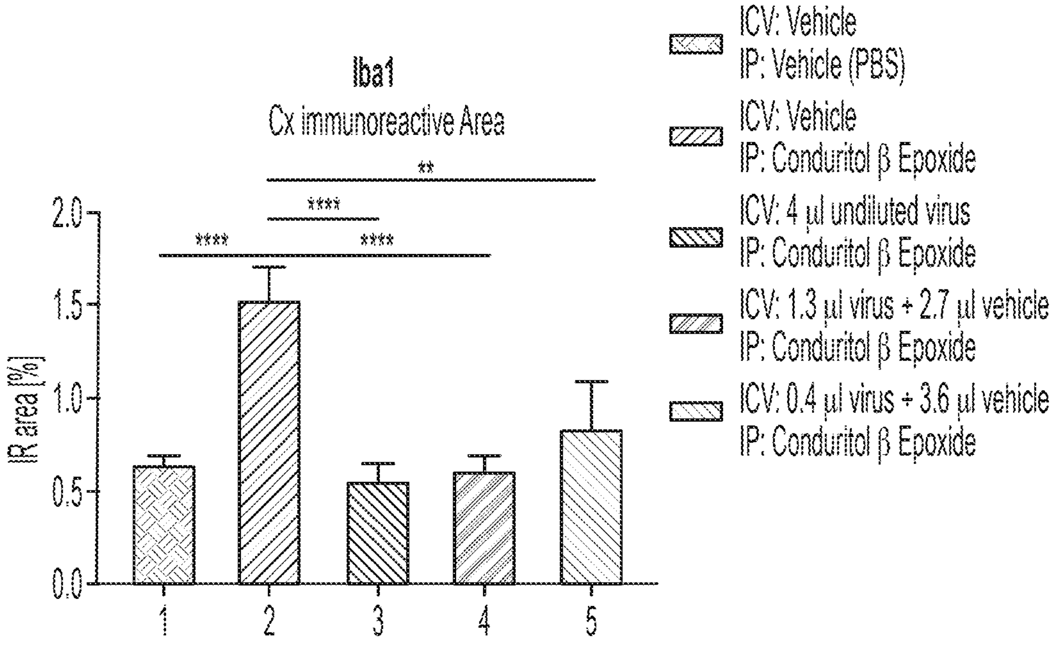

FIG. 29A-FIG. 29B show representative data for the means of immunofluorescent signal measured within the cortex (n=6-10 per group) of mice administered rAAV-GBA1 or excipient. Quantification of GCase (FIG. 19A) immunolabeling revealed strongest immunofluorescent labeling in high-dose rAAV-GBA1 treated animals, followed by mid- and low-dose rAAV-GBA1 treated animals. Iba1 (FIG. 29B) immunoreactive area was significantly higher in CBE/Excipient treated animals than in mice of all other groups investigated. Data were analyzed with one-way ANOVA and Sidak's post hoc test for multiple comparisons. Bar graphs represent group means+SEM.

Figure 30:
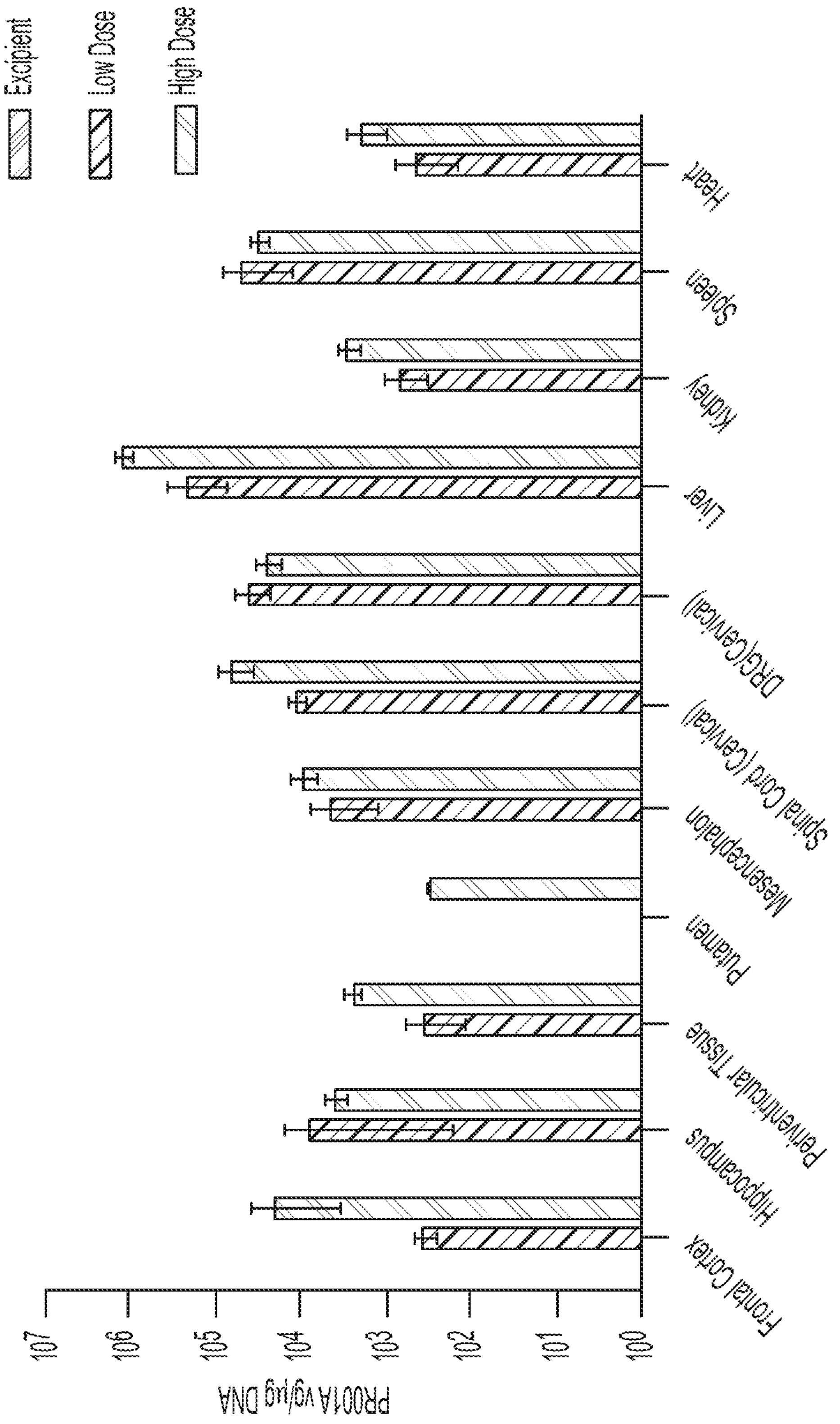

FIG. 30 is a bar graph showing representative data for biodistribution of PR001A transgene in study PRV-2018-016 at Day 183. The study is described in Example 12. Transgene levels were analyzed using qPCR methodologies in NHP (non-human primates) 183 days after intra-cisterna *magna* (ICM) injection of either excipient, low dose of PR001A ($6.2\times10^{10}$ vg/g brain), or high dose of PR001A ($2.3\times10^{11}$ vg/g brain). Each bar represents the average±SEM of 3 animals per group; values that were below the limit of quantitation were plotted as zero. As the qPCR values for the excipient-treated animals were zero for each region, the excipient bars are not shown on the graph with this scale.

Figure 31A:
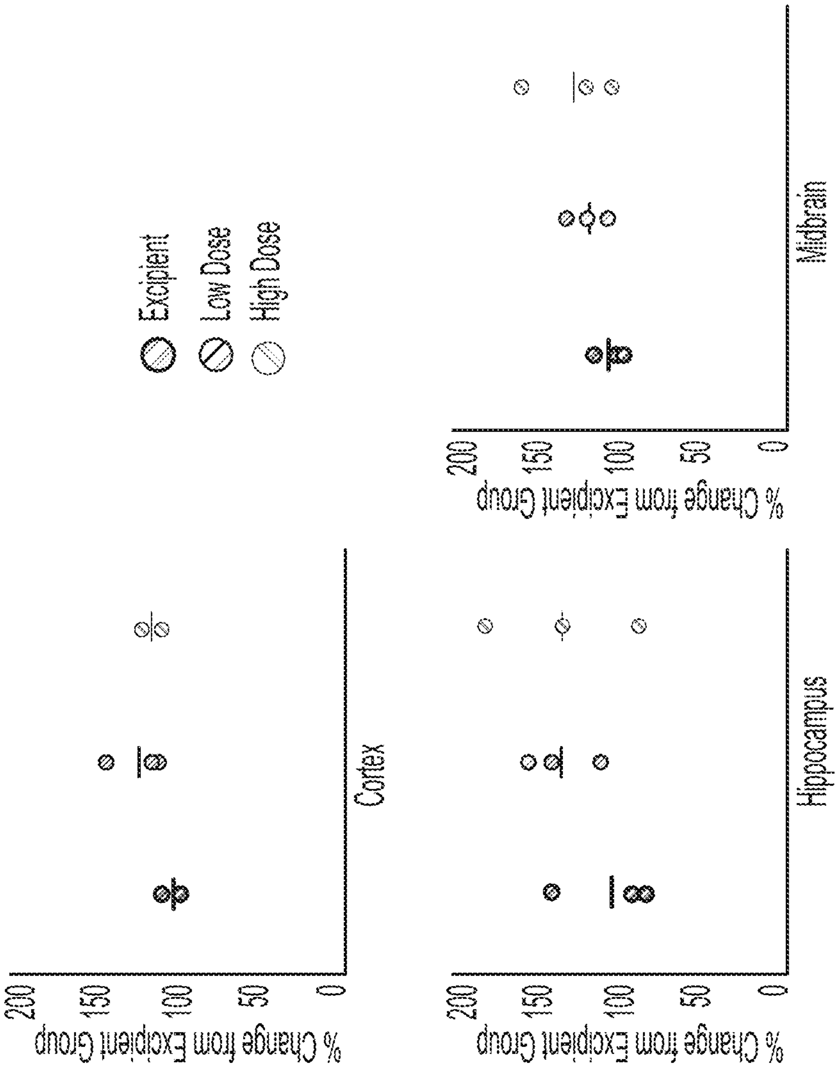
Figure 31B:
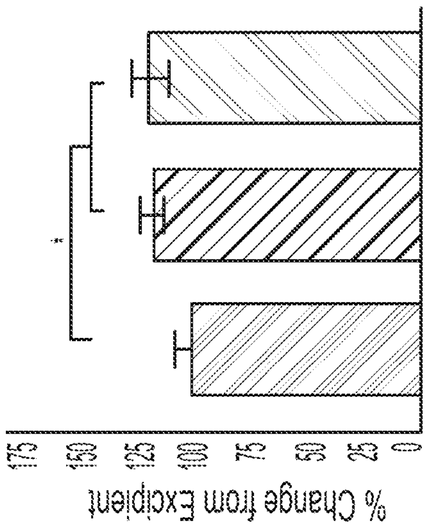

FIG. 31A-FIG. 31B are graphs showing representative data for human GCase expression at day 183 in study PRV-2018-016. The study is described in Example 12. GCase expression levels were determined in NHP (non-human primate) cortex, hippocampus, and midbrain samples that were collected at Day 183 by a Simple Western™ (Jess) analysis. GCase expression levels from NHPs treated with excipient (left in each panel), low dose of PR001A ($6.2\times10^{10}$ vg/g brain weight; center in each panel) or high dose of PR001A ($2.3\times10^{11}$ vg/g brain weight; right in each panel) are shown. FIG. 31A presents the data from individual cortex, hippocampus, and midbrain regions. FIG. 31B shows the percent change from the excipient-treated group (left), low dose (center), and high dose (right) groups. The data for this plot was mean-normalized within tissue and combined for cortex, hippocampus, and midbrain. Each bar represents percent of the excipient group median for each dose of the mean normalized data. To calculate significance, a one-way ANOVA was performed to consider significance for a combined treatment group that included both the low- and high-dose treated animals to the excipient group. P value=0.014 (*<0.05).

Figure 32:
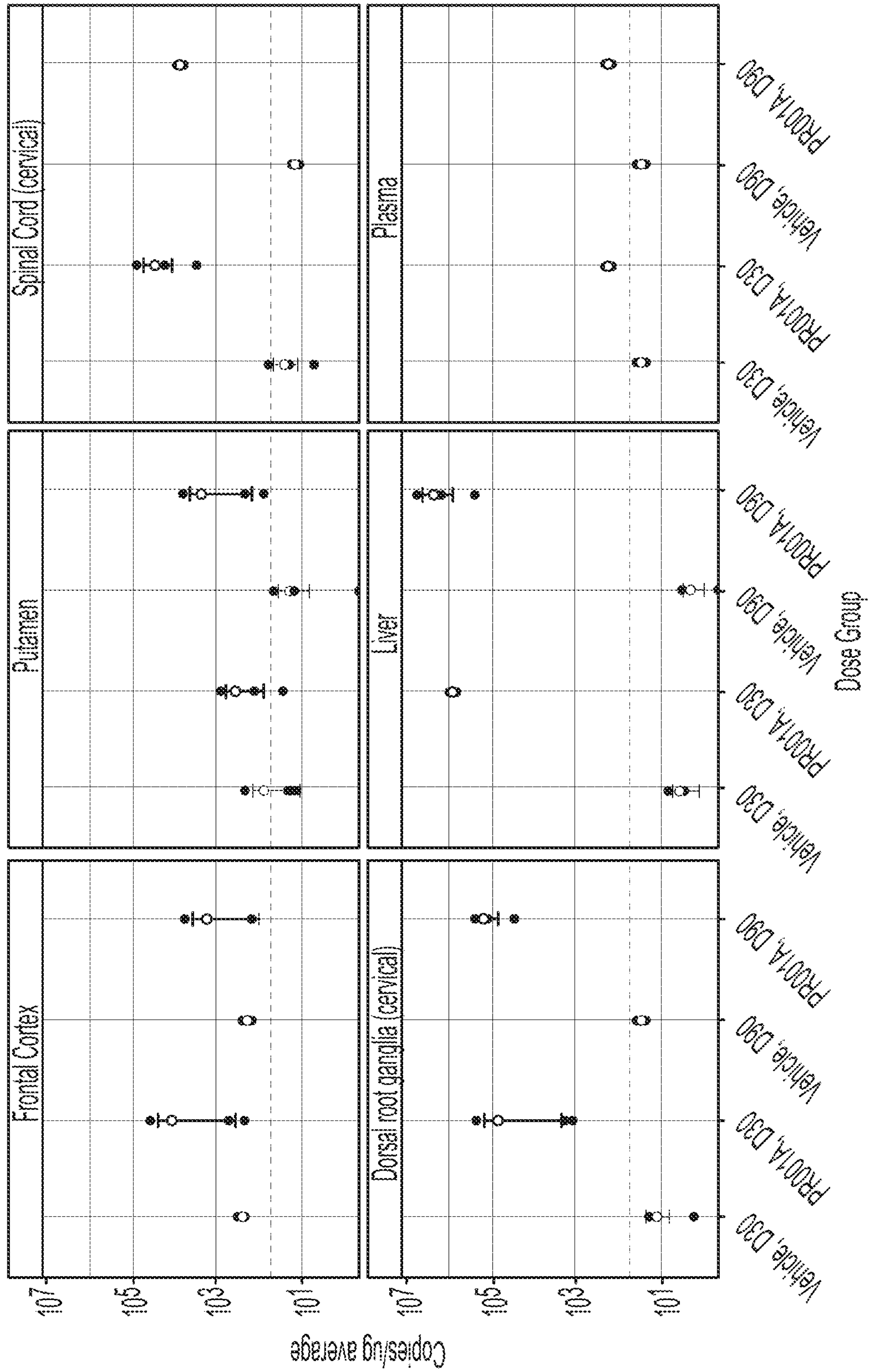

FIG. 32 is a series of plots showing representative data for biodistribution of PR001A transgene quantified by qPCR in Study PRV-2019-005. The study is described in Example 12. Transgene levels were analyzed using qPCR methodologies in NHPs (non-human primates) 30 and 90 days after intra-cisterna *magna* (ICM) injection of either excipient or PR001A ($7.0\times10^{11}$ vg/g brain). Each plot represents each individual animal (n=3/group) with the average±SEM.

Figure 33:
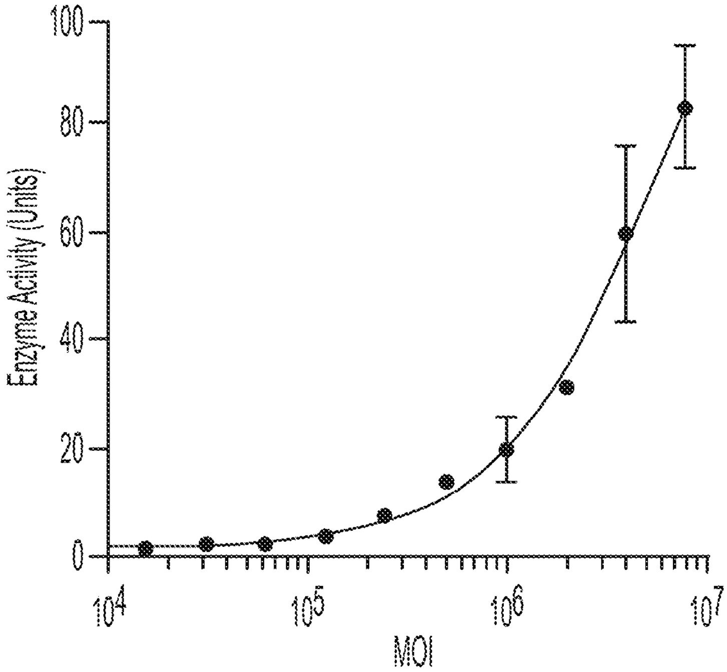

FIG. 33 is a line graph showing representative data for GCase activity after in vitro transduction of HEK293T cells with PR001A. HEK293T cells transduced with PR001A at different multiplicity of infection (MOI) were assayed for GCase activity. Activity was measured by hydrolysis of the pro-fluorescent substrate resorufin β-D-glucopyranoside. Fluorescence of the cleaved substrate was determined using a plate reader at an excitation of 573 nm and an emission of 610 nm. Values are means±SEM, n=2; a unit is equivalent to the activity of 1 ng/mL of recombinant purified GCase.

Figure 34A:
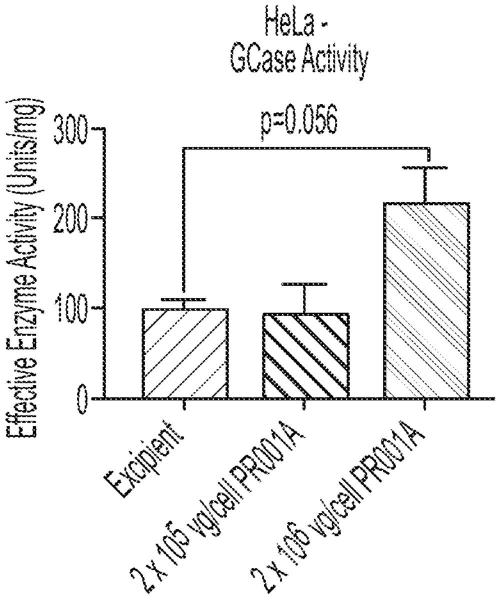
Figure 34B:
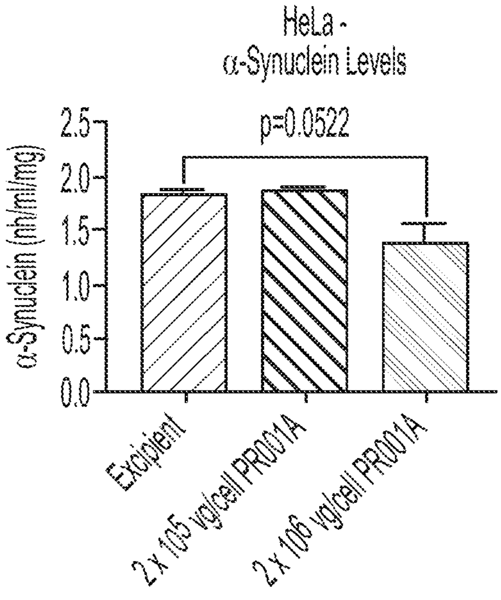

FIG. 34A-FIG. 34B are bar graphs showing representative data for GCase activity (FIG. 34A) and α-Synuclein levels (FIG. 34B) after in vitro transduction of HeLa cells with PR001A. HeLa cells treated with excipient (left bar) or transduced with $2\times10^5$ vg/cell PR001A (center bar) or $2\times10^6$ vg/cell PR001A (right bar) were collected 72 hours post treatment and analyzed for GCase activity levels (FIG. 34A) by a fluorometric enzyme assay or α-Synuclein levels (FIG. 34B) by ELISA. Effective enzymatic GCase activity is shown as units per mg of total protein with one unit defined as the activity of 1 ng/mL of recombinant purified GCase. α-Synuclein concentration is presented as ng/mL per mg of total protein. Studies were performed in biological triplicate. Means are presented. Error bars are SEM. One-way ANOVA was used followed by Dunnett's multiple comparisons test.

Figure 35B:
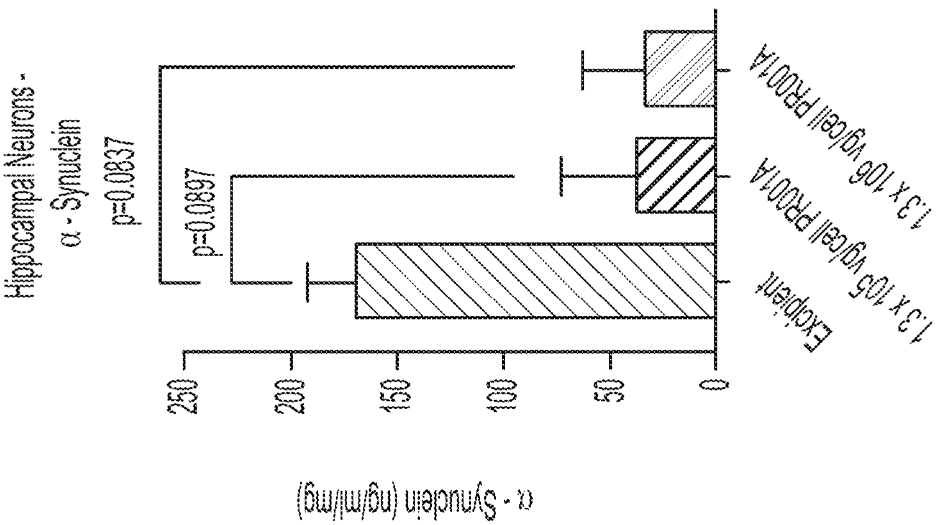
Figure 35A:
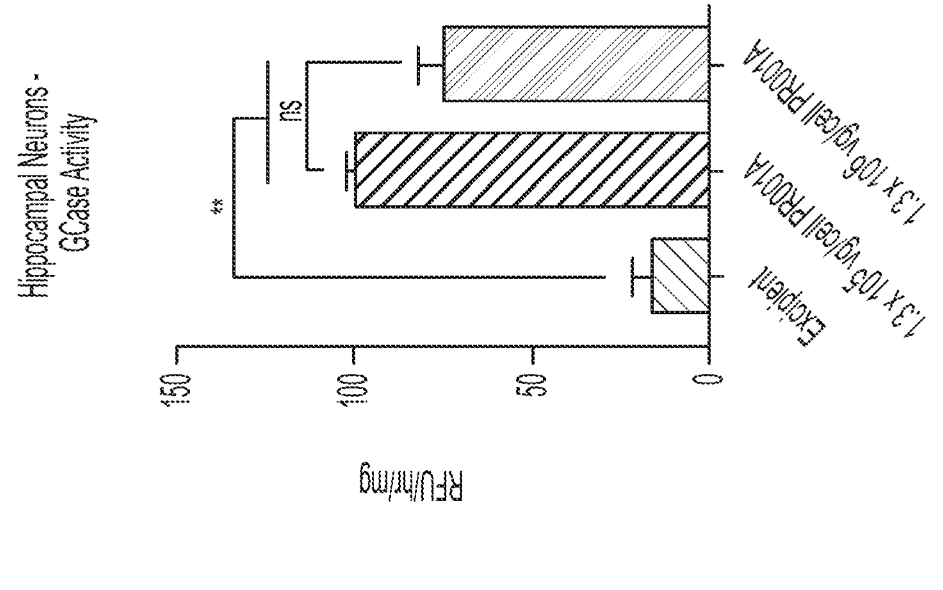

FIG. 35A-FIG. 35B are bar graphs showing representative data for GCase activity (FIG. 35A) and α-Synuclein levels (FIG. 35B) after in vitro transduction of mouse hippocampal neurons with PR001A. Primary cultures of mouse hippocampal neurons were treated with excipient (left bar) or transduced with $1.3\times10^5$ vg/cell PR001A (center bar) or $1.3\times10^6$ vg/cell PR001A (right bar) on Day in vitro (DIV) 2. On DIV9, cells were collected and analyzed for GCase activity levels (FIG. 35A) by a fluorometric enzyme assay or α-Synuclein levels (FIG. 35B) by ELISA. GCase activity is shown as relative fluorescent units (RFU) per hour per mg of total protein. α-Synuclein concentration is presented as ng/mL per mg of total protein. Studies were performed in biological duplicate. Means are presented. Error bars are SEM. One-way ANOVA was used followed by Dunnett's multiple comparisons test.

Figure 36:
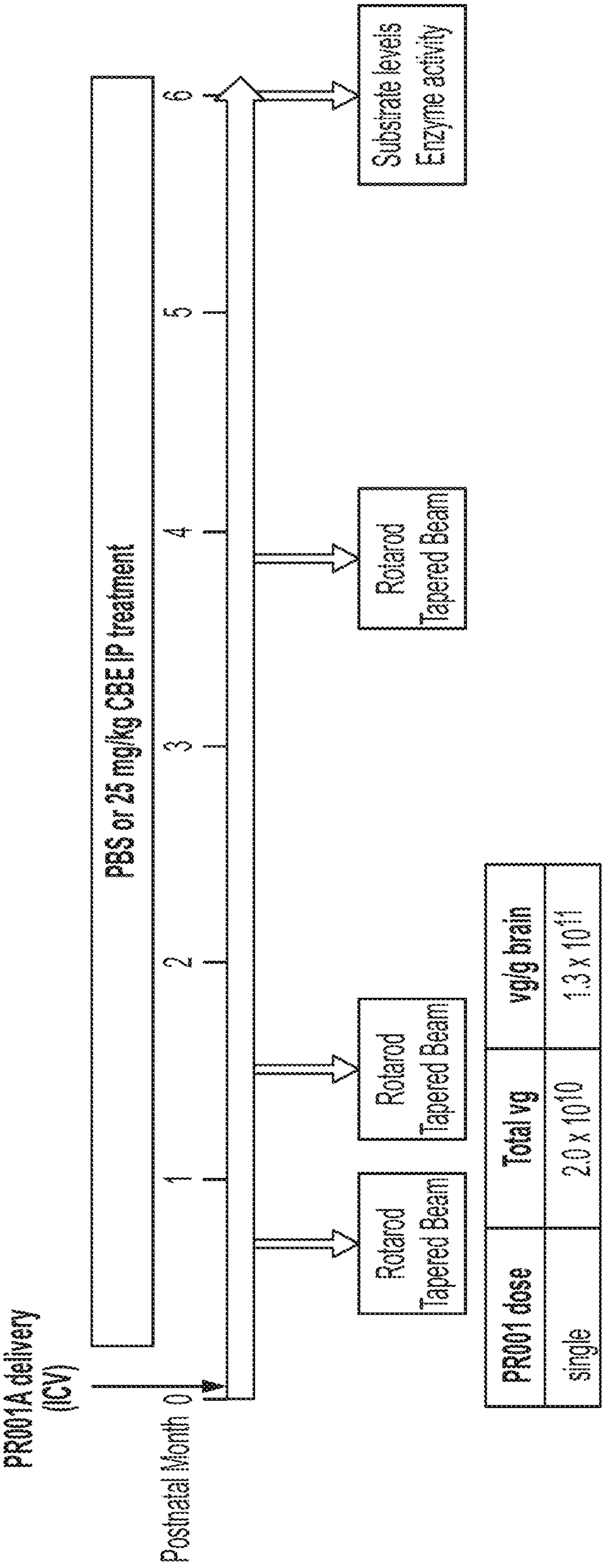

FIG. 36 is a schematic depicting one embodiment of a study design for long-term treatment with a rAAV encoding GCase in a CBE mouse model. PR001A was delivered by ICV injection at P3, and daily CBE treatment was initiated at P8. Behavior was assessed in the rotarod assay at Weeks 3, 6, and 15 and the tapered beam assay at Weeks 4, 7, 13. The animals were sacrificed around Week 26, 1 day after their final CBE dose. The cerebral cortices were analyzed for GluSph and GluCer substrate levels and GCase activity. There were 10-11 animals per treatment group, each including male and female mice.

FIG. 37A-FIG. 37D show representative data for assessment of long-term PR001A treatment in a CBE model. The cortex of all treatment groups (PBS+excipient: left bar, CBE+excipient: center bar, CBE+$2.0\times10^{10}$ vg PR001A: right bar) was used to measure vector genomes (FIG. 37A), GCase activity (FIG. 37B), GluSph levels (FIG. 37C), and GluCer levels (FIG. 37D). Presence of vector genomes was assessed in each tissue and all treatment groups, shown as number of vector copies per 1 μg of genomic DNA. Vector genome presence was quantified by qPCR using a vector reference standard curve. Effective enzymatic GCase activity is shown as units per mg of total protein with one unit defined as the activity of 1 ng/mL of recombinant purified GCase. GluSph, and GluCer levels are shown as pmol per nmol of phosphate. Means are presented. Error bars are SEM. N=10, 11, 10 per group, respectively. (*) $P<0.1$, *$P<0.05$; $P<0.01$; *$P<0.001$ by ANOVA followed by Tukey's HSD multiple tests correction.

Figure 38A:
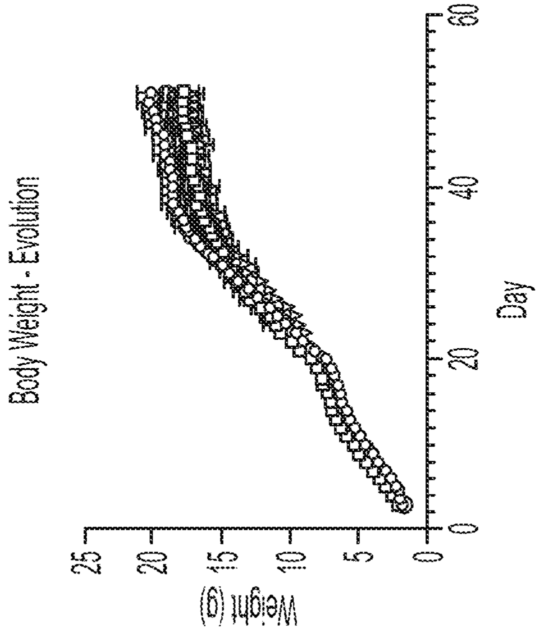
Figure 38B:
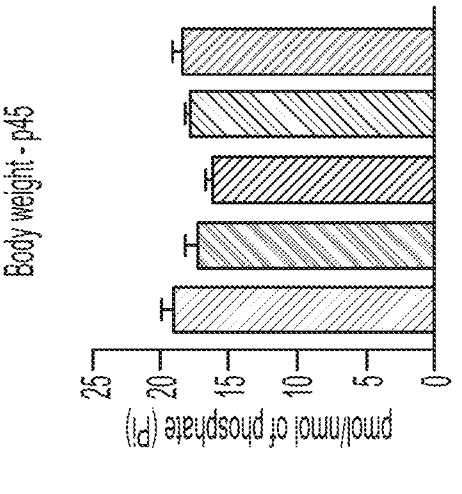
Figure 38C:
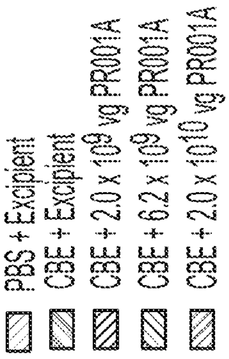
Figure 38C:
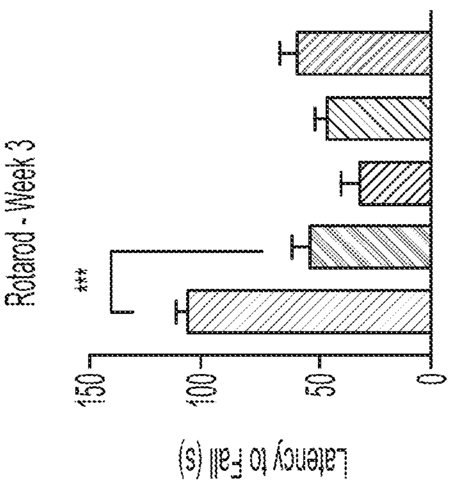
Figure 38D:
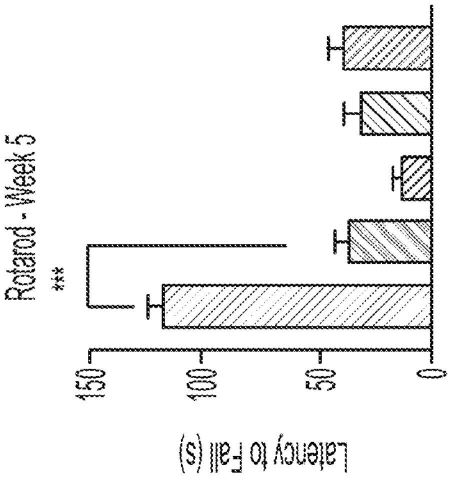
Figure 38E:
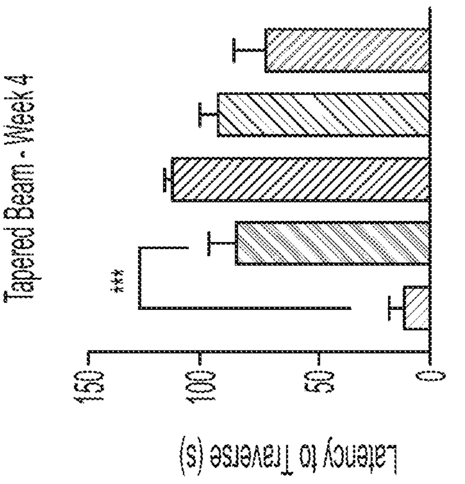

FIG. 38A-FIG. 38E show representative data for in-life assessment of additional dose-ranging PR001A in a CBE model. All treatment groups were weighed daily (FIG. 38A), and their weight was analyzed at P45 (FIG. 38B). Motor performance was assessed by latency to fall on rotarod at Week 3 (FIG. 38C) and Week 5 (FIG. 38D), and latency to traverse the tapered beam (FIG. 38E) at Week 4. n=8-11 per group. Means are presented. Error bars are SEM. Statistical results are presented for comparisons against the CBE+ excipient group (second bar from left). ***P<0.001 by ANOVA followed by Tukey's HSD test.

Figure 39:
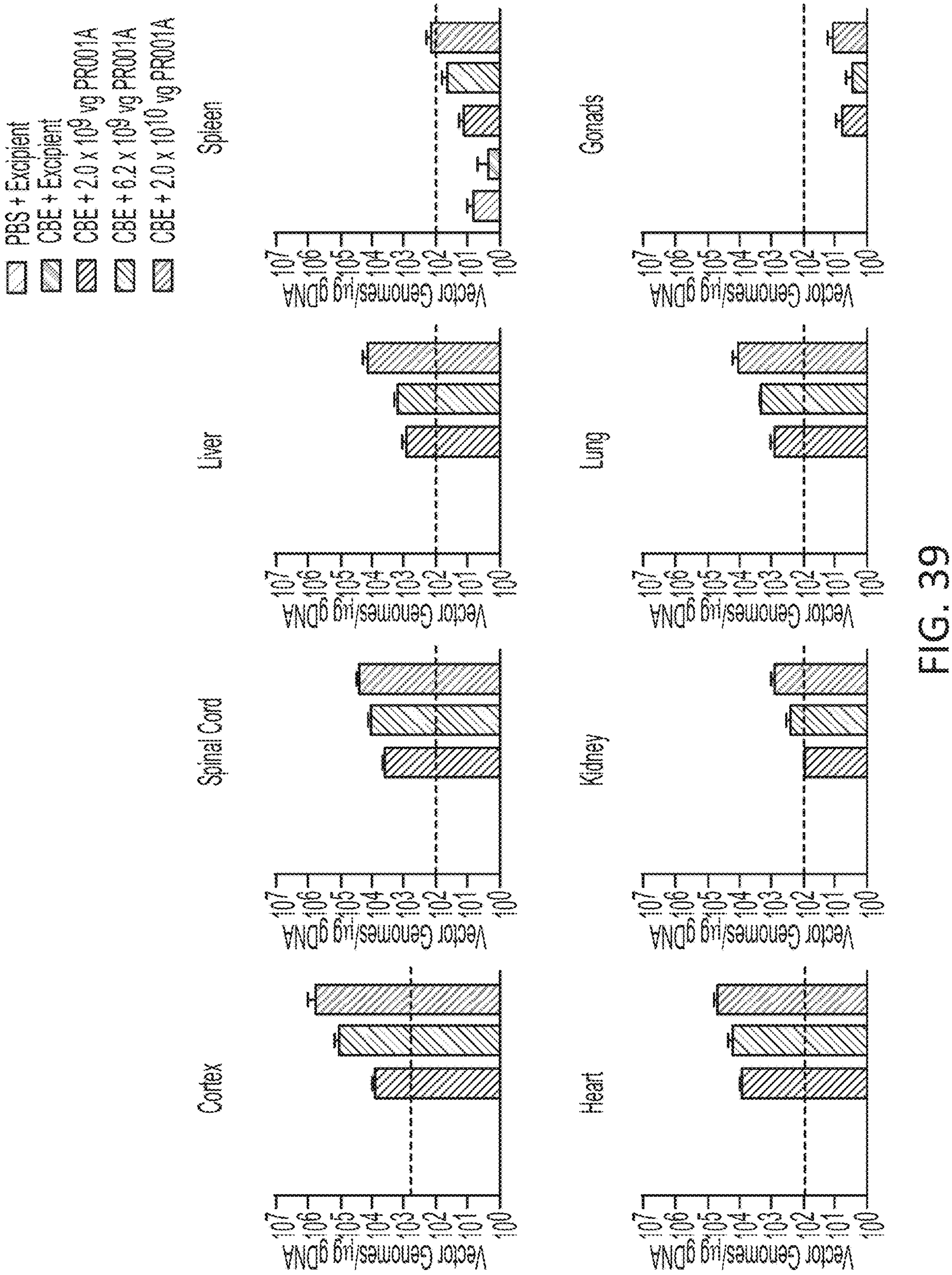

FIG. 39 shows representative data for biodistribution in an additional dose-ranging CBE model study. Presence of vector genomes was assessed in each tissue and all treatment groups, shown as number of vector copies per 1 μg of gDNA. Vector genome presence was quantified by qPCR using a vector reference standard curve; n=9-11 per group. Black dashed line (at 100 vector genomes/μg gDNA) represents the detection threshold for positive vector presence. Means are presented. Error bars are SEM.

Figure 40:
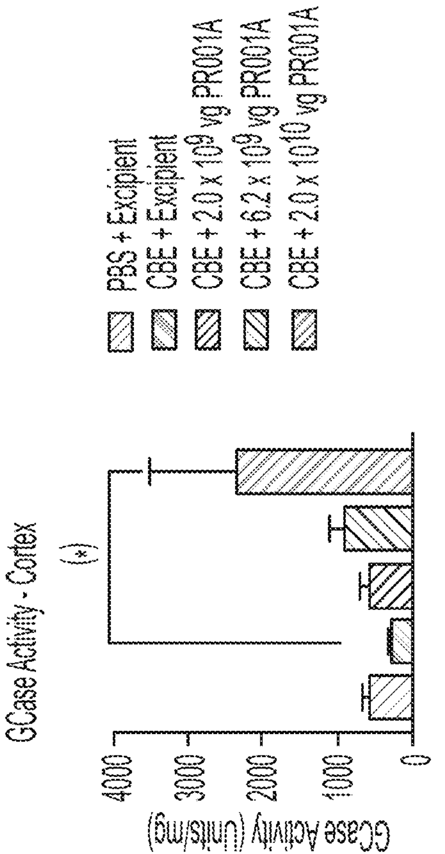

FIG. 40 shows representative data for GCase enzymatic activity in an additional dose-ranging CBE model study. Effective enzymatic GCase activity was measured and is shown for the cerebral cortex of all treatment groups. Activity is shown as units per mg of total protein with one unit defined as the activity of 1 ng/mL of recombinant purified GCase. Means are presented. Error bars are SEM. Statistical results are presented for comparisons against the CBE+excipient group (second bar from left). n=9-11 per group. (*)P<0.1 by ANOVA followed by Tukey's HSD test.

Figure 41A:
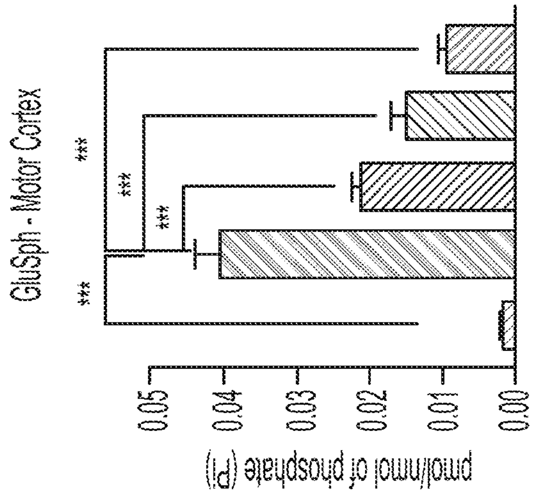
Figure 41B:
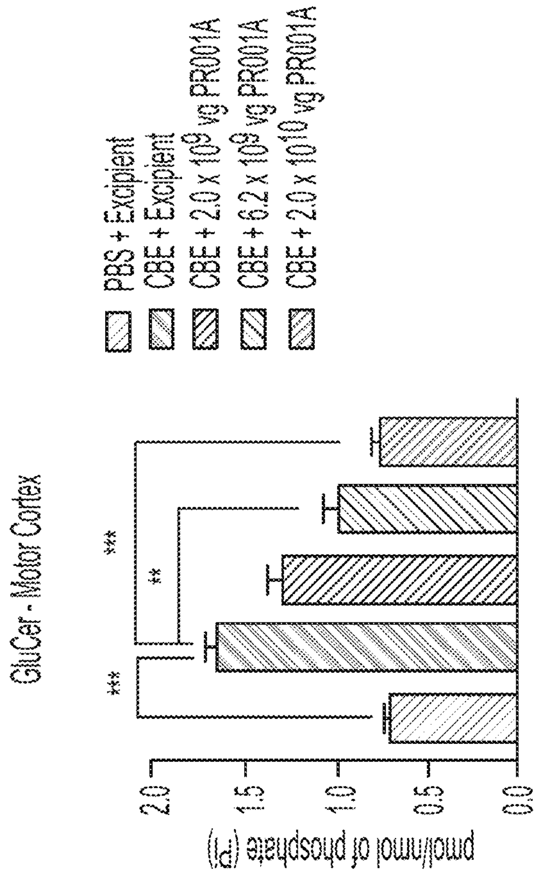

FIG. 41A-FIG. 41B show representative data for glycolipid analysis in an additional dose-ranging CBE model study. GluSph (FIG. 41A) and GluCer (FIG. 41B) levels are shown as pmol per nmol of phosphate. Means are presented. Error bars are SEM. Statistical results are presented for comparisons against the CBE+excipient group (second bar from left). n=9-11 per group. P<0.01; *P<0.001, by ANOVA followed by Tukey's HSD test.

Figures 42A, 42B, 42C, 42D:
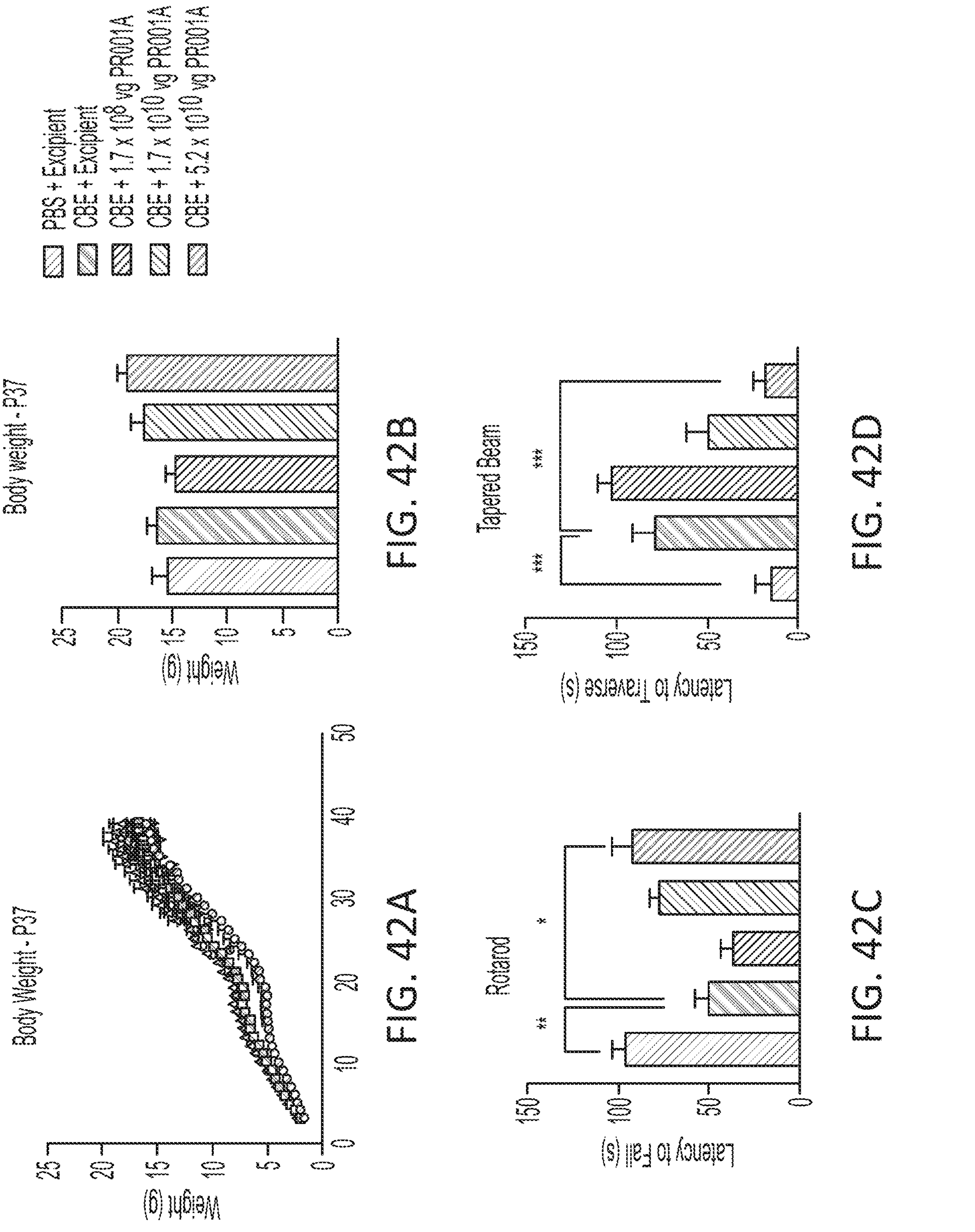

FIG. 42A-FIG. 42D show representative data for in-life assessment of further dose-ranging PR001A in a CBE model study. All treatment groups were weighed daily (FIG. 42A), and their weight was analyzed at P37 (FIG. 42B). Motor performance was assessed by latency to fall on rotarod at Week 3 (FIG. 42C) and latency to traverse the tapered beam (FIG. 42D) at Week 4. n=9-10 per group. Means are presented. Error bars are SEM. Statistical results are presented for comparisons against the CBE+excipient group (second bar from left). ***P<0.001 by ANOVA followed by Tukey's HSD test.

Figure 43A:
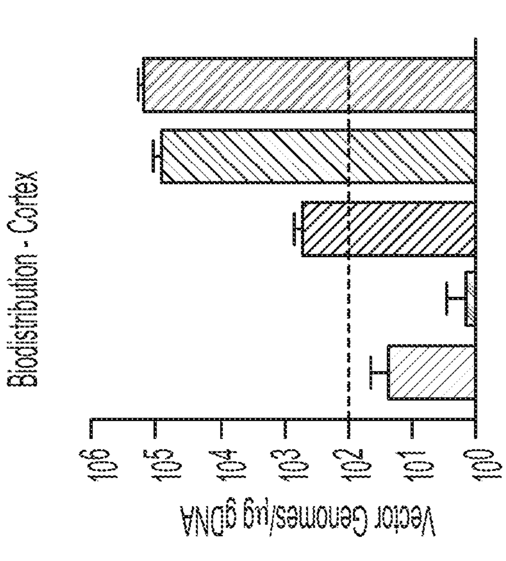
Figure 43B:
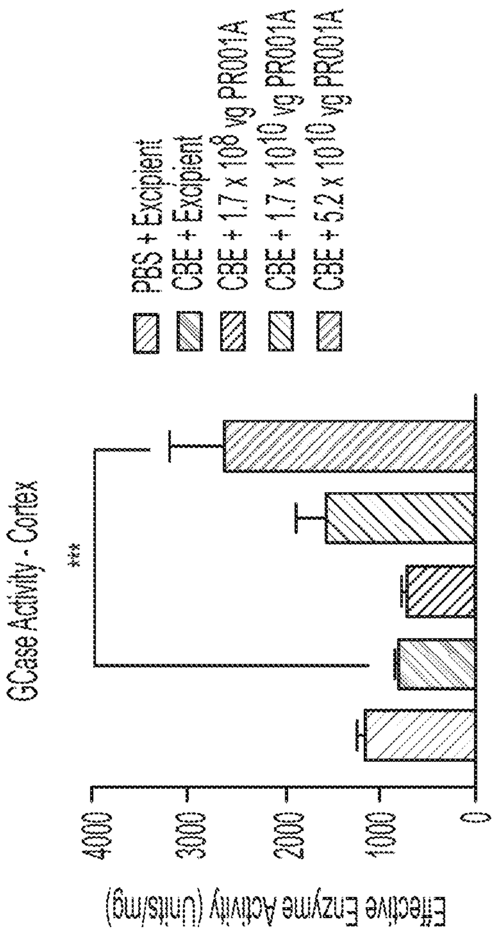

FIG. 43A-FIG. 43B show representative data for biodistribution and GCase enzymatic activity in further dose-ranging PR001A in a CBE model study. Vector genomes were measured in the cerebral cortex (FIG. 43A) of all treatment groups and are shown as number of vector copies per 1 μg of genomic DNA (gDNA). Vector genome presence was quantified by qPCR using a vector reference standard curve. Black dashed line represents the detection threshold for positive vector presence (at 100 vector genomes/μg gDNA). Effective enzymatic GCase activity was measured in the cerebral cortex (FIG. 43B) and is shown as units per mg of total protein with one unit defined as the activity of 1 ng/mL of recombinant purified GCase. Means are presented. Error bars are SEM. N=9-10 per group. ***P<0.001; by ANOVA followed by Tukey's HSD test.

Figure 44A:
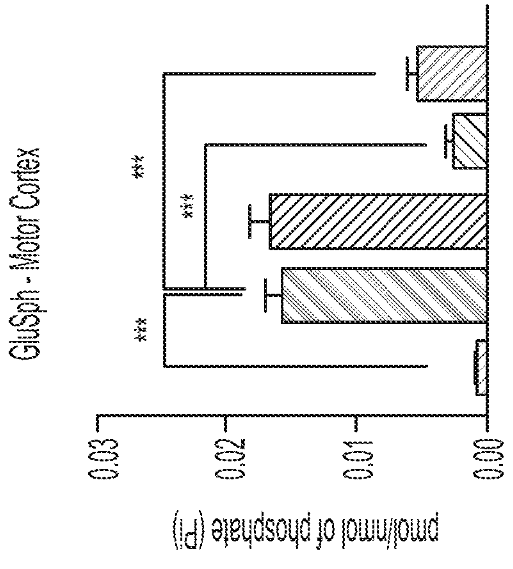
Figure 44B:
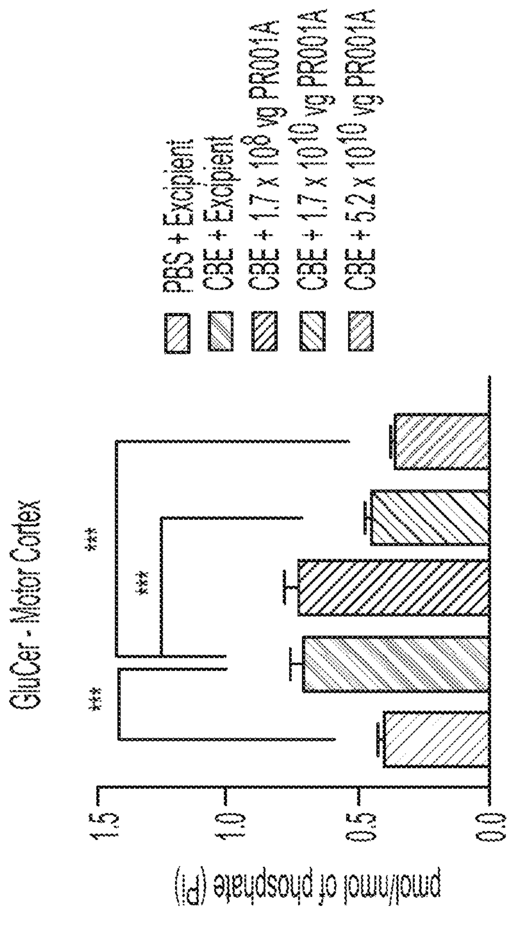

FIG. 44A-FIG. 44B show representative data for glycolipid analysis in further dose-ranging PR001A in a CBE model study. GluSph (FIG. 44A) and GluCer (FIG. 44B) levels are shown as pmol per nmol of phosphate. Means are presented. Error bars are SEM. Statistical results are presented for comparisons against the CBE+excipient group (second bar from left). n=9-10 per group. ***P<0.001 by ANOVA followed by Tukey's HSD test.

Figure 45:
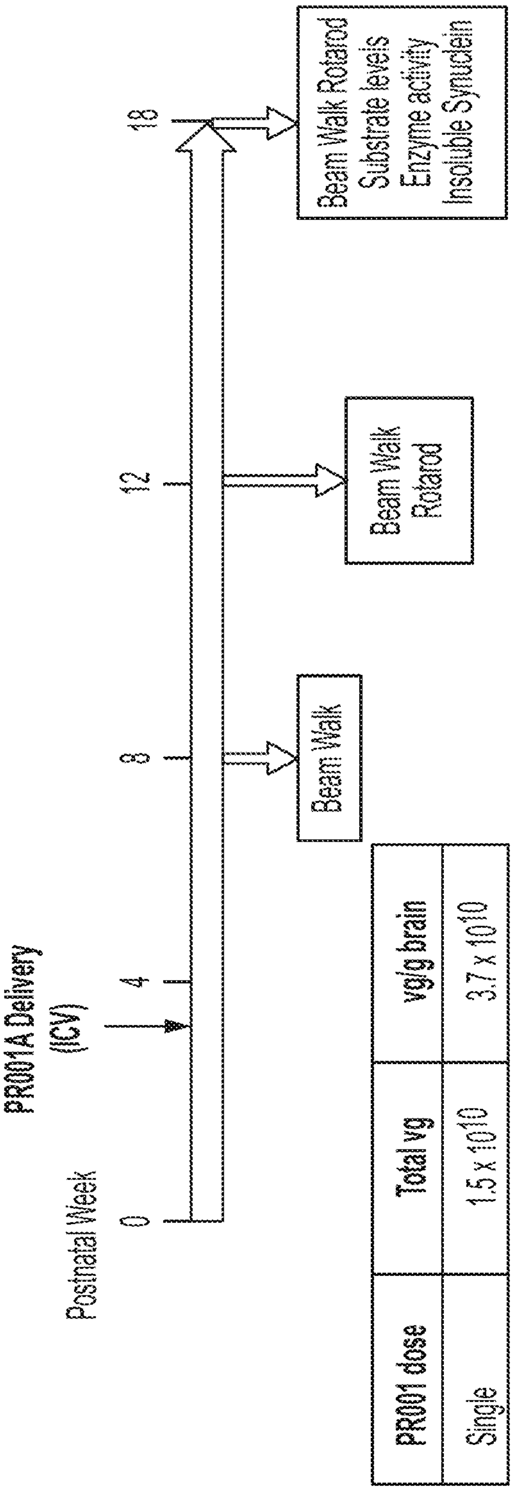

FIG. 45 is a schematic depicting one embodiment of a study design for treatment with a rAAV encoding GCase in a 4L/PS-NA genetic mouse model. PR001A was delivered by ICV injection to 4L/PS-NA mice at 3-4 weeks of age. Beam walk was tested at Weeks 8, 12, and 18 of life (5, 9, and 15 weeks post-ICV treatment) and rotarod was tested at Weeks 12 and 18 of life (9 and 15 weeks post-ICV treatment). Mice were sacrificed at Week 18. The cerebral cortices were analyzed for GCase enzymatic activity and the cerebella were analyzed for GluSph and GluCer substrate levels. There were 3 male and 3 female mice in each treatment group.

Figure 46:
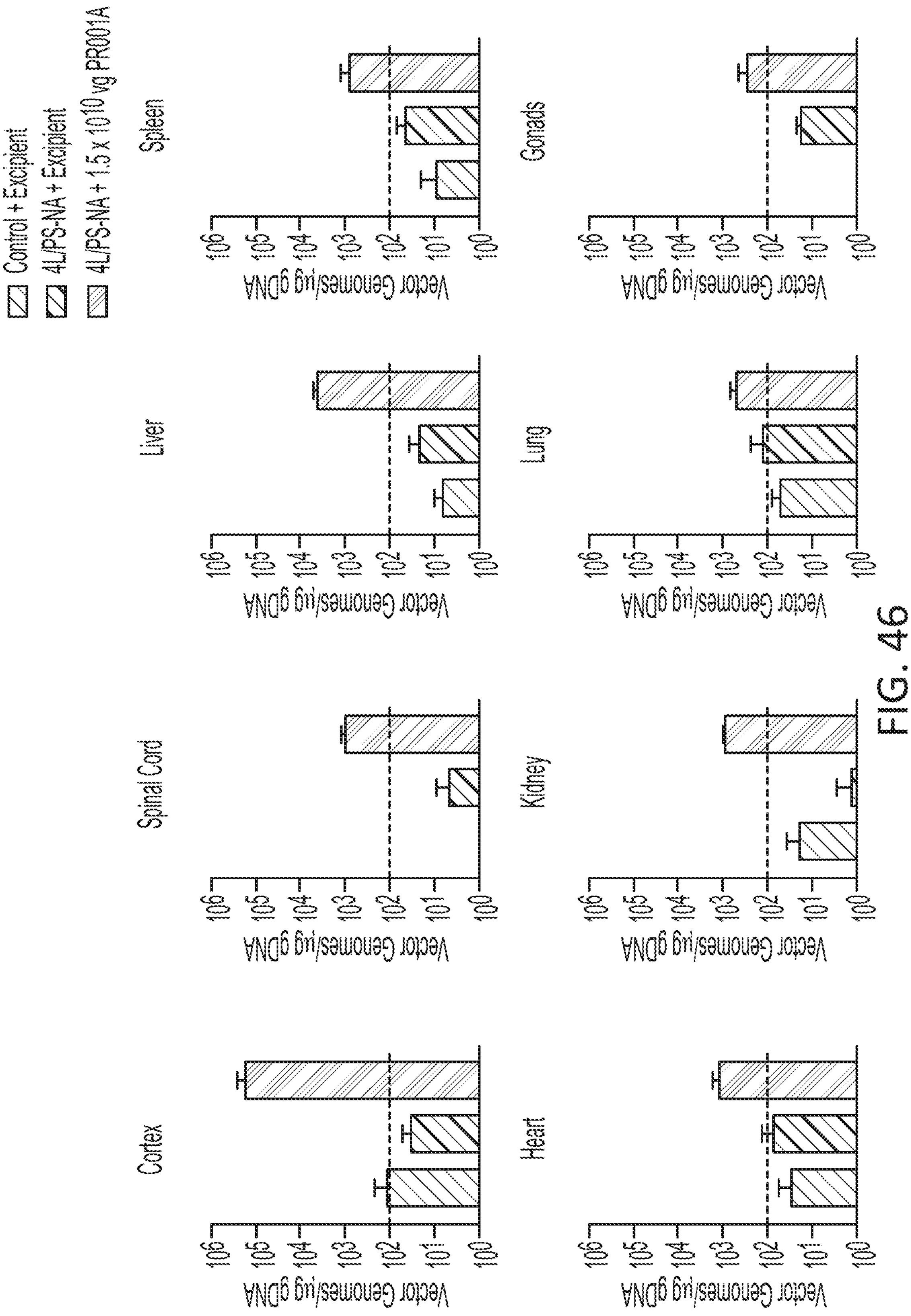

FIG. 46 shows representative data for biodistribution in maximal dose PR001A in a 4L/PS-NA genetic mouse model. Presence of vector genomes was assessed in each tissue and all treatment groups, shown as number of vector copies per 1 μg of genomic DNA (gDNA). Vector genome presence was quantified by qPCR using a vector reference standard curve. Means are presented. Error bars are SEM. n=4-5 per group. Dashed lines represent the detection threshold for positive vector presence (at 100 vector genomes/μg gDNA).

Figure 47:
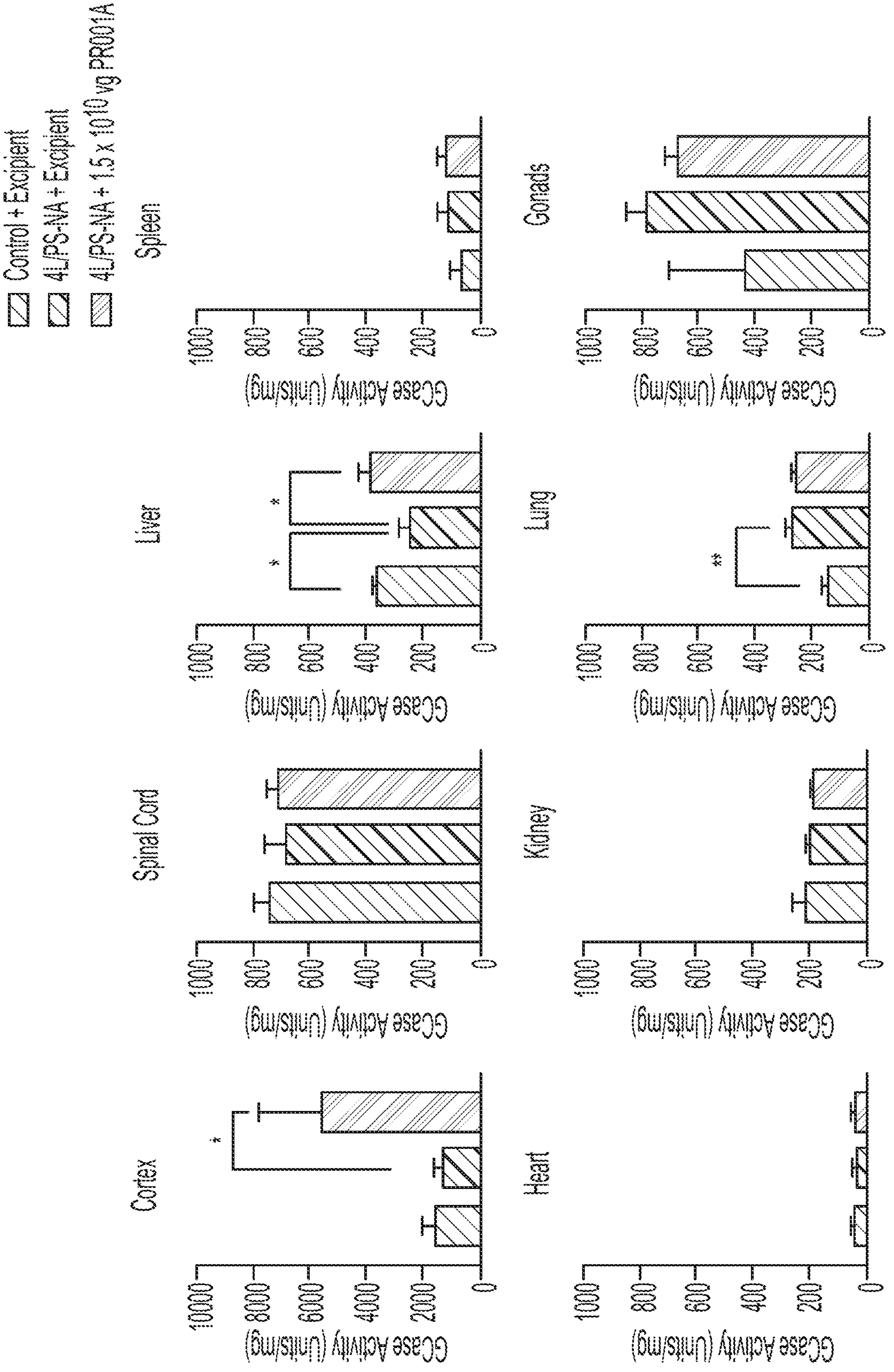

FIG. 47 shows representative data for GCase enzymatic activity in maximal dose PR001A in a 4L/PS-NA genetic mouse model. Effective enzymatic GCase activity was measured and is shown for each tissue and all treatment groups. Activity is shown as units per mg of total protein with one unit defined as the activity of 1 ng/mL of recombinant purified GCase. Means are presented. Error bars are SEM. N=4-5 per group. *: P<0.05; : P<0.01; *: P<0.001 by ANOVA followed by Tukey's HSD multiple tests correction.

Figure 48A:
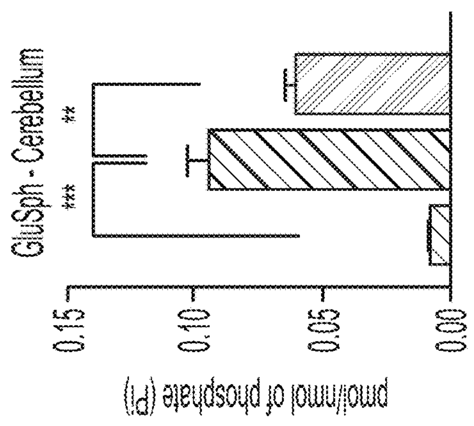
Figure 48B:
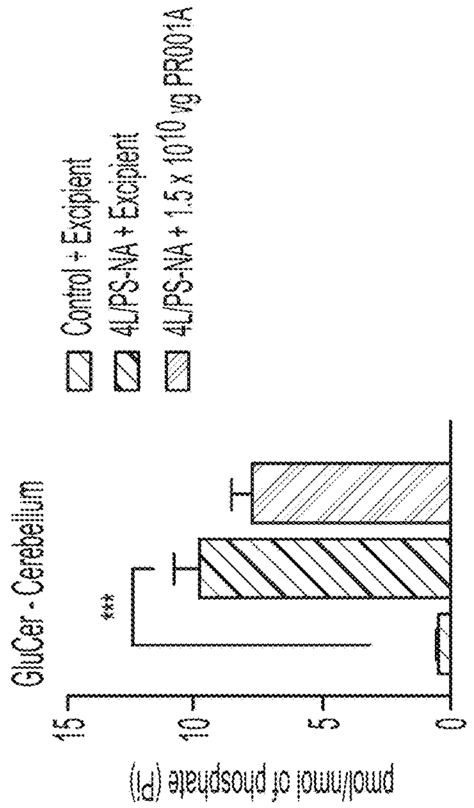

FIG. 48A-FIG. 48B show representative data for glycolipid analysis of PR001A in a 4L/PS-NA genetic mouse model. 4L/PS-NA mice received excipient (center bar) or $1.5\times10^{10}$ vg PR001A (right bar), and control mice received excipient (left bar) by ICV delivery at postnatal Day P23. The cerebellum was used to measure GluSph (FIG. 48A) and GluCer (FIG. 48B) levels. Levels are shown as pmol per nmol of phosphate. Means are presented. Error bars are SEM. n=4,5,5 per group, respectively. *: P<0.05; : P<0.01; *: P<0.001 by ANOVA followed by Tukey's HSD multiple tests correction.

Figure 49A:
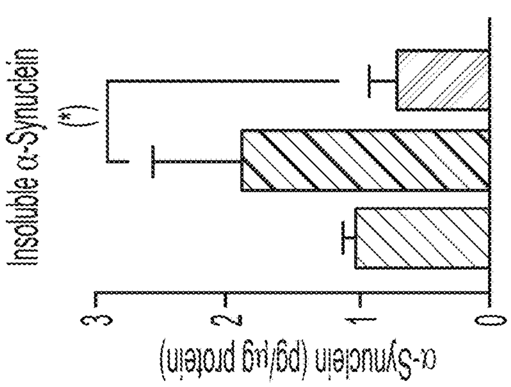
Figure 49B:
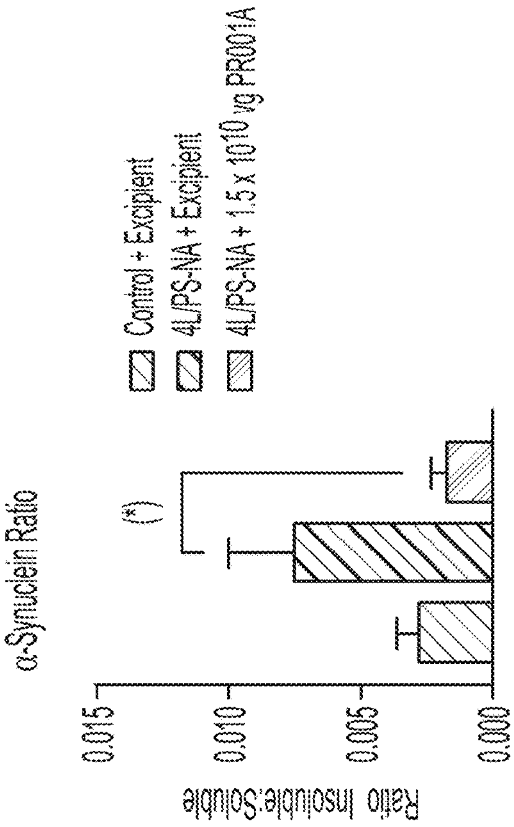

FIG. 49A-FIG. 49B show representative data for biochemical assessment of cerebral cortex α-Synuclein accumulation in a 4L/PS-NA genetic mouse model. 4L/PS-NA mice received ICV excipient (center bar) or $1.5\times10^{10}$ vg PR001A (right bar), and control mice received ICV excipient (left bar) at postnatal Day 23. The Triton X-soluble and Triton X-insoluble fractions of brain lysates from the cerebral cortex were analyzed for α-Synuclein protein levels using a customized immunosorbent assay. Insoluble α-Synuclein (FIG. 49A) and the ratio of insoluble to soluble α-Synuclein (FIG. 49B) are shown. Means are presented. Error bars are SEM. N=3-5 per group. (*): P<0.20, ANOVA followed by Tukey's HSD multiple tests correction.

Figure 50:
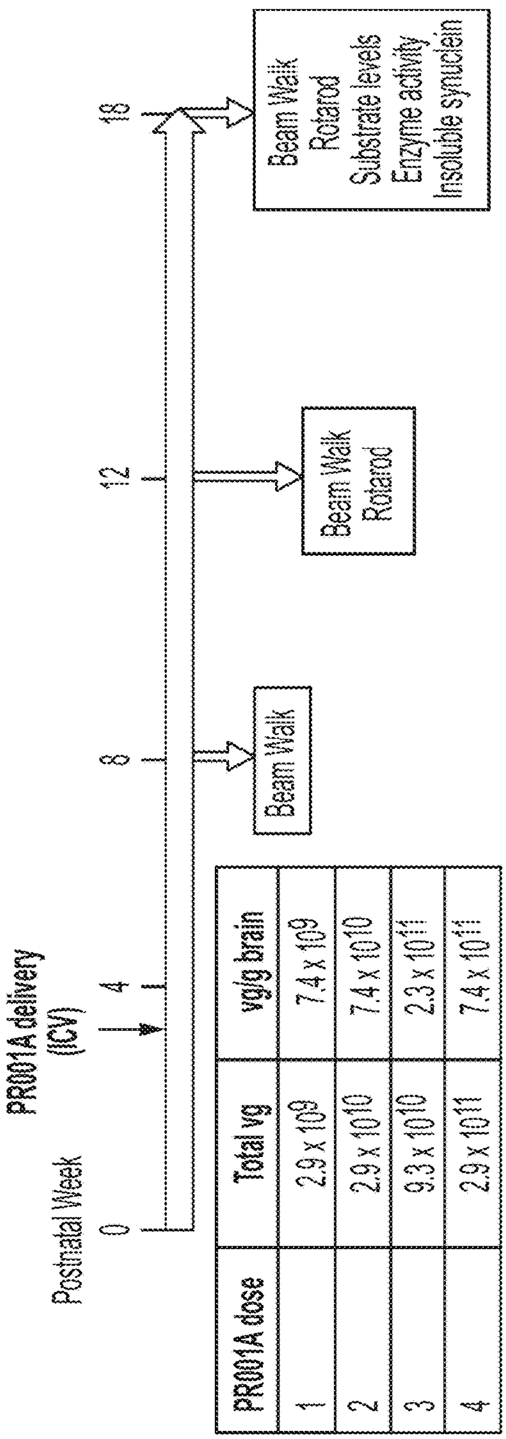

FIG. 50 is a schematic depicting one embodiment of a study design for dose-ranging PR001A rAAV in a 4L/PS-NA genetic mouse model. PR001A was delivered by ICV injection to 4L/PS-NA mice at 3-4 weeks. Beam walk was assessed at Weeks 8, 12, and 18 of life (5, 9, and 15 weeks post-ICV treatment) and rotarod was assessed at Weeks 12 and 18 of life (9 and weeks post-ICV treatment). Mice were sacrificed at Week 18. The cerebral cortices were analyzed for GCase enzymatic activity, and the cerebella were analyzed for GluSph and GluCer substrate levels. There were 10-11 mice per treatment group.

Figure 51:
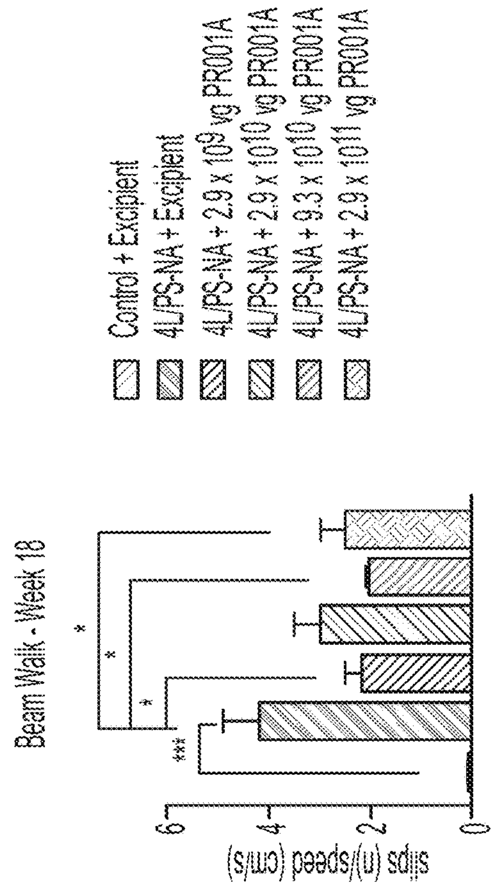

FIG. 51 shows representative data for week 18 behavioral analyses in dose-ranging PR001A in a 4L/PS-NA genetic mouse model. Motor performance in beam walk was evaluated, and the average total slips per speed are shown over 2 trials on different beams. N=10, 6, 5, 7, 4, 8 for group, respectively. Means are presented. Error bars are SEM; *: $P<0.05$; ***: $P<0.001$ by ANOVA followed by Tukey's HSD multiple tests correction.

Figure 52A:
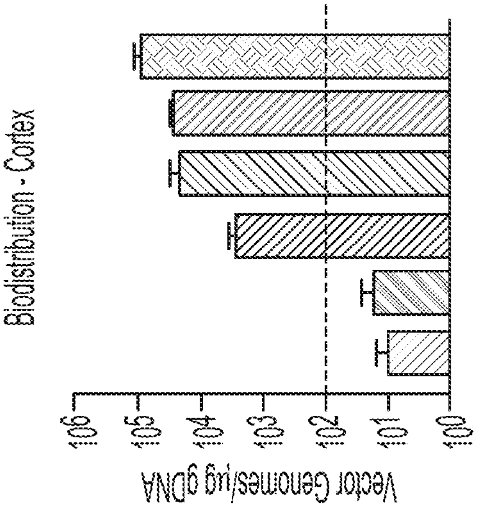
Figure 52B:
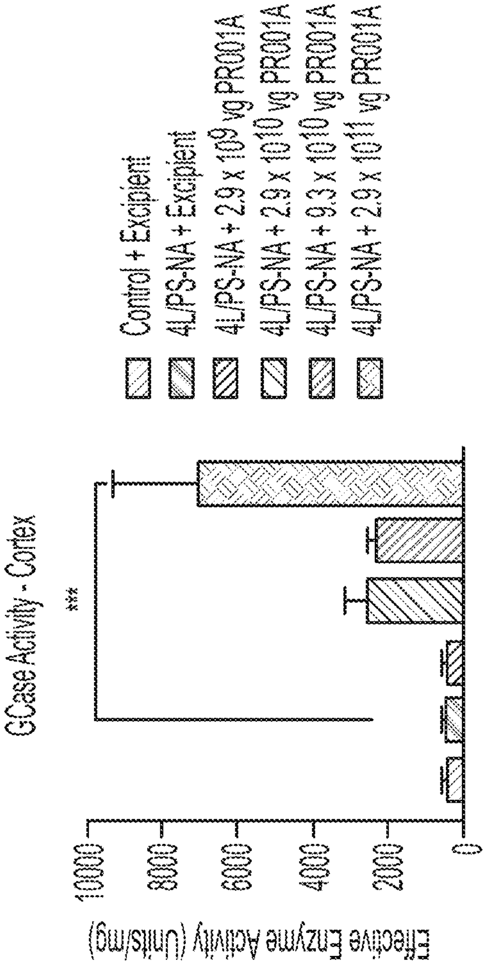

FIG. 52A-FIG. 52B show representative data for biodistribution and GCase enzymatic activity in dose-ranging PR001A in a 4L/PS-NA genetic mouse model. Vector genomes were measured in the cerebral cortex (FIG. 52A) of all treatment groups and are shown as number of vector copies per 1 μg of genomic DNA (gDNA). Vector genome presence was quantified by qPCR using a vector reference standard curve. Dashed line represents the detection threshold for positive vector genome presence (at 100 vector genomes/μg gDNA). Effective enzymatic GCase activity was measured in the cerebral cortex (FIG. 52B) and is shown as units per mg of total protein with one unit defined as the activity of 1 ng/mL of recombinant purified GCase. Means are presented. Error bars are SEM. n=10, 10, 10, 10, 7, 8 per group, respectively. ***$P<0.001$ by ANOVA followed by Tukey's HSD multiple tests correction.

Figure 53A:
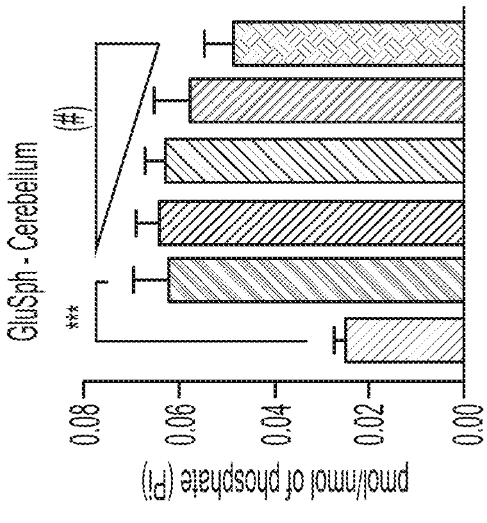
Figure 53B:
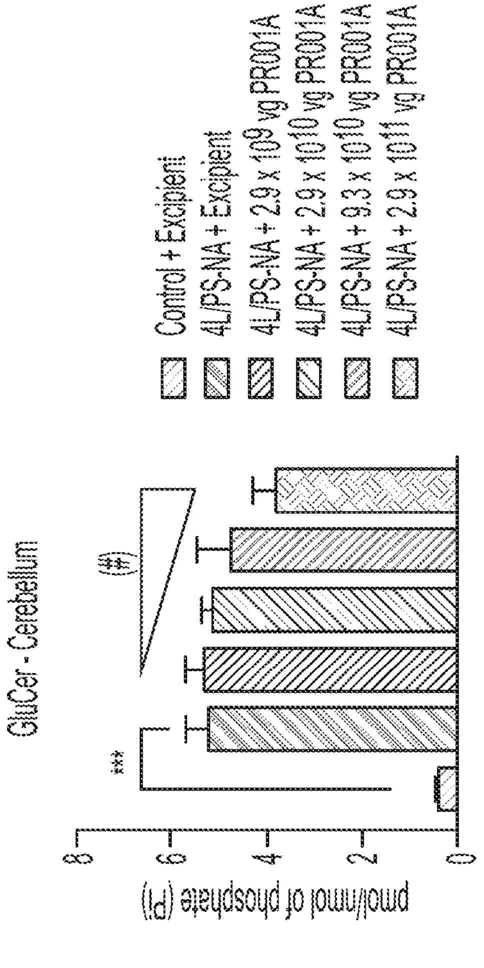

FIG. 53A-FIG. 53B show representative data for glycolipid analysis in dose-ranging PROW A in a 4L/PS-NA genetic mouse model. The cerebellum was used to measure GluSph (FIG. 53A) and GluCer (FIG. 53B) levels. Levels are shown as pmol per nmol of phosphate. Means are presented. Error bars are SEM. n=10, 10, 10, 10, 7, 8 per group, respectively. ***: $P<0.001$ by ANOVA followed by Tukey's HSD multiple tests correction. (#): $P<0.1$; #: $P<0.05$ by multiple linear regression for genotype and dose across all animals.

Figure 54A:
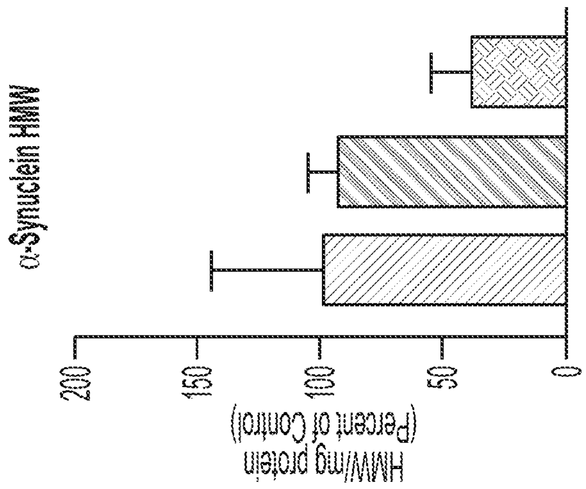
Figure 54B:
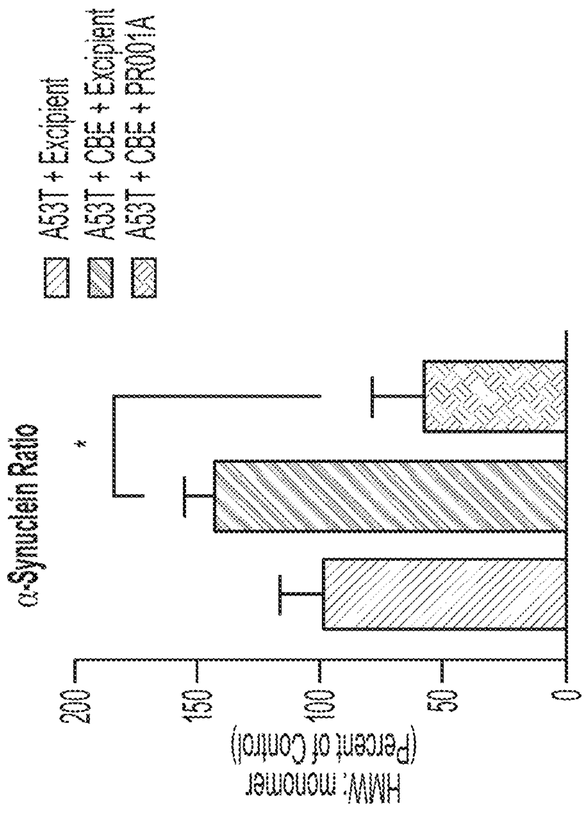

FIG. 54A-FIG. 54B show representative data for biochemical assessment of α-Synuclein protein levels in CBE-treated α-Synuclein transgenic mice. Hippocampal brain lysates were analyzed for α-Synuclein concentration using the Simple Western™ (Jess) automated capillary western blot system and the MJFR-14-6-4-2 α-Synuclein antibody. Multiple bands were observed between 48 kDa and 230 kDa and were grouped as "high molecular weight" (HMW). A single band was present at 18 kDa, consistent with the predicted molecular weight of α-Synuclein monomer. Mean fold change over the normalized mean of the A53T+excipient group is presented. Error bars are SEM. N=3-5 per group. *: $P<0.05$ by ANOVA followed by Tukey's HSD multiple test correction.

Figure 55:
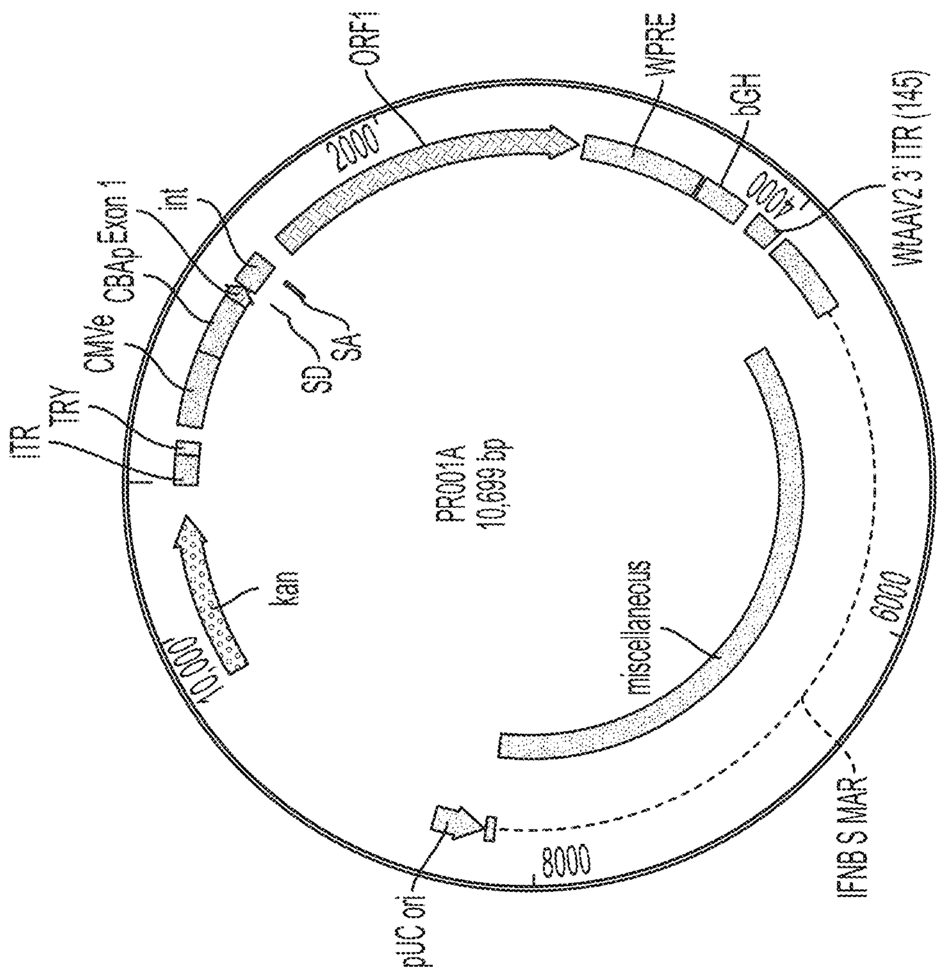

FIG. 55 is a schematic depicting one embodiment of a plasmid encoding a recombinant adeno-associated virus vector (PR001A) comprising an expression construct encoding human Gcase. "bp" refers to "base pairs". "kan" refers to a gene that confers resistance to kanamycin. "ORF1" refers to an open reading frame for Gcase. "ITR" refers to an adeno-associated virus inverted terminal repeat sequence. "TRY" refers to a sequence comprising three transcriptional regulatory activation sites: TATA, RBS, and YY1. "CBAp" refers to a chicken β-actin promoter. "CMVe" refers to a cytomegalovirus enhancer. "WPRE" refers to a woodchuck hepatitis virus post-transcriptional regulatory element. "bGH" refers to a bovine Growth Hormone polyA signal tail. "int" refers to an intron. The nucleotide sequences of the two strands of PR001A are provided in SEQ ID NOs: 39 and 40.

Figure 56:
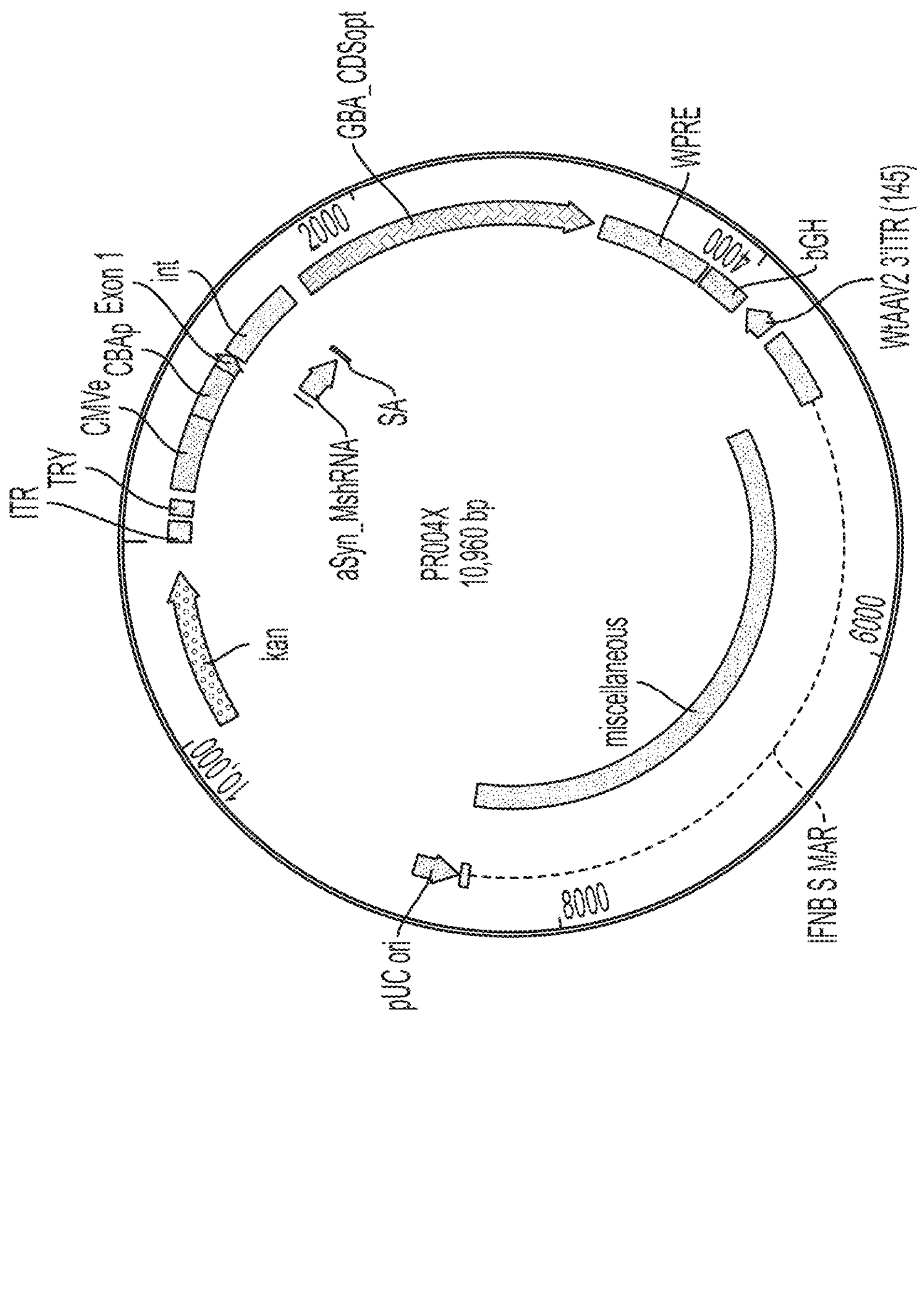

FIG. 56 is a schematic depicting one embodiment of a plasmid encoding a recombinant adeno-associated virus vector (PR004X) comprising an expression construct encoding human Gcase and a shRNA targeting α-Synuclein. "bp" refers to "base pairs". "kan" refers to a gene that confers resistance to kanamycin. "aSyn_MshRNA" refers to a region encoding a shRNA inhibiting α-Synuclein. "GBA_CDSopt" refers to an open reading frame for Gcase. "ITR" refers to an adeno-associated virus inverted terminal repeat sequence. "TRY" refers to a sequence comprising three transcriptional regulatory activation sites: TATA, RBS, and YY1. "CBAp" refers to a chicken β-actin promoter. "CMVe" refers to a cytomegalovirus enhancer. "WPRE" refers to a woodchuck hepatitis virus post-transcriptional regulatory element. "bGH" refers to a bovine Growth Hormone polyA signal tail. "int" refers to an intron. The nucleotide sequences (sequence verified) of the two strands of PR004X are provided in SEQ ID NOs: 41 and 42.

Figure 57:
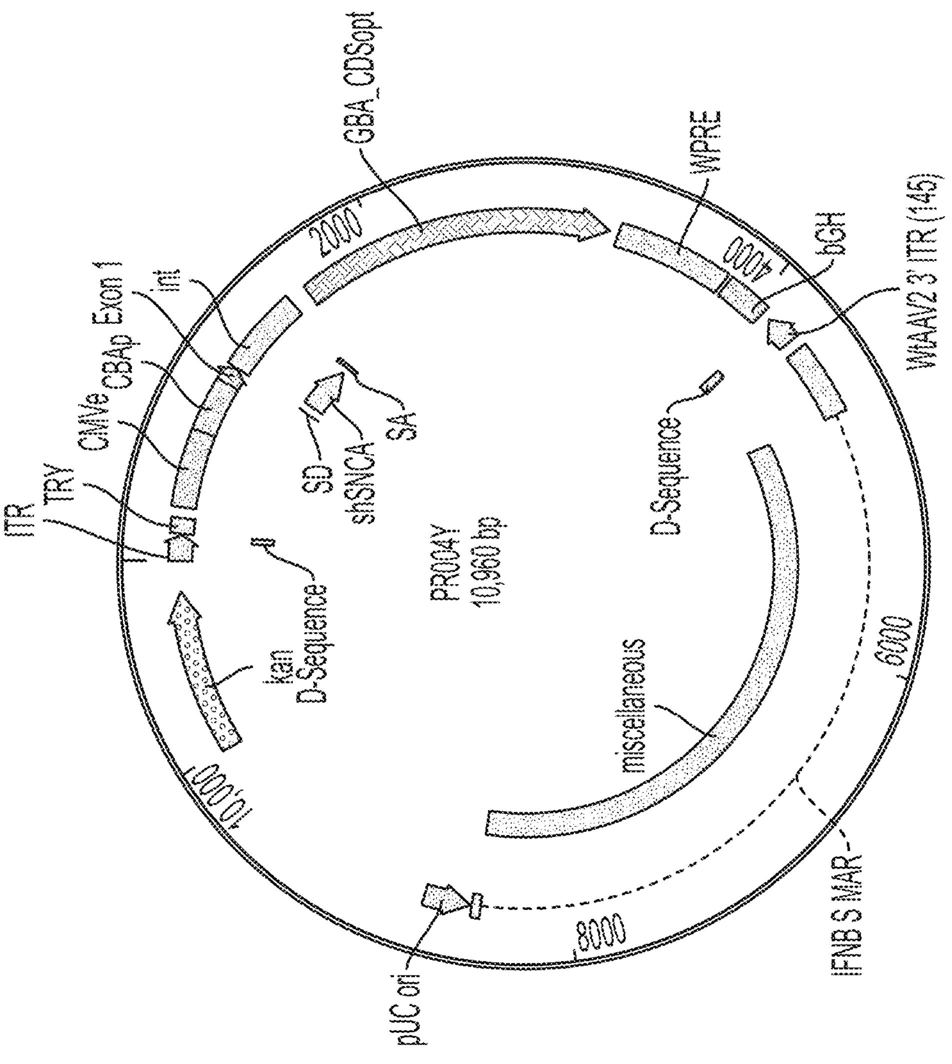

FIG. 57 is a schematic depicting one embodiment of a plasmid encoding a recombinant adeno-associated virus vector (PR004Y) comprising an expression construct encoding human Gcase and a shRNA targeting α-Synuclein. "bp" refers to "base pairs". "kan" refers to a gene that confers resistance to kanamycin. "shSNCA" refers to a region encoding a shRNA inhibiting α-Synuclein. "GBA_CDSopt" refers to an open reading frame for Gcase. "ITR" refers to an adeno-associated virus inverted terminal repeat sequence. "TRY" refers to a sequence comprising three transcriptional regulatory activation sites: TATA, RBS, and YY1. "CBAp" refers to a chicken β-actin promoter. "CMVe" refers to a cytomegalovirus enhancer. "WPRE" refers to a woodchuck hepatitis virus post-transcriptional regulatory element. "bGH" refers to a bovine Growth Hormone polyA signal tail. "int" refers to an intron. The nucleotide sequences (theoretical) of the two strands of PR004Y are provided in SEQ ID NOs: 43 and 44.

Figure 58:
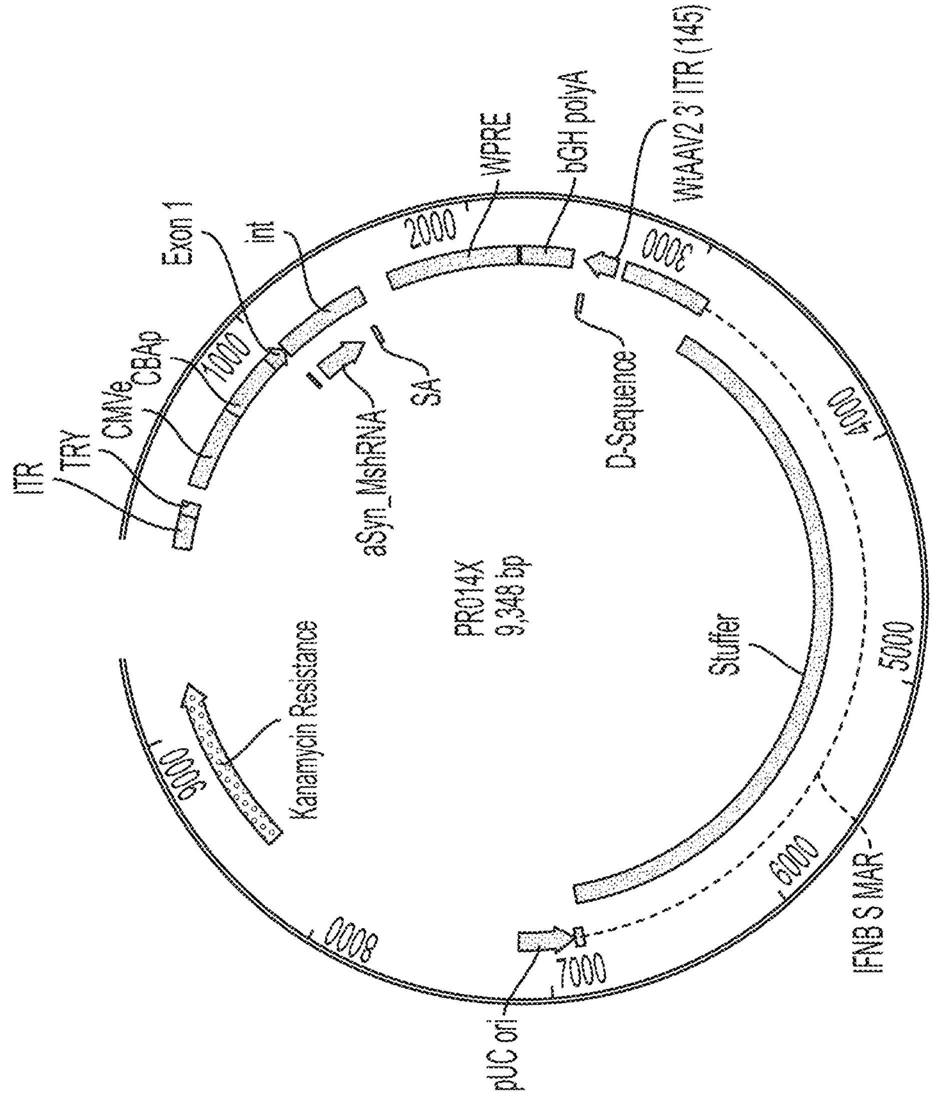

FIG. 58 is a schematic depicting one embodiment of a plasmid encoding a recombinant adeno-associated virus vector (PR014X) comprising an expression construct encoding a shRNA targeting α-Synuclein. "bp" refers to "base pairs". "kan" refers to a gene that confers resistance to kanamycin. "aSyn_MshRNA" refers to a region encoding a shRNA inhibiting α-Synuclein. "ITR" refers to an adeno-associated virus inverted terminal repeat sequence. "TRY" refers to a sequence comprising three transcriptional regulatory activation sites: TATA, RBS, and YY1. "CBAp" refers to a chicken β-actin promoter. "CMVe" refers to a cytomegalovirus enhancer. "WPRE" refers to a woodchuck hepatitis virus post-transcriptional regulatory element. "bGH" refers to a bovine Growth Hormone polyA signal tail. "int" refers to an intron. The nucleotide sequences (theoretical) of the two strands of PR014X are provided in SEQ ID NOs: 45 and 46. The nucleotide sequences (theoretical) of the two strands of the region encoding the shRNA are provided in SEQ ID NOs: 47 and 48.

Figure 59:
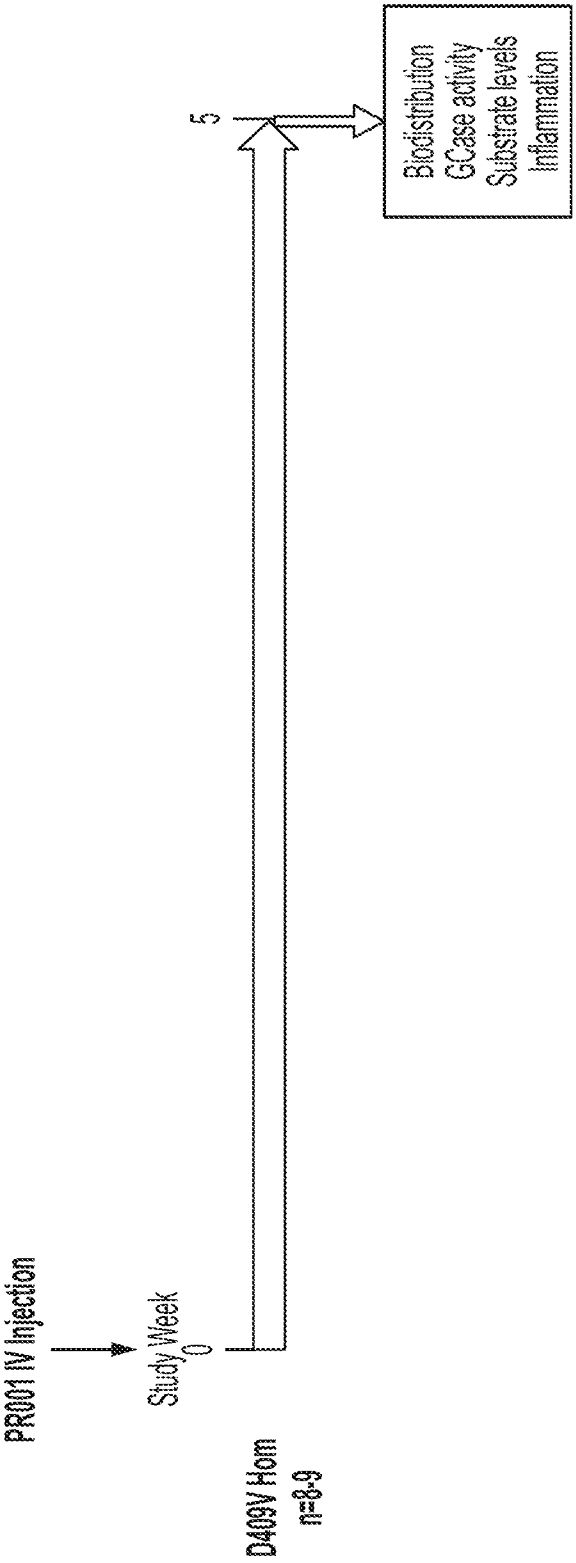

FIG. 59 is a schematic depicting one embodiment of a study design for dose-ranging PR001 rAAV in a D409V Horn genetic mouse model. PR001 was delivered by intravenous (IV) injection to D409V Horn mice. The parameters listed in the figure were assessed 5 weeks later.

Figure 60A:
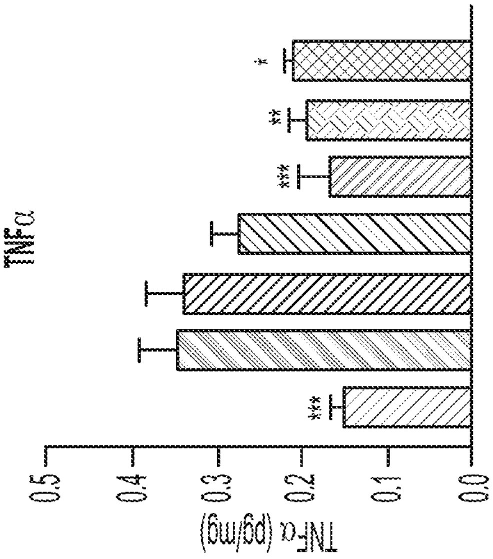
Figure 60B:
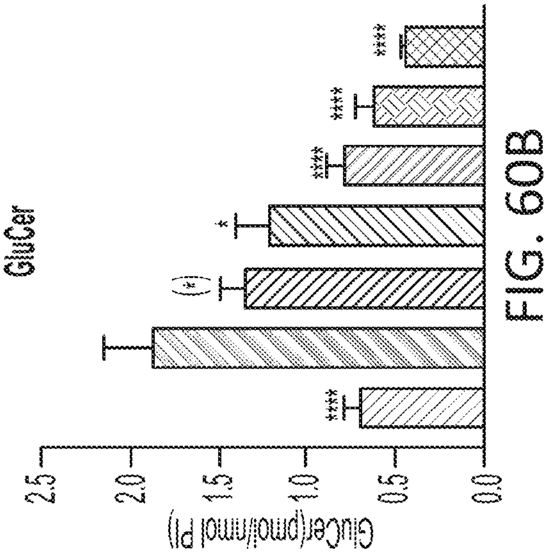
Figure 60C:
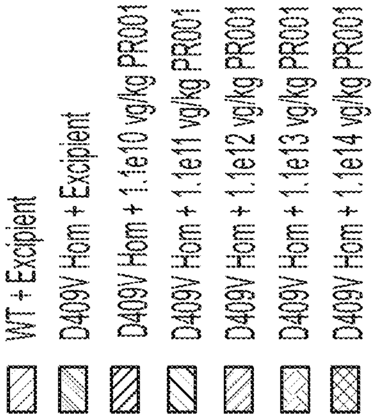
Figure 60C:
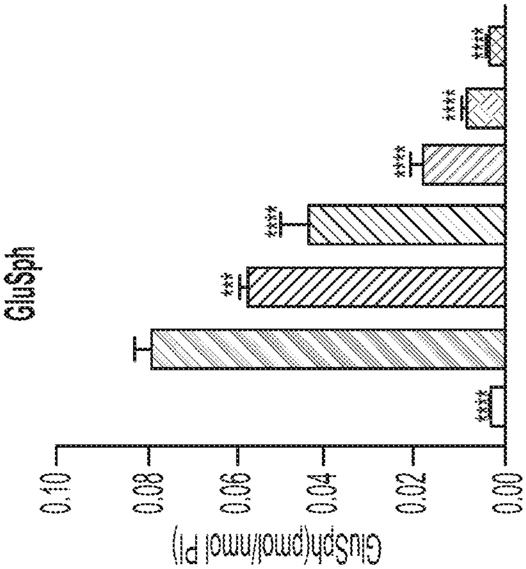

FIG. 60A-FIG. 60C show representative data for liver biochemistry of PR001 intravenous (IV) administration in a D409V Horn genetic mouse model. Mice were sacrificed 5-weeks post-IV injection. Cytokine levels (FIG. 60A) and glycolipid levels (FIG. 60B; FIG. 60C) were quantified. Statistics were determined using ANOVA followed by Dunnett's test comparing to the D409V Horn+Excipient group.

Means are presented+/−SEM (n=8-**: p<0.0001; *: p<0.001; **: p<0.01; *: p<0.05; (*): p=0.10. GluCer=glucosylceramide. GluSph=glucosylsphingosine. WT=wild type.

Figures 61A, 61B:
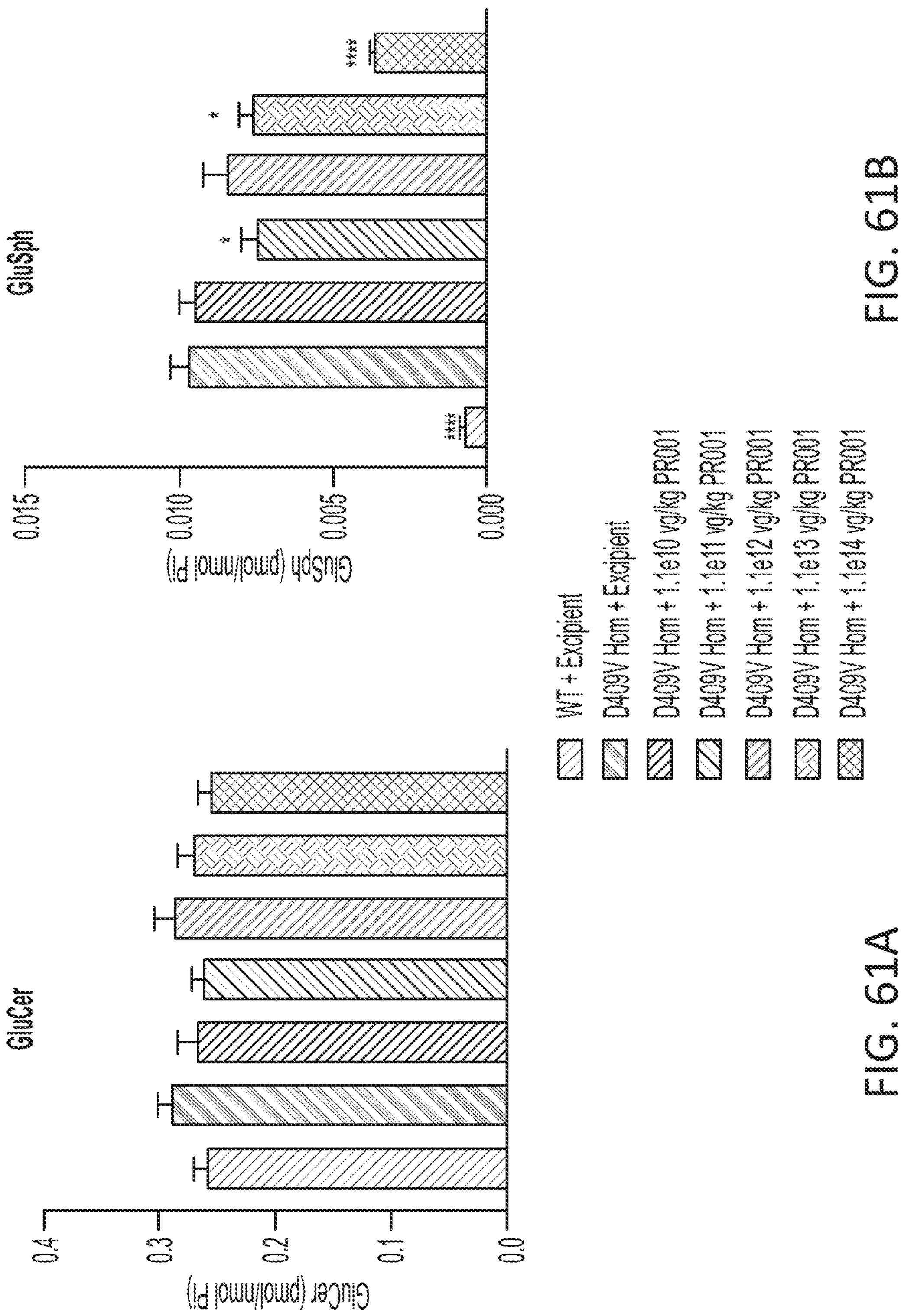

FIG. 61A-FIG. 61B show representative data for brain biochemistry of PR001 intravenous (IV) administration in a D409V Horn genetic mouse model. Mice were sacrificed 5-weeks post-IV injection. Glycolipid levels were quantified. Statistics were determined using ANOVA followed by Dunnett's test comparing to the D409V Hom+Excipient group. Means are presented+/−SEM (n=8-10/group). ****: p<0.0001; *: p<0.05. GluCer=glucosylceramide. GluSph=glucosylsphingosine. WT=wild type.

Figure 62:
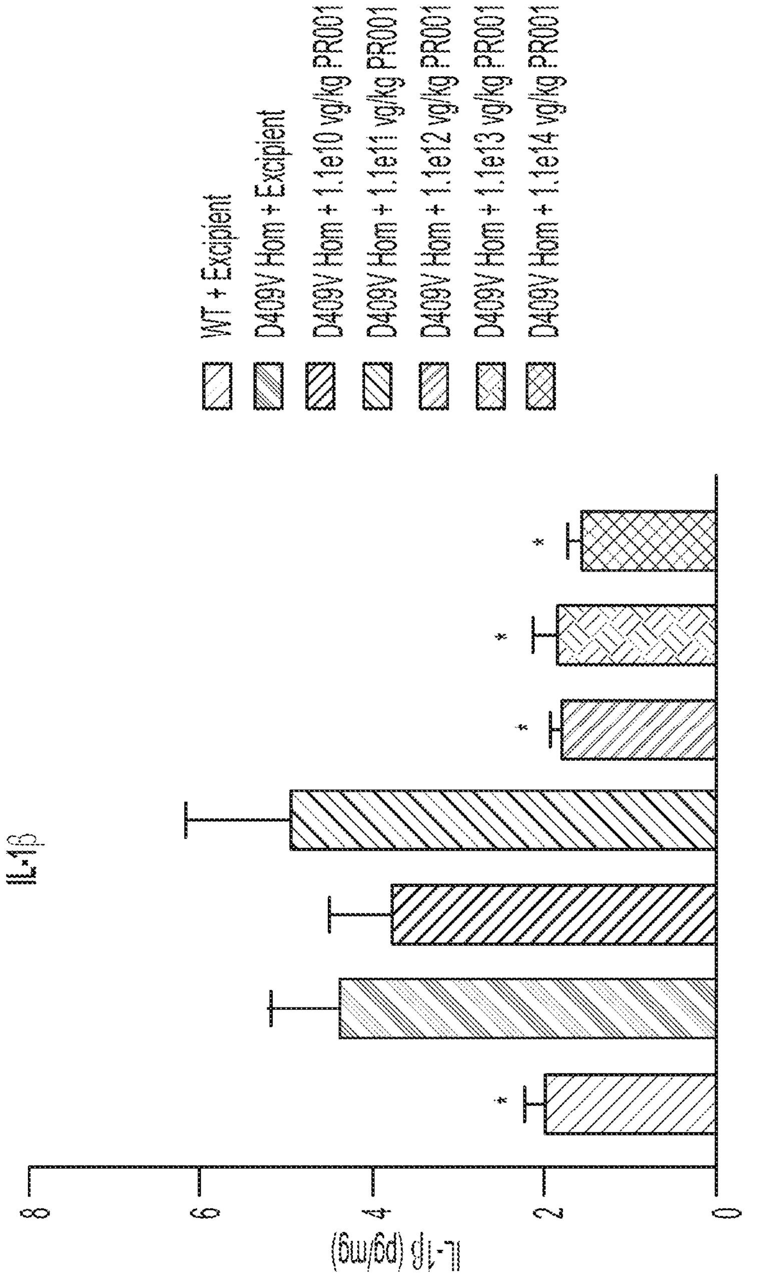

FIG. 62 shows representative data for lung biochemistry of PR001 intravenous (IV) administration in a D409V Horn genetic mouse model. Mice were sacrificed 5-weeks post-IV injection. Cytokine levels were quantified. Statistics were determined using ANOVA followed by Dunnett's test comparing to the D409V Horn+Excipient group. Means are presented+/−SEM (n=8-10/group). *: p<0.05. WT=wild type.

Figure 63:
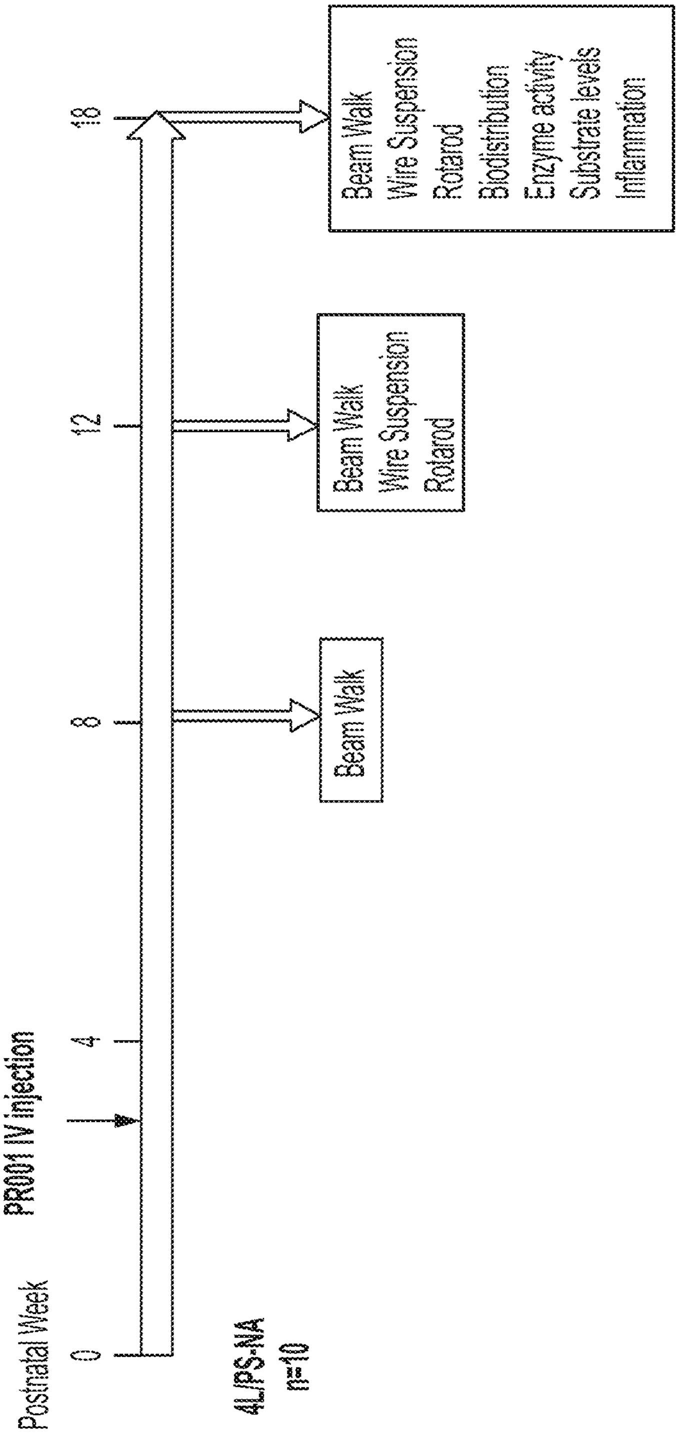

FIG. 63 is a schematic depicting one embodiment of a study design for dose-ranging PR001 rAAV in a 4L/PS-NA genetic mouse model. PR001 was delivered by intravenous (IV) injection to 4L/PS-NA mice. The parameters listed in the figure were assessed at the time points shown.

Figures 64A, 64B:
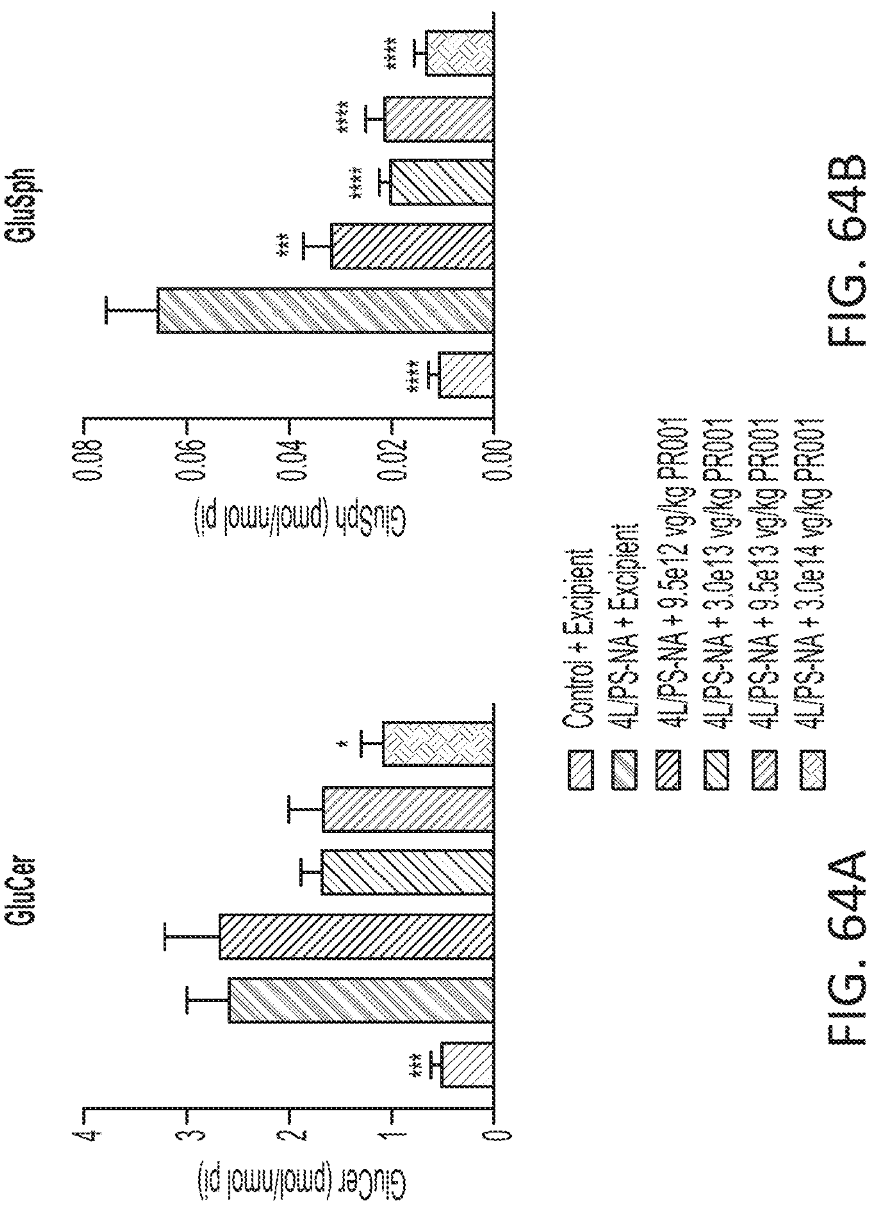

FIG. 64A-FIG. 64B show representative data for liver biochemistry of PR001 intravenous (IV) administration in a 4L/PS-NA genetic mouse model. Mice were sacrificed 15-weeks post-IV injection. Glycolipid levels were quantified. Statistics were determined using ANOVA followed by Dunnett's test comparing to the 4L/PS-NA+Excipient group. Means are presented+/−SEM (n=10/group). **: p<0.0001; *: p<0.001; *: p<0.05. GluCer=glucosylceramide. GluSph=glucosylsphingosine.

Figures 65A, 65B:
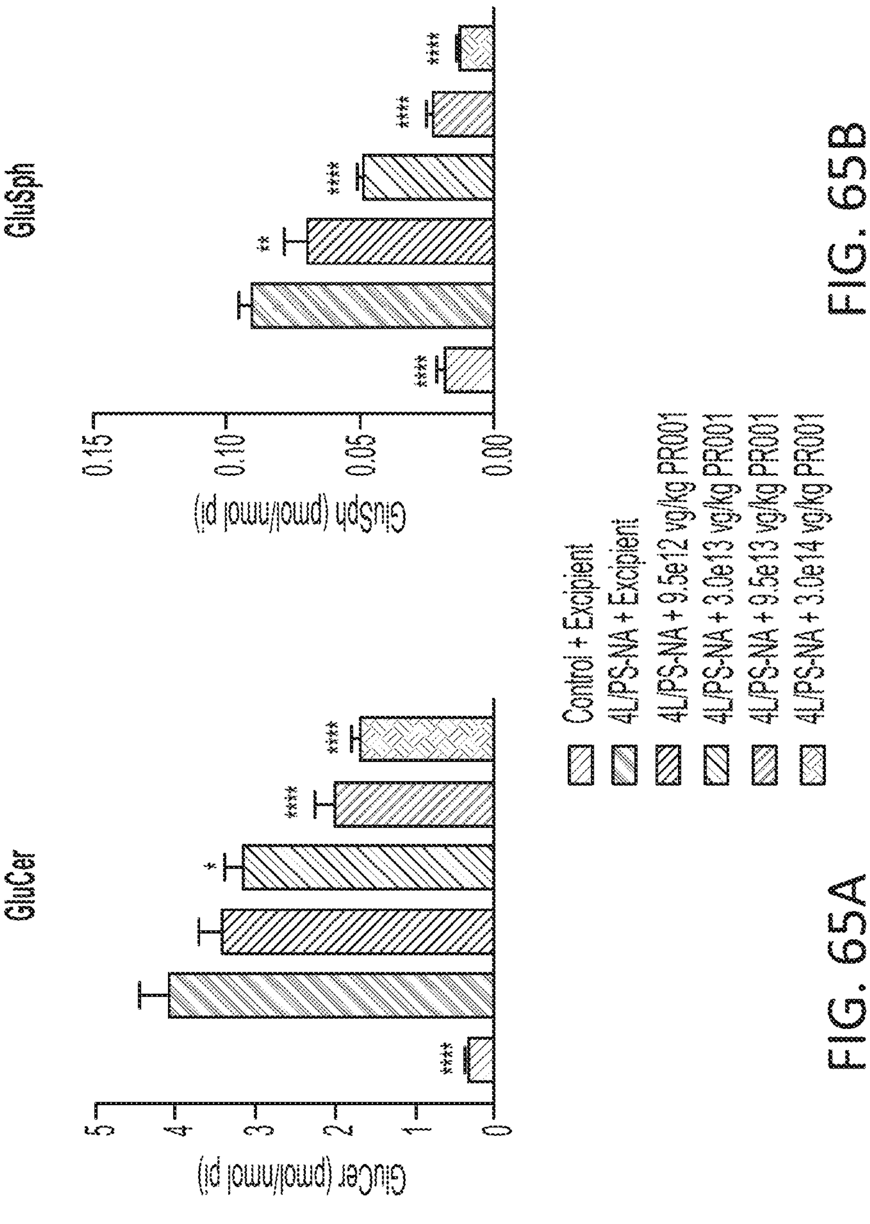

FIG. 65A-FIG. 65B show representative data for brain biochemistry of PR001 intravenous (IV) administration in a 4L/PS-NA genetic mouse model. Mice were sacrificed 15-weeks post-IV injection. Glycolipid levels were quantified. Statistics were determined using ANOVA followed by Dunnett's test comparing to the 4L/PS-NA+Excipient group. Means are presented+/−SEM (n=10/group). **: p<0.0001; : p<0.01; *: p<0.05. GluCer=glucosylceramide. GluSph=glucosylsphingosine.

Figure 66A:
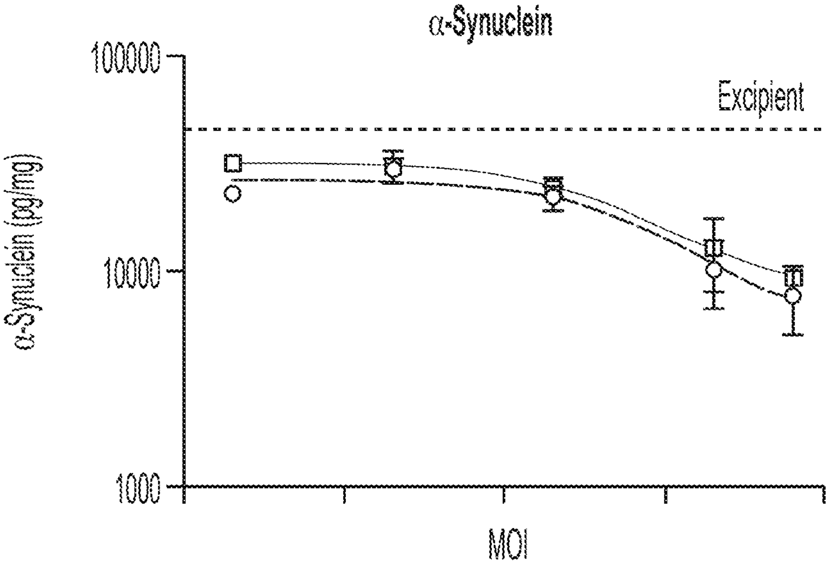
Figure 66B:
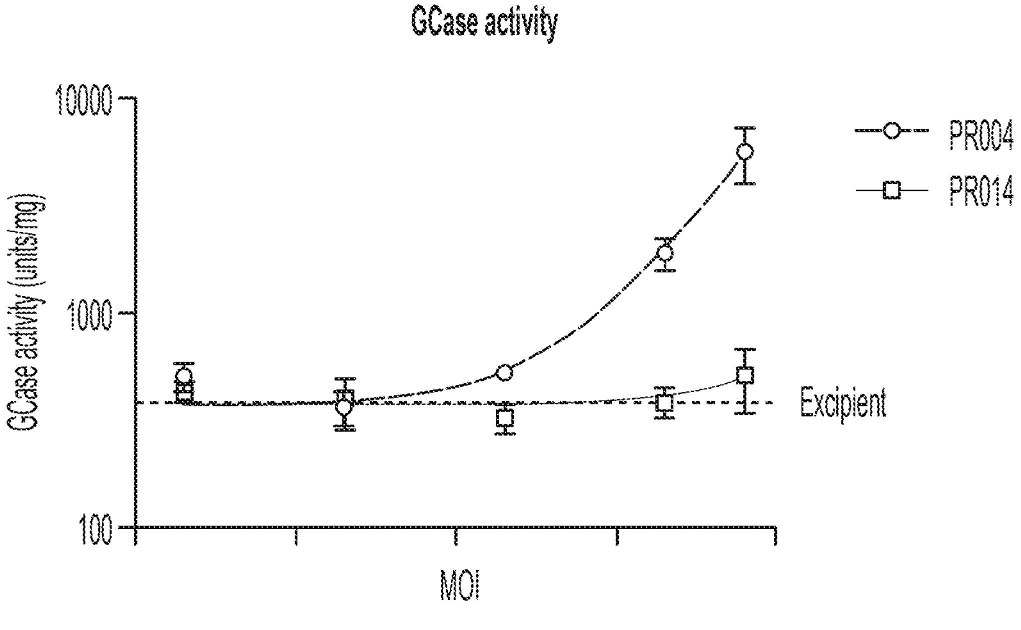

FIG. 66A-FIG. 66B show representative data for α-Synuclein protein levels and Gcase activity in HeLa cells after transduction with PR004 or PR014. HeLa cells were treated with PR004, PR014 or excipient, and α-Synuclein levels (FIG. 66A) and GCase activity (FIG. 66B) in cell lysates were measured after 72 hours. Data is presented as mean±SEM (n=3/condition).

Figure 67A:
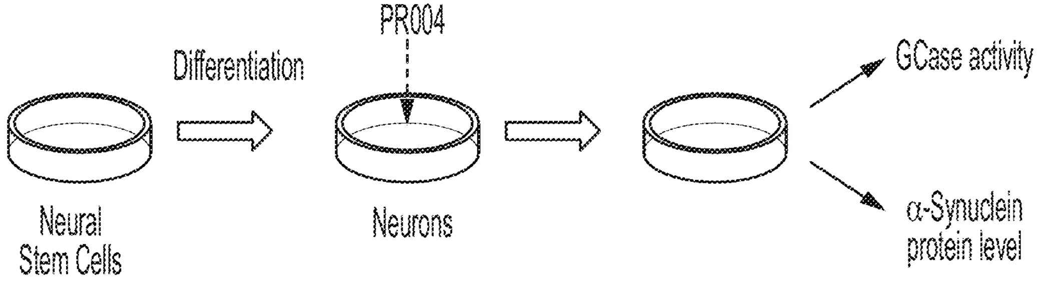
Figure 67A:
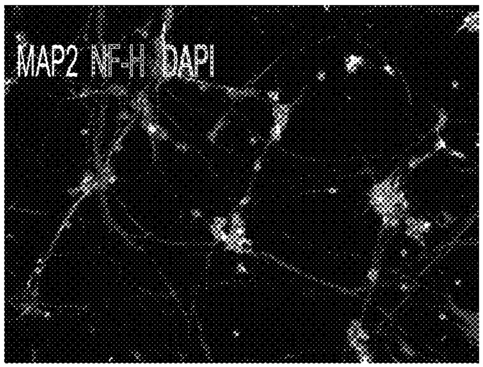
Figure 67B:
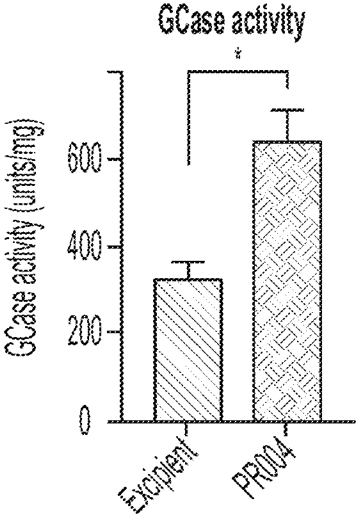
Figure 67C:
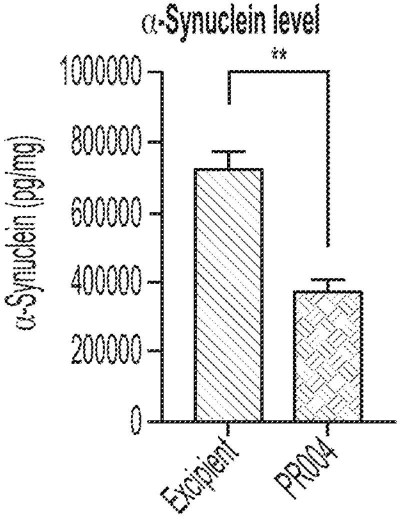

FIG. 67A-FIG. 67C show representative data for PR004 efficacy in neuronal cultures from Parkinson's disease patient-derived induced pluripotent stem cells (iPSC). Induced pluripotent stem cells derived from a Parkinson's disease patient with a SNCA triplication were differentiated into neurons (FIG. 67A). iPSC-derived neurons were treated with PR004 or excipient, and GCase activity (FIG. 67B) and α-Synuclein levels (FIG. 67C) were measured in cell lysates after two weeks. Statistics determined by unpaired t-test; *=p<0.05, **=p<0.01. Data is presented as mean±SEM (n=2-3/group).

Figure 68A:
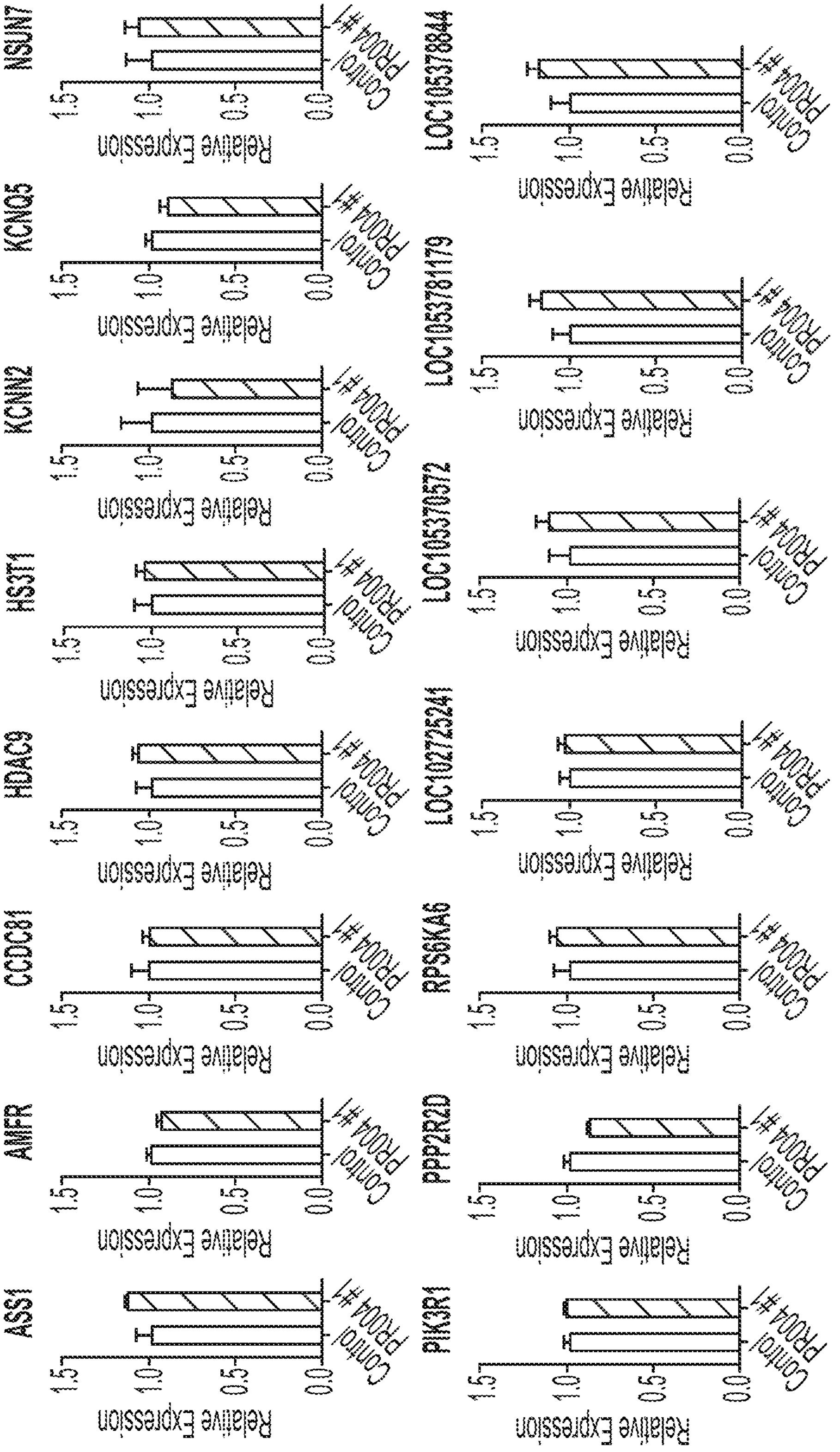
Figure 68B:
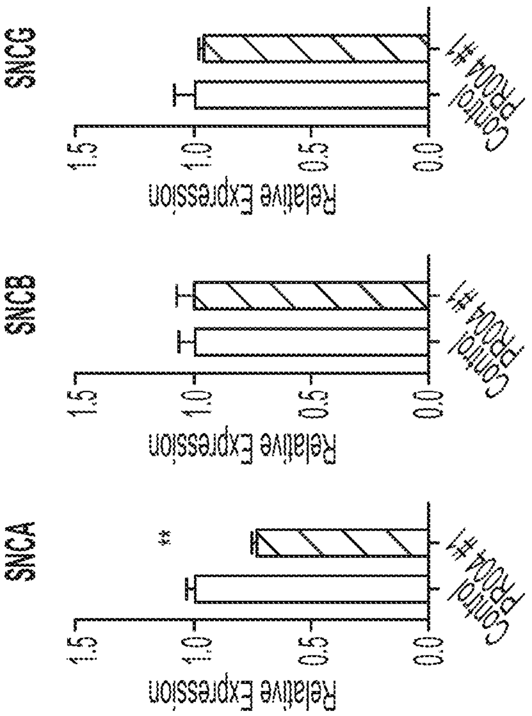

FIG. 68A-FIG. 68B show representative data for studies assessing shRNA targeting SNCA from the PR004 vector in HEK293 cells by qRT-PCR. HEK293 cells were transfected with PR004 or control, and RNA was extracted after 72 hours. qRT-PCR for various genes was performed and normalized to GAPDH expression. Data is normalized to the control condition and presented as mean±SEM (n=3/group).

Figure 69:
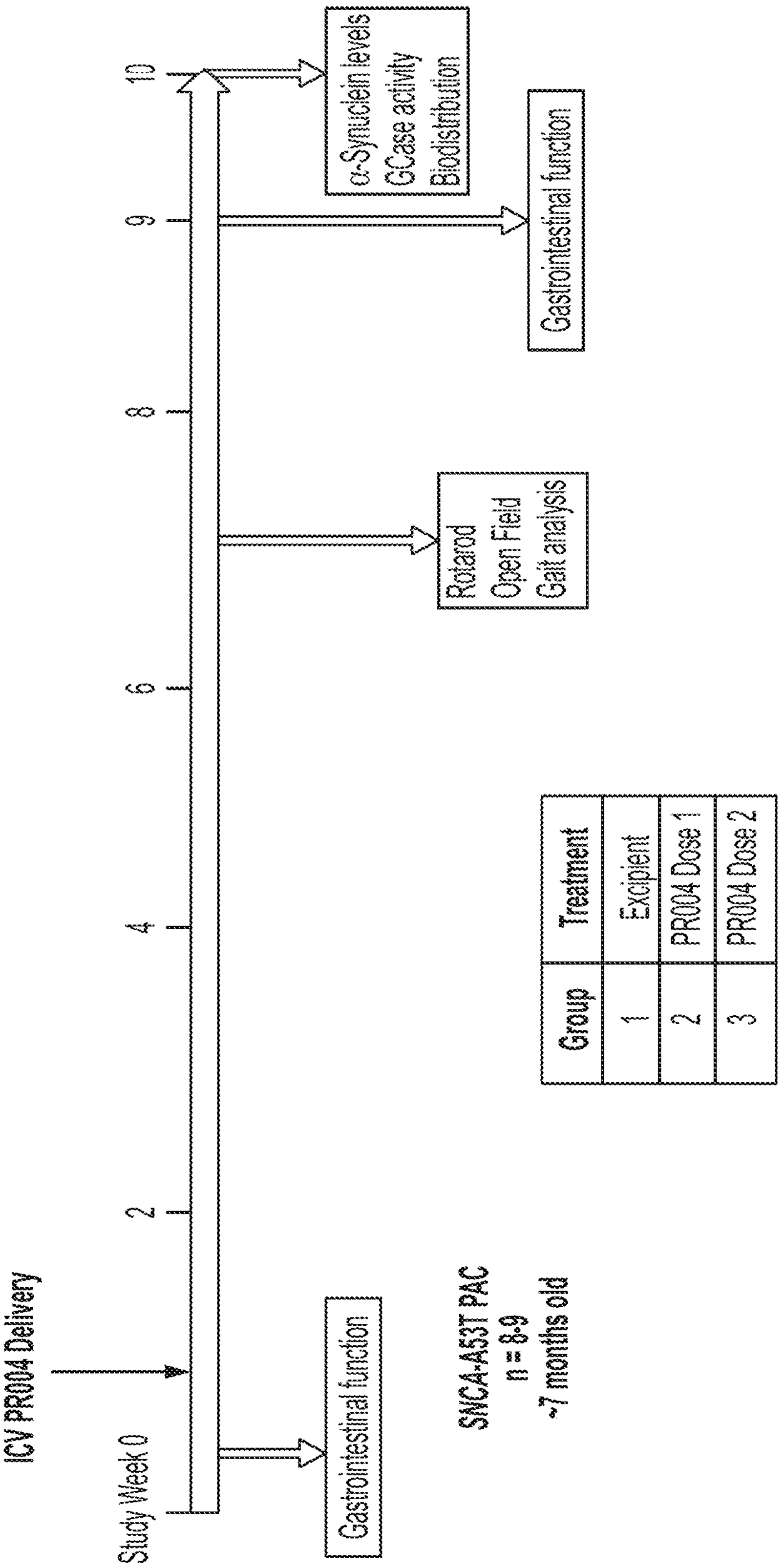

FIG. 69 is a schematic depicting one embodiment of a study design examining gastrointestinal, motor behavior, and biochemical endpoints in the SNCA-A53T PAC mouse model after administration of PR004. ICV=intracerebroventricular.

Figure 70:
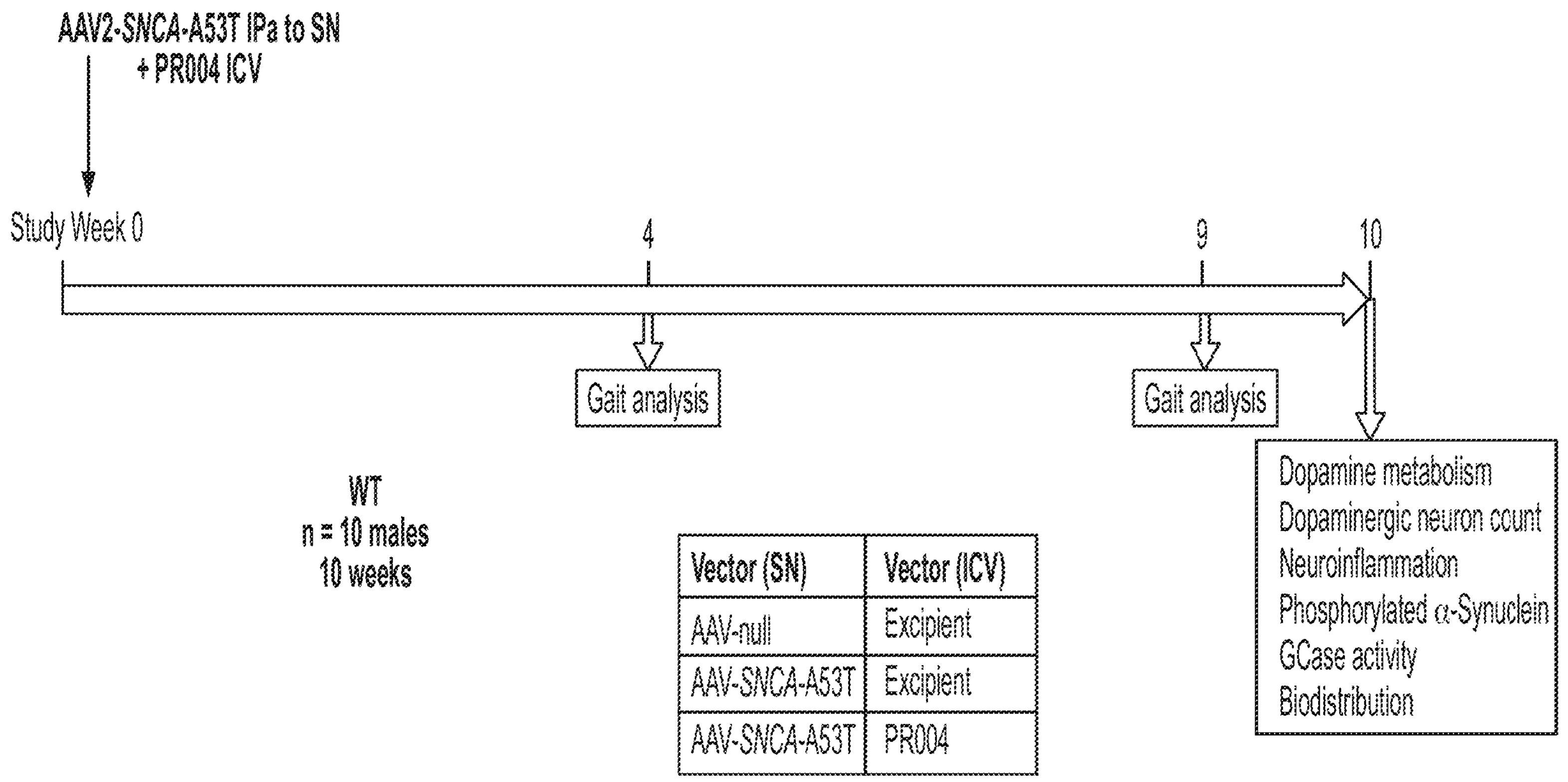

FIG. 70 is a schematic depicting one embodiment of a study design examining motor behavior and biochemical analysis in the AAV2-SNCA-A53T IPa injection mouse model after administration of PR004. IPa=intraparenchymal. SN=substantia nigra. ICV=intracerebroventricular.

Figure 71A:
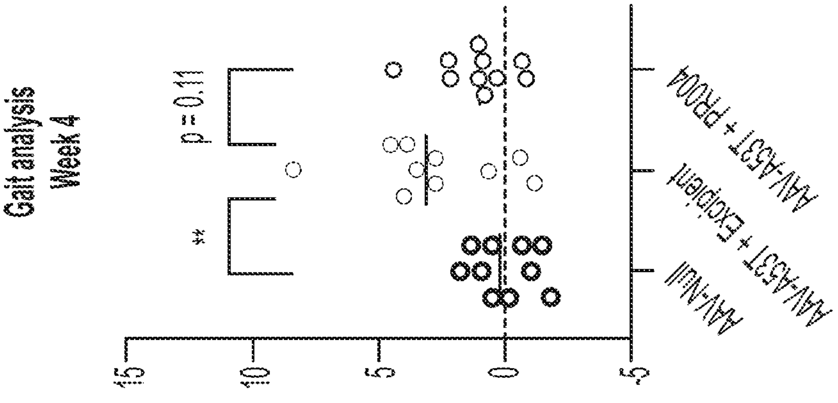
Figure 71B:
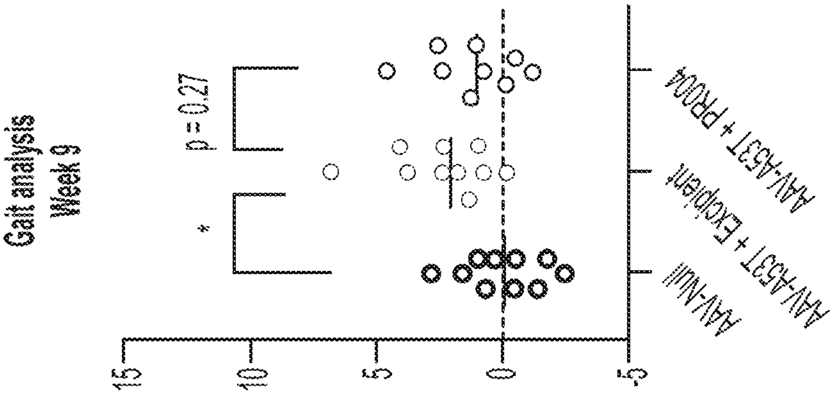

FIG. 71A-FIG. 71B show representative data for studies assessing motor phenotypes after PR004 administration in the AAV2-SNCA-A53T mouse model. Ten-week old mice were dosed with (1) AAV-Null or AAV-SNCA-A53T via IPa injection to the SN, and (2) excipient or PR004 via ICV injection. Fine motor kinematic gait analysis (MotoRater) was performed at 4 weeks (FIG. 71A) and 9 weeks (FIG. 71B) after treatment. Statistics determined by ANOVA followed by Dunnett's multiple tests correction; *=p<0.05, **=p<0.01. Data is presented as mean±SEM (n=10/group). IPa=intraparenchymal. SN=substantia nigra. ICV=intracerebroventricular.

DETAILED DESCRIPTION

The disclosure is based, in part, on compositions and methods for expression of combinations of certain gene products (e.g., gene products associated with CNS disease) in a subject. A gene product can be a protein, a fragment (e.g., portion) of a protein, an interfering nucleic acid that inhibits a CNS disease-associated gene, etc. In some embodiments, a gene product is a protein or a protein fragment encoded by a CNS disease-associated gene. In some embodiments, a gene product is an interfering nucleic acid (e.g., shRNA, siRNA, miRNA, amiRNA, etc.) that inhibits a CNS disease-associated gene.

A CNS disease-associated gene refers to a gene encoding a gene product that is genetically, biochemically or functionally associated with a central nervous system (CNS) disease, such as Parkinson's disease (PD), Gaucher disease (GD) or a synucleinopathy. For example, individuals having mutations in the GBA1 gene (which encodes the protein Gcase), have been observed to be have an increased risk of developing PD compared to individuals that do not have a mutation in GBA1. In another example, PD is associated with accumulation of protein aggregates comprising α-Synuclein (α-Syn) protein; accordingly, SNCA (which encodes α-Syn) is a CNS disease-associated gene. In some embodiments, an expression cassette described herein encodes a wild-type or non-mutant form of a CNS disease-associated gene (or coding sequence thereof). Examples of CNS disease-associated genes are listed in Table 1.

TABLE 1

| Examples of CNS disease-associated genes | | | |
|---|---|---|---|
| Name | Gene | Function | NCBI Accession No. |
| Lysosome membrane protein 2 | SCARB2/LIMP2 | lysosomal receptor for glucosylceramidase (GBA targeting) | NP_005497.1 (Isoform 1), NP_001191184.1 (Isoform 2) |
| Prosaposin | PSAP | precursor for saposins A, B, C, and D, which localize to the lysosomal compartment and facilitate the catabolism of glycosphingolipids with short oligosaccharide groups | AAH01503.1, AAH07612.1, AAH04275.1, AAA60303.1 |
| beta-Glucocerebrosidase | GBA1 | cleaves the beta-glucosidic linkage of glucocerebroside | NP_001005742.1 (Isoform 1), NP_001165282.1 (Isoform 2), NP_001165283.1 (Isoform 3) |
| alpha-Synuclein | SNCA | plays a role in maintaining a supply of synaptic vesicles in presynaptic terminals by clustering synaptic vesicles, and may help regulate the release of dopamine | NP_001139527.1 |

Deficits in enzymes such as lysosomal acid β-glucocerebrosidase (e.g., the gene product of GBA1 gene; also referred to as GCase), as well as common variants in many genes implicated in lysosome function or trafficking of macromolecules to the lysosome (e.g., Lysosomal Membrane Protein 1 (LIMP), also referred to as SCARB2), have been associated with increased PD risk and/or increased risk of Gaucher disease (e.g., neuronopathic Gaucher disease, such as Type 2 Gaucher disease or Type 3 Gaucher disease). The disclosure is based, in part, on expression constructs (e.g., vectors) encoding Gcase (or a portion thereof), prosaposin (or a portion thereof), LIMP2 (or a portion thereof), or a combination of Gcase (or a portion thereof) and one or more additional gene products from genes (e.g., LIMP2, Prosaposin, and/or α-Synuclein (α-Syn)) associated with central nervous system (CNS) diseases, for example PD, Gaucher disease, etc. In some embodiments, combinations of gene products described herein act together (e.g., synergistically) to reduce one or more signs and symptoms of a CNS disease when expressed in a subject.

Accordingly, in some aspects, the disclosure provides an isolated nucleic acid comprising an expression construct encoding a Gcase (e.g., the gene product of GBA1 gene). In some embodiments, the isolated nucleic acid comprises a Gcase-encoding sequence that has been codon optimized (e.g., codon optimized for expression in mammalian cells, for example human cells). In some embodiments, the nucleic acid sequence encoding the Gcase encodes a protein comprising an amino acid sequence as set forth in SEQ ID NO: 14 (e.g., as set forth in NCBI Reference Sequence NP_000148.2). In some embodiments, the isolated nucleic acid comprises the sequence set forth in SEQ ID NO: 15. In some embodiments the expression construct comprises adeno-associated virus (AAV) inverted terminal repeats (ITRs), for example AAV ITRs flanking the nucleic acid sequence encoding the Gcase.

In some aspects, the disclosure provides an isolated nucleic acid comprising an expression construct encoding Prosaposin (e.g., the gene product of PSAP gene). In some embodiments, the isolated nucleic acid comprises a prosaposin-encoding sequence that has been codon optimized (e.g., codon optimized for expression in mammalian cells, for example human cells). In some embodiments, the nucleic acid sequence encoding the prosaposin encodes a protein comprising an amino acid sequence as set forth in SEQ ID NO: 16 (e.g., as set forth in NCBI Reference Sequence NP_002769.1). In some embodiments, the isolated nucleic acid comprises the sequence set forth in SEQ ID NO: 17. In some embodiments the expression construct comprises adeno-associated virus (AAV) inverted terminal repeats (ITRs), for example AAV ITRs flanking the nucleic acid sequence encoding the prosaposin.

In some aspects, the disclosure provides an isolated nucleic acid comprising an expression construct encoding LIMP2/SCARB2 (e.g., the gene product of SCARB2 gene). In some embodiments, the isolated nucleic acid comprises a SCARB2-encoding sequence that has been codon optimized (e.g., codon optimized for expression in mammalian cells, for example human cells). In some embodiments, the nucleic acid sequence encoding the LIMP2/SCARB2 encodes a protein comprising an amino acid sequence as set forth in SEQ ID NO: 18 (e.g., as set forth in NCBI Reference Sequence NP_005497.1). In some embodiments, the isolated nucleic acid comprises the sequence set forth in SEQ ID NO: 29. In some embodiments the expression construct comprises adeno-associated virus (AAV) inverted terminal repeats (ITRs), for example AAV ITRs flanking the nucleic acid sequence encoding the SCARB2.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, a first gene product or a second gene product is a Gcase protein, or a portion thereof. In some embodiments, a first gene product or a second gene product is LIMP2 or a portion thereof, or Prosaposin or a portion thereof. In some embodiments, the first gene product is a Gcase protein, and the second gene product is LIMP2 or a portion thereof, or Prosaposin or a portion thereof.

In some embodiments, an expression construct encodes (e.g., alone or in addition to another gene product) an interfering nucleic acid (e.g., shRNA, miRNA, dsRNA, etc.). In some embodiments, an interfering nucleic acid inhibits expression of α-Synuclein (α-Synuclein). In some embodiments, an interfering nucleic acid that targets α-Synuclein comprises a sequence set forth in any one of SEQ ID NOs: 20-25. In some embodiments, an interfering nucleic acid that targets α-Synuclein comprises a sequence set forth in SEQ ID NO: 20. In some embodiments, an interfering nucleic acid that targets α-Synuclein binds to (e.g., hybridizes with) a sequence set forth in any one of SEQ ID NO: 20-25. In some embodiments, an interfering nucleic acid that targets α-Synuclein binds to (e.g., hybridizes with) a sequence set forth in SEQ ID NO: 20.

In some embodiments, an expression construct further comprises one or more promoters. In some embodiments, a promoter is a chicken-beta actin (CBA) promoter, a CAG promoter, a CD68 promoter, or a JeT promoter. In some embodiments, a promoter is a RNA pol II promoter or an RNA pol III promoter (e.g., U6, etc.).

In some embodiments, an expression construct further comprises an internal ribosomal entry site (IRES). In some embodiments, an IRES is located between a first gene product and a second gene product.

In some embodiments, an expression construct further comprises a self-cleaving peptide coding sequence. In some embodiments, a self-cleaving peptide is a T2A peptide.

In some embodiments, an expression construct comprises two adeno-associated virus (AAV) inverted terminal repeat (ITR) sequences. In some embodiments, ITR sequences flank a first gene product and a second gene product (e.g., are arranged as follows from 5'-end to 3'-end: ITR-first gene product-second gene product-ITR). In some embodiments, one of the ITR sequences of an isolated nucleic acid lacks a functional terminal resolution site (trs). For example, in some embodiments, one of the ITRs is a ΔITR.

The disclosure relates, in some aspects, to rAAV vectors comprising an ITR having a modified "D" region (e.g., a D sequence that is modified relative to wild-type AAV2 ITR, SEQ ID NO: 29). In some embodiments, the ITR having the modified D region is the 5' ITR of the rAAV vector. In some embodiments, a modified "D" region comprises an "S" sequence, for example as set forth in SEQ ID NO: 26. In some embodiments, the ITR having the modified "D" region is the 3' ITR of the rAAV vector. In some embodiments, a modified "D" region comprises a 3'ITR in which the "D" region is positioned at the 3' end of the ITR (e.g., on the outside or terminal end of the ITR relative to the transgene insert of the vector). In some embodiments, a modified "D" region comprises a sequence as set forth in SEQ ID NO: 26 or 27.

In some embodiments, an isolated nucleic acid (e.g., an rAAV vector) comprises a TRY region. In some embodiments, a TRY region comprises the sequence set forth in SEQ ID NO: 28.

In some embodiments, an isolated nucleic acid described by the disclosure comprises or consists of the sequence set forth in any one of SEQ ID NOs: 1 to 13, 15, 17, 19, and 32-48. In some embodiments, an isolated nucleic acid described by the disclosure encodes a peptide comprising or consisting of the sequence set forth in any one of SEQ ID NOs: 14, 16, and 18.

In some aspects, the disclosure provides a vector comprising an isolated nucleic acid as described by the disclosure. In some embodiments, a vector is a plasmid, or a viral vector. In some embodiments, a viral vector is a recombinant AAV (rAAV) vector. In some embodiments, an rAAV vector is single-stranded (e.g., single-stranded DNA).

In some aspects, the disclosure provides a host cell comprising an isolated nucleic acid as described by the disclosure or a vector as described by the disclosure.

In some aspects, the disclosure provides a recombinant adeno-associated virus (rAAV) comprising a capsid protein and an isolated nucleic acid or a vector as described by the disclosure.

In some embodiments, a capsid protein is capable of crossing the blood-brain barrier, for example an AAV9 capsid protein or an AAVrh.10 capsid protein. In some embodiments, an rAAV transduces neuronal cells and non-neuronal cells of the central nervous system (CNS).

In some aspects, the disclosure provides a method for treating a subject having or suspected of having or suspected of having a central nervous system (CNS) disease, the method comprising administering to the subject a composition (e.g., a composition comprising an isolated nucleic acid or a vector or a rAAV) as described by the disclosure. In some embodiments, the CNS disease is a neurodegenerative disease, such as a neurodegenerative disease listed in Table 4. In some embodiments, the CNS disease is a synucleinopathy, such as a synucleinopathy listed in Table 5. In some embodiments, the CNS disease is a tauopathy, such as a tauopathy listed in Table 6. In some embodiments, the CNS disease is a lysosomal storage disease, such as a lysosomal storage disease listed in Table 7. In some embodiments, the lysosomal storage disease is neuronopathic Gaucher disease, such as Type 1 Gaucher disease, Type 2 Gaucher disease or Type 3 Gaucher disease.

In some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

In some embodiments, the disclosure provides a method for treating a subject having Type 2 Gaucher disease or Type 3 Gaucher disease, the method comprising administering to the subject a rAAV comprising a nucleic acid comprising an expression construct comprising a promoter operably linked to a sequence encoding a Gcase protein, wherein the sequence encoding a Gcase protein comprises SEQ ID NO:15; and wherein the rAAV comprises a capsid protein having an AAV9 serotype. In some embodiments, the rAAV is administered to a subject having Type 2 Gaucher disease or Type 3 Gaucher disease at a dose of about $1.3\times10^{11}$ vector genomes (vg)/g brain.

In some embodiments, the disclosure provides a method for treating a subject having Parkinson's disease with a glucocerebrosidase-1 (GBA1) mutation, the method comprising administering to the subject a rAAV comprising a nucleic acid comprising an expression construct comprising a promoter operably linked to a sequence encoding a Gcase protein, wherein the sequence encoding a Gcase protein comprises SEQ ID NO:15; and wherein the rAAV comprises a capsid protein having an AAV9 serotype. In some embodiments, the rAAV is administered to a subject having Parkinson's disease at a dose of about $1\times10^{14}$ vector genomes (vg) or about $2\times10^{14}$ vg.

In some embodiments, the rAAV is administered via a suboccipital injection into the cisterna *magna.*

In some embodiments, a composition comprises a nucleic acid (e.g., an rAAV genome, for example encapsidated by AAV capsid proteins) that encodes two or more gene products (e.g., CNS disease-associated gene products), for example 2, 3, 4, 5, or more gene products described in this application. In some embodiments, a composition comprises two or more (e.g., 2, 3, 4, 5, or more) different nucleic acids (e.g., two or more rAAV genomes, for example separately encapsidated by AAV capsid proteins), each encoding one or more different gene products. In some embodiments, two or more different compositions are administered to a subject, each composition comprising one or more nucleic acids encoding different gene products. In some embodiments, different gene products are operably linked to the same promoter type (e.g., the same promoter). In some embodiments, different gene products are operably linked to different promoters.

Isolated Nucleic Acids and Vectors

An isolated nucleic acid may be DNA or RNA. The disclosure provides, in some aspects, an isolated nucleic acid comprising an expression construct encoding a Gcase (e.g., the gene product of GBA1 gene) or a portion thereof. Gcase, also referred to as β-glucocerebrosidase or GBA, refers to a lysosomal protein that cleaves the beta-glucosidic linkage of the chemical glucocerebroside, an intermediate in glycolipid metabolism. Deficiency in Gcase, a key lysosomal enzyme required for the normal metabolism of glycolipids, leads to the accumulation of the Gcase glycolipid substrates glucosylceramide (GluCer) and glucosylsphingosine (GluSph). In humans, Gcase is encoded by the GBA1 gene, located on chromosome 1. In some embodiments, GBA1 encodes a peptide that is represented by NCBI Reference Sequence NP_000148.2 (SEQ ID NO: 14). In some embodiments, the isolated nucleic acid comprises a Gcase-encoding sequence that has been codon optimized (e.g., codon optimized for expression in mammalian cells, for example human cells), such as the sequence set forth in SEQ ID NO: 15.

In some aspects, the disclosure provides an isolated nucleic acid comprising an expression construct encoding Prosaposin (e.g., the gene product of PSAP gene). Prosaposin is a precursor glycoprotein for sphingolipid activator proteins (saposins) A, B, C, and D, which facilitate the catabolism of glycosphingolipids with short oligosaccharide groups. In humans, the PSAP gene is located on chromosome 10. In some embodiments, PSAP encodes a peptide that is represented by NCBI Reference Sequence NP_002769.1 (e.g., SEQ ID NO: 16). In some embodiments, the isolated nucleic acid comprises a prosaposin-encoding sequence that has been codon optimized (e.g., codon optimized for expression in mammalian cells, for example human cells), such as the sequence set forth in SEQ ID NO: 17.

Aspects of the disclosure relate to an isolated nucleic acid comprising an expression construct encoding LIMP2/SCARB2 (e.g., the gene product of SCARB2 gene). SCARB2 refers to a membrane protein that regulates lysosomal and endosomal transport within a cell. In humans, SCARB2 gene is located on chromosome 4. In some embodiments, the SCARB2 gene encodes a peptide that is represented by NCBI Reference Sequence NP_005497.1 (SEQ ID NO: 18). In some embodiments, the isolated nucleic acid comprises the sequence set forth in SEQ ID NO: 19. In some embodiments the isolated nucleic acid comprises a SCARB2-encoding sequence that has been codon optimized.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, an isolated nucleic acid or vector (e.g., rAAV vector) described by the disclosure comprises or consists of a sequence set forth in any one of SEQ ID NOs: 1-48. In some embodiments, an isolated nucleic acid or vector (e.g., rAAV vector) described by the disclosure comprises or consists of a sequence that is complementary (e.g., the complement of) a sequence set forth in any one of SEQ ID NOs: 1-48. In some embodiments, an isolated nucleic acid or vector (e.g., rAAV vector) described by the disclosure comprises or consists of a sequence that is a reverse complement of a sequence set forth in any one of SEQ ID NOs: 1-48. In some embodiments, an isolated nucleic acid or vector (e.g., rAAV vector) described by the disclosure comprises or consists of a portion of a sequence set forth in any one of SEQ ID NOs: 1-48. A portion may comprise at least 25%, 50%, 60%, 70%, 80%, 90%, 95%, or 99% of a sequence set forth in any one of SEQ ID NOs: 1-48. In some embodiments, a nucleic acid sequence described by the disclosure is a nucleic acid sense strand (e.g., 5' to 3' strand), or in the context of a viral sequences a plus (+) strand. In some embodiments, a nucleic acid sequence described by the disclosure is a nucleic acid antisense strand (e.g., 3' to 5' strand), or in the context of viral sequences a minus (−) strand.

In some embodiments, a gene product is encoded by a coding portion (e.g., a cDNA) of a naturally occurring gene. In some embodiments, a first gene product is a protein (or a fragment thereof) encoded by the GBA1 gene. In some embodiments, a gene product is a protein (or a fragment thereof) encoded by the SCARB2/LIMP2 gene and/or the PSAP gene. However, the skilled artisan recognizes that the order of expression of a first gene product (e.g., Gcase) and a second gene product (e.g., LIMP2) can generally be reversed (e.g., LIMP2 is the first gene product and Gcase is the second gene product). In some embodiments, a gene product is a fragment (e.g., portion) of a gene listed in Table 1. A protein fragment may comprise about 50%, about 60%, about 70%, about 80% about 90% or about 99% of a protein encoded by the genes listed in Table 1. In some embodiments, a protein fragment comprises between 50% and 99.9% (e.g., any value between 50% and 99.9%) of a protein encoded by a gene listed in Table 1.

In some embodiments, an expression construct is monocistronic (e.g., the expression construct encodes a single fusion protein comprising a first gene product and a second gene product). In some embodiments, an expression construct is polycistronic (e.g., the expression construct encodes two distinct gene products, for example two different proteins or protein fragments).

A polycistronic expression vector may comprise a one or more (e.g., 1, 2, 3, 4, 5, or more) promoters. Any suitable promoter can be used, for example, a constitutive promoter, an inducible promoter, an endogenous promoter, a tissue-specific promoter (e.g., a CNS-specific promoter), etc. In some embodiments, a promoter is a chicken beta-actin promoter (CBA promoter), a CAG promoter (for example as described by Alexopoulou et al. (2008) *BMC Cell Biol.* 9:2; doi: 10.1186/1471-2121-9-2), a CD68 promoter, or a JeT promoter (for example as described by Tornøe et al. (2002)

*Gene* 297(1-2):21-32). In some embodiments, a promoter is operably-linked to a nucleic acid sequence encoding a first gene product, a second gene product, or a first gene product and a second gene product. In some embodiments, an expression cassette comprises one or more additional regulatory sequences, including but not limited to transcription factor binding sequences, intron splice sites, poly(A) addition sites, enhancer sequences, repressor binding sites, or any combination of the foregoing.

In some embodiments, a nucleic acid sequence encoding a first gene product and a nucleic acid sequence encoding a second gene product are separated by a nucleic acid sequence encoding an internal ribosomal entry site (IRES). Examples of IRES sites are described, for example, by Mokrejs et al. (2006) *Nucleic Acids Res.* 34(Database issue): D125-30. In some embodiments, a nucleic acid sequence encoding a first gene product and a nucleic acid sequence encoding a second gene product are separated by a nucleic acid sequence encoding a self-cleaving peptide. Examples of self-cleaving peptides include but are not limited to T2A, P2A, E2A, F2A, BmCPV 2A, and BmIFV 2A, and those described by Liu et al. (2017) *Sci Rep.* 7: 2193. In some embodiments, the self-cleaving peptide is a T2A peptide.

Pathologically, disorders such as PD and Gaucher disease are associated with accumulation of protein aggregates composed largely of α-Synuclein (α-Syn) protein. Accordingly, in some embodiments, isolated nucleic acids described herein comprise an inhibitory nucleic acid that reduces or prevents expression of α-Syn protein. A sequence encoding an inhibitory nucleic acid may be placed in an untranslated region (e.g., intron, 5'UTR, 3'UTR, etc.) of the expression vector.

In some embodiments, an inhibitory nucleic acid is positioned in an intron of an expression construct, for example in an intron upstream of the sequence encoding a first gene product. An inhibitory nucleic acid can be a double stranded RNA (dsRNA), siRNA, shRNA, micro RNA (miRNA), artificial miRNA (amiRNA), or an RNA aptamer. Generally, an inhibitory nucleic acid binds to (e.g., hybridizes with) between about 6 and about 30 (e.g., any integer between 6 and 30, inclusive) contiguous nucleotides of a target RNA (e.g., mRNA). In some embodiments, the inhibitory nucleic acid molecule is an miRNA or an amiRNA, for example an miRNA that targets SNCA (the gene encoding α-Syn protein). In some embodiments, the miRNA does not comprise any mismatches with the region of SNCA mRNA to which it hybridizes (e.g., the miRNA is "perfected"). In some embodiments, the inhibitory nucleic acid is an shRNA (e.g., an shRNA targeting SNCA). In some embodiments, an shRNA that targets SNCA is encoded by SEQ ID NO: 47. In some embodiments, an shRNA that targets SNCA is encoded by a sequence comprising SEQ ID NO: 20.

The skilled artisan recognizes that when referring to nucleic acid sequences comprising or encoding inhibitory nucleic acids (e.g., dsRNA, siRNA, shRNA, miRNA, amiRNA, etc.) any one or more thymidine (T) nucleotides or uridine (U) nucleotides in a sequence provided herein may be replaced with any other nucleotide suitable for base pairing (e.g., via a Watson-Crick base pair) with an adenosine nucleotide. For example, T may be replaced with U, and U may be replaced with T.

An isolated nucleic acid as described herein may exist on its own, or as part of a vector. Generally, a vector can be a plasmid, cosmid, phagemid, bacterial artificial chromosome (BAC), or a viral vector (e.g., adenoviral vector, adeno-associated virus (AAV) vector, retroviral vector, baculoviral vector, etc.). In some embodiments, the vector is a plasmid (e.g., a plasmid comprising an isolated nucleic acid as described herein). In some embodiments, the vector is a recombinant AAV (rAAV) vector. In some embodiments, an rAAV vector is single-stranded (e.g., single-stranded DNA). In some embodiments, a vector is a Baculovirus vector (e.g., an *Autographa californica* nuclear polyhedrosis (AcNPV) vector).

Typically an rAAV vector (e.g., rAAV genome) comprises a transgene (e.g., an expression construct comprising one or more of each of the following: promoter, intron, enhancer sequence, protein coding sequence, inhibitory RNA coding sequence, polyA tail sequence, etc.) flanked by two AAV inverted terminal repeat (ITR) sequences. In some embodiments the transgene of an rAAV vector comprises an isolated nucleic acid as described by the disclosure. In some embodiments, each of the two ITR sequences of an rAAV vector is a full-length ITR (e.g., approximately 145 bp in length, and containing functional Rep binding site (RBS) and terminal resolution site (trs)). In some embodiments, one of the ITRs of an rAAV vector is truncated (e.g., shortened or not full-length). In some embodiments, a truncated ITR lacks a functional terminal resolution site (trs) and is used for production of self-complementary AAV vectors (scAAV vectors). In some embodiments, a truncated ITR is a ΔITR, for example as described by McCarty et al. (2003) *Gene Ther.* 10(26):2112-8.

Aspects of the disclosure relate to isolated nucleic acids (e.g., rAAV vectors) comprising an ITR having one or more modifications (e.g., nucleic acid additions, deletions, substitutions, etc.) relative to a wild-type AAV ITR, for example relative to wild-type AAV2 ITR (e.g., SEQ ID NO: 29). The structure of wild-type AAV2 ITR is shown in FIG. 19. Generally, a wild-type ITR comprises a 125 nucleotide region that self-anneals to form a palindromic double-stranded T-shaped, hairpin structure consisting of two cross arms (formed by sequences referred to as B/B' and C/C', respectively), a longer stem region (formed by sequences A/A'), and a single-stranded terminal region referred to as the "D" region. (FIG. 19). Generally, the "D" region of an ITR is positioned between the stem region formed by the A/A' sequences and the insert containing the transgene of the rAAV vector (e.g., positioned on the "inside" of the ITR relative to the terminus of the ITR or proximal to the transgene insert or expression construct of the rAAV vector). In some embodiments, a "D" region comprises the sequence set forth in SEQ ID NO: 27. The "D" region has been observed to play an important role in encapsidation of rAAV vectors by capsid proteins, for example as disclosed by Ling et al. (2015) *J Mol Genet Med* 9(3).

The disclosure is based, in part, on the surprising discovery that rAAV vectors comprising a "D" region located on the "outside" of the ITR (e.g., proximal to the terminus of the ITR relative to the transgene insert or expression construct) are efficiently encapsidated by AAV capsid proteins than rAAV vectors having ITRs with unmodified (e.g., wild-type) ITRs. In some embodiments, rAAV vectors having a modified "D" sequence (e.g., a "D" sequence in the "outside" position) have reduced toxicity relative to rAAV vectors having wild-type ITR sequences.

In some embodiments, a modified "D" sequence comprises at least one nucleotide substitution relative to a wild-type "D" sequence (e.g., SEQ ID NO: 27). A modified "D" sequence may have at least 1, 2, 3, 4, 5, 6, 7, 8, 9, 10, or more than 10 nucleotide substitutions relative to a wild-type "D" sequence (e.g., SEQ ID NO: 27). In some embodiments, a modified "D" sequence comprises at least 10, 11, 12, 13, 14, 15, 16, 17, 18, or 19 nucleic acid substitutions relative to a wild-type "D" sequence (e.g., SEQ ID NO: 27). In some embodiments, a modified "D" sequence is between about 10% and about 99% (e.g., 10%, 15%, 20%, 25%, 30%, 40%, 45%, 50%, 55%, 60%, 65%, 70%, 75%, 80%, 85%, 90%, 95%, or 99%) identical to a wild-type "D" sequence (e.g., SEQ ID NO: 27). In some embodiments, a modified "D" sequence comprises the sequence set forth in SEQ ID NO: 26, also referred to as an "S" sequence as described in Wang et al. (1995) *J Mol Biol* 250(5):573-80.

An isolated nucleic acid or rAAV vector as described by the disclosure may further comprise a "TRY" sequence, for example as set forth in SEQ ID NO: 28 or as described in Francois et al., (2005) *J. Virol.* 79(17):11082-11094. In some embodiments, a TRY sequence is positioned between an ITR (e.g., a 5' ITR) and an expression construct (e.g., a transgene-encoding insert) of an isolated nucleic acid or rAAV vector.

In some aspects, the disclosure relates to Baculovirus vectors comprising an isolated nucleic acid or rAAV vector as described by the disclosure. In some embodiments, the Baculovirus vector is an *Autographa californica* nuclear polyhedrosis (AcNPV) vector, for example as described by Urabe et al. (2002) *Hum Gene Ther* 13(16):1935-43 and Smith et al. (2009) *Mol Ther* 17(11):1888-1896.

In some aspects, the disclosure provides a host cell comprising an isolated nucleic acid or vector as described herein. A host cell can be a prokaryotic cell or a eukaryotic cell. For example, a host cell can be a mammalian cell, bacterial cell, yeast cell, insect cell, etc. In some embodiments, a host cell is a mammalian cell, for example a HEK293T cell. In some embodiments, a host cell is a bacterial cell, for example an *E. coli* cell.

rAAVs

In some aspects, the disclosure relates to recombinant AAVs (rAAVs) comprising a transgene that encodes a nucleic acid as described herein (e.g., an rAAV vector as described herein). The term "rAAVs" generally refers to viral particles comprising an rAAV vector encapsidated by one or more AAV capsid proteins. An rAAV described by the disclosure may comprise a capsid protein having a serotype selected from AAV1, AAV2, AAV3, AAV4, AAV5, AAV6, AAV7, AAV8, AAV9, and AAV10. In some embodiments, an rAAV comprises a capsid protein from a non-human host, for example a rhesus AAV capsid protein such as AAVrh.10, AAVrh.39, etc. In some embodiments, an rAAV described by the disclosure comprises a capsid protein that is a variant of a wild-type capsid protein, such as a capsid protein variant that includes at least 1, 2, 3, 4, 5, 6, 7, 8, 9, 10, or more than 10 (e.g., 15, 20, 25, 50, 100, etc.) amino acid substitutions (e.g., mutations) relative to the wild-type AAV capsid protein from which it is derived. In some embodiments, an AAV capsid protein variant is an AAV1RX capsid protein, for example as described by Albright et al. *Mol Ther.* 2018 Feb. 7; 26(2):510-523. In some embodiments, a capsid protein variant is an AAV TM6 capsid protein, for example as described by Rosario et al. *Mol Ther Methods Clin Dev.* 2016; 3: 16026.

In some embodiments, rAAVs described by the disclosure readily spread through the CNS, particularly when introduced into the CSF space or directly into the brain parenchyma. Accordingly, in some embodiments, rAAVs described by the disclosure comprise a capsid protein that is capable of crossing the blood-brain barrier (BBB). For example, in some embodiments, an rAAV comprises a capsid protein having an AAV9 or AAVrh.10 serotype. Production of rAAVs is described, for example, by Samulski et al. (1989) *J Virol.* 63(9):3822-8 and Wright (2009) *Hum Gene Ther.* 20(7): 698-706. In some embodiments, an rAAV comprises a capsid protein that specifically or preferentially targets myeloid cells, for example microglial cells.

In some embodiments, the disclosure provides an rAAV referred to as "PR001". This rAAV expresses the codon-optimized coding sequence of human GBA1 (SEQ ID NO:15). In some embodiments, the disclosure provides an rAAV referred to as "PR001A". PR001A (AAV9.CBA.GBA1.A) is a rAAV that delivers a functional human GBA1 gene, leading to increased expression of functional human Gcase. The PR001A vector insert comprises the chicken β-actin (CBA) promoter element, comprising 4 parts: the cytomegalovirus (CMV) enhancer, CBA promoter, exon 1, and intron (int) to constitutively express the codon-optimized coding sequence of human GBA1 (SEQ ID NO:15). The 3' region also contains a woodchuck hepatitis virus post-transcriptional regulatory element (WPRE) followed by a bovine growth hormone polyadenylation signal tail. Three well described transcriptional regulatory activation sites are included at the 5' end of the promoter region: TATA, RBS, and YY1 (see, e.g., Francois et al., (2005) *J. Virol.* 79(17):11082-11094). The flanking inverted terminal repeats (ITRs) allow for the correct packaging of the intervening sequences. Two variants of the 5' ITR sequence (FIG. 7, inset box, bottom sequence) are provided; these variants have several nucleotide differences within the 20-nucleotide "D" region of the ITR, which is believed to impact the efficiency of packaging and expression. PR001A contains the "D" domain nucleotide sequence shown in FIG. 7 (inset box, top sequence; SEQ ID NO:30). In some embodiment, the disclosure provides a variant vector referred to as "PR001B", which harbors a mutant "D" domain (termed an "S" domain herein, with the nucleotide changes shown by shading in SEQ ID NO:31 in FIG. 7). Except for the different 5'ITR sequence, PR001B is identical to PR001A. The backbone contains the gene to confer resistance to kanamycin as well as a stuffer sequence to prevent reverse packaging. A schematic depicting a plasmid encoding the rAAV vector is shown in FIG. 55. SEQ ID NO: 39 provides the nucleotide sequence of the first strand (in 5' to 3' order) of the plasmid encoding the PR001A vector shown in FIG. 55. SEQ ID NO: 40 provides the nucleotide sequence of the second strand (in 5' to 3' order) of the plasmid encoding PR001A vector shown in FIG. 55. PR001A comprises AAV9 capsid proteins.

In some embodiments, the disclosure provides an rAAV referred to as "PR004". This rAAV expresses the codon-optimized coding sequence of human GBA1 (SEQ ID NO:15) and an inhibitory nucleic acid coding sequence that targets reduces α-Synuclein and comprises the nucleotide sequence of SEQ ID NO: 20. In some embodiments, the disclosure provides an rAAV referred to as "PR004X". In some embodiments, the disclosure provides an rAAV referred to as "PR004Y". Each of PR004X and PR004Y is a rAAV that (i) delivers a functional human GBA1 gene, leading to increased expression of functional human Gcase, and (ii) encodes a shRNA that reduces α-Synuclein levels via RNA interference. The PR004 vector insert comprises the chicken β-actin (CBA) promoter element, comprising 4 parts: the cytomegalovirus (CMV) enhancer, CBA promoter, exon 1, and intron (int) to constitutively express the codon-optimized coding sequence of human GBA1 (SEQ ID NO:15) and an inhibitory nucleic acid coding sequence comprising the nucleotide sequence of SEQ ID NO: 20. The 3' region also contains a woodchuck hepatitis virus post-transcriptional regulatory element (WPRE) followed by a bovine growth hormone polyadenylation signal tail. Three well described transcriptional regulatory activation sites are included at the 5' end of the promoter region: TATA, RBS, and YY1 (see, e.g., Francois et al., (2005) *J. Virol.* 79(17): 11082-11094). The flanking inverted terminal repeats (ITRs) allow for the correct packaging of the intervening sequences. The backbone contains the gene to confer resistance to kanamycin as well as a stuffer sequence to prevent reverse packaging. A schematic depicting a plasmid encoding the rAAV PR004X vector is shown in FIG. 56. SEQ ID NO: 41 provides the nucleotide sequence of the first strand (in 5' to 3' order) of the plasmid encoding the PR004X vector shown in FIG. 56. SEQ ID NO: 42 provides the nucleotide sequence of the second strand (in 5' to 3' order) of the plasmid encoding the PR004X vector shown in FIG. 56. A schematic depicting a plasmid encoding the rAAV PR004Y vector is shown in FIG. 57. SEQ ID NO: 43 provides the nucleotide sequence of the first strand (in 5' to 3' order) of the plasmid encoding the PR004Y vector shown in FIG. 57. SEQ ID NO: 44 provides the nucleotide sequence of the second strand (in 5' to 3' order) of the plasmid encoding the PR004Y vector shown in FIG. 57. PR004X and PR004Y each comprise AAV9 capsid proteins. The PR004X and PR004Y vectors are designed to reduce accumulation of all forms of α-Synuclein, including aggregated and extracellular forms.

In some embodiments, the disclosure provides an rAAV referred to as "PR014". This rAAV expresses an inhibitory nucleic acid coding sequence that targets reduces α-Synuclein and comprises the nucleotide sequence of SEQ ID NO: 20. In some embodiments, the disclosure provides an rAAV referred to as "PR014X". PR014X is a rAAV that encodes a shRNA that reduces α-Synuclein levels via RNA interference. The PR014X vector insert comprises the chicken β-actin (CBA) promoter element, comprising 4 parts: the cytomegalovirus (CMV) enhancer, CBA promoter, exon 1, and intron (int) to constitutively express an inhibitory nucleic acid coding sequence comprising the nucleotide sequence of SEQ ID NO: 20. The 3' region also contains a woodchuck hepatitis virus post-transcriptional regulatory element (WPRE) followed by a bovine growth hormone polyadenylation signal tail. Three well described transcriptional regulatory activation sites are included at the 5' end of the promoter region: TATA, RBS, and YY1 (see, e.g., Francois et al., (2005) *J. Virol.* 79(17):11082-11094). The flanking inverted terminal repeats (ITRs) allow for the correct packaging of the intervening sequences. The backbone contains the gene to confer resistance to kanamycin as well as a stuffer sequence to prevent reverse packaging. A schematic depicting a plasmid encoding the rAAV vector is shown in FIG. 58. SEQ ID NO: 45 provides the nucleotide sequence of the first strand (in 5' to 3' order) of the plasmid encoding the PR014X vector shown in FIG. 60. SEQ ID NO: 46 provides the nucleotide sequence of the second strand (in 5' to 3' order) of the plasmid encoding the PR014X vector shown in FIG. 60. SEQ ID NO: 47 provides the nucleotide sequence of the first strand (in 5' to 3' order) of the shRNA in the plasmid encoding the PR014X vector shown in FIG. 58. SEQ ID NO: 48 provides the nucleotide sequence of the second strand (in 5' to 3' order) of the shRNA in the plasmid encoding the PR014X vector shown in FIG. 58. PR014X comprises AAV9 capsid proteins. The PR014X vector is designed to reduce accumulation of all forms of α-Synuclein, including aggregated and extracellular forms.

In some embodiments, an rAAV as described by the disclosure (e.g., comprising a recombinant rAAV genome encapsidated by AAV capsid proteins to form an rAAV capsid particle) is produced in a Baculovirus vector expression system (BEVS). Production of rAAVs using BEVS are described, for example by Urabe et al. (2002) *Hum Gene Ther* 13(16):1935-43, Smith et al. (2009) *Mol Ther* 17(11): 1888-1896, U.S. Pat. Nos. 8,945,918, 9,879,282, and International PCT Publication WO 2017/184879. However, an rAAV can be produced using any suitable method (e.g., using recombinant rep and cap genes). In some embodiments, an rAAV as disclosed herein is produced in HEK293 (human embryonic kidney) cells.

Pharmaceutical Compositions

In some aspects, the disclosure provides pharmaceutical compositions comprising an isolated nucleic acid or rAAV as described herein and a pharmaceutically acceptable carrier. As used herein, the term "pharmaceutically acceptable" refers to a material, such as a carrier or diluent, which does not abrogate the biological activity or properties of the compound, and is relatively non-toxic, e.g., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

Compositions (e.g., pharmaceutical compositions) provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

In some embodiments, the disclosure provides a PR001 (e.g., PR001A) finished drug product comprising the PR001 rAAV described above presented in aqueous solution. In some embodiments, the final formulation buffer comprises about 20 mM Tris [pH 8.0], about 1 mM $MgCl_2$, about 200 mM NaCl, and about 0.001% [w/v] poloxamer 188. In some embodiments, the finished drug product and the final formulation buffer are suitable for intra-cisterna *magna* (ICM) injection or intravenous administration.

Methods

Aspects of the disclosure relate to delivery of compositions (e.g., isolated nucleic acids, rAAVs, etc.) engineered to express CNS disease-associated gene products to a cell or cells (e.g., a cell or cells of a subject).

As described further in the Examples section, aspects of the disclosure relate to compositions expressing gene products that inhibit or prevent glial scarring (e.g., gliosis). Accordingly, in some aspects, the disclosure provides a method for inhibiting glial scarring in a subject, the method comprising administering to the subject a composition (e.g., an isolated nucleic acid or rAAV) as described herein.

In some embodiments, the subject has or is suspected of having a central nervous system (CNS) disease. In some embodiments, the subject has Gaucher disease (GD). In some embodiments, the subject has neuronopathic GD (nGD) (e.g., Type 2 GD or Type 3 GD). In some embodiments, the subject has Type 1 GD. In some embodiments, a subject having GD does not have PD or PD symptoms. In some embodiments, the subject has parkinsonism. In some embodiments, a subject has Parkinson's disease (PD). In some embodiments, the subject has an atypical Parkinsonian disorder. In some embodiments, an atypical Parkinsonian disorder is dementia with Lewy bodies, progressive supranuclear palsy, multiple system atrophy or corticobasal syndrome.

The disclosure is based, in part, on compositions for expression of one or more CNS disease-associated gene products in a subject to treat CNS-associated diseases. The one or more CNS disease-associated gene products may be encoded by one or more isolated nucleic acids or rAAV vectors. In some embodiments, a subject is administered a single vector (e.g., isolated nucleic acid, rAAV, etc.) encoding one or more (1, 2, 3, 4, 5, or more) gene products. In some embodiments, a subject is administered a plurality (e.g., 2, 3, 4, 5, or more) vectors (e.g., isolated nucleic acids, rAAVs, etc.), where each vector encodes a different CNS disease-associated gene product. In some embodiments, the composition expresses GBA or a portion thereof. In some embodiments, the composition expresses an interfering RNA that targets alpha-Synuclein. In some embodiments, the composition expresses GBA or a portion thereof and an interfering RNA that targets alpha-Synuclein.

A CNS-associated disease may be a neurodegenerative disease, synucleinopathy, tauopathy, or a lysosomal storage disease. Examples of neurodegenerative diseases and their associated genes are listed in Table 4.

A "synucleinopathy" refers to a disease or disorder characterized by the accumulation of alpha-Synuclein (the gene product of SNCA) in a subject (e.g., relative to a healthy subject, for example a subject not having a synucleinopathy). Examples of synucleinopathies and their associated genes are listed in Table 5.

A "tauopathy" refers to a disease or disorder characterized by accumulation of abnormal Tau protein in a subject (e.g., relative to a healthy subject not having a tauopathy). Examples of tauopathies and their associated genes are listed in Table 6.

A "lysosomal storage disease" refers to a disease characterized by abnormal build-up of toxic cellular products in lysosomes of a subject. Examples of lysosomal storage diseases and their associated genes are listed in Table 7.

As used herein "treat" or "treating" refers to (a) preventing or delaying onset of a CNS disease; (b) reducing severity of a CNS disease; (c) reducing or preventing development of symptoms characteristic of a CNS disease; (d) and/or preventing worsening of symptoms characteristic of a CNS disease. Symptoms of CNS disease may include, for example, motor dysfunction (e.g., shaking, rigidity, slowness of movement, difficulty with walking, paralysis), cognitive dysfunction (e.g., dementia, depression, anxiety, psychosis), difficulty with memory, and emotional and behavioral dysfunction.

The disclosure is based, in part, on compositions for expression of one or more PD-associated gene products in a subject that act together (e.g., synergistically) to treat Parkinson's disease.

Accordingly, in some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

The disclosure is based, in part, on compositions for expression of one or more CNS disease-associated gene products in a subject to treat Gaucher disease (GD). The diagnosis of GD is established by the presence of biallelic pathogenic mutations in GBA1 or a finding of less than 15% of normal GCase activity in peripheral blood leukocytes. GBA1 mutations causing more profound enzyme deficiencies are associated with earlier onset of disease, faster progression of symptoms, and a higher likelihood to develop neurological symptoms (Svennerholm et al., *Clin Genet.* 1986; 30(2):131-5; Cox, *Biologics.* 2010; 4:299-313). GD has traditionally been subdivided into three broader phenotypes distinguished by the presence of neurologic manifestations (neuronopathic [Type 2 GD and Type 3 GD; nGD] or non-neuronopathic [Type 1 GD]).

Within nGD, the distinctions between Type 2 GD and Type 3 GD may represent a phenotypic continuum of an acute to chronic presentation of CNS and visceral symptoms. Infants with Type 2 GD, known as the acute neuronopathic form, classically present with early bulbar signs (such as squint and/or swallowing difficulty), opisthotonus or spasticity, supranuclear gaze palsy, and failure to achieve motor, behavior, and cognitive milestones. Most children die by age 2. (Goker-Alpan et al., *J Pediatr.* 2003; 143(2):273-6; Roshan and Sidransky, *Diseases.* 2017; 5(1):pii:E10). In Type 3 GD, the hallmark clinical sign is a slow horizontal supranuclear gaze palsy, with other neurologic manifestations ranging from cognitive impairment to ataxia to seizures to death in childhood or early adolescence (Goker-Alpan et al., *J Pediatr.* 2003; 143(2):273-6; Tylki-Szynáliska et al., *J Inherit Metab Dis.* 2010; 33(4):339-46).

Accordingly, in some aspects, the disclosure provides a method for treating a subject having or suspected of having neuronopathic Gaucher disease, the method comprising administering to the subject a composition (e.g., a composition comprising an isolated nucleic acid or a vector or a rAAV) as described by the disclosure.

In some aspects, the disclosure provides a method for treating a subject having Type 2 Gaucher disease or Type 3 Gaucher disease, the method comprising administering to the subject a rAAV comprising a nucleic acid comprising an expression construct comprising a promoter operably linked to a sequence encoding a Gcase protein, wherein the sequence encoding a Gcase protein comprises SEQ ID NO:15; and wherein the rAAV comprises a capsid protein having an AAV9 serotype. In some embodiments, the disclosure provides a method for treating a neurological symptom of a subject having Type 2 Gaucher disease or Type 3 Gaucher disease, the method comprising administering to the subject a rAAV comprising a nucleic acid comprising an expression construct comprising a promoter operably linked to a sequence encoding a Gcase protein, wherein the sequence encoding a Gcase protein comprises SEQ ID NO:15; and wherein the rAAV comprises a capsid protein having an AAV9 serotype. In some embodiments, a neurological symptom of Type 2 Gaucher disease or Type 3 Gaucher disease is supranuclear gaze palsy, hypotonia, seizures, spasticity, hypokinesia, motor or behavioral developmental delay or impairment, cognitive delay or impairment, ataxia, intention tremor, or rigidity.

In some embodiments, patients having certain forms of Gaucher disease exhibit symptoms of peripheral neuropathy, for example as described in Biegstraaten et al. (2010) *Brain* 133(10):2909-2919. In some embodiments, the disclosure provides a method for treating peripheral neuropathy in a subject having Gaucher disease (e.g., Type 1 Gaucher disease), the method comprising administering to the subject a rAAV comprising a nucleic acid comprising an expression construct comprising a promoter operably linked to a sequence encoding a Gcase protein, wherein the sequence encoding a Gcase protein comprises SEQ ID NO:15; and wherein the rAAV comprises a capsid protein having an AAV9 serotype. In some embodiments, the disclosure provides a method for treating Type 1 Gaucher disease in a subject, the method comprising administering to the subject a rAAV comprising a nucleic acid comprising an expression construct comprising a promoter operably linked to a sequence encoding a Gcase protein, wherein the sequence encoding a Gcase protein comprises SEQ ID NO:15; and wherein the rAAV comprises a capsid protein having an AAV9 serotype. In some embodiments, the rAAV is administered to the subject intravenously for treating Type 1 Gaucher disease.

In some embodiments, the disclosure provides a method for treating a subject having Parkinson's disease (PD) with a glucocerebrosidase-1 (GBA1) mutation (e.g., a pathogenic GBA1 mutation), the method comprising administering to the subject a rAAV comprising a nucleic acid comprising an expression construct comprising a promoter operably linked to a sequence encoding a Gcase protein, wherein the sequence encoding a Gcase protein comprises SEQ ID NO:15; and wherein the rAAV comprises a capsid protein having an AAV9 serotype. In some embodiments, the disclosure provides a method for treating a symptom of a subject having PD with a GBA1 mutation, the method comprising administering to the subject a rAAV comprising a nucleic acid comprising an expression construct comprising a promoter operably linked to a sequence encoding a Gcase protein, wherein the sequence encoding a Gcase protein comprises SEQ ID NO:15; and wherein the rAAV comprises a capsid protein having an AAV9 serotype. In some embodiments, a motor symptom of PD is resting tremor, bradykinesia, rigidity, or gait difficulty. In some embodiments, a non-motor symptom of PD is cognitive impairment/dementia, depression, delusions/hallucinations, psychosis, sleep disturbances, constipation, urinary symptoms, pain, anosmia, difficulty swallowing, or hypotension. In some embodiments, the subject having PD has one GBA1 mutation. In some embodiments, the subject having PD has two GBA1 mutations.

In some embodiments, a rAAV encoding a Gcase protein for treating Type 1 Gaucher disease, Type 2 Gaucher disease or Type 3 Gaucher disease or Parkinson's disease with a GBA1 mutation is administered to a subject at a dose ranging from about $1\times10^{12}$ vector genomes (vg) to about $1\times10^{15}$ vg, or from about $1\times10^{13}$ vg to about $5\times10^{14}$ vg, or from about $5\times10^{13}$ vg to about $5\times10^{14}$ vg, or from about $3.4\times10^{13}$ vg to about $1\times10^{14}$ vg, or from about $1\times10^{14}$ vg to about $5\times10^{14}$ vg, or from about $1\times10^{14}$ vg to about $3\times10^{14}$ vg, or from about $1\times10^{14}$ vg to about $2\times10^{14}$ vg. The total dose assumes an adult brain mass of 1.3 kg (Hakim and Mathieson, *Neurology,* 1979; 29(9 Pt 1):1209-14). For pediatric subjects, the dose may be scaled accordingly. In some embodiments, the dose for pediatric subjects may be adjusted using estimates of brain weight by age, for example, based on a composite dataset that includes derived brain weights from 21 autopsy and neuroimaging publications (Vannucci and Vannucci, *Am J Phys Anthropol.* 2019; 168(2):247-61).

In some embodiments, a rAAV encoding a Gcase protein for treating Parkinson's disease with a GBA1 mutation is administered to a subject (e.g., a human adult subject) at a dose of about $1\times10^{14}$ vg, about $2\times10^{14}$ vg, about $3\times10^{14}$ vg, about $4\times10^{14}$ vg, or about $5\times10^{14}$ vg. In some embodiments, a rAAV for treating Parkinson's disease with a GBA1 mutation is administered to a subject (e.g., a human adult subject) at a dose of about $1\times10^{14}$ vg (about $7.7\times10^{10}$ vg/g brain), about $2\times10^{14}$ vg (about $1.5\times10^{11}$ vg/g brain), or about $3\times10^{14}$ vg (about $1.9\times10^{11}$ vg/g brain).

In some embodiments, a rAAV encoding a Gcase protein for treating Type 2 or Type 3 Gaucher disease is administered to a subject (e.g., a human pediatric subject) at a dose ranging from about $5\times10^{10}$ vg/g brain to about $5\times10^{11}$ vg/g brain. In some embodiments, a rAAV for treating Type 2 Gaucher disease or Type 3 Gaucher disease is administered to a subject (e.g., a human pediatric subject) at a dose of about $1.3\times10^{11}$ vg/g brain (from about $5.9\times10^{13}$ vg to about $1.7\times10^{14}$ vg). In some embodiments, a rAAV for treating Type 2 Gaucher disease or Type 3 Gaucher disease is administered to a subject (e.g., a human pediatric subject) at a dose of about $1.9\times10^{11}$ vg/g brain (from about $8.6\times10^{13}$ vg to about $2.5\times10^{14}$ vg). In some embodiments, a rAAV for treating Type 2 Gaucher disease or Type 3 Gaucher disease is administered to a subject (e.g., a human pediatric subject) at a dose of about $7.7\times10^{10}$ vg/g brain (from about $3.4\times10^{13}$ vg to about $1\times10^{14}$ vg) or a dose of about $2.3\times10^{11}$ vg/g brain (from about $1\times10^{14}$ vg to about $3\times10^{14}$ vg).

In some embodiments, a rAAV encoding a Gcase protein for treating Type 1, Type 2 or Type 3 Gaucher disease or Parkinson's disease with a GBA1 mutation is administered to a subject as a single dose, and the rAAV is not administered to the subject subsequently.

In some embodiments, a rAAV encoding a Gcase protein is administered via a single suboccipital injection into the cisterna *magna*. In some embodiments, the injection into the cisterna *magna* is performed under radiographic guidance.

In some embodiments, the disclosure provides a method for treating a subject having a synucleinopathy or parkinsonism, the method comprising administering to the subject a rAAV comprising a nucleic acid comprising an expression construct comprising a transgene comprising (a) a Gcase protein coding sequence comprising the nucleotide sequence of SEQ ID NO: 15; and (b) an inhibitory nucleic acid coding sequence comprising the nucleotide sequence of SEQ ID NO: 20 or SEQ ID NO: 47; wherein the rAAV comprises a capsid protein having an AAV9 serotype.

In some embodiments, the disclosure provides a method for treating a subject having multiple system atrophy, Parkinson's disease, Parkinson's disease with GBA1 mutation, Lewy body disease, dementia with Lewy bodies, dementia with Lewy bodies with GBA1 mutation, progressive supranuclear palsy, or corticobasal syndrome, the method comprising administering to the subject a rAAV comprising a nucleic acid comprising an expression construct comprising a transgene comprising (a) a Gcase protein coding sequence comprising the nucleotide sequence of SEQ ID NO: 15; and (b) an inhibitory nucleic acid coding sequence comprising the nucleotide sequence of SEQ ID NO: 20 or SEQ ID NO: 47; wherein the rAAV comprises a capsid protein having an AAV9 serotype.

In some embodiments, the disclosure provides a method for treating a subject having a synucleinopathy or parkinsonism, the method comprising administering to the subject a rAAV comprising a nucleic acid comprising an expression construct comprising a transgene comprising an inhibitory nucleic acid coding sequence comprising the nucleotide sequence of SEQ ID NO: 20 or SEQ ID NO: 47; wherein the rAAV comprises a capsid protein having an AAV9 serotype.

In some embodiments, the disclosure provides a method for treating a subject having multiple system atrophy, Parkinson's disease, Parkinson's disease with GBA1 mutation, Lewy body disease, dementia with Lewy bodies, dementia with Lewy bodies with GBA1 mutation, progressive supranuclear palsy, or corticobasal syndrome, the method comprising administering to the subject a rAAV comprising a nucleic acid comprising an expression construct comprising a transgene comprising an inhibitory nucleic acid coding sequence comprising the nucleotide sequence of SEQ ID NO: 20 or SEQ ID NO: 47; wherein the rAAV comprises a capsid protein having an AAV9 serotype.

A subject is typically a mammal, preferably a human. In some embodiments, a subject is between the ages of 1 month old and 10 years old (e.g., 1 month, 2 months, 3 months, 4, months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 3, years, 4 years, 5 years, 6 years, 7 years, 8 years, 9 years, 10 years, or any age therebetween). In some embodiments, a subject is between 2 years old and 20 years old. In some embodiments, a subject is between 30 years old and 100 years old. In some embodiments, a subject is older than 55 years old.

In some embodiments, a composition is administered directly to the CNS of the subject, for example by direct injection into the brain and/or spinal cord of the subject. Examples of CNS-direct administration modalities include but are not limited to intracerebral injection, intraventricular injection, intracisternal injection, intraparenchymal injection, intrathecal injection, and any combination of the foregoing. In some embodiments, a composition is administered to a subject by intra-cisterna *magna* (ICM) injection. In some embodiments, direct injection into the CNS of a subject results in transgene expression (e.g., expression of the first gene product, second gene product, and if applicable, third gene product) in the midbrain, striatum and/or cerebral cortex of the subject. In some embodiments, direct injection into the CNS results in transgene expression (e.g., expression of the first gene product, second gene product, and if applicable, third gene product) in the spinal cord and/or CSF of the subject.

In some embodiments, direct injection to the CNS of a subject comprises convection enhanced delivery (CED). Convection enhanced delivery is a therapeutic strategy that involves surgical exposure of the brain and placement of a small-diameter catheter directly into a target area of the brain, followed by infusion of a therapeutic agent (e.g., a composition or rAAV as described herein) directly to the brain of the subject. CED is described, for example by Debinski et al. (2009) *Expert Rev Neurother.* 9(10):1519-27.

In some embodiments, a composition is administered peripherally to a subject, for example by peripheral injection. Examples of peripheral injection include subcutaneous injection, intravenous injection, intra-arterial injection, intraperitoneal injection, or any combination of the foregoing. In some embodiments, the peripheral injection is intra-arterial injection, for example injection into the carotid artery of a subject.

In some embodiments, a composition (e.g., a composition comprising an isolated nucleic acid or a vector or a rAAV) as described by the disclosure is administered both peripherally and directly to the CNS of a subject. For example, in some embodiments, a subject is administered a composition by intra-arterial injection (e.g., injection into the carotid artery) and by intraparenchymal injection (e.g., intraparenchymal injection by CED). In some embodiments, the direct injection to the CNS and the peripheral injection are simultaneous (e.g., happen at the same time). In some embodiments, the direct injection occurs prior (e.g., between 1 minute and 1 week, or more before) to the peripheral injection. In some embodiments, the direct injection occurs after (e.g., between 1 minute and 1 week, or more after) the peripheral injection.

In some embodiments, a subject is administered an immunosuppressant prior to (e.g., between 1 month and 1 minute prior to) or at the same time as a composition as described herein. In some embodiments, the immunosuppressant is a corticosteroid (e.g., prednisone, budesonide, etc.), an mTOR inhibitor (e.g., sirolimus, everolimus, etc.), an antibody (e.g., adalimumab, etanercept, natalizumab, etc.), or methotrexate.

The amount of composition (e.g., a composition comprising an isolated nucleic acid or a vector or a rAAV) as described by the disclosure administered to a subject will vary depending on the administration method. For example, in some embodiments, a rAAV as described herein is administered to a subject at a titer between about $10^9$ Genome copies (GC)/kg and about $10^{14}$ GC/kg (e.g., about $10^9$ GC/kg, about $10^{10}$ GC/kg, about $10^{11}$ GC/kg, about $10^{12}$ GC/kg, about $10^{12}$ GC/kg, or about $10^{14}$ GC/kg). In some embodiments, a subject is administered a high titer (e.g., $>10^{12}$ Genome Copies GC/kg of an rAAV) by injection to the CSF space, or by intraparenchymal injection. In some embodiments, a rAAV as described herein is administered to a subject at a dose ranging from about $1\times10^{10}$ vector genomes (vg) to about $1\times10^{17}$ vg by intravenous injection. In some embodiments, a rAAV as described herein is administered to a subject at a dose ranging from about $1\times10^{10}$ vg to about $1\times10^{16}$ vg by injection into the cisterna *magna.*

A composition (e.g., a composition comprising an isolated nucleic acid or a vector or a rAAV) as described by the disclosure can be administered to a subject once or multiple times (e.g., 2, 3, 4, 5, 6, 7, 8, 9, 10, 20, or more) times. In some embodiments, a composition is administered to a subject continuously (e.g., chronically), for example via an infusion pump.

EXAMPLES

Example 1: rAAV Vectors

AAV vectors are generated using cells, such as HEK293 cells for triple-plasmid transfection. The ITR sequences flank an expression construct comprising a promoter/enhancer element for each transgene of interest, a 3' polyA signal, and posttranslational signals such as the WPRE element. Multiple gene products can be expressed simultaneously such as GBA1 and LIMP2 and/or Prosaposin, by fusion of the protein sequences; or using a 2A peptide linker, such as T2A or P2A, which leads 2 peptide fragments with added amino acids due to prevention of the creation of a peptide bond; or using an IRES element; or by expression with 2 separate expression cassettes. The presence of a short intronic sequence that is efficiently spliced, upstream of the expressed gene, can improve expression levels. shRNAs and other regulatory RNAs can potentially be included within these sequences. Examples of plasmids comprising rAAV vectors described by the disclosure are shown in FIGS. 1-6, FIGS. 21-27, and FIGS. 55-58 and in Table 2 below.

Efficacy Measures (α-Synuclein)

In vitro studies were also conducted in HeLa cells, a human cell line, and in primary mouse hippocampal neurons. In HeLa cells treated with $2\times10^6$ vg/cell PR001A, an approximately 2-fold increase in GCase activity levels and a reduction in total α-Synuclein levels compared to excipient-treated control cells was observed (FIG. 34A and FIG. 34B). A similar effect was not observed with a lower dose of PR001A.

TABLE 2

| Name | Promoter 1 | shRNA | CDS1 | PolyA 1 | Bicistronic element | Promoter 2 | CDS2 | PolyA2 | Length between ITRs |
|---|---|---|---|---|---|---|---|---|---|
| CMVe_CBAp_GBA1_WPRE_bGH | CBA | | GBA1 | WPRE-bGH | | | | | 3741 |
| LT1s_JetLong_mRNAiaSYn_SCARB2-T2A-GBA1_bGH | JetLong | aSyn | SCARB2 | bGH | T2A | | GBA1 | | 4215 |
| LI1_JetLong_SCARB2-IRES-GBA1_bGH | JetLong | | SCARB2 | bGH | IRES | | GBA1 | | 4399 |
| FP1_JetLong_GBA1_bGH_JetLong_SCARB2_SV40L | JetLong | | GBA1 | bGH | | JetLong | SCARB2 | SV40L | 4464 |
| PrevailVector_LT2s_JetLong_mRNAiaSYn_PSAP-T2A-GBA1_bGH_4353nt | JetLong | aSyn | PSAP | bGH | T2A | — | GBA1 | — | 4353 |
| PrevailVector_LI2_JetLong_PSAP_IRES_GBA1_SymtheticpolyA_4337nt | JetLong | — | PSAP | Synthetic pA | IRES | — | GBA1 | — | 4337 |

Example 2: Cell Based Assays of Viral Transduction into GBA-Deficient Cells

Cells deficient in GBA1 are obtained, for example as fibroblasts from GD patients, monocytes, or hES cells, or patient-derived induced pluripotent stem cells (iPSCs). These cells accumulate substrates such as glucosylceramide and glucosylsphingosine (GluCer and GluSph). Treatment of wild-type or mutant cultured cell lines with Gcase inhibitors, such as CBE, is also be used to obtain GBA deficient cells.

Using such cell models, lysosomal defects are quantified in terms of accumulation of protein aggregates, such as of α-Synuclein with an antibody for this protein or phospho-αSyn, followed by imaging using fluorescent microscopy. Imaging for lysosomal abnormalities by ICC for protein markers such as LAMP1, LAMP2, LIMP1, LIMP2, or using dyes such as Lysotracker, or by uptake through the endocytic compartment of fluorescent dextran or other markers is also performed. Imaging for autophagy marker accumulation due to defective fusion with the lysosome, such as for LC3, can also be performed. Western blotting and/or ELISA is used to quantify abnormal accumulation of these markers. Also, the accumulation of glycolipid substrates and products of GBA1 is measured using standard approaches.

Therapeutic endpoints (e.g., reduction of PD-associated pathology) are measured in the context of expression of transduction of the AAV vectors, to confirm and quantify activity and function. Gcase can also be quantified using protein ELISA measures, or by standard Gcase activity assays.

Example 2.1: In Vitro Pharmacology Studies with rAAV Encoding Gcase

Transduction and Potency

An in vitro study to evaluate the ability of PR001A (AAV9.CBA.GBA1.A) (schematic of a plasmid encoding the vector provided in FIG. 55), comprising the codon-optimized coding sequence of human GBA1 (SEQ ID NO:15), to express the GBA1 transgene in HEK293T cells demonstrated a dose-dependent increase in GCase activity following PR001A transduction in HEK293T cells (FIG. 33).

Mouse hippocampal neurons transduced with $1.3\times10^5$ vg/cell or $1.3\times10^6$ vg/cell PR001A showed increased GCase activity levels and trended to decreased total α-Synuclein levels (FIG. 35A and FIG. 35B).

In summary, PR001A transduction in cell lines and primary neuron cultures resulted in increased GCase activity. In HeLa cells and mouse hippocampal neurons, PR001A transduction also resulted in decreased α-Synuclein levels, supporting the link between GCase activity and α-Synuclein levels (Mazzulli et al., *Cell.* 2011; 146(1):37-52).

Example 3: In Vivo Assays Using Mutant Mice

This example describes in vivo assays of AAV vectors using mutant mice. In vivo studies of AAV vectors as above in mutant mice are performed using assays described, for example, by Liou et al. (2006) *J. Biol. Chem.* 281(7): 4242-4253, Sun et al. (2005) *J. Lipid Res.* 46:2102-2113, and Farfel-Becker et al. (2011) *Dis. Model Mech.* 4(6):746-752.

The intrathecal or intraventricular delivery of vehicle control and AAV vectors (e.g., at a dose of $2\times10^{11}$ vg/mouse) are performed using concentrated AAV stocks, for example at an injection volume between 5-10 μL. Intraparenchymal delivery by convection enhanced delivery is performed.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 4: Chemical Models of Disease

This example describes in vivo assays of AAV vectors using a chemically-induced mouse model of Gaucher disease (e.g., the CBE mouse model). In vivo studies of these AAV vectors are performed in a chemically-induced mouse model of Gaucher disease, for example as described by Vardi et al. (2016) *J Pathol.* 239(4):496-509.

Intrathecal or intraventricular delivery of vehicle control and AAV vectors (e.g., at a dose of $2\times10^{11}$ vg/mouse) are performed using concentrated AAV stocks, for example with injection volume between 5-10 μL. Intraparenchymal delivery by convection enhanced delivery is performed. Peripheral delivery is achieved by tail vein injection.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 5: Clinical Trials in PD, LBD, Gaucher Disease Patients

In some embodiments, patients having certain forms of Gaucher disease (e.g., GD1) have an increased risk of developing Parkinson's disease (PD) or Lewy body dementia (LBD). This Example describes clinical trials to assess the safety and efficacy of rAAVs as described by the disclosure, in patients having Gaucher disease, PD and/or LBD.

Clinical trials of such vectors for treatment of Gaucher disease, PD and/or LBD are performed using a study design similar to that described in Grabowski et al. (1995) *Ann. Intern. Med.* 122(1):33-39.

Example 6: Treatment of Peripheral Disease

In some embodiments, patients having certain forms of Gaucher disease exhibit symptoms of peripheral neuropathy, for example as described in Biegstraaten et al. (2010) *Brain* 133(10):2909-2919.

This example describes in vivo assays of AAV vectors as described herein for treatment of peripheral neuropathy associated with Gaucher disease (e.g., Type 1 Gaucher disease). Briefly, Type 1 Gaucher disease patients identified as having signs or symptoms of peripheral neuropathy are administered a rAAV as described by the disclosure. In some embodiments, the peripheral neuropathic signs and symptoms of the subject are monitored, for example using methods described in Biegstraaten et al., after administration of the rAAV.

Levels of transduced gene products as described by the disclosure present in patients (e.g., in serum of a patient, in peripheral tissue (e.g., liver tissue, spleen tissue, etc.)) of a patient are assayed, for example by Western blot analysis, enzymatic functional assays, or imaging studies.

Example 7: Treatment of CNS Forms

This example describes in vivo assays of rAAVs as described herein for treatment of CNS forms of Gaucher disease. Briefly, Gaucher disease patients identified as having a CNS form of Gaucher disease (e.g., Type 2 or Type 3 Gaucher disease) are administered a rAAV as described by the disclosure. Levels of transduced gene products as described by the disclosure present in the CNS of patients (e.g., in serum of the CNS of a patient, in cerebrospinal fluid (CSF) of a patient, or in CNS tissue of a patient) are assayed, for example by Western blot analysis, enzymatic functional assays, or imaging studies.

Example 8: Gene Therapy of Parkinson's Disease in Subjects Having Mutations in GBA1

This example describes administration of a recombinant adeno-associated virus (rAAV) encoding GBA1 to a subject having Parkinson's disease characterized by a mutation in GBA1 gene.

The rAAV vector insert contains the CBA promoter element (CBA), consisting of four parts: the CMV enhancer (CMVe), CBA promoter (CBAp), Exon 1, and intron (int) to constitutively express the codon optimized coding sequence (CDS) of human GBA1 (maroon). The 3' region also contains a Woodchuck hepatitis virus Posttranscriptional Regulatory Element (WPRE) followed by a bovine Growth Hormone polyA signal (bGH polyA) tail. The flanking ITRs allow for the correct packaging of the intervening sequences. Two variants of the 5' ITR sequence (FIG. 7, inset box, bottom sequence) were evaluated; these variants have several nucleotide differences within the 20-nucleotide "D" region of the ITR, which is believed to impact the efficiency of packaging and expression. The rAAV product contains the "D" domain nucleotide sequence shown in FIG. 7 (inset box, top sequence). A variant vector, harbors a mutant "D" domain (termed an "S" domain herein, with the nucleotide changes shown by shading), performed similarly in preclinical studies. The backbone contains the gene to confer resistance to kanamycin as well as a stuffer sequence to prevent reverse packaging. A schematic depicting the rAAV vector is shown in FIG. 8. The rAAV vector is packaged into an rAAV using AAV9 serotype capsid proteins.

GBA1-rAAV is administered to a subject as a single dose via a fluoroscopy guided suboccipital injection into the cisterna *magna* (intracisternal *magna*; ICM). One embodiment of a dosing regimen study is as follows:

Example 8.1: In Vivo Pharmacology Studies with rAAV Encoding Gcase

Initial studies were conducted in a chemical mouse model involving daily delivery of conduritol-β-epoxide (CBE), an inhibitor of GCase to assess the efficacy and safety of the PR001A rAAV vector (AAV9.CBA.GBA1.A) (schematic of a plasmid encoding the vector provided in FIG. 55), comprising the codon-optimized coding sequence of human GBA1 (SEQ ID NO:15), and a PR001B rAAV S-variant construct (as described further below). Additionally, initial studies were performed in a genetic mouse model, which carries a homozygous GBA1 mutation and is partially deficient in saposins (4L/PS-NA). Additional dose-ranging studies in mice and nonhuman primates (NHPs) are conducted to further evaluate vector safety and efficacy.

These mouse models exhibit phenotypes characteristic of nGD (neuronopathic Gaucher disease) and PD-GBA (having Parkinson's disease characterized by a mutation in GBA1 gene), including reduced GCase activity, accumulation of the glycolipid substrates of GCase, deficits in motor behavior, and neuropathological changes including astrogliosis and microgliosis, reflecting inflammation. Intracerebroventricular injection of PR001A suppressed all of these disease-associated phenotypes. Additionally, the 4L/PS-NA mouse model displayed accumulation of α-Synuclein, and ICV administration of PR001A in the 4L/PS-NA model reduced the accumulation of α-Synuclein.

Figure 7:
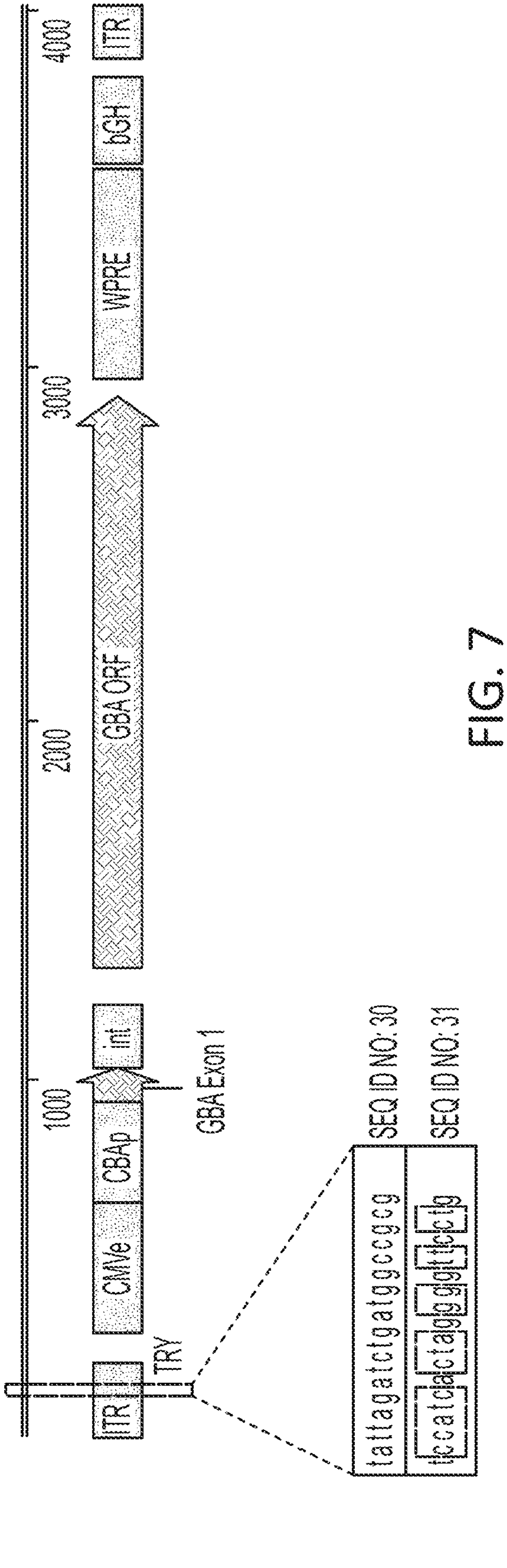
FIG. 7 is a schematic depicting one embodiment of an rAAV vector that includes an expression construct encoding a Gcase (e.g., GBA1 or a portion thereof). In this embodiment, the vector comprises a CBA promoter element (CBA), consisting of four parts: the CMV enhancer (CMVe), CBA promoter (CBAp), Exon 1, and intron (int) to constitutively express the codon optimized coding sequence of human GBA1. The 3' region also contains a WPRE regulatory element followed by a bGH polyA tail. Three transcriptional regulatory activation sites are included at the 5' end of the promoter region: TATA, RBS, and YY1. The flanking ITRs allow for the correct packaging of the intervening sequences. Two variants of the 5' ITR sequence (inset box) were evaluated; these have several nucleotide differences within the 20-nucleotide "D" region of wild-type AAV2 ITR. In some embodiments, an rAAV vector contains the "D" domain nucleotide sequence shown on the top line. In some embodiments, an rAAV vector comprises a mutant "D" domain (e.g., an "S" domain, with the nucleotide changes shown on the bottom line).
Figure 8:
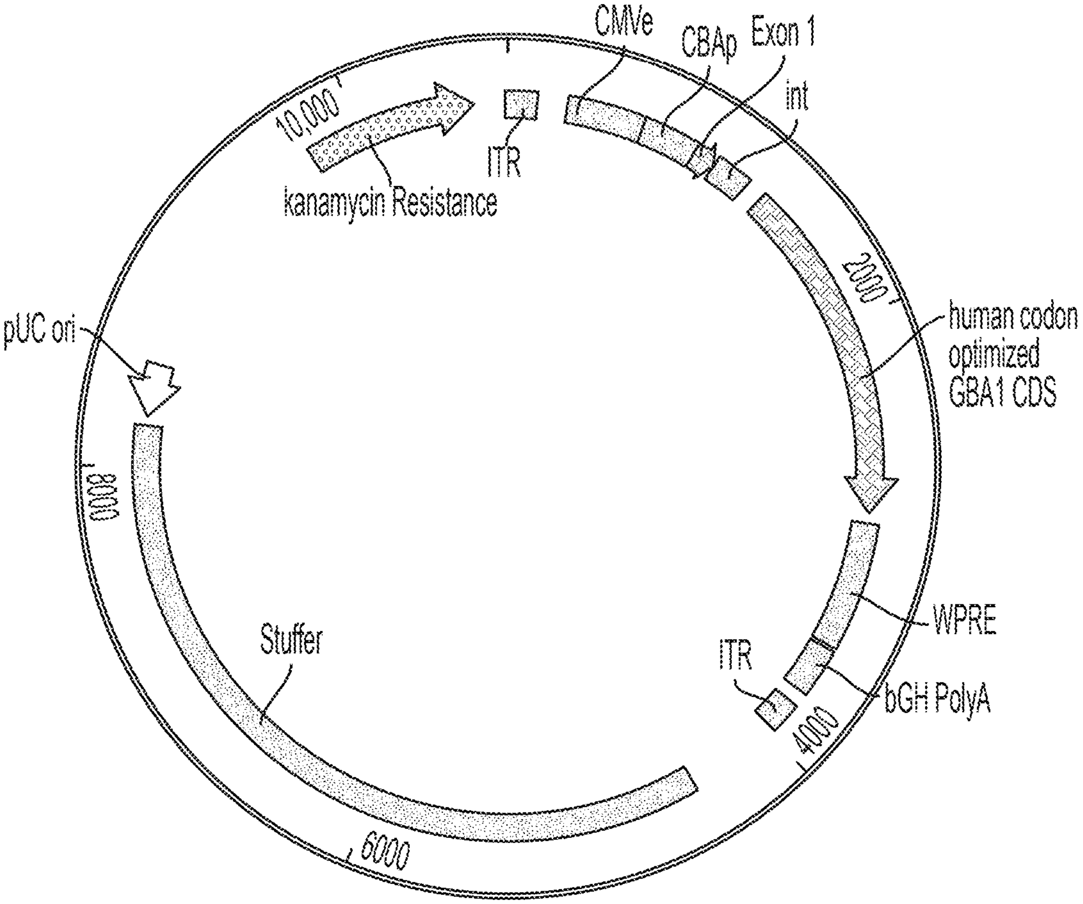
FIG. 8 is a schematic depicting one embodiment of a plasmid encoding the rAAV vector described in FIG. 7.

Two slightly different versions of the 5' inverted terminal repeat (ITR) in the AAV backbone were tested to assess manufacturability and transgene expression (FIG. 7). The 20 bp "D" domain within the 145 bp 5' ITR is thought to be necessary for optimal viral vector production, but mutations within the "D" domain have also been reported to increase transgene expression in some cases. Thus, in addition to the PR001A viral vector, which harbors an intact "D" domain, a second vector form (PR001B) with a mutant D domain (termed an "S" domain herein) was also evaluated. Both PR001A rAAV and variant PR001B rAAV express the same transgene. While both vectors produced virus that was efficacious in vivo as detailed below, the PR001A rAAV, which contains a wild-type "D" domain, was selected for further development.

The nonclinical in vivo pharmacology (efficacy) studies are summarized in Table 14. A total of 10 studies were completed; the 4 principal studies are discussed in detail in subsequent sections.

Example 8.1.1: CBE Mouse Model Studies

Overview of the CBE Model

In the CBE chemical mouse model, a pharmacological inhibition of GCase activity is achieved using a selective and irreversible covalent competitive inhibitor of GCase, leading to glycolipid (GluCer and GluSph) accumulation, neuropathological changes including astrogliosis and microgliosis, and motor behavior deficits (Manning-Bog et al., *Neurotoxicology.* 2009; 30(6):1127-32; Farfel-Becker et al., *Dis Model Mech.* 2011; 4(6):746-52; Rocha et al., *Antioxid Redox Signal.* 2015; 23(6):550-64).

CBE is a pharmacological inhibitor of GCase, and mice treated with CBE display phenotypes consistent with GCase loss-of-function. By varying CBE dosage and, thus, the degree of GCase inhibition in vivo, it is possible to recapitulate the varied degrees of enzyme deficiency seen in different GBA1-associated disorders, thereby modulating the severity of the resulting phenotype. For this reason, the CBE mouse model has significant technical advantages over genetic models of GCase deficiency, making it an attractive model for PD-GBA. The systemic reduction in GCase activity in the CBE model recapitulates the human disease as patients with PD-GBA present with a reduction in GCase activity throughout the CNS and peripheral organs. It is expected that this model will underestimate the effects of PR001A since CBE will inhibit both endogenous GCase activity as well as exogenous GCase activity resulting from PR001A treatment.

Study PRV-2017-001: CBE Dose-Ranging Study

Figure 9A:
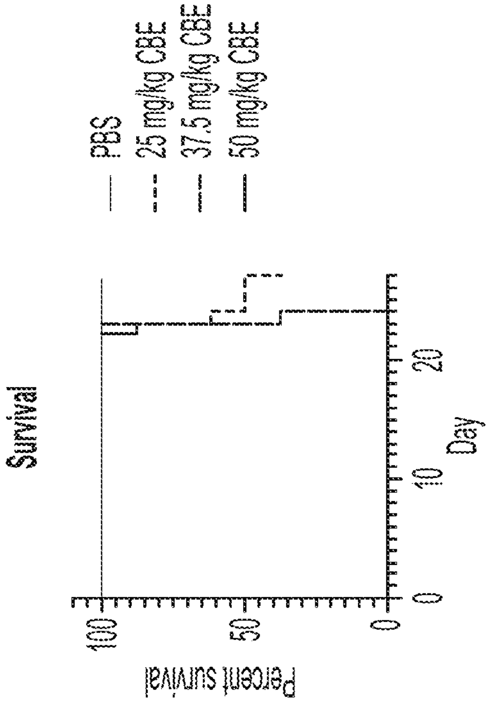
FIG. 9A-FIG. 9F show representative data for CBE mouse model validation. Survival (FIG. 9A) was checked 2 times a day and weight (FIG. 9B) was recorded daily and analyzed at P27 (FIG. 9C). All groups started with n=8. Behavior was assessed by latency to fall on rotarod (FIG. 9D) at P24 and by total distance traveled in Open Field (FIG. 9F). Due to early lethality, the number of animals in each group differs: n=8 for PBS and 25 mg/kg CBE, n=4 for the 37.5 mg/kg CBE. The 50 mg/kg CBE treatment group was not assessed in rotarod due to complete lethality by P24. Statistical results are presented for comparisons against the PBS group using ANOVA followed by Tukey's HSD test. Levels of the GCase substrates were analyzed in the cerebral cortex of mice in the PBS and 25 mg/kg CBE treatment groups. Aggregate GluSph and GalSph levels (FIG. 9E) are shown as pmol per mg wet weight of the tissue. Statistical results are presented using student's t-test. Means are presented. Error bars are standard error of the mean (SEM). $^*P<0.05$; $^{}P<0.01$; $^{*}P<0.001$.
Figure 9B:
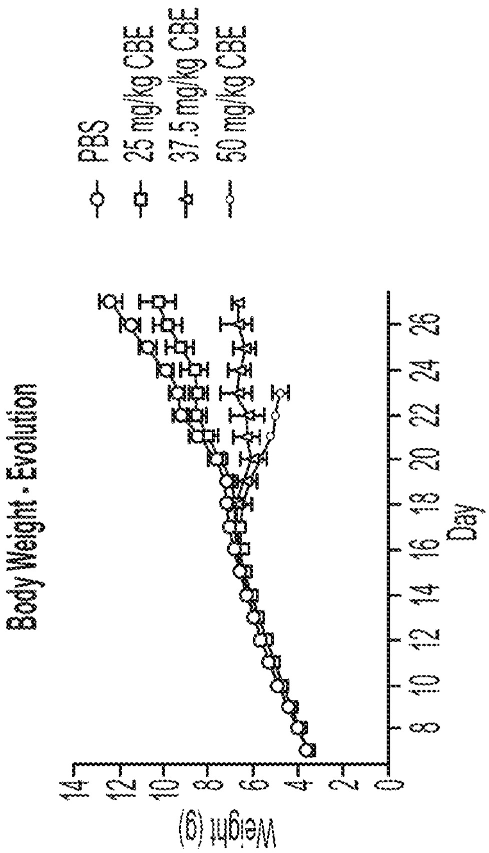
Figure 9C:
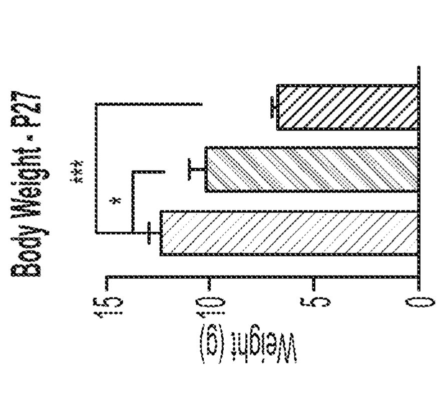
Figure 9D:
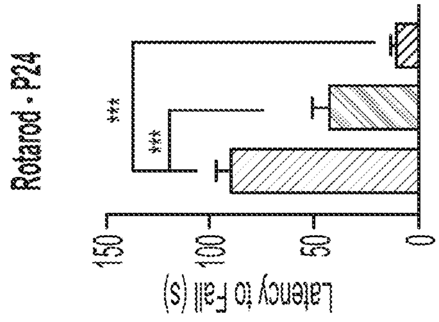
Figure 9E:
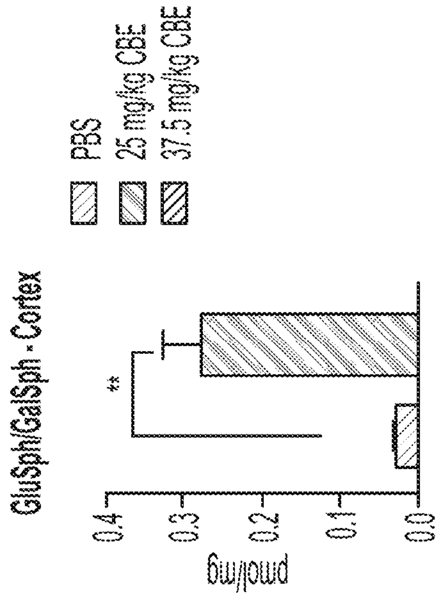
Figure 9F:
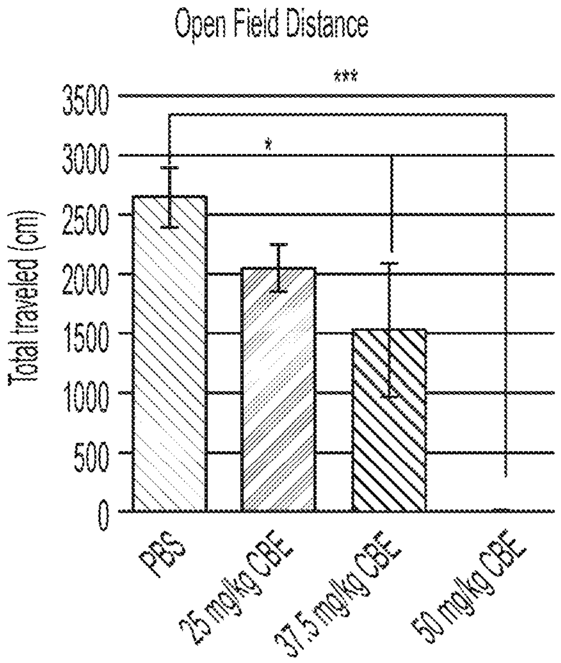

To establish the CBE model of GCase deficiency, juvenile mice were dosed with CBE, a specific inhibitor of GCase. Mice were given CBE by IP injection daily, starting at postnatal day 8 (P8). Three different CBE doses (25 mg/kg, 37.5 mg/kg, 50 mg/kg) or daily intraperitoneal (IP) vehicle (PBS) were tested to establish a model that exhibits a behavioral phenotype (FIG. 9A-FIG. 9F). Higher doses of CBE led to lethality in a dose-dependent manner. All mice treated with 50 mg/kg CBE died by P23, and 5 of the 8 mice treated with 37.5 mg/kg CBE died by P27 (FIG. 9A). There was no lethality in mice treated with 25 mg/kg CBE. Mice treated with CBE showed a failure to gain weight that correlated with CBE dose. At P27, the end of the in-life portion of the study, the weight difference was statistically significant between control animals and those treated with either 25 or 37.5 mg/kg CBE; no mice treated with 50 mg/kg CBE survived to P27 (FIG. 9B, FIG. 9C). Whereas CBE-injected mice showed no general motor deficits in the open field assay (traveling the same distance and at the same velocity as mice given PBS; FIG. 9F), CBE-treated mice exhibited a motor coordination and balance deficit as measured by the rotarod assay (FIG. 9D).

Mice surviving to the end of the study were sacrificed on the day after their last CBE dose (P27, "Day 1") or after three days of CBE withdrawal (P29, "Day 3"). Lipid analysis was performed on the cortex of mice given 25 mg/kg CBE to evaluate the accumulation of GCase substrates in both the Day 1 and Day 3 cohorts. GluSph and GalSph levels (measured in aggregate in this example) were significantly accumulated in the CBE-treated mice compared to PBS-treated controls, consistent with GCase insufficiency (FIG. 9E).

In summary, a dose of 25 mg/kg CBE injected IP daily resulted in motor behavior deficits and accumulation of GCase substrates (aggregate of GluSph and GalSph levels), which is consistent with inhibition of GCase activity. Therefore, the 25 mg/kg dose was selected for subsequent studies since this recapitulated the core features of the human disease while permitting longer studies to evaluate persistence of vector.

Study PRV-2018-002: Efficacy of PR001B in the CBE Model

Figure 10:
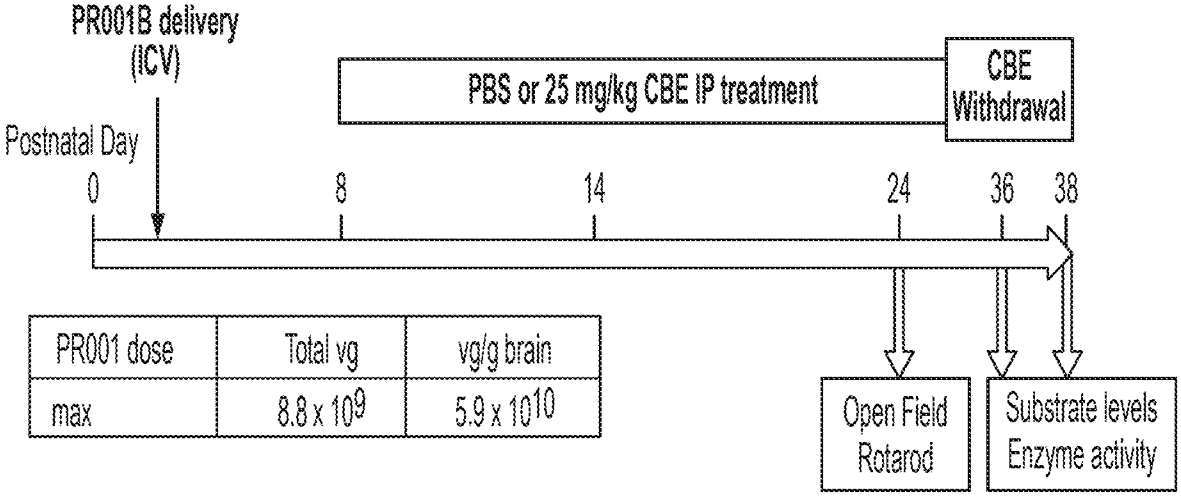
FIG. 10 is a schematic depicting one embodiment of a study design for maximal dose of a rAAV encoding GCase in a CBE mouse model. 4 μL PR001B or dPBS was delivered by ICV injection at P3, and daily 25 mg/kg CBE treatment was initiated at P8. Behavior was assessed in the rotarod assay at P24. Half of the animals were sacrificed at P36, 1 day after their final CBE dose at P35, while the remaining half were sacrificed at P38, 3 days after their final CBE dose at P35. "vg" refers to vector genomes.

Based on the study described above, the 25 mg/kg CBE dose was selected since it produced behavioral deficits without impacting survival. For all nonclinical mouse studies, intracerebroventricular (ICV) injection was chosen as the route of administration (ROA). As intra-cisterna *magna* (ICM) injection (the intended clinical ROA) is technically difficult in mice, ICV injection was deemed the most suitable alternative approach to recapitulate the ICM delivery of the therapeutic agent into the cerebrospinal fluid (CSF). To achieve widespread GBA1 distribution throughout the brain and transgene expression during CBE treatment, 4 vehicle (dPBS+0.001% Pluronic F68, "dPBS") or $8.8\times10^{9}$ vg ($5.9\times10^{10}$ vg/g brain, based on a brain weight of 150 mg) PR001B was delivered via ICV injection at P3 and daily IP injection of PBS or 25 mg/kg CBE treatment was initiated at P8 (FIG. 10). To determine if CBE treatment would completely mask the effect of PR001B, half the animals were sacrificed on P36, 1 day after their final CBE injection, while the other half underwent CBE withdrawal and were sacrificed on P38, 3 days after their final CBE injection. For all measures, the groups were combined for analysis correcting for day of collection as a covariate.

Figure 11B:
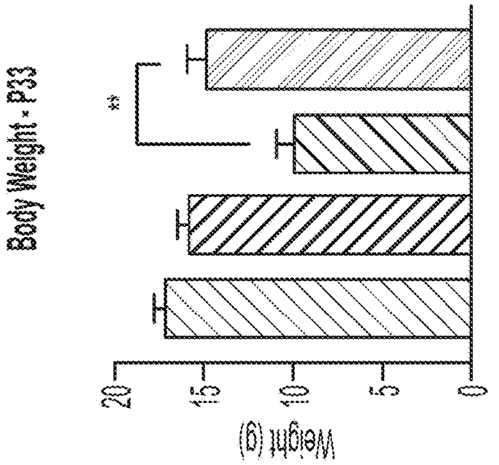
FIG. 11A-FIG. 11D show representative data for in-life assessment of maximal PR001B rAAV dose in a CBE mouse model. At P3, mice were treated with either excipient or 8.8e9 vg rAAV via ICV delivery. Daily IP delivery of either PBS or 25 mg/kg CBE was initiated at P8. At the end of the study, half the mice were sacrificed one day after their last CBE dose at P36 (Day 1) while the remaining half went through 3 days of CBE withdrawal before sacrifice at P38 (Day3). All treatment groups (excipient+PBS n=8, rAAV+PBS n=7, excipient+CBE n=8, and rAAV+CBE n=9) were weighed daily (FIG. 11A), and the weight at P33 was analyzed (FIG. 11B). Behavior was assessed by total distance traveled in Open Field at P23 (FIG. 11D) and latency to fall on Rotarod at P24 (FIG. 11C), evaluated for each animal as the median across 3 trials. Due to lethality, n=7 for the excipient+CBE group for the behavioral assays, while n=8 for all other groups. Means across animals are presented. Error bars are SEM. $^*p<0.05$; $^{***}p<0.001$, nominal p-values for treatment groups by linear regression in the CBE-treated animals.
Figure 11D:
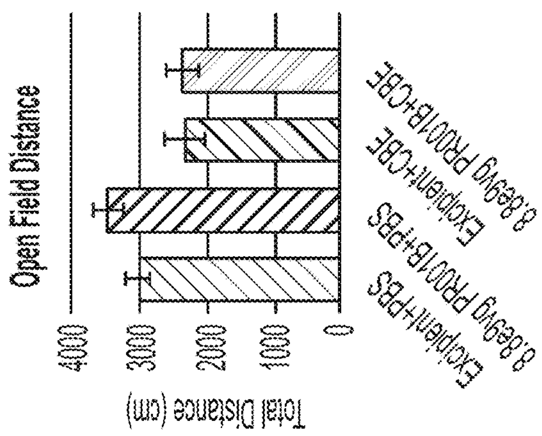
Figure 11A:
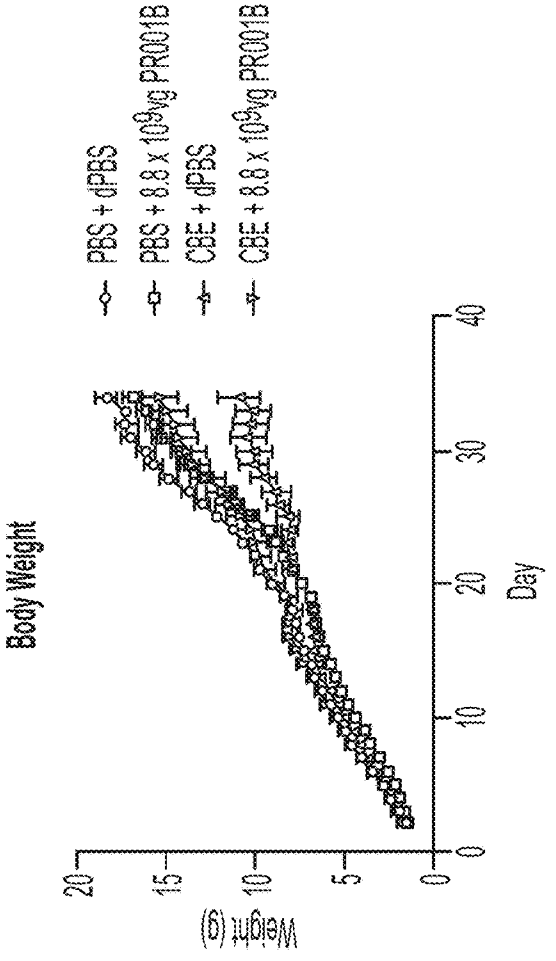
Figure 11C:
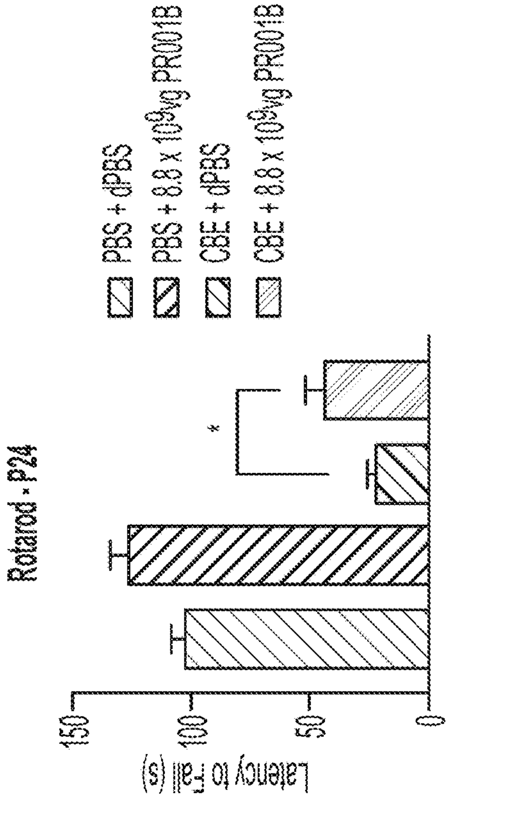

The CBE-treated mice showed decreased body weight evolution that was attenuated with PR001B treatment (FIG. 11A; FIG. 11B). CBE-treated mice that received rAAV performed statistically significantly better on the rotarod than those that received excipient (FIG. 11C). Mice in the variant vector treatment group did not differ from excipient treated mice in terms of total distance traveled during testing (FIG. 11D).

Figure 12A:
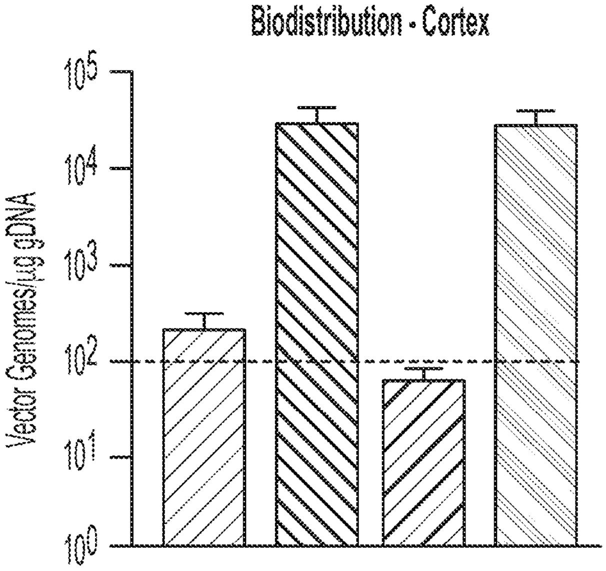
FIG. 12A-FIG. 12B show representative data for biochemical assessment of maximal PR001B rAAV dose in a CBE mouse model. The cerebral cortex of all treatment groups was used to measure vector genomes (FIG. 12A) and GCase activity (FIG. 12B). Biodistribution is shown as vector genomes per 1 μg of genomic DNA (gDNA). Dashed line (at 100 vector genomes/μg gDNA) represents the detection threshold for positive vector presence. Enzymatic activity was evaluated by measuring the rate of glucose production by GCase using Amplex Red (Invitrogen; #A22189), then converted to an effective GCase activity level using a recombinant GCase reference standard curve. One unit was defined as the activity of 1 ng/mL of recombinant purified GCase normalized to mg of total protein. n=6-9 per group. Means are presented. Error bars are SEM. $^*P<0.05$; nominal P values for treatment groups in the CBE-treated animals, with collection days and gender corrected for as covariates.
Figure 12B:
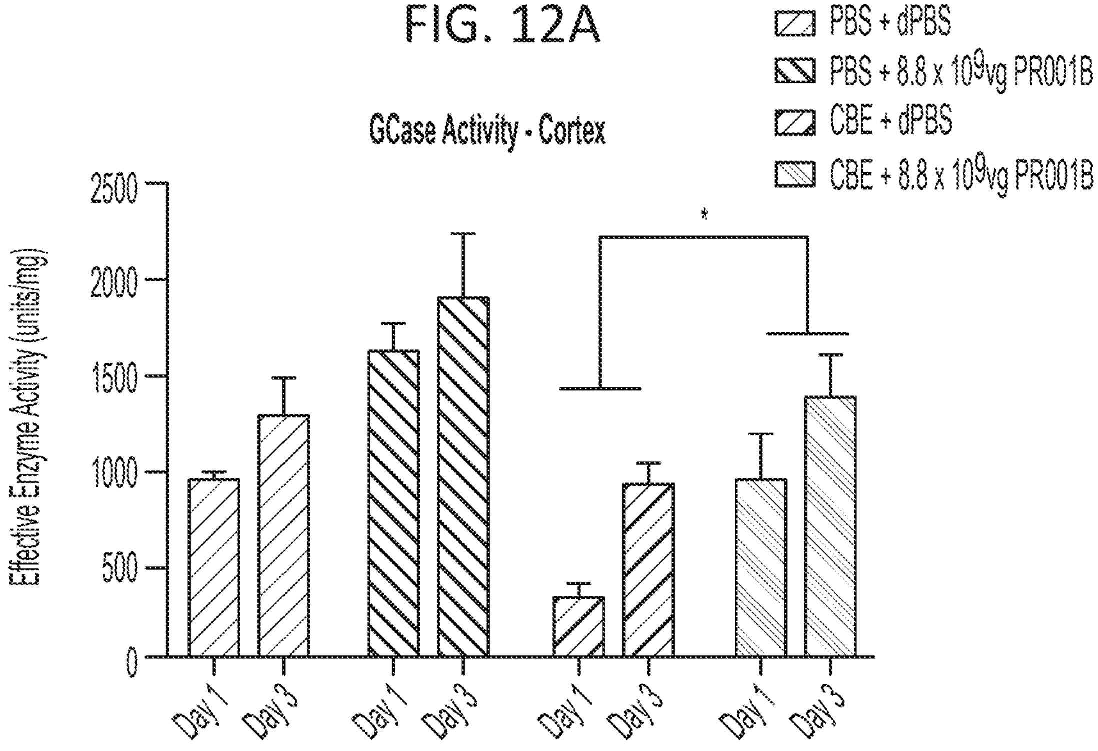
Figure 12C:
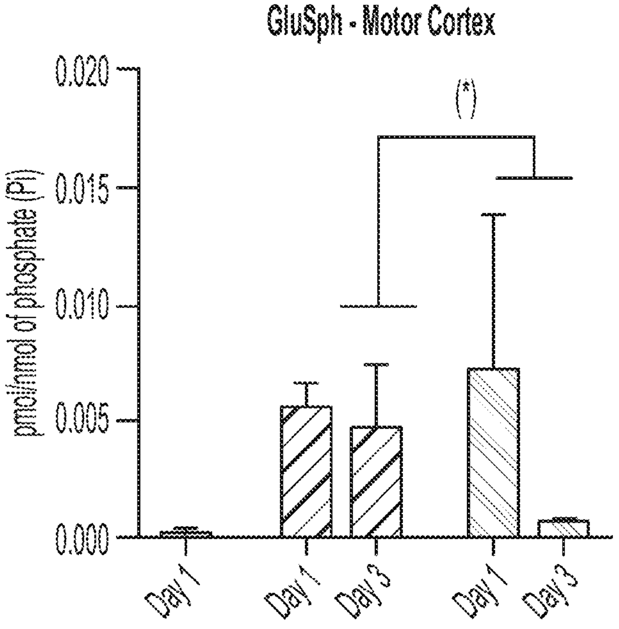
FIG. 12C-FIG. 12D show representative data for glycolipid analysis of maximal PR001B rAAV dose in a CBE mouse model. The cerebral cortex of all treatment groups (PBS+dPBS [left bars in each graph] n=4, CBE+dPBS [center bars in each graph] n=6, and CBE+PR001B [right bars in each graph] n=9) was used to measure GluSph levels (FIG. 12C) and GluCer levels (FIG. 12D) in the groups before (Day 1) or after (Day 3) CBE withdrawal. GluSph and GluCer levels are shown as pmol per nmol of phosphate. Means are presented. Error bars are SEM. $^*P<0.1$; $^{}P<0.01$; $^{*}P<0.001$, nominal P values for treatment groups in the CBE-treated animals from multiple linear regression, with collection days and gender corrected for as covariates.
Figure 12D:
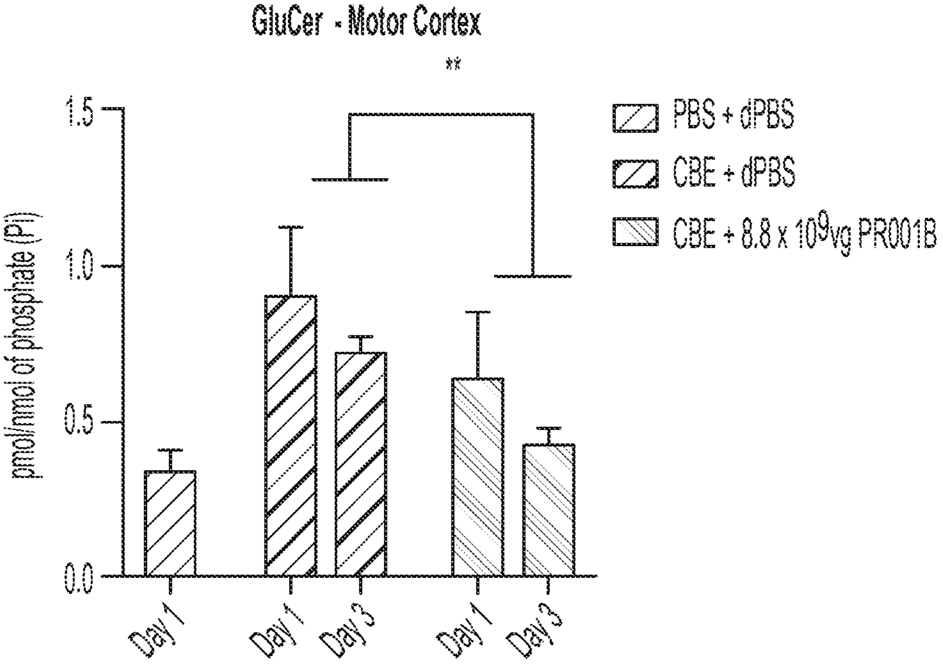

At the completion of the in-life study, half of the mice were sacrificed the day after the last CBE dose (P36, "Day 1") or after three days of CBE withdrawal (P38, "Day 3") for biochemical analysis (FIG. 12B-FIG. 12D). Using a fluorometric enzyme assay performed in biological triplicate, GCase activity was assessed in the cortex. GCase activity was increased in mice that were treated with PR001B rAAV, while CBE treatment reduced GCase activity (FIG. 12B). Additionally, mice that received both CBE and PR001B rAAV had GCase activity levels that were similar to the PBS-treated group, indicating that delivery of rAAV is able to overcome the inhibition of GCase activity induced by CBE treatment. Lipid analysis was performed on the motor cortex of the mice to examine levels of the substrates GluCer and GluSph. Both lipids accumulated in the brains of mice given CBE, and rAAV treatment significantly reduced GluCer accumulation and tended to reduce GluSph accumulation (FIG. 12C; FIG. 12D).

Figure 13:
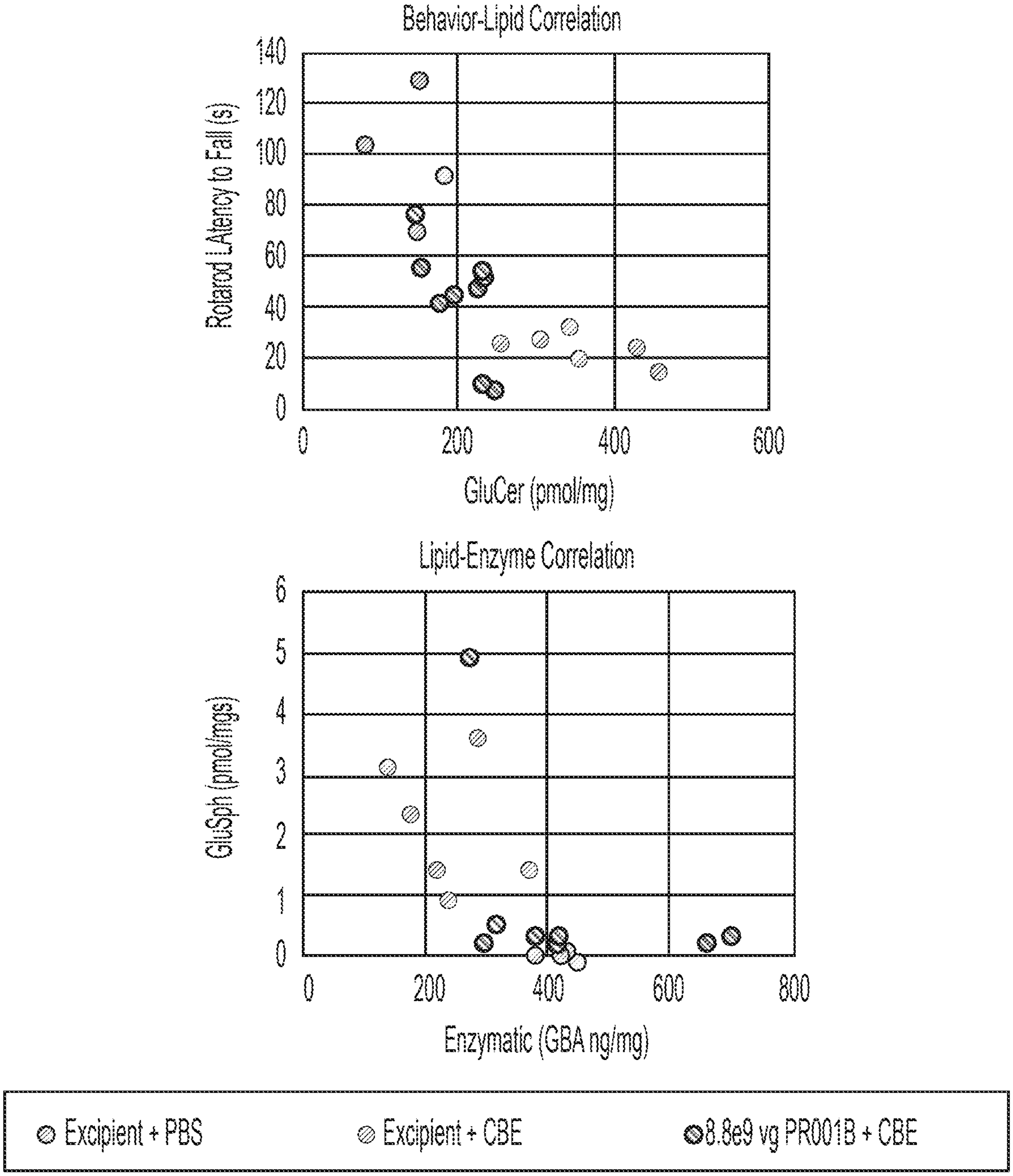
FIG. 13 shows representative data for behavioral and biochemical correlations in a CBE mouse model after administration of excipient+PBS, excipient+CBE, and PR001B rAAV+CBE treatment groups. Across treatment groups, performance on Rotarod was negatively correlated with GluCer accumulation (A, p=0.0012 by linear regression), and GluSph accumulation was negatively correlated with increased GCase activity (B, p=0.0086 by linear regression).

Lipid levels were negatively correlated with both GCase activity and performance on the Rotarod across treatment groups. The increased GCase activity after rAAV administration was associated with substrate reduction and enhanced motor function (FIG. 13).

Figure 14:
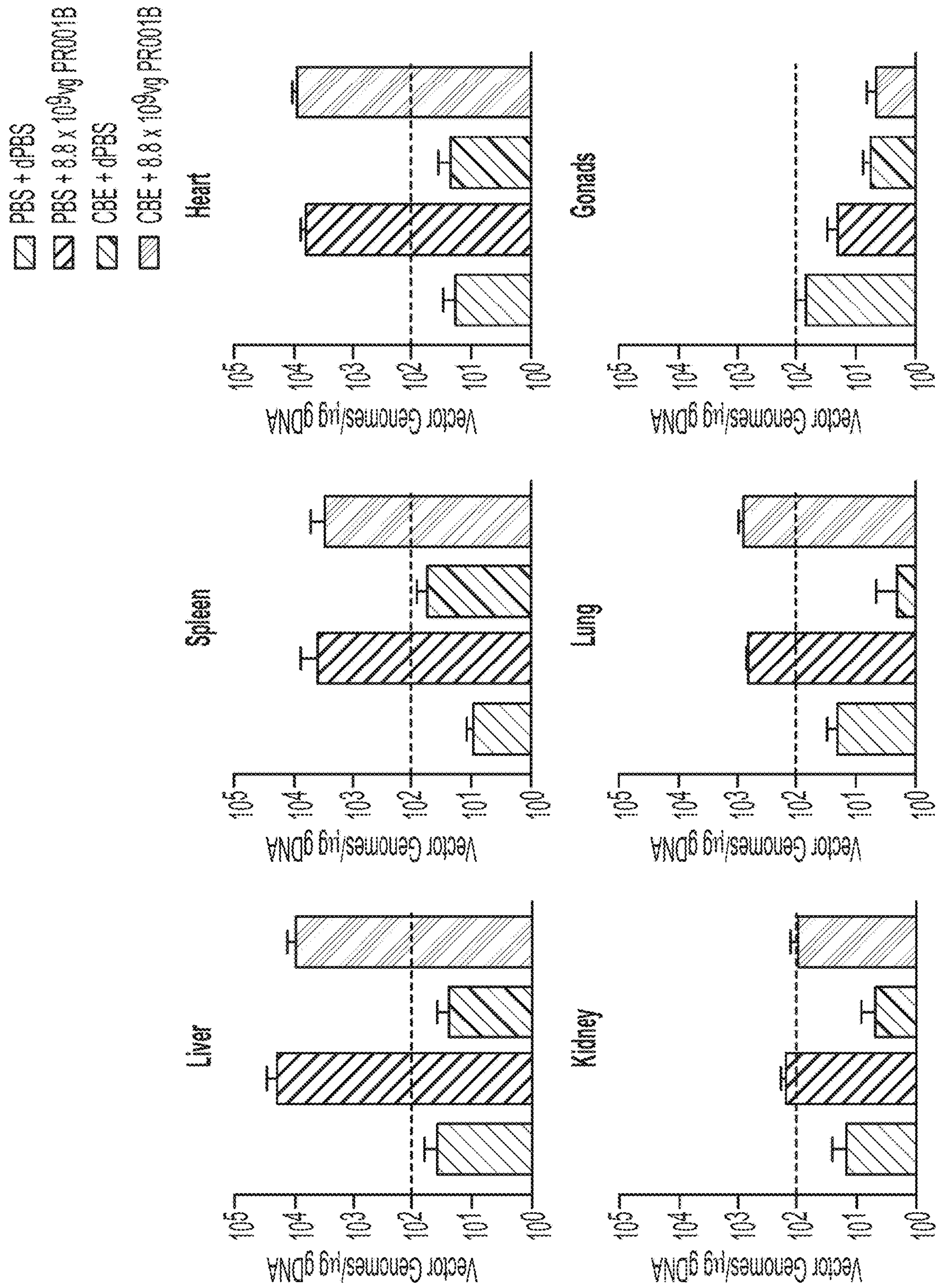
FIG. 14 shows representative data for biodistribution of PROM rAAV in a CBE mouse model. Vector genome presence was quantified by quantitative PCR using a vector reference standard curve; genomic DNA concentration was evaluated by A260 optical density measurement. Dashed line (at 100 vector genomes/14 gDNA) represents the detection threshold for positive vector presence. Means are presented. Error bars are SEM. n=7-9, per group.

As shown in FIG. 14, preliminary biodistribution was assessed by vector genome presence, as measured by qPCR (with >100 vector genomes per 1 μg genomic DNA defined as positive). Mice that received PR001B rAAV, both with and without CBE, were positive for rAAV vector genomes in the cortex (FIG. 12A), indicating that ICV delivery results in rAAV delivery to the cortex. Additionally, vector genomes were detected in the liver, spleen, heart, and lung, with lower levels in the kidney, and none in the gonads (FIG. 14). For all measures, there was no statistically significant difference between the Day 1 and Day 3 groups (data not shown).

In summary, at a dose of $8.8\times10^{9}$ vg ($5.9\times10^{10}$ vg/g brain) injected ICV, PR001B was distributed in the brain and peripheral tissues, and enzymatically active GCase was expressed in the brain. PR001B improved the biochemical (i.e., glycolipid levels) deficits and performance on rotarod. Because CBE withdrawal was not necessary in order to see the effects of PR001B, mice were sacrificed 1 day following the last CBE dose in all future studies.

Study PRV-2018-005: Dose-Ranging PR001A in CBE Model

Figure 15A:
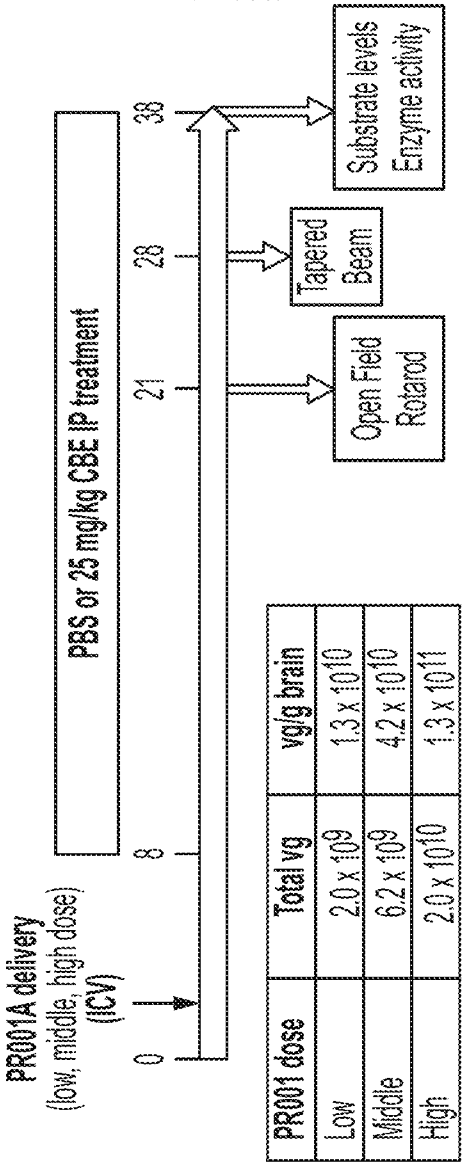
FIG. 15A is a schematic depicting one embodiment of a study design for dose-ranging of a rAAV encoding GCase in a CBE mouse model. PR001A was delivered by ICV injection at P3, and daily 25 mg/kg CBE treatment was initiated at P8. Behavior was assessed in the open field and rotarod assays at P21-P22, and by tapered beam at P28. Animals were sacrificed at P38-P40, 1 day after their final CBE dose. The cortices were analyzed for GluSph and GluCer substrate levels and GCase activity. There were 10 mice (5 males, 5 females) in each treatment group.
Figure 15B:
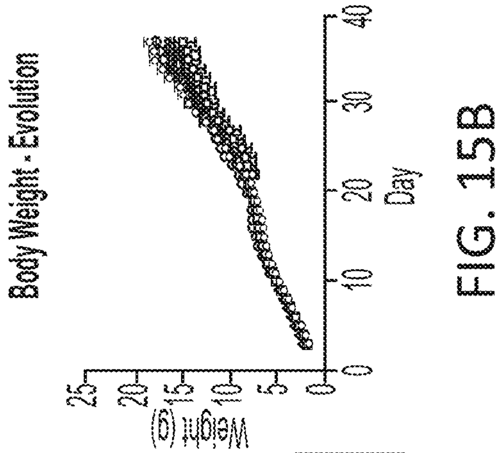
FIG. 15B-FIG. 15E show representative data for in-life assessment of PR001 rAAV dose-ranging in a CBE mouse model. Mice received excipient or 1 of 3 different doses of PR001A by ICV delivery in 4 μL at P3: low dose (middle bar), medium dose (bar second from right), or high dose (right-most bar). At P8, daily IP treatment of 25 mg/kg CBE was initiated. Mice that received excipient and CBE (bar second from left) or excipient and PBS (left-most bar) served as controls. All treatment groups started with n=10
Figure 15C:
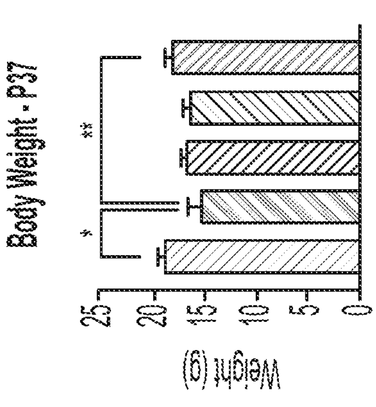
Figure 15D:
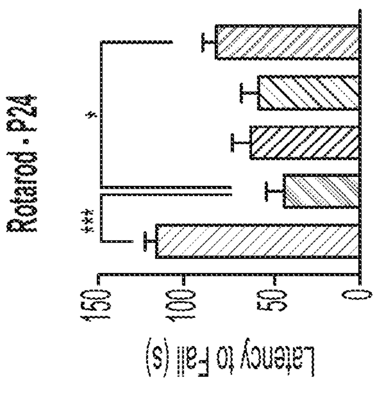
Figure 15E:
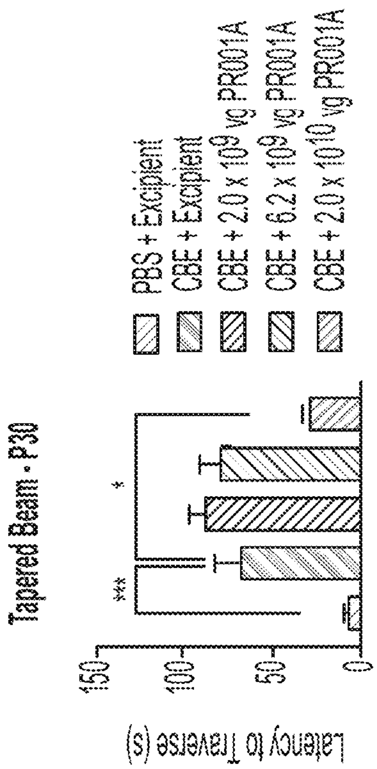

A schematic showing an illustrative dose-ranging study design is provided in FIG. 15A.

A larger study in the CBE model further explored efficacious doses of PR001 rAAV in the CBE model. Using the 25 mg/kg CBE dose model, excipient or PR001 rAAV was delivered via ICV at P3, and daily IP PBS or CBE treatment initiated at P8. Given the similarity between the groups with and without CBE withdrawal observed in the previous studies, all mice were sacrificed one day after the final CBE dose (P38-40). The effect of three different rAAV doses was assessed, resulting in the following five groups, with 10 mice (5M/5F) per group:

Excipient ICV+PBS IP

Excipient ICV+25 mg/kg CBE IP 2.0e9 vg (1.3e10 vg/g brain) rAAV ICV+25 mg/kg CBE IP 6.2e10 vg (4.2e10 vg/g brain) rAAV ICV+25 mg/kg CBE IP 2.0e10 vg (1.3e11 vg/g brain) rAAV ICV+25 mg/kg CBE IP.

The CBE-treated animals gained weight at a lower rate than control animals, a typical observation in this animal model. At the highest dose, PR001A corrected the CBE treatment-related failure to gain weight. Additionally, this dose resulted in a statistically significant improvement on the rotarod and tapered beam tasks, compared to the CBE-treated group that did not receive PR001A (FIG. 15B-FIG. 15E). Brain GCase activity was positively correlated with performance on the rotarod. Lethality was observed in several groups, including both excipient-treated and rAAV-treated group.

At the completion of the in-life study, mice were sacrificed for biodistribution and biochemical analysis (FIG. 16A-FIG. 16D). Of the tissues examined, brain, spinal cord, liver, spleen, heart, kidney, and lungs were positive for vector genomes at the middle and highest doses. The brain, spinal cord, lung, and heart were also positive at the low dose (FIG. 16A). Gonads were not positive at any dose. Effective GCase activity, evaluated by measuring enzymatic activity in all tissues using a fluorometric assay, was reduced by up to 60% following treatment with CBE (FIG. 16B). At the highest dose of PR001A, GCase activity was significantly increased in the brain, spinal cord, and heart. Note that because CBE treatment inhibits the activity of PR001A-encoded GCase to the same extent as endogenous GCase by approximately 50%, CBE model studies likely underestimate the potency of PR001A as measured by GCase activity by approximately 2-fold. The CBE-treated mice exhibited accumulation of GluCer and GluSph in the brain cortex. The high dose of PR001A reduced their accumulation (FIG. 16C; FIG. 16D).

Reactive astrogliosis and microglial activation are prominent inflammatory aspects of the CNS pathology described in neuronopathic GD and PD-GBA patients (Wong et al 2004; Ginns et al 2014). In this study, CBE-treated mice displayed glial scarring, a manifestation of reactive astrogliosis, in the cerebral cortex, consistent with prior studies showing CNS activation in the context of CBE (Sun et al 2011). PR001A treatment led to a statistically significant, dose-dependent reduction of the glial scarring phenotype (FIG. 16E). Thus, PR001 treatment suppresses the neuropathology associated with GCase deficiency in the CNS. A full description of the histopathological findings from this study are discussed in the toxicology section.

Immunohistochemistry was performed for GCase and ionizing calcium-binding adaptor molecule 1 (Iba1; a marker of microgliosis) expression in the cortex (FIG. 16F) (Wong et al 2004; Vitner et al 2016). The expression of GCase was significantly increased in all mice treated with PR001A compared to CBE+excipient-treated animals and correlated with the dose delivered. Iba1 staining was significantly reduced in a dose-dependent manner in mice treated with PR001A compared with mice receiving CBE+excipient, in which Iba1 staining was significantly increased compared with mice receiving PBS.

In summary, the results of Study PRV-2018-005 show that ICV administration of PR001A at 3 dose levels led to broad vector genome biodistribution, increase in GCase activity, improvement on motor behavioral endpoints, and reduction in glycolipid accumulation. Two different measures of neuroinflammation (microgliosis and astrogliosis) showed a dose dependent, statistically significant decrease in mice treated with PR001A. The CBE model inherently underestimates the potency of PR001A since CBE also inhibits enzyme activity due to PR001A treatment. Taken together, these results indicate that ICV administration of PR001A at $2.0\times10^{10}$ vg ($1.3\times10^{11}$ vg/g brain) was effective in the CBE mouse model. A trend towards efficacy was observed at lower doses of PR001A in a subset of endpoints.

Study PRV-2018-007: Long-Term PR001A Effects in CBE Model

This study assessed the persistence of PR001A vector copy number biodistribution and the durability of PR001A-mediated expression of GCase in the CBE mouse model. A single dose of excipient or PR001A was delivered via ICV at P3, and daily IP PBS or CBE treatment was initiated at P8 and continued until P183 through P185 (FIG. 36). All mice were sacrificed 1 day after the final CBE dose. No lethality was observed in any group.

A single ICV dose of PR001A in CBE-treated mice led to the presence of vector genome copies 6 months after dosing (FIG. 37A) at levels comparable to levels seen at approximately 1 month after ICV dosing (see Study PRV-2018-005). Chronic CBE treatment resulted in reduced GCase activity levels; GCase activity was nearly normalized in the mice receiving PR001A, indicating that a single dose of PR001A leads to a durable expression of GCase (FIG. 37B). Six month CBE-treated mice showed a pronounced accumulation of the glycolipid substrates GluCer and GluSph in the cerebral cortex, compared to those receiving 1 month of CBE treatment. A single administration of PR001A at P3 resulted in a significant reduction of GluCer and GluSph levels to near wildtype levels (FIG. 37C; FIG. 37D).

Study PRV-2018-008: Additional Dose-Ranging PR001A in CBE Model

This study was intended to evaluate additional doses of PR001A to determine the minimum effective dose and examine higher doses for tolerability. However, due to an unexpected dosing deviation, this study replicated the doses from PRV-2018-005. Following a similar design as PRV-2018-005 (FIG. 15A), 4 μL excipient or PR001A was delivered via ICV at P3, and daily IP PBS or CBE treatment was initiated at P8 and continued until P51 through P53.

Unlike previous studies, CBE treatment did not lead to a significant change in body weight. Although CBE treatment resulted in significantly poorer performance on the rotarod and tapered beam, treatment with PR001A did not significantly alter this performance (FIG. 38A-FIG. 38E).

Of the tissues examined, brain, spinal cord, liver, heart, and lungs were positive for PROW A at all dose levels. The kidney was also positive at the middle and highest doses, while the spleen was only positive at the highest dose. Gonads were also examined but were not positive at any dose level (FIG. 39). GCase activity was assessed only in select organs. In the cerebral cortex, the low and middle dose of PR001A restored GCase activity levels to the equivalent of PBS+excipient levels or greater, although this did not reach statistical significance. The high dose of PR001A trended toward a significant increase in GCase activity compared to levels in CBE+excipient-treated animals (FIG. 40).

Consistent with the other studies in this model, CBE-treated mice exhibited accumulation of GluSph and GluCer in the brain, which was reduced by administering PR001A (FIG. 41; FIG. 41B). In a dose-dependent manner, all doses of PR001A significantly decreased GluSph levels while the middle and high dose significantly decreased GluCer levels.

This study confirmed the findings from PRV-2018-005, showing that PR001A treatment results in broad biodistribution and a robust elevation of GCase activity that significantly reduces the glycolipid substrate accumulation caused by CBE treatment. This study did not replicate the behavioral phenotypes observed in PRV-2018-005; however, these phenotypes are known to be variable and less reliable in mice.

PRV-2018-025: Further Dose-Ranging PR001A in CBE Model

Given the study deviation in PRV-2018-008, an additional study was performed in the CBE model to expand on previous dose-ranging studies. The ICV dosing of PR001A and IP injection of PBS or CBE followed the same protocol as PRV-2018-005. However, this study included a lower PR001A dose to examine the minimum effective dose and a higher dose to examine tolerability.

In this study, CBE treatment did not lead to a failure to gain weight over time; however, a statistically significant decrease in motor performance was observed in CBE+ excipient animals in both the rotarod and tapered beam. Treatment with PR001A at $5.2\times10^{10}$ vg significantly improved motor performance to nearly the same level as PBS+excipient animals. An improvement was also observed in animals treated with $1.7\times10^{10}$ vg PR001A, though this did not reach significance (FIG. 42A-FIG. 42D).

The cerebral cortex of animals treated with PR001A was positive for vector genomes at all doses, and treatment with $5.2\times10^{10}$ vg PR001A led to a significant increase in GCase activity. Treatment with $1.7\times10^{10}$ vg PROM restored activity to near wildtype levels (FIG. 43A-FIG. 43B), although this did not reach statistical significance.

Consistent with the other studies in this model, CBE-treated mice exhibited an accumulation of GluSph and GluCer in the brain, which was significantly reduced by administering PR001A at either $1.7\times10^{10}$ vg or $5.2\times10^{10}$ vg (FIG. 44A-FIG. 44B).

This study confirmed and expanded on the findings from the previous studies in the CBE model. Although this study did not completely replicate the behavioral phenotypes observed in PRV-2018-005, nonsignificant improvements were seen in both rotarod and tapered beam with $1.7\times10^{10}$ vg PR001A, and treatment with $5.2\times10^{10}$ vg PR001A significantly improved performance in both tasks. Additionally, treatment at either dose decreased glycolipid substrate accumulation, confirming the results from the other CBE studies.

Summary of CBE Model Studies

Results from CBE model studies show that PR001A can be effectively delivered to the CNS and also peripheral tissues by ICV injection. Within the CNS, ICV delivery of PR001A resulted in a consistent increase in GCase activity, a reduction of the glycolipid substrates GluCer and GluSph, a reduction of glial scarring, and improvement in some motor deficits. These effects, where assessed, persisted at 6 months post treatment.

Example 8.1.2: 4L/PS-NA Genetic Mouse Model Studies

Overview of the 4L/PS-NA model

4L/PS-NA mice are an established genetic model of GD and PD-GBA (Sun et al., *J Lipid Res.* 2005; 46(10):2102-13; Mazzulli et al., *Cell.* 2011; 146(1):37-52; Xu et al., *Mol Genet Metab.* 2011; 102(4):436-47). These mice are homozygous for the V394L mutation in GBA1 and additionally harbor mutations in PSAP, which encodes saposin C, an activator of GCase; the presence of a mutant GCase enzyme and the low levels of the GCase activator saposin C together lead to a severe reduction in GCase activity, accumulation of glycolipid substrates, as well as motor behavior deficits. These mice exhibit motor strength, coordination, and balance deficits, as evidenced by their performance in the beam walk, rotarod, and wire hang assays. Typically the lifespan of these mice is less than 22 weeks. The "control" mice in this study are homozygous for the V394L mutation in Gba1, but wild-type for the endogenous prosaposin gene, and thus harbor a more modest reduction in GCase activity. Note that because treatment with PR001A does not have an effect on saposin C, results obtained in the 4L/PS-NA mice likely underestimate the predicted effect in humans. Two studies were conducted with PR001A in these mice.

Study PRV-2018-006: PR001A in 4L/PS-NA Genetic Model

In Study PRV-2018-006, PR001A or excipient was delivered ICV to 3 to 4 week old 4L/PS-NA mice, and animals were sacrificed 15 weeks post-PR001A administration. A dose of 3 μL, of undiluted vector ($1.5\times10^{10}$ vg total; $3.7\times10^{10}$ vg/g brain) was administered (FIG. 45).

Progressive motor deficits were observed in the 4L/PS-NA mice, and treatment with PROW A resulted in a non-significant improvement on beam walk 5 and 9 weeks after treatment. At 15 weeks post treatment, there was no statistically significant difference among the groups. Biodistribution of PR001A vector genomes in the 4L/PS-NA mice was quantified approximately weeks after dosing. All tissues examined, including cerebral cortex, spinal cord, liver, kidney, heart, lung, spleen, and gonads, were positive for vector genomes. (FIG. 46). Analysis of GCase activity in tissue lysates, evaluated using a fluorometric assay, revealed significant increases in effective GCase activity in the cortex and liver (FIG. 47).

There was a statistically significant accumulation of GluSph and GluCer in the brain lysates from 4L/PS-NA mice relative to lysates from control animals. In the 4L/PS-NA mice, treatment with PR001A led to a statistically significant reduction in GluSph accumulation and a trend (P=0.16) towards a reduction in GluCer (FIG. 48A; FIG. 48B).

Prior studies have demonstrated increased accumulation of α-Synuclein protein in the cortex of the 4L/PS-NA mouse model, consistent with the proposed role of GCase in α-Synuclein pathology (Sun et al., *J Lipid Res.* 2005; 46(10):2102-13; Mazzulli et al., *Cell.* 2011; 146(1):37-52; Xu et al., *Mol Genet Metab.* 2011; 102(4):436-47). Cerebral cortical levels of soluble and insoluble α-Synuclein were examined biochemically. In 4L/PS-NA mice treated with excipient, there was a nonsignificant increase in insoluble α-Synuclein and the ratio of insoluble to soluble α-Synuclein in the cerebral cortex; treatment with ICV PR001A reversed these effects (P=0.19, P=0.87, respectively) (FIG. 49A; FIG. 49B). These data are consistent with in vitro studies described in Example 2.1 that demonstrate reduced accumulation of α-Synuclein.

Motor performance by the beam walk test was assessed 4 weeks post-rAAV delivery. The group of mutant mice that received PR001A rAAV showed a trend towards fewer total slips and fewer slips per speed when compared to mutant mice treated with excipient, restoring motor function to near wild-type levels (FIG. 17).

Study PRV-2018-011: Dose-Ranging PR001A in 4L/PS-NA Genetic Model

The second study with 4L/PS-NA mice explored a range of PR001A doses using a design similar to the one used in Study PRV-2018-006 (FIG. 50).

On the beam walk test, 4L/PS-NA mice performed significantly worse than control mice. 4L/PS-NA mice treated with $2.9\times10^{11}$ vg, $9.3\times10^{10}$ vg, or $2.9\times10^{10}$ vg PR001A showed significant improvement when compared to 4L/PS-NA mice treated with excipient at Week 18 (FIG. 51). There was no effect of PR001A at the earlier timepoints. There was no difference in rotarod test results between 4L/PS-NA mice and control mice, and PR001A treatment did not appear to have an effect on this outcome.

All PR001A treatment groups were positive for vector genomes in the cortex. Effective GCase activity, evaluated using a fluorometric assay, was measured in the cortex and was found to be significantly increased in mice treated with $2.9\times10^{11}$ vg PR001A (FIG. 52A; FIG. 52B).

Cerebral cortical and hippocampal levels of soluble and insoluble α-Synuclein were examined biochemically. There was no difference in these levels between 4L/PS-NA mice and control animals; published reports in the literature have shown variable α-Synuclein phenotypes.

There was a statistically significant accumulation of GluSph and GluCer in the cerebellum of 4L/PS-NA mice treated with excipient. Treatment with PR001A led to a dose-dependent trend to reduced levels of GluSph and a statistically significant dose-dependent reduction in GluCer (FIG. 53A; FIG. 53B).

Summary of 4L/PS-NA Genetic Mouse Model

Although the 4L/PS-NA mice displayed variability with respect to the measured phenotypes across 2 studies, the overall data were consistent with the CBE model findings and published data: GCase deficiency was associated with an increased level of glycolipid substrates and motor behavioral deficits. Treatment with ICV PR001A strongly attenuated these phenotypes. In Study PRV-2018-006, insoluble α-Synuclein levels in the cerebral cortex were nonsignificantly increased in the 4L/PS-NA relative to control mice, as reported in published studies (Sun et al., *J Lipid Res.* 2005; 46(10):2102-13; Mazzulli et al., *Cell.* 2011; 146(1):37-52; Xu et al., *Mol Genet Metab.* 2011; 102(4):436-47). Treatment with ICV PR001A reversed such accumulation, consistent with in vitro analyses disclosed herein. Taken together, these studies support the clinical development of PR001A.

Example 8.1.3: In Vivo α-Synuclein Model Studies

Study PRV-2018-019 and PRV-2019-001: PR001A in α-Synuclein Transgenic Mice Treated with CBE To further examine the effect of PR001A on α-Synuclein pathology, 2 studies were performed in db1-PAC-Tg (SNCAA53T);$Snca^{-/-}$ mice, which are homozygous for a human PD-associated α-Synuclein A53T mutant transgene on a Snca knockout background (Snca encodes the murine α-Synuclein protein). These mice are reported to display gastrointestinal phenotypes and subtle motor abnormalities between 6 to 12 months of age but not widespread α-Synuclein pathology in the brain (Kuo et al., *Hum Mol Genet.* 2010; 19(9):1633-50). Previous studies in human α-Synuclein A53T transgenic mouse models have reported that the treatment of such mice with CBE leads to elevated α-Synuclein levels (Rockenstein et al., *Hum Mol Genet.* 2016; Papadopoulos et al., *Hum Mol Genet.* 2018; 27(10): 1696-1710). Due to these published findings, and to validate the effects of GCase deficiency in this model, we treated these mice with CBE. At 9 to 10 weeks of age, mice were treated with 10 μL of excipient or $2.9\times10^{11}$ vg ($7.4\times10^{11}$ vg/g brain, based on a brain weight of 400 mg) PR001A via ICV injection. Two weeks post-ICV treatment, IP PBS or 100 mg/kg CBE was given daily for 1 week.

The presence of vector genomes and GCase activity was assessed in the cerebral cortex. For PRV-2018-019, increased cortical glycolipid substrates with CBE treatment were confirmed, and assessed α-Synuclein levels from hippocampal lysates using an automated capillary Simple Western™ immunoblot system on a Jess instrument. Multiple α-Synuclein immunoreactive bands were observed, consistent with the presence of monomers and high molecular weight (HMW) species. A statistically significant reduction in the ratio of HMW α-Synuclein species to monomeric α-Synuclein levels was observed with PR001A treatment of CBE-dosed α-Synuclein transgenic mice (FIG. 54A; FIG. 54B).

Summary of Nonclinical Efficacy Studies

The studies above show that a single ICY injection of PR001A effectively delivers GBA1 to the CNS and peripheral tissues of mice. In two animal models of PD-GBA and nGD, PR001A elevated GCase activity in the CNS. Increased GCase activity reduced the accumulation of glycolipid substrates in the brain; these glycolipid substrates are proposed as a biomarker outcome measure for the intended clinical trial. Importantly, these benefits persist for at least 6 months after a single treatment with PR001A. The CBE model presents with reactive astrogliosis as well as microgliosis, which are typical histopathological findings in patients with PD-GBA, nGD, and animal models of these disorders (Hamby and Sofroniew, Neurotherapeutics. 2010; 7(4):494-506; Farfel-Becker et al., *Dis. Model Mech.* 2011; 4(6):746-752; Farfel-Becker et al., *Hum Mol Genet.* 2011; 20(7):1375-86; Booth et al., *Trends Neurosci.* 2017; 40(6):

358-70; McMahon et al., *Mol Genet Metab.* 2018;123(2): 593). PR001A is able to prevent or reverse the CBE-induced reactive gliosis and microgliosis. Both models display motor deficits, and treatment with PR001A improves some of these deficits in both models. Alongside these two models, an additional mouse model was used to investigate α-Synuclein pathology. While α-Synuclein phenotypes are variable in mouse models, PR001A was able to suppress or reverse the phenotypes when they were observed; additional in vitro studies support the effectiveness of PR001A in reducing α-Synuclein levels. Together, these studies support the efficacy of PR001A in models of PD-GBA and nGD.

Example 8.1.4: Toxicology

Single-Dose Mouse Studies

Safety and toxicology studies conducted with PR001A in mouse models are summarized in Table 15. Two of the mouse model efficacy studies (PRV-2018-005 and PRV-2018-006) also included select safety endpoints such as histopathology to evaluate the safety of PR001A in a disease model.

Study PRV-2018-005: Dose-Ranging PR001A in CBE Model

Histopathological analysis was performed by hematoxylin and eosin (H&E) staining of the brain, thoracic spinal cord, heart, liver, spleen, lung, and kidney; results were evaluated by a board-certified veterinary pathologist. In the mice treated with CBE, findings in the CNS included glial scars and neuronal necrosis in the cerebral cortex, brain stem, and thoracic spinal cord. Intracerebroventricular PR001A at doses up to $1.3\times10^{11}$ vg/g was well tolerated in these mice, and this highest dose resulted in a notable reduction in the incidence of these CNS findings; low and mid dose PR001A had a dose-dependent reduction in the number of animals with glial scars in the cerebral cortex, with equivocal effects on the other CNS findings such as neuronal necrosis. No adverse effects of either CBE or PR001A were observed in peripheral tissues. In summary, there were no adverse histopathology findings or evidence of toxicity due to treatment with PR001A in studies with the CBE mouse model.

Example 9: In Vitro Analysis of rAAV Vectors

A pilot study was performed to assess in vitro activity of rAAV vectors encoding Prosaposin (PSAP) and SCARB2, alone or in combination with GBA1 and/or one or more inhibitory RNAs. One construct encoding PSAP and progranulin (PGRN) was also tested. Vectors tested include those shown in Table 3. "Opt" refers to a nucleic acid sequence codon optimized for expression in mammalian cells (e.g., human cells). FIG. 18 shows representative data indicating that transfection of HEK293 cells with each of the constructs resulted in overexpression of the corresponding gene product compared to mock transfected cells.

TABLE 3

| ID | Promoter | Inhibitory RNA | Promoter | Transgene |
|---|---|---|---|---|
| 100015 | JL_intronic | SNCA | JetLong | Opt-PSAP_GBA1 |
| 100039 | — | — | JetLong | Opt-PSAP-GRN |
| 100046 | — | — | | Opt-PSAP |
| 100014 | JetLong | SNCA | JetLong | Opt-SCARB2_GBA1 |

Example 10: ITR "D" Sequence Placement and Cell Transduction

The effect of placement of ITR "D" sequence on cell transduction of rAAV vectors was investigated. HEK 293 cells were transduced with Gcase-encoding rAAVs having 1) wild-type ITRs (e.g., "D" sequences proximal to the transgene insert and distal to the terminus of the ITR) or 2) ITRs with the "D" sequence located on the "outside" of the vector (e.g., "D" sequence located proximal to the terminus of the ITR and distal to the transgene insert), as shown in FIG. 19. Surprisingly, data indicate that rAAVs having the "D" sequence located in the "outside" position retain the ability to be packaged and transduce cells efficiently (FIG. 20).

Example 11: In Vivo Toxicity Studies

Fifty (50) mice were administered GBA1-encoding rAAVs via a 4 μl intracerebroventricular (ICV) injection on post-natal day 3. All mice received daily intraperitoneal (IP) injections of conduritol B-epoxide (CBE) or PBS, depending on treatment group, from post-natal day 8 to the end of the study. Animals were euthanized 24 hours after their last IP dose. After euthanasia, target tissues were harvested, drop fixed in chilled 4% paraformaldehyde and stored at 4° C., then sent for histopathological processing and evaluation.

Tissues from the forty-two (42) animals euthanized at 38-40 days were trimmed, processed, and embedded in paraffin blocks. They were then sectioned at ~5 μm, stained with hematoxylin and eosin (H&E) and affixed to slides for evaluation.

There were no histopathologic findings or evidence of toxicity due to treatment with the rAAVs. In the mice treated with conduritol B-epoxide (CBE), there were findings in the central nervous system (CNS) that included glial scars and neuronal necrosis in the cerebral cortex, and neuronal necrosis in the brain stem and thoracic spinal cord. High dose rAAV treatment resulted in a notable reduction in the incidence of these CNS findings, while the low and mid dose virus had a dose dependent reduction in the incidence of glial scars in the cerebral cortex, with equivocal effects on the other CNS findings (FIG. 28).

Immunohistochemistry was performed to assess GCase and Iba1 expression in the cortex (FIGS. 29A-29B). GCase expression was significantly increased in all animals treated with rAAV-GBA1 compared to CBE/Excipient treated animals. The increase in GCase expression correlated with the dose delivered, with the highest GCase expression observed in the high-dose treated animals followed by mid- and low-dose treated animals. Iba1, a marker of microgliosis, was significantly increased in animals treated with CBE/Excipient. All doses of rAAV-GBA1 reduced Iba1 staining, thus alleviating microgliosis in the CBE model. Microgliosis is a well described endpoint in neuronopathic GD and models of this disorder.

TABLE 4

Examples of neurodegenerative diseases

Figure 1:
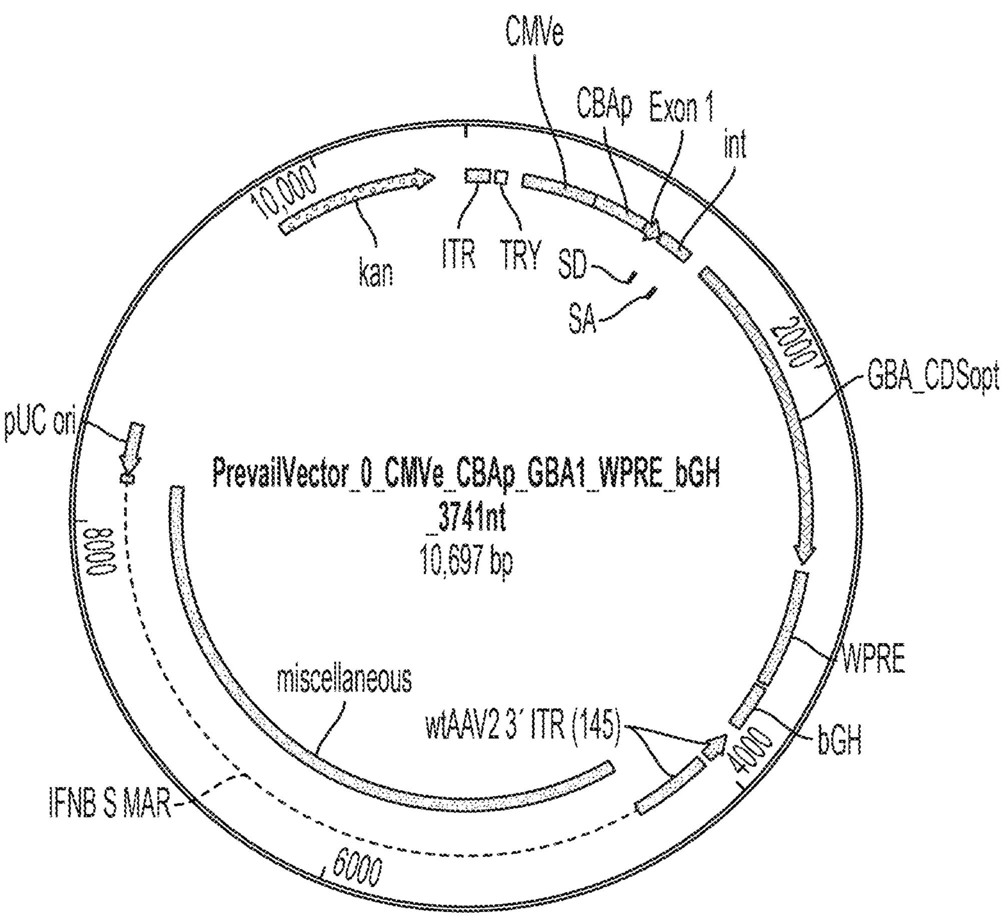
FIG. 1 is a schematic depicting one embodiment of a plasmid comprising an rAAV vector that includes an expression construct encoding Gcase (e.g., GBA1 or a portion thereof).
Figure 2:
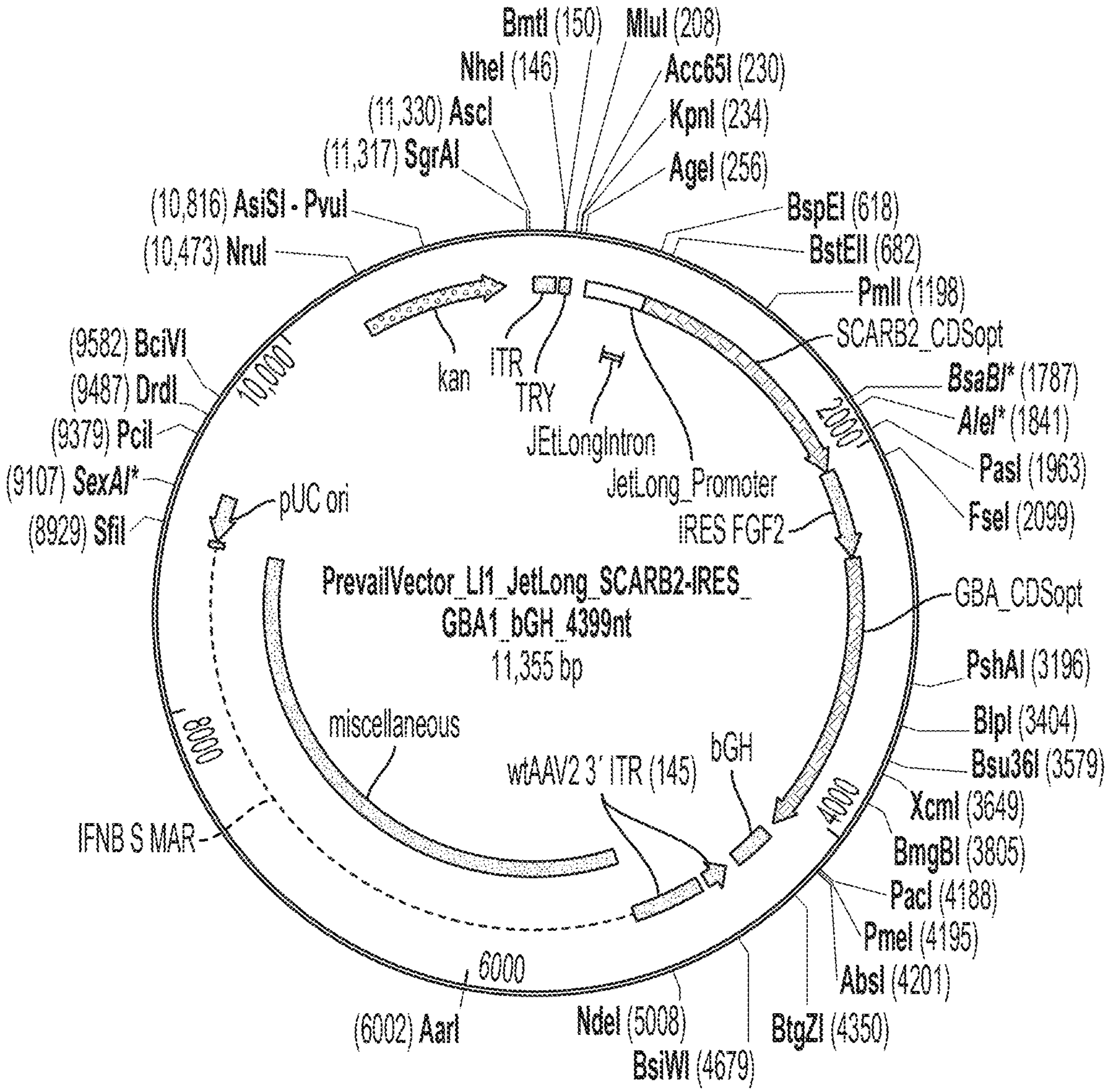
FIG. 2 is a schematic depicting one embodiment of a plasmid comprising an rAAV vector that includes an expression construct encoding Gcase (e.g., GBA1 or a portion thereof) and LIMP2 (SCARB2) or a portion thereof. The coding sequences of Gcase and LIMP2 are separated by an internal ribosomal entry site (IRES).
Figure 3:
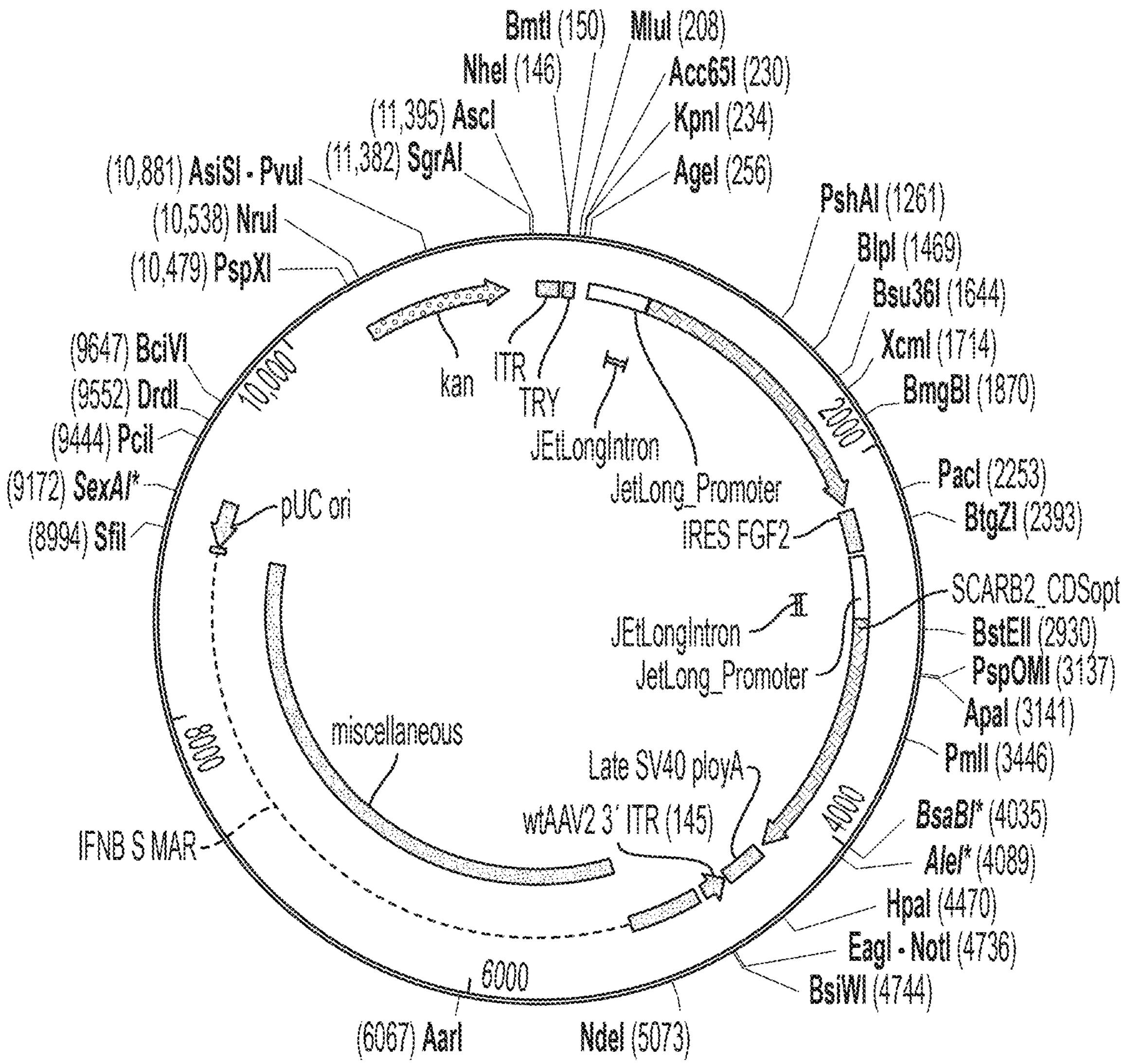
FIG. 3 is a schematic depicting one embodiment of a plasmid comprising an rAAV vector that includes an expression construct encoding Gcase (e.g., GBA1 or a portion thereof) and LIMP2 (SCARB2) or a portion thereof. Expression of the coding sequences of Gcase and LIMP2 are each driven by a separate promoter.
Figure 4:
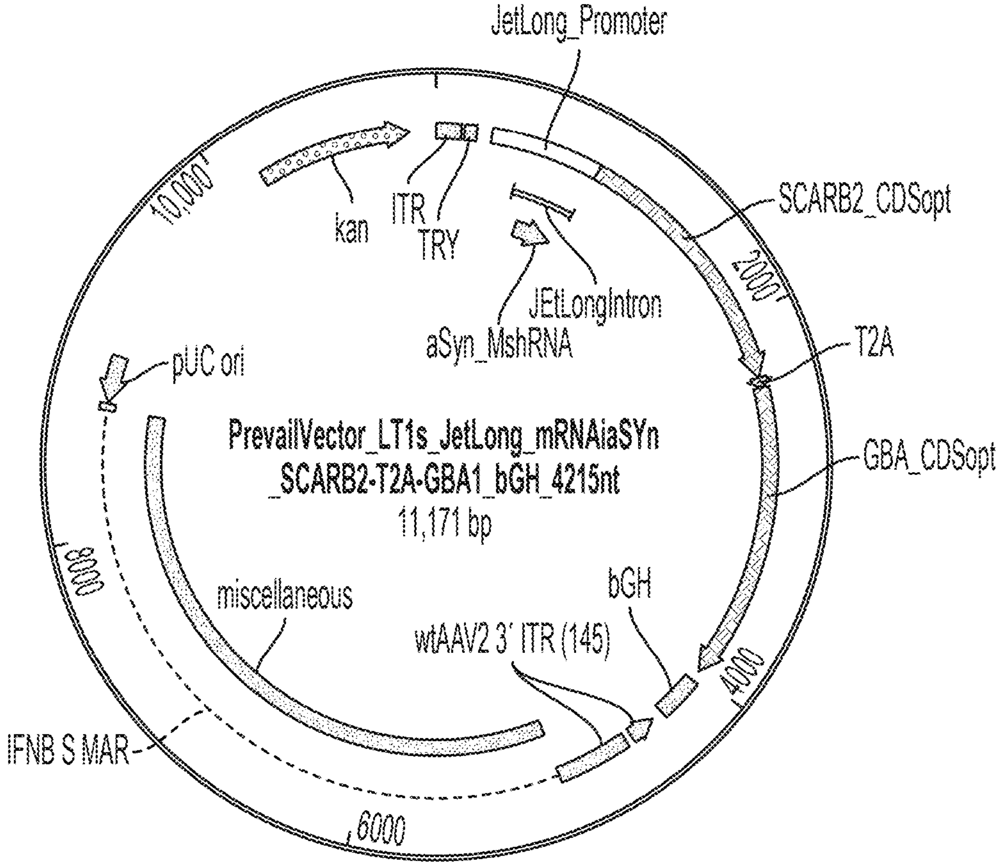
FIG. 4 is a schematic depicting one embodiment of a plasmid comprising an rAAV vector that includes an expression construct encoding Gcase (e.g., GBA1 or a portion thereof), LIMP2 (SCARB2) or a portion thereof, and an interfering RNA for α-Syn.
Figure 5:
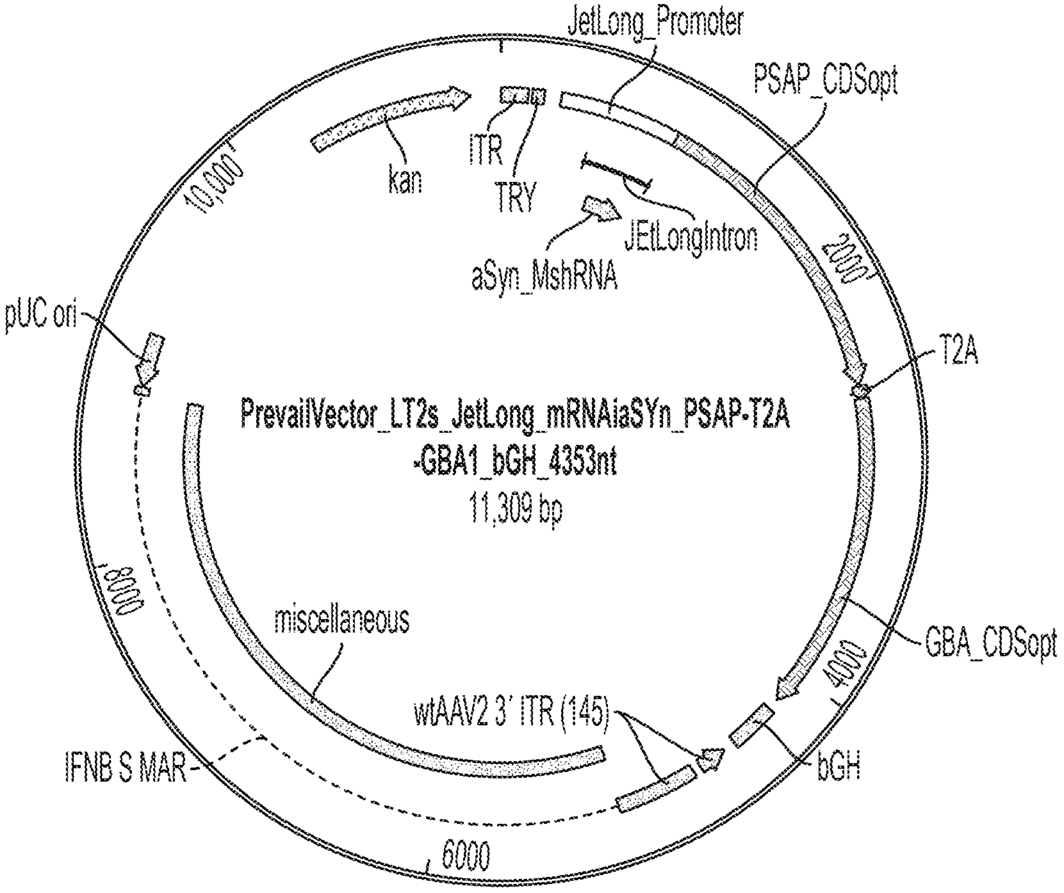
FIG. 5 is a schematic depicting one embodiment of a plasmid comprising an rAAV vector that includes an expression construct encoding Gcase (e.g., GBA1 or a portion thereof), Prosaposin (e.g., PSAP or a portion thereof), and an interfering RNA for α-Syn.
Figure 6:
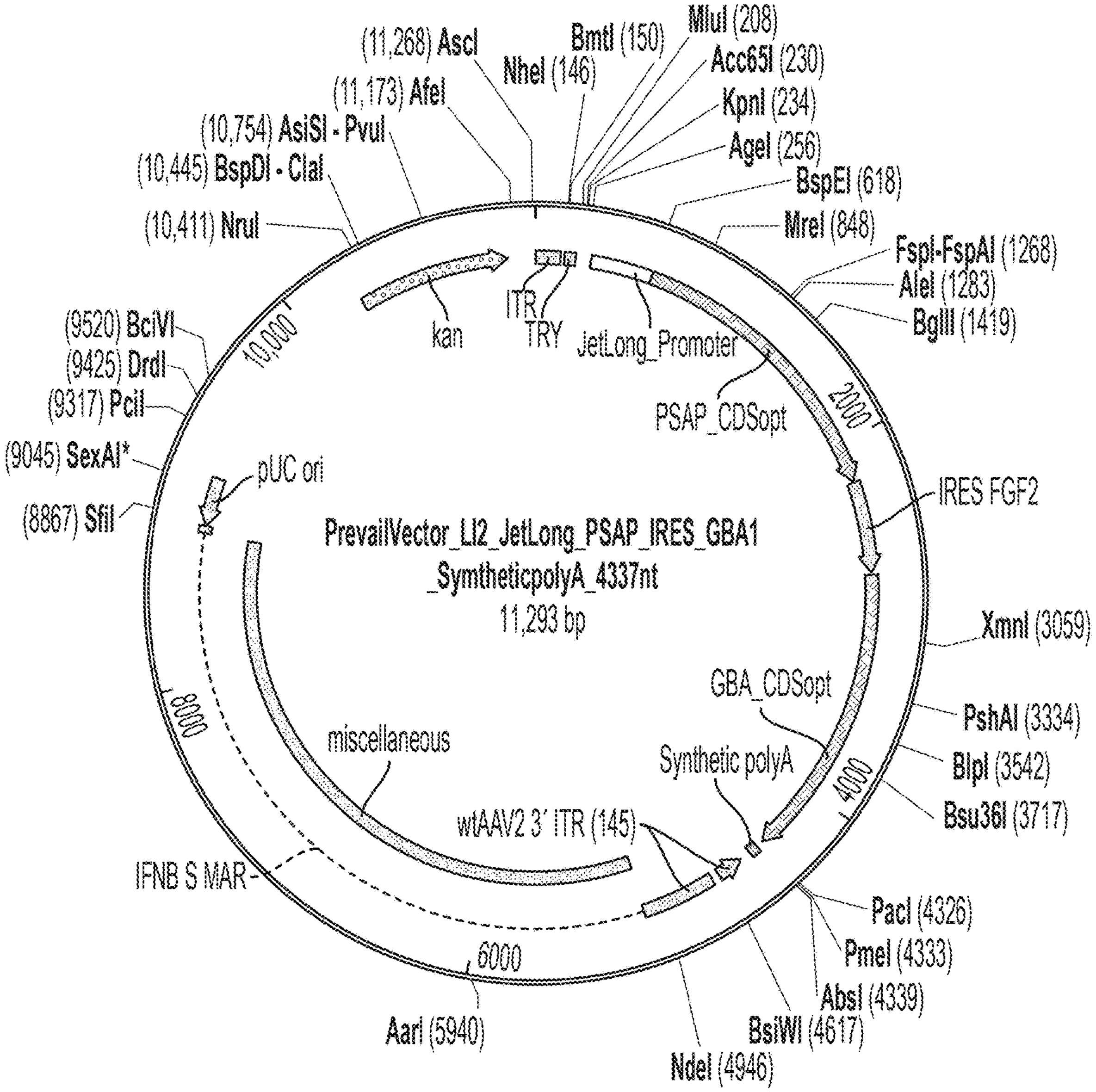
FIG. 6 is a schematic depicting one embodiment of a plasmid comprising an rAAV vector that includes an expression construct encoding Gcase (e.g., GBA1 or a portion thereof) and Prosaposin (e.g., PSAP or a portion thereof). The coding sequences of Gcase and Prosaposin are separated by an internal ribosomal entry site (IRES).

| Disease | Associated genes |
|---|---|
| Alzheimer's disease | APP, PSEN1, PSEN2, APOE |
| Parkinson's disease | LRRK2, PARK7, PINK1, PRKN, SNCA, GBA, UCHL1, ATP13A2, VPS35 |
| Huntington's disease | HTT |
| Amyotrophic lateral sclerosis | ALS2, ANG, ATXN2, C9orf72, CHCHD10, CHMP2B, DCTN1, ERBB4, FIG4, FUS, HNRNPA1, MATR3, NEFH, OPTN, PFN1, PRPH, SETX, SIGMAR1, SMN1, SOD1, SPG11, SQSTM1, TARDBP, TBK1, TRPM7, TUBA4A, UBQLN2, VAPB, VCP |
| Batten disease (Neuronal ceroid lipofunscinosis) | PPT1, TPP1, CLN3, CLN5, CLN6, MFSD8, CLN8, CTSD, DNAJC5, CTSF, ATP13A2, GRN, KCTD7 |
| Friedreich's ataxia | FXN |
| Lewy body disease | APOE, GBA, SNCA, SNCB |
| Spinal muscular atrophy | SMN1, SMN2 |
| Multiple sclerosis | CYP2761, HLA-DRB1, IL2RA, IL7R, TNFRSF1A |
| Prion disease (Creutzfeldt-Jakob disease, Fatal familial insomnia, Gertsmann-Straussler-Scheinker syndrome, Variably protease-sensitive prionopathy) | PRNP |

TABLE 5

Examples of synucleinopathies

| Disease | Associated genes |
|---|---|
| Parkinson's disease | LRRK2, PARK7, PINK1, PRKN, SNCA, GBA, UCHL1, ATP13A2, VPS35 |
| Dementia with Lewy bodies | APOE, GBA, SNCA, SNCB |
| Multiple system atrophy | COQ2, SNCA |

TABLE 6

Examples of tauopathies

| Disease | Associated genes |
|---|---|
| Alzheimer's disease | APP, PSEN1, PSEN2, APOE |
| Primary age-related tauopathy | MAPT |
| Progressive supranuclear palsy | MAPT |
| Corticobasal degeneration | MAPT, GRN, C9orf72, VCP, CHMP2B, TARDBP, FUS |
| Frontotemporal dementia with parkinsonism-17 | MAPT |
| Subacute sclerosing panencephalitis | SCN1A |
| Lytico-Bodig disease | |
| Gangioglioma, gangliocytoma | |
| Meningioangiomatosis | |
| Postencephalitic parkinsonism | |
| Chronic traumatic encephalopathy | |

TABLE 7

Examples of lysosomal storage diseases

| Disease | Associated genes |
|---|---|
| Niemann-Pick disease | NPC1, NPC2, SMPD1 |
| Fabry disease | GLA |
| Krabbe disease | GALC |
| Gaucher disease | GBA |
| Tach-Sachs disease | HEXA |
| Metachromatic leukodystrophy | ARSA, PSAP |
| Farber disease | ASAH1 |
| Galactosialidosis | CTSA |
| Schindler disease | NAGA |
| GM1 gangliosidosis | GLB1 |
| GM2 gangliosidosis | GM2A |
| Sandhoff disease | HEXB |
| Lysosomal acid lipase deficiency | LIPA |
| Multiple sulfatase deficiency | SUMF1 |
| Mucopolysaccharidosis Type I | IDUA |
| Mucopolysaccharidosis Type II | IDS |
| Mucopolysaccharidosis Type III | GNS, HGSNAT, NAGLU, SGSH |
| Mucopolysaccharidosis Type IV | GALNS, GLB1 |
| Mucopolysaccharidosis Type VI | ARSB |
| Mucopolysaccharidosis Type VII | GUSB |
| Mucopolysaccharidosis Type IX | HYAL1 |
| Mucolipidosis Type II | GNPTAB |
| Mucolipidosis Type III alpha/beta | GNPTAB |
| Mucolipidosis Type III gamma | GNPTG |
| Mucolipidosis Type IV | MCOLN1 |
| Neuronal ceroid lipofuscinosis | PPT1, TPP1, CLN3, CLN5, CLN6, MFSD8, CLN8, CTSD, DNAJC5, CTSF, ATP13A2, GRN, KCTD7 |
| Alpha-mannosidosis | MAN2B1 |
| Beta-mannosidosis | MANBA |
| Aspartylglucosaminuria | AGA |
| Fucosidosis | FUCA1 |

Example 12: Non-Human Primate Studies with rAAV Encoding Gcase

The safety of PR001A (AAV9.CBA.GBA1.A), comprising the codon-optimized coding sequence of human GBA1 (SEQ ID NO:15), was evaluated in vivo in non-human primates (NHPs). Additional details of the PR001A components are provided above. The brain of the NHP is most similar to that of humans, and the anatomical features of the NHP spinal cord and CSF volume and flow permits an ICM (intra-cisterna *magna*) injection. Because of the anatomical similarities to humans, it was expected that NHP studies would provide reliable biodistribution data supporting clinical dosing of PR001A.

Safety and biodistribution of PR001A were evaluated in three toxicology studies in cynomolgus macaques (Table 8): two non-GLP (Good Laboratory Practice) studies (PRV-2018-015 and PRV-2019-005) and a larger 21CFR58 GLP-compliant study (PRV-2018-016).

TABLE 8

| Overview of NHP Nonclinical Safety Studies Using PR001A | | | | | | | |
|---|---|---|---|---|---|---|---|
| Study number | Regulatory Oversight | Species (Age) | ROA | Dose Groups (vg/g brain) | Total PR001A Dose (vg) | Necropsy Time Points | Endpoints |
| PRV-2018-015 | Non-GLP | Cynomolgus (2-3 years of age) | ICM<br>ICM + IPa | 0<br>$2.0 \times 10^{11}$<br>$2.1 \times 10^{11}$ | 0<br>$1.47 \times 10^{13}$<br>$1.53 \times 10^{13}$ | D18 | In-Life Safety; Biodistribution; Histopathology |
| PRV-2018-016 | GLP | Cynomolgus (2-4 years of age) | ICM | 0<br>$6.2 \times 10^{10}$<br>$2.3 \times 10^{11}$ | 0<br>$4.6 \times 10^{12}$<br>$1.7 \times 10^{13}$ | D7, D30, D183 | In-Life Safety; Biodistribution; Histopathology; CBC; Vector Shedding |
| PRV-2019-005 | Non-GLP | Cynomolgus (2-3 years of age) | ICM | 0<br>$7.0 \times 10^{11}$ | 0<br>$5.2 \times 10^{13}$ | D30, D90 | In-Life Safety; Biodistribution; Histopathology |

Abbreviations:
CBC, complete blood count;
D, day;
GLP, Good Laboratory Practice;
ICM; intra-cisterna magna;
IPa, intraparenchymal;
NHP, nonhuman primate;
ROA, route of administration;
vg, vector genome.

A pilot non-GLP study (PRV-2018-015) was conducted in NHPs to confirm that the final PR001A product is delivered to the NHP brain following ICM administration. The GLP toxicology and biodistribution study in NHPs (PRV-2018-016) assessed the safety and biodistribution of PR001A.

The doses tested in NHPs include the maximum feasible dose as determined by the volume administered and test product titer. In addition, a lower dose was also evaluated in the GLP study. The time points of the GLP study were selected to evaluate safety after treatment but before peak expression (Day 7), the start of peak expression (Day 30), and long-term expression post peak (Day 183).

Study PRV-2018-015: Non-GLP NHP Study of PR001A

A non-GLP pilot tolerance and biodistribution study of PR001A was conducted in male cynomolgus monkeys. The goal of this study was to verify biodistribution of PR001A to various brain areas and major peripheral organs following ICM delivery. The time point for sacrifice was selected because it was predicted to allow for a meaningful measure of potential early toxicity to inform the planned GLP NHP toxicology study, most notably with early in-life observations as measured by a functional observational battery (FOB). Studies of intrathecal AAV delivery have demonstrated that transgene expression peaks 2 to 3 weeks after injection (Hinderer et al., *Mol Ther.* 2014; 22(12):2018-27; Hinderer et al., *Mol Ther Methods Clin Dev.* 2014; 1:14051; Hinderer et al., *Mol Ther.* 2015;23(8)1298-307; Hinderer et al., *Mol Genet Metab.* 2016;119(1-2):124-30). Day 18 evaluations, therefore, should detect immediate toxicity due to the injection procedure or an innate inflammatory response to the test article, as well as provide information regarding transgene biodistribution and expression at a time point corresponding to early peak expression. The study design included an arm with rapamycin treatment (0.3 mg/kg oral, Day −3 to Day 18) in combination with PR001A to determine if immunosuppression would be beneficial in mitigating potential toxicity. To increase transgene expression in the brain, one arm in the study included intraparenchymal (IPa) administration of PR001A directly into the midbrain targeting bilateral substantia nigra pars *compacta* in combination with ICM delivery. The ICM dose volume was 0.5 mL, the maximum volume there was experience with administering, and the IPa dose was 10 μL bilateral, translating to doses of $1.47\times10^{13}$ vg for ICM alone and $1.53\times10^{13}$ vg for treatment with both ICM and IPa. With an estimated brain weight of 74 g, this translates to an ICM dose of $2.0\times10^{11}$ vg/g brain and a dose of $2.1\times10^{11}$ vg/g brain for the group receiving ICM administration in combination with IPa. A tabulated summary of this study's design is provided in Table 9.

TABLE 9

| Overview of the Non-GLP NHP Study PRV-2018-015<br>Biodistribution and Safety Study Following PR001A Administration in NHPs | |
|---|---|
| Purpose | Assess the tolerance and biodistribution of PR001A in NHPs |
| Regulatory Compliance | Non-GLP |
| Test Article | PR001A |
| Total No. of Animals | 8 male cynomolgus monkeys |
| Weight (age) | 3-4 kg (2-3 years) |
| Number of Animals/Group | 2/group |
| Study Design | Group Assignments (see Table 9A) |
| Dosing Route and Frequency | ICM using a syringe; single injection of 0.5 mL IPa using Hamilton syringe; bilateral injection of 10 μL to each hemisphere |

TABLE 9-continued

Overview of the Non-GLP NHP Study PRV-2018-015
Biodistribution and Safety Study Following PR001A Administration in NHPs

| | | | |
|---|---|---|---|
| Formulations | Dosing solution provided at concentration of $2.9 \times 10^{13}$ vg/mL; excipient used in the control group is a similar formulation as intended for the clinic (20 mM Tris pH 8.0, 200 mM NaCl, 1 mM $MgCl_2$, and 0.001% [w/v] poloxamer 188) | | |
| FOB | Weekly | | |
| Body Weights | Weekly | | |
| Necropsy | Day 18 | | |
| H&E and qPCR | The following tissues were examined from all animals in all groups: | | |
| | liver | frontal cortex | paraventricular |
| | lung | parietal cortex | nucleus |
| | kidney | occipital cortex | pons |
| | gonads | insular cortex | entorhinal cortex |
| | heart | cingulate cortex | medulla |
| | spleen | hippocampus | cerebellum dorsal |
| | root ganglia | putamen | midbrain cervical |
| | | | spinal cord |
| | For midbrain H&E, includes at least 12 sections that include 6 sections around the infusion site in the IPa group; the ICM alone groups (1-3) include the same anatomical levels | | |

Abbreviations: FOB, functional observational battery; GLP, Good Laboratory Practice; H&E, hematoxylin and eosin; ICM; intra-cisterna magna; Immunosupp, immunosuppressed; IPa, intraparenchymal; $MgCl_2$; magnesium chloride; NaCl, sodium chloride; NHP, nonhuman primate; qPCR, quantitative polymerase chain reaction; ROA, route of administration; vg, vector genome(s).

TABLE 9A

Group Assignments

| Group | Dose (vg/g brain) | ROA | Immunosupp. | Number of Animals |
|---|---|---|---|---|
| 1 | 0 | ICM | No | 2 |
| 2 | $2.0 \times 10^{11}$ | ICM | No | 2 |
| 3 | $2.0 \times 10^{11}$ | ICM | Yes | 2 |
| 4 | $2.1 \times 10^{11}$ | ICM + IPa | No | 2 |

The H&E analysis was performed by two independent board-certified veterinary pathologists, and both concluded there were no PR001A-related toxicity findings. Spinal cord changes observed were likely the result of trauma at the time of ICM injection and were not considered related to PR001A. All histopathology findings in non-nervous system tissue were considered spontaneous or incidental changes commonly seen in control monkeys. Overall, there were no definitive adverse PR001A effects in the brain or spinal cord.

The reviewing pathologist noted nonspecific changes (predominantly variable infiltrates of mononuclear cells) in the meninges, brain or spinal cord parenchyma, and/or at the injection site (in these tissues) were likely associated with the test article, but the pathologist did not consider these changes to be adverse. At the severities noted, similar infiltrates might reasonably be expected to be observed in any monkey with an experimental procedure that disrupts the meninges and/or the blood brain barrier. Additionally, some infiltrates (notably those within the choroid plexus and occasionally in the parenchyma) are commonly observed in control monkeys (Butt et al., *Toxicol Pathol.* 2015; 43:513-8). All other histopathologic findings observed were considered incidental and/or were of similar incidence and severity in excipient and PR001A-treated animals and, therefore, were considered unrelated to administration of PR001A. A second independent, board-certified veterinary pathologist reviewing the same tissue samples noted that all findings were indistinguishable from incidental findings or trauma incurred during the injection procedure as findings were nonspecific and across all groups, including the control group receiving only excipient. In addition, a different board-certified veterinary pathologist reviewed the non-GLP tissues and concluded there were no PR001A-related effects.

Overall, there were no changes in FOB scores, body weight gain, or food consumption during the course of the study irrespective of group and across time points. Microglia morphology in the midbrain did not appear to differ across treatment groups (as determined with Iba1 staining). Expression and morphology of tyrosine hydroxylase positive neurons of the midbrain did not appear to differ across treatment groups. By Day 18, AAV9-nAb titers were increased in all PR001A-treated animals, while the excipient-treated control animals showed only modest changes compared to baseline. One of the monkeys in the group receiving oral rapamycin had a lower AAV9 nAb titer (1:64) at Day 18 compared to the other animals receiving PR001A treatment (>1:256); the difference in titers did not appear to affect biodistribution, but the sample size is too low to be conclusive.

Biodistribution was evaluated in all test samples collected using quantitative polymerase chain reaction (qPCR); tissues were considered positive with at least 100 vg/μg DNA (these criteria were also used to assess positive tissues in the mouse efficacy studies). All tissues tested were positive in all groups that were treated with PR001A, indicating widespread distribution throughout the CNS and periphery. In addition, animals that received ICM administration of PR001A in combination with bilateral IPa administration into the midbrain had increased localized expression. Treatment with rapamycin did not appear to have any effect on safety or biodistribution (select representative regions shown in FIG. 30). Of note, several of the tissues from control animals (pons, spinal cord, paraventricular, dorsal root ganglia, and lung) were also positive as determined by qPCR. Several issues were noted about the necropsy procedures that indicated an increased risk for cross-contamination across animals in different treatment groups and between different organs within each animal. Changes were implemented in the necropsy procedure to minimize contamination for future studies. However, there were no adverse toxicity findings in any of the animals that were positive for qPCR. Analysis of the transgene expression (GCase activity) indicated no significant increase in GCase activity in the PR001A-treated animals compared to controls; GCase activity was explored in more detail in the GLP NHP toxicity Study PRV-2018-016.

Taken together, the results of non-GLP NHP Study PRV-2018-015 indicated no safety or toxicity concerns with any of the in-life or postmortem assessments. All animals survived until their scheduled necropsy date, and postmortem pathology analysis indicated no adverse toxicity concerns. The study also showed uniform biodistribution of PR001A in the brain.

Study PRV-2018-016: A GLP NHP Study of PR001A

Study Design

The purpose of this GLP study was to evaluate the toxicity and biodistribution of PR001A when administered once via ICM injection in cynomolgus monkeys with a 7-, 30-, or 183-day post-administration observation period. The study was designed to evaluate 2 dose levels: the highest dose is the maximum feasible dose achievable with 1.2 mL volume (the highest volume there was experience with administering) of undiluted test product, and a lower dose ½ log unit lower than the high dose. The doses equated to a low dose of $4.6\times10^{12}$ vg and a high dose of $1.7\times10^{13}$ vg; with a brain weight estimate of 74 g in a cynomolgus monkey, this translates to approximately $6.2\times10^{10}$ vg/g brain and $2.3\times10^{11}$ vg/g brain. The study also included a control arm in which animals receive 1.2 mL of excipient only (20 mM Tris pH 8.0, 200 mM NaCl, 1 mM $MgCl_2$, and 0.001% [w/v] poloxamer 188). This study utilized both male and female cynomolgus macaques. The Day 7 group included 1 male at the highest dose and was designed as a sentinel for early toxicity; the remaining 2 time points (Day 30 and Day 183) included 2 males and 1 female at each dose. In addition to samples from multiple brain regions, peripheral tissue samples were collected for qPCR analysis. All samples that were positive with qPCR were analyzed for transgene expression. A tabulated summary of this study's design is provided in Table 10.

TABLE 10

Overview of the GLP NHP Study PRV-2018-016
A Single-dose Intra-cisternal Toxicity and Biodistribution Study in Cynomolgus Monkeys with a 7-day, 30-day, or 183-day Observation Period

| | | |
|---|---|---|
| Purpose | Assess the tolerance and biodistribution of PR001A in NHPs | |
| Regulatory Compliance | GLP | |
| Test Article | PR001A | |
| Total No. of Animals | 19 cynomolgus monkeys | |
| Weight (age) | 2-5 kg (25-50 months) | |
| Study Design | Group Assignments (see Table 10A) | |
| Dosing Route and Frequency | ICM using a syringe; 1-3 cc syringe and spinal needle (Pencan 25 G × 2.5 cm BBraun); single slow bolus delivered at a maximum rate of 0.5 cc/min | |
| Formulations | Dosing solution provided at concentration of $1.42\times10^{13}$ vg/mL | |
| Clinical Signs | Daily (including food consumption); detailed observations weekly | |
| Body weights | Weekly | |
| Neurological, Ophthalmic, and Electrocardiogram Examinations | Once pre-dose and during Weeks 2 and 26 | |
| Clinical Pathology | All groups hematology, clinical chemistry, coagulation parameters | |
| Hematology | red blood cell count | mean corpuscular volume |
| | hemoglobin | platelet count |
| | hematocrit | white blood cell count |
| | mean corpuscular | blood smear |
| | hemoglobin | absolute reticulocyte count |
| | mean corpuscular | leukocyte count |
| | hemoglobin concentration | differential blood cell count |
| Clinical Chemistry | glucose | alanine aminotransferase |
| | urea nitrogen | alkaline phosphatase |
| | creatinine | gamma glutamyltransferase |
| | total protein | aspartate aminotransferase |
| | albumin | calcium |
| | globulin | inorganic phosphorus |
| | albumin/globulin ratio | sodium |
| | cholesterol | potassium |
| | total bilirubin | chloride |
| | creatine kinase | triglycerides |
| Coagulation | prothrombin time | |
| | fibrinogen | |
| | activated partial thromboplastin time | |
| Vector Shedding (urine/feces) | At sacrifice | |
| Necropsy | Day 7, Day 30, Day 183 | |
| Tissue Preservation for Histopathology | The following tissues from each animal will be collected in 10% neutral-buffered formalin (unless otherwise indicated) or recorded as missing, if applicable: | |
| Histopathology | All groups - all tissues | |
| Biodistribution | The following tissues will be analyzed for biodistribution by qPCR: | |
| | Frontal cortex | Liver |
| | Hippocampus | DRG (cervical) |
| | Ventral mesencephalon | DRG (thoracic) |
| | Periventricular gray | DRG (lumbar) |

TABLE 10-continued

Overview of the GLP NHP Study PRV-2018-016
A Single-dose Intra-cisternal Toxicity and Biodistribution Study in Cynomolgus Monkeys with a 7-day, 30-day, or 183-day Observation Period

| | | | |
|---|---|---|---|
| | Putamen | Spinal cord (thoracic) | |
| | Testis | Spinal cord (lumbar) | |
| | Ovary | Spinal cord (cervical) | |
| | Kidney | Spleen | |
| | Stomach (pyloric) | Heart (apex) | |
| | Blood | CSF | |
| GCase Expression | All samples that are positive for qPCR will be evaluated for GCase expression | | |
| Tissue Preservation | Adrenal[a] | Injection site | Rectum |
| | Aorta | (overlying skin) | Salivary gland |
| | Bone, femur with | Jejunum | Sciatic nerve |
| | Bone marrow | Kidney[a] | Seminal vesicle[a] |
| | with bone marrow | Liver[a] | Spinal cord |
| | Brain[a] | Lung with large | (cervical, |
| | thoracic, | bronchi | lumbar) |
| | Cecum | Lymph node | Spleen[a] |
| | Cervix | (mandibular) | Stomach |
| | Colon | Lymph node | Testis[a] |
| | Duodenum | (mesenteric) | Thymus[a] |
| | Epididymis[a] | Mammary gland | Thyroid with |
| | Esophagus | Muscle, biceps | parathyroid[a] |
| | Eye[b] | femoris | Tongue |
| | Gall bladder | Optic nerve | Trachea |
| | GALT (Peyer's | Ovary[a] | Urinary bladder |
| | patch) | Oviducts | Uterus[a] |
| | Heart[a] | Pancreas | Vagina |
| | Ileum | Pituitary gland | |
| | | Prostrate[a] | |

[a]Organs (when present) will be weighed or noted as missing:
[b]Collected in modified Davidson's fixative and stored in10% neutral buffered formalin
Abbreviations: CSF, cerebrospinal fluid; DRG, dorsal root ganglia; F, female; GALT, gut-associated lymphoid tissue; GLP, Good Laboratory Practice; ICM; intra-cisterna magna; M, male; $MgCl_2$; magnesium chloride; NaCl, sodium chloride; NHP, nonhuman primate; qPCR, quantitative polymerase chain reaction; vg, vector genome(s).[a]
20 mM Tris pH 8.0, 200 mM NaCl, 1 mM $MgCl_2$, and 0.001% (w/v) poloxamer 188.

TABLE 10A

Group Assignments

| Group | Dose (vg/g brain) | Number of animals: Necropsy (Day 7) | Necropsy (Day 30) | Necropsy (Day 183) |
|---|---|---|---|---|
| 1 | 0 | 0 | 2M/1F | 2M/1F |
| 2 | $6.2 \times 10^{10}$ | 0 | 2M/1F | 2M/1F |
| 3 | $2.3 \times 10^{11}$ | IM | 2M/1F | 2M/1F |

Cynomolgus NHPs were assessed by multiple in-life observations and measurements, including mortality/morbidity (daily), clinical observations (daily), body weight (baseline and weekly thereafter), visual inspection of food consumption (daily), neurological observations (baseline and during Weeks 2 and 26), indirect ophthalmoscopy (baseline and during Weeks 2 and 26), and electrocardiographic measurement (baseline and during Weeks 2 and 26).

Analysis of nAb to the AAV9 capsid was performed at baseline and at sacrifice on Days 7, 30, or 183. Clinical pathology consisting of hematology, coagulation, clinical chemistry, and urinalysis was performed twice at baseline (blood tests; once for urinalysis) and once during Weeks 1 and 13 of the dosing phase.

Animals were euthanized, and tissues harvested on Days 7, 30, or 183. The tissues were collected from all animals, weighed (if applicable), and divided into replicates. One replicate was preserved in 10% neutral-buffered formalin (except when special fixatives are required for optimum fixation) for histopathological evaluation (all animals). Additional replicates were collected for qPCR and transgene expression analysis.

Safety and Toxicity

All animals survived to the scheduled necropsy date with no unexpected deaths. There were no concerns or issues with the in-life assessments for any of the groups; gross macroscopic examination at necropsy showed no PR001A-related abnormalities in any of the cohorts.

No PR001A-related organ weight differences or macroscopic or microscopic findings were present in any of the groups at the interim sacrifices on Day 7 or 30 or at the terminal sacrifice on Day 183. Hemorrhage, characterized by focal areas of perivascular hemorrhage mainly in region of the brain stem, was present across all groups including controls, and, therefore, was considered procedure-related (CSF collection prior to necropsy) and not related to PR001A. All other microscopic findings, including minimal mononuclear infiltrates in the brain or spinal cord, were considered spontaneous and/or incidental because they occurred at a low incidence, were randomly distributed across groups (including concurrent controls), and/or their severity was as expected for monkeys of this age; therefore, they were considered not related to PR001A.

No PR001A-related findings were observed in clinical pathology test results; increased fibrinogen was noted in the animal exhibiting the highest anti-AAV9 titer consistent with an immune response against the vector. Positive titers for anti-AAV9 antibodies were observed by Day 7 in all animals administered PR001A. No PR001A-related clinical observations, body weight changes, ophthalmic observations, or physical or neurological examination findings were noted. No PR001A-related differences in mean PR interval, QRS duration, QT interval, corrected QT (QTc) interval, or heart rate were observed in males only or combined sexes administered either dose of PR001A. No PR001A-related arrhythmias or abnormal waveforms were observed.

Dose levels of 0, $6.2 \times 10^{10}$, or $2.3 \times 10^{11}$ vg/g brain PR001A were well tolerated when administered via single injection at the cisterna *magna* to male and female monkeys. No in-life, clinical pathology, or anatomic pathology observations were observed that were considered related to the gene product in PR001A.

Biodistribution and Immune Response

Biodistribution analysis of vector genome copies was performed using a qPCR-based assay (vector presence); expression of the transgene (GBA1) was measured in samples that were positive for vector genome presence. At Days 30 and 183, all tissues examined (including CNS and peripheral) were positive by qPCR analysis following treatment with the high dose ($2.3 \times 10^{11}$ vg/g brain) (select representative regions from Day 183 shown in FIG. 30). At Day 30, tissue samples collected from the testes and ovaries were positive for transduction in all NHPs treated with the high dose of PR001A ($2.3 \times 10^{11}$ vg/g brain). In addition, 1 male NHP treated with the low dose of PROM A ($6.2 \times 10^{10}$ vg/g brain) was positive in the testes at Day 30. At Day 183, 1 male and 1 female were positive for PR001A transduction in the gonads after treatment with the high dose, and 2 males treated with the low dose were positive in the testes.

To confirm that human GCase was produced in the treated NHPs, protein levels were evaluated on a Simple Western™ immunoblot system on a Jess instrument. Results from cortex, hippocampus, and midbrain samples obtained from NHPs dosed with PR001A indicated elevated levels of GCase expression when analyzed in aggregate compared to the samples from normal NHPs that only received excipient; both low dose and high dose groups were combined for statistical comparison to the control group (FIG. 31A and FIG. 31B). These results indicate that the effective and broad transduction of PR001A in NHPs following ICM administration lead to increased GCase expression.

In conclusion, the biodistribution findings indicate that ICM administration of PR001A in NHPs results in robust and broad transduction of the human GBA1 transgene in the brain and peripheral organs. In summary of the NHP biodistribution data, ICM administration of PR001A results in broad biodistribution throughout the brain comparable to levels shown to be efficacious in the mouse models; this transduction leads to the elevation of GCase protein levels in the brain.

Study PRV-2019-005: Non-GLP NHP Study of PR001A

Study Design

A non-GLP study was conducted in 12 male cynomolgus macaques to evaluate toxicity and biodistribution of PR001A when administered once via ICM injection with a 30- and 90-day post-administration observation period. The study was designed to evaluate a single dose level: $5.2 \times 10^{13}$ vg, or $7.0 \times 10^{11}$ vg/g brain assuming an average brain weight of 74 g in cynomolgus macaques. The dose administered is the maximum feasible dose achievable with 1.2 mL volume (the highest volume there was experience with administering) of undiluted PR001A product. The study included a control arm in which animals receive 1.2 mL of excipient only (20 mM Tris pH 8.0, 200 mM NaCl, and 1 mM $MgCl_2$+0.001% [w/v] Pluronic F68). Samples from multiple brain regions and peripheral organs were collected for qPCR analysis to measure biodistribution, and clinical pathology measurements and histopathology were performed to evaluate safety. A tabulated summary of this study's design is provided in Table 11.

TABLE 11

Overview of the Non-GLP NHP Study PRV-2019-005
Non-GLP toxicology and biodistribution study following intra-cisterna magna PR001A administration in non-human

| | | |
|---|---|---|
| Purpose | Assess the tolerance and biodistribution of PR001A in NHPs | |
| Regulatory Compliance | Non-GLP | |
| Test Article | PR001A | |
| Total No. of Animals | 12 cynomolgus monkeys | |
| Weight (age) | 2-4 kg (2-3 years) | |
| Study Design | Group Assignments (see Table 11A) | |
| Dosing Route and Frequency | Intra-cisterna magna; single slow bolus delivered over 3 minutes | |
| Formulations | Dosing solution provided at concentration of $4.3 \times 10^{13}$ vg/mL | |
| Clinical Signs | Daily (including food consumption) | |
| Body Weights | Daily | |
| FOB | Days −14, 7, 30, 60, 90 | |
| Clinical Pathology (chemistry and hematology) | Days −14, 7, 30, 60, 90 | |
| Hematology | red blood cell count | mean corpuscular volume |
| | hemoglobin | platelet count |
| | hematocrit | white blood cell count |
| | mean corpuscular hemoglobin | blood smear |
| | | reticulocyte count |
| | mean corpuscular hemoglobin concentration | differential blood cell count |
| Clinical Chemistry | glucose | alanine aminotransferase |
| | alkaline | phosphatase |
| | urea nitrogen | gamma glutamyltrasnferase |
| | creatinine | aspartate aminotransferase |
| | total protein | calcium |
| | albumin | inorganic phosphorus |
| | globulin | sodium |
| | albumin/globulin ratio | potassium |
| | cholesterol | chloride |
| | total bilirubin | triglycerides |

TABLE 11-continued

Overview of the Non-GLP NHP Study PRV-2019-005
Non-GLP toxicology and biodistribution study following intra-cisterna magna PR001A administration in non-human

| | | |
|---|---|---|
| Necropsy | Day 30 and Day 90 | |
| Tissue Preservation | The following tissues were examined from all animals in all groups: | |
| | frontal cortex | liver |
| | hippocampus | kidney |
| | ventral mesencephalon | heart (apex) |
| | periventricular nucleus | spleen |
| | putamen | stomach (pyloric) |
| | dorsal root ganglion (cervical) | testes |
| | dorsal root ganglion (thoracis) | spinal cord (cervical) |
| | dorsal root ganglion (lumbar) | spinal cord (thoracic) |
| | CSF | spinal cord (lumbar) |
| Histopathology | Samples from the tissue list above will be preserved and paraffin wax embedded for H&E histology | |
| Biodistribution | The tissue list shown above will be collected and stored. Samples from all animals will be analyzed for biodistribution by quantitative PCR (qPCR). | |

Abbreviations: CSF, cerebrospinal fluid; FOB, functional observational battery; GLP, Good Laboratory Practice; H&E, hematoxylin and eosin; NHP, nonhuman primate; qPCR, quantitative polymerase chain reaction; vg, vector genome(s).

TABLE 11A

Group Assignments

| Group | Dose (vg/g brain) | Number of Animals Day 30 | Day 90 |
|---|---|---|---|
| 1 | 0 | 3 | 3 |
| 2 | $7.0 \times 10^{11}$ | 3 | 3 |

As part of this study, tissues were fixed in 10% formalin, embedded in paraffin, and processed to produce H&E-stained slides. Digital slides were prepared and examined by an independent board-certified veterinary pathologist. At both 30 and 90 days post treatment, there were no findings attributed to treatment with PR001A as findings in the PR001A-treated animals were either consistent with those commonly observed in cynomolgus macaque monkeys (Chamanza et al., *Toxicol Pathol.* 2010; 38(4):642-57), and/or were observed in both vehicle control animals and animals treated with PR001A, and, therefore, were considered incidental.

There was no effect of PR001A, administered to the cisterna *magna*, on weight gain or food consumption as there was no statistical difference between the treatment and control groups during the course of the study. In addition, there was no change in FOB scores irrespective of group and across timepoints, indicating no issues or concerns during the in-life phase of the study. Plasma levels of nAb against AAV9 were measured using an in vitro assay. Samples were prepared from animals in the study at baseline (pre-ICM administration) and at time of sacrifice (either Day 30 or 90). Treatment with PR001A resulted in increases in AAV9 nAb titers between baseline and time of necropsy at both Days 30 and 90, while vehicle-treated animals' titers overall remained stable or decreased.

Biodistribution and Expression of PR001A

Biodistribution of the PR001A transgene was evaluated in all test samples collected using qPCR; tissues were considered positive with at least 50 vg/μg DNA, the lower limit of quantitation for the assay. All tissues tested were positive in all groups that were treated with PR001A, indicating widespread distribution throughout the CNS and periphery. Data from select representative regions from both the Day 30 and Day 90 cohorts are shown in FIG. 32.

Taken together, the results of non-GLP NHP Study PRV-2019-005 indicate no safety or toxicity concerns with any of the in-life or post-mortem assessments. All animals survived until their scheduled necropsy date, and post-mortem pathology analysis indicated no adverse toxicity concerns.

Safety and toxicology studies conducted with PR001A in NHPs are summarized in Table 16.

Example 13: Phase 1/2 Trials in Human Subjects

Parkinson's Disease with GBA1 Mutation

Human subjects will be enrolled in a randomized, double-blind, sham procedure-controlled trial of the PR001A rAAV. The subject inclusion criteria comprise: single or biallelic GBA1 mutations, moderate to severe Parkinson's disease, and has stable use of background Parkinson's disease medications prior to investigational product dosing. The subjects will be divided into two groups: (1) PR001 Low Dose ($1\times10^{14}$ vg) vs. Placebo (N=8, 6:2); and (2) PR001 High Dose ($2\times10^{14}$ vg) vs. Placebo (N=8, 6:2). Each subject will receive the investigational product as a single ICM (intra-cisterna *magna*) injection. The trial will include a 3-month biomarker readout, a 12-month clinical readout and a 5-year safety and clinical follow-up. The trial will analyze: (1) safety and tolerability; (2) key biomarkers, including: Gcase, GluCer, and GluSph (CSF and blood); (3) additional biomarkers, including: α-Synuclein, NIL (neurofilament light), DAT (Dopamine transporter) SPECT (single photon emission computed tomography); and MRI (magnetic resonance imaging); and (4) Efficacy: MDS-UPDRS (Movement Disorders Society Unified Parkinson's disease Rating Scale); cognition; and ADLs (Activities of Daily Living).

Type 2 Gaucher Disease

Human subjects (n=15) will be enrolled in an open-label trial of the PR001A rAAV. The subject inclusion criteria comprise: infants 0-24 months old; biallelic GBA1 mutations; neurological signs and symptoms consistent with Type 2 Gaucher disease; and stable standard of care background medications. Each subject will receive the investigational product as a single ICM (intra-cisterna *magna*) injection. The trial will include a 3-month biomarker readout, a 12-month clinical readout and a 5-year safety and clinical follow-up. The trial will analyze: (1) safety and tolerability; (2) key biomarkers, including: Gcase, GluCer, and GluSph (CSF and blood); (3) time to clinical event (e.g., tracheostomy, PEG (percutaneous endoscopic gastrostomy) placement, death); and (4) Efficacy: behavior, cognition, gross motor, function, QoL (quality of life).

Example 14: Studies of Intravenous Administration of rAAV Encoding Gcase

A PR001 intravenous dose ranging study was carried out in the D409V Hom mouse model. Homozygous Gba1$^{D409V/D409V}$ (D409V Horn) mice (The Jackson Laboratory, Bar Harbor, ME) display Gaucher disease-related phenotypes including decreased GCase activity (see, e.g., Sardi et al., *Proc Natl Acad Sci USA.* 2011; 108(29):12101-6). The study design is provided in FIG. 59. The groups and doses are provided in Table 12.

TABLE 12

Groups and doses for study of PR001 intravenous administration in D409V Hom mice

| Group | Vector genomes/kg |
|---|---|
| WT† + Excipient | N/A |
| D409V + Excipient | N/A |
| D409V + PR001 Dose 1 | $1.1 \times 10^{10}$ |
| D409V + PR001 Dose 2 | $1.1 \times 10^{11}$ |
| D409V + PR001 Dose 3 | $1.1 \times 10^{12}$ |
| D409V + PR001 Dose 4 | $1.1 \times 10^{13}$ |
| D409V + PR001 Dose 5 | $1.1 \times 10^{14}$ |

†Wild type animals purchased from The Jackson Laboratory (Bar Harbor, ME), not littermates.

Intravenous administration of PR001 decreased inflammation in the liver (FIG. 60A). D409V Horn mice showed glycolipid accumulation in the liver which was suppressed in a dose-dependent manner by PR001 treatment (FIG. 60B; FIG. 60C). D409V Horn mice showed GluSph accumulation in the brain, which was decreased by PROW treatment (FIG. 61B). Intravenous administration of PR001 decreased inflammation in the lung (FIG. 62).

A PR001 intravenous dose ranging study was also carried out in the 4L/PS-NA mouse model. The study design is provided in FIG. 63. The groups and doses are provided in Table 13.

TABLE 13

Groups and doses for study of PR001 intravenous administration in 4L/PS-NA mice

| Group | Vector genomes/kg |
|---|---|
| Control + Excipient | N/A |
| 4L/PS-NA + Excipient | N/A |
| 4L/PS-NA + PR001 Dose 1 | $9.5 \times 10^{12}$ |
| 4L/PS-NA + PR001 Dose 2 | $3.0 \times 10^{13}$ |
| 4L/PS-NA + PR001 Dose 3 | $9.5 \times 10^{13}$ |
| 4L/PS-NA + PR001 Dose 4 | $3.0 \times 10^{14}$ |

4L/PS-NA mice showed glycolipid accumulation in the liver which was reduced by PR001 treatment (FIG. 64A; FIG. 64B). 4L/PS-NA mice showed glycolipid accumulation in the brain which was reduced by PR001 treatment (FIG. 65A; FIG. 65B).

Example 15: Studies of rAAVs Encoding Inhibitory RNA Targeting α-Synuclein

HeLa cells were transduced with PR004 or PR014 at several multiplicities of infection (MOI). Both PR004 and PR014 decreased α-Synuclein protein levels in a dose-dependent manner (FIG. 66A). PR004 increased GCase activity in a dose-dependent manner (FIG. 66B).

PR004 efficacy was assessed in neuronal cultures from Parkinson's disease patient-derived induced pluripotent stem cells (iPSCs). Induced pluripotent stem cells derived from a Parkinson's disease patient with a SNCA triplication were differentiated into neurons (FIG. 67A). Neurons transduced with PR004 had increased GCase activity (FIG. 67B) and decreased α-Synuclein protein level (FIG. 67C).

No off-target effects of the PR004 rAAV vector were observed. Off-target effects of shRNA targeting SNCA from the PR004 vector were assessed in HEK293 cells by qRT-PCR. The expression of the 15 genes most similar in sequence to the target region of SNCA was evaluated (FIG. 68A). The expression of SNCA family members beta- and gamma-synuclein (SNCB and SNCG, respectively) was also evaluated (FIG. 68B). mRNA levels of these genes were not affected by PR004.

PR004 efficacy was assessed in the AAV2-SNCA-A53T AAV mouse model of Parkinson's disease (FIG. 69; FIG. 70). An AAV2 encoding human SNCA with the A53T mutation is directly injected into the substantia nigra of adult wild type mice. Starting at 4 weeks after injection, animals exhibit gait abnormalities, changes in dopamine metabolism, loss of dopaminergic neurons, neuroinflammation, and phosphorylated α-Synuclein expression. Automated kinematic gait analysis (MotoRater) was performed 4 weeks (FIG. 71A) and 9 weeks (FIG. 71B) after PR004 intracerebroventricular injection. A trend of a PR004 treatment effect was observed at both timepoints.

This Application incorporates by reference the contents of the following documents in their entirety: International PCT Application Publication No. WO 2019/070894; International PCT Application Publication No. WO 2019/070891; U.S. Provisional Application Ser. No. 62/567,311, filed Oct. 3, 2017, entitled "GENE THERAPIES FOR LYSOSOMAL DISORDERS"; 62/567,319, filed Oct. 3, 2017, entitled "GENE THERAPIES FOR LYSOSOMAL DISORDERS"; 62/567,301, filed Oct. 3, 2018, entitled "GENE THERAPIES FOR LYSOSOMAL DISORDERS"; 62/567,310, filed Oct. 3, 2017, entitled "GENE THERAPIES FOR LYSOSOMAL DISORDERS"; 62/567,303, filed Oct. 3, 2017, entitled "GENE THERAPIES FOR LYSOSOMAL DISORDERS"; and 62/567,305, filed Oct. 3, 2017, entitled "GENE THERAPIES FOR LYSOSOMAL DISORDERS".

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

Each of the U.S. patents, U.S. patent application publications, U.S. patent applications, foreign patents, foreign patent applications and non-patent publications referred to in this application is incorporated herein by reference, in its entirety.

SEQUENCES

In some embodiments, an expression cassette encoding one or more gene products (e.g., a first, second and/or third gene product) comprises or consists of (or encodes a peptide having) a sequence set forth in any one of SEQ ID NOs: 1, 2, 3, 4, 5, 6, 7, 8, 9, 10, 11, 12, 13, 14, 15, 16, 17, 18, 19, 20, 21, 22, 23, 24, 25, 32, 33, 34, 35, 36, 37, 38, 39, 40, 41, 42, 43, 44, 45, 46, 47, or 48. In some embodiments, a gene product is encoded by a portion (e.g., fragment) of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 32, 33, 34, 35, 36, 37, 38, 39, 40, 41, 42, 43, 44, 45, 46, 47, or 48.

NUMBERED EMBODIMENTS

Notwithstanding the appended claims, the disclosure sets forth the following numbered embodiments:

1. An isolated nucleic acid comprising an expression construct encoding a Gcase protein flanked by two adeno-associated virus (AAV) inverted terminal repeats (ITRs), wherein (i) at least one of the ITRs comprises a modified "D" region relative to a wild-type AAV2 ITR (SEQ ID NO: 29); and/or (ii) the Gcase is encoded by a codon optimized nucleic acid sequence.

2. The isolated nucleic acid of embodiment 1, wherein the Gcase protein comprises the amino acid sequence set forth in SEQ ID NO: 14 or a portion thereof.

3. The isolated nucleic acid of embodiment 1 or 2, wherein the Gcase protein is encoded by a codon-optimized nucleic acid sequence, optionally the nucleic acid sequence set forth in SEQ ID NO: 15.

4. The isolated nucleic acid of any one of embodiments 1 to 3, wherein the modified "D" region is a "D" sequence located on the outside of the ITR relative to the expression construct.

5. The isolated nucleic acid of any one of embodiments 1 to 4, wherein the ITR comprising the modified "D" sequence is a 3' ITR 6. The isolated nucleic acid of any one of embodiments 1 to 5, further comprising a TRY sequence, optionally wherein the TRY sequence is set forth in SEQ ID NO: 28.

7. An isolated nucleic acid comprising an expression construct encoding a prosaposin protein flanked by two adeno-associated virus (AAV) inverted terminal repeats (ITRs), wherein
(i) at least one of the ITRs comprises a modified "D" region relative to a wild-type AAV2 ITR (SEQ ID NO: 29); and/or
(ii) the prosaposin is encoded by a codon optimized nucleic acid sequence.
8. The isolated nucleic acid of embodiment 7, wherein the prosaposin protein comprises the amino acid sequence set forth in SEQ ID NO: 16 or a portion thereof.
9. The isolated nucleic acid of embodiment 7 or 8, wherein the prosaposin protein is encoded by a codon-optimized nucleic acid sequence, optionally the nucleic acid sequence set forth in SEQ ID NO: 17.
10. The isolated nucleic acid of any one of embodiments 7 to 9, wherein the modified "D" region is a "D" sequence located on the outside of the ITR relative to the expression construct.
11. The isolated nucleic acid of any one of embodiments 7 to 10, wherein the ITR comprising the modified "D" sequence is a 3' ITR.
12. The isolated nucleic acid of any one of embodiments 7 to 11, further comprising a TRY sequence, optionally wherein the TRY sequence is set forth in SEQ ID NO: 28.
13. An isolated nucleic acid comprising an expression construct encoding a SCARB2 protein flanked by two adeno-associated virus (AAV) inverted terminal repeats (ITRs), wherein
(i) at least one of the ITRs comprises a modified "D" region relative to a wild-type AAV2 ITR (SEQ ID NO: 29); and/or
(ii) the SCARB2 is encoded by a codon optimized nucleic acid sequence.
14. The isolated nucleic acid of embodiment 13, wherein the SCARB2 protein comprises the amino acid sequence set forth in SEQ ID NO: 18 or a portion thereof.
15. The isolated nucleic acid of embodiment 13 or 14, wherein the SCARB2 protein is encoded by a codon-optimized nucleic acid sequence or the nucleic acid sequence set forth in SEQ ID NO: 19.
16. The isolated nucleic acid of any one of embodiments 13 to 15, wherein the modified "D" region is a "D" sequence located on the outside of the ITR relative to the expression construct.
17. The isolated nucleic acid of any one of embodiments 13 to 16, wherein the ITR comprising the modified "D" sequence is a 3' ITR.
18. The isolated nucleic acid of any one of embodiments 13 to 17, further comprising a TRY sequence, optionally wherein the TRY sequence is set forth in SEQ ID NO: 28.
19. An isolated nucleic acid comprising an expression construct encoding a first gene product and a second gene product, wherein each gene product independently is selected from the gene products, or portions thereof, set forth in Table 1.
20. The isolated nucleic acid of embodiment 19, wherein the first gene product is a Gcase protein, or a portion thereof.
21. The isolated nucleic acid of embodiment 19 or embodiment 20, wherein the second gene product is LIMP2 or a portion thereof, or Prosaposin or a portion thereof.
22. The isolated nucleic acid of any one of embodiments 19 to 21, further encoding an interfering nucleic acid (e.g., shRNA, miRNA, dsRNA, etc.), optionally wherein the interfering nucleic acid inhibits expression of α-Syn.
23. The isolated nucleic acid of any one of embodiments 19 to 22, further comprising one or more promoters, optionally wherein each of the one or more promoters is independently a chicken-beta actin (CBA) promoter, a CAG promoter, a CD68 promoter, or a JeT promoter.
24. The isolated nucleic acid of any one of embodiments 19 to 23, further comprising an internal ribosomal entry site (IRES), optionally wherein the IRES is located between the first gene product and the second gene product.
25. The isolated nucleic acid of any one of embodiments 19 to 23, further comprising a self-cleaving peptide coding sequence, optionally wherein the self-cleaving peptide is T2A.
26. The isolated nucleic acid of any one of embodiments 19 to 24, wherein the expression construct comprises two adeno-associated virus (AAV) inverted terminal repeat (ITR) sequences flanking the first gene product and the second gene product, optionally wherein one of the ITR sequences lacks a functional terminal resolution site.
27. The isolated nucleic acids of embodiment 26, wherein at least one of the ITRs comprises a modified "D" region relative to a wild-type AAV2 ITR (SEQ ID NO: 29).
28. The isolated nucleic acid of embodiment 27, wherein the modified "D" region is a "D" sequence located on the outside of the ITR relative to the expression construct.
29. The isolated nucleic acid of embodiment 27 or 28, wherein the ITR comprising the modified "D" sequence is a 3' ITR.
30. The isolated nucleic acid of any one of embodiments 27 to 29, further comprising a TRY sequence, optionally wherein the TRY sequence is set forth in SEQ ID NO: 28.
31. The isolated nucleic acid of any one of embodiments 1 to 30 having the sequence set forth in any one of SEQ ID NOs: 1 to 12, 14, 16, and 18.
32. A vector comprising the isolated nucleic acid of any one of embodiments 1 to 31.
33. The vector of embodiment 32, wherein the vector is a plasmid.
34. The vector of embodiment 32, wherein the vector is a viral vector, optionally wherein the viral vector is a recombinant AAV (rAAV) vector or a Baculovirus vector.
35. A composition comprising the isolated nucleic acid of any one of embodiments 1 to 31 or the vector of any one of embodiments 32 to 34.
36. A host cell comprising the isolated nucleic acid of any one of embodiments 1 to 31 or the vector of any one of embodiments 32 to 34.
37. A recombinant adeno-associated virus (rAAV) comprising:
(i) a capsid protein; and
(ii) the isolated nucleic acid of any one of embodiments 1 to 31, or the vector of any one of embodiments 32 to 34.
38. The rAAV of embodiment 37, wherein the capsid protein is capable of crossing the blood-brain barrier, optionally wherein the capsid protein is an AAV9 capsid protein or an AAVrh.10 capsid protein.

39. The rAAV of embodiment 37 or embodiment 38, wherein the rAAV transduces neuronal cells and non-neuronal cells of the central nervous system (CNS).

40. A method for treating a subject having or suspected of having Parkinson's disease, the method comprising administering to the subject an isolated nucleic acid of any one of embodiments 1 to 31, the vector of any one of embodiments 32 to 34, the composition of embodiment 35, or the rAAV of any one of embodiments 37 to 39.

41. The method of embodiment 40, wherein the administration comprises direct injection to the CNS of the subject, optionally wherein the direct injection is intracerebral injection, intraparenchymal injection, intrathecal injection, intra-cisterna *magna* injection or any combination thereof 42. The method of embodiment 41, wherein the direct injection to the CNS of the subject comprises convection enhanced delivery (CED).

43. The method of any one of embodiments 40 to 42, wherein the administration comprises peripheral injection, optionally wherein the peripheral injection is intravenous injection.

44. A method for treating a subject having Type 2 Gaucher disease or Type 3 Gaucher disease, the method comprising administering to the subject a recombinant adeno-associated virus (rAAV) comprising:

(i) a rAAV vector comprising a nucleic acid comprising an expression construct comprising a promoter operably linked to a transgene insert encoding a glucocerebrosidase (Gcase) protein, wherein the transgene insert comprises the nucleotide sequence of SEQ ID NO: 15; and (ii) an AAV9 capsid protein.

45. The method of embodiment 44, wherein the rAAV is administered to the subject at a dose ranging from about $5\times10^{10}$ vg/g brain to about $5\times10^{11}$ vg/g brain.

46. The method of embodiment 44, wherein the rAAV is administered to the subject at a dose of about $1.3\times10^{11}$ vg/g brain.

47. A method for treating a subject having Parkinson's disease with a glucocerebrosidase-1 (GBA1) mutation, the method comprising administering to the subject a recombinant adeno-associated virus (rAAV) comprising:

(i) a rAAV vector comprising a nucleic acid comprising an expression construct comprising a promoter operably linked to a transgene insert encoding a Gcase protein, wherein the transgene insert comprises the nucleotide sequence of SEQ ID NO: 15; and (ii) an AAV9 capsid protein.

47. The method of embodiment 46, wherein the rAAV is administered to the subject at a dose ranging from about $5\times10^{13}$ vg to about $5\times10^{14}$ vg.

48. The method of embodiment 46, wherein the rAAV is administered to the subject at a dose of about $1\times10^{14}$ vg or about $2\times10^{14}$ vg.

49. The method of any one of embodiments 44-48, wherein the rAAV is administered via a suboccipital injection into the cisterna *magna.*

50. A method for treating a subject having Type 1 Gaucher disease, the method comprising administering to the subject a recombinant adeno-associated virus (rAAV) comprising:

(i) a rAAV vector comprising a nucleic acid comprising an expression construct comprising a promoter operably linked to a transgene insert encoding a Gcase protein, wherein the transgene insert comprises the nucleotide sequence of SEQ ID NO: 15; and (ii) an AAV9 capsid protein.

51. The method of embodiment 50, wherein the rAAV is administered to the subject at a dose ranging from about $5\times10^{13}$ vg to about $5\times10^{14}$ vg.

52. The method of embodiment 50 or 51, wherein the rAAV is administered intravenously.

53. A method for treating a subject having a synucleinopathy or parkinsonism, the method comprising administering to the subject a recombinant adeno-associated virus (rAAV) comprising:

(i) a rAAV vector comprising a nucleic acid comprising an expression construct comprising a transgene comprising (a) a Gcase protein coding sequence comprising the nucleotide sequence of SEQ ID NO: 15; and (b) an inhibitory nucleic acid coding sequence comprising the nucleotide sequence of SEQ ID NO: 20; and (ii) an AAV9 capsid protein.

54. A method for treating a subject having a synucleinopathy or parkinsonism, the method comprising administering to the subject a recombinant adeno-associated virus (rAAV) comprising:

(i) a rAAV vector comprising a nucleic acid comprising an expression construct comprising a transgene comprising an inhibitory nucleic acid coding sequence comprising the nucleotide sequence of SEQ ID NO: 20; and (ii) an AAV9 capsid protein.

55. The method of embodiment 53 or 54, wherein the synucleinopathy or parkinsonism is multiple system atrophy, Parkinson's disease, Parkinson's disease with GBA1 mutation, Lewy body disease, dementia with Lewy bodies, dementia with Lewy bodies with GBA1 mutation, progressive supranuclear palsy, or corticobasal syndrome.

56. The method of any one of embodiments 44-55, wherein the promoter is a chicken beta actin (CBA) promoter.

57. The method of any one of embodiments 44-56, wherein the rAAV vector further comprises a cytomegalovirus (CMV) enhancer.

58. The method of any one of embodiments 44-57, wherein the rAAV vector further comprises a Woodchuck Hepatitis Virus Posttranscriptional Regulatory Element (WPRE).

59. The method of any one of embodiments 44-58, wherein the rAAV vector further comprises a Bovine Growth Hormone polyA signal tail.

60. The method of any one of embodiments 44-59, wherein the nucleic acid comprises two adeno-associated virus inverted terminal repeats (ITR) sequences flanking the expression construct.

61. The method of embodiment 60, wherein each ITR sequence is a wild-type AAV2 ITR sequence.

62. The method of any one of embodiments 44-61, wherein the rAAV vector further comprises a TRY region between the 5' ITR and the expression construct, wherein the TRY region comprises SEQ ID NO: 28.

63. A method for treating a subject having Type 2 Gaucher disease or Type 3 Gaucher disease, the method comprising administering to the subject a rAAV comprising:

(i) a rAAV vector comprising a nucleic acid comprising, in 5' to 3' order:

(a) an AAV2 ITR;

(b) a CMV enhancer;

(c) a CBA promoter;

(d) a transgene insert encoding a Gcase protein, wherein the transgene insert comprises the nucleotide sequence of SEQ ID NO: 15;

(e) a WPRE;

(f) a Bovine Growth Hormone polyA signal tail; and (g) an AAV2 ITR; and (ii) an AAV9 capsid protein;

wherein the rAAV is administered to the subject at a dose ranging from about $5\times10^{10}$ vg/g brain to about $5\times10^{11}$ vg/g brain.

64. A method for treating a subject having Parkinson's disease with a GBA1 mutation, the method comprising administering to the subject a rAAV comprising:

(i) a rAAV vector comprising a nucleic acid comprising, in 5' to 3' order:

(a) an AAV2 ITR;

(b) a CMV enhancer;

(c) a CBA promoter;

(d) a transgene insert encoding a Gcase protein, wherein the transgene insert comprises the nucleotide sequence of SEQ ID NO: 15;

(e) a WPRE;

(f) a Bovine Growth Hormone polyA signal tail; and (g) an AAV2 ITR; and (ii) an AAV9 capsid protein;

wherein the rAAV is administered to the subject at a dose ranging from about $5\times10^{13}$ vg to about $5\times10^{14}$ vg.

65. The method of embodiment 63 or 64, wherein the rAAV is administered via a suboccipital injection into the cisterna *magna*.

66. The method of any one of embodiments 44-52 and 63-65, wherein the rAAV is administered in a formulation comprising about 20 mM Tris, pH 8.0, about 1 mM $MgCl_2$, about 200 mM NaCl, and about 0.001% w/v poloxamer 188.

67. A pharmaceutical composition comprising (i) a rAAV comprising:

(a) a rAAV vector comprising a nucleic acid comprising an expression construct comprising a promoter operably linked to a transgene insert a Gcase protein, wherein the transgene insert comprises the nucleotide sequence of SEQ ID NO: 15; and (b) an AAV9 capsid protein; and (ii) about 20 mM Tris, pH 8.0, (iii) about 1 mM $MgCl_2$, (iv) about 200 mM NaCl, and (v) about 0.001% w/v poloxamer 188.

68. A rAAV comprising:

(i) a rAAV vector comprising a nucleic acid comprising an expression construct comprising a promoter operably linked to a transgene insert encoding a Gcase protein, wherein the transgene insert comprises the nucleotide sequence of SEQ ID NO: 15; and (ii) an AAV9 capsid protein, for use in a method of treating Type 1 Gaucher disease, Type 2 Gaucher disease, Type 3 Gaucher disease or Parkinson's disease with a GBA1 mutation in a subject.

69. A rAAV comprising:

(i) a rAAV vector comprising a nucleic acid comprising an expression construct comprising a promoter operably linked to a transgene insert comprising:

(a) a Gcase protein coding sequence comprising the nucleotide sequence of SEQ ID NO: 15; and (b) an inhibitory nucleic acid coding sequence comprising the nucleotide sequence of SEQ ID NO: 20; and (ii) an AAV9 capsid protein, for use in a method of treating a synucleinopathy or parkinsonism in a subject.

70. A rAAV comprising:

(i) a rAAV vector comprising a nucleic acid comprising an expression construct comprising a promoter operably linked to a transgene insert comprising an inhibitory nucleic acid coding sequence comprising the nucleotide sequence of SEQ ID NO: 20; and (ii) an AAV9 capsid protein, for use in a method of treating a synucleinopathy or parkinsonism in a subject.

TABLE 14

Summary of Nonclinical In Vivo Pharmacology (Efficacy) Studies

| Study Number | Objective | Status | Results |
|---|---|---|---|
| PRV-2017-001 | Validate CBE mouse as a model of GCase deficiency | Completed | 25 mg/kg CBE recapitulates core features of GCase deficiency<br>Glycolipid (aggregate GluSph and galactosylsphingosine [GalSph]) accumulation relative to controls<br>Motor deficits in rotarod assay |
| PRV-2018-002 | Demonstrate efficacy of highest possible dose of PR001Ba in CBE mouse | Completed | Broad vector genome biodistribution of PR001B<br>Increase in GCase activity correlated with reduction of glycolipid substrate accumulation<br>Improved behavioral performance on rotarod assay<br>No PR001B-related adverse effects observed |
| PRV-2018-005 | Determine efficacious doses of ICV PR001A in CBE mouse model | Completed | Broad vector genome biodistribution of PR001A<br>Increase in GCase activity and reduction in abnormal glycolipid substrate accumulation<br>Reduction of astrogliosis and microgliosis<br>Improvement of motor behavior deficits<br>No PR001A-related adverse effects observed |
| PRV-2018-007 | Long-term (6 month) persistence of ICV PR001A in CBE mouse model | Completed | Vector genome persistence, durable increased GCase activity, and reduction in glycolipids 6 months post treatment<br>No PR001A-related adverse effects observed |
| PRV-2018-008 | Additional dose-ranging ICV PR001A in CBE mouse model | Completed | Broad vector genome biodistribution of PR001A<br>Increase in cortical GCase activity and reduction in abnormal glycolipid substrate accumulation<br>No PR001A-related adverse effects observed |

TABLE 14-continued

Summary of Nonclinical In Vivo Pharmacology (Efficacy) Studies

| Study Number | Objective | Status | Results |
|---|---|---|---|
| PRV-2018-025 | Further dose-ranging ICV PR001A in CBE mouse model | Ongoing | Cortical vector genome biodistribution of PR001A<br>Increase in cortical GCase activity and reduction in abnormal glycolipid substrate accumulation<br>Improvement of motor behavior deficits |
| PRV-2018-006 | Demonstrate efficacy of ICV PR001A in 4L/PS-NA mouse model | Completed | Broad vector genome biodistribution of PR001A<br>Increase GCase activity in CNS and periphery associated with reduction of glycolipid substrate accumulation<br>Trend towards improved motor behavior<br>Reduction in accumulation of insoluble cc-Synuclein<br>No PR001A-related adverse effects observed |
| PRV-2018-011 | Dose-ranging ICV PR001A in 4L/PS-NA genetic mouse model | Completed | Broad vector genome biodistribution of PR001A<br>Increase in GCase activity and reduction in abnormal glycolipid substrate accumulation<br>Improvement of motor behavior deficits<br>No PR001A-related adverse effects observed |
| PRV-2018-019 | Effect of ICV PR001A on α-Synuclein in transgenic mice treated with CBE | Ongoing | Cortical vector genome biodistribution of PR001A and reduction in glycolipids<br>Reduction in accumulation of insoluble α-Synuclein and ratio of insoluble to soluble accumulation of insoluble α-Synuclein<br>No PR001A-related adverse effects observed |
| PRV-2019-001 | Effect of ICV PR001A on α-Synuclein in transgenic mice treated with CBE | Ongoing | Cortical vector genome biodistribution of PR001A and increase in cortical GCase activity<br>No PR001A-related adverse effects observed |

Abbreviations: CBE, conduritol-β-epoxide; CNS, central nervous system; GCase, glucocerebrosidase; GluSph, glucosylsphingosine; ICV, intracerebroventricular; vg, vector genome.
[a]PR001B is a version of PR001A with an altered D domain; PR001A and PR001B are otherwise identical.

TABLE 15

Summary of Safety Evaluations in Mouse Efficacy Studies of PR001A

| Study Purpose | Study Number | Administration Route | Species | Dose (vg/g brain) | Total PR001A Dose (vg) | Injection Volume(s) (μl) | Necropsy Time Point[a] |
|---|---|---|---|---|---|---|---|
| Efficacy with select safety endpoints | PRV-2018-005 | ICV | CBE-injected C57BL/6J mice | $1.3 \times 10^{10}$<br>$4.2 \times 10^{10}$<br>$1.3 \times 10^{11}$ | $2.0 \times 10^{9}$<br>$6.2 \times 10^{9}$<br>$2.0 \times 10^{10}$ | 4 | Days 35-37 |
| Efficacy with select safety endpoints | PRV-2018-006 | ICV | 4L/PS-NA mice | $3.7 \times 10^{10}$ | $1.5 \times 10^{10}$ | 3 | Week 15 |

Abbreviations:
CBE, conduritol-β-epoxide;
ICV, intracerebroventricular;
vg, vector genome.
[a]Post-PR001A treatment

45

TABLE 16

Summary of Safety Evaluations in NHP Safety Studies of PR001A

| Study Purpose | Study Number | Administration Route | Species | Dose (vg/g brain) | Total PR001A Dose (vg) | Injection Volume(s) (μl) | Necropsy Time Point[a] |
|---|---|---|---|---|---|---|---|
| Pilot non-GLP toxicology | PRV-2018-015 | ICM<br>ICM + IPa (midbrain) | Cynomolgus monkeys | $2.0 \times 10^{11}$<br>$2.1 \times 10^{11}$ | $1.47 \times 10^{13}$<br>$1.53 \times 10^{13}$ | 500<br>520 | Day 18 |
| GLP toxicology | PRV-2018-016 | ICM | Cynomolgus monkeys | $6.2 \times 10^{10}$<br>$2.3 \times 10^{11}$ | $4.6 \times 10^{12}$<br>$1.7 \times 10^{13}$ | 1200 | Days 7, 30, 183 |
| Non-GLP toxicology | PRV-2019-005 | ICM | Cynomolgus monkeys | $7.0 \times 10^{11}$ | $5.2 \times 10^{13}$ | 1200 | Days 30, 90 |

Abbreviations:
GLP, Good Laboratory Practice;
ICM, intra-cisterna magna;
IPa, intraparenchymal;
NHP, nonhuman primate;
vg, vector genome.

What is claimed is:

1. A method for treating a subject having Type 2 Gaucher disease or Type 3 Gaucher disease, the method comprising administering to the subject a recombinant adeno-associated virus (rAAV) comprising:

(i) a rAAV vector comprising a nucleic acid comprising an expression construct comprising a promoter operably linked to a transgene insert encoding a glucocerebrosidase (Gcase) protein, wherein the transgene insert comprises the nucleotide sequence of SEQ ID NO: 15; and (ii) an AAV9 capsid protein;

wherein the rAAV is administered to the subject at a dose ranging from about $5\times10^{10}$ vg/g brain to about $5\times10^{11}$ vg/g brain.

2. The method of claim 1, wherein the rAAV is administered to the subject at a dose of about $1.3\times10^{11}$ vg/g brain.

3. The method of claim 1, wherein the rAAV is administered via a suboccipital injection into the cisterna *magna*.

4. A method for treating a subject having Type 1 Gaucher disease, the method comprising administering to the subject a recombinant adeno-associated virus (rAAV) comprising:

(i) a rAAV vector comprising a nucleic acid comprising an expression construct comprising a promoter operably linked to a transgene insert encoding a Gcase protein, wherein the transgene insert comprises the nucleotide sequence of SEQ ID NO: 15; and (ii) an AAV9 capsid protein.

5. The method of claim 4, wherein the rAAV is administered to the subject at a dose ranging from about $5\times10^{13}$ vg to about $5\times10^{14}$ vg.

6. The method of claim 4, wherein the rAAV is administered intravenously.

7. The method of claim 1, wherein the promoter is a chicken beta actin (CBA) promoter.

8. The method of claim 1, wherein the rAAV vector further comprises a cytomegalovirus (CMV) enhancer.

9. The method of claim 1, wherein the rAAV vector further comprises a Woodchuck Hepatitis Virus Posttranscriptional Regulatory Element (WPRE).

10. The method of claim 1, wherein the rAAV vector further comprises a Bovine Growth Hormone polyA signal tail.

11. The method of claim 1, wherein the nucleic acid comprises two adeno-associated virus inverted terminal repeat (ITR) sequences flanking the expression construct, wherein the first ITR sequence is a 5' ITR, and the second ITR sequence is a 3' ITR.

12. The method of claim 11, wherein each of the two ITR sequences is a wild-type AAV2 ITR sequence.

13. The method of claim 11, wherein the rAAV vector further comprises a TRY region between the 5' ITR and the expression construct, wherein the TRY region comprises SEQ ID NO: 28.

14. The method of claim 1, wherein the rAAV is administered in a formulation comprising about 20 mM Tris, pH 8.0, about 1 mM $MgCl_2$, about 200 mM NaCl, and about 0.001% w/v poloxamer 188.

15. A method for treating a subject having Type 2 Gaucher disease or Type 3 Gaucher disease, the method comprising administering to the subject a rAAV comprising:
- (i) a rAAV vector comprising a nucleic acid comprising, in 5' to 3' order:
  - (a) an AAV2 ITR;
  - (b) a CMV enhancer;
  - (c) a CBA promoter;
  - (d) a transgene insert encoding a Gcase protein, wherein the transgene insert comprises the nucleotide sequence of SEQ ID NO: 15;
  - (e) a WPRE;
  - (f) a Bovine Growth Hormone polyA signal tail; and
  - (g) an AAV2 ITR; and
- (ii) an AAV9 capsid protein;

wherein the rAAV is administered to the subject at a dose ranging from about $5\times10^{10}$ vg/g brain to about $5\times10^{11}$ vg/g brain.

16. The method of claim 15, wherein the rAAV is administered via a suboccipital injection into the cisterna *magna.*

17. The method of claim 15, wherein the rAAV is administered to the subject at a dose of about $1.3\times10^{11}$ vg/g brain.

18. The method of claim 15, wherein the rAAV is administered in a formulation comprising about 20 mM Tris, pH 8.0, about 1 mM $MgCl_2$, about 200 mM NaCl, and about 0.001% w/v poloxamer 188.

19. A method for treating a subject having Parkinson's disease with a glucocerebrosidase-1 (GBA1) mutation, the method comprising administering to the subject a recombinant adeno-associated virus (rAAV) comprising:
- (i) a rAAV vector comprising a nucleic acid comprising an expression construct comprising a promoter operably linked to a transgene insert encoding a Gcase protein, wherein the transgene insert comprises the nucleotide sequence of SEQ ID NO: 15; and
- (ii) an AAV9 capsid protein.

20. The method of claim 19, wherein the rAAV is administered to the subject at a dose ranging from about $5\times10^{13}$ vg to about $5\times10^{14}$ vg.

21. The method of claim 19, wherein the rAAV is administered to the subject at a dose of about $1\times10^{14}$ vg or about $2\times10^{14}$ vg.

22. The method of claim 19, wherein the rAAV is administered via a suboccipital injection into the cisterna *magna.*

23. A method for treating a subject having Parkinson's disease with a GBA1 mutation, the method comprising administering to the subject a rAAV comprising:
- (i) a rAAV vector comprising a nucleic acid comprising, in 5' to 3' order:
  - (a) an AAV2 ITR;
  - (b) a CMV enhancer;
  - (c) a CBA promoter;
  - (d) a transgene insert encoding a Gcase protein, wherein the transgene insert comprises the nucleotide sequence of SEQ ID NO: 15;
  - (e) a WPRE;
  - (f) a Bovine Growth Hormone polyA signal tail; and
  - (g) an AAV2 ITR; and
- (ii) an AAV9 capsid protein;

wherein the rAAV is administered to the subject at a dose ranging from about $5\times10^{13}$ vg to about $5\times10^{14}$ vg.

24. The method of claim 23, wherein the rAAV is administered via a suboccipital injection into the cisterna *magna.*

* * * * *

SEQUENCE LISTING

<160> NUMBER OF SEQ ID NOS: 48

<210> SEQ ID NO 1
<211> LENGTH: 10697
<212> TYPE: DNA
<213> ORGANISM: Artificial Sequence
<220> FEATURE:
<223> OTHER INFORMATION: Synthetic polynucleotide

<400> SEQUENCE: 1
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
cctagttatt aatagtaatc aattacgggg tcattagttc atagcccata tatggagttc 360
cgcgttacat aacttacggt aaatggcccg cctggctgac cgcccaacga cccccgccca 420
ttgacgtcaa taatgacgta tgttcccata gtaacgccaa tagggacttt ccattgacgt 480
caatgggtgg actatttacg gtaaactgcc cacttggcag tacatcaagt gtatcatatg 540
ccaagtacgc cccctattga cgtcaatgac ggtaaatggc ccgcctggca ttatgcccag 600
tacatgacct tatgggactt tcctacttgg cagtacatct acgtattagt catcgctatt 660
accatggtcg aggtgagccc cacgttctgc ttcactctcc ccatctcccc cccctcccca 720
cccccaattt tgtatttatt tattttttaa ttattttgtg cagcgatggg ggcggggggg 780 ggggggggc gcgcgccagg cggggcgggg cggggcgagg ggcggggcgg ggcgaggcgg 840
agaggtgcgg cggcagccaa tcagagcggc gcgctccgaa agtttccttt tatggcgagg 900
cggcggcggc ggcggcccta taaaaagcga agcgcgcggc gggcgggagt cgctgcgacg 960
ctgccttcgc cccgtgcccc gctccgccgc cgcctcgcgc cgcccgcccc ggctctgact 1020
gaccgcgtta ctcccacagg tgagcgggcg ggacggccct tctcctccgg gctgtaatta 1080
gcgcttggtt taatgacggc ttgtttcttg tggctgcgtg aaagccttga ggggctccgg 1140
gagctagagc ctctgctaac catgttcatg ccttcttctt tttcctacag ctcctgggca 1200
acgtgctggt tattgtgctg tctcatcatt ttggcaaaga attcctcgaa gatccgaagg 1260
gaaagtcttc cacgactgtg ggatccgttc gaagatatca ccggttgagc caccatggaa 1320
ttcagcagcc ccagcagaga ggaatgcccc aagcctctga gccgggtgtc aatcatggcc 1380
ggatctctga caggactgct gctgcttcag gccgtgtctt gggcttctgg cgctagacct 1440
tgcatcccca agagcttcgg ctacagcagc gtcgtgtgcg tgtgcaatgc cacctactgc 1500
gacagcttcg accctcctac ctttcctgct ctgggcacct tcagcagata cgagagcacc 1560
agatccggca gacggatgga actgagcatg ggacccatcc aggccaatca cacaggcact 1620
ggcctgctgc tgacactgca gcctgagcag aaattccaga aagtgaaagg cttcggcgga 1680
gccatgacag atgccgccgc tctgaatatc ctggctctgt ctccaccagc tcagaacctg 1740
ctgctcaaga gctacttcag cgaggaaggc atcggctaca acatcatcag agtgcccatg 1800
gccagctgcg acttcagcat caggacctac acctacgccg acacacccga cgatttccag 1860
ctgcacaact tcagcctgcc tgaagaggac accaagctga agatccctct gatccacaga 1920
gccctgcagc tggcacaaag acccgtgtca ctgctggcct ctccatggac atctcccacc 1980
tggctgaaaa caaatggcgc cgtgaatggc aagggcagcc tgaaaggcca acctggcgac 2040

-continued

```
atctaccacc agacctgggc cagatacttc gtgaagttcc tggacgccta tgccgagcac   2100
aagctgcagt tttgggccgt gacagccgag aacgaacctt ctgctggact gctgagcggc   2160
taccccttc agtgcctggg ctttacaccc gagcaccagc gggactttat cgcccgtgat    2220
ctgggaccca cactggccaa tagcacccac cataatgtgc ggctgctgat gctggacgac   2280
cagagactgc ttctgcccca ctgggctaaa gtggtgctga cagatcctga ggccgccaaa   2340
tacgtgcacg gaatcgccgt gcactggtat ctggactttc tggcccctgc caaggccaca   2400
ctgggagaga cacacagact gttccccaac accatgctgt tcgccagcga agcctgtgtg   2460
ggcagcaagt tttgggaaca gagcgtgcgg ctcggcagct gggatagagg catgcagtac   2520
agccacagca tcatcaccaa cctgctgtac cacgtcgtcg gctggaccga ctggaatctg   2580
gccctgaatc ctgaaggcgg ccctaactgg gtccgaaact tcgtggacag ccccatcatc   2640
gtggacatca ccaaggacac cttctacaag cagcccatgt tctaccacct gggacacttc   2700
agcaagttca tccccgaggg ctctcagcgc gttggactgg tggcttccca gaagaacgat   2760
ctggacgccg tggctctgat gcaccctgat ggatctgctg tggtggtggt cctgaaccgc   2820
agcagcaaag atgtgcccct gaccatcaag gatcccgccg tgggattcct ggaaacaatc   2880
agccctggct actccatcca cacctacctg tggcgtagac agtgacaatt gttaattaag   2940
tttaaaccct cgaggccgca agcttatcga taatcaacct ctggattaca aaatttgtga   3000
aagattgact ggtattctta actatgttgc tccttttacg ctatgtggat acgctgcttt   3060
aatgcctttg tatcatgcta ttgcttcccg tatggctttc attttctcct ccttgtataa   3120
atcctggttg ctgtctcttt atgaggagtt gtggcccgtt gtcaggcaac gtggcgtggt   3180
gtgcactgtg tttgctgacg caacccccac tggttggggc attgccacca cctgtcagct   3240
cctttccggg actttcgctt tccccctccc tattgccacg gcggaactca tcgccgcctg   3300
ccttgcccgc tgctggacag gggctcggct gttgggcact gacaattccg tggtgttgtc   3360
ggggaaatca tcgtcctttc cttggctgct cgcctgtgtt gccacctgga ttctgcgcgg   3420
gacgtccttc tgctacgtcc cttcggccct caatccagcg gaccttcctt cccgcggcct   3480
gctgccggct ctgcggcctc ttccgcgtct tcgccttcgc cctcagacga gtcggatctc   3540
cctttgggcc gcctccccgc atcgataccg tcgactagag ctcgctgatc agcctcgact   3600
gtgccttcta gttgccagcc atctgttgtt tgcccctccc ccgtgccttc cttgaccctg   3660
gaaggtgcca ctcccactgt cctttcctaa taaaatgagg aaattgcatc gcattgtctg   3720
agtaggtgtc attctattct ggggggtggg gtggggcagg acagcaaggg ggaggattgg   3780
gaagacaata gcaggcatgc tggggagaga tccacgataa caaacagctt ttttggggtg   3840
aacatattga ctgaattccc tgcaggttgg ccactccctc tctgcgcgct cgctcgctca   3900
ctgaggccgc ccgggcaaag cccgggcgtc gggcgacctt tggtcgcccg gcctcagtga   3960
gcgagcgagc gcgcagagag ggagtggcca actccatcac taggggttcc tgcggccgct   4020
cgtacggtct cgaggaattc ctgcaggata acttgccaac ctcattctaa aatgtatata   4080
gaagcccaaa agacaataac aaaaatattc ttgtagaaca aaatgggaaa gaatgttcca   4140
ctaaatatca agatttagag caaagcatga gatgtgtggg gatagacagt gaggctgata   4200
aaatagagta gagctcagaa acagacccat tgatatatgt aagtgaccta tgaaaaaaat   4260
atggcatttt acaatgggaa aatgatggtc tttttctttt ttagaaaaac agggaaatat   4320
atttatatgt aaaaaataaa agggaaccca tatgtcatac catacacaca aaaaaattcc   4380
```

agtgaattat aagtctaaat ggagaaggca aaactttaaa tcttttagaa aataatatag 4440
aagcatgcag accagcctgg ccaacatgat gaaaccctct ctactaataa taaaatcagt 4500
agaactactc aggactactt tgagtgggaa gtccttttct atgaagactt ctttggccaa 4560
aattaggctc taaatgcaag gagatagtgc atcatgcctg gctgcactta ctgataaatg 4620
atgttatcac catctttaac caaatgcaca ggaacaagtt atggtactga tgtgctggat 4680
tgagaaggag ctctacttcc ttgacaggac acatttgtat caacttaaaa aagcagattt 4740
ttgccagcag aactattcat tcagaggtag gaaacttaga atagatgatg tcactgatta 4800
gcatggcttc cccatctcca cagctgcttc ccacccaggt tgcccacagt tgagtttgtc 4860
cagtgctcag ggctgcccac tctcagtaag aagccccaca ccagcccctc tccaaatatg 4920
ttggctgttc cttccattaa agtgacccca ctttagagca gcaagtggat ttctgtttct 4980
tacagttcag gaaggaggag tcagctgtga gaacctggag cctgagatgc ttctaagtcc 5040
cactgctact ggggtcaggg aagccagact ccagcatcag cagtcaggag cactaagccc 5100
ttgccaacat cctgtttctc agagaaactg cttccattat aatggttgtc ctttttttaag 5160
ctatcaagcc aaacaaccag tgtctaccat tattctcatc acctgaagcc aagggttcta 5220
gcaaaagtca agctgtcttg taatggttga tgtgcctcca gcttctgtct tcagtcactc 5280
cactcttagc ctgctctgaa tcaactctga ccacagttcc ctggagcccc tgccacctgc 5340
tgcccctgcc accttctcca tctgcagtgc tgtgcagcct tctgcactct tgcagagcta 5400
ataggtggag acttgaagga agaggaggaa agtttctcat aatagccttg ctgcaagctc 5460
aaatgggagg tgggcactgt gcccaggagc cttggagcaa aggctgtgcc caacctctga 5520
ctgcatccag gtttggtctt gacagagata agaagccctg gcttttggag ccaaaatcta 5580
ggtcagactt aggcaggatt ctcaaagttt atcagcagaa catgaggcag aagacccttt 5640
ctgctccagc ttcttcaggc tcaaccttca tcagaataga tagaaagaga ggctgtgagg 5700
gttcttaaaa cagaagcaaa tctgactcag agaataaaca acctcctagt aaactacagc 5760
ttagacagag catctggtgg tgagtgtgct cagtgtccta ctcaactgtc tggtatcagc 5820
cctcatgagg acttctcttc tttccctcat agacctccat ctctgttttc cttagcctgc 5880
agaaatctgg atggctattc acagaatgcc tgtgctttca gagttgcatt ttttctctgg 5940
tattctggtt caagcatttg aaggtaggaa aggttctcca agtgcaagaa agccagccct 6000
gagcctcaac tgcctggcta gtgtggtcag taggatgcaa aggctgttga atgccacaag 6060
gccaaacttt aacctgtgta ccacaagcct agcagcagag gcagctctgc tcactggaac 6120
tctctgtctt ctttctcctg agccttttct tttcctgagt tttctagctc tcctcaacct 6180
tacctctgcc ctacccagga caaacccaag agccactgtt tctgtgatgt cctctccagc 6240
cctaattagg catcatgact tcagcctgac cttccatgct cagaagcagt gctaatccac 6300
ttcagatgag ctgctctatg caacacaggc agagcctaca aacctttgca ccagagccct 6360
ccacatatca gtgtttgttc atactcactt caacagcaaa tgtgactgct gagattaaga 6420
ttttacacaa gatggtctgt aatttcacag ttagttttat cccattaggt atgaaagaat 6480
tagcataatt ccccttaaac atgaatgaat cttagatttt ttaataaata gttttggaag 6540
taaagacaga gacatcagga gcacaaggaa tagcctgaga ggacaaacag aacaagaaag 6600
agtctggaaa tacacaggat gttcttggcc tcctcaaagc aagtgcaagc agatagtacc 6660
agcagcccca ggctatcaga gcccagtgaa gagaagtacc atgaaagcca cagctctaac 6720
caccctgttc cagagtgaca gacagtcccc aagacaagcc agcctgagcc agagagagaa 6780

```
ctgcaagaga aagtttctaa tttaggttct gttagattca gacaagtgca ggtcatcctc   6840
tctccacagc tactcacctc tccagcctaa caaagcctgc agtccacact ccaaccctgg   6900
tgtctcacct cctagcctct cccaacatcc tgctctctga ccatcttctg catctctcat   6960
ctcaccatct cccactgtct acagcctact cttgcaacta ccatctcatt ttctgacatc   7020
ctgtctacat cttctgccat actctgccat ctaccatacc acctcttacc atctaccaca   7080
ccatctttta tctccatccc tctcagaagc ctccaagctg aatcctgctt tatgtgttca   7140
tctcagcccc tgcatggaaa gctgacccca gaggcagaac tattcccaga gagcttggcc   7200
aagaaaaaca aaactaccag cctggccagg ctcaggagta gtaagctgca gtgtctgttg   7260
tgttctagct tcaacagctg caggagttcc actctcaaat gctccacatt tctcacatcc   7320
tcctgattct ggtcactacc catcttcaaa gaacagaata tctcacatca gcatactgtg   7380
aaggactagt catgggtgca gctgctcaga gctgcaaagt cattctggat ggtggagagc   7440
ttacaaacat ttcatgatgc tccccccgct ctgatggctg gagcccaatc cctacacaga   7500
ctcctgctgt atgtgtttc ctttcactct gagccacagc cagagggcag gcattcagtc    7560
tcctcttcag gctggggctg gggcactgag aactcaccca acaccttgct ctcactcctt   7620
ctgcaaaaca agaaagagct ttgtgctgca gtagccatga agaatgaaag gaaggcttta   7680
actaaaaaat gtcagagatt attttcaacc ccttactgtg gatcaccagc aaggaggaaa   7740
cacaacacag agacattttt tcccctcaaa ttatcaaaag aatcactgca tttgttaaag   7800
agagcaactg aatcaggaag cagagttttg aacatatcag aagttaggaa tctgcatcag   7860
agacaaatgc agtcatggtt gtttgctgca taccagccct aatcattaga agcctcatgg   7920
acttcaaaca tcattccctc tgacaagatg ctctagccta actccatgag ataaaataaa   7980
tctgcctttc agagccaaag aagagtccac cagcttcttc tcagtgtgaa caagagctcc   8040
agtcaggtta gtcagtccag tgcagtagag gagaccagtc tgcatcctct aattttcaaa   8100
ggcaagaaga tttgtttacc ctggacacca ggcacaagtg aggtcacaga gctcttagat   8160
atgcagtcct catgagtgag gagactaaag cgcatgccat caagacttca gtgtagagaa   8220
aacctccaaa aaagcctcct cactacttct ggaatagctc agaggccgag gcggcctcgg   8280
cctctgcata aataaaaaaa attagtcagc catggggcgg agaatgggcg gaactgggcg   8340
gagttagggg cgggatgggc ggagttaggg gcgggactat ggttgctgac taattgagat   8400
gcatgctttg catacttctg cctgctgggg agcctgggga ctttccacac ctggttgctg   8460
actaattgag atgcatgctt tgcatacttc tgcctgctgg ggagcctggg gactttccac   8520
accctaactg acacacattc cacagctgca ttaatgaatc ggccaacgcg cggggagagg   8580
cggtttgcgt attgggcgct cttccgcttc ctcgctcact gactcgctgc gctcggtcgt   8640
tcggctgcgg cgagcggtat cagctcactc aaaggcggta atacggttat ccacagaatc   8700
aggggataac gcaggaaaga acatgtgagc aaaaggccag caaaaggcca ggaaccgtaa   8760
aaaggccgcg ttgctggcgt ttttccatag gctccgcccc cctgacgagc atcacaaaaa   8820
tcgacgctca agtcagaggt ggcgaaaccc gacaggacta taaagatacc aggcgtttcc   8880
ccctggaagc tccctcgtgc gctctcctgt tccgaccctg ccgcttaccg gatacctgtc   8940
cgcctttctc ccttcgggaa gcgtggcgct ttctcatagc tcacgctgta ggtatctcag   9000
ttcggtgtag gtcgttcgct ccaagctggg ctgtgtgcac gaaccccccg ttcagcccga   9060
ccgctgcgcc ttatccggta actatcgtct tgagtccaac ccggtaagac acgacttatc   9120
```

gccactggca gcagccactg gtaacaggat tagcagagcg aggtatgtag gcggtgctac 9180
agagttcttg aagtggtggc ctaactacgg ctacactaga agaacagtat ttggtatctg 9240
cgctctgctg aagccagtta ccttcggaaa aagagttggt agctcttgat ccggcaaaca 9300
aaccaccgct ggtagcggtg gtttttttgt ttgcaagcag cagattacgc gcagaaaaaa 9360
aggatctcaa gaagatcctt tgatcttttc tacggggtct gacgctcagt ggaacgaaaa 9420
ctcacgttaa gggattttgg tcatgagatt atcaaaaagg atcttcacct agatcctttt 9480
aaattaaaaa tgaagtttta aatcaatcta aagtatatat gagtaaactt ggtctgacag 9540
ttaccaatgc ttaatcagtg aggcacctat ctcagcgatc tgtctatttc gttcatccat 9600
agttgcctga ctcctgcaaa ccacgttgtg tctcaaaatc tctgatgtta cattgcacaa 9660
gataaaaata tatcatcatg aacaataaaa ctgtctgctt acataaacag taatacaagg 9720
ggtgttatga gccatattca acgggaaacg tcttgctcga ggccgcgatt aaattccaac 9780
atggatgctg atttatatgg gtataaatgg gctcgcgata atgtcgggca atcaggtgcg 9840
acaatctatc gattgtatgg gaagcccgat gcgccagagt tgtttctgaa acatggcaaa 9900
ggtagcgttg ccaatgatgt tacagatgag atggtcagac taaactggct gacggaattt 9960
atgcctcttc cgaccatcaa gcattttatc cgtactcctg atgatgcatg gttactcacc 10020
actgcgatcc ccgggaaaac agcattccag gtattagaag aatatcctga ttcaggtgaa 10080
aatattgttg atgcgctggc agtgttcctg cgccggttgc attcgattcc tgtttgtaat 10140
tgtcctttta acagcgatcg cgtatttcgt ctcgctcagg cgcaatcacg aatgaataac 10200
ggtttggttg atgcgagtga ttttgatgac gagcgtaatg gctggcctgt tgaacaagtc 10260
tggaaagaaa tgcataagct tttgccattc tcaccggatt cagtcgtcac tcatggtgat 10320
ttctcacttg ataaccttat ttttgacgag gggaaattaa taggttgtat tgatgttgga 10380
cgagtcggaa tcgcagaccg ataccaggat cttgccatcc tatggaactg cctcggtgag 10440
ttttctcctt cattacagaa acggcttttt caaaaatatg gtattgataa tcctgatatg 10500
aataaattgc agtttcattt gatgctcgat gagtttttct aagggcggcc tgccaccata 10560
cccacgccga aacaagcgct catgagcccg aagtggcgag cccgatcttc cccatcggtg 10620
atgtcggcga tataggcgcc agcaaccgca cctgtggcgc cggtgatgag ggcgcgccaa 10680
gtcgacgtcc ggcagtc 10697

<210> SEQ ID NO 2
<211> LENGTH: 11355
<212> TYPE: DNA
<213> ORGANISM: Artificial Sequence
<220> FEATURE:
<223> OTHER INFORMATION: Synthetic polynucleotide

<400> SEQUENCE: 2
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg agggcggagt 300
tagggcggag ccaatcagcg tgcgccgttc cgaaagttgc cttttatggc tgggcggaga 360
atgggcggtg aacgccgatg attatataag gacgcgccgg gtgtggcaca gctagttccg 420
tcgcagccgg gatttgggtc gcggttcttg tttgtggatc cctgtgatcg tcacttggta 480

```
agtcactgac tgtctatgcc tgggaaaggg tgggcaggag atggggcagt gcaggaaaag    540
tggcactatg aaccctgcag ccctaggaat gcatctagac aattgtacta accttcttct    600
ctttcctctc ctgacagtcc ggaaagccac catgggccgc tgctgcttct acaccgccgg    660
caccctgagc ctgctgctgc tggtgaccag cgtgaccctg ctggtggccc gcgtgttcca    720
gaaggccgtg gaccagagca tcgagaagaa gatcgtgctg cgcaacggca ccgaggcctt    780
cgacagctgg gagaagcccc ccctgcccgt gtacacccag ttctacttct tcaacgtgac    840
caaccccgag gagatcctgc gcggcgagac cccccgcgtg gaggaggtgg gcccctacac    900
ctaccgcgag ctgcgcaaca aggccaacat ccagttcggc gacaacggca ccaccatcag    960
cgccgtgagc aacaaggcct acgtgttcga gcgcgaccag agcgtgggcg accccaagat   1020
cgacctgatc cgcaccctga acatccccgt gctgaccgtg atcgagtgga gccaggtgca   1080
cttcctgcgc gagatcatcg aggccatgct gaaggcctac cagcagaagc tgttcgtgac   1140
ccacaccgtg gacgagctgc tgtggggcta caaggacgag atcctgagcc tgatccacgt   1200
gttccgcccc gacatcagcc cctacttcgg cctgttctac gagaagaacg gcaccaacga   1260
cggcgactac gtgttcctga ccggcgagga cagctacctg aacttcacca agatcgtgga   1320
gtggaacggc aagaccagcc tggactggtg gatcaccgac aagtgcaaca tgatcaacgg   1380
caccgacggc gacagcttcc acccccctgat caccaaggac gaggtgctgt acgtgttccc   1440
cagcgacttc tgccgcagcg tgtacatcac cttcagcgac tacgagagcg tgcagggcct   1500
gcccgccttc cgctacaagg tgcccgccga gatcctggcc aacaccagcg acaacgccgg   1560
cttctgcatc cccgagggca actgcctggg cagcggcgtg ctgaacgtga gcatctgcaa   1620
gaacggcgcc cccatcatca tgagcttccc ccacttctac caggccgacg agcgcttcgt   1680
gagcgccatc gagggcatgc accccaacca ggaggaccac gagaccttcg tggacatcaa   1740
ccccctgacc ggcatcatcc tgaaggccgc caagcgcttc cagatcaaca tctacgtgaa   1800
gaagctggac gacttcgtgg agaccggcga catccgcacc atggtgttcc ccgtgatgta   1860
cctgaacgag agcgtgcaca tcgacaagga gaccgccagc cgcctgaaga gcatgatcaa   1920
caccaccctg atcatcacca acatccccta catcatcatg gccctgggcg tgttcttcgg   1980
cctggtgttc acctggctgg cctgcaaggg ccagggcagc atggacgagg gcaccgccga   2040
cgagcgcgcc cccctgatcc gcacctgatt gtggccgaac cgccgaactc agaggccggc   2100
cccagaaaac ccgagcgagt agggggcggc gcgcaggagg gaggagaact gggggcgcgg   2160
gaggctggtg ggtgtggggg gtggagatgt agaagatgtg acgccgcggc ccggcgggtg   2220
ccagattagc ggacgcggtg cccgcggttg caacgggatc ccgggcgctg cagcttggga   2280
ggcggctctc cccaggcggc gtccgcggag acacccatcc gtgaacccca ggtcccgggc   2340
cgccggctcg ccgcgcacca ggggccggcg gacagaagag cggccgagcg gctcgaggct   2400
gggggaccgc gggcgcggcc gcgcgctgcc gggcgggagg ctgggggggcc ggggccgggg   2460
ccgtgccccg gagcgggtcg gaggccgggg ccggggccgg gggacggcgg ctccccgcgc   2520
ggctccagcg gctcggggat cccggccggg ccccgcaggg accatgatgg aattcagcag   2580
ccccagcaga gaggaatgcc ccaagcctct gagccgggtg tcaatcatgg ccggatctct   2640
gacaggactg ctgctgcttc aggccgtgtc ttgggcttct ggcgctagac cttgcatccc   2700
caagagcttc ggctacagca gcgtcgtgtg cgtgtgcaat gccacctact gcgacagctt   2760
cgaccctcct acctttcctg ctctgggcac cttcagcaga tacgagagca ccagatccgg   2820
```

```
cagacggatg gaactgagca tgggacccat ccaggccaat cacacaggca ctggcctgct   2880
gctgacactg cagcctgagc agaaattcca gaaagtgaaa ggcttcggcg gagccatgac   2940
agatgccgcc gctctgaata tcctggctct gtctccacca gctcagaacc tgctgctcaa   3000
gagctacttc agcgaggaag gcatcggcta caacatcatc agagtgccca tggccagctg   3060
cgacttcagc atcaggacct acacctacgc cgacacaccc gacgatttcc agctgcacaa   3120
cttcagcctg cctgaagagg acaccaagct gaagatccct ctgatccaca gagccctgca   3180
gctggcacaa agacccgtgt cactgctggc ctctccatgg acatctccca cctggctgaa   3240
aacaaatggc gccgtgaatg gcaagggcag cctgaaaggc caacctggcg acatctacca   3300
ccagacctgg gccagatact tcgtgaagtt cctggacgcc tatgccgagc acaagctgca   3360
gttttgggcc gtgacagccg agaacgaacc ttctgctgga ctgctgagcg gctacccctt   3420
tcagtgcctg ggctttacac ccgagcacca gcgggacttt atcgcccgtg atctgggacc   3480
cacactggcc aatagcaccc accataatgt gcggctgctg atgctggacg accagagact   3540
gcttctgccc cactgggcta aagtggtgct gacagatcct gaggccgcca aatacgtgca   3600
cggaatcgcc gtgcactggt atctggactt tctggcccct gccaaggcca cactgggaga   3660
gacacacaga ctgttcccca acaccatgct gttcgccagc gaagcctgtg tgggcagcaa   3720
gttttgggaa cagagcgtgc ggctcggcag ctgggataga ggcatgcagt acagccacag   3780
catcatcacc aacctgctgt accacgtcgt cggctggacc gactggaatc tggccctgaa   3840
tcctgaaggc ggccctaact gggtccgaaa cttcgtggac agccccatca tcgtggacat   3900
caccaaggac accttctaca agcagcccat gttctaccac ctgggacact tcagcaagtt   3960
catccccgag ggctctcagc gcgttggact ggtggcttcc cagaagaacg atctggacgc   4020
cgtggctctg atgcaccctg atggatctgc tgtggtggtg gtcctgaacc gcagcagcaa   4080
agatgtgccc ctgaccatca aggatcccgc cgtgggattc ctggaaacaa tcagccctgg   4140
ctactccatc cacacctacc tgtggcgtag acagtgacaa ttgttaatta agtttaaacc   4200
ctcgaggccg caagccgcat cgataccgtc gactagagct cgctgatcag cctcgactgt   4260
gccttctagt tgccagccat ctgttgtttg cccctccccc gtgccttcct tgaccctgga   4320
aggtgccact cccactgtcc tttcctaata aaatgaggaa attgcatcgc attgtctgag   4380
taggtgtcat tctattctgg ggggtggggt ggggcaggac agcaaggggg aggattggga   4440
agacaatagc aggcatgctg gggagagatc cacgataaca aacagctttt ttggggtgaa   4500
catattgact gaattccctg caggttggcc actccctctc tgcgcgctcg ctcgctcact   4560
gaggccgccc gggcaaagcc cgggcgtcgg gcgacctttg gtcgcccggc ctcagtgagc   4620
gagcgagcgc gcagagaggg agtggccaac tccatcacta ggggttcctg cggccgctcg   4680
tacggtctcg aggaattcct gcaggataac ttgccaacct cattctaaaa tgtatataga   4740
agcccaaaag acaataacaa aaatattctt gtagaacaaa atgggaaaga atgttccact   4800
aaatatcaag atttagagca aagcatgaga tgtgtggggga tagacagtga ggctgataaa   4860
atagagtaga gctcagaaac agacccattg atatatgtaa gtgacctatg aaaaaaatat   4920
ggcattttac aatgggaaaa tgatggtctt tttctttttt agaaaaacag ggaaatatat   4980
ttatatgtaa aaaataaaag ggaacccata tgtcatacca tacacacaaa aaaattccag   5040
tgaattataa gtctaaatgg agaaggcaaa actttaaatc ttttagaaaa taatatagaa   5100
gcatgcagac cagcctggcc aacatgatga aaccctctct actaataata aaatcagtag   5160
aactactcag gactactttg agtgggaagt ccttttctat gaagacttct ttggccaaaa   5220
```

ttaggctcta aatgcaagga gatagtgcat catgcctggc tgcacttact gataaatgat 5280
gttatcacca tctttaacca aatgcacagg aacaagttat ggtactgatg tgctggattg 5340
agaaggagct ctacttcctt gacaggacac atttgtatca acttaaaaaa gcagattttt 5400
gccagcagaa ctattcattc agaggtagga aacttagaat agatgatgtc actgattagc 5460
atggcttccc catctccaca gctgcttccc acccaggttg cccacagttg agtttgtcca 5520
gtgctcaggg ctgcccactc tcagtaagaa gccccacacc agcccctctc caaatatgtt 5580
ggctgttcct tccattaaag tgaccccact ttagagcagc aagtggattt ctgtttctta 5640
cagttcagga aggaggagtc agctgtgaga acctggagcc tgagatgctt ctaagtccca 5700
ctgctactgg ggtcagggaa gccagactcc agcatcagca gtcaggagca ctaagccctt 5760
gccaacatcc tgtttctcag agaaactgct tccattataa tggttgtcct tttttaagct 5820
atcaagccaa acaaccagtg tctaccatta ttctcatcac ctgaagccaa gggttctagc 5880
aaaagtcaag ctgtcttgta atggttgatg tgcctccagc ttctgtcttc agtcactcca 5940
ctcttagcct gctctgaatc aactctgacc acagttccct ggagcccctg ccacctgctg 6000
cccctgccac cttctccatc tgcagtgctg tgcagccttc tgcactcttg cagagctaat 6060
aggtggagac ttgaaggaag aggaggaaag tttctcataa tagccttgct gcaagctcaa 6120
atgggaggtg ggcactgtgc ccaggagcct tggagcaaag gctgtgccca acctctgact 6180
gcatccaggt ttggtcttga cagagataag aagccctggc ttttggagcc aaaatctagg 6240
tcagacttag gcaggattct caaagtttat cagcagaaca tgaggcagaa gaccctttct 6300
gctccagctt cttcaggctc aaccttcatc agaatagata gaaagagagg ctgtgagggt 6360
tcttaaaaca gaagcaaatc tgactcagag aataaacaac ctcctagtaa actacagctt 6420
agacagagca tctggtggtg agtgtgctca gtgtcctact caactgtctg gtatcagccc 6480
tcatgaggac ttctcttctt tccctcatag acctccatct ctgttttcct tagcctgcag 6540
aaatctggat ggctattcac agaatgcctg tgctttcaga gttgcatttt ttctctggta 6600
ttctggttca agcatttgaa ggtaggaaag gttctccaag tgcaagaaag ccagccctga 6660
gcctcaactg cctggctagt gtggtcagta ggatgcaaag gctgttgaat gccacaaggc 6720
caaactttaa cctgtgtacc acaagcctag cagcagaggc agctctgctc actggaactc 6780
tctgtcttct ttctcctgag ccttttcttt tcctgagttt tctagctctc ctcaacctta 6840
cctctgccct acccaggaca aacccaagag ccactgtttc tgtgatgtcc tctccagccc 6900
taattaggca tcatgacttc agcctgacct tccatgctca gaagcagtgc taatccactt 6960
cagatgagct gctctatgca acacaggcag agcctacaaa cctttgcacc agagccctcc 7020
acatatcagt gtttgttcat actcacttca acagcaaatg tgactgctga gattaagatt 7080
ttacacaaga tggtctgtaa tttcacagtt agttttatcc cattaggtat gaaagaatta 7140
gcataattcc ccttaaacat gaatgaatct tagatttttt aataaatagt tttggaagta 7200
aagacagaga catcaggagc acaaggaata gcctgagagg acaaacagaa caagaaagag 7260
tctggaaata cacaggatgt tcttggcctc ctcaaagcaa gtgcaagcag atagtaccag 7320
cagccccagg ctatcagagc ccagtgaaga gaagtaccat gaaagccaca gctctaacca 7380
ccctgttcca gagtgacaga cagtccccaa gacaagccag cctgagccag agagagaact 7440
gcaagagaaa gtttctaatt taggttctgt tagattcaga caagtgcagg tcatcctctc 7500
tccacagcta ctcacctctc cagcctaaca aagcctgcag tccacactcc aaccctggtg 7560

-continued

```
tctcacctcc tagcctctcc caacatcctg ctctctgacc atcttctgca tctctcatct   7620
caccatctcc cactgtctac agcctactct tgcaactacc atctcatttt ctgacatcct   7680
gtctacatct tctgccatac tctgccatct accataccac ctcttaccat ctaccacacc   7740
atcttttatc tccatccctc tcagaagcct ccaagctgaa tcctgcttta tgtgttcatc   7800
tcagcccctg catggaaagc tgaccccaga ggcagaacta ttcccagaga gcttggccaa   7860
gaaaaacaaa actaccagcc tggccaggct caggagtagt aagctgcagt gtctgttgtg   7920
ttctagcttc aacagctgca ggagttccac tctcaaatgc tccacatttc tcacatcctc   7980
ctgattctgg tcactaccca tcttcaaaga acagaatatc tcacatcagc atactgtgaa   8040
ggactagtca tgggtgcagc tgctcagagc tgcaaagtca ttctggatgg tggagagctt   8100
acaaacattt catgatgctc cccccgctct gatggctgga gcccaatccc tacacagact   8160
cctgctgtat gtgttttcct ttcactctga gccacagcca gagggcaggc attcagtctc   8220
ctcttcaggc tggggctggg gcactgagaa ctcacccaac accttgctct cactccttct   8280
gcaaaacaag aaagagcttt gtgctgcagt agccatgaag aatgaaagga aggctttaac   8340
taaaaaatgt cagagattat tttcaacccc ttactgtgga tcaccagcaa ggaggaaaca   8400
caacacagag acatttttc ccctcaaatt atcaaaagaa tcactgcatt tgttaaagag   8460
agcaactgaa tcaggaagca gagttttgaa catatcagaa gttaggaatc tgcatcagag   8520
acaaatgcag tcatggttgt ttgctgcata ccagccctaa tcattagaag cctcatggac   8580
ttcaaacatc attccctctg acaagatgct ctagcctaac tccatgagat aaaataaatc   8640
tgcctttcag agccaaagaa gagtccacca gcttcttctc agtgtgaaca agagctccag   8700
tcaggttagt cagtccagtg cagtagagga gaccagtctg catcctctaa ttttcaaagg   8760
caagaagatt tgtttaccct ggacaccagg cacaagtgag gtcacagagc tcttagatat   8820
gcagtcctca tgagtgagga gactaaagcg catgccatca agacttcagt gtagagaaaa   8880
cctccaaaaa agcctcctca ctacttctgg aatagctcag aggccgaggc ggcctcggcc   8940
tctgcataaa taaaaaaaat tagtcagcca tggggcggag aatgggcgga actgggcgga   9000
gttaggggcg ggatgggcgg agttaggggc gggactatgg ttgctgacta attgagatgc   9060
atgctttgca tacttctgcc tgctggggag cctggggact ttccacacct ggttgctgac   9120
taattgagat gcatgctttg catacttctg cctgctgggg agcctgggga ctttccacac   9180
cctaactgac acacattcca cagctgcatt aatgaatcgg ccaacgcgcg gggagaggcg   9240
gtttgcgtat tgggcgctct tccgcttcct cgctcactga ctcgctgcgc tcggtcgttc   9300
ggctgcggcg agcggtatca gctcactcaa aggcggtaat acggttatcc acagaatcag   9360
gggataacgc aggaaagaac atgtgagcaa aaggccagca aaaggccagg aaccgtaaaa   9420
aggccgcgtt gctggcgttt ttccataggc tccgcccccc tgacgagcat cacaaaaatc   9480
gacgctcaag tcagaggtgg cgaaacccga caggactata aagataccag gcgtttcccc   9540
ctggaagctc cctcgtgcgc tctcctgttc cgaccctgcc gcttaccgga tacctgtccg   9600
cctttctccc ttcgggaagc gtggcgcttt ctcatagctc acgctgtagg tatctcagtt   9660
cggtgtaggt cgttcgctcc aagctgggct gtgtgcacga accccccgtt cagcccgacc   9720
gctgcgcctt atccggtaac tatcgtcttg agtccaaccc ggtaagacac gacttatcgc   9780
cactggcagc agccactggt aacaggatta gcagagcgag gtatgtaggc ggtgctacag   9840
agttcttgaa gtggtggcct aactacggct acactagaag aacagtattt ggtatctgcg   9900
ctctgctgaa gccagttacc ttcggaaaaa gagttggtag ctcttgatcc ggcaaacaaa   9960
```

ccaccgctgg tagcggtggt ttttttgttt gcaagcagca gattacgcgc agaaaaaaag 10020
gatctcaaga agatcctttg atcttttcta cggggtctga cgctcagtgg aacgaaaact 10080
cacgttaagg gattttggtc atgagattat caaaaaggat cttcacctag atcctttttaa 10140 attaaaaatg aagttttaaa tcaatctaaa gtatatatga gtaaacttgg tctgacagtt 10200
accaatgctt aatcagtgag gcacctatct cagcgatctg tctatttcgt tcatccatag 10260
ttgcctgact cctgcaaacc acgttgtgtc tcaaaatctc tgatgttaca ttgcacaaga 10320
taaaaatata tcatcatgaa caataaaact gtctgcttac ataaacagta atacaagggg 10380
tgttatgagc catattcaac gggaaacgtc ttgctcgagg ccgcgattaa attccaacat 10440
ggatgctgat ttatatgggt ataaatgggc tcgcgataat gtcgggcaat caggtgcgac 10500
aatctatcga ttgtatggga agcccgatgc gccagagttg tttctgaaac atggcaaagg 10560
tagcgttgcc aatgatgtta cagatgagat ggtcagacta aactggctga cggaatttat 10620
gcctcttccg accatcaagc attttatccg tactcctgat gatgcatggt tactcaccac 10680
tgcgatcccc gggaaaacag cattccaggt attagaagaa tatcctgatt caggtgaaaa 10740
tattgttgat gcgctggcag tgttcctgcg ccggttgcat tcgattcctg tttgtaattg 10800
tccttttaac agcgatcgcg tatttcgtct cgctcaggcg caatcacgaa tgaataacgg 10860
tttggttgat gcgagtgatt ttgatgacga gcgtaatggc tggcctgttg aacaagtctg 10920
gaaagaaatg cataagcttt tgccattctc accggattca gtcgtcactc atggtgattt 10980
ctcacttgat aaccttattt ttgacgaggg gaaattaata ggttgtattg atgttggacg 11040
agtcggaatc gcagaccgat accaggatct tgccatccta tggaactgcc tcggtgagtt 11100
ttctccttca ttacagaaac ggctttttca aaaatatggt attgataatc ctgatatgaa 11160
taaattgcag tttcatttga tgctcgatga gtttttctaa gggcggcctg ccaccatacc 11220
cacgccgaaa caagcgctca tgagcccgaa gtggcgagcc cgatcttccc catcggtgat 11280
gtcggcgata taggcgccag caaccgcacc tgtggcgccg gtgatgaggg cgcgccaagt 11340
cgacgtccgg cagtc 11355

<210> SEQ ID NO 3
<211> LENGTH: 11420
<212> TYPE: DNA
<213> ORGANISM: Artificial Sequence
<220> FEATURE:
<223> OTHER INFORMATION: Synthetic polynucleotide

<400> SEQUENCE: 3
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg agggcggagt 300
tagggcggag ccaatcagcg tgcgccgttc cgaaagttgc cttttatggc tgggcggaga 360
atgggcggtg aacgccgatg attatataag gacgcgccgg gtgtggcaca gctagttccg 420
tcgcagccgg gatttgggtc gcggttcttg tttgtggatc cctgtgatcg tcacttggta 480
agtcactgac tgtctatgcc tgggaaaggg tgggcaggag atggggcagt gcaggaaaag 540
tggcactatg aaccctgcag ccctaggaat gcatctagac aattgtacta accttcttct 600

-continued

```
ctttcctctc ctgacagtcc ggaaagccac catggaattc agcagcccca gcagagagga    660
atgccccaag cctctgagcc gggtgtcaat catggccgga tctctgacag gactgctgct    720
gcttcaggcc gtgtcttggg cttctggcgc tagaccttgc atccccaaga gcttcggcta    780
cagcagcgtc gtgtgcgtgt gcaatgccac ctactgcgac agcttcgacc ctcctacctt    840
tcctgctctg ggcaccttca gcagatacga gagcaccaga tccggcagac ggatggaact    900
gagcatggga cccatccagg ccaatcacac aggcactggc ctgctgctga cactgcagcc    960
tgagcagaaa ttccagaaag tgaaaggctt cggcggagcc atgacagatg ccgccgctct   1020
gaatatcctg gctctgtctc caccagctca gaacctgctg ctcaagagct acttcagcga   1080
ggaaggcatc ggctacaaca tcatcagagt gcccatggcc agctgcgact tcagcatcag   1140
gacctacacc tacgccgaca cacccgacga tttccagctg cacaacttca gcctgcctga   1200
agaggacacc aagctgaaga tccctctgat ccacagagcc ctgcagctgg cacaaagacc   1260
cgtgtcactg ctggcctctc catggacatc tcccacctgg ctgaaaacaa atggcgccgt   1320
gaatggcaag ggcagcctga aaggccaacc tggcgacatc taccaccaga cctgggccag   1380
atacttcgtg aagttcctgg acgcctatgc cgagcacaag ctgcagtttt gggccgtgac   1440
agccgagaac gaaccttctg ctggactgct gagcggctac ccctttcagt gcctgggctt   1500
tacacccgag caccagcggg actttatcgc ccgtgatctg ggacccacac tggccaatag   1560
cacccaccat aatgtgcggc tgctgatgct ggacgaccag agactgcttc tgccccactg   1620
ggctaaagtg gtgctgacag atcctgaggc cgccaaatac gtgcacggaa tcgccgtgca   1680
ctggtatctg gactttctgg cccctgccaa ggccacactg ggagagacac acagactgtt   1740
ccccaacacc atgctgttcg ccagcgaagc ctgtgtgggc agcaagtttt gggaacagag   1800
cgtgcggctc ggcagctggg atagaggcat gcagtacagc cacagcatca tcaccaacct   1860
gctgtaccac gtcgtcggct ggaccgactg gaatctggcc ctgaatcctg aaggcggccc   1920
taactgggtc cgaaacttcg tggacagccc catcatcgtg gacatcacca aggacacctt   1980
ctacaagcag cccatgttct accacctggg acacttcagc aagttcatcc ccgagggctc   2040
tcagcgcgtt ggactggtgg cttcccagaa gaacgatctg gacgccgtgg ctctgatgca   2100
ccctgatgga tctgctgtgg tggtggtcct gaaccgcagc agcaaagatg tgcccctgac   2160
catcaaggat cccgccgtgg gattcctgga aacaatcagc cctggctact ccatccacac   2220
ctacctgtgg cgtagacagt gacaattgtt aattaagttt catcgatacc gtcgactaga   2280
gctcgctgat cagcctcgac tgtgccttct agttgccagc catctgttgt ttgcccctcc   2340
cccgtgcctt ccttgaccct ggaaggtgcc actcccactg tcctttccta ataaaatgag   2400
gaaattgcat cgcattgtct gagtaggtgt cattctattc tggggggtgg ggtggggcag   2460
gacagcaagg gggaggattg ggaagacaat agcaggcatg ctggggagag atccacgata   2520
acaaacagct tttttggggg ggcggagtta gggcggagcc aatcagcgtg cgccgttccg   2580
aaagttgcct tttatggctg ggcggagaat gggcggtgaa cgccgatgat tatataagga   2640
cgcgccgggt gtggcacagc tagttccgtc gcagccggga tttgggtcgc ggttcttgtt   2700
tgtggatccc tgtgatcgtc acttggtaag tcactgactg tctatgcctg ggaaagggtg   2760
ggcaggagat ggggcagtgc aggaaaagtg gcactatgaa ccctgcagcc ctaggaatgc   2820
atctagacaa ttgtactaac cttcttctct ttcctctcct gacagtccgg aaagccacca   2880
tgggccgctg ctgcttctac accgccggca ccctgagcct gctgctgctg gtgaccagcg   2940
tgaccctgct ggtggcccgc gtgttccaga aggccgtgga ccagagcatc gagaagaaga   3000
```

-continued

```
tcgtgctgcg caacggcacc gaggccttcg acagctggga gaagcccccc ctgcccgtgt   3060
acacccagtt ctacttcttc aacgtgacca accccgagga gatcctgcgc ggcgagaccc   3120
cccgcgtgga ggaggtgggc ccctacacct accgcgagct gcgcaacaag gccaacatcc   3180
agttcggcga caacggcacc accatcagcg ccgtgagcaa caaggcctac gtgttcgagc   3240
gcgaccagag cgtgggcgac cccaagatcg acctgatccg caccctgaac atccccgtgc   3300
tgaccgtgat cgagtggagc caggtgcact tcctgcgcga gatcatcgag gccatgctga   3360
aggcctacca gcagaagctg ttcgtgaccc acaccgtgga cgagctgctg tggggctaca   3420
aggacgagat cctgagcctg atccacgtgt tccgccccga catcagcccc tacttcggcc   3480
tgttctacga gaagaacggc accaacgacg gcgactacgt gttcctgacc ggcgaggaca   3540
gctacctgaa cttcaccaag atcgtggagt ggaacggcaa gaccagcctg gactggtgga   3600
tcaccgacaa gtgcaacatg atcaacggca ccgacggcga cagcttccac cccctgatca   3660
ccaaggacga ggtgctgtac gtgttcccca gcgacttctg ccgcagcgtg tacatcacct   3720
tcagcgacta cgagagcgtg cagggcctgc ccgccttccg ctacaaggtg cccgccgaga   3780
tcctggccaa caccagcgac aacgccggct tctgcatccc cgagggcaac tgcctgggca   3840
gcggcgtgct gaacgtgagc atctgcaaga acggcgcccc catcatcatg agcttccccc   3900
acttctacca ggccgacgag cgcttcgtga gcgccatcga gggcatgcac cccaaccagg   3960
aggaccacga gaccttcgtg gacatcaacc ccctgaccgg catcatcctg aaggccgcca   4020
agcgcttcca gatcaacatc tacgtgaaga agctggacga cttcgtggag accggcgaca   4080
tccgcaccat ggtgttcccc gtgatgtacc tgaacgagag cgtgcacatc gacaaggaga   4140
ccgccagccg cctgaagagc atgatcaaca ccaccctgat catcaccaac atcccctaca   4200
tcatcatggc cctgggcgtg ttcttcggcc tggtgttcac ctggctggcc tgcaagggcc   4260
agggcagcat ggacgagggc accgccgacg agcgcgcccc cctgatccgc acctgaccca   4320
ggggactcaa tcagcctcga agacatgata agatacattg atgagtttgg acaaaccaca   4380
acaagaatgc agtgaaaaaa atgctttatt tgtgaaattt gtgatgctat tgctttattt   4440
gtaaccatta taagctgcaa taaacaagtt aacaacaaca attgcattca ttttatgttt   4500
caggttcagg gggagatgtg ggaggttttt taaagcaagt aaaacctcta caaatgtggt   4560
atgaacatat tgactgaatt ccctgcaggt tggccactcc ctctctgcgc gctcgctcgc   4620
tcactgaggc cgcccgggca aagcccgggc gtcgggcgac ctttggtcgc ccggcctcag   4680
tgagcgagcg agcgcgcaga gagggagtgg ccaactccat cactaggggt tcctgcggcc   4740
gctcgtacgg tctcgaggaa ttcctgcagg ataacttgcc aacctcattc taaaatgtat   4800
atagaagccc aaaagacaat aacaaaaata ttcttgtaga acaaaatggg aaagaatgtt   4860
ccactaaata tcaagattta gagcaaagca tgagatgtgt ggggatagac agtgaggctg   4920
ataaaataga gtagagctca gaaacagacc cattgatata tgtaagtgac ctatgaaaaa   4980
aatatggcat tttacaatgg gaaaatgatg gtctttttct tttttagaaa aacagggaaa   5040
tatatttata tgtaaaaaat aaaagggaac ccatatgtca taccatacac acaaaaaaat   5100
tccagtgaat tataagtcta aatggagaag gcaaaacttt aaatctttta gaaaataata   5160
tagaagcatg cagaccagcc tggccaacat gatgaaaccc tctctactaa taataaaatc   5220
agtagaacta ctcaggacta ctttgagtgg gaagtccttt tctatgaaga cttctttggc   5280
caaaattagg ctctaaatgc aaggagatag tgcatcatgc ctggctgcac ttactgataa   5340
```

atgatgttat caccatcttt aaccaaatgc acaggaacaa gttatggtac tgatgtgctg 5400
gattgagaag gagctctact tccttgacag gacacatttg tatcaactta aaaaagcaga 5460
tttttgccag cagaactatt cattcagagg taggaaactt agaatagatg atgtcactga 5520
ttagcatggc ttccccatct ccacagctgc ttcccaccca ggttgcccac agttgagttt 5580
gtccagtgct cagggctgcc cactctcagt aagaagcccc acaccagccc ctctccaaat 5640
atgttggctg ttccttccat taaagtgacc ccactttaga gcagcaagtg gatttctgtt 5700
tcttacagtt caggaaggag gagtcagctg tgagaacctg gagcctgaga tgcttctaag 5760
tcccactgct actggggtca gggaagccag actccagcat cagcagtcag gagcactaag 5820
cccttgccaa catcctgttt ctcagagaaa ctgcttccat tataatggtt gtcctttttt 5880
aagctatcaa gccaaacaac cagtgtctac cattattctc atcacctgaa gccaagggtt 5940
ctagcaaaag tcaagctgtc ttgtaatggt tgatgtgcct ccagcttctg tcttcagtca 6000
ctccactctt agcctgctct gaatcaactc tgaccacagt tccctggagc ccctgccacc 6060
tgctgcccct gccaccttct ccatctgcag tgctgtgcag ccttctgcac tcttgcagag 6120
ctaataggtg gagacttgaa ggaagaggag gaaagtttct cataatagcc ttgctgcaag 6180
ctcaaatggg aggtgggcac tgtgcccagg agccttggag caaaggctgt gcccaacctc 6240
tgactgcatc caggtttggt cttgacagag ataagaagcc ctggcttttg gagccaaaat 6300
ctaggtcaga cttaggcagg attctcaaag tttatcagca gaacatgagg cagaagaccc 6360
tttctgctcc agcttcttca ggctcaacct tcatcagaat agatagaaag agaggctgtg 6420
agggttctta aaacagaagc aaatctgact cagagaataa acaacctcct agtaaactac 6480
agcttagaca gagcatctgg tggtgagtgt gctcagtgtc ctactcaact gtctggtatc 6540
agccctcatg aggacttctc ttctttccct catagacctc catctctgtt ttccttagcc 6600
tgcagaaatc tggatggcta ttcacagaat gcctgtgctt tcagagttgc atttttttctc 6660 tggtattctg gttcaagcat ttgaaggtag gaaaggttct ccaagtgcaa gaaagccagc 6720
cctgagcctc aactgcctgg ctagtgtggt cagtaggatg caaaggctgt tgaatgccac 6780
aaggccaaac tttaacctgt gtaccacaag cctagcagca gaggcagctc tgctcactgg 6840
aactctctgt cttctttctc ctgagccttt tcttttcctg agttttctag ctctcctcaa 6900
ccttacctct gccctaccca ggacaaaccc aagagccact gtttctgtga tgtcctctcc 6960
agccctaatt aggcatcatg acttcagcct gaccttccat gctcagaagc agtgctaatc 7020
cacttcagat gagctgctct atgcaacaca ggcagagcct acaaaccttt gcaccagagc 7080
cctccacata tcagtgtttg ttcatactca cttcaacagc aaatgtgact gctgagatta 7140 agatttaca caagatggtc tgtaatttca cagttagttt tatcccatta ggtatgaaag 7200
aattagcata attcccctta aacatgaatg aatcttagat tttttaataa atagttttgg 7260
aagtaaagac agagacatca ggagcacaag gaatagcctg agaggacaaa cagaacaaga 7320
aagagtctgg aaatacacag gatgttcttg gcctcctcaa agcaagtgca agcagatagt 7380
accagcagcc ccaggctatc agagcccagt gaagagaagt accatgaaag ccacagctct 7440
aaccaccctg ttccagagtg acagacagtc cccaagacaa gccagcctga gccagagaga 7500
gaactgcaag agaaagtttc taatttaggt tctgttagat tcagacaagt gcaggtcatc 7560
ctctctccac agctactcac ctctccagcc taacaaagcc tgcagtccac actccaaccc 7620
tggtgtctca cctcctagcc tctcccaaca tcctgctctc tgaccatctt ctgcatctct 7680
catctcacca tctcccactg tctacagcct actcttgcaa ctaccatctc attttctgac 7740

```
atcctgtcta catcttctgc catactctgc catctaccat accacctctt accatctacc   7800
acaccatctt ttatctccat ccctctcaga agcctccaag ctgaatcctg ctttatgtgt   7860
tcatctcagc ccctgcatgg aaagctgacc ccagaggcag aactattccc agagagcttg   7920
gccaagaaaa acaaaactac cagcctggcc aggctcagga gtagtaagct gcagtgtctg   7980
ttgtgttcta gcttcaacag ctgcaggagt tccactctca aatgctccac atttctcaca   8040
tcctcctgat tctggtcact acccatcttc aaagaacaga atatctcaca tcagcatact   8100
gtgaaggact agtcatgggt gcagctgctc agagctgcaa agtcattctg gatggtggag   8160
agcttacaaa catttcatga tgctccccc gctctgatgg ctggagccca atccctacac   8220
agactcctgc tgtatgtgtt ttcctttcac tctgagccac agccagaggg caggcattca   8280
gtctcctctt caggctgggg ctggggcact gagaactcac ccaacacctt gctctcactc   8340
cttctgcaaa acaagaaaga gctttgtgct gcagtagcca tgaagaatga aaggaaggct   8400
ttaactaaaa aatgtcagag attattttca accccttact gtggatcacc agcaaggagg   8460
aaacacaaca cagagacatt ttttcccctc aaattatcaa aagaatcact gcatttgtta   8520
aagagagcaa ctgaatcagg aagcagagtt ttgaacatat cagaagttag gaatctgcat   8580
cagagacaaa tgcagtcatg gttgtttgct gcataccagc cctaatcatt agaagcctca   8640
tggacttcaa acatcattcc ctctgacaag atgctctagc ctaactccat gagataaaat   8700
aaatctgcct ttcagagcca aagaagagtc caccagcttc ttctcagtgt gaacaagagc   8760
tccagtcagg ttagtcagtc cagtgcagta gaggagacca gtctgcatcc tctaattttc   8820
aaaggcaaga agatttgttt accctggaca ccaggcacaa gtgaggtcac agagctctta   8880
gatatgcagt cctcatgagt gaggagacta aagcgcatgc catcaagact tcagtgtaga   8940
gaaaacctcc aaaaaagcct cctcactact tctggaatag ctcagaggcc gaggcggcct   9000
cggcctctgc ataaataaaa aaaattagtc agccatgggg cggagaatgg gcggaactgg   9060
gcggagttag gggcgggatg ggcggagtta ggggcgggac tatggttgct gactaattga   9120
gatgcatgct ttgcatactt ctgcctgctg gggagcctgg ggactttcca cacctggttg   9180
ctgactaatt gagatgcatg ctttgcatac ttctgcctgc tggggagcct ggggactttc   9240
cacaccctaa ctgacacaca ttccacagct gcattaatga atcggccaac gcgcggggag   9300
aggcggtttg cgtattgggc gctcttccgc ttcctcgctc actgactcgc tgcgctcggt   9360
cgttcggctg cggcgagcgg tatcagctca ctcaaaggcg gtaatacggt tatccacaga   9420
atcaggggat aacgcaggaa agaacatgtg agcaaaaggc cagcaaaagg ccaggaaccg   9480
taaaaaggcc gcgttgctgg cgtttttcca taggctccgc ccccctgacg agcatcacaa   9540
aaatcgacgc tcaagtcaga ggtggcgaaa cccgacagga ctataaagat accaggcgtt   9600
tccccctgga agctccctcg tgcgctctcc tgttccgacc ctgccgctta ccggatacct   9660
gtccgccttt ctcccttcgg gaagcgtggc gctttctcat agctcacgct gtaggtatct   9720
cagttcggtg taggtcgttc gctccaagct gggctgtgtg cacgaacccc ccgttcagcc   9780
cgaccgctgc gccttatccg gtaactatcg tcttgagtcc aacccggtaa gacacgactt   9840
atcgccactg gcagcagcca ctggtaacag gattagcaga gcgaggtatg taggcggtgc   9900
tacagagttc ttgaagtggt ggcctaacta cggctacact agaagaacag tatttggtat   9960
ctgcgctctg ctgaagccag ttaccttcgg aaaaagagtt ggtagctctt gatccggcaa  10020
acaaaccacc gctggtagcg gtggtttttt tgtttgcaag cagcagatta cgcgcagaaa  10080
```

aaaaggatct caagaagatc ctttgatctt ttctacgggg tctgacgctc agtggaacga 10140
aaactcacgt taagggattt tggtcatgag attatcaaaa aggatcttca cctagatcct 10200
tttaaattaa aaatgaagtt ttaaatcaat ctaaagtata tatgagtaaa cttggtctga 10260
cagttaccaa tgcttaatca gtgaggcacc tatctcagcg atctgtctat ttcgttcatc 10320
catagttgcc tgactcctgc aaaccacgtt gtgtctcaaa atctctgatg ttacattgca 10380
caagataaaa atatatcatc atgaacaata aaactgtctg cttacataaa cagtaataca 10440
aggggtgtta tgagccatat tcaacgggaa acgtcttgct cgaggccgcg attaaattcc 10500
aacatggatg ctgatttata tgggtataaa tgggctcgcg ataatgtcgg gcaatcaggt 10560
gcgacaatct atcgattgta tgggaagccc gatgcgccag agttgtttct gaaacatggc 10620
aaaggtagcg ttgccaatga tgttacagat gagatggtca gactaaactg gctgacggaa 10680
tttatgcctc ttccgaccat caagcatttt atccgtactc ctgatgatgc atggttactc 10740
accactgcga tccccgggaa aacagcattc caggtattag aagaatatcc tgattcaggt 10800
gaaaatattg ttgatgcgct ggcagtgttc ctgcgccggt tgcattcgat tcctgtttgt 10860
aattgtcctt ttaacagcga tcgcgtattt cgtctcgctc aggcgcaatc acgaatgaat 10920
aacggtttgg ttgatgcgag tgattttgat gacgagcgta atggctggcc tgttgaacaa 10980
gtctggaaag aaatgcataa gcttttgcca ttctcaccgg attcagtcgt cactcatggt 11040
gatttctcac ttgataacct tatttttgac gaggggaaat taataggttg tattgatgtt 11100
ggacgagtcg gaatcgcaga ccgataccag gatcttgcca tcctatggaa ctgcctcggt 11160
gagttttctc cttcattaca gaaacggctt tttcaaaaat atggtattga taatcctgat 11220
atgaataaat tgcagtttca tttgatgctc gatgagtttt tctaagggcg gcctgccacc 11280
atacccacgc cgaaacaagc gctcatgagc ccgaagtggc gagcccgatc ttccccatcg 11340
gtgatgtcgg cgatataggc gccagcaacc gcacctgtgg cgccggtgat gagggcgcgc 11400
caagtcgacg tccggcagtc 11420

<210> SEQ ID NO 4
<211> LENGTH: 11171
<212> TYPE: DNA
<213> ORGANISM: Artificial Sequence
<220> FEATURE:
<223> OTHER INFORMATION: Synthetic polynucleotide

<400> SEQUENCE: 4
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg agggcggagt 300
tagggcggag ccaatcagcg tgcgccgttc cgaaagttgc cttttatggc tgggcggaga 360
atgggcggtg aacgccgatg attatataag gacgcgccgg gtgtggcaca gctagttccg 420
tcgcagccgg gatttgggtc gcggttcttg tttgtggatc cctgtgatcg tcacttggta 480
agtcactgac tgtctatgcc tgggaaaggg tgggcaggag atggggcagt gcaggaaaag 540
tggcactatg aaccctcctg gtggcgaggg gaggggggtg gtcctcgaac gccttgcaga 600
actggcctgg atacagagtg gaccggctgg ccccatctgg aagacttcga gatacactgt 660
tgtcttactg cgctcaacag tgtatctcga agtcttccaa atggtgccag ccatcgcagc 720

-continued

```
ggggtgcagg aaatgggggc agccccccctt tttggctatc cttccacgtg ttcttttttg    780
tatcttttgt gtttcctaga aaacatctca gtcaccaccg cagccctagg aatgcatcta    840
gacaattgta ctaaccttct tctctttcct ctcctgacag tccggaaagc caccatgggc    900
cgctgctgct tctacaccgc cggcaccctg agcctgctgc tgctggtgac cagcgtgacc    960
ctgctggtgg cccgcgtgtt ccagaaggcc gtggaccaga gcatcgagaa gaagatcgtg   1020
ctgcgcaacg gcaccgaggc cttcgacagc tgggagaagc cccccctgcc cgtgtacacc   1080
cagttctact tcttcaacgt gaccaacccc gaggagatcc tgcgcggcga gaccccccgc   1140
gtggaggagg tgggccccta cacctaccgc gagctgcgca acaaggccaa catccagttc   1200
ggcgacaacg gcaccaccat cagcgccgtg agcaacaagg cctacgtgtt cgagcgcgac   1260
cagagcgtgg gcgaccccaa gatcgacctg atccgcaccc tgaacatccc cgtgctgacc   1320
gtgatcgagt ggagccaggt gcacttcctg cgcgagatca tcgaggccat gctgaaggcc   1380
taccagcaga agctgttcgt gacccacacc gtggacgagc tgctgtgggg ctacaaggac   1440
gagatcctga gcctgatcca cgtgttccgc cccgacatca gcccctactt cggcctgttc   1500
tacgagaaga acggcaccaa cgacggcgac tacgtgttcc tgaccggcga ggacagctac   1560
ctgaacttca ccaagatcgt ggagtggaac ggcaagacca gcctggactg gtggatcacc   1620
gacaagtgca acatgatcaa cggcaccgac ggcgacagct tccacccccct gatcaccaag   1680
gacgaggtgc tgtacgtgtt ccccagcgac ttctgccgca gcgtgtacat caccttcagc   1740
gactacgaga gcgtgcaggg cctgcccgcc ttccgctaca aggtgcccgc cgagatcctg   1800
gccaacacca gcgacaacgc cggcttctgc atccccgagg gcaactgcct gggcagcggc   1860
gtgctgaacg tgagcatctg caagaacggc gcccccatca tcatgagctt cccccacttc   1920
taccaggccg acgagcgctt cgtgagcgcc atcgagggca tgcaccccaa ccaggaggac   1980
cacgagacct tcgtggacat caaccccctg accggcatca tcctgaaggc cgccaagcgc   2040
ttccagatca acatctacgt gaagaagctg gacgacttcg tggagaccgg cgacatccgc   2100
accatggtgt tccccgtgat gtacctgaac gagagcgtgc acatcgacaa ggagaccgcc   2160
agccgcctga agagcatgat caacaccacc ctgatcatca ccaacatccc ctacatcatc   2220
atggccctgg gcgtgttctt cggcctggtg ttcacctggc tggcctgcaa gggccagggc   2280
agcatggacg agggcaccgc cgacgagcgc gccccccctga tccgcaccga gggcagagga   2340
agtcttctga catgcggaga cgtggaagag aatcccggcc ctatggaatt cagcagcccc   2400
agcagagagg aatgccccaa gcctctgagc cgggtgtcaa tcatggccgg atctctgaca   2460
ggactgctgc tgcttcaggc cgtgtcttgg gcttctggcg ctagaccttg catccccaag   2520
agcttcggct acagcagcgt cgtgtgcgtg tgcaatgcca cctactgcga cagcttcgac   2580
cctcctacct ttcctgctct gggcaccttc agcagatacg agagcaccag atccggcaga   2640
cggatggaac tgagcatggg acccatccag gccaatcaca caggcactgg cctgctgctg   2700
acactgcagc ctgagcagaa attccagaaa gtgaaaggct tcggcggagc catgacagat   2760
gccgccgctc tgaatatcct ggctctgtct ccaccagctc agaacctgct gctcaagagc   2820
tacttcagcg aggaaggcat cggctacaac atcatcagag tgcccatggc cagctgcgac   2880
ttcagcatca ggacctacac ctacgccgac acacccgacg atttccagct gcacaacttc   2940
agcctgcctg aagaggacac caagctgaag atccctctga tccacagagc cctgcagctg   3000
gcacaaagac ccgtgtcact gctggcctct ccatggacat ctcccacctg gctgaaaaca   3060
```

-continued

```
aatggcgccg tgaatggcaa gggcagcctg aaaggccaac ctggcgacat ctaccaccag   3120
acctgggcca gatacttcgt gaagttcctg gacgcctatg ccgagcacaa gctgcagttt   3180
tgggccgtga cagccgagaa cgaaccttct gctggactgc tgagcggcta cccctttcag   3240
tgcctgggct ttacacccga gcaccagcgg gactttatcg cccgtgatct gggacccaca   3300
ctggccaata gcacccacca taatgtgcgg ctgctgatgc tggacgacca gagactgctt   3360
ctgccccact gggctaaagt ggtgctgaca gatcctgagg ccgccaaata cgtgcacgga   3420
atcgccgtgc actggtatct ggactttctg gcccctgcca aggccacact gggagagaca   3480
cacagactgt tccccaacac catgctgttc gccagcgaag cctgtgtggg cagcaagttt   3540
tgggaacaga gcgtgcggct cggcagctgg gatagaggca tgcagtacag ccacagcatc   3600
atcaccaacc tgctgtacca cgtcgtcggc tggaccgact ggaatctggc cctgaatcct   3660
gaaggcggcc ctaactgggt ccgaaacttc gtggacagcc ccatcatcgt ggacatcacc   3720
aaggacacct tctacaagca gcccatgttc taccacctgg gacacttcag caagttcatc   3780
cccgagggct ctcagcgcgt tggactggtg gcttcccaga agaacgatct ggacgccgtg   3840
gctctgatgc accctgatgg atctgctgtg gtggtggtcc tgaaccgcag cagcaaagat   3900
gtgcccctga ccatcaagga tcccgccgtg ggattcctgg aaacaatcag ccctggctac   3960
tccatccaca cctacctgtg gcgtagacag tgacaattgt taattaagtt taaaccctcg   4020
aggccgcaag ccgcatcgat accgtcgact agagctcgct gatcagcctc gactgtgcct   4080
tctagttgcc agccatctgt tgtttgcccc tcccccgtgc cttccttgac cctggaaggt   4140
gccactccca ctgtcctttc ctaataaaat gaggaaattg catcgcattg tctgagtagg   4200
tgtcattcta ttctgggggg tggggtgggg caggacagca agggggagga ttgggaagac   4260
aatagcaggc atgctgggga gagatccacg ataacaaaca gctttttttgg ggtgaacata   4320
ttgactgaat tccctgcagg ttggccactc cctctctgcg cgctcgctcg ctcactgagg   4380
ccgcccgggc aaagcccggg cgtcgggcga cctttggtcg cccggcctca gtgagcgagc   4440
gagcgcgcag agagggagtg gccaactcca tcactagggg ttcctgcggc cgctcgtacg   4500
gtctcgagga attcctgcag gataacttgc caacctcatt ctaaaatgta tatagaagcc   4560
caaaagacaa taacaaaaat attcttgtag aacaaaatgg gaaagaatgt tccactaaat   4620
atcaagattt agagcaaagc atgagatgtg tggggataga cagtgaggct gataaaatag   4680
agtagagctc agaaacagac ccattgatat atgtaagtga cctatgaaaa aaatatggca   4740
ttttacaatg ggaaaatgat ggtctttttc tttttttagaa aaacagggaa atatatttat   4800
atgtaaaaaa taaaagggaa cccatatgtc ataccataca cacaaaaaaa ttccagtgaa   4860
ttataagtct aaatggagaa ggcaaaactt taaatctttt agaaaataat atagaagcat   4920
gcagaccagc ctggccaaca tgatgaaacc ctctctacta ataataaaat cagtagaact   4980
actcaggact actttgagtg ggaagtcctt ttctatgaag acttctttgg ccaaaattag   5040
gctctaaatg caaggagata gtgcatcatg cctggctgca cttactgata aatgatgtta   5100
tcaccatctt taaccaaatg cacaggaaca agttatggta ctgatgtgct ggattgagaa   5160
ggagctctac ttccttgaca ggacacattt gtatcaactt aaaaaagcag atttttgcca   5220
gcagaactat tcattcagag gtaggaaact tagaatagat gatgtcactg attagcatgg   5280
cttccccatc tccacagctg cttcccaccc aggttgccca cagttgagtt tgtccagtgc   5340
tcagggctgc ccactctcag taagaagccc cacaccagcc cctctccaaa tatgttggct   5400
gttccttcca ttaaagtgac cccactttag agcagcaagt ggatttctgt ttcttacagt   5460
```

```
tcaggaagga ggagtcagct gtgagaacct ggagcctgag atgcttctaa gtcccactgc   5520
tactggggtc agggaagcca gactccagca tcagcagtca ggagcactaa gcccttgcca   5580
acatcctgtt tctcagagaa actgcttcca ttataatggt tgtccttttt taagctatca   5640
agccaaacaa ccagtgtcta ccattattct catcacctga agccaagggt tctagcaaaa   5700
gtcaagctgt cttgtaatgg ttgatgtgcc tccagcttct gtcttcagtc actccactct   5760
tagcctgctc tgaatcaact ctgaccacag ttccctggag cccctgccac ctgctgcccc   5820
tgccaccttc tccatctgca gtgctgtgca gccttctgca ctcttgcaga gctaataggt   5880
ggagacttga aggaagagga ggaaagtttc tcataatagc cttgctgcaa gctcaaatgg   5940
gaggtgggca ctgtgcccag gagccttgga gcaaaggctg tgcccaacct ctgactgcat   6000
ccaggtttgg tcttgacaga gataagaagc cctggctttt ggagccaaaa tctaggtcag   6060
acttaggcag gattctcaaa gtttatcagc agaacatgag gcagaagacc ctttctgctc   6120
cagcttcttc aggctcaacc ttcatcagaa tagatagaaa gagaggctgt gagggttctt   6180
aaaacagaag caaatctgac tcagagaata aacaacctcc tagtaaacta cagcttagac   6240
agagcatctg gtggtgagtg tgctcagtgt cctactcaac tgtctggtat cagccctcat   6300
gaggacttct cttctttccc tcatagacct ccatctctgt tttccttagc ctgcagaaat   6360
ctggatggct attcacagaa tgcctgtgct ttcagagttg catttttttct ctggtattct   6420
ggttcaagca tttgaaggta ggaaaggttc tccaagtgca agaaagccag ccctgagcct   6480
caactgcctg gctagtgtgg tcagtaggat gcaaaggctg ttgaatgcca caaggccaaa   6540
ctttaacctg tgtaccacaa gcctagcagc agaggcagct ctgctcactg gaactctctg   6600
tcttctttct cctgagcctt ttcttttcct gagttttcta gctctcctca accttacctc   6660
tgccctaccc aggacaaacc caagagccac tgtttctgtg atgtcctctc cagccctaat   6720
taggcatcat gacttcagcc tgaccttcca tgctcagaag cagtgctaat ccacttcaga   6780
tgagctgctc tatgcaacac aggcagagcc tacaaacctt tgcaccagag ccctccacat   6840
atcagtgttt gttcatactc acttcaacag caaatgtgac tgctgagatt aagattttac   6900
acaagatggt ctgtaatttc acagttagtt ttatcccatt aggtatgaaa gaattagcat   6960
aattcccctt aaacatgaat gaatcttaga tttttttaata aatagttttg gaagtaaaga   7020
cagagacatc aggagcacaa ggaatagcct gagaggacaa acagaacaag aaagagtctg   7080
gaaatacaca ggatgttctt ggcctcctca aagcaagtgc aagcagatag taccagcagc   7140
cccaggctat cagagcccag tgaagagaag taccatgaaa gccacagctc taaccaccct   7200
gttccagagt gacagacagt ccccaagaca agccagcctg agccagagag agaactgcaa   7260
gagaaagttt ctaatttagg ttctgttaga ttcagacaag tgcaggtcat cctctctcca   7320
cagctactca cctctccagc ctaacaaagc ctgcagtcca cactccaacc ctggtgtctc   7380
acctcctagc ctctcccaac atcctgctct ctgaccatct tctgcatctc tcatctcacc   7440
atctcccact gtctacagcc tactcttgca actaccatct cattttctga catcctgtct   7500
acatcttctg ccatactctg ccatctacca taccacctct taccatctac cacaccatct   7560
tttatctcca tccctctcag aagcctccaa gctgaatcct gctttatgtg ttcatctcag   7620
cccctgcatg gaaagctgac cccagaggca gaactattcc cagagagctt ggccaagaaa   7680
aacaaaacta ccagcctggc caggctcagg agtagtaagc tgcagtgtct gttgtgttct   7740
agcttcaaca gctgcaggag ttccactctc aaatgctcca catttctcac atcctcctga   7800
```

-continued

```
ttctggtcac tacccatctt caaagaacag aatatctcac atcagcatac tgtgaaggac   7860
tagtcatggg tgcagctgct cagagctgca aagtcattct ggatggtgga gagcttacaa   7920
acatttcatg atgctccccc cgctctgatg gctggagccc aatccctaca cagactcctg   7980
ctgtatgtgt tttcctttca ctctgagcca cagccagagg gcaggcattc agtctcctct   8040
tcaggctggg gctggggcac tgagaactca cccaacacct tgctctcact ccttctgcaa   8100
aacaagaaag agctttgtgc tgcagtagcc atgaagaatg aaaggaaggc tttaactaaa   8160
aaatgtcaga gattattttc aaccccttac tgtggatcac cagcaaggag gaaacacaac   8220
acagagacat tttttcccct caaattatca aaagaatcac tgcatttgtt aaagagagca   8280
actgaatcag gaagcagagt tttgaacata tcagaagtta ggaatctgca tcagagacaa   8340
atgcagtcat ggttgtttgc tgcataccag ccctaatcat tagaagcctc atggacttca   8400
aacatcattc cctctgacaa gatgctctag cctaactcca tgagataaaa taaatctgcc   8460
tttcagagcc aaagaagagt ccaccagctt cttctcagtg tgaacaagag ctccagtcag   8520
gttagtcagt ccagtgcagt agaggagacc agtctgcatc ctctaatttt caaaggcaag   8580
aagatttgtt taccctggac accaggcaca agtgaggtca cagagctctt agatatgcag   8640
tcctcatgag tgaggagact aaagcgcatg ccatcaagac ttcagtgtag agaaaacctc   8700
caaaaaagcc tcctcactac ttctggaata gctcagaggc cgaggcggcc tcggcctctg   8760
cataaataaa aaaaattagt cagccatggg gcggagaatg ggcggaactg ggcggagtta   8820
ggggcgggat gggcggagtt aggggcggga ctatggttgc tgactaattg agatgcatgc   8880
tttgcatact tctgcctgct ggggagcctg gggactttcc acacctggtt gctgactaat   8940
tgagatgcat gctttgcata cttctgcctg ctggggagcc tggggacttt ccacacccta   9000
actgacacac attccacagc tgcattaatg aatcggccaa cgcgcgggga gaggcggttt   9060
gcgtattggg cgctcttccg cttcctcgct cactgactcg ctgcgctcgg tcgttcggct   9120
gcggcgagcg gtatcagctc actcaaaggc ggtaatacgg ttatccacag aatcagggga   9180
taacgcagga aagaacatgt gagcaaaagg ccagcaaaag gccaggaacc gtaaaaaggc   9240
cgcgttgctg gcgtttttcc ataggctccg cccccctgac gagcatcaca aaaatcgacg   9300
ctcaagtcag aggtggcgaa acccgacagg actataaaga taccaggcgt ttccccctgg   9360
aagctccctc gtgcgctctc ctgttccgac cctgccgctt accggatacc tgtccgcctt   9420
tctcccttcg ggaagcgtgg cgctttctca tagctcacgc tgtaggtatc tcagttcggt   9480
gtaggtcgtt cgctccaagc tgggctgtgt gcacgaaccc cccgttcagc ccgaccgctg   9540
cgccttatcc ggtaactatc gtcttgagtc caacccggta agacacgact tatcgccact   9600
ggcagcagcc actggtaaca ggattagcag agcgaggtat gtaggcggtg ctacagagtt   9660
cttgaagtgg tggcctaact acggctacac tagaagaaca gtatttggta tctgcgctct   9720
gctgaagcca gttaccttcg gaaaaagagt tggtagctct tgatccggca aacaaaccac   9780
cgctggtagc ggtggttttt ttgtttgcaa gcagcagatt acgcgcagaa aaaaaggatc   9840
tcaagaagat cctttgatct tttctacggg gtctgacgct cagtggaacg aaaactcacg   9900
ttaagggatt ttggtcatga gattatcaaa aaggatcttc acctagatcc ttttaaatta   9960
aaaatgaagt tttaaatcaa tctaaagtat atatgagtaa acttggtctg acagttacca  10020
atgcttaatc agtgaggcac ctatctcagc gatctgtcta tttcgttcat ccatagttgc  10080
ctgactcctg caaaccacgt tgtgtctcaa aatctctgat gttacattgc acaagataaa  10140
aatatatcat catgaacaat aaaactgtct gcttacataa acagtaatac aaggggtgtt  10200
```

atgagccata ttcaacggga aacgtcttgc tcgaggccgc gattaaattc caacatggat 10260
gctgatttat atgggtataa atgggctcgc gataatgtcg ggcaatcagg tgcgacaatc 10320
tatcgattgt atgggaagcc cgatgcgcca gagttgtttc tgaaacatgg caaaggtagc 10380
gttgccaatg atgttacaga tgagatggtc agactaaact ggctgacgga atttatgcct 10440
cttccgacca tcaagcattt tatccgtact cctgatgatg catggttact caccactgcg 10500
atccccggga aaacagcatt ccaggtatta gaagaatatc ctgattcagg tgaaaatatt 10560
gttgatgcgc tggcagtgtt cctgcgccgg ttgcattcga ttcctgtttg taattgtcct 10620
tttaacagcg atcgcgtatt tcgtctcgct caggcgcaat cacgaatgaa taacggtttg 10680
gttgatgcga gtgattttga tgacgagcgt aatggctggc ctgttgaaca agtctggaaa 10740
gaaatgcata agcttttgcc attctcaccg gattcagtcg tcactcatgg tgatttctca 10800
cttgataacc ttatttttga cgaggggaaa ttaataggtt gtattgatgt tggacgagtc 10860
ggaatcgcag accgatacca ggatcttgcc atcctatgga actgcctcgg tgagttttct 10920
ccttcattac agaaacggct ttttcaaaaa tatggtattg ataatcctga tatgaataaa 10980
ttgcagtttc atttgatgct cgatgagttt ttctaagggc ggcctgccac catacccacg 11040
ccgaaacaag cgctcatgag cccgaagtgg cgagcccgat cttccccatc ggtgatgtcg 11100
gcgatatagg cgccagcaac cgcacctgtg gcgccggtga tgagggcgcg ccaagtcgac 11160
gtccggcagt c 11171

<210> SEQ ID NO 5
<211> LENGTH: 11309
<212> TYPE: DNA
<213> ORGANISM: Artificial Sequence
<220> FEATURE:
<223> OTHER INFORMATION: Synthetic polynucleotide

<400> SEQUENCE: 5
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg agggcggagt 300
tagggcggag ccaatcagcg tgcgccgttc cgaaagttgc cttttatggc tgggcggaga 360
atgggcggtg aacgccgatg attatataag gacgcgccgg gtgtggcaca gctagttccg 420
tcgcagccgg gatttgggtc gcggttcttg tttgtggatc cctgtgatcg tcacttggta 480
agtcactgac tgtctatgcc tgggaaaggg tgggcaggag atggggcagt gcaggaaaag 540
tggcactatg aaccctcctg gtggcgaggg gaggggggtg gtcctcgaac gccttgcaga 600
actggcctgg atacagagtg gaccggctgg ccccatctgg aagacttcga gatacactgt 660
tgtcttactg cgctcaacag tgtatctcga agtcttccaa atggtgccag ccatcgcagc 720
ggggtgcagg aaatgggggc agcccccctt tttggctatc cttccacgtg ttcttttttg 780
tatcttttgt gtttcctaga aaacatctca gtcaccaccg cagccctagg aatgcatcta 840
gacaattgta ctaaccttct tctctttcct ctcctgacag tccggaaagc caccatgtac 900
gccctgttcc tgctggccag cctgctgggc gccgccctgg ccggccccgt gctgggcctg 960
aaggagtgca cccgcggcag cgccgtgtgg tgccagaacg tgaagaccgc cagcgactgc 1020

-continued

```
ggcgccgtga agcactgcct gcagaccgtg tggaacaagc ccaccgtgaa gagcctgccc   1080
tgcgacatct gcaaggacgt ggtgaccgcc gccggcgaca tgctgaagga caacgccacc   1140
gaggaggaga tcctggtgta cctggagaag acctgcgact ggctgcccaa gcccaacatg   1200
agcgccagct gcaaggagat cgtggacagc tacctgcccg tgatcctgga catcatcaag   1260
ggcgagatga gccgccccgg cgaggtgtgc agcgccctga acctgtgcga gagcctgcag   1320
aagcacctgg ccgagctgaa ccaccagaag cagctggaga gcaacaagat ccccgagctg   1380
gacatgaccg aggtggtggc cccctcatg gccaacatcc ccctgctgct gtacccccag   1440
gacggccccc gcagcaagcc ccagcccaag gacaacggcg acgtgtgcca ggactgcatc   1500
cagatggtga ccgacatcca gaccgccgtg cgcaccaaca gcaccttcgt gcaggccctg   1560
gtggagcacg tgaaggagga gtgcgaccgc ctgggccccg gcatggccga catctgcaag   1620
aactacatca gccagtacag cgagatcgcc atccagatga tgatgcacat gcagcccaag   1680
gagatctgcg ccctggtggg cttctgcgac gaggtgaagg agatgcccat gcagaccctg   1740
gtgcccgcca aggtggccag caagaacgtg atccccgccc tggagctggt ggagcccatc   1800
aagaagcacg aggtgcccgc caagagcgac gtgtactgcg aggtgtgcga gttcctggtg   1860
aaggaggtga ccaagctgat cgacaacaac aagaccgaga aggagatcct ggacgccttc   1920
gacaagatgt gcagcaagct gcccaagagc ctgagcgagg agtgccagga ggtggtggac   1980
acctacggca gcagcatcct gagcatcctg ctggaggagg tgagccccga gctggtgtgc   2040
agcatgctgc acctgtgcag cggcacccgc ctgcccgccc tgaccgtgca cgtgacccag   2100
cccaaggacg gcggcttctg cgaggtgtgc aagaagctgg tgggctacct ggaccgcaac   2160
ctggagaaga acagcaccaa gcaggagatc ctggccgccc tggagaaggg ctgcagcttc   2220
ctgcccgacc cctaccagaa gcagtgcgac cagttcgtgg ccgagtacga gcccgtgctg   2280
atcgagatcc tggtggaggt gatggacccc agcttcgtgt gcctgaagat cggcgcctgc   2340
cccagcgccc acaagcccct gctgggcacc gagaagtgca tctggggccc cagctactgg   2400
tgccagaaca ccgagaccgc cgcccagtgc aacgccgtgg agcactgcaa gcgccacgtg   2460
tggaacgagg gcagaggaag tcttctgaca tgcggagacg tggaagagaa tcccggccct   2520
atggaattca gcagccccag cagagaggaa tgccccaagc ctctgagccg ggtgtcaatc   2580
atggccggat ctctgacagg actgctgctg cttcaggccg tgtcttgggc ttctggcgct   2640
agaccttgca tccccaagag cttcggctac agcagcgtcg tgtgcgtgtg caatgccacc   2700
tactgcgaca gcttcgaccc tcctaccttt cctgctctgg gcaccttcag cagatacgag   2760
agcaccagat ccggcagacg gatggaactg agcatgggac ccatccaggc caatcacaca   2820
ggcactggcc tgctgctgac actgcagcct gagcagaaat tccagaaagt gaaaggcttc   2880
ggcggagcca tgacagatgc cgccgctctg aatatcctgg ctctgtctcc accagctcag   2940
aacctgctgc tcaagagcta cttcagcgag gaaggcatcg gctacaacat catcagagtg   3000
cccatggcca gctgcgactt cagcatcagg acctacacct acgccgacac acccgacgat   3060
ttccagctgc acaacttcag cctgcctgaa gaggacacca agctgaagat ccctctgatc   3120
cacagagccc tgcagctggc acaaagaccc gtgtcactgc tggcctctcc atggacatct   3180
cccacctggc tgaaaacaaa tggcgccgtg aatggcaagg gcagcctgaa aggccaacct   3240
ggcgacatct accaccagac ctgggccaga tacttcgtga agttcctgga cgcctatgcc   3300
gagcacaagc tgcagttttg ggccgtgaca gccgagaacg aaccttctgc tggactgctg   3360
agcggctacc cctttcagtg cctgggcttt acacccgagc accagcggga ctttatcgcc   3420
```

cgtgatctgg gacccacact ggccaatagc acccaccata atgtgcggct gctgatgctg 3480
gacgaccaga gactgcttct gccccactgg gctaaagtgg tgctgacaga tcctgaggcc 3540
gccaaatacg tgcacggaat cgccgtgcac tggtatctgg actttctggc ccctgccaag 3600
gccacactgg gagagacaca cagactgttc cccaacacca tgctgttcgc cagcgaagcc 3660
tgtgtgggca gcaagttttg ggaacagagc gtgcggctcg gcagctggga tagaggcatg 3720
cagtacagcc acagcatcat caccaacctg ctgtaccacg tcgtcggctg gaccgactgg 3780
aatctggccc tgaatcctga aggcggccct aactgggtcc gaaacttcgt ggacagcccc 3840
atcatcgtgg acatcaccaa ggacaccttc tacaagcagc ccatgttcta ccacctggga 3900
cacttcagca agttcatccc cgagggctct cagcgcgttg gactggtggc ttcccagaag 3960
aacgatctgg acgccgtggc tctgatgcac cctgatggat ctgctgtggt ggtggtcctg 4020
aaccgcagca gcaaagatgt gcccctgacc atcaaggatc ccgccgtggg attcctggaa 4080
acaatcagcc ctggctactc catccacacc tacctgtggc gtagacagtg acaattgtta 4140
attaagttta aaccctcgag gccgcaagcc gcatcgatac cgtcgactag agctcgctga 4200
tcagcctcga ctgtgccttc tagttgccag ccatctgttg tttgcccctc ccccgtgcct 4260
tccttgaccc tggaaggtgc cactcccact gtcctttcct aataaaatga ggaaattgca 4320
tcgcattgtc tgagtaggtg tcattctatt ctggggggtg gggtggggca ggacagcaag 4380
ggggaggatt gggaagacaa tagcaggcat gctggggaga gatccacgat aacaaacagc 4440
tttttggggg tgaacatatt gactgaattc cctgcaggtt ggccactccc tctctgcgcg 4500
ctcgctcgct cactgaggcc gcccgggcaa agcccgggcg tcgggcgacc tttggtcgcc 4560
cggcctcagt gagcgagcga gcgcgcagag agggagtggc caactccatc actaggggtt 4620
cctgcggccg ctcgtacggt ctcgaggaat tcctgcagga taacttgcca acctcattct 4680
aaaatgtata tagaagccca aaagacaata acaaaaatat tcttgtagaa caaaatggga 4740
aagaatgttc cactaaatat caagatttag agcaaagcat gagatgtgtg gggatagaca 4800
gtgaggctga taaaatagag tagagctcag aaacagaccc attgatatat gtaagtgacc 4860
tatgaaaaaa atatggcatt ttacaatggg aaaatgatgg tctttttctt ttttagaaaa 4920
acagggaaat atatttatat gtaaaaaata aaagggaacc catatgtcat accatacaca 4980
caaaaaaatt ccagtgaatt ataagtctaa atggagaagg caaaacttta aatcttttag 5040
aaaataatat agaagcatgc agaccagcct ggccaacatg atgaaaccct ctctactaat 5100
aataaaatca gtagaactac tcaggactac tttgagtggg aagtcctttt ctatgaagac 5160
ttctttggcc aaaattaggc tctaaatgca aggagatagt gcatcatgcc tggctgcact 5220
tactgataaa tgatgttatc accatcttta accaaatgca caggaacaag ttatggtact 5280
gatgtgctgg attgagaagg agctctactt ccttgacagg acacatttgt atcaacttaa 5340
aaaagcagat ttttgccagc agaactattc attcagaggt aggaaactta gaatagatga 5400
tgtcactgat tagcatggct tccccatctc cacagctgct tcccacccag gttgcccaca 5460
gttgagtttg tccagtgctc agggctgccc actctcagta agaagcccca caccagcccc 5520
tctccaaata tgttggctgt tccttccatt aaagtgaccc cactttagag cagcaagtgg 5580
atttctgttt cttacagttc aggaaggagg agtcagctgt gagaacctgg agcctgagat 5640
gcttctaagt cccactgcta ctggggtcag ggaagccaga ctccagcatc agcagtcagg 5700
agcactaagc ccttgccaac atcctgtttc tcagagaaac tgcttccatt ataatggttg 5760

-continued

```
tcctttttta agctatcaag ccaaacaacc agtgtctacc attattctca tcacctgaag   5820
ccaagggttc tagcaaaagt caagctgtct tgtaatggtt gatgtgcctc cagcttctgt   5880
cttcagtcac tccactctta gcctgctctg aatcaactct gaccacagtt ccctggagcc   5940
cctgccacct gctgcccctg ccaccttctc catctgcagt gctgtgcagc cttctgcact   6000
cttgcagagc taataggtgg agacttgaag gaagaggagg aaagtttctc ataatagcct   6060
tgctgcaagc tcaaatggga ggtgggcact gtgcccagga gccttggagc aaaggctgtg   6120
cccaacctct gactgcatcc aggtttggtc ttgacagaga taagaagccc tggcttttgg   6180
agccaaaatc taggtcagac ttaggcagga ttctcaaagt ttatcagcag aacatgaggc   6240
agaagaccct ttctgctcca gcttcttcag gctcaacctt catcagaata gatagaaaga   6300
gaggctgtga gggttcttaa aacagaagca aatctgactc agagaataaa caacctccta   6360
gtaaactaca gcttagacag agcatctggt ggtgagtgtg ctcagtgtcc tactcaactg   6420
tctggtatca gccctcatga ggacttctct tctttccctc atagacctcc atctctgttt   6480
tccttagcct gcagaaatct ggatggctat tcacagaatg cctgtgcttt cagagttgca   6540
tttttctct ggtattctgg ttcaagcatt tgaaggtagg aaaggttctc caagtgcaag    6600
aaagccagcc ctgagcctca actgcctggc tagtgtggtc agtaggatgc aaaggctgtt   6660
gaatgccaca aggccaaact ttaacctgtg taccacaagc ctagcagcag aggcagctct   6720
gctcactgga actctctgtc ttctttctcc tgagcctttt cttttcctga gttttctagc   6780
tctcctcaac cttacctctg ccctacccag gacaaaccca agagccactg tttctgtgat   6840
gtcctctcca gccctaatta ggcatcatga cttcagcctg accttccatg ctcagaagca   6900
gtgctaatcc acttcagatg agctgctcta tgcaacacag gcagagccta caaacctttg   6960
caccagagcc ctccacatat cagtgtttgt tcatactcac ttcaacagca aatgtgactg   7020
ctgagattaa gattttacac aagatggtct gtaatttcac agttagtttt atcccattag   7080
gtatgaaaga attagcataa ttccccttaa acatgaatga atcttagatt ttttaataaa   7140
tagttttgga agtaaagaca gagacatcag gagcacaagg aatagcctga gaggacaaac   7200
agaacaagaa agagtctgga aatacacagg atgttcttgg cctcctcaaa gcaagtgcaa   7260
gcagatagta ccagcagccc caggctatca gagcccagtg aagagaagta ccatgaaagc   7320
cacagctcta accaccctgt tccagagtga cagacagtcc ccaagacaag ccagcctgag   7380
ccagagagag aactgcaaga gaaagtttct aatttaggtt ctgttagatt cagacaagtg   7440
caggtcatcc tctctccaca gctactcacc tctccagcct aacaaagcct gcagtccaca   7500
ctccaaccct ggtgtctcac ctcctagcct ctcccaacat cctgctctct gaccatcttc   7560
tgcatctctc atctcaccat ctcccactgt ctacagccta ctcttgcaac taccatctca   7620
ttttctgaca tcctgtctac atcttctgcc atactctgcc atctaccata ccacctctta   7680
ccatctacca caccatcttt tatctccatc cctctcagaa gcctccaagc tgaatcctgc   7740
tttatgtgtt catctcagcc cctgcatgga aagctgaccc cagaggcaga actattccca   7800
gagagcttgg ccaagaaaaa caaaactacc agcctggcca ggctcaggag tagtaagctg   7860
cagtgtctgt tgtgttctag cttcaacagc tgcaggagtt ccactctcaa atgctccaca   7920
tttctcacat cctcctgatt ctggtcacta cccatcttca aagaacagaa tatctcacat   7980
cagcatactg tgaaggacta gtcatgggtg cagctgctca gagctgcaaa gtcattctgg   8040
atggtggaga gcttacaaac atttcatgat gctccccccg ctctgatggc tggagcccaa   8100
tccctacaca gactcctgct gtatgtgttt tcctttcact ctgagccaca gccagagggc   8160
```

```
aggcattcag tctcctcttc aggctggggc tggggcactg agaactcacc caacaccttg   8220
ctctcactcc ttctgcaaaa caagaaagag ctttgtgctg cagtagccat gaagaatgaa   8280
aggaaggctt taactaaaaa atgtcagaga ttattttcaa ccccttactg tggatcacca   8340
gcaaggagga aacacaacac agagacattt tttcccctca aattatcaaa agaatcactg   8400
catttgttaa agagagcaac tgaatcagga agcagagttt tgaacatatc agaagttagg   8460
aatctgcatc agagacaaat gcagtcatgg ttgtttgctg cataccagcc ctaatcatta   8520
gaagcctcat ggacttcaaa catcattccc tctgacaaga tgctctagcc taactccatg   8580
agataaaata aatctgcctt tcagagccaa agaagagtcc accagcttct tctcagtgtg   8640
aacaagagct ccagtcaggt tagtcagtcc agtgcagtag aggagaccag tctgcatcct   8700
ctaattttca aaggcaagaa gatttgttta ccctggacac caggcacaag tgaggtcaca   8760
gagctcttag atatgcagtc ctcatgagtg aggagactaa agcgcatgcc atcaagactt   8820
cagtgtagag aaaacctcca aaaaagcctc ctcactactt ctggaatagc tcagaggccg   8880
aggcggcctc ggcctctgca taaataaaaa aaattagtca gccatggggc ggagaatggg   8940
cggaactggg cggagttagg ggcgggatgg gcggagttag gggcgggact atggttgctg   9000
actaattgag atgcatgctt tgcatacttc tgcctgctgg ggagcctggg gactttccac   9060
acctggttgc tgactaattg agatgcatgc tttgcatact tctgcctgct ggggagcctg   9120
gggactttcc acaccctaac tgacacacat tccacagctg cattaatgaa tcggccaacg   9180
cgcggggaga ggcggtttgc gtattgggcg ctcttccgct tcctcgctca ctgactcgct   9240
gcgctcggtc gttcggctgc ggcgagcggt atcagctcac tcaaaggcgg taatacggtt   9300
atccacagaa tcaggggata acgcaggaaa gaacatgtga gcaaaaggcc agcaaaaggc   9360
caggaaccgt aaaaaggccg cgttgctggc gtttttccat aggctccgcc cccctgacga   9420
gcatcacaaa aatcgacgct caagtcagag gtggcgaaac ccgacaggac tataaagata   9480
ccaggcgttt ccccctggaa gctccctcgt gcgctctcct gttccgaccc tgccgcttac   9540
cggatacctg tccgcctttc tcccttcggg aagcgtggcg ctttctcata gctcacgctg   9600
taggtatctc agttcggtgt aggtcgttcg ctccaagctg ggctgtgtgc acgaaccccc   9660
cgttcagccc gaccgctgcg ccttatccgg taactatcgt cttgagtcca acccggtaag   9720
acacgactta tcgccactgg cagcagccac tggtaacagg attagcagag cgaggtatgt   9780
aggcggtgct acagagttct tgaagtggtg gcctaactac ggctacacta gaagaacagt   9840
atttggtatc tgcgctctgc tgaagccagt taccttcgga aaaagagttg gtagctcttg   9900
atccggcaaa caaaccaccg ctggtagcgg tggttttttt gtttgcaagc agcagattac   9960
gcgcagaaaa aaaggatctc aagaagatcc tttgatcttt tctacggggt ctgacgctca  10020
gtggaacgaa aactcacgtt aagggatttt ggtcatgaga ttatcaaaaa ggatcttcac  10080
ctagatcctt ttaaattaaa aatgaagttt taaatcaatc taaagtatat atgagtaaac  10140
ttggtctgac agttaccaat gcttaatcag tgaggcacct atctcagcga tctgtctatt  10200
tcgttcatcc atagttgcct gactcctgca aaccacgttg tgtctcaaaa tctctgatgt  10260
tacattgcac aagataaaaa tatatcatca tgaacaataa aactgtctgc ttacataaac  10320
agtaatacaa ggggtgttat gagccatatt caacgggaaa cgtcttgctc gaggccgcga  10380
ttaaattcca acatggatgc tgatttatat gggtataaat gggctcgcga taatgtcggg  10440
caatcaggtg cgacaatcta tcgattgtat gggaagcccg atgcgccaga gttgtttctg  10500
```

aaacatggca aaggtagcgt tgccaatgat gttacagatg agatggtcag actaaactgg 10560
ctgacggaat ttatgcctct tccgaccatc aagcatttta tccgtactcc tgatgatgca 10620
tggttactca ccactgcgat ccccgggaaa acagcattcc aggtattaga agaatatcct 10680
gattcaggtg aaaatattgt tgatgcgctg gcagtgttcc tgcgccggtt gcattcgatt 10740
cctgtttgta attgtccttt taacagcgat cgcgtatttc gtctcgctca ggcgcaatca 10800
cgaatgaata acggtttggt tgatgcgagt gattttgatg acgagcgtaa tggctggcct 10860
gttgaacaag tctggaaaga aatgcataag cttttgccat tctcaccgga ttcagtcgtc 10920
actcatggtg atttctcact tgataacctt atttttgacg aggggaaatt aataggttgt 10980
attgatgttg gacgagtcgg aatcgcagac cgataccagg atcttgccat cctatggaac 11040
tgcctcggtg agttttctcc ttcattacag aaacggcttt ttcaaaaata tggtattgat 11100
aatcctgata tgaataaatt gcagtttcat ttgatgctcg atgagttttt ctaagggcgg 11160
cctgccacca tacccacgcc gaaacaagcg ctcatgagcc cgaagtggcg agcccgatct 11220
tccccatcgg tgatgtcggc gatataggcg ccagcaaccg cacctgtggc gccggtgatg 11280
agggcgcgcc aagtcgacgt ccggcagtc 11309

<210> SEQ ID NO 6
<211> LENGTH: 11293
<212> TYPE: DNA
<213> ORGANISM: Artificial Sequence
<220> FEATURE:
<223> OTHER INFORMATION: Synthetic polynucleotide

<400> SEQUENCE: 6
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg agggcggagt 300
tagggcggag ccaatcagcg tgcgccgttc cgaaagttgc cttttatggc tgggcggaga 360
atgggcggtg aacgccgatg attatataag gacgcgccgg gtgtggcaca gctagttccg 420
tcgcagccgg gatttgggtc gcggttcttg tttgtggatc cctgtgatcg tcacttggta 480
agtcactgac tgtctatgcc tgggaaaggg tgggcaggag atggggcagt gcaggaaaag 540
tggcactatg aaccctgcag ccctaggaat gcatctagac aattgtacta accttcttct 600
ctttcctctc ctgacagtcc ggaaagccac catgtacgcc ctgttcctgc tggccagcct 660
gctgggcgcc gccctggccg gccccgtgct gggcctgaag gagtgcaccc gcggcagcgc 720
cgtgtggtgc cagaacgtga agaccgccag cgactgcggc gccgtgaagc actgcctgca 780
gaccgtgtgg aacaagccca ccgtgaagag cctgccctgc gacatctgca aggacgtggt 840
gaccgccgcc ggcgacatgc tgaaggacaa cgccaccgag gaggagatcc tggtgtacct 900
ggagaagacc tgcgactggc tgcccaagcc caacatgagc gccagctgca aggagatcgt 960
ggacagctac ctgcccgtga tcctggacat catcaagggc gagatgagcc gccccggcga 1020
ggtgtgcagc gccctgaacc tgtgcgagag cctgcagaag cacctggccg agctgaacca 1080
ccagaagcag ctggagagca acaagatccc cgagctggac atgaccgagg tggtggcccc 1140
cttcatggcc aacatccccc tgctgctgta cccccaggac ggcccccgca gcaagcccca 1200
gcccaaggac aacggcgacg tgtgccagga ctgcatccag atggtgaccg acatccagac 1260
cgccgtgcgc accaacagca ccttcgtgca ggccctggtg gagcacgtga aggaggagtg 1320
cgaccgcctg ggccccggca tggccgacat ctgcaagaac tacatcagcc agtacagcga 1380
gatcgccatc cagatgatga tgcacatgca gcccaaggag atctgcgccc tggtgggctt 1440
ctgcgacgag gtgaaggaga tgcccatgca gaccctggtg cccgccaagg tggccagcaa 1500
gaacgtgatc cccgccctgg agctggtgga gcccatcaag aagcacgagg tgcccgccaa 1560
gagcgacgtg tactgcgagg tgtgcgagtt cctggtgaag gaggtgacca agctgatcga 1620
caacaacaag accgagaagg agatcctgga cgccttcgac aagatgtgca gcaagctgcc 1680
caagagcctg agcgaggagt gccaggaggt ggtggacacc tacggcagca gcatcctgag 1740
catcctgctg gaggaggtga gccccgagct ggtgtgcagc atgctgcacc tgtgcagcgg 1800
cacccgcctg cccgccctga ccgtgcacgt gacccagccc aaggacggcg gcttctgcga 1860
ggtgtgcaag aagctggtgg gctacctgga ccgcaacctg gagaagaaca gcaccaagca 1920
ggagatcctg gccgccctgg agaagggctg cagcttcctg cccgacccct accagaagca 1980
gtgcgaccag ttcgtggccg agtacgagcc cgtgctgatc gagatcctgg tggaggtgat 2040
ggaccccagc ttcgtgtgcc tgaagatcgg cgcctgcccc agcgcccaca agcccctgct 2100
gggcaccgag aagtgcatct ggggccccag ctactggtgc cagaacaccg agaccgccgc 2160
ccagtgcaac gccgtggagc actgcaagcg ccacgtgtgg aactgattgt ggccgaaccg 2220
ccgaactcag aggccggccc cagaaaaccc gagcgagtag gggcggcgc gcaggaggga 2280
ggagaactgg gggcgcggga ggctggtggg tgtgggggt ggagatgtag aagatgtgac 2340
gccgcggccc ggcgggtgcc agattagcgg acgcggtgcc cgcggttgca acgggatccc 2400
gggcgctgca gcttgggagg cggctctccc caggcggcgt ccgcggagac acccatccgt 2460
gaaccccagg tcccgggccg ccggctcgcc gcgcaccagg ggccggcgga cagaagagcg 2520
gccgagcggc tcgaggctgg gggaccgcgg gcgcggccgc gcgctgccgg gcgggaggct 2580
ggggggccgg ggccggggcc gtgccccgga gcgggtcgga ggccggggcc ggggccgggg 2640
gacggcggct ccccgcgcgg ctccagcggc tcggggatcc cggccgggcc ccgcagggac 2700
catgatggaa ttcagcagcc ccagcagaga ggaatgcccc aagcctctga gccgggtgtc 2760
aatcatggcc ggatctctga caggactgct gctgcttcag gccgtgtctt gggcttctgg 2820
cgctagacct tgcatcccca agagcttcgg ctacagcagc gtcgtgtgcg tgtgcaatgc 2880
cacctactgc gacagcttcg accctcctac ctttcctgct ctgggcacct tcagcagata 2940
cgagagcacc agatccggca gacggatgga actgagcatg ggacccatcc aggccaatca 3000
cacaggcact ggcctgctgc tgacactgca gcctgagcag aaattccaga aagtgaaagg 3060
cttcggcgga gccatgacag atgccgccgc tctgaatatc ctggctctgt ctccaccagc 3120
tcagaacctg ctgctcaaga gctacttcag cgaggaaggc atcggctaca acatcatcag 3180
agtgcccatg gccagctgcg acttcagcat caggacctac acctacgccg acacacccga 3240
cgatttccag ctgcacaact tcagcctgcc tgaagaggac accaagctga agatccctct 3300
gatccacaga gccctgcagc tggcacaaag acccgtgtca ctgctggcct ctccatggac 3360
atctcccacc tggctgaaaa caaatggcgc cgtgaatggc aagggcagcc tgaaaggcca 3420
acctggcgac atctaccacc agacctgggc cagatacttc gtgaagttcc tggacgccta 3480
tgccgagcac aagctgcagt tttgggccgt gacagccgag aacgaacctt ctgctggact 3540
gctgagcggc tacccctttc agtgcctggg ctttacaccc gagcaccagc gggactttat 3600

```
cgcccgtgat ctgggaccca cactggccaa tagcacccac cataatgtgc ggctgctgat   3660
gctggacgac cagagactgc ttctgcccca ctgggctaaa gtggtgctga cagatcctga   3720
ggccgccaaa tacgtgcacg gaatcgccgt gcactggtat ctggactttc tggcccctgc   3780
caaggccaca ctgggagaga cacacagact gttccccaac accatgctgt tcgccagcga   3840
agcctgtgtg ggcagcaagt tttgggaaca gagcgtgcgg ctcggcagct gggatagagg   3900
catgcagtac agccacagca tcatcaccaa cctgctgtac cacgtcgtcg gctggaccga   3960
ctggaatctg gccctgaatc ctgaaggcgg ccctaactgg gtccgaaact tcgtggacag   4020
ccccatcatc gtggacatca ccaaggacac cttctacaag cagcccatgt tctaccacct   4080
gggacacttc agcaagttca tccccgaggg ctctcagcgc gttggactgg tggcttccca   4140
gaagaacgat ctggacgccg tggctctgat gcaccctgat ggatctgctg tggtggtggt   4200
cctgaaccgc agcagcaaag atgtgcccct gaccatcaag gatcccgccg tgggattcct   4260
ggaaacaatc agccctggct actccatcca cacctacctg tggcgtagac agtgacaatt   4320
gttaattaag tttaaaccct cgaggccgca agcaataaaa tatctttatt ttcattacat   4380
ctgtgtgttg gttttttgtg tggagatcca cgataacaaa cagctttttt ggggtgaaca   4440
tattgactga attccctgca ggttggccac tccctctctg cgcgctcgct cgctcactga   4500
ggccgcccgg gcaaagcccg ggcgtcgggc gacctttggt cgcccggcct cagtgagcga   4560
gcgagcgcgc agagagggag tggccaactc catcactagg ggttcctgcg gccgctcgta   4620
cggtctcgag gaattcctgc aggataactt gccaacctca ttctaaaatg tatatagaag   4680
cccaaaagac aataacaaaa atattcttgt agaacaaaat gggaaagaat gttccactaa   4740
atatcaagat ttagagcaaa gcatgagatg tgtggggata gacagtgagg ctgataaaat   4800
agagtagagc tcagaaacag acccattgat atatgtaagt gacctatgaa aaaaatatgg   4860
cattttacaa tgggaaaatg atggtctttt tctttttttag aaaaacaggg aaatatattt   4920
atatgtaaaa aataaaaggg aacccatatg tcataccata cacacaaaaa aattccagtg   4980
aattataagt ctaaatggag aaggcaaaac tttaaatctt ttagaaaata atatagaagc   5040
atgcagacca gcctggccaa catgatgaaa ccctctctac taataataaa atcagtagaa   5100
ctactcagga ctactttgag tgggaagtcc ttttctatga agacttcttt ggccaaaatt   5160
aggctctaaa tgcaaggaga tagtgcatca tgcctggctg cacttactga taaatgatgt   5220
tatcaccatc tttaaccaaa tgcacaggaa caagttatgg tactgatgtg ctggattgag   5280
aaggagctct acttccttga caggacacat ttgtatcaac ttaaaaaagc agatttttgc   5340
cagcagaact attcattcag aggtaggaaa cttagaatag atgatgtcac tgattagcat   5400
ggcttcccca tctccacagc tgcttcccac ccaggttgcc cacagttgag tttgtccagt   5460
gctcagggct gcccactctc agtaagaagc cccacaccag cccctctcca aatatgttgg   5520
ctgttccttc cattaaagtg accccacttt agagcagcaa gtggatttct gtttcttaca   5580
gttcaggaag gaggagtcag ctgtgagaac ctggagcctg agatgcttct aagtcccact   5640
gctactgggg tcagggaagc cagactccag catcagcagt caggagcact aagcccttgc   5700
caacatcctg tttctcagag aaactgcttc cattataatg gttgtccttt tttaagctat   5760
caagccaaac aaccagtgtc taccattatt ctcatcacct gaagccaagg gttctagcaa   5820
aagtcaagct gtcttgtaat ggttgatgtg cctccagctt ctgtcttcag tcactccact   5880
cttagcctgc tctgaatcaa ctctgaccac agttccctgg agcccctgcc acctgctgcc   5940
cctgccacct tctccatctg cagtgctgtg cagccttctg cactcttgca gagctaatag   6000
```

-continued

```
gtggagactt gaaggaagag gaggaaagtt tctcataata gccttgctgc aagctcaaat   6060
gggaggtggg cactgtgccc aggagccttg gagcaaaggc tgtgcccaac ctctgactgc   6120
atccaggttt ggtcttgaca gagataagaa gccctggctt ttggagccaa aatctaggtc   6180
agacttaggc aggattctca aagtttatca gcagaacatg aggcagaaga cccttttctgc   6240
tccagcttct tcaggctcaa ccttcatcag aatagataga aagagaggct gtgagggttc   6300
ttaaaacaga agcaaatctg actcagagaa taaacaacct cctagtaaac tacagcttag   6360
acagagcatc tggtggtgag tgtgctcagt gtcctactca actgtctggt atcagccctc   6420
atgaggactt ctcttctttc cctcatagac ctccatctct gttttcctta gcctgcagaa   6480
atctggatgg ctattcacag aatgcctgtg ctttcagagt tgcatttttt ctctggtatt   6540
ctggttcaag catttgaagg taggaaaggt tctccaagtg caagaaagcc agccctgagc   6600
ctcaactgcc tggctagtgt ggtcagtagg atgcaaaggc tgttgaatgc cacaaggcca   6660
aactttaacc tgtgtaccac aagcctagca gcagaggcag ctctgctcac tggaactctc   6720
tgtcttcttt ctcctgagcc ttttcttttc ctgagttttc tagctctcct caaccttacc   6780
tctgccctac ccaggacaaa cccaagagcc actgtttctg tgatgtcctc tccagcccta   6840
attaggcatc atgacttcag cctgaccttc catgctcaga agcagtgcta atccacttca   6900
gatgagctgc tctatgcaac acaggcagag cctacaaacc tttgcaccag agccctccac   6960
atatcagtgt ttgttcatac tcacttcaac agcaaatgtg actgctgaga ttaagatttt   7020
acacaagatg gtctgtaatt tcacagttag ttttatccca ttaggtatga aagaattagc   7080
ataattcccc ttaaacatga atgaatctta gattttttaa taaatagttt tggaagtaaa   7140
gacagagaca tcaggagcac aaggaatagc ctgagaggac aaacagaaca agaaagagtc   7200
tggaaataca caggatgttc ttggcctcct caaagcaagt gcaagcagat agtaccagca   7260
gccccaggct atcagagccc agtgaagaga agtaccatga aagccacagc tctaaccacc   7320
ctgttccaga gtgacagaca gtccccaaga caagccagcc tgagccagag agagaactgc   7380
aagagaaagt ttctaattta ggttctgtta gattcagaca agtgcaggtc atcctctctc   7440
cacagctact cacctctcca gcctaacaaa gcctgcagtc cacactccaa ccctggtgtc   7500
tcacctccta gcctctccca acatcctgct ctctgaccat cttctgcatc tctcatctca   7560
ccatctccca ctgtctacag cctactcttg caactaccat ctcattttct gacatcctgt   7620
ctacatcttc tgccatactc tgccatctac cataccacct cttaccatct accacaccat   7680
cttttatctc catccctctc agaagcctcc aagctgaatc ctgctttatg tgttcatctc   7740
agcccctgca tggaaagctg accccagagg cagaactatt cccagagagc ttggccaaga   7800
aaaacaaaac taccagcctg gccaggctca ggagtagtaa gctgcagtgt ctgttgtgtt   7860
ctagcttcaa cagctgcagg agttccactc tcaaatgctc cacatttctc acatcctcct   7920
gattctggtc actacccatc ttcaaagaac agaatatctc acatcagcat actgtgaagg   7980
actagtcatg ggtgcagctg ctcagagctg caaagtcatt ctggatggtg gagagcttac   8040
aaacatttca tgatgctccc cccgctctga tggctggagc ccaatcccta cacagactcc   8100
tgctgtatgt gttttccttt cactctgagc cacagccaga gggcaggcat tcagtctcct   8160
cttcaggctg gggctggggc actgagaact cacccaacac cttgctctca ctccttctgc   8220
aaaacaagaa agagctttgt gctgcagtag ccatgaagaa tgaaaggaag gctttaacta   8280
aaaaatgtca gagattattt tcaacccctt actgtggatc accagcaagg aggaaacaca   8340
```

-continued

```
acacagagac atttttttccc ctcaaattat caaaagaatc actgcatttg ttaaagagag   8400
caactgaatc aggaagcaga gttttgaaca tatcagaagt taggaatctg catcagagac   8460
aaatgcagtc atggttgttt gctgcatacc agccctaatc attagaagcc tcatggactt   8520
caaacatcat tccctctgac aagatgctct agcctaactc catgagataa aataaatctg   8580
cctttcagag ccaaagaaga gtccaccagc ttcttctcag tgtgaacaag agctccagtc   8640
aggttagtca gtccagtgca gtagaggaga ccagtctgca tcctctaatt ttcaaaggca   8700
agaagatttg tttaccctgg acaccaggca caagtgaggt cacagagctc ttagatatgc   8760
agtcctcatg agtgaggaga ctaaagcgca tgccatcaag acttcagtgt agagaaaacc   8820
tccaaaaaag cctcctcact acttctggaa tagctcagag gccgaggcgg cctcggcctc   8880
tgcataaata aaaaaaatta gtcagccatg gggcggagaa tgggcggaac tgggcggagt   8940
taggggcggg atgggcggag ttaggggcgg gactatggtt gctgactaat tgagatgcat   9000
gctttgcata cttctgcctg ctggggagcc tggggacttt ccacacctgg ttgctgacta   9060
attgagatgc atgctttgca tacttctgcc tgctggggag cctggggact ttccacaccc   9120
taactgacac acattccaca gctgcattaa tgaatcggcc aacgcgcggg gagaggcggt   9180
ttgcgtattg ggcgctcttc cgcttcctcg ctcactgact cgctgcgctc ggtcgttcgg   9240
ctgcggcgag cggtatcagc tcactcaaag gcggtaatac ggttatccac agaatcaggg   9300
gataacgcag gaaagaacat gtgagcaaaa ggccagcaaa aggccaggaa ccgtaaaaag   9360
gccgcgttgc tggcgttttt ccataggctc cgcccccctg acgagcatca caaaaatcga   9420
cgctcaagtc agaggtggcg aaacccgaca ggactataaa gataccaggc gtttccccct   9480
ggaagctccc tcgtgcgctc tcctgttccg accctgccgc ttaccggata cctgtccgcc   9540
tttctccctt cgggaagcgt ggcgctttct catagctcac gctgtaggta tctcagttcg   9600
gtgtaggtcg ttcgctccaa gctgggctgt gtgcacgaac cccccgttca gcccgaccgc   9660
tgcgccttat ccggtaacta tcgtcttgag tccaacccgg taagacacga cttatcgcca   9720
ctggcagcag ccactggtaa caggattagc agagcgaggt atgtaggcgg tgctacagag   9780
ttcttgaagt ggtggcctaa ctacggctac actagaagaa cagtatttgg tatctgcgct   9840
ctgctgaagc cagttacctt cggaaaaaga gttggtagct cttgatccgg caaacaaacc   9900
accgctggta gcggtggttt ttttgtttgc aagcagcaga ttacgcgcag aaaaaaagga   9960
tctcaagaag atcctttgat cttttctacg gggtctgacg ctcagtggaa cgaaaactca  10020
cgttaaggga ttttggtcat gagattatca aaaaggatct tcacctagat ccttttaaat  10080
taaaaatgaa gttttaaatc aatctaaagt atatatgagt aaacttggtc tgacagttac  10140
caatgcttaa tcagtgaggc acctatctca gcgatctgtc tatttcgttc atccatagtt  10200
gcctgactcc tgcaaaccac gttgtgtctc aaaatctctg atgttacatt gcacaagata  10260
aaaatatatc atcatgaaca ataaaactgt ctgcttacat aaacagtaat acaaggggtg  10320
ttatgagcca tattcaacgg gaaacgtctt gctcgaggcc gcgattaaat tccaacatgg  10380
atgctgattt atatgggtat aaatgggctc gcgataatgt cgggcaatca ggtgcgacaa  10440
tctatcgatt gtatgggaag cccgatgcgc cagagttgtt tctgaaacat ggcaaaggta  10500
gcgttgccaa tgatgttaca gatgagatgg tcagactaaa ctggctgacg gaatttatgc  10560
ctcttccgac catcaagcat tttatccgta ctcctgatga tgcatggtta ctcaccactg  10620
cgatccccgg gaaaacagca ttccaggtat tagaagaata tcctgattca ggtgaaaata  10680
ttgttgatgc gctggcagtg ttcctgcgcc ggttgcattc gattcctgtt tgtaattgtc  10740
```

-continued

```
cttttaacag cgatcgcgta tttcgtctcg ctcaggcgca atcacgaatg aataacggtt  10800

tggttgatgc gagtgatttt gatgacgagc gtaatggctg gcctgttgaa caagtctgga  10860

aagaaatgca taagcttttg ccattctcac cggattcagt cgtcactcat ggtgatttct  10920

cacttgataa ccttattttt gacgagggga aattaatagg ttgtattgat gttggacgag  10980

tcggaatcgc agaccgatac caggatcttg ccatcctatg gaactgcctc ggtgagtttt  11040

ctccttcatt acagaaacgg ctttttcaaa aatatggtat tgataatcct gatatgaata  11100

aattgcagtt tcatttgatg ctcgatgagt ttttctaagg gcggcctgcc accataccca  11160

cgccgaaaca agcgctcatg agcccgaagt ggcgagcccg atcttcccca tcggtgatgt  11220

cggcgatata ggcgccagca accgcacctg tggcgccggt gatgagggcg cgccaagtcg  11280

acgtccggca gtc                                                     11293
```

<210> SEQ ID NO 7
<211> LENGTH: 10700
<212> TYPE: DNA
<213> ORGANISM: Artificial Sequence
<220> FEATURE:
<223> OTHER INFORMATION: Synthetic polynucleotide

<400> SEQUENCE: 7

```
ttggccactc cctctctgcg cgctcgctcg ctcactgagg ccgcccgggc aaagcccggg     60

cgtcgggcga cctttggtcg cccggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg aattcggtac    300

ctagttatta atagtaatca attacggggt cattagttca tagcccatat atggagttcc    360

gcgttacata acttacggta aatggcccgc ctggctgacc gcccaacgac ccccgcccat    420

tgacgtcaat aatgacgtat gttcccatag taacgccaat agggactttc cattgacgtc    480

aatgggtgga gtatttacgg taaactgccc acttggcagt acatcaagtg tatcatatgc    540

caagtacgcc ccctattgac gtcaatgacg gtaaatggcc cgcctggcat tatgcccagt    600

acatgacctt atgggacttt cctacttggc agtacatcta cgtattagtc atcgctatta    660

ccatggtcga ggtgagcccc acgttctgct tcactctccc catctccccc ccctccccac    720

ccccaatttt gtatttattt atttttttaat tatttttgtgc agcgatgggg gcgggggggg    780

gggggggggcg cgcgccaggc ggggcggggc ggggcgaggg gcggggcggg gcgaggcgga    840

gaggtgcggc ggcagccaat cagagcggcg cgctccgaaa gtttcctttt atggcgaggc    900

ggcggcggcg gcggccctat aaaaagcgaa gcgcgcggcg ggcgggagtc gctgcgacgc    960

tgccttcgcc ccgtgccccg ctccgccgcc gcctcgcgcc gcccgccccg gctctgactg   1020

accgcgttac tcccacaggt gagcgggcgg gacggccctt ctcctccggg ctgtaattag   1080

cgcttggttt aatgacggct tgtttctttt ctgtggctgc gtgaaagcct tgaggggctc   1140

cgggagctag agcctctgct aaccatgttc atgccttctt ctttttccta cagctcctgg   1200

gcaacgtgct ggttattgtg ctgtctcatc attttggcaa agaattcctc gaagatccga   1260

agggaaagtc ttccacgact gtgggatccg ttcgaagata tcaccggttg agccaccatg   1320

gaattcagca gccccagcag agaggaatgc cccaagcctc tgagccgggt gtcaatcatg   1380

gccggatctc tgacaggact gctgctgctt caggccgtgt cttgggcttc tggcgctaga   1440
```

-continued

```
ccttgcatcc ccaagagctt cggctacagc agcgtcgtgt gcgtgtgcaa tgccacctac   1500
tgcgacagct tcgaccctcc tacctttcct gctctgggca ccttcagcag atacgagagc   1560
accagatccg gcagacggat ggaactgagc atgggaccca tccaggccaa tcacacaggc   1620
actggcctgc tgctgacact gcagcctgag cagaaattcc agaaagtgaa aggcttcggc   1680
ggagccatga cagatgccgc cgctctgaat atcctggctc tgtctccacc agctcagaac   1740
ctgctgctca agagctactt cagcgaggaa ggcatcggct acaacatcat cagagtgccc   1800
atggccagct gcgacttcag catcaggacc tacacctacg ccgacacacc cgacgatttc   1860
cagctgcaca acttcagcct gcctgaagag gacaccaagc tgaagatccc tctgatccac   1920
agagccctgc agctggcaca aagacccgtg tcactgctgg cctctccatg gacatctccc   1980
acctggctga aaacaaatgg cgccgtgaat ggcaagggca gcctgaaagg ccaacctggc   2040
gacatctacc accagacctg ggccagatac ttcgtgaagt tcctggacgc ctatgccgag   2100
cacaagctgc agttttgggc cgtgacagcc gagaacgaac cttctgctgg actgctgagc   2160
ggctacccct ttcagtgcct gggctttaca cccgagcacc agcgggactt tatcgcccgt   2220
gatctgggac ccacactggc caatagcacc caccataatg tgcggctgct gatgctggac   2280
gaccagagac tgcttctgcc ccactgggct aaagtggtgc tgacagatcc tgaggccgcc   2340
aaatacgtgc acggaatcgc cgtgcactgg tatctggact ttctggcccc tgccaaggcc   2400
acactgggag agacacacag actgttcccc aacaccatgc tgttcgccag cgaagcctgt   2460
gtgggcagca agttttggga acagagcgtg cggctcggca gctgggatag aggcatgcag   2520
tacagccaca gcatcatcac caacctgctg taccacgtcg tcggctggac cgactggaat   2580
ctggccctga atcctgaagg cggccctaac tgggtccgaa acttcgtgga cagccccatc   2640
atcgtggaca tcaccaagga caccttctac aagcagccca tgttctacca cctgggacac   2700
ttcagcaagt tcatccccga gggctctcag cgcgttggac tggtggcttc ccagaagaac   2760
gatctggacg ccgtggctct gatgcaccct gatggatctg ctgtggtggt ggtcctgaac   2820
cgcagcagca aagatgtgcc cctgaccatc aaggatcccg ccgtgggatt cctggaaaca   2880
atcagccctg gctactccat ccacacctac ctgtggcgta gacagtgaca attgttaatt   2940
aagtttaaac cctcgaggcc gcaagcttat cgataatcaa cctctggatt acaaaatttg   3000
tgaaagattg actggtattc ttaactatgt tgctcctttt acgctatgtg gatacgctgc   3060
tttaatgcct ttgtatcatg ctattgcttc ccgtatggct ttcattttct cctccttgta   3120
taaatcctgg ttgctgtctc tttatgagga gttgtggccc gttgtcaggc aacgtggcgt   3180
ggtgtgcact gtgtttgctg acgcaacccc cactggttgg ggcattgcca ccacctgtca   3240
gctcctttcc gggactttcg ctttccccct ccctattgcc acggcggaac tcatcgccgc   3300
ctgccttgcc cgctgctgga caggggctcg gctgttgggc actgacaatt ccgtggtgtt   3360
gtcggggaaa tcatcgtcct ttccttggct gctcgcctgt gttgccacct ggattctgcg   3420
cgggacgtcc ttctgctacg tcccttcggc cctcaatcca gcggaccttc cttcccgcgg   3480
cctgctgccg gctctgcggc ctcttccgcg tcttcgcctt cgccctcaga cgagtcggat   3540
ctccctttgg gccgcctccc cgcatcgata ccgtcgacta gagctcgctg atcagcctcg   3600
actgtgcctt ctagttgcca gccatctgtt gtttgcccct cccccgtgcc ttccttgacc   3660
ctggaaggtg ccactcccac tgtcctttcc taataaaatg aggaaattgc atcgcattgt   3720
ctgagtaggt gtcattctat tctggggggt ggggtggggc aggacagcaa gggggaggat   3780
tgggaagaca atagcaggca tgctggggag agatccacga taacaaacag ctttttttggg   3840
```

```
gtgaacatat tgactgaatt ccctgcaggt tggccactcc ctctctgcgc gctcgctcgc   3900
tcactgaggc cgcccgggca aagcccgggc gtcgggcgac ctttggtcgc ccggcctcag   3960
tgagcgagcg agcgcgcaga gagggagtgg ccaactccat cactaggggt tcctgcggcc   4020
gctcgtacgg tctcgaggaa ttcctgcagg ataacttgcc aacctcattc taaaatgtat   4080
atagaagccc aaaagacaat aacaaaaata ttcttgtaga acaaaatggg aaagaatgtt   4140
ccactaaata tcaagattta gagcaaagca tgagatgtgt ggggatagac agtgaggctg   4200
ataaaataga gtagagctca gaaacagacc cattgatata tgtaagtgac ctatgaaaaa   4260
aatatggcat tttacaatgg gaaaatgatg gtctttttct tttttagaaa aacagggaaa   4320
tatatttata tgtaaaaaat aaaagggaac ccatatgtca taccatacac acaaaaaaat   4380
tccagtgaat tataagtcta aatggagaag gcaaaacttt aaatctttta gaaaataata   4440
tagaagcatg cagaccagcc tggccaacat gatgaaaccc tctctactaa taataaaatc   4500
agtagaacta ctcaggacta ctttgagtgg gaagtccttt tctatgaaga cttctttggc   4560
caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacatttg tatcaactta aaaaagcaga   4740
tttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtcctttttt   5160
aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttctttccct catagacctc catctctgtt ttccttagcc   5880
tgcagaaatc tggatggcta ttcacagaat gcctgtgctt tcagagttgc atttttttctc   5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
```

-continued

```
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agattttaca caagatggtc tgtaatttca cagttagttt tatcccatta ggtatgaaag   6480
aattagcata attcccctta aacatgaatg aatcttagat tttttaataa atagttttgg   6540
aagtaaagac agagacatca ggagcacaag gaatagcctg agaggacaaa cagaacaaga   6600
aagagtctgg aaatacacag gatgttcttg gcctcctcaa agcaagtgca agcagatagt   6660
accagcagcc ccaggctatc agagcccagt gaagagaagt accatgaaag ccacagctct   6720
aaccaccctg ttccagagtg acagacagtc cccaagacaa gccagcctga gccagagaga   6780
gaactgcaag agaaagtttc taatttaggt tctgttagat tcagacaagt gcaggtcatc   6840
ctctctccac agctactcac ctctccagcc taacaaagcc tgcagtccac actccaaccc   6900
tggtgtctca cctcctagcc tctcccaaca tcctgctctc tgaccatctt ctgcatctct   6960
catctcacca tctcccactg tctacagcct actcttgcaa ctaccatctc attttctgac   7020
atcctgtcta catcttctgc catactctgc catctaccat accacctctt accatctacc   7080
acaccatctt ttatctccat ccctctcaga agcctccaag ctgaatcctg ctttatgtgt   7140
tcatctcagc ccctgcatgg aaagctgacc ccagaggcag aactattccc agagagcttg   7200
gccaagaaaa acaaaactac cagcctggcc aggctcagga gtagtaagct gcagtgtctg   7260
ttgtgttcta gcttcaacag ctgcaggagt tccactctca aatgctccac atttctcaca   7320
tcctcctgat tctggtcact acccatcttc aaagaacaga atatctcaca tcagcatact   7380
gtgaaggact agtcatgggt gcagctgctc agagctgcaa agtcattctg gatggtggag   7440
agcttacaaa catttcatga tgctccccccc gctctgatgg ctggagccca atccctacac   7500
agactcctgc tgtatgtgtt ttcctttcac tctgagccac agccagaggg caggcattca   7560
gtctcctctt caggctgggg ctggggcact gagaactcac ccaacacctt gctctcactc   7620
cttctgcaaa acaagaaaga gctttgtgct gcagtagcca tgaagaatga aaggaaggct   7680
ttaactaaaa aatgtcagag attattttca accccttact gtggatcacc agcaaggagg   7740
aaacacaaca cagagacatt ttttcccctc aaattatcaa aagaatcact gcatttgtta   7800
aagagagcaa ctgaatcagg aagcagagtt ttgaacatat cagaagttag gaatctgcat   7860
cagagacaaa tgcagtcatg gttgtttgct gcataccagc cctaatcatt agaagcctca   7920
tggacttcaa acatcattcc ctctgacaag atgctctagc ctaactccat gagataaaat   7980
aaatctgcct ttcagagcca aagaagagtc caccagcttc ttctcagtgt gaacaagagc   8040
tccagtcagg ttagtcagtc cagtgcagta gaggagacca gtctgcatcc tctaattttc   8100
aaaggcaaga agatttgttt accctggaca ccaggcacaa gtgaggtcac agagctctta   8160
gatatgcagt cctcatgagt gaggagacta aagcgcatgc catcaagact tcagtgtaga   8220
gaaaacctcc aaaaaagcct cctcactact tctggaatag ctcagaggcc gaggcggcct   8280
cggcctctgc ataaataaaa aaaattagtc agccatgggg cggagaatgg gcggaactgg   8340
gcggagttag gggcgggatg ggcggagtta ggggcgggac tatggttgct gactaattga   8400
gatgcatgct ttgcatactt ctgcctgctg gggagcctgg ggactttcca cacctggttg   8460
ctgactaatt gagatgcatg ctttgcatac ttctgcctgc tggggagcct ggggactttc   8520
cacaccctaa ctgacacaca ttccacagct gcattaatga atcggccaac gcgcggggag   8580
```

```
aggcggtttg cgtattgggc gctcttccgc ttcctcgctc actgactcgc tgcgctcggt   8640
cgttcggctg cggcgagcgg tatcagctca ctcaaaggcg gtaatacggt tatccacaga   8700
atcaggggat aacgcaggaa agaacatgtg agcaaaaggc cagcaaaagg ccaggaaccg   8760
taaaaaggcc gcgttgctgg cgtttttcca taggctccgc cccctgacg agcatcacaa    8820
aaatcgacgc tcaagtcaga ggtggcgaaa cccgacagga ctataaagat accaggcgtt   8880
tccccctgga agctccctcg tgcgctctcc tgttccgacc ctgccgctta ccggatacct   8940
gtccgccttt ctcccttcgg gaagcgtggc gctttctcat agctcacgct gtaggtatct   9000
cagttcggtg taggtcgttc gctccaagct gggctgtgtg cacgaacccc ccgttcagcc   9060
cgaccgctgc gccttatccg gtaactatcg tcttgagtcc aacccggtaa gacacgactt   9120
atcgccactg gcagcagcca ctggtaacag gattagcaga gcgaggtatg taggcggtgc   9180
tacagagttc ttgaagtggt ggcctaacta cggctacact agaagaacag tatttggtat   9240
ctgcgctctg ctgaagccag ttaccttcgg aaaaagagtt ggtagctctt gatccggcaa   9300
acaaaccacc gctggtagcg gtggtttttt tgtttgcaag cagcagatta cgcgcagaaa   9360
aaaaggatct caagaagatc ctttgatctt ttctacgggg tctgacgctc agtggaacga   9420
aaactcacgt taagggattt tggtcatgag attatcaaaa aggatcttca cctagatcct   9480
tttaaattaa aaatgaagtt ttaaatcaat ctaaagtata tatgagtaaa cttggtctga   9540
cagttaccaa tgcttaatca gtgaggcacc tatctcagcg atctgtctat ttcgttcatc   9600
catagttgcc tgactcctgc aaaccacgtt gtgtctcaaa atctctgatg ttacattgca   9660
caagataaaa atatatcatc atgaacaata aaactgtctg cttacataaa cagtaataca   9720
aggggtgtta tgagccatat tcaacgggaa acgtcttgct cgaggccgcg attaaattcc   9780
aacatggatg ctgatttata tgggtataaa tgggctcgcg ataatgtcgg gcaatcaggt   9840
gcgacaatct atcgattgta tgggaagccc gatgcgccag agttgtttct gaaacatggc   9900
aaaggtagcg ttgccaatga tgttacagat gagatggtca gactaaactg gctgacggaa   9960
tttatgcctc ttccgaccat caagcatttt atccgtactc ctgatgatgc atggttactc  10020
accactgcga tccccgggaa aacagcattc caggtattag aagaatatcc tgattcaggt  10080
gaaaatattg ttgatgcgct ggcagtgttc ctgcgccggt tgcattcgat tcctgtttgt  10140
aattgtcctt ttaacagcga tcgcgtattt cgtctcgctc aggcgcaatc acgaatgaat  10200
aacggtttgg ttgatgcgag tgattttgat gacgagcgta atggctggcc tgttgaacaa  10260
gtctggaaag aaatgcataa gcttttgcca ttctcaccgg attcagtcgt cactcatggt  10320
gatttctcac ttgataacct tatttttgac gaggggaaat taataggttg tattgatgtt  10380
ggacgagtcg gaatcgcaga ccgataccag gatcttgcca tcctatggaa ctgcctcggt  10440
gagttttctc cttcattaca gaaacggctt tttcaaaaat atggtattga taatcctgat  10500
atgaataaat tgcagtttca tttgatgctc gatgagtttt tctaagggcg gcctgccacc  10560
atacccacgc cgaaacaagc gctcatgagc ccgaagtggc gagcccgatc ttccccatcg  10620
gtgatgtcgg cgatataggc gccagcaacc gcacctgtgg cgccggtgat gagggcgcgc  10680
caagtcgacg tccggcagtc                                              10700
```

<210> SEQ ID NO 8
<211> LENGTH: 10700
<212> TYPE: DNA
<213> ORGANISM: Artificial Sequence
<220> FEATURE:

<223> OTHER INFORMATION: Synthetic polynucleotide

<400> SEQUENCE: 8

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactatt agatctgatg gccgcgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg aattcggtac    300
ctagttatta atagtaatca attacggggt cattagttca tagcccatat atggagttcc    360
gcgttacata acttacggta aatggcccgc ctggctgacc gcccaacgac ccccgcccat    420
tgacgtcaat aatgacgtat gttcccatag taacgccaat agggactttc cattgacgtc    480
aatgggtgga gtatttacgg taaactgccc acttggcagt acatcaagtg tatcatatgc    540
caagtacgcc ccctattgac gtcaatgacg gtaaatggcc cgcctggcat tatgcccagt    600
acatgacctt atgggacttt cctacttggc agtacatcta cgtattagtc atcgctatta    660
ccatggtcga ggtgagcccc acgttctgct tcactctccc catctccccc ccctccccac    720
ccccaatttt gtatttattt atttttaat tattttgtgc agcgatgggg gcgggggggg    780
gggggggcg cgcgccaggc ggggcggggc ggggcgaggg gcggggcggg gcgaggcgga    840
gaggtgcggc ggcagccaat cagagcggcg cgctccgaaa gtttcctttt atggcgaggc    900
ggcggcggcg gcggccctat aaaaagcgaa gcgcgcggcg ggcgggagtc gctgcgacgc    960
tgccttcgcc ccgtgccccg ctccgccgcc gcctcgcgcc gcccgccccg gctctgactg   1020
accgcgttac tcccacaggt gagcgggcgg gacggccctt ctcctccggg ctgtaattag   1080
cgcttggttt aatgacggct tgtttctttt ctgtggctgc gtgaaagcct tgaggggctc   1140
cgggagctag agcctctgct aaccatgttc atgccttctt ctttttccta cagctcctgg   1200
gcaacgtgct ggttattgtg ctgtctcatc attttggcaa agaattcctc gaagatccga   1260
agggaaagtc ttccacgact gtgggatccg ttcgaagata tcaccggttg agccaccatg   1320
gaattcagca gccccagcag agaggaatgc cccaagcctc tgagccgggt gtcaatcatg   1380
gccggatctc tgacaggact gctgctgctt caggccgtgt cttgggcttc tggcgctaga   1440
ccttgcatcc ccaagagctt cggctacagc agcgtcgtgt gcgtgtgcaa tgccacctac   1500
tgcgacagct tcgaccctcc tacctttcct gctctgggca ccttcagcag atacgagagc   1560
accagatccg gcagacggat ggaactgagc atgggaccca tccaggccaa tcacacaggc   1620
actggcctgc tgctgacact gcagcctgag cagaaattcc agaaagtgaa aggcttcggc   1680
ggagccatga cagatgccgc cgctctgaat atcctggctc tgtctccacc agctcagaac   1740
ctgctgctca agagctactt cagcgaggaa ggcatcggct acaacatcat cagagtgccc   1800
atggccagct gcgacttcag catcaggacc tacacctacg ccgacacacc cgacgatttc   1860
cagctgcaca acttcagcct gcctgaagag gacaccaagc tgaagatccc tctgatccac   1920
agagccctgc agctggcaca aagacccgtg tcactgctgg cctctccatg gacatctccc   1980
acctggctga aaacaaatgg cgccgtgaat ggcaagggca gcctgaaagg ccaacctggc   2040
gacatctacc accagacctg ggccagatac ttcgtgaagt tcctggacgc ctatgccgag   2100
cacaagctgc agttttgggc cgtgacagcc gagaacgaac cttctgctgg actgctgagc   2160
ggctacccct ttcagtgcct gggctttaca cccgagcacc agcgggactt tatcgcccgt   2220
gatctgggac ccacactggc caatagcacc caccataatg tgcggctgct gatgctggac   2280
```

-continued

```
gaccagagac tgcttctgcc ccactgggct aaagtggtgc tgacagatcc tgaggccgcc   2340
aaatacgtgc acggaatcgc cgtgcactgg tatctggact ttctggcccc tgccaaggcc   2400
acactgggag agacacacag actgttcccc aacaccatgc tgttcgccag cgaagcctgt   2460
gtgggcagca agttttggga acagagcgtg cggctcggca gctgggatag aggcatgcag   2520
tacagccaca gcatcatcac caacctgctg taccacgtcg tcggctggac cgactggaat   2580
ctggccctga atcctgaagg cggccctaac tgggtccgaa acttcgtgga cagccccatc   2640
atcgtggaca tcaccaagga caccttctac aagcagccca tgttctacca cctgggacac   2700
ttcagcaagt tcatccccga gggctctcag cgcgttggac tggtggcttc ccagaagaac   2760
gatctggacg ccgtggctct gatgcaccct gatggatctg ctgtggtggt ggtcctgaac   2820
cgcagcagca aagatgtgcc cctgaccatc aaggatcccg ccgtgggatt cctggaaaca   2880
atcagccctg gctactccat ccacacctac ctgtggcgta gacagtgaca attgttaatt   2940
aagtttaaac cctcgaggcc gcaagcttat cgataatcaa cctctggatt acaaaatttg   3000
tgaaagattg actggtattc ttaactatgt tgctcctttt acgctatgtg gatacgctgc   3060
tttaatgcct ttgtatcatg ctattgcttc ccgtatggct ttcattttct cctccttgta   3120
taaatcctgg ttgctgtctc tttatgagga gttgtggccc gttgtcaggc aacgtggcgt   3180
ggtgtgcact gtgtttgctg acgcaacccc cactggttgg ggcattgcca ccacctgtca   3240
gctcctttcc gggactttcg ctttccccct ccctattgcc acggcggaac tcatcgccgc   3300
ctgccttgcc cgctgctgga caggggctcg gctgttgggc actgacaatt ccgtggtgtt   3360
gtcggggaaa tcatcgtcct ttccttggct gctcgcctgt gttgccacct ggattctgcg   3420
cgggacgtcc ttctgctacg tcccttcggc cctcaatcca gcggaccttc cttcccgcgg   3480
cctgctgccg gctctgcggc ctcttccgcg tcttcgcctt cgccctcaga cgagtcggat   3540
ctccctttgg gccgcctccc cgcatcgata ccgtcgacta gagctcgctg atcagcctcg   3600
actgtgcctt ctagttgcca gccatctgtt gtttgcccct cccccgtgcc ttccttgacc   3660
ctggaaggtg ccactcccac tgtcctttcc taataaaatg aggaaattgc atcgcattgt   3720
ctgagtaggt gtcattctat tctggggggt ggggtggggc aggacagcaa gggggaggat   3780
tgggaagaca atagcaggca tgctggggag agatccacga taacaaacag ctttttgggg   3840
gtgaacatat tgactgaatt ccctgcaggt tggccactcc ctctctgcgc gctcgctcgc   3900
tcactgaggc cgcccgggca aagcccgggc gtcgggcgac ctttggtcgc ccggcctcag   3960
tgagcgagcg agcgcgcaga gagggagtgg ccaactccat cactaggggt tcctgcggcc   4020
gctcgtacgg tctcgaggaa ttcctgcagg ataacttgcc aacctcattc taaaatgtat   4080
atagaagccc aaaagacaat aacaaaaata ttcttgtaga acaaaatggg aaagaatgtt   4140
ccactaaata tcaagattta gagcaaagca tgagatgtgt ggggatagac agtgaggctg   4200
ataaaataga gtagagctca gaaacagacc cattgatata tgtaagtgac ctatgaaaaa   4260
aatatggcat tttacaatgg gaaaatgatg gtctttttct tttttagaaa aacagggaaa   4320
tatatttata tgtaaaaaat aaaagggaac ccatatgtca taccatacac acaaaaaaat   4380
tccagtgaat tataagtcta aatggagaag gcaaaacttt aaatctttta gaaaataata   4440
tagaagcatg cagaccagcc tggccaacat gatgaaaccc tctctactaa taataaaatc   4500
agtagaacta ctcaggacta ctttgagtgg gaagtccttt tctatgaaga cttctttggc   4560
caaaattagg ctctaaatgc aaggagatag tgcatcatgc ctggctgcac ttactgataa   4620
```

-continued

```
atgatgttat caccatcttt aaccaaatgc acaggaacaa gttatggtac tgatgtgctg   4680
gattgagaag gagctctact tccttgacag gacacatttg tatcaactta aaaaagcaga   4740
tttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtcctttttt   5160
aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc cctgccacc    5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttctttccct catagacctc catctctgtt ttccttagcc   5880
tgcagaaatc tggatggcta ttcacagaat gcctgtgctt tcagagttgc atttttttctc   5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agatttaca caagatggtc tgtaatttca cagttagttt tatcccatta ggtatgaaag   6480
aattagcata attcccctta aacatgaatg aatcttagat tttttaataa atagttttgg   6540
aagtaaagac agagacatca ggagcacaag gaatagcctg agaggacaaa cagaacaaga   6600
aagagtctgg aaatacacag gatgttcttg gcctcctcaa agcaagtgca agcagatagt   6660
accagcagcc ccaggctatc agagcccagt gaagagaagt accatgaaag ccacagctct   6720
aaccaccctg ttccagagtg acagacagtc cccaagacaa gccagcctga gccagagaga   6780
gaactgcaag agaaagtttc taatttaggt tctgttagat tcagacaagt gcaggtcatc   6840
ctctctccac agctactcac ctctccagcc taacaaagcc tgcagtccac actccaaccc   6900
tggtgtctca cctcctagcc tctcccaaca tcctgctctc tgaccatctt ctgcatctct   6960
catctcacca tctcccactg tctacagcct actcttgcaa ctaccatctc attttctgac   7020
```

atcctgtcta catcttctgc catactctgc catctaccat accacctctt accatctacc 7080
acaccatctt ttatctccat ccctctcaga agcctccaag ctgaatcctg ctttatgtgt 7140
tcatctcagc ccctgcatgg aaagctgacc ccagaggcag aactattccc agagagcttg 7200
gccaagaaaa acaaaactac cagcctggcc aggctcagga gtagtaagct gcagtgtctg 7260
ttgtgttcta gcttcaacag ctgcaggagt tccactctca aatgctccac atttctcaca 7320
tcctcctgat tctggtcact acccatcttc aaagaacaga atatctcaca tcagcatact 7380
gtgaaggact agtcatgggt gcagctgctc agagctgcaa agtcattctg gatggtggag 7440
agcttacaaa catttcatga tgctcccccc gctctgatgg ctggagccca atccctacac 7500
agactcctgc tgtatgtgtt ttcctttcac tctgagccac agccagaggg caggcattca 7560
gtctcctctt caggctgggg ctggggcact gagaactcac ccaacacctt gctctcactc 7620
cttctgcaaa acaagaaaga gctttgtgct gcagtagcca tgaagaatga aaggaaggct 7680
ttaactaaaa aatgtcagag attattttca accccttact gtggatcacc agcaaggagg 7740
aaacacaaca cagagacatt ttttcccctc aaattatcaa aagaatcact gcatttgtta 7800
aagagagcaa ctgaatcagg aagcagagtt ttgaacatat cagaagttag gaatctgcat 7860
cagagacaaa tgcagtcatg gttgtttgct gcataccagc cctaatcatt agaagcctca 7920
tggacttcaa acatcattcc ctctgacaag atgctctagc ctaactccat gagataaaat 7980
aaatctgcct ttcagagcca aagaagagtc caccagcttc ttctcagtgt gaacaagagc 8040
tccagtcagg ttagtcagtc cagtgcagta gaggagacca gtctgcatcc tctaattttc 8100
aaaggcaaga agatttgttt accctggaca ccaggcacaa gtgaggtcac agagctctta 8160
gatatgcagt cctcatgagt gaggagacta aagcgcatgc catcaagact tcagtgtaga 8220
gaaaacctcc aaaaaagcct cctcactact tctggaatag ctcagaggcc gaggcggcct 8280
cggcctctgc ataaataaaa aaaattagtc agccatgggg cggagaatgg gcggaactgg 8340
gcggagttag gggcgggatg ggcggagtta ggggcgggac tatggttgct gactaattga 8400
gatgcatgct ttgcatactt ctgcctgctg gggagcctgg ggactttcca cacctggttg 8460
ctgactaatt gagatgcatg ctttgcatac ttctgcctgc tggggagcct ggggactttc 8520
cacaccctaa ctgacacaca ttccacagct gcattaatga atcggccaac gcgcggggag 8580
aggcggtttg cgtattgggc gctcttccgc ttcctcgctc actgactcgc tgcgctcggt 8640
cgttcggctg cggcgagcgg tatcagctca ctcaaaggcg gtaatacggt tatccacaga 8700
atcaggggat aacgcaggaa agaacatgtg agcaaaaggc cagcaaaagg ccaggaaccg 8760
taaaaaggcc gcgttgctgg cgtttttcca taggctccgc ccccctgacg agcatcacaa 8820
aaatcgacgc tcaagtcaga ggtggcgaaa cccgacagga ctataaagat accaggcgtt 8880
tccccctgga agctccctcg tgcgctctcc tgttccgacc ctgccgctta ccggatacct 8940
gtccgccttt ctcccttcgg gaagcgtggc gctttctcat agctcacgct gtaggtatct 9000
cagttcggtg taggtcgttc gctccaagct gggctgtgtg cacgaacccc ccgttcagcc 9060
cgaccgctgc gccttatccg gtaactatcg tcttgagtcc aacccggtaa gacacgactt 9120
atcgccactg gcagcagcca ctggtaacag gattagcaga gcgaggtatg taggcggtgc 9180
tacagagttc ttgaagtggt ggcctaacta cggctacact agaagaacag tatttggtat 9240
ctgcgctctg ctgaagccag ttaccttcgg aaaaagagtt ggtagctctt gatccggcaa 9300
acaaaccacc gctggtagcg gtggtttttt tgtttgcaag cagcagatta cgcgcagaaa 9360

```
aaaaggatct caagaagatc ctttgatctt ttctacgggg tctgacgctc agtggaacga   9420

aaactcacgt taagggattt tggtcatgag attatcaaaa aggatcttca cctagatcct   9480

tttaaattaa aaatgaagtt ttaaatcaat ctaaagtata tatgagtaaa cttggtctga   9540

cagttaccaa tgcttaatca gtgaggcacc tatctcagcg atctgtctat ttcgttcatc   9600

catagttgcc tgactcctgc aaaccacgtt gtgtctcaaa atctctgatg ttacattgca   9660

caagataaaa atatatcatc atgaacaata aaactgtctg cttacataaa cagtaataca   9720

aggggtgtta tgagccatat tcaacgggaa acgtcttgct cgaggccgcg attaaattcc   9780

aacatggatg ctgatttata tgggtataaa tgggctcgcg ataatgtcgg gcaatcaggt   9840

gcgacaatct atcgattgta tgggaagccc gatgcgccag agttgtttct gaaacatggc   9900

aaaggtagcg ttgccaatga tgttacagat gagatggtca gactaaactg gctgacggaa   9960

tttatgcctc ttccgaccat caagcatttt atccgtactc ctgatgatgc atggttactc  10020

accactgcga tccccgggaa aacagcattc caggtattag aagaatatcc tgattcaggt  10080

gaaaatattg ttgatgcgct ggcagtgttc ctgcgccggt tgcattcgat tcctgtttgt  10140

aattgtcctt ttaacagcga tcgcgtattt cgtctcgctc aggcgcaatc acgaatgaat  10200

aacggtttgg ttgatgcgag tgattttgat gacgagcgta atggctggcc tgttgaacaa  10260

gtctggaaag aaatgcataa gcttttgcca ttctcaccgg attcagtcgt cactcatggt  10320

gatttctcac ttgataacct tatttttgac gaggggaaat taataggttg tattgatgtt  10380

ggacgagtcg gaatcgcaga ccgataccag gatcttgcca tcctatggaa ctgcctcggt  10440

gagttttctc cttcattaca gaaacggctt tttcaaaaat atggtattga taatcctgat  10500

atgaataaat tgcagtttca tttgatgctc gatgagtttt tctaagggcg gcctgccacc  10560

atacccacgc cgaaacaagc gctcatgagc ccgaagtggc gagcccgatc ttccccatcg  10620

gtgatgtcgg cgatataggc gccagcaacc gcacctgtgg cgccggtgat gagggcgcgc  10680

caagtcgacg tccggcagtc                                               10700
```

<210> SEQ ID NO 9
<211> LENGTH: 10700
<212> TYPE: DNA
<213> ORGANISM: Artificial Sequence
<220> FEATURE:
<223> OTHER INFORMATION: Synthetic polynucleotide

<400> SEQUENCE: 9

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg aattcggtac    300

ctagttatta atagtaatca attacggggt cattagttca tagcccatat atggagttcc    360

gcgttacata acttacggta aatggcccgc ctggctgacc gcccaacgac ccccgcccat    420

tgacgtcaat aatgacgtat gttcccatag taacgccaat agggactttc cattgacgtc    480

aatgggtgga gtatttacgg taaactgccc acttggcagt acatcaagtg tatcatatgc    540

caagtacgcc ccctattgac gtcaatgacg gtaaatggcc cgcctggcat tatgcccagt    600

acatgacctt atgggacttt cctacttggc agtacatcta cgtattagtc atcgctatta    660

ccatggtcga ggtgagcccc acgttctgct tcactctccc catctccccc ccctccccac    720
```

```
ccccaatttt gtatttattt attttttaat tattttgtgc agcgatgggg gcgggggggg    780
gggggggcg cgcgccaggc ggggcggggc ggggcgaggg gcggggcggg gcgaggcgga    840
gaggtgcggc ggcagccaat cagagcggcg cgctccgaaa gtttcctttt atggcgaggc    900
ggcggcggcg gcggccctat aaaaagcgaa gcgcgcggcg ggcgggagtc gctgcgacgc    960
tgccttcgcc ccgtgccccg ctccgccgcc gcctcgcgcc gcccgccccg gctctgactg   1020
accgcgttac tcccacaggt gagcgggcgg gacggccctt ctcctccggg ctgtaattag   1080
cgcttggttt aatgacggct tgtttctttt ctgtggctgc gtgaaagcct tgaggggctc   1140
cgggagctag agcctctgct aaccatgttc atgccttctt ctttttccta cagctcctgg   1200
gcaacgtgct ggttattgtg ctgtctcatc attttggcaa agaattcctc gaagatccga   1260
agggaaagtc ttccacgact gtgggatccg ttcgaagata tcaccggttg agccaccatg   1320
gaattcagca gccccagcag agaggaatgc cccaagcctc tgagccgggt gtcaatcatg   1380
gccggatctc tgacaggact gctgctgctt caggccgtgt cttgggcttc tggcgctaga   1440
ccttgcatcc ccaagagctt cggctacagc agcgtcgtgt gcgtgtgcaa tgccacctac   1500
tgcgacagct tcgaccctcc tacctttcct gctctgggca ccttcagcag atacgagagc   1560
accagatccg gcagacggat ggaactgagc atgggaccca tccaggccaa tcacacaggc   1620
actggcctgc tgctgacact gcagcctgag cagaaattcc agaaagtgaa aggcttcggc   1680
ggagccatga cagatgccgc cgctctgaat atcctggctc tgtctccacc agctcagaac   1740
ctgctgctca agagctactt cagcgaggaa ggcatcggct acaacatcat cagagtgccc   1800
atggccagct gcgacttcag catcaggacc tacacctacg ccgacacacc cgacgatttc   1860
cagctgcaca acttcagcct gcctgaagag gacaccaagc tgaagatccc tctgatccac   1920
agagccctgc agctggcaca aagacccgtg tcactgctgg cctctccatg gacatctccc   1980
acctggctga aaacaaatgg cgccgtgaat ggcaagggca gcctgaaagg ccaacctggc   2040
gacatctacc accagacctg ggccagatac ttcgtgaagt tcctggacgc ctatgccgag   2100
cacaagctgc agttttgggc cgtgacagcc gagaacgaac cttctgctgg actgctgagc   2160
ggctacccct ttcagtgcct gggctttaca cccgagcacc agcgggactt tatcgcccgt   2220
gatctgggac ccacactggc caatagcacc caccataatg tgcggctgct gatgctggac   2280
gaccagagac tgcttctgcc ccactgggct aaagtggtgc tgacagatcc tgaggccgcc   2340
aaatacgtgc acggaatcgc cgtgcactgg tatctggact ttctggcccc tgccaaggcc   2400
acactgggag agacacacag actgttcccc aacaccatgc tgttcgccag cgaagcctgt   2460
gtgggcagca agttttggga acagagcgtg cggctcggca gctgggatag aggcatgcag   2520
tacagccaca gcatcatcac caacctgctg taccacgtcg tcggctggac cgactggaat   2580
ctggccctga atcctgaagg cggccctaac tgggtccgaa acttcgtgga cagccccatc   2640
atcgtggaca tcaccaagga caccttctac aagcagccca tgttctacca cctgggacac   2700
ttcagcaagt tcatccccga gggctctcag cgcgttggac tggtggcttc ccagaagaac   2760
gatctggacg ccgtggctct gatgcaccct gatggatctg ctgtggtggt ggtcctgaac   2820
cgcagcagca aagatgtgcc cctgaccatc aaggatcccg ccgtgggatt cctggaaaca   2880
atcagccctg gctactccat ccacacctac ctgtggcgta gacagtgaca attgttaatt   2940
aagtttaaac cctcgaggcc gcaagcttat cgataatcaa cctctggatt acaaaatttg   3000
tgaaagattg actggtattc ttaactatgt tgctcctttt acgctatgtg gatacgctgc   3060
```

```
tttaatgcct ttgtatcatg ctattgcttc ccgtatggct ttcattttct cctccttgta   3120
taaatcctgg ttgctgtctc tttatgagga gttgtggccc gttgtcaggc aacgtggcgt   3180
ggtgtgcact gtgtttgctg acgcaacccc cactggttgg ggcattgcca ccacctgtca   3240
gctcctttcc gggactttcg ctttccccct ccctattgcc acggcggaac tcatcgccgc   3300
ctgccttgcc cgctgctgga caggggctcg gctgttgggc actgacaatt ccgtggtgtt   3360
gtcggggaaa tcatcgtcct ttccttggct gctcgcctgt gttgccacct ggattctgcg   3420
cgggacgtcc ttctgctacg tcccttcggc cctcaatcca gcggaccttc cttcccgcgg   3480
cctgctgccg gctctgcggc ctcttccgcg tcttcgcctt cgccctcaga cgagtcggat   3540
ctccctttgg gccgcctccc cgcatcgata ccgtcgacta gagctcgctg atcagcctcg   3600
actgtgcctt ctagttgcca gccatctgtt gtttgcccct cccccgtgcc ttccttgacc   3660
ctggaaggtg ccactcccac tgtcctttcc taataaaatg aggaaattgc atcgcattgt   3720
ctgagtaggt gtcattctat tctggggggt ggggtggggc aggacagcaa gggggaggat   3780
tgggaagaca atagcaggca tgctggggag agatccacga taacaaacag ctttttttggg  3840
gtgaacatat tgactgaatt ccctgcaggt tggccactcc ctctctgcgc gctcgctcgc   3900
tcactgaggc cgcccgggca aagcccgggc gtcgggcgac ctttggtcgc ccggcctcag   3960
tgagcgagcg agcgcgcaga gagggagtgg ccaactccat cactaggggt tcctgcggcc   4020
gctcgtacgg tctcgaggaa ttcctgcagg ataacttgcc aacctcattc taaaatgtat   4080
atagaagccc aaaagacaat aacaaaaata ttcttgtaga acaaaatggg aaagaatgtt   4140
ccactaaata tcaagattta gagcaaagca tgagatgtgt ggggatagac agtgaggctg   4200
ataaaataga gtagagctca gaaacagacc cattgatata tgtaagtgac ctatgaaaaa   4260
aatatggcat tttacaatgg gaaaatgatg gtctttttct tttttagaaa aacagggaaa   4320
tatatttata tgtaaaaaat aaaagggaac ccatatgtca taccatacac acaaaaaaat   4380
tccagtgaat tataagtcta aatggagaag gcaaaacttt aaatctttta gaaaataata   4440
tagaagcatg cagaccagcc tggccaacat gatgaaaccc tctctactaa taataaaatc   4500
agtagaacta ctcaggacta ctttgagtgg gaagtccttt tctatgaaga cttctttggc   4560
caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacatttg tatcaactta aaaaagcaga   4740
tttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtcctttttt   5160
aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
```

```
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttctttccct catagacctc catctctgtt ttccttagcc   5880
tgcagaaatc tggatggcta ttcacagaat gcctgtgctt tcagagttgc atttttctc    5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agattttaca caagatggtc tgtaatttca cagttagttt tatcccatta ggtatgaaag   6480
aattagcata attcccctta aacatgaatg aatcttagat tttttaataa atagttttgg   6540
aagtaaagac agagacatca ggagcacaag gaatagcctg agaggacaaa cagaacaaga   6600
aagagtctgg aaatacacag gatgttcttg gcctcctcaa agcaagtgca agcagatagt   6660
accagcagcc ccaggctatc agagcccagt gaagagaagt accatgaaag ccacagctct   6720
aaccaccctg ttccagagtg acagacagtc cccaagacaa gccagcctga gccagagaga   6780
gaactgcaag agaaagtttc taatttaggt tctgttagat tcagacaagt gcaggtcatc   6840
ctctctccac agctactcac ctctccagcc taacaaagcc tgcagtccac actccaaccc   6900
tggtgtctca cctcctagcc tctcccaaca tcctgctctc tgaccatctt ctgcatctct   6960
catctcacca tctcccactg tctacagcct actcttgcaa ctaccatctc attttctgac   7020
atcctgtcta catcttctgc catactctgc catctaccat accacctctt accatctacc   7080
acaccatctt ttatctccat ccctctcaga agcctccaag ctgaatcctg ctttatgtgt   7140
tcatctcagc ccctgcatgg aaagctgacc ccagaggcag aactattccc agagagcttg   7200
gccaagaaaa acaaaactac cagcctggcc aggctcagga gtagtaagct gcagtgtctg   7260
ttgtgttcta gcttcaacag ctgcaggagt tccactctca aatgctccac atttctcaca   7320
tcctcctgat tctggtcact acccatcttc aaagaacaga atatctcaca tcagcatact   7380
gtgaaggact agtcatgggt gcagctgctc agagctgcaa agtcattctg gatggtggag   7440
agcttacaaa catttcatga tgctccccc gctctgatgg ctggagccca atccctacac    7500
agactcctgc tgtatgtgtt ttcctttcac tctgagccac agccagaggg caggcattca   7560
gtctcctctt caggctgggg ctggggcact gagaactcac ccaacacctt gctctcactc   7620
cttctgcaaa acaagaaaga gctttgtgct gcagtagcca tgaagaatga aaggaaggct   7680
ttaactaaaa aatgtcagag attattttca accccttact gtggatcacc agcaaggagg   7740
aaacacaaca cagagacatt ttttcccctc aaattatcaa aagaatcact gcatttgtta   7800
```

aagagagcaa ctgaatcagg aagcagagtt ttgaacatat cagaagttag gaatctgcat 7860
cagagacaaa tgcagtcatg gttgtttgct gcataccagc cctaatcatt agaagcctca 7920
tggacttcaa acatcattcc ctctgacaag atgctctagc ctaactccat gagataaaat 7980
aaatctgcct ttcagagcca aagaagagtc caccagcttc ttctcagtgt gaacaagagc 8040
tccagtcagg ttagtcagtc cagtgcagta gaggagacca gtctgcatcc tctaattttc 8100
aaaggcaaga agatttgttt accctggaca ccaggcacaa gtgaggtcac agagctctta 8160
gatatgcagt cctcatgagt gaggagacta aagcgcatgc catcaagact tcagtgtaga 8220
gaaaacctcc aaaaaagcct cctcactact tctggaatag ctcagaggcc gaggcggcct 8280
cggcctctgc ataaataaaa aaaattagtc agccatgggg cggagaatgg gcggaactgg 8340
gcggagttag gggcgggatg ggcggagtta ggggcgggac tatggttgct gactaattga 8400
gatgcatgct ttgcatactt ctgcctgctg gggagcctgg ggactttcca cacctggttg 8460
ctgactaatt gagatgcatg ctttgcatac ttctgcctgc tggggagcct ggggactttc 8520
cacaccctaa ctgacacaca ttccacagct gcattaatga atcggccaac gcgcggggag 8580
aggcggtttg cgtattgggc gctcttccgc ttcctcgctc actgactcgc tgcgctcggt 8640
cgttcggctg cggcgagcgg tatcagctca ctcaaaggcg gtaatacggt tatccacaga 8700
atcaggggat aacgcaggaa agaacatgtg agcaaaaggc cagcaaaagg ccaggaaccg 8760
taaaaaggcc gcgttgctgg cgtttttcca taggctccgc ccccctgacg agcatcacaa 8820
aaatcgacgc tcaagtcaga ggtggcgaaa cccgacagga ctataaagat accaggcgtt 8880
tccccctgga agctccctcg tgcgctctcc tgttccgacc ctgccgctta ccggatacct 8940
gtccgccttt ctcccttcgg gaagcgtggc gctttctcat agctcacgct gtaggtatct 9000
cagttcggtg taggtcgttc gctccaagct gggctgtgtg cacgaacccc ccgttcagcc 9060
cgaccgctgc gccttatccg gtaactatcg tcttgagtcc aacccggtaa gacacgactt 9120
atcgccactg gcagcagcca ctggtaacag gattagcaga gcgaggtatg taggcggtgc 9180
tacagagttc ttgaagtggt ggcctaacta cggctacact agaagaacag tatttggtat 9240
ctgcgctctg ctgaagccag ttaccttcgg aaaaagagtt ggtagctctt gatccggcaa 9300
acaaaccacc gctggtagcg gtggtttttt tgtttgcaag cagcagatta cgcgcagaaa 9360
aaaaggatct caagaagatc ctttgatctt ttctacgggg tctgacgctc agtggaacga 9420
aaactcacgt taagggattt tggtcatgag attatcaaaa aggatcttca cctagatcct 9480
tttaaattaa aaatgaagtt ttaaatcaat ctaaagtata tatgagtaaa cttggtctga 9540
cagttaccaa tgcttaatca gtgaggcacc tatctcagcg atctgtctat ttcgttcatc 9600
catagttgcc tgactcctgc aaaccacgtt gtgtctcaaa atctctgatg ttacattgca 9660
caagataaaa atatatcatc atgaacaata aaactgtctg cttacataaa cagtaataca 9720
aggggtgtta tgagccatat tcaacgggaa acgtcttgct cgaggccgcg attaaattcc 9780
aacatggatg ctgatttata tgggtataaa tgggctcgcg ataatgtcgg gcaatcaggt 9840
gcgacaatct atcgattgta tgggaagccc gatgcgccag agttgtttct gaaacatggc 9900
aaaggtagcg ttgccaatga tgttacagat gagatggtca gactaaactg gctgacggaa 9960
tttatgcctc ttccgaccat caagcatttt atccgtactc ctgatgatgc atggttactc 10020
accactgcga tccccgggaa aacagcattc caggtattag aagaatatcc tgattcaggt 10080
gaaaatattg ttgatgcgct ggcagtgttc ctgcgccggt tgcattcgat tcctgtttgt 10140
aattgtcctt ttaacagcga tcgcgtattt cgtctcgctc aggcgcaatc acgaatgaat 10200
aacggtttgg ttgatgcgag tgattttgat gacgagcgta atggctggcc tgttgaacaa 10260
gtctggaaag aaatgcataa gcttttgcca ttctcaccgg attcagtcgt cactcatggt 10320
gatttctcac ttgataacct tatttttgac gaggggaaat taataggttg tattgatgtt 10380
ggacgagtcg gaatcgcaga ccgataccag gatcttgcca tcctatggaa ctgcctcggt 10440
gagttttctc cttcattaca gaaacggctt tttcaaaaat atggtattga taatcctgat 10500
atgaataaat tgcagtttca tttgatgctc gatgagtttt tctaagggcg gcctgccacc 10560
atacccacgc cgaaacaagc gctcatgagc ccgaagtggc gagcccgatc ttccccatcg 10620
gtgatgtcgg cgatataggc gccagcaacc gcacctgtgg cgccggtgat gagggcgcgc 10680
caagtcgacg tccggcagtc 10700

<210> SEQ ID NO 10
<211> LENGTH: 10700
<212> TYPE: DNA
<213> ORGANISM: Artificial Sequence
<220> FEATURE:
<223> OTHER INFORMATION: Synthetic polynucleotide

<400> SEQUENCE: 10
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttaat tattttgtgc agcgatgggg gcgggggggg 780 gggggggcg cgcgccaggc ggggcggggc ggggcgaggg gcggggcggg gcgaggcgga 840
gaggtgcggc ggcagccaat cagagcggcg cgctccgaaa gtttcctttt atggcgaggc 900
ggcggcggcg gcggccctat aaaaagcgaa gcgcgcggcg ggcgggagtc gctgcgacgc 960
tgccttcgcc ccgtgccccg ctccgccgcc gcctcgcgcc gcccgccccg gctctgactg 1020
accgcgttac tcccacaggt gagcgggcgg gacggccctt ctcctccggg ctgtaattag 1080
cgcttggttt aatgacggct tgtttctttt ctgtggctgc gtgaaagcct tgaggggctc 1140
cgggagctag agcctctgct aaccatgttc atgccttctt ctttttccta cagctcctgg 1200
gcaacgtgct ggttattgtg ctgtctcatc attttggcaa agaattcctc gaagatccga 1260
agggaaagtc ttccacgact gtgggatccg ttcgaagata tcaccggttg agccaccatg 1320
gaattcagca gccccagcag agaggaatgc cccaagcctc tgagccgggt gtcaatcatg 1380
gccggatctc tgacaggact gctgctgctt caggccgtgt cttgggcttc tggcgctaga 1440
ccttgcatcc ccaagagctt cggctacagc agcgtcgtgt gcgtgtgcaa tgccacctac 1500

-continued

```
tgcgacagct tcgaccctcc tacctttcct gctctgggca ccttcagcag atacgagagc   1560
accagatccg gcagacggat ggaactgagc atgggaccca tccaggccaa tcacacaggc   1620
actggcctgc tgctgacact gcagcctgag cagaaattcc agaaagtgaa aggcttcggc   1680
ggagccatga cagatgccgc cgctctgaat atcctggctc tgtctccacc agctcagaac   1740
ctgctgctca agagctactt cagcgaggaa ggcatcggct acaacatcat cagagtgccc   1800
atggccagct gcgacttcag catcaggacc tacacctacg ccgacacacc cgacgatttc   1860
cagctgcaca acttcagcct gcctgaagag gacaccaagc tgaagatccc tctgatccac   1920
agagccctgc agctggcaca aagacccgtg tcactgctgg cctctccatg gacatctccc   1980
acctggctga aaacaaatgg cgccgtgaat ggcaagggca gcctgaaagg ccaacctggc   2040
gacatctacc accagacctg ggccagatac ttcgtgaagt tcctggacgc ctatgccgag   2100
cacaagctgc agttttgggc cgtgacagcc gagaacgaac cttctgctgg actgctgagc   2160
ggctacccct ttcagtgcct gggctttaca cccgagcacc agcgggactt tatcgcccgt   2220
gatctgggac ccacactggc caatagcacc caccataatg tgcggctgct gatgctggac   2280
gaccagagac tgcttctgcc ccactgggct aaagtggtgc tgacagatcc tgaggccgcc   2340
aaatacgtgc acggaatcgc cgtgcactgg tatctggact ttctggcccc tgccaaggcc   2400
acactgggag agacacacag actgttcccc aacaccatgc tgttcgccag cgaagcctgt   2460
gtgggcagca agttttggga acagagcgtg cggctcggca gctgggatag aggcatgcag   2520
tacagccaca gcatcatcac caacctgctg taccacgtcg tcggctggac cgactggaat   2580
ctggccctga atcctgaagg cggccctaac tgggtccgaa acttcgtgga cagccccatc   2640
atcgtggaca tcaccaagga caccttctac aagcagccca tgttctacca cctgggacac   2700
ttcagcaagt tcatccccga gggctctcag cgcgttggac tggtggcttc ccagaagaac   2760
gatctggacg ccgtggctct gatgcaccct gatggatctg ctgtggtggt ggtcctgaac   2820
cgcagcagca aagatgtgcc cctgaccatc aaggatcccg ccgtgggatt cctggaaaca   2880
atcagccctg gctactccat ccacacctac ctgtggcgta gacagtgaca attgttaatt   2940
aagtttaaac cctcgaggcc gcaagcttat cgataatcaa cctctggatt acaaaatttg   3000
tgaaagattg actggtattc ttaactatgt tgctcctttt acgctatgtg gatacgctgc   3060
tttaatgcct ttgtatcatg ctattgcttc ccgtatggct ttcattttct cctccttgta   3120
taaatcctgg ttgctgtctc tttatgagga gttgtggccc gttgtcaggc aacgtggcgt   3180
ggtgtgcact gtgtttgctg acgcaacccc cactggttgg ggcattgcca ccacctgtca   3240
gctcctttcc gggactttcg ctttccccct ccctattgcc acggcggaac tcatcgccgc   3300
ctgccttgcc cgctgctgga caggggctcg gctgttgggc actgacaatt ccgtggtgtt   3360
gtcggggaaa tcatcgtcct ttccttggct gctcgcctgt gttgccacct ggattctgcg   3420
cgggacgtcc ttctgctacg tcccttcggc cctcaatcca gcggaccttc cttcccgcgg   3480
cctgctgccg gctctgcggc ctcttccgcg tcttcgcctt cgccctcaga cgagtcggat   3540
ctccctttgg gccgcctccc cgcatcgata ccgtcgacta gagctcgctg atcagcctcg   3600
actgtgcctt ctagttgcca gccatctgtt gtttgcccct cccccgtgcc ttccttgacc   3660
ctggaaggtg ccactcccac tgtcctttcc taataaaatg aggaaattgc atcgcattgt   3720
ctgagtaggt gtcattctat tctggggggt ggggtggggc aggacagcaa gggggaggat   3780
tgggaagaca atagcaggca tgctggggag agatccacga taacaaacag ctttttttggg  3840
gtgaacatat tgactgaatt ccctgcagga ggaacccctA gtgatggagt tggccactcc   3900
```

```
ctctctgcgc gctcgctcgc tcactgaggc cgcccgggca aagcccgggc gtcgggcgac   3960
ctttggtcgc ccggcctcag tgagcgagcg agcgcgcaga gagggagtgg ccaagcggcc   4020
gctcgtacgg tctcgaggaa ttcctgcagg ataacttgcc aacctcattc taaaatgtat   4080
atagaagccc aaaagacaat aacaaaaata ttcttgtaga acaaaatggg aaagaatgtt   4140
ccactaaata tcaagattta gagcaaagca tgagatgtgt ggggatagac agtgaggctg   4200
ataaaataga gtagagctca gaaacagacc cattgatata tgtaagtgac ctatgaaaaa   4260
aatatggcat tttacaatgg gaaaatgatg gtcttttttct tttttagaaa aacagggaaa   4320
tatatttata tgtaaaaaat aaaagggaac ccatatgtca taccatacac acaaaaaaat   4380
tccagtgaat tataagtcta aatggagaag gcaaaacttt aaatctttta gaaaataata   4440
tagaagcatg cagaccagcc tggccaacat gatgaaaccc tctctactaa taataaaatc   4500
agtagaacta ctcaggacta ctttgagtgg gaagtccttt tctatgaaga cttctttggc   4560
caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacatttg tatcaactta aaaaagcaga   4740
tttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtcctttttt   5160
aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttctttccct catagacctc catctctgtt ttccttagcc   5880
tgcagaaatc tggatggcta ttcacagaat gcctgtgctt tcagagttgc atttttttctc   5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
ccttacctct gccctaccca ggacaaaccc aagagccact gtttctgtga tgtcctctcc   6240
```

-continued

```
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agattttaca caagatggtc tgtaatttca cagttagttt tatcccatta ggtatgaaag   6480
aattagcata attcccctta aacatgaatg aatcttagat tttttaataa atagttttgg   6540
aagtaaagac agagacatca ggagcacaag gaatagcctg agaggacaaa cagaacaaga   6600
aagagtctgg aaatacacag gatgttcttg gcctcctcaa agcaagtgca agcagatagt   6660
accagcagcc ccaggctatc agagcccagt gaagagaagt accatgaaag ccacagctct   6720
aaccaccctg ttccagagtg acagacagtc cccaagacaa gccagcctga gccagagaga   6780
gaactgcaag agaaagtttc taatttaggt tctgttagat tcagacaagt gcaggtcatc   6840
ctctctccac agctactcac ctctccagcc taacaaagcc tgcagtccac actccaaccc   6900
tggtgtctca cctcctagcc tctcccaaca tcctgctctc tgaccatctt ctgcatctct   6960
catctcacca tctcccactg tctacagcct actcttgcaa ctaccatctc attttctgac   7020
atcctgtcta catcttctgc catactctgc catctaccat accacctctt accatctacc   7080
acaccatctt ttatctccat ccctctcaga agcctccaag ctgaatcctg ctttatgtgt   7140
tcatctcagc ccctgcatgg aaagctgacc ccagaggcag aactattccc agagagcttg   7200
gccaagaaaa acaaaactac cagcctggcc aggctcagga gtagtaagct gcagtgtctg   7260
ttgtgttcta gcttcaacag ctgcaggagt tccactctca aatgctccac atttctcaca   7320
tcctcctgat tctggtcact acccatcttc aaagaacaga atatctcaca tcagcatact   7380
gtgaaggact agtcatgggt gcagctgctc agagctgcaa agtcattctg gatggtggag   7440
agcttacaaa catttcatga tgctccccc gctctgatgg ctggagccca atccctacac   7500
agactcctgc tgtatgtgtt ttcctttcac tctgagccac agccagaggg caggcattca   7560
gtctcctctt caggctgggg ctggggcact gagaactcac ccaacacctt gctctcactc   7620
cttctgcaaa acaagaaaga gctttgtgct gcagtagcca tgaagaatga aaggaaggct   7680
ttaactaaaa aatgtcagag attattttca accccttact gtggatcacc agcaaggagg   7740
aaacacaaca cagagacatt ttttcccctc aaattatcaa aagaatcact gcatttgtta   7800
aagagagcaa ctgaatcagg aagcagagtt ttgaacatat cagaagttag gaatctgcat   7860
cagagacaaa tgcagtcatg gttgtttgct gcataccagc cctaatcatt agaagcctca   7920
tggacttcaa acatcattcc ctctgacaag atgctctagc ctaactccat gagataaaat   7980
aaatctgcct ttcagagcca aagaagagtc caccagcttc ttctcagtgt gaacaagagc   8040
tccagtcagg ttagtcagtc cagtgcagta gaggagacca gtctgcatcc tctaattttc   8100
aaaggcaaga agatttgttt accctggaca ccaggcacaa gtgaggtcac agagctctta   8160
gatatgcagt cctcatgagt gaggagacta aagcgcatgc catcaagact tcagtgtaga   8220
gaaaacctcc aaaaaagcct cctcactact tctggaatag ctcagaggcc gaggcggcct   8280
cggcctctgc ataaataaaa aaaattagtc agccatgggg cggagaatgg gcggaactgg   8340
gcggagttag gggcgggatg ggcggagtta ggggcgggac tatggttgct gactaattga   8400
gatgcatgct ttgcatactt ctgcctgctg gggagcctgg ggactttcca cacctggttg   8460
ctgactaatt gagatgcatg ctttgcatac ttctgcctgc tggggagcct ggggactttc   8520
cacaccctaa ctgacacaca ttccacagct gcattaatga atcggccaac gcgcggggag   8580
aggcggtttg cgtattgggc gctcttccgc ttcctcgctc actgactcgc tgcgctcggt   8640
```

cgttcggctg cggcgagcgg tatcagctca ctcaaaggcg gtaatacggt tatccacaga 8700
atcaggggat aacgcaggaa agaacatgtg agcaaaaggc cagcaaaagg ccaggaaccg 8760
taaaaaggcc gcgttgctgg cgtttttcca taggctccgc ccccctgacg agcatcacaa 8820
aaatcgacgc tcaagtcaga ggtggcgaaa cccgacagga ctataaagat accaggcgtt 8880
tccccctgga agctccctcg tgcgctctcc tgttccgacc ctgccgctta ccggatacct 8940
gtccgccttt ctcccttcgg gaagcgtggc gctttctcat agctcacgct gtaggtatct 9000
cagttcggtg taggtcgttc gctccaagct gggctgtgtg cacgaacccc ccgttcagcc 9060
cgaccgctgc gccttatccg gtaactatcg tcttgagtcc aacccggtaa gacacgactt 9120
atcgccactg gcagcagcca ctggtaacag gattagcaga gcgaggtatg taggcggtgc 9180
tacagagttc ttgaagtggt ggcctaacta cggctacact agaagaacag tatttggtat 9240
ctgcgctctg ctgaagccag ttaccttcgg aaaaagagtt ggtagctctt gatccggcaa 9300
acaaaccacc gctggtagcg gtggtttttt tgtttgcaag cagcagatta cgcgcagaaa 9360
aaaaggatct caagaagatc ctttgatctt ttctacgggg tctgacgctc agtggaacga 9420
aaactcacgt taagggattt tggtcatgag attatcaaaa aggatcttca cctagatcct 9480
tttaaattaa aaatgaagtt ttaaatcaat ctaaagtata tatgagtaaa cttggtctga 9540
cagttaccaa tgcttaatca gtgaggcacc tatctcagcg atctgtctat ttcgttcatc 9600
catagttgcc tgactcctgc aaaccacgtt gtgtctcaaa atctctgatg ttacattgca 9660
caagataaaa atatatcatc atgaacaata aaactgtctg cttacataaa cagtaataca 9720
aggggtgtta tgagccatat tcaacgggaa acgtcttgct cgaggccgcg attaaattcc 9780
aacatggatg ctgatttata tgggtataaa tgggctcgcg ataatgtcgg gcaatcaggt 9840
gcgacaatct atcgattgta tgggaagccc gatgcgccag agttgtttct gaaacatggc 9900
aaaggtagcg ttgccaatga tgttacagat gagatggtca gactaaactg gctgacggaa 9960
tttatgcctc ttccgaccat caagcatttt atccgtactc ctgatgatgc atggttactc 10020
accactgcga tccccgggaa aacagcattc caggtattag aagaatatcc tgattcaggt 10080
gaaaatattg ttgatgcgct ggcagtgttc ctgcgccggt tgcattcgat tcctgtttgt 10140
aattgtcctt ttaacagcga tcgcgtattt cgtctcgctc aggcgcaatc acgaatgaat 10200
aacggtttgg ttgatgcgag tgattttgat gacgagcgta atggctggcc tgttgaacaa 10260
gtctggaaag aaatgcataa gcttttgcca ttctcaccgg attcagtcgt cactcatggt 10320
gatttctcac ttgataacct tatttttgac gaggggaaat taataggttg tattgatgtt 10380
ggacgagtcg gaatcgcaga ccgataccag gatcttgcca tcctatggaa ctgcctcggt 10440
gagttttctc cttcattaca gaaacggctt tttcaaaaat atggtattga taatcctgat 10500
atgaataaat tgcagtttca tttgatgctc gatgagtttt tctaagggcg gcctgccacc 10560
atacccacgc cgaaacaagc gctcatgagc ccgaagtggc gagcccgatc ttccccatcg 10620
gtgatgtcgg cgatataggc gccagcaacc gcacctgtgg cgccggtgat gagggcgcgc 10680
caagtcgacg tccggcagtc 10700

<210> SEQ ID NO 11
<211> LENGTH: 11188
<212> TYPE: DNA
<213> ORGANISM: Artificial Sequence
<220> FEATURE:
<223> OTHER INFORMATION: Synthetic polynucleotide

<400> SEQUENCE: 11
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactatt agatctgatg gccgcgctag ctctgggtat ttaagcccga gtgagcacgc 180
agggtctcca ttttgaagcg ggaggttacg cgttcgtcga ctactagtgg gtaccagagc 240
gtggtgactg agatgttttc taggaaacac aaaagataca aaaaagaaca cgtggaagga 300
tagccaaaaa ggggggctgc ccccatttcc tgcaccccgc tgcgatggct ggcaccattt 360
ggaagacttc gagatacact gttgagcgca gtaagacaac agtgtatctc gaagtcttcc 420
agatggggcc agccggtcca ctctgtatcc aggccagttc tgcaaggcgt tcgaggacca 480 ccccccctccc ctcgccacca gggtggtctc atacagaact tataagattc ccaaatccaa 540
agacatttca cgtttatggt gatttcccag aacacatagc gacatgcaaa tattgcaggg 600
cgccactccc ctgtccctca cagccatctt cctgccaggg cgcacgcgcg ctgggtgttc 660
ccgcctagtg acactgggcc cgcgattcct tggagcgggt tgatgacgtc agcgtttccc 720
atggtgaatc cctaggttct agaaccggtg acgtctccca tggtgaagct tggatctgaa 780
ttcggtacct agttattaat agtaatcaat tacggggtca ttagttcata gcccatatat 840
ggagttccgc gttacataac ttacggtaaa tggcccgcct ggctgaccgc ccaacgaccc 900
ccgcccattg acgtcaataa tgacgtatgt tcccatagta acgccaatag ggactttcca 960
ttgacgtcaa tgggtggagt atttacggta aactgcccac ttggcagtac atcaagtgta 1020
tcatatgcca agtacgcccc ctattgacgt caatgacggt aaatggcccg cctggcatta 1080
tgcccagtac atgaccttat gggactttcc tacttggcag tacatctacg tattagtcat 1140
cgctattacc atggtcgagg tgagccccac gttctgcttc actctcccca tctccccccc 1200
ctccccaccc ccaattttgt atttatttat tttttaatta ttttgtgcag cgatgggggc 1260
gggggggggg ggggggcgcg cgccaggcgg ggcggggcgg ggcgaggggc ggggcggggc 1320
gaggcggaga ggtgcggcgg cagccaatca gagcggcgcg ctccgaaagt ttccttttat 1380
ggcgaggcgg cggcggcggc ggccctataa aaagcgaagc gcgcggcggg cgggagtcgc 1440
tgcgacgctg ccttcgcccc gtgccccgct ccgccgccgc ctcgcgccgc ccgccccggc 1500
tctgactgac cgcgttactc ccacaggtga gcgggcggga cggcccttct cctccgggct 1560
gtaattagcg cttggtttaa tgacggcttg tttcttttct gtggctgcgt gaaagccttg 1620
aggggctccg ggagctagag cctctgctaa ccatgttcat gccttcttct tttcctaca 1680 gctcctgggc aacgtgctgg ttattgtgct gtctcatcat tttggcaaag aattcctcga 1740
agatccgaag ggaaagtctt ccacgactgt gggatccgtt cgaagatatc accggttgag 1800
ccaccatgga attcagcagc cccagcagag aggaatgccc caagcctctg agccgggtgt 1860
caatcatggc cggatctctg acaggactgc tgctgcttca ggccgtgtct tgggcttctg 1920
gcgctagacc ttgcatcccc aagagcttcg gctacagcag cgtcgtgtgc gtgtgcaatg 1980
ccacctactg cgacagcttc gaccctccta cctttcctgc tctgggcacc ttcagcagat 2040
acgagagcac cagatccggc agacggatgg aactgagcat gggacccatc caggccaatc 2100
acacaggcac tggcctgctg ctgacactgc agcctgagca gaaattccag aaagtgaaag 2160
gcttcggcgg agccatgaca gatgccgccg ctctgaatat cctggctctg tctccaccag 2220
ctcagaacct gctgctcaag agctacttca gcgaggaagg catcggctac aacatcatca 2280
gagtgcccat ggccagctgc gacttcagca tcaggaccta cacctacgcc gacacacccg 2340

```
acgatttcca gctgcacaac ttcagcctgc ctgaagagga caccaagctg aagatccctc   2400
tgatccacag agccctgcag ctggcacaaa gacccgtgtc actgctggcc tctccatgga   2460
catctcccac ctggctgaaa acaaatggcg ccgtgaatgg caagggcagc ctgaaaggcc   2520
aacctggcga catctaccac cagacctggg ccagatactt cgtgaagttc ctggacgcct   2580
atgccgagca caagctgcag ttttgggccg tgacagccga gaacgaacct tctgctggac   2640
tgctgagcgg ctaccccttt cagtgcctgg gctttacacc cgagcaccag cgggacttta   2700
tcgcccgtga tctgggaccc acactggcca atagcaccca ccataatgtg cggctgctga   2760
tgctggacga ccagagactg cttctgcccc actgggctaa agtggtgctg acagatcctg   2820
aggccgccaa atacgtgcac ggaatcgccg tgcactggta tctggacttt ctggcccctg   2880
ccaaggccac actgggagag acacacagac tgttccccaa caccatgctg ttcgccagcg   2940
aagcctgtgt gggcagcaag ttttgggaac agagcgtgcg gctcggcagc tgggatagag   3000
gcatgcagta cagccacagc atcatcacca acctgctgta ccacgtcgtc ggctggaccg   3060
actggaatct ggccctgaat cctgaaggcg gccctaactg ggtccgaaac ttcgtggaca   3120
gccccatcat cgtggacatc accaaggaca ccttctacaa gcagcccatg ttctaccacc   3180
tgggacactt cagcaagttc atccccgagg gctctcagcg cgttggactg gtggcttccc   3240
agaagaacga tctggacgcc gtggctctga tgcaccctga tggatctgct gtggtggtgg   3300
tcctgaaccg cagcagcaaa gatgtgcccc tgaccatcaa ggatcccgcc gtgggattcc   3360
tggaaacaat cagccctggc tactccatcc acacctacct gtggcgtaga cagtgacaat   3420
tgttaattaa gtttaaaccc tcgaggccgc aagcttatcg ataatcaacc tctggattac   3480
aaaatttgtg aaagattgac tggtattctt aactatgttg ctccttttac gctatgtgga   3540
tacgctgctt taatgccttt gtatcatgct attgcttccc gtatggcttt cattttctcc   3600
tccttgtata aatcctggtt gctgtctctt tatgaggagt tgtggcccgt tgtcaggcaa   3660
cgtggcgtgg tgtgcactgt gtttgctgac gcaaccccca ctggttgggg cattgccacc   3720
acctgtcagc tcctttccgg gactttcgct ttccccctcc ctattgccac ggcggaactc   3780
atcgccgcct gccttgcccg ctgctggaca ggggctcggc tgttgggcac tgacaattcc   3840
gtggtgttgt cggggaaatc atcgtccttt ccttggctgc tcgcctgtgt tgccacctgg   3900
attctgcgcg ggacgtcctt ctgctacgtc ccttcggccc tcaatccagc ggaccttcct   3960
tcccgcggcc tgctgccggc tctgcggcct cttccgcgtc ttcgccttcg ccctcagacg   4020
agtcggatct ccctttgggc cgcctccccg catcgatacc gtcgactaga gctcgctgat   4080
cagcctcgac tgtgccttct agttgccagc catctgttgt ttgcccctcc cccgtgcctt   4140
ccttgaccct ggaaggtgcc actcccactg tcctttccta ataaaatgag gaaattgcat   4200
cgcattgtct gagtaggtgt cattctattc tggggggtgg ggtggggcag gacagcaagg   4260
gggaggattg ggaagacaat agcaggcatg ctggggagag atccacgata acaaacagct   4320
tttttggggt gaacatattg actgaattcc ctgcaggttg gccactccct ctctgcgcgc   4380
tcgctcgctc actgaggccg cccgggcaaa gcccgggcgt cgggcgacct ttggtcgccc   4440
ggcctcagtg agcgagcgag cgcgcagaga gggagtggcc aactccatca ctaggggttc   4500
ctgcggccgc tcgtacggtc tcgaggaatt cctgcaggat aacttgccaa cctcattcta   4560
aaatgtatat agaagcccaa aagacaataa caaaaatatt cttgtagaac aaaatgggaa   4620
agaatgttcc actaaatatc aagatttaga gcaaagcatg agatgtgtgg ggatagacag   4680
```

```
tgaggctgat aaaatagagt agagctcaga aacagaccca ttgatatatg taagtgacct   4740
atgaaaaaaa tatggcattt tacaatggga aaatgatggt ctttttcttt tttagaaaaa   4800
cagggaaata tatttatatg taaaaaataa aagggaaccc atatgtcata ccatacacac   4860
aaaaaaattc cagtgaatta taagtctaaa tggagaaggc aaaactttaa atcttttaga   4920
aaataatata gaagcatgca gaccagcctg gccaacatga tgaaaccctc tctactaata   4980
ataaaatcag tagaactact caggactact ttgagtggga agtccttttc tatgaagact   5040
tctttggcca aaattaggct ctaaatgcaa ggagatagtg catcatgcct ggctgcactt   5100
actgataaat gatgttatca ccatctttaa ccaaatgcac aggaacaagt tatggtactg   5160
atgtgctgga ttgagaagga gctctacttc cttgacagga cacatttgta tcaacttaaa   5220
aaagcagatt tttgccagca gaactattca ttcagaggta ggaaacttag aatagatgat   5280
gtcactgatt agcatggctt ccccatctcc acagctgctt cccacccagg ttgcccacag   5340
ttgagtttgt ccagtgctca gggctgccca ctctcagtaa gaagccccac accagcccct   5400
ctccaaatat gttggctgtt ccttccatta aagtgacccc actttagagc agcaagtgga   5460
tttctgtttc ttacagttca ggaaggagga gtcagctgtg agaacctgga gcctgagatg   5520
cttctaagtc ccactgctac tggggtcagg gaagccagac tccagcatca gcagtcagga   5580
gcactaagcc cttgccaaca tcctgtttct cagagaaact gcttccatta taatggttgt   5640
cctttttttaa gctatcaagc caaacaacca gtgtctacca ttattctcat cacctgaagc   5700
caagggttct agcaaaagtc aagctgtctt gtaatggttg atgtgcctcc agcttctgtc   5760
ttcagtcact ccactcttag cctgctctga atcaactctg accacagttc cctggagccc   5820
ctgccacctg ctgcccctgc caccttctcc atctgcagtg ctgtgcagcc ttctgcactc   5880
ttgcagagct aataggtgga gacttgaagg aagaggagga aagtttctca taatagcctt   5940
gctgcaagct caaatgggag gtgggcactg tgcccaggag ccttggagca aaggctgtgc   6000
ccaacctctg actgcatcca ggtttggtct tgacagagat aagaagccct ggcttttgga   6060
gccaaaatct aggtcagact taggcaggat tctcaaagtt tatcagcaga acatgaggca   6120
gaagaccctt tctgctccag cttcttcagg ctcaaccttc atcagaatag atagaaagag   6180
aggctgtgag ggttcttaaa acagaagcaa atctgactca gagaataaac aacctcctag   6240
taaactacag cttagacaga gcatctggtg gtgagtgtgc tcagtgtcct actcaactgt   6300
ctggtatcag ccctcatgag gacttctctt ctttccctca tagacctcca tctctgtttt   6360
ccttagcctg cagaaatctg gatggctatt cacagaatgc ctgtgctttc agagttgcat   6420
tttttctctg gtattctggt tcaagcattt gaaggtagga aaggttctcc aagtgcaaga   6480
aagccagccc tgagcctcaa ctgcctggct agtgtggtca gtaggatgca aaggctgttg   6540
aatgccacaa ggccaaactt taacctgtgt accacaagcc tagcagcaga ggcagctctg   6600
ctcactggaa ctctctgtct tctttctcct gagccttttc ttttcctgag ttttctagct   6660
ctcctcaacc ttacctctgc cctacccagg acaaacccaa gagccactgt ttctgtgatg   6720
tcctctccag ccctaattag gcatcatgac ttcagcctga ccttccatgc tcagaagcag   6780
tgctaatcca cttcagatga gctgctctat gcaacacagg cagagcctac aaacctttgc   6840
accagagccc tccacatatc agtgtttgtt catactcact tcaacagcaa atgtgactgc   6900
tgagattaag attttacaca agatggtctg taatttcaca gttagtttta tcccattagg   6960
tatgaaagaa ttagcataat tccccttaaa catgaatgaa tcttagattt tttaataaat   7020
agttttggaa gtaaagacag agacatcagg agcacaagga atagcctgag aggacaaaca   7080
```

gaacaagaaa gagtctggaa atacacagga tgttcttggc ctcctcaaag caagtgcaag 7140
cagatagtac cagcagcccc aggctatcag agcccagtga agagaagtac catgaaagcc 7200
acagctctaa ccaccctgtt ccagagtgac agacagtccc caagacaagc cagcctgagc 7260
cagagagaga actgcaagag aaagtttcta atttaggttc tgttagattc agacaagtgc 7320
aggtcatcct ctctccacag ctactcacct ctccagccta acaaagcctg cagtccacac 7380
tccaaccctg gtgtctcacc tcctagcctc tcccaacatc ctgctctctg accatcttct 7440
gcatctctca tctcaccatc tcccactgtc tacagcctac tcttgcaact accatctcat 7500
tttctgacat cctgtctaca tcttctgcca tactctgcca tctaccatac cacctcttac 7560
catctaccac accatctttt atctccatcc ctctcagaag cctccaagct gaatcctgct 7620
ttatgtgttc atctcagccc ctgcatggaa agctgacccc agaggcagaa ctattcccag 7680
agagcttggc caagaaaaac aaaactacca gcctggccag gctcaggagt agtaagctgc 7740
agtgtctgtt gtgttctagc ttcaacagct gcaggagttc cactctcaaa tgctccacat 7800
ttctcacatc ctcctgattc tggtcactac ccatcttcaa agaacagaat atctcacatc 7860
agcatactgt gaaggactag tcatgggtgc agctgctcag agctgcaaag tcattctgga 7920
tggtggagag cttacaaaca tttcatgatg ctccccccgc tctgatggct ggagcccaat 7980
ccctacacag actcctgctg tatgtgtttt cctttcactc tgagccacag ccagagggca 8040
ggcattcagt ctcctcttca ggctggggct ggggcactga gaactcaccc aacaccttgc 8100
tctcactcct tctgcaaaac aagaaagagc tttgtgctgc agtagccatg aagaatgaaa 8160
ggaaggcttt aactaaaaaa tgtcagagat tattttcaac cccttactgt ggatcaccag 8220
caaggaggaa acacaacaca gagacatttt ttcccctcaa attatcaaaa gaatcactgc 8280
atttgttaaa gagagcaact gaatcaggaa gcagagtttt gaacatatca gaagttagga 8340
atctgcatca gagacaaatg cagtcatggt tgtttgctgc ataccagccc taatcattag 8400
aagcctcatg gacttcaaac atcattccct ctgacaagat gctctagcct aactccatga 8460
gataaaataa atctgccttt cagagccaaa gaagagtcca ccagcttctt ctcagtgtga 8520
acaagagctc cagtcaggtt agtcagtcca gtgcagtaga ggagaccagt ctgcatcctc 8580
taattttcaa aggcaagaag atttgtttac cctggacacc aggcacaagt gaggtcacag 8640
agctcttaga tatgcagtcc tcatgagtga ggagactaaa gcgcatgcca tcaagacttc 8700
agtgtagaga aaacctccaa aaaagcctcc tcactacttc tggaatagct cagaggccga 8760
ggcggcctcg gcctctgcat aaataaaaaa aattagtcag ccatggggcg gagaatgggc 8820
ggaactgggc ggagttaggg gcgggatggg cggagttagg ggcgggacta tggttgctga 8880
ctaattgaga tgcatgcttt gcatacttct gcctgctggg gagcctgggg actttccaca 8940
cctggttgct gactaattga gatgcatgct ttgcatactt ctgcctgctg gggagcctgg 9000
ggactttcca caccctaact gacacacatt ccacagctgc attaatgaat cggccaacgc 9060
gcggggagag gcggtttgcg tattgggcgc tcttccgctt cctcgctcac tgactcgctg 9120
cgctcggtcg ttcggctgcg gcgagcggta tcagctcact caaaggcggt aatacggtta 9180
tccacagaat caggggataa cgcaggaaag aacatgtgag caaaaggcca gcaaaaggcc 9240
aggaaccgta aaaaggccgc gttgctggcg tttttccata ggctccgccc ccctgacgag 9300
catcacaaaa atcgacgctc aagtcagagg tggcgaaacc cgacaggact ataaagatac 9360
caggcgtttc cccctggaag ctccctcgtg cgctctcctg ttccgaccct gccgcttacc 9420

```
ggatacctgt ccgcctttct cccttcggga agcgtggcgc tttctcatag ctcacgctgt   9480

aggtatctca gttcggtgta ggtcgttcgc tccaagctgg gctgtgtgca cgaacccccc   9540

gttcagcccg accgctgcgc cttatccggt aactatcgtc ttgagtccaa cccggtaaga   9600

cacgacttat cgccactggc agcagccact ggtaacagga ttagcagagc gaggtatgta   9660

ggcggtgcta cagagttctt gaagtggtgg cctaactacg gctacactag aagaacagta   9720

tttggtatct gcgctctgct gaagccagtt accttcggaa aaagagttgg tagctcttga   9780

tccggcaaac aaaccaccgc tggtagcggt ggtttttttg tttgcaagca gcagattacg   9840

cgcagaaaaa aaggatctca agaagatcct ttgatctttt ctacggggtc tgacgctcag   9900

tggaacgaaa actcacgtta agggattttg gtcatgagat tatcaaaaag gatcttcacc   9960

tagatccttt taaattaaaa atgaagtttt aaatcaatct aaagtatata tgagtaaact  10020

tggtctgaca gttaccaatg cttaatcagt gaggcaccta tctcagcgat ctgtctattt  10080

cgttcatcca tagttgcctg actcctgcaa accacgttgt gtctcaaaat ctctgatgtt  10140

acattgcaca agataaaaat atatcatcat gaacaataaa actgtctgct tacataaaca  10200

gtaatacaag gggtgttatg agccatattc aacgggaaac gtcttgctcg aggccgcgat  10260

taaattccaa catggatgct gatttatatg ggtataaatg ggctcgcgat aatgtcgggc  10320

aatcaggtgc gacaatctat cgattgtatg ggaagcccga tgcgccagag ttgtttctga  10380

aacatggcaa aggtagcgtt gccaatgatg ttacagatga gatggtcaga ctaaactggc  10440

tgacggaatt tatgcctctt ccgaccatca agcattttat ccgtactcct gatgatgcat  10500

ggttactcac cactgcgatc cccgggaaaa cagcattcca ggtattagaa gaatatcctg  10560

attcaggtga aaatattgtt gatgcgctgg cagtgttcct gcgccggttg cattcgattc  10620

ctgtttgtaa ttgtcctttt aacagcgatc gcgtatttcg tctcgctcag gcgcaatcac  10680

gaatgaataa cggtttggtt gatgcgagtg attttgatga cgagcgtaat ggctggcctg  10740

ttgaacaagt ctggaaagaa atgcataagc ttttgccatt ctcaccggat tcagtcgtca  10800

ctcatggtga tttctcactt gataacctta tttttgacga ggggaaatta ataggttgta  10860

ttgatgttgg acgagtcgga atcgcagacc gataccagga tcttgccatc ctatggaact  10920

gcctcggtga gttttctcct tcattacaga aacggctttt tcaaaaatat ggtattgata  10980

atcctgatat gaataaattg cagtttcatt tgatgctcga tgagtttttc taagggcggc  11040

ctgccaccat acccacgccg aaacaagcgc tcatgagccc gaagtggcga gcccgatctt  11100

ccccatcggt gatgtcggcg atataggcgc cagcaaccgc acctgtggcg ccggtgatga  11160

gggcgcgcca agtcgacgtc cggcagtc                                    11188
```

<210> SEQ ID NO 12
<211> LENGTH: 11187
<212> TYPE: DNA
<213> ORGANISM: Artificial Sequence
<220> FEATURE:
<223> OTHER INFORMATION: Synthetic polynucleotide

<400> SEQUENCE: 12

```
ctagaaccgg tgacgtctcc catggtgaag cttggatctg aattcggtac ctagttataa     60

tagtaatcaa ttacggggtc attagttcat agcccatata tggagttccg cgttacataa    120

cttacggtaa atggcccgcc tggctgaccg cccaacgacc cccgcccatt gacgtcaata    180

atgacgtatg ttcccatagt aacgccaata gggactttcc attgacgtca atgggtggag    240

tatttacggt aaactgccca cttggcagta catcaagtgt atcatatgcc aagtacgccc    300
```

```
cctattgacg tcaatgacgg taaatggccc gcctggcatt atgcccagta catgacctta    360
tgggactttc ctacttggca gtacatctac gtattagtca tcgctattac catggtcgag    420
gtgagcccca cgttctgctt cactctcccc atctcccccc cctccccacc cccaattttg    480
tatttattta tttttaatt attttgtgca gcgatggggg cggggggggg gggggggcgc    540
gcgccaggcg gggcggggcg gggcgagggg cggggcgggg cgaggcggag aggtgcggcg    600
gcagccaatc agagcggcgc gctccgaaag tttcctttta tggcgaggcg gcggcggcgg    660
cggccctata aaaagcgaag cgcgcggcgg gcgggagtcg ctgcgacgct gccttcgccc    720
cgtgccccgc tccgccgccg cctcgcgccg cccgccccgg ctctgactga ccgcgttact    780
cccacaggtg agcgggcggg acggcccttc tcctccgggc tgtaattagc gcttggttta    840
atgacggctt gtttcttttc tgtggctgcg tgaaagcctt gaggggctcc gggagctaga    900
gcctctgcta accatgttca tgccttcttc tttttcctac agctcctggg caacgtgctg    960
gttattgtgc tgtctcatca ttttggcaaa gaattcctcg aagatccgaa gggaaagtct   1020
tccacgactg tgggatccgt tcgaagatat caccggttga gccaccatgg aattcagcag   1080
ccccagcaga gaggaatgcc ccaagcctct gagccgggtg tcaatcatgg ccggatctct   1140
gacaggactg ctgctgcttc aggccgtgtc ttgggcttct ggcgctagac cttgcatccc   1200
caagagcttc ggctacagca gcgtcgtgtg cgtgtgcaat gccacctact gcgacagctt   1260
cgaccctcct acctttcctg ctctgggcac cttcagcaga tacgagagca ccagatccgg   1320
cagacggatg gaactgagca tgggacccat ccaggccaat cacacaggca ctggcctgct   1380
gctgacactg cagcctgagc agaaattcca gaaagtgaaa ggcttcggcg gagccatgac   1440
agatgccgcc gctctgaata tcctggctct gtctccacca gctcagaacc tgctgctcaa   1500
gagctacttc agcgaggaag gcatcggcta caacatcatc agagtgccca tggccagctg   1560
cgacttcagc atcaggacct acacctacgc cgacacaccc gacgatttcc agctgcacaa   1620
cttcagcctg cctgaagagg acaccaagct gaagatccct ctgatccaca gagccctgca   1680
gctggcacaa agacccgtgt cactgctggc ctctccatgg acatctccca cctggctgaa   1740
aacaaatggc gccgtgaatg gcaagggcag cctgaaaggc caacctggcg acatctacca   1800
ccagacctgg gccagatact tcgtgaagtt cctggacgcc tatgccgagc acaagctgca   1860
gttttgggcc gtgacagccg agaacgaacc ttctgctgga ctgctgagcg gctacccctt   1920
tcagtgcctg ggctttacac ccgagcacca gcgggacttt atcgcccgtg atctgggacc   1980
cacactggcc aatagcaccc accataatgt gcggctgctg atgctggacg accagagact   2040
gcttctgccc cactgggcta aagtggtgct gacagatcct gaggccgcca aatacgtgca   2100
cggaatcgcc gtgcactggt atctggactt tctggcccct gccaaggcca cactgggaga   2160
gacacacaga ctgttcccca acaccatgct gttcgccagc gaagcctgtg tgggcagcaa   2220
gttttgggaa cagagcgtgc ggctcggcag ctgggataga ggcatgcagt acagccacag   2280
catcatcacc aacctgctgt accacgtcgt cggctggacc gactggaatc tggccctgaa   2340
tcctgaaggc ggccctaact gggtccgaaa cttcgtggac agccccatca tcgtggacat   2400
caccaaggac accttctaca agcagcccat gttctaccac ctgggacact tcagcaagtt   2460
catccccgag ggctctcagc gcgttggact ggtggcttcc cagaagaacg atctggacgc   2520
cgtggctctg atgcaccctg atggatctgc tgtggtggtg gtcctgaacc gcagcagcaa   2580
agatgtgccc ctgaccatca aggatcccgc cgtgggattc ctggaaacaa tcagccctgg   2640
```

-continued

```
ctactccatc cacacctacc tgtggcgtag acagtgacaa ttgttaatta agtttaaacc   2700
ctcgaggccg caagcttatc gataatcaac ctctggatta caaaatttgt gaaagattga   2760
ctggtattct taactatgtt gctcctttta cgctatgtgg atacgctgct ttaatgcctt   2820
tgtatcatgc tattgcttcc cgtatggctt tcattttctc ctccttgtat aaatcctggt   2880
tgctgtctct ttatgaggag ttgtggcccg ttgtcaggca acgtggcgtg gtgtgcactg   2940
tgtttgctga cgcaaccccc actggttggg gcattgccac cacctgtcag ctcctttccg   3000
ggactttcgc tttccccctc cctattgcca cggcggaact catcgccgcc tgccttgccc   3060
gctgctggac aggggctcgg ctgttgggca ctgacaattc cgtggtgttg tcggggaaat   3120
catcgtcctt tccttggctg ctcgcctgtg ttgccacctg gattctgcgc gggacgtcct   3180
tctgctacgt cccttcggcc ctcaatccag cggaccttcc ttcccgcggc ctgctgccgg   3240
ctctgcggcc tcttccgcgt cttcgccttc gccctcagac gagtcggatc tccctttggg   3300
ccgcctcccc gcatcgatac cgtcgactag agctcgctga tcagcctcga ctgtgccttc   3360
tagttgccag ccatctgttg tttgcccctc ccccgtgcct tccttgaccc tggaaggtgc   3420
cactcccact gtcctttcct aataaaatga ggaaattgca tcgcattgtc tgagtaggtg   3480
tcattctatt ctggggggtg gggtggggca ggacagcaag ggggaggatt gggaagacaa   3540
tagcaggcat gctggggaga gatccacgat aacaaacagc tttttggggg tgaacatatt   3600
gactgaattc cctgcaggtt ggccactccc tctctgcgcg ctcgctcgct cactgaggcc   3660
gcccgggcaa agcccgggcg tcgggcgacc tttggtcgcc cggcctcagt gagcgagcga   3720
gcgcgcagag agggagtggc caactccatc actaggggtt cctgcggccg ctcgtacggt   3780
ctcgaggaat tcctgcagga taacttgcca acctcattct aaaatgtata tagaagccca   3840
aaagacaata acaaaaatat tcttgtagaa caaaatggga aagaatgttc cactaaatat   3900
caagatttag agcaaagcat gagatgtgtg gggatagaca gtgaggctga taaaatagag   3960
tagagctcag aaacagaccc attgatatat gtaagtgacc tatgaaaaaa atatggcatt   4020
ttacaatggg aaaatgatgg tctttttctt ttttagaaaa acagggaaat atatttatat   4080
gtaaaaaata aaagggaacc catatgtcat accatacaca caaaaaaatt ccagtgaatt   4140
ataagtctaa atggagaagg caaaacttta aatcttttag aaaataatat agaagcatgc   4200
agaccagcct ggccaacatg atgaaaccct ctctactaat aataaaatca gtagaactac   4260
tcaggactac tttgagtggg aagtcctttt ctatgaagac ttctttggcc aaaattaggc   4320
tctaaatgca aggagatagt gcatcatgcc tggctgcact tactgataaa tgatgttatc   4380
accatcttta accaaatgca caggaacaag ttatggtact gatgtgctgg attgagaagg   4440
agctctactt ccttgacagg acacatttgt atcaacttaa aaaagcagat ttttgccagc   4500
agaactattc attcagaggt aggaaactta gaatagatga tgtcactgat tagcatggct   4560
tccccatctc cacagctgct tcccacccag gttgcccaca gttgagtttg tccagtgctc   4620
agggctgccc actctcagta agaagcccca caccagcccc tctccaaata tgttggctgt   4680
tccttccatt aaagtgaccc cactttagag cagcaagtgg atttctgttt cttacagttc   4740
aggaaggagg agtcagctgt gagaacctgg agcctgagat gcttctaagt cccactgcta   4800
ctggggtcag ggaagccaga ctccagcatc agcagtcagg agcactaagc ccttgccaac   4860
atcctgtttc tcagagaaac tgcttccatt ataatggttg tcctttttta agctatcaag   4920
ccaaacaacc agtgtctacc attattctca tcacctgaag ccaagggttc tagcaaaagt   4980
caagctgtct tgtaatggtt gatgtgcctc cagcttctgt cttcagtcac tccactctta   5040
```

gcctgctctg aatcaactct gaccacagtt ccctggagcc cctgccacct gctgcccctg 5100
ccaccttctc catctgcagt gctgtgcagc cttctgcact cttgcagagc taataggtgg 5160
agacttgaag gaagaggagg aaagtttctc ataatagcct tgctgcaagc tcaaatggga 5220
ggtgggcact gtgcccagga gccttggagc aaaggctgtg cccaacctct gactgcatcc 5280
aggtttggtc ttgacagaga taagaagccc tggcttttgg agccaaaatc taggtcagac 5340
ttaggcagga ttctcaaagt ttatcagcag aacatgaggc agaagaccct ttctgctcca 5400
gcttcttcag gctcaacctt catcagaata gatagaaaga gaggctgtga gggttcttaa 5460
aacagaagca aatctgactc agagaataaa caacctccta gtaaactaca gcttagacag 5520
agcatctggt ggtgagtgtg ctcagtgtcc tactcaactg tctggtatca gccctcatga 5580
ggacttctct tctttccctc atagacctcc atctctgttt tccttagcct gcagaaatct 5640
ggatggctat tcacagaatg cctgtgcttt cagagttgca ttttttctct ggtattctgg 5700
ttcaagcatt tgaaggtagg aaaggttctc caagtgcaag aaagccagcc ctgagcctca 5760
actgcctggc tagtgtggtc agtaggatgc aaaggctgtt gaatgccaca aggccaaact 5820
ttaacctgtg taccacaagc ctagcagcag aggcagctct gctcactgga actctctgtc 5880
ttctttctcc tgagcctttt cttttcctga gttttctagc tctcctcaac cttacctctg 5940
ccctacccag gacaaaccca agagccactg tttctgtgat gtcctctcca gccctaatta 6000
ggcatcatga cttcagcctg accttccatg ctcagaagca gtgctaatcc acttcagatg 6060
agctgctcta tgcaacacag gcagagccta caaacctttg caccagagcc ctccacatat 6120
cagtgtttgt tcatactcac ttcaacagca aatgtgactg ctgagattaa gattttacac 6180
aagatggtct gtaatttcac agttagtttt atcccattag gtatgaaaga attagcataa 6240
ttccccttaa acatgaatga atcttagatt ttttaataaa tagttttgga agtaaagaca 6300
gagacatcag gagcacaagg aatagcctga gaggacaaac agaacaagaa agagtctgga 6360
aatacacagg atgttcttgg cctcctcaaa gcaagtgcaa gcagatagta ccagcagccc 6420
caggctatca gagcccagtg aagagaagta ccatgaaagc cacagctcta accaccctgt 6480
tccagagtga cagacagtcc ccaagacaag ccagcctgag ccagagagag aactgcaaga 6540
gaaagtttct aatttaggtt ctgttagatt cagacaagtg caggtcatcc tctctccaca 6600
gctactcacc tctccagcct aacaaagcct gcagtccaca ctccaaccct ggtgtctcac 6660
ctcctagcct ctcccaacat cctgctctct gaccatcttc tgcatctctc atctcaccat 6720
ctcccactgt ctacagccta ctcttgcaac taccatctca ttttctgaca tcctgtctac 6780
atcttctgcc atactctgcc atctaccata ccacctctta ccatctacca caccatcttt 6840
tatctccatc cctctcagaa gcctccaagc tgaatcctgc tttatgtgtt catctcagcc 6900
cctgcatgga aagctgaccc cagaggcaga actattccca gagagcttgg ccaagaaaaa 6960
caaaactacc agcctggcca ggctcaggag tagtaagctg cagtgtctgt tgtgttctag 7020
cttcaacagc tgcaggagtt ccactctcaa atgctccaca tttctcacat cctcctgatt 7080
ctggtcacta cccatcttca aagaacagaa tatctcacat cagcatactg tgaaggacta 7140
gtcatgggtg cagctgctca gagctgcaaa gtcattctgg atggtggaga gcttacaaac 7200
atttcatgat gctccccccg ctctgatggc tggagcccaa tccctacaca gactcctgct 7260
gtatgtgttt tcctttcact ctgagccaca gccagagggc aggcattcag tctcctcttc 7320
aggctggggc tggggcactg agaactcacc caacaccttg ctctcactcc ttctgcaaaa 7380

-continued

```
caagaaagag ctttgtgctg cagtagccat gaagaatgaa aggaaggctt taactaaaaa   7440
atgtcagaga ttattttcaa cccttactg tggatcacca gcaaggagga aacacaacac   7500
agagacattt tttcccctca aattatcaaa agaatcactg catttgttaa agagagcaac   7560
tgaatcagga agcagagttt tgaacatatc agaagttagg aatctgcatc agagacaaat   7620
gcagtcatgg ttgtttgctg cataccagcc ctaatcatta gaagcctcat ggacttcaaa   7680
catcattccc tctgacaaga tgctctagcc taactccatg agataaaata aatctgcctt   7740
tcagagccaa agaagagtcc accagcttct tctcagtgtg aacaagagct ccagtcaggt   7800
tagtcagtcc agtgcagtag aggagaccag tctgcatcct ctaattttca aaggcaagaa   7860
gatttgttta ccctggacac caggcacaag tgaggtcaca gagctcttag atatgcagtc   7920
ctcatgagtg aggagactaa agcgcatgcc atcaagactt cagtgtagag aaaacctcca   7980
aaaaagcctc ctcactactt ctggaatagc tcagaggccg aggcggcctc ggcctctgca   8040
taaataaaaa aaattagtca gccatggggc ggagaatggg cggaactggg cggagttagg   8100
ggcgggatgg gcggagttag gggcgggact atggttgctg actaattgag atgcatgctt   8160
tgcatacttc tgcctgctgg ggagcctggg gactttccac acctggttgc tgactaattg   8220
agatgcatgc tttgcatact tctgcctgct ggggagcctg gggactttcc acaccctaac   8280
tgacacacat tccacagctg cattaatgaa tcggccaacg cgcggggaga ggcggtttgc   8340
gtattgggcg ctcttccgct tcctcgctca ctgactcgct gcgctcggtc gttcggctgc   8400
ggcgagcggt atcagctcac tcaaaggcgg taatacggtt atccacagaa tcaggggata   8460
acgcaggaaa gaacatgtga gcaaaaggcc agcaaaaggc caggaaccgt aaaaaggccg   8520
cgttgctggc gtttttccat aggctccgcc cccctgacga gcatcacaaa aatcgacgct   8580
caagtcagag gtggcgaaac ccgacaggac tataaagata ccaggcgttt ccccctggaa   8640
gctccctcgt gcgctctcct gttccgaccc tgccgcttac cggatacctg tccgcctttc   8700
tcccttcggg aagcgtggcg ctttctcata gctcacgctg taggtatctc agttcggtgt   8760
aggtcgttcg ctccaagctg ggctgtgtgc acgaaccccc cgttcagccc gaccgctgcg   8820
ccttatccgg taactatcgt cttgagtcca acccggtaag acacgactta tcgccactgg   8880
cagcagccac tggtaacagg attagcagag cgaggtatgt aggcggtgct acagagttct   8940
tgaagtggtg gcctaactac ggctacacta gaagaacagt atttggtatc tgcgctctgc   9000
tgaagccagt taccttcgga aaaagagttg gtagctcttg atccggcaaa caaaccaccg   9060
ctggtagcgg tggttttttt gtttgcaagc agcagattac gcgcagaaaa aaaggatctc   9120
aagaagatcc tttgatcttt tctacggggt ctgacgctca gtggaacgaa aactcacgtt   9180
aagggatttt ggtcatgaga ttatcaaaaa ggatcttcac ctagatcctt ttaaattaaa   9240
aatgaagttt taaatcaatc taaagtatat atgagtaaac ttggtctgac agttaccaat   9300
gcttaatcag tgaggcacct atctcagcga tctgtctatt tcgttcatcc atagttgcct   9360
gactcctgca aaccacgttg tgtctcaaaa tctctgatgt tacattgcac aagataaaaa   9420
tatatcatca tgaacaataa aactgtctgc ttacataaac agtaatacaa ggggtgttat   9480
gagccatatt caacgggaaa cgtcttgctc gaggccgcga ttaaattcca acatggatgc   9540
tgatttatat gggtataaat gggctcgcga taatgtcggg caatcaggtg cgacaatcta   9600
tcgattgtat gggaagcccg atgcgccaga gttgtttctg aaacatggca aaggtagcgt   9660
tgccaatgat gttacagatg agatggtcag actaaactgg ctgacggaat ttatgcctct   9720
tccgaccatc aagcatttta tccgtactcc tgatgatgca tggttactca ccactgcgat   9780
```

ccccgggaaa acagcattcc aggtattaga agaatatcct gattcaggtg aaaatattgt 9840
tgatgcgctg gcagtgttcc tgcgccggtt gcattcgatt cctgtttgta attgtccttt 9900
taacagcgat cgcgtatttc gtctcgctca ggcgcaatca cgaatgaata acggtttggt 9960
tgatgcgagt gattttgatg acgagcgtaa tggctggcct gttgaacaag tctggaaaga 10020
aatgcataag cttttgccat tctcaccgga ttcagtcgtc actcatggtg atttctcact 10080
tgataacctt atttttgacg aggggaaatt aataggttgt attgatgttg gacgagtcgg 10140
aatcgcagac cgataccagg atcttgccat cctatggaac tgcctcggtg agttttctcc 10200
ttcattacag aaacggcttt ttcaaaaata tggtattgat aatcctgata tgaataaatt 10260
gcagtttcat ttgatgctcg atgagttttt ctaagggcgg cctgccacca tacccacgcc 10320
gaaacaagcg ctcatgagcc cgaagtggcg agcccgatct tccccatcgg tgatgtcggc 10380
gatataggcg ccagcaaccg cacctgtggc gccggtgatg agggcgcgcc aagtcgacgt 10440
ccggcagtct tggccactcc ctctctgcgc gctcgctcgc tcactgaggc cgggcgacca 10500
aaggtcgccc gacgcccggg ctttgcccgg gcggcctcag tgagcgagcg agcgcgcaga 10560
gagggagtgg ccaactccat cactaggggt tcctgctagc tctgggtatt taagcccgag 10620
tgagcacgca gggtctccat tttgaagcgg gaggttacgc gttcgtcgac tactagtggg 10680
taccagagcg tggtgactga gatgttttct aggaaacaca aaagatacaa aaaagaacac 10740
gtggaaggat agccaaaaag gggggctgcc cccatttcct gcaccccgct gcgatggctg 10800
gcaccatttg gaagacttcg agatacactg ttgagcgcag taagacaaca gtgtatctcg 10860
aagtcttcca gatggggcca gccggtccac tctgtatcca ggccagttct gcaaggcgtt 10920
cgaggaccac ccccctcccc tcgccaccag ggtggtctca tacagaactt ataagattcc 10980
caaatccaaa gacatttcac gtttatggtg atttcccaga acacatagcg acatgcaaat 11040
attgcagggc gccactcccc tgtccctcac agccatcttc ctgccagggc gcacgcgcgc 11100
tgggtgttcc cgcctagtga cactgggccc gcgattcctt ggagcgggtt gatgacgtca 11160
gcgtttccca tggtgaatcc ctaggtt 11187

<210> SEQ ID NO 13
<211> LENGTH: 10960
<212> TYPE: DNA
<213> ORGANISM: Artificial Sequence
<220> FEATURE:
<223> OTHER INFORMATION: Synthetic polynucleotide

<400> SEQUENCE: 13
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
cctagttatt aatagtaatc aattacgggg tcattagttc atagcccata tatggagttc 360
cgcgttacat aacttacggt aaatggcccg cctggctgac cgcccaacga cccccgccca 420
ttgacgtcaa taatgacgta tgttcccata gtaacgccaa tagggacttt ccattgacgt 480
caatgggtgg actatttacg gtaaactgcc cacttggcag tacatcaagt gtatcatatg 540
ccaagtacgc cccctattga cgtcaatgac ggtaaatggc ccgcctggca ttatgcccag 600

-continued

```
tacatgacct tatgggactt tcctacttgg cagtacatct acgtattagt catcgctatt     660
accatggtcg aggtgagccc cacgttctgc ttcactctcc ccatctcccc cccctcccca     720
cccccaattt tgtatttatt tatttttttaa ttattttgtg cagcgatggg ggcggggggg     780
gggggggggc gcgcgccagg cggggcgggg cggggcgagg ggcggggcgg ggcgaggcgg     840
agaggtgcgg cggcagccaa tcagagcggc gcgctccgaa agtttccttt tatggcgagg     900
cggcggcggc ggcggcccta taaaaagcga agcgcgcggc gggcgggagt cgctgcgacg     960
ctgccttcgc cccgtgcccc gctccgccgc cgcctcgcgc cgcccgcccc ggctctgact    1020
gaccgcgtta ctcccacagg tgagcgggcg ggacggccct tctcctccgg gctgtaatta    1080
gcgcttggtt taatgacggc ttgtcctggt ggcgagggga gggggggtggt cctcgaacgc    1140
cttgcagaac tggcctggat acagagtgga ccggctggcc ccatctggaa gacttcgaga    1200
tacactgttg tcttactgcg ctcaacagtg tatctcgaag tcttccaaat ggtgccagcc    1260
atcgcagcgg ggtgcaggaa atgggggcag cccccctttt tggctatcct tccacgtgtt    1320
ctttttgta tcttttgtgt ttcctagaaa acatctcagt caccaccttt ctgtggctgc    1380
gtgaaagcct tgaggggctc cgggagctag agcctctgct aaccatgttc atgccttctt    1440
ctttttccta cagctcctgg gcaacgtgct ggttattgtg ctgtctcatc attttggcaa    1500
agaattcctc gaagatccga agggaaagtc ttccacgact gtgggatccg ttcgaagata    1560
tcaccggttg agccaccatg gaattcagca gccccagcag agaggaatgc cccaagcctc    1620
tgagccgggt gtcaatcatg gccggatctc tgacaggact gctgctgctt caggccgtgt    1680
cttgggcttc tggcgctaga ccttgcatcc ccaagagctt cggctacagc agcgtcgtgt    1740
gcgtgtgcaa tgccacctac tgcgacagct tcgaccctcc taccttcct gctctgggca    1800
ccttcagcag atacgagagc accagatccg gcagacggat ggaactgagc atgggaccca    1860
tccaggccaa tcacacaggc actggcctgc tgctgacact gcagcctgag cagaaattcc    1920
agaaagtgaa aggcttcggc ggagccatga cagatgccgc cgctctgaat atcctggctc    1980
tgtctccacc agctcagaac ctgctgctca agagctactt cagcgaggaa ggcatcggct    2040
acaacatcat cagagtgccc atggccagct gcgacttcag catcaggacc tacacctacg    2100
ccgacacacc cgacgatttc cagctgcaca acttcagcct gcctgaagag gacaccaagc    2160
tgaagatccc tctgatccac agagccctgc agctggcaca aagacccgtg tcactgctgg    2220
cctctccatg gacatctccc acctggctga aaacaaatgg cgccgtgaat ggcaagggca    2280
gcctgaaagg ccaacctggc gacatctacc accagacctg ggccagatac ttcgtgaagt    2340
tcctggacgc ctatgccgag cacaagctgc agttttgggc cgtgacagcc gagaacgaac    2400
cttctgctgg actgctgagc ggctacccct ttcagtgcct gggctttaca cccgagcacc    2460
agcgggactt tatcgcccgt gatctgggac ccacactggc caatagcacc caccataatg    2520
tgcggctgct gatgctggac gaccagagac tgcttctgcc ccactgggct aaagtggtgc    2580
tgacagatcc tgaggccgcc aaatacgtgc acggaatcgc cgtgcactgg tatctggact    2640
ttctggcccc tgccaaggcc acactgggag agacacacag actgttcccc aacaccatgc    2700
tgttcgccag cgaagcctgt gtgggcagca agttttggga acagagcgtg cggctcggca    2760
gctgggatag aggcatgcag tacagccaca gcatcatcac caacctgctg taccacgtcg    2820
tcggctggac cgactggaat ctggccctga atcctgaagg cggccctaac tgggtccgaa    2880
acttcgtgga cagccccatc atcgtggaca tcaccaagga caccttctac aagcagccca    2940
tgttctacca cctgggacac ttcagcaagt tcatccccga gggctctcag cgcgttggac    3000
```

```
tggtggcttc ccagaagaac gatctggacg ccgtggctct gatgcaccct gatggatctg   3060
ctgtggtggt ggtcctgaac cgcagcagca aagatgtgcc cctgaccatc aaggatcccg   3120
ccgtgggatt cctggaaaca atcagccctg gctactccat ccacacctac ctgtggcgta   3180
gacagtgaca attgttaatt aagtttaaac cctcgaggcc gcaagcttat cgataatcaa   3240
cctctggatt acaaaatttg tgaaagattg actggtattc ttaactatgt tgctcctttt   3300
acgctatgtg gatacgctgc tttaatgcct ttgtatcatg ctattgcttc ccgtatggct   3360
ttcattttct cctccttgta taaatcctgg ttgctgtctc tttatgagga gttgtggccc   3420
gttgtcaggc aacgtggcgt ggtgtgcact gtgtttgctg acgcaacccc cactggttgg   3480
ggcattgcca ccacctgtca gctcctttcc gggactttcg ctttccccct ccctattgcc   3540
acggcggaac tcatcgccgc ctgccttgcc cgctgctgga caggggctcg gctgttgggc   3600
actgacaatt ccgtggtgtt gtcggggaaa tcatcgtcct ttccttggct gctcgcctgt   3660
gttgccacct ggattctgcg cgggacgtcc ttctgctacg tcccttcggc cctcaatcca   3720
gcggaccttc cttcccgcgg cctgctgccg gctctgcggc ctcttccgcg tcttcgcctt   3780
cgccctcaga cgagtcggat ctccctttgg gccgcctccc cgcatcgata ccgtcgacta   3840
gagctcgctg atcagcctcg actgtgcctt ctagttgcca gccatctgtt gtttgcccct   3900
cccccgtgcc ttccttgacc ctggaaggtg ccactcccac tgtcctttcc taataaaatg   3960
aggaaattgc atcgcattgt ctgagtaggt gtcattctat tctggggggt ggggtggggc   4020
aggacagcaa gggggaggat tgggaagaca atagcaggca tgctggggag agatccacga   4080
taacaaacag ctttttgggg gtgaacatat tgactgaatt ccctgcaggt tggccactcc   4140
ctctctgcgc gctcgctcgc tcactgaggc cgcccgggca aagcccgggc gtcgggcgac   4200
ctttggtcgc ccggcctcag tgagcgagcg agcgcgcaga gagggagtgg ccaactccat   4260
cactaggggt tcctgcggcc gctcgtacgg tctcgaggaa ttcctgcagg ataacttgcc   4320
aacctcattc taaaatgtat atagaagccc aaaagacaat aacaaaaata ttcttgtaga   4380
acaaaatggg aaagaatgtt ccactaaata tcaagattta gagcaaagca tgagatgtgt   4440
ggggatagac agtgaggctg ataaaataga gtagagctca gaaacagacc cattgatata   4500
tgtaagtgac ctatgaaaaa aatatggcat tttacaatgg gaaaatgatg gtcttttttct   4560
tttttagaaa aacagggaaa tatatttata tgtaaaaaat aaaagggaac ccatatgtca   4620
taccatacac acaaaaaaat tccagtgaat tataagtcta aatggagaag gcaaaacttt   4680
aaatctttta gaaaataata tagaagcatg cagaccagcc tggccaacat gatgaaaccc   4740
tctctactaa taataaaatc agtagaacta ctcaggacta ctttgagtgg gaagtccttt   4800
tctatgaaga cttctttggc caaaattagg ctctaaatgc aaggagatag tgcatcatgc   4860
ctggctgcac ttactgataa atgatgttat caccatcttt aaccaaatgc acaggaacaa   4920
gttatggtac tgatgtgctg gattgagaag gagctctact tccttgacag gacacatttg   4980
tatcaactta aaaaagcaga tttttgccag cagaactatt cattcagagg taggaaactt   5040
agaatagatg atgtcactga ttagcatggc ttccccatct ccacagctgc ttcccaccca   5100
ggttgcccac agttgagttt gtccagtgct cagggctgcc cactctcagt aagaagcccc   5160
acaccagccc ctctccaaat atgttggctg ttccttccat taaagtgacc ccactttaga   5220
gcagcaagtg gatttctgtt tcttacagtt caggaaggag gagtcagctg tgagaacctg   5280
gagcctgaga tgcttctaag tcccactgct actggggtca gggaagccag actccagcat   5340
```

cagcagtcag gagcactaag cccttgccaa catcctgttt ctcagagaaa ctgcttccat 5400
tataatggtt gtcctttttt aagctatcaa gccaaacaac cagtgtctac cattattctc 5460
atcacctgaa gccaagggtt ctagcaaaag tcaagctgtc ttgtaatggt tgatgtgcct 5520
ccagcttctg tcttcagtca ctccactctt agcctgctct gaatcaactc tgaccacagt 5580
tccctggagc cctgccaccc tgctgcccct gccaccttct ccatctgcag tgctgtgcag 5640
ccttctgcac tcttgcagag ctaataggtg gagacttgaa ggaagaggag gaaagtttct 5700
cataatagcc ttgctgcaag ctcaaatggg aggtgggcac tgtgcccagg agccttggag 5760
caaaggctgt gcccaacctc tgactgcatc caggtttggt cttgacagag ataagaagcc 5820
ctggcttttg gagccaaaat ctaggtcaga cttaggcagg attctcaaag tttatcagca 5880
gaacatgagg cagaagaccc tttctgctcc agcttcttca ggctcaacct tcatcagaat 5940
agatagaaag agaggctgtg agggttctta aaacagaagc aaatctgact cagagaataa 6000
acaacctcct agtaaactac agcttagaca gagcatctgg tggtgagtgt gctcagtgtc 6060
ctactcaact gtctggtatc agccctcatg aggacttctc ttctttccct catagacctc 6120
catctctgtt ttccttagcc tgcagaaatc tggatggcta ttcacagaat gcctgtgctt 6180
tcagagttgc atttttctc tggtattctg gttcaagcat ttgaaggtag gaaaggttct 6240
ccaagtgcaa gaaagccagc cctgagcctc aactgcctgg ctagtgtggt cagtaggatg 6300
caaaggctgt tgaatgccac aaggccaaac tttaacctgt gtaccacaag cctagcagca 6360
gaggcagctc tgctcactgg aactctctgt cttctttctc ctgagccttt tcttttcctg 6420
agttttctag ctctcctcaa ccttacctct gccctaccca ggacaaaccc aagagccact 6480
gtttctgtga tgtcctctcc agccctaatt aggcatcatg acttcagcct gaccttccat 6540
gctcagaagc agtgctaatc cacttcagat gagctgctct atgcaacaca ggcagagcct 6600
acaaaccttt gcaccagagc cctccacata tcagtgtttg ttcatactca cttcaacagc 6660
aaatgtgact gctgagatta agattttaca caagatggtc tgtaatttca cagttagttt 6720
tatcccatta ggtatgaaag aattagcata attcccctta aacatgaatg aatcttagat 6780
tttttaataa atagttttgg aagtaaagac agagacatca ggagcacaag gaatagcctg 6840
agaggacaaa cagaacaaga aagagtctgg aaatacacag gatgttcttg gcctcctcaa 6900
agcaagtgca agcagatagt accagcagcc ccaggctatc agagcccagt gaagagaagt 6960
accatgaaag ccacagctct aaccaccctg ttccagagtg acagacagtc cccaagacaa 7020
gccagcctga gccagagaga gaactgcaag agaaagtttc taatttaggt tctgttagat 7080
tcagacaagt gcaggtcatc ctctctccac agctactcac ctctccagcc taacaaagcc 7140
tgcagtccac actccaaccc tggtgtctca cctcctagcc tctcccaaca tcctgctctc 7200
tgaccatctt ctgcatctct catctcacca tctcccactg tctacagcct actcttgcaa 7260
ctaccatctc attttctgac atcctgtcta catcttctgc catactctgc catctaccat 7320
accacctctt accatctacc acaccatctt ttatctccat ccctctcaga agcctccaag 7380
ctgaatcctg ctttatgtgt tcatctcagc ccctgcatgg aaagctgacc ccagaggcag 7440
aactattccc agagagcttg gccaagaaaa acaaaactac cagcctggcc aggctcagga 7500
gtagtaagct gcagtgtctg ttgtgttcta gcttcaacag ctgcaggagt tccactctca 7560
aatgctccac atttctcaca tcctcctgat tctggtcact acccatcttc aaagaacaga 7620
atatctcaca tcagcatact gtgaaggact agtcatgggt gcagctgctc agagctgcaa 7680
agtcattctg gatggtggag agcttacaaa catttcatga tgctcccccc gctctgatgg 7740

```
ctggagccca atccctacac agactcctgc tgtatgtgtt ttcctttcac tctgagccac   7800
agccagaggg caggcattca gtctcctctt caggctgggg ctggggcact gagaactcac   7860
ccaacacctt gctctcactc cttctgcaaa acaagaaaga gctttgtgct gcagtagcca   7920
tgaagaatga aaggaaggct ttaactaaaa aatgtcagag attattttca accccttact   7980
gtggatcacc agcaaggagg aaacacaaca cagagacatt ttttcccctc aaattatcaa   8040
aagaatcact gcatttgtta aagagagcaa ctgaatcagg aagcagagtt ttgaacatat   8100
cagaagttag gaatctgcat cagagacaaa tgcagtcatg gttgtttgct gcataccagc   8160
cctaatcatt agaagcctca tggacttcaa acatcattcc ctctgacaag atgctctagc   8220
ctaactccat gagataaaat aaatctgcct ttcagagcca aagaagagtc caccagcttc   8280
ttctcagtgt gaacaagagc tccagtcagg ttagtcagtc cagtgcagta gaggagacca   8340
gtctgcatcc tctaattttc aaaggcaaga agatttgttt accctggaca ccaggcacaa   8400
gtgaggtcac agagctctta gatatgcagt cctcatgagt gaggagacta aagcgcatgc   8460
catcaagact tcagtgtaga gaaaacctcc aaaaaagcct cctcactact tctggaatag   8520
ctcagaggcc gaggcggcct cggcctctgc ataaataaaa aaaattagtc agccatgggg   8580
cggagaatgg gcggaactgg gcggagttag gggcgggatg ggcggagtta ggggcgggac   8640
tatggttgct gactaattga gatgcatgct ttgcatactt ctgcctgctg gggagcctgg   8700
ggactttcca cacctggttg ctgactaatt gagatgcatg ctttgcatac ttctgcctgc   8760
tggggagcct ggggactttc cacaccctaa ctgacacaca ttccacagct gcattaatga   8820
atcggccaac gcgcggggag aggcggtttg cgtattgggc gctcttccgc ttcctcgctc   8880
actgactcgc tgcgctcggt cgttcggctg cggcgagcgg tatcagctca ctcaaaggcg   8940
gtaatacggt tatccacaga atcaggggat aacgcaggaa agaacatgtg agcaaaaggc   9000
cagcaaaagg ccaggaaccg taaaaaggcc gcgttgctgg cgtttttcca taggctccgc   9060
ccccctgacg agcatcacaa aaatcgacgc tcaagtcaga ggtggcgaaa cccgacagga   9120
ctataaagat accaggcgtt tccccctgga agctccctcg tgcgctctcc tgttccgacc   9180
ctgccgctta ccggatacct gtccgccttt ctcccttcgg gaagcgtggc gctttctcat   9240
agctcacgct gtaggtatct cagttcggtg taggtcgttc gctccaagct gggctgtgtg   9300
cacgaacccc ccgttcagcc cgaccgctgc gccttatccg gtaactatcg tcttgagtcc   9360
aacccggtaa gacacgactt atcgccactg gcagcagcca ctggtaacag gattagcaga   9420
gcgaggtatg taggcggtgc tacagagttc ttgaagtggt ggcctaacta cggctacact   9480
agaagaacag tatttggtat ctgcgctctg ctgaagccag ttaccttcgg aaaaagagtt   9540
ggtagctctt gatccggcaa acaaaccacc gctggtagcg gtggtttttt tgtttgcaag   9600
cagcagatta cgcgcagaaa aaaaggatct caagaagatc ctttgatctt ttctacgggg   9660
tctgacgctc agtggaacga aaactcacgt taagggattt tggtcatgag attatcaaaa   9720
aggatcttca cctagatcct tttaaattaa aaatgaagtt ttaaatcaat ctaaagtata   9780
tatgagtaaa cttggtctga cagttaccaa tgcttaatca gtgaggcacc tatctcagcg   9840
atctgtctat ttcgttcatc catagttgcc tgactcctgc aaaccacgtt gtgtctcaaa   9900
atctctgatg ttacattgca caagataaaa atatatcatc atgaacaata aaactgtctg   9960
cttacataaa cagtaataca aggggtgtta tgagccatat tcaacgggaa acgtcttgct  10020
cgaggccgcg attaaattcc aacatggatg ctgatttata tgggtataaa tgggctcgcg  10080
```

```
ataatgtcgg gcaatcaggt gcgacaatct atcgattgta tgggaagccc gatgcgccag  10140

agttgtttct gaaacatggc aaaggtagcg ttgccaatga tgttacagat gagatggtca  10200

gactaaactg gctgacggaa tttatgcctc ttccgaccat caagcatttt atccgtactc  10260

ctgatgatgc atggttactc accactgcga tccccgggaa aacagcattc caggtattag  10320

aagaatatcc tgattcaggt gaaaatattg ttgatgcgct ggcagtgttc ctgcgccggt  10380

tgcattcgat tcctgtttgt aattgtcctt ttaacagcga tcgcgtattt cgtctcgctc  10440

aggcgcaatc acgaatgaat aacggtttgg ttgatgcgag tgattttgat gacgagcgta  10500

atggctggcc tgttgaacaa gtctggaaag aaatgcataa gcttttgcca ttctcaccgg  10560

attcagtcgt cactcatggt gatttctcac ttgataacct tatttttgac gaggggaaat  10620

taataggttg tattgatgtt ggacgagtcg gaatcgcaga ccgataccag gatcttgcca  10680

tcctatggaa ctgcctcggt gagttttctc cttcattaca gaaacggctt tttcaaaaat  10740

atggtattga taatcctgat atgaataaat tgcagtttca tttgatgctc gatgagtttt  10800

tctaagggcg gcctgccacc atacccacgc cgaaacaagc gctcatgagc ccgaagtggc  10860

gagcccgatc ttccccatcg gtgatgtcgg cgatataggc gccagcaacc gcacctgtgg  10920

cgccggtgat gagggcgcgc caagtcgacg tccggcagtc                        10960
```

<210> SEQ ID NO 14
<211> LENGTH: 536
<212> TYPE: PRT
<213> ORGANISM: Homo sapiens

<400> SEQUENCE: 14

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220
```

Lys Thr Asn Gly Ala Val Asn Gly Lys Gly Ser Leu Lys Gly Gln Pro
225 230 235 240

Gly Asp Ile Tyr His Gln Thr Trp Ala Arg Tyr Phe Val Lys Phe Leu
245 250 255

Asp Ala Tyr Ala Glu His Lys Leu Gln Phe Trp Ala Val Thr Ala Glu
260 265 270

Asn Glu Pro Ser Ala Gly Leu Leu Ser Gly Tyr Pro Phe Gln Cys Leu
275 280 285

Gly Phe Thr Pro Glu His Gln Arg Asp Phe Ile Ala Arg Asp Leu Gly
290 295 300

Pro Thr Leu Ala Asn Ser Thr His His Asn Val Arg Leu Leu Met Leu
305 310 315 320

Asp Asp Gln Arg Leu Leu Leu Pro His Trp Ala Lys Val Val Leu Thr
325 330 335

Asp Pro Glu Ala Ala Lys Tyr Val His Gly Ile Ala Val His Trp Tyr
340 345 350

Leu Asp Phe Leu Ala Pro Ala Lys Ala Thr Leu Gly Glu Thr His Arg
355 360 365

Leu Phe Pro Asn Thr Met Leu Phe Ala Ser Glu Ala Cys Val Gly Ser
370 375 380

Lys Phe Trp Glu Gln Ser Val Arg Leu Gly Ser Trp Asp Arg Gly Met
385 390 395 400

Gln Tyr Ser His Ser Ile Ile Thr Asn Leu Leu Tyr His Val Val Gly
405 410 415

Trp Thr Asp Trp Asn Leu Ala Leu Asn Pro Glu Gly Gly Pro Asn Trp
420 425 430

Val Arg Asn Phe Val Asp Ser Pro Ile Ile Val Asp Ile Thr Lys Asp
435 440 445

Thr Phe Tyr Lys Gln Pro Met Phe Tyr His Leu Gly His Phe Ser Lys
450 455 460

Phe Ile Pro Glu Gly Ser Gln Arg Val Gly Leu Val Ala Ser Gln Lys
465 470 475 480

Asn Asp Leu Asp Ala Val Ala Leu Met His Pro Asp Gly Ser Ala Val
485 490 495

Val Val Val Leu Asn Arg Ser Ser Lys Asp Val Pro Leu Thr Ile Lys
500 505 510

Asp Pro Ala Val Gly Phe Leu Glu Thr Ile Ser Pro Gly Tyr Ser Ile
515 520 525

His Thr Tyr Leu Trp Arg Arg Gln
530 535

<210> SEQ ID NO 15
<211> LENGTH: 1608
<212> TYPE: DNA
<213> ORGANISM: Homo sapiens

<400> SEQUENCE: 15
atggaattca gcagccccag cagagaggaa tgccccaagc ctctgagccg ggtgtcaatc 60
atggccggat ctctgacagg actgctgctg cttcaggccg tgtcttgggc ttctggcgct 120
agaccttgca tccccaagag cttcggctac agcagcgtcg tgtgcgtgtg caatgccacc 180
tactgcgaca gcttcgaccc tcctaccttt cctgctctgg gcaccttcag cagatacgag 240
agcaccagat ccggcagacg gatggaactg agcatgggac ccatccaggc caatcacaca 300
ggcactggcc tgctgctgac actgcagcct gagcagaaat tccagaaagt gaaaggcttc 360
ggcggagcca tgacagatgc cgccgctctg aatatcctgg ctctgtctcc accagctcag 420
aacctgctgc tcaagagcta cttcagcgag gaaggcatcg gctacaacat catcagagtg 480
cccatggcca gctgcgactt cagcatcagg acctacacct acgccgacac acccgacgat 540
ttccagctgc acaacttcag cctgcctgaa gaggacacca agctgaagat ccctctgatc 600
cacagagccc tgcagctggc acaaagaccc gtgtcactgc tggcctctcc atggacatct 660
cccacctggc tgaaaacaaa tggcgccgtg aatggcaagg gcagcctgaa aggccaacct 720
ggcgacatct accaccagac ctgggccaga tacttcgtga agttcctgga cgcctatgcc 780
gagcacaagc tgcagttttg ggccgtgaca gccgagaacg aaccttctgc tggactgctg 840
agcggctacc cctttcagtg cctgggcttt acacccgagc accagcggga ctttatcgcc 900
cgtgatctgg gacccacact ggccaatagc acccaccata atgtgcggct gctgatgctg 960
gacgaccaga gactgcttct gccccactgg gctaaagtgg tgctgacaga tcctgaggcc 1020
gccaaatacg tgcacggaat cgccgtgcac tggtatctgg actttctggc ccctgccaag 1080
gccacactgg gagagacaca cagactgttc cccaacacca tgctgttcgc cagcgaagcc 1140
tgtgtgggca gcaagttttg ggaacagagc gtgcggctcg gcagctggga tagaggcatg 1200
cagtacagcc acagcatcat caccaacctg ctgtaccacg tcgtcggctg gaccgactgg 1260
aatctggccc tgaatcctga aggcggccct aactgggtcc gaaacttcgt ggacagcccc 1320
atcatcgtgg acatcaccaa ggacaccttc tacaagcagc ccatgttcta ccacctggga 1380
cacttcagca agttcatccc cgagggctct cagcgcgttg gactggtggc ttcccagaag 1440
aacgatctgg acgccgtggc tctgatgcac cctgatggat ctgctgtggt ggtggtcctg 1500
aaccgcagca gcaaagatgt gcccctgacc atcaaggatc ccgccgtggg attcctggaa 1560
acaatcagcc ctggctactc catccacacc tacctgtggc gtagacag 1608

<210> SEQ ID NO 16
<211> LENGTH: 524
<212> TYPE: PRT
<213> ORGANISM: Homo sapiens

<400> SEQUENCE: 16

Met Tyr Ala Leu Phe Leu Leu Ala Ser Leu Leu Gly Ala Ala Leu Ala
1 5 10 15

Gly Pro Val Leu Gly Leu Lys Glu Cys Thr Arg Gly Ser Ala Val Trp
20 25 30

Cys Gln Asn Val Lys Thr Ala Ser Asp Cys Gly Ala Val Lys His Cys
35 40 45

Leu Gln Thr Val Trp Asn Lys Pro Thr Val Lys Ser Leu Pro Cys Asp
50 55 60

Ile Cys Lys Asp Val Val Thr Ala Ala Gly Asp Met Leu Lys Asp Asn
65 70 75 80

Ala Thr Glu Glu Glu Ile Leu Val Tyr Leu Glu Lys Thr Cys Asp Trp
85 90 95

Leu Pro Lys Pro Asn Met Ser Ala Ser Cys Lys Glu Ile Val Asp Ser
100 105 110

Tyr Leu Pro Val Ile Leu Asp Ile Ile Lys Gly Glu Met Ser Arg Pro
115 120 125

Gly Glu Val Cys Ser Ala Leu Asn Leu Cys Glu Ser Leu Gln Lys His
130 135 140

-continued

```
Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
            260                 265                 270

Glu Val Lys Glu Met Pro Met Gln Thr Leu Val Pro Ala Lys Val Ala
        275                 280                 285

Ser Lys Asn Val Ile Pro Ala Leu Glu Leu Val Glu Pro Ile Lys Lys
    290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350

Leu Ser Glu Glu Cys Gln Glu Val Val Asp Thr Tyr Gly Ser Ser Ile
        355                 360                 365

Leu Ser Ile Leu Leu Glu Glu Val Ser Pro Glu Leu Val Cys Ser Met
    370                 375                 380

Leu His Leu Cys Ser Gly Thr Arg Leu Pro Ala Leu Thr Val His Val
385                 390                 395                 400

Thr Gln Pro Lys Asp Gly Gly Phe Cys Glu Val Cys Lys Lys Leu Val
                405                 410                 415

Gly Tyr Leu Asp Arg Asn Leu Glu Lys Asn Ser Thr Lys Gln Glu Ile
            420                 425                 430

Leu Ala Ala Leu Glu Lys Gly Cys Ser Phe Leu Pro Asp Pro Tyr Gln
        435                 440                 445

Lys Gln Cys Asp Gln Phe Val Ala Glu Tyr Glu Pro Val Leu Ile Glu
    450                 455                 460

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
                485                 490                 495

Trp Gly Pro Ser Tyr Trp Cys Gln Asn Thr Glu Thr Ala Ala Gln Cys
            500                 505                 510

Asn Ala Val Glu His Cys Lys Arg His Val Trp Asn
        515                 520
```

<210> SEQ ID NO 17
<211> LENGTH: 1572
<212> TYPE: DNA
<213> ORGANISM: Homo sapiens

<400> SEQUENCE: 17
atgtacgccc tgttcctgct ggccagcctg ctgggcgccg ccctggccgg ccccgtgctg 60
ggcctgaagg agtgcacccg cggcagcgcc gtgtggtgcc agaacgtgaa gaccgccagc 120
gactgcggcg ccgtgaagca ctgcctgcag accgtgtgga acaagcccac cgtgaagagc 180
ctgccctgcg acatctgcaa ggacgtggtg accgccgccg gcgacatgct gaaggacaac 240
gccaccgagg aggagatcct ggtgtacctg gagaagacct gcgactggct gcccaagccc 300
aacatgagcg ccagctgcaa ggagatcgtg gacagctacc tgcccgtgat cctggacatc 360
atcaagggcg agatgagccg ccccggcgag gtgtgcagcg ccctgaacct gtgcgagagc 420
ctgcagaagc acctggccga gctgaaccac cagaagcagc tggagagcaa caagatcccc 480
gagctggaca tgaccgaggt ggtggccccc ttcatggcca acatccccct gctgctgtac 540
ccccaggacg gcccccgcag caagccccag cccaaggaca acggcgacgt gtgccaggac 600
tgcatccaga tggtgaccga catccagacc gccgtgcgca ccaacagcac cttcgtgcag 660
gccctggtgg agcacgtgaa ggaggagtgc gaccgcctgg gccccggcat ggccgacatc 720
tgcaagaact acatcagcca gtacagcgag atcgccatcc agatgatgat gcacatgcag 780
cccaaggaga tctgcgccct ggtgggcttc tgcgacgagg tgaaggagat gcccatgcag 840
accctggtgc ccgccaaggt ggccagcaag aacgtgatcc ccgccctgga gctggtggag 900
cccatcaaga agcacgaggt gcccgccaag agcgacgtgt actgcgaggt gtgcgagttc 960
ctggtgaagg aggtgaccaa gctgatcgac aacaacaaga ccgagaagga gatcctggac 1020
gccttcgaca agatgtgcag caagctgccc aagagcctga gcgaggagtg ccaggaggtg 1080
gtggacacct acggcagcag catcctgagc atcctgctgg aggaggtgag ccccgagctg 1140
gtgtgcagca tgctgcacct gtgcagcggc acccgcctgc ccgccctgac cgtgcacgtg 1200
acccagccca aggacggcgg cttctgcgag gtgtgcaaga agctggtggg ctacctggac 1260
cgcaacctgg agaagaacag caccaagcag gagatcctgg ccgccctgga gaagggctgc 1320
agcttcctgc ccgaccccta ccagaagcag tgcgaccagt tcgtggccga gtacgagccc 1380
gtgctgatcg agatcctggt ggaggtgatg gaccccagct tcgtgtgcct gaagatcggc 1440
gcctgcccca gcgcccacaa gcccctgctg ggcaccgaga agtgcatctg gggccccagc 1500
tactggtgcc agaacaccga gaccgccgcc cagtgcaacg ccgtggagca ctgcaagcgc 1560
cacgtgtgga ac 1572

<210> SEQ ID NO 18
<211> LENGTH: 478
<212> TYPE: PRT
<213> ORGANISM: Homo sapiens

<400> SEQUENCE: 18

Met Gly Arg Cys Cys Phe Tyr Thr Ala Gly Thr Leu Ser Leu Leu Leu
1 5 10 15

Leu Val Thr Ser Val Thr Leu Leu Val Ala Arg Val Phe Gln Lys Ala
20 25 30

Val Asp Gln Ser Ile Glu Lys Lys Ile Val Leu Arg Asn Gly Thr Glu
35 40 45

Ala Phe Asp Ser Trp Glu Lys Pro Pro Leu Pro Val Tyr Thr Gln Phe
50 55 60

Tyr Phe Phe Asn Val Thr Asn Pro Glu Glu Ile Leu Arg Gly Glu Thr
65 70 75 80

Pro Arg Val Glu Glu Val Gly Pro Tyr Thr Tyr Arg Glu Leu Arg Asn

-continued

```
                85                  90                  95

Lys Ala Asn Ile Gln Phe Gly Asp Asn Gly Thr Thr Ile Ser Ala Val
            100                 105                 110

Ser Asn Lys Ala Tyr Val Phe Glu Arg Asp Gln Ser Val Gly Asp Pro
        115                 120                 125

Lys Ile Asp Leu Ile Arg Thr Leu Asn Ile Pro Val Leu Thr Val Ile
    130                 135                 140

Glu Trp Ser Gln Val His Phe Leu Arg Glu Ile Ile Glu Ala Met Leu
145                 150                 155                 160

Lys Ala Tyr Gln Gln Lys Leu Phe Val Thr His Thr Val Asp Glu Leu
                165                 170                 175

Leu Trp Gly Tyr Lys Asp Glu Ile Leu Ser Leu Ile His Val Phe Arg
            180                 185                 190

Pro Asp Ile Ser Pro Tyr Phe Gly Leu Phe Tyr Glu Lys Asn Gly Thr
        195                 200                 205

Asn Asp Gly Asp Tyr Val Phe Leu Thr Gly Glu Asp Ser Tyr Leu Asn
    210                 215                 220

Phe Thr Lys Ile Val Glu Trp Asn Gly Lys Thr Ser Leu Asp Trp Trp
225                 230                 235                 240

Ile Thr Asp Lys Cys Asn Met Ile Asn Gly Thr Asp Gly Asp Ser Phe
                245                 250                 255

His Pro Leu Ile Thr Lys Asp Glu Val Leu Tyr Val Phe Pro Ser Asp
            260                 265                 270

Phe Cys Arg Ser Val Tyr Ile Thr Phe Ser Asp Tyr Glu Ser Val Gln
        275                 280                 285

Gly Leu Pro Ala Phe Arg Tyr Lys Val Pro Ala Glu Ile Leu Ala Asn
    290                 295                 300

Thr Ser Asp Asn Ala Gly Phe Cys Ile Pro Glu Gly Asn Cys Leu Gly
305                 310                 315                 320

Ser Gly Val Leu Asn Val Ser Ile Cys Lys Asn Gly Ala Pro Ile Ile
                325                 330                 335

Met Ser Phe Pro His Phe Tyr Gln Ala Asp Glu Arg Phe Val Ser Ala
            340                 345                 350

Ile Glu Gly Met His Pro Asn Gln Glu Asp His Glu Thr Phe Val Asp
        355                 360                 365

Ile Asn Pro Leu Thr Gly Ile Ile Leu Lys Ala Ala Lys Arg Phe Gln
    370                 375                 380

Ile Asn Ile Tyr Val Lys Lys Leu Asp Asp Phe Val Glu Thr Gly Asp
385                 390                 395                 400

Ile Arg Thr Met Val Phe Pro Val Met Tyr Leu Asn Glu Ser Val His
                405                 410                 415

Ile Asp Lys Glu Thr Ala Ser Arg Leu Lys Ser Met Ile Asn Thr Thr
            420                 425                 430

Leu Ile Ile Thr Asn Ile Pro Tyr Ile Ile Met Ala Leu Gly Val Phe
        435                 440                 445

Phe Gly Leu Val Phe Thr Trp Leu Ala Cys Lys Gly Gln Gly Ser Met
    450                 455                 460

Asp Glu Gly Thr Ala Asp Glu Arg Ala Pro Leu Ile Arg Thr
465                 470                 475
```

<210> SEQ ID NO 19
<211> LENGTH: 1434
<212> TYPE: DNA
<213> ORGANISM: Homo sapiens

<400> SEQUENCE: 19
atgggccgct gctgcttcta caccgccggc accctgagcc tgctgctgct ggtgaccagc 60
gtgaccctgc tggtggcccg cgtgttccag aaggccgtgg accagagcat cgagaagaag 120
atcgtgctgc gcaacggcac cgaggccttc gacagctggg agaagccccc cctgcccgtg 180
tacacccagt tctacttctt caacgtgacc aaccccgagg agatcctgcg cggcgagacc 240
ccccgcgtgg aggaggtggg cccctacacc taccgcgagc tgcgcaacaa ggccaacatc 300
cagttcggcg acaacggcac caccatcagc gccgtgagca acaaggccta cgtgttcgag 360
cgcgaccaga gcgtgggcga ccccaagatc gacctgatcc gcaccctgaa catccccgtg 420
ctgaccgtga tcgagtggag ccaggtgcac ttcctgcgcg agatcatcga ggccatgctg 480
aaggcctacc agcagaagct gttcgtgacc cacaccgtgg acgagctgct gtggggctac 540
aaggacgaga tcctgagcct gatccacgtg ttccgccccg acatcagccc ctacttcggc 600
ctgttctacg agaagaacgg caccaacgac ggcgactacg tgttcctgac cggcgaggac 660
agctacctga acttcaccaa gatcgtggag tggaacggca agaccagcct ggactggtgg 720
atcaccgaca agtgcaacat gatcaacggc accgacggcg acagcttcca cccccctgatc 780
accaaggacg aggtgctgta cgtgttcccc agcgacttct gccgcagcgt gtacatcacc 840
ttcagcgact acgagagcgt gcagggcctg cccgccttcc gctacaaggt gcccgccgag 900
atcctggcca acaccagcga caacgccggc ttctgcatcc ccgagggcaa ctgcctgggc 960
agcggcgtgc tgaacgtgag catctgcaag aacggcgccc ccatcatcat gagcttcccc 1020
cacttctacc aggccgacga gcgcttcgtg agcgccatcg agggcatgca ccccaaccag 1080
gaggaccacg agaccttcgt ggacatcaac cccctgaccg gcatcatcct gaaggccgcc 1140
aagcgcttcc agatcaacat ctacgtgaag aagctggacg acttcgtgga gaccggcgac 1200
atccgcacca tggtgttccc cgtgatgtac ctgaacgaga gcgtgcacat cgacaaggag 1260
accgccagcc gcctgaagag catgatcaac accaccctga tcatcaccaa catcccctac 1320
atcatcatgg ccctgggcgt gttcttcggc ctggtgttca cctggctggc ctgcaagggc 1380
cagggcagca tggacgaggg caccgccgac gagcgcgccc ccctgatccg cacc 1434

<210> SEQ ID NO 20
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 20
tggaagactt cgagatacac tgt 23

<210> SEQ ID NO 21
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 21
acagtgtatc tcgaagtctt cca 23

<210> SEQ ID NO 22
<211> LENGTH: 21
<212> TYPE: DNA

<213> ORGANISM: Artificial Sequence
<220> FEATURE:
<223> OTHER INFORMATION: Synthetic polynucleotide

<400> SEQUENCE: 22
tttagaaata agtggtagtc a 21

<210> SEQ ID NO 23
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 23
tgactaccac ttatttctaa a 21

<210> SEQ ID NO 24
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 24
agggtatcaa gactacgaa 19

<210> SEQ ID NO 25
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 25
ttcgtagtct tgataccct 19

<210> SEQ ID NO 26
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 26
tattagatct gatggccgc 19

<210> SEQ ID NO 27
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 27
ctccatcact aggggttcct 20

<210> SEQ ID NO 28
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 28
agctctgggt atttaagccc gagtgagcac gcagggtctc cattttgaag cgggaggtta 60

<210> SEQ ID NO 29
<211> LENGTH: 145
<212> TYPE: DNA
<213> ORGANISM: Unknown
<220> FEATURE:
<223> OTHER INFORMATION: AAV2 ITR

<400> SEQUENCE: 29
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag agagggagtg gccaa 145

<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 30
tattagatct gatggccgcg 20

<210> SEQ ID NO 31
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 31
tccatcacta ggggttcctg 20

<210> SEQ ID NO 32
<211> LENGTH: 4013
<212> TYPE: DNA
<213> ORGANISM: Artificial Sequence
<220> FEATURE:
<223> OTHER INFORMATION: Synthetic polynucleotide

<400> SEQUENCE: 32
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttaat tattttgtgc agcgatgggg gcgggggggg 780 gggggggcg cgcgccaggc ggggcggggc ggggcgaggg gcggggcggg gcgaggcgga 840

-continued

```
gaggtgcggc ggcagccaat cagagcggcg cgctccgaaa gtttcctttt atggcgaggc    900
ggcggcggcg gcggccctat aaaaagcgaa gcgcgcggcg ggcgggagtc gctgcgcgct    960
gccttcgccc cgtgccccgc tccgccgccg cctcgcgccg cccgccccgg ctctgactga   1020
ccgcgttact cccacaggtg agcgggcggg acggcccttc tcctccgggc tgtaattagc   1080
gcttggttta atgacggctt gtttcttttc tgtggctgcg tgaaagcctt gaggggctcc   1140
gggagctaga gcctctgcta accatgttca tgccttcttc tttttcctac agctcctggg   1200
caacgtgctg gttattgtgc tgtctcatca ttttggcaaa gaattcctcg aagatccgaa   1260
gggaaagtct tccacgactg tgggatccgt tcgaagatat caccggttga gccaccatgg   1320
aattcagcag ccccagcaga gaggaatgcc ccaagcctct gagccgggtg tcaatcatgg   1380
ccggatctct gacaggactg ctgctgcttc aggccgtgtc ttgggcttct ggcgctagac   1440
cttgcatccc caagagcttc ggctacagca gcgtcgtgtg cgtgtgcaat gccacctact   1500
gcgacagctt cgaccctcct acctttcctg ctctgggcac cttcagcaga tacgagagca   1560
ccagatccgg cagacggatg gaactgagca tgggacccat ccaggccaat cacacaggca   1620
ctggcctgct gctgacactg cagcctgagc agaaattcca gaaagtgaaa ggcttcggcg   1680
gagccatgac agatgccgcc gctctgaata tcctggctct gtctccacca gctcagaacc   1740
tgctgctcaa gagctacttc agcgaggaag gcatcggcta caacatcatc agagtgccca   1800
tggccagctg cgacttcagc atcaggacct acacctacgc cgacacaccc gacgatttcc   1860
agctgcacaa cttcagcctg cctgaagagg acaccaagct gaagatccct ctgatccaca   1920
gagccctgca gctggcacaa agacccgtgt cactgctggc ctctccatgg acatctccca   1980
cctggctgaa aacaaatggc gccgtgaatg gcaagggcag cctgaaaggc caacctggcg   2040
acatctacca ccagacctgg gccagatact tcgtgaagtt cctggacgcc tatgccgagc   2100
acaagctgca gttttgggcc gtgacagccg agaacgaacc ttctgctgga ctgctgagcg   2160
gctacccctt tcagtgcctg ggctttacac ccgagcacca gcgggacttt atcgcccgtg   2220
atctgggacc cacactggcc aatagcaccc accataatgt gcggctgctg atgctggacg   2280
accagagact gcttctgccc cactgggcta aagtggtgct gacagatcct gaggccgcca   2340
aatacgtgca cggaatcgcc gtgcactggt atctggactt tctggcccct gccaaggcca   2400
cactgggaga gacacacaga ctgttcccca acaccatgct gttcgccagc gaagcctgtg   2460
tgggcagcaa gttttgggaa cagagcgtgc ggctcggcag ctgggataga ggcatgcagt   2520
acagccacag catcatcacc aacctgctgt accacgtcgt cggctggacc gactggaatc   2580
tggccctgaa tcctgaaggc ggccctaact gggtccgaaa cttcgtggac agccccatca   2640
tcgtggacat caccaaggac accttctaca agcagcccat gttctaccac ctgggacact   2700
tcagcaagtt catccccgag ggctctcagc gcgttggact ggtggcttcc cagaagaacg   2760
atctggacgc cgtggctctg atgcaccctg atggatctgc tgtggtggtg gtcctgaacc   2820
gcagcagcaa agatgtgccc ctgaccatca aggatcccgc cgtgggattc ctggaaacaa   2880
tcagccctgg ctactccatc cacacctacc tgtggcgtag acagtgacaa ttgttaatta   2940
agtttaaacc ctcgaggccg caagcttatc gataatcaac ctctggatta caaaatttgt   3000
gaaagattga ctggtattct taactatgtt gctcctttta cgctatgtgg atacgctgct   3060
ttaatgcctt tgtatcatgc tattgcttcc cgtatggctt tcattttctc ctccttgtat   3120
aaatcctggt tgctgtctct ttatgaggag ttgtggcccg ttgtcaggca acgtggcgtg   3180
gtgtgcactg tgtttgctga cgcaaccccc actggttggg gcattgccac cacctgtcag   3240
```

ctcctttccg ggactttcgc tttccccctc cctattgcca cggcggaact catcgccgcc 3300
tgccttgccc gctgctggac aggggctcgg ctgttgggca ctgacaattc cgtggtgttg 3360
tcggggaaat catcgtcctt tccttggctg ctcgcctgtg ttgccacctg gattctgcgc 3420
gggacgtcct tctgctacgt cccttcggcc ctcaatccag cggaccttcc ttcccgcggc 3480
ctgctgccgg ctctgcggcc tcttccgcgt cttcgccttc gccctcagac gagtcggatc 3540
tccctttggg ccgcctcccc gcatcgatac cgtcgactag agctcgctga tcagcctcga 3600
ctgtgccttc tagttgccag ccatctgttg tttgcccctc ccccgtgcct tccttgaccc 3660
tggaaggtgc cactcccact gtcctttcct aataaaatga ggaaattgca tcgcattgtc 3720
tgagtaggtg tcattctatt ctggggggtg gggtggggca ggacagcaag ggggaggatt 3780
gggaagacaa tagcaggcat gctggggaga gatccacgat aacaaacagc tttttggggg 3840
tgaacatatt gactgaattc cctgcaggtt ggccactccc tctctgcgcg ctcgctcgct 3900
cactgaggcc gcccgggcaa agcccgggcg tcgggcgacc tttggtcgcc cggcctcagt 3960
gagcgagcga gcgcgcagag agggagtggc caactccatc actaggggtt cct 4013

<210> SEQ ID NO 33
<211> LENGTH: 4013
<212> TYPE: DNA
<213> ORGANISM: Artificial Sequence
<220> FEATURE:
<223> OTHER INFORMATION: Synthetic polynucleotide

<400> SEQUENCE: 33
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttaat tattttgtgc agcgatgggg gcgggggggg 780 gggggggcg cgcgccaggc ggggcggggc ggggcgaggg gcggggcggg gcgaggcgga 840
gaggtgcggc ggcagccaat cagagcggcg cgctccgaaa gtttcctttt atggcgaggc 900
ggcggcggcg gcggccctat aaaaagcgaa gcgcgcggcg ggcgggagtc gctgcgcgct 960
gccttcgccc cgtgccccgc tccgccgccg cctcgcgccg cccgccccgg ctctgactga 1020
ccgcgttact cccacaggtg agcgggcggg acggcccttc tcctccgggc tgtaattagc 1080
gcttggttta atgacggctt gtttcttttc tgtggctgcg tgaaagcctt gaggggctcc 1140
gggagctaga gcctctgcta accatgttca tgccttcttc tttttcctac agctcctggg 1200
caacgtgctg gttattgtgc tgtctcatca ttttggcaaa gaattcctcg aagatccgaa 1260

-continued gggaaagtct tccacgactg tgggatccgt tcgaagatat caccggttga gccaccatgg 1320
aattcagcag ccccagcaga gaggaatgcc ccaagcctct gagccgggtg tcaatcatgg 1380
ccggatctct gacaggactg ctgctgcttc aggccgtgtc ttgggcttct ggcgctagac 1440
cttgcatccc caagagcttc ggctacagca gcgtcgtgtg cgtgtgcaat gccacctact 1500
gcgacagctt cgaccctcct acctttcctg ctctgggcac cttcagcaga tacgagagca 1560
ccagatccgg cagacggatg gaactgagca tgggacccat ccaggccaat cacacaggca 1620
ctggcctgct gctgacactg cagcctgagc agaaattcca gaaagtgaaa ggcttcggcg 1680
gagccatgac agatgccgcc gctctgaata tcctggctct gtctccacca gctcagaacc 1740
tgctgctcaa gagctacttc agcgaggaag gcatcggcta caacatcatc agagtgccca 1800
tggccagctg cgacttcagc atcaggacct acacctacgc cgacacaccc gacgatttcc 1860
agctgcacaa cttcagcctg cctgaagagg acaccaagct gaagatccct ctgatccaca 1920
gagccctgca gctggcacaa agacccgtgt cactgctggc ctctccatgg acatctccca 1980
cctggctgaa aacaaatggc gccgtgaatg gcaagggcag cctgaaaggc caacctggcg 2040
acatctacca ccagacctgg gccagatact tcgtgaagtt cctggacgcc tatgccgagc 2100
acaagctgca gttttgggcc gtgacagccg agaacgaacc ttctgctgga ctgctgagcg 2160
gctacccctt tcagtgcctg ggctttacac ccgagcacca gcgggacttt atcgcccgtg 2220
atctgggacc cacactggcc aatagcaccc accataatgt gcggctgctg atgctggacg 2280
accagagact gcttctgccc cactgggcta aagtggtgct gacagatcct gaggccgcca 2340
aatacgtgca cggaatcgcc gtgcactggt atctggactt tctggcccct gccaaggcca 2400
cactgggaga gacacacaga ctgttcccca acaccatgct gttcgccagc gaagcctgtg 2460
tgggcagcaa gttttgggaa cagagcgtgc ggctcggcag ctgggataga ggcatgcagt 2520
acagccacag catcatcacc aacctgctgt accacgtcgt cggctggacc gactggaatc 2580
tggccctgaa tcctgaaggc ggccctaact gggtccgaaa cttcgtggac agccccatca 2640
tcgtggacat caccaaggac accttctaca agcagcccat gttctaccac ctgggacact 2700
tcagcaagtt catccccgag ggctctcagc gcgttggact ggtggcttcc cagaagaacg 2760
atctggacgc cgtggctctg atgcaccctg atggatctgc tgtggtggtg gtcctgaacc 2820
gcagcagcaa agatgtgccc ctgaccatca aggatcccgc cgtgggattc ctggaaacaa 2880
tcagccctgg ctactccatc cacacctacc tgtggcgtag acagtgacaa ttgttaatta 2940
agtttaaacc ctcgaggccg caagcttatc gataatcaac ctctggatta caaaatttgt 3000
gaaagattga ctggtattct taactatgtt gctcctttta cgctatgtgg atacgctgct 3060
ttaatgcctt tgtatcatgc tattgcttcc cgtatggctt tcattttctc ctccttgtat 3120
aaatcctggt tgctgtctct ttatgaggag ttgtggcccg ttgtcaggca acgtggcgtg 3180
gtgtgcactg tgtttgctga cgcaaccccc actggttggg gcattgccac cacctgtcag 3240
ctcctttccg ggactttcgc tttccccctc cctattgcca cggcggaact catcgccgcc 3300
tgccttgccc gctgctggac aggggctcgg ctgttgggca ctgacaattc cgtggtgttg 3360
tcggggaaat catcgtcctt tccttggctg ctcgcctgtg ttgccacctg gattctgcgc 3420
gggacgtcct tctgctacgt cccttcggcc ctcaatccag cggaccttcc ttcccgcggc 3480
ctgctgccgg ctctgcggcc tcttccgcgt cttcgccttc gccctcagac gagtcggatc 3540
tccctttggg ccgcctcccc gcatcgatac cgtcgactag agctcgctga tcagcctcga 3600
ctgtgccttc tagttgccag ccatctgttg tttgcccctc ccccgtgcct tccttgaccc 3660
tggaaggtgc cactcccact gtcctttcct aataaaatga ggaaattgca tcgcattgtc 3720
tgagtaggtg tcattctatt ctggggggtg gggtggggca ggacagcaag ggggaggatt 3780
gggaagacaa tagcaggcat gctggggaga gatccacgat aacaaacagc tttttggggg 3840
tgaacatatt gactgaattc cctgcaggtt ggccactccc tctctgcgcg ctcgctcgct 3900
cactgaggcc gcccgggcaa agcccgggcg tcgggcgacc tttggtcgcc cggcctcagt 3960
gagcgagcga gcgcgcagag agggagtggc caactccatc actaggggtt cct 4013

<210> SEQ ID NO 34
<211> LENGTH: 4162
<212> TYPE: DNA
<213> ORGANISM: Artificial Sequence
<220> FEATURE:
<223> OTHER INFORMATION: Synthetic polynucleotide

<400> SEQUENCE: 34
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttaat tattttgtgc agcgatgggg gcgggggggg 780 gggggggcg cgcgccaggc ggggcggggc ggggcgaggg gcggggcggg gcgaggcgga 840
gaggtgcggc ggcagccaat cagagcggcg cgctccgaaa gtttcctttt atggcgaggc 900
ggcggcggcg gcggccctat aaaaagcgaa gcgcgcggcg ggcgggagtc gctgcgacgc 960
tgccttcgcc ccgtgccccg ctccgccgcc gcctcgcgcc gcccgccccg gctctgactg 1020
accgcgttac tcccacaggt gagcgggcgg gacggccctt ctcctcagcg ctgtaattag 1080
cgcttggttt aatgacggct tgttggaggc ttgctgaagg ctgtatgctg ttgtctttag 1140
aaataagtgg tagtcaagtg aagccacaga tgtgactacc acttatttct aaaaggacac 1200
aaggcctgtt actagcactc acatggaaca aatggccacc gtgggaggat gacaatttct 1260
gtggctgcgt gaaagccttg aggggctccg ggagctagag cctctgctaa ccatgttcat 1320
gccttcttct ttttcctaca gctcctgggc aacgtgctgg ttattgtgct gtctcatcat 1380
tttggcaaag aattcctcga agatccgaag ggaaagtctt ccacgactgt gggatccgtt 1440
cgaagatatc accggttgag ccaccatgga attcagcagc cccagcagag aggaatgccc 1500
caagcctctg agccgggtgt caatcatggc cggatctctg acaggactgc tgctgcttca 1560
ggccgtgtct tgggcttctg gcgctagacc ttgcatcccc aagagcttcg gctacagcag 1620
cgtcgtgtgc gtgtgcaatg ccacctactg cgacagcttc gaccctccta cctttcctgc 1680

```
tctgggcacc ttcagcagat acgagagcac cagatccggc agacggatgg aactgagcat   1740
gggacccatc caggccaatc acacaggcac tggcctgctg ctgacactgc agcctgagca   1800
gaaattccag aaagtgaaag gcttcggcgg agccatgaca gatgccgccg ctctgaatat   1860
cctggctctg tctccaccag ctcagaacct gctgctcaag agctacttca gcgaggaagg   1920
catcggctac aacatcatca gagtgcccat ggccagctgc gacttcagca tcaggaccta   1980
cacctacgcc gacacacccg acgatttcca gctgcacaac ttcagcctgc ctgaagagga   2040
caccaagctg aagatccctc tgatccacag agccctgcag ctggcacaaa gacccgtgtc   2100
actgctggcc tctccatgga catctcccac ctggctgaaa acaaatggcg ccgtgaatgg   2160
caagggcagc ctgaaaggcc aacctggcga catctaccac cagacctggg ccagatactt   2220
cgtgaagttc ctggacgcct atgccgagca caagctgcag ttttgggccg tgacagccga   2280
gaacgaacct tctgctggac tgctgagcgg ctaccccttt cagtgcctgg gctttacacc   2340
cgagcaccag cgggacttta tcgcccgtga tctgggaccc acactggcca atagcaccca   2400
ccataatgtg cggctgctga tgctggacga ccagagactg cttctgcccc actgggctaa   2460
agtggtgctg acagatcctg aggccgccaa atacgtgcac ggaatcgccg tgcactggta   2520
tctggacttt ctggcccctg ccaaggccac actgggagag acacacagac tgttccccaa   2580
caccatgctg ttcgccagcg aagcctgtgt gggcagcaag ttttgggaac agagcgtgcg   2640
gctcggcagc tgggatagag gcatgcagta cagccacagc atcatcacca acctgctgta   2700
ccacgtcgtc ggctggaccg actggaatct ggccctgaat cctgaaggcg gccctaactg   2760
ggtccgaaac ttcgtggaca gccccatcat cgtggacatc accaaggaca ccttctacaa   2820
gcagcccatg ttctaccacc tgggacactt cagcaagttc atccccgagg gctctcagcg   2880
cgttggactg gtggcttccc agaagaacga tctggacgcc gtggctctga tgcaccctga   2940
tggatctgct gtggtggtgg tcctgaaccg cagcagcaaa gatgtgcccc tgaccatcaa   3000
ggatcccgcc gtgggattcc tggaaacaat cagccctggc tactccatcc acacctacct   3060
gtggcgtaga cagtgacaat tgttaattaa gtttaaaccc tcgaggccgc aagcttatcg   3120
ataatcaacc tctggattac aaaatttgtg aaagattgac tggtattctt aactatgttg   3180
ctccttttac gctatgtgga tacgctgctt taatgccttt gtatcatgct attgcttccc   3240
gtatggcttt cattttctcc tccttgtata aatcctggtt gctgtctctt tatgaggagt   3300
tgtggcccgt tgtcaggcaa cgtggcgtgg tgtgcactgt gtttgctgac gcaaccccca   3360
ctggttgggg cattgccacc acctgtcagc tcctttccgg gactttcgct ttccccctcc   3420
ctattgccac ggcggaactc atcgccgcct gccttgcccg ctgctggaca ggggctcggc   3480
tgttgggcac tgacaattcc gtggtgttgt cggggaaatc atcgtccttt ccttggctgc   3540
tcgcctgtgt tgccacctgg attctgcgcg ggacgtcctt ctgctacgtc ccttcggccc   3600
tcaatccagc ggaccttcct tcccgcggcc tgctgccggc tctgcggcct cttccgcgtc   3660
ttcgccttcg ccctcagacg agtcggatct ccctttgggc cgcctccccg catcgatacc   3720
gtcgactaga gctcgctgat cagcctcgac tgtgccttct agttgccagc catctgttgt   3780
ttgcccctcc cccgtgcctt ccttgaccct ggaaggtgcc actcccactg tcctttccta   3840
ataaaatgag gaaattgcat cgcattgtct gagtaggtgt cattctattc tggggggtgg   3900
ggtggggcag gacagcaagg gggaggattg ggaagacaat agcaggcatg ctggggagag   3960
atccacgata acaaacagct tttttggggc ccacatgtac actgaattcc ctgcaggttg   4020
gccactccct ctctgcgcgc tcgctcgctc actgaggccg cccgggcaaa gcccgggcgt   4080
```

cgggcgacct ttggtcgccc ggcctcagtg agcgagcgag cgcgcagaga gggagtggcc 4140
aactccatca ctaggggttc ct 4162

<210> SEQ ID NO 35
<211> LENGTH: 4162
<212> TYPE: DNA
<213> ORGANISM: Artificial Sequence
<220> FEATURE:
<223> OTHER INFORMATION: Synthetic polynucleotide

<400> SEQUENCE: 35
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttaat tattttgtgc agcgatgggg gcgggggggg 780 gggggggcg cgcgccaggc ggggcggggc ggggcgaggg gcggggcggg gcgaggcgga 840
gaggtgcggc ggcagccaat cagagcggcg cgctccgaaa gtttcctttt atggcgaggc 900
ggcggcggcg gcggccctat aaaaagcgaa gcgcgcggcg ggcgggagtc gctgcgacgc 960
tgccttcgcc ccgtgccccg ctccgccgcc gcctcgcgcc gcccgccccg gctctgactg 1020
accgcgttac tcccacaggt gagcgggcgg gacggccctt ctcctcagcg ctgtaattag 1080
cgcttggttt aatgacggct tgttggaggc ttgctgaagg ctgtatgctg ttgtctttag 1140
aaataagtgg tagtcaagtg aagccacaga tgtgactacc acttatttct aaaaggacac 1200
aaggcctgtt actagcactc acatggaaca aatggccacc gtgggaggat gacaatttct 1260
gtggctgcgt gaaagccttg aggggctccg ggagctagag cctctgctaa ccatgttcat 1320
gccttcttct ttttcctaca gctcctgggc aacgtgctgg ttattgtgct gtctcatcat 1380
tttggcaaag aattcctcga agatccgaag ggaaagtctt ccacgactgt gggatccgtt 1440
cgaagatatc accggttgag ccaccatgga attcagcagc cccagcagag aggaatgccc 1500
caagcctctg agccgggtgt caatcatggc cggatctctg acaggactgc tgctgcttca 1560
ggccgtgtct tgggcttctg gcgctagacc ttgcatcccc aagagcttcg gctacagcag 1620
cgtcgtgtgc gtgtgcaatg ccacctactg cgacagcttc gaccctccta cctttcctgc 1680
tctgggcacc ttcagcagat acgagagcac cagatccggc agacggatgg aactgagcat 1740
gggacccatc caggccaatc acacaggcac tggcctgctg ctgacactgc agcctgagca 1800
gaaattccag aaagtgaaag gcttcggcgg agccatgaca gatgccgccg ctctgaatat 1860
cctggctctg tctccaccag ctcagaacct gctgctcaag agctacttca gcgaggaagg 1920
catcggctac aacatcatca gagtgcccat ggccagctgc gacttcagca tcaggaccta 1980
cacctacgcc gacacacccg acgatttcca gctgcacaac ttcagcctgc ctgaagagga 2040
caccaagctg aagatccctc tgatccacag agccctgcag ctggcacaaa gacccgtgtc 2100
actgctggcc tctccatgga catctcccac ctggctgaaa acaaatggcg ccgtgaatgg 2160
caagggcagc ctgaaaggcc aacctggcga catctaccac cagacctggg ccagatactt 2220
cgtgaagttc ctggacgcct atgccgagca caagctgcag ttttgggccg tgacagccga 2280
gaacgaacct tctgctggac tgctgagcgg ctacccettt cagtgcctgg gctttacacc 2340
cgagcaccag cgggacttta tcgcccgtga tctgggaccc acactggcca atagcaccca 2400
ccataatgtg cggctgctga tgctggacga ccagagactg cttctgcccc actgggctaa 2460
agtggtgctg acagatcctg aggccgccaa atacgtgcac ggaatcgccg tgcactggta 2520
tctggacttt ctggcccctg ccaaggccac actgggagag acacacagac tgttccccaa 2580
caccatgctg ttcgccagcg aagcctgtgt gggcagcaag ttttgggaac agagcgtgcg 2640
gctcggcagc tgggatagag gcatgcagta cagccacagc atcatcacca acctgctgta 2700
ccacgtcgtc ggctggaccg actggaatct ggccctgaat cctgaaggcg gccctaactg 2760
ggtccgaaac ttcgtggaca gccccatcat cgtggacatc accaaggaca ccttctacaa 2820
gcagcccatg ttctaccacc tgggacactt cagcaagttc atccccgagg gctctcagcg 2880
cgttggactg gtggcttccc agaagaacga tctggacgcc gtggctctga tgcaccctga 2940
tggatctgct gtggtggtgg tcctgaaccg cagcagcaaa gatgtgcccc tgaccatcaa 3000
ggatcccgcc gtgggattcc tggaaacaat cagccctggc tactccatcc acacctacct 3060
gtggcgtaga cagtgacaat tgttaattaa gtttaaaccc tcgaggccgc aagcttatcg 3120
ataatcaacc tctggattac aaaatttgtg aaagattgac tggtattctt aactatgttg 3180
ctccttttac gctatgtgga tacgctgctt taatgccttt gtatcatgct attgcttccc 3240
gtatggcttt cattttctcc tccttgtata aatcctggtt gctgtctctt tatgaggagt 3300
tgtggcccgt tgtcaggcaa cgtggcgtgg tgtgcactgt gtttgctgac gcaaccccca 3360
ctggttgggg cattgccacc acctgtcagc tcctttccgg gactttcgct ttccccctcc 3420
ctattgccac ggcggaactc atcgccgcct gccttgcccg ctgctggaca ggggctcggc 3480
tgttgggcac tgacaattcc gtggtgttgt cggggaaatc atcgtccttt ccttggctgc 3540
tcgcctgtgt tgccacctgg attctgcgcg ggacgtcctt ctgctacgtc ccttcggccc 3600
tcaatccagc ggaccttcct tcccgcggcc tgctgccggc tctgcggcct cttccgcgtc 3660
ttcgccttcg ccctcagacg agtcggatct ccctttgggc cgcctccccg catcgatacc 3720
gtcgactaga gctcgctgat cagcctcgac tgtgccttct agttgccagc catctgttgt 3780
ttgcccctcc cccgtgcctt ccttgaccct ggaaggtgcc actcccactg tcctttccta 3840
ataaaatgag gaaattgcat cgcattgtct gagtaggtgt cattctattc tggggggtgg 3900
ggtggggcag gacagcaagg gggaggattg ggaagacaat agcaggcatg ctggggagag 3960
atccacgata acaaacagct tttttggggc ccacatgtac actgaattcc ctgcaggttg 4020
gccactccct ctctgcgcgc tcgctcgctc actgaggccg cccgggcaaa gcccgggcgt 4080
cgggcgacct ttggtcgccc ggcctcagtg agcgagcgag cgcgcagaga gggagtggcc 4140
aactccatca ctaggggttc ct 4162

<210> SEQ ID NO 36
<211> LENGTH: 3977

<212> TYPE: DNA
<213> ORGANISM: Artificial Sequence
<220> FEATURE:
<223> OTHER INFORMATION: Synthetic polynucleotide

<400> SEQUENCE: 36
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttaat tattttgtgc agcgatgggg gcgggggggg 780 gggggggcg cgcgccaggc ggggcggggc ggggcgaggg gcggggcggg gcgaggcgga 840
gaggtgcggc ggcagccaat cagagcggcg cgctccgaaa gtttcctttt atggcgaggc 900
ggcggcggcg gcggccctat aaaaagcgaa gcgcgcggcg ggcgggagtc gctgcgcgct 960
gccttcgccc cgtgccccgc tccgccgccg cctcgcgccg cccgccccgg ctctgactga 1020
ccgcgttact cccacaggtg agcgggcggg acggcccttc tcctccgggc tgtaattagc 1080
gcttggttta atgacggctt gtttcttttc tgtggctgcg tgaaagcctt gaggggctcc 1140
gggagctaga gcctctgcta accatgttca tgccttcttc tttttcctac agctcctggg 1200
caacgtgctg gttattgtgc tgtctcatca ttttggcaaa gaattcctcg aagatccgaa 1260
gggaaagtct tccacgactg tgggatccgt tcgaagatat caccggttga gccaccatgt 1320
acgccctgtt cctgctggcc agcctgctgg gcgccgccct ggccggcccc gtgctgggcc 1380
tgaaggagtg cacccgcggc agcgccgtgt ggtgccagaa cgtgaagacc gccagcgact 1440
gcggcgccgt gaagcactgc ctgcagaccg tgtggaacaa gcccaccgtg aagagcctgc 1500
cctgcgacat ctgcaaggac gtggtgaccg ccgccggcga catgctgaag gacaacgcca 1560
ccgaggagga gatcctggtg tacctggaga agacctgcga ctggctgccc aagcccaaca 1620
tgagcgccag ctgcaaggag atcgtggaca gctacctgcc cgtgatcctg gacatcatca 1680
agggcgagat gagccgcccc ggcgaggtgt gcagcgccct gaacctgtgc gagagcctgc 1740
agaagcacct ggccgagctg aaccaccaga agcagctgga gagcaacaag atccccgagc 1800
tggacatgac cgaggtggtg gccccttca tggccaacat cccccctgctg ctgtaccccc 1860 aggacggccc ccgcagcaag ccccagccca aggacaacgg cgacgtgtgc caggactgca 1920
tccagatggt gaccgacatc cagaccgccg tgcgcaccaa cagcaccttc gtgcaggccc 1980
tggtggagca cgtgaaggag gagtgcgacc gcctgggccc cggcatggcc gacatctgca 2040
agaactacat cagccagtac agcgagatcg ccatccagat gatgatgcac atgcagccca 2100
aggagatctg cgccctggtg ggcttctgcg acgaggtgaa ggagatgccc atgcagaccc 2160

-continued tggtgcccgc caaggtggcc agcaagaacg tgatccccgc cctggagctg gtggagccca 2220
tcaagaagca cgaggtgccc gccaagagcg acgtgtactg cgaggtgtgc gagttcctgg 2280
tgaaggaggt gaccaagctg atcgacaaca acaagaccga gaaggagatc ctggacgcct 2340
tcgacaagat gtgcagcaag ctgcccaaga gcctgagcga ggagtgccag gaggtggtgg 2400
acacctacgg cagcagcatc ctgagcatcc tgctggagga ggtgagcccc gagctggtgt 2460
gcagcatgct gcacctgtgc agcggcaccc gcctgcccgc cctgaccgtg cacgtgaccc 2520
agcccaagga cggcggcttc tgcgaggtgt gcaagaagct ggtgggctac ctggaccgca 2580
acctggagaa gaacagcacc aagcaggaga tcctggccgc cctggagaag ggctgcagct 2640
tcctgcccga cccctaccag aagcagtgcg accagttcgt ggccgagtac gagcccgtgc 2700
tgatcgagat cctggtggag gtgatggacc ccagcttcgt gtgcctgaag atcggcgcct 2760
gccccagcgc ccacaagccc ctgctgggca ccgagaagtg catctggggc cccagctact 2820
ggtgccagaa caccgagacc gccgcccagt gcaacgccgt ggagcactgc aagcgccacg 2880
tgtggaactg acaattgtta attaagttta aaccctcgag gccgcaagct tatcgataat 2940
caacctctgg attacaaaat ttgtgaaaga ttgactggta ttcttaacta tgttgctcct 3000
tttacgctat gtggatacgc tgctttaatg cctttgtatc atgctattgc ttcccgtatg 3060
gctttcattt tctcctcctt gtataaatcc tggttgctgt ctctttatga ggagttgtgg 3120
cccgttgtca ggcaacgtgg cgtggtgtgc actgtgtttg ctgacgcaac ccccactggt 3180
tggggcattg ccaccacctg tcagctcctt tccgggactt tcgctttccc cctccctatt 3240
gccacggcgg aactcatcgc cgcctgcctt gcccgctgct ggacaggggc tcggctgttg 3300
ggcactgaca attccgtggt gttgtcgggg aaatcatcgt cctttccttg gctgctcgcc 3360
tgtgttgcca cctggattct gcgcgggacg tccttctgct acgtcccttc ggccctcaat 3420
ccagcggacc ttccttcccg cggcctgctg ccggctctgc ggcctcttcc gcgtcttcgc 3480
cttcgccctc agacgagtcg gatctccctt tgggccgcct ccccgcatcg ataccgtcga 3540
ctagagctcg ctgatcagcc tcgactgtgc cttctagttg ccagccatct gttgtttgcc 3600
cctcccccgt gccttccttg accctggaag gtgccactcc cactgtcctt tcctaataaa 3660
atgaggaaat tgcatcgcat tgtctgagta ggtgtcattc tattctgggg ggtggggtgg 3720
ggcaggacag caagggggag gattgggaag acaatagcag gcatgctggg gagagatcca 3780
cgataacaaa cagctttttt ggggcccaca tgtacactga attccctgca ggttggccac 3840
tccctctctg cgcgctcgct cgctcactga ggccgcccgg gcaaagcccg ggcgtcgggc 3900
gacctttggt cgcccggcct cagtgagcga gcgagcgcgc agagagggag tggccaactc 3960
catcactagg ggttcct 3977

<210> SEQ ID NO 37
<211> LENGTH: 4013
<212> TYPE: DNA
<213> ORGANISM: Artificial Sequence
<220> FEATURE:
<223> OTHER INFORMATION: Synthetic polynucleotide

<400> SEQUENCE: 37
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240

-continued

```
tccctaggtt ctagaaccgg tgacgtctcc catggtgaag cttggatctg aattcggtac    300
ctagttatta atagtaatca attacggggt cattagttca tagcccatat atggagttcc    360
gcgttacata acttacggta aatggcccgc ctggctgacc gcccaacgac ccccgcccat    420
tgacgtcaat aatgacgtat gttcccatag taacgccaat agggactttc cattgacgtc    480
aatgggtgga gtatttacgg taaactgccc acttggcagt acatcaagtg tatcatatgc    540
caagtacgcc ccctattgac gtcaatgacg gtaaatggcc cgcctggcat tatgcccagt    600
acatgacctt atgggacttt cctacttggc agtacatcta cgtattagtc atcgctatta    660
ccatggtcga ggtgagcccc acgttctgct tcactctccc catctccccc ccctccccac    720
ccccaatttt gtatttattt atttttttaat tattttgtgc agcgatgggg gcgggggggg    780
gggggggcg cgcgccaggc ggggcggggc ggggcgaggg gcggggcggg gcgaggcgga    840
gaggtgcggc ggcagccaat cagagcggcg cgctccgaaa gtttcctttt atggcgaggc    900
ggcggcggcg gcggccctat aaaaagcgaa gcgcgcggcg ggcgggagtc gctgcgcgct    960
gccttcgccc cgtgccccgc tccgccgccg cctcgcgccg cccgccccgg ctctgactga   1020
ccgcgttact cccacaggtg agcgggcggg acggcccttc tcctccgggc tgtaattagc   1080
gcttggttta atgacggctt gtttcttttc tgtggctgcg tgaaagcctt gaggggctcc   1140
gggagctaga gcctctgcta accatgttca tgccttcttc tttttcctac agctcctggg   1200
caacgtgctg gttattgtgc tgtctcatca ttttggcaaa gaattcctcg aagatccgaa   1260
gggaaagtct tccacgactg tgggatccgt tcgaagatat caccggttga gccaccatgg   1320
aattcagcag ccccagcaga gaggaatgcc ccaagcctct gagccgggtg tcaatcatgg   1380
ccggatctct gacaggactg ctgctgcttc aggccgtgtc ttgggcttct ggcgctagac   1440
cttgcatccc caagagcttc ggctacagca gcgtcgtgtg cgtgtgcaat gccacctact   1500
gcgacagctt cgaccctcct acctttcctg ctctgggcac cttcagcaga tacgagagca   1560
ccagatccgg cagacggatg gaactgagca tgggacccat ccaggccaat cacacaggca   1620
ctggcctgct gctgacactg cagcctgagc agaaattcca gaaagtgaaa ggcttcggcg   1680
gagccatgac agatgccgcc gctctgaata tcctggctct gtctccacca gctcagaacc   1740
tgctgctcaa gagctacttc agcgaggaag gcatcggcta caacatcatc agagtgccca   1800
tggccagctg cgacttcagc atcaggacct acacctacgc cgacacaccc gacgatttcc   1860
agctgcacaa cttcagcctg cctgaagagg acaccaagct gaagatccct ctgatccaca   1920
gagccctgca gctggcacaa agacccgtgt cactgctggc ctctccatgg acatctccca   1980
cctggctgaa aacaaatggc gccgtgaatg gcaagggcag cctgaaaggc caacctggcg   2040
acatctacca ccagacctgg gccagatact tcgtgaagtt cctggacgcc tatgccgagc   2100
acaagctgca gttttgggcc gtgacagccg agaacgaacc ttctgctgga ctgctgagcg   2160
gctacccctt tcagtgcctg ggctttacac ccgagcacca gcgggacttt atcgcccgtg   2220
atctgggacc cacactggcc aatagcaccc accataatgt gcggctgctg atgctggacg   2280
accagagact gcttctgccc cactgggcta aagtggtgct gacagatcct gaggccgcca   2340
aatacgtgca cggaatcgcc gtgcactggt atctggactt tctggcccct gccaaggcca   2400
cactgggaga gacacacaga ctgttcccca acaccatgct gttcgccagc gaagcctgtg   2460
tgggcagcaa gttttgggaa cagagcgtgc ggctcggcag ctgggataga ggcatgcagt   2520
acagccacag catcatcacc aacctgctgt accacgtcgt cggctggacc gactggaatc   2580
```

tggccctgaa tcctgaaggc ggccctaact gggtccgaaa cttcgtggac agccccatca 2640
tcgtggacat caccaaggac accttctaca agcagcccat gttctaccac ctgggacact 2700
tcagcaagtt catccccgag ggctctcagc gcgttggact ggtggcttcc cagaagaacg 2760
atctggacgc cgtggctctg atgcaccctg atggatctgc tgtggtggtg gtcctgaacc 2820
gcagcagcaa agatgtgccc ctgaccatca aggatcccgc cgtgggattc ctggaaacaa 2880
tcagccctgg ctactccatc cacacctacc tgtggcgtag acagtgacaa ttgttaatta 2940
agtttaaacc ctcgaggccg caagcttatc gataatcaac ctctggatta caaaatttgt 3000
gaaagattga ctggtattct taactatgtt gctcctttta cgctatgtgg atacgctgct 3060
ttaatgcctt tgtatcatgc tattgcttcc cgtatggctt tcattttctc ctccttgtat 3120
aaatcctggt tgctgtctct ttatgaggag ttgtggcccg ttgtcaggca acgtggcgtg 3180
gtgtgcactg tgtttgctga cgcaaccccc actggttggg gcattgccac cacctgtcag 3240
ctcctttccg ggactttcgc tttccccctc cctattgcca cggcggaact catcgccgcc 3300
tgccttgccc gctgctggac aggggctcgg ctgttgggca ctgacaattc cgtggtgttg 3360
tcggggaaat catcgtcctt tccttggctg ctcgcctgtg ttgccacctg gattctgcgc 3420
gggacgtcct tctgctacgt cccttcggcc ctcaatccag cggaccttcc ttcccgcggc 3480
ctgctgccgg ctctgcggcc tcttccgcgt cttcgccttc gccctcagac gagtcggatc 3540
tccctttggg ccgcctcccc gcatcgatac cgtcgactag agctcgctga tcagcctcga 3600
ctgtgccttc tagttgccag ccatctgttg tttgcccctc ccccgtgcct tccttgaccc 3660
tggaaggtgc cactcccact gtcctttcct aataaaatga ggaaattgca tcgcattgtc 3720
tgagtaggtg tcattctatt ctggggggtg gggtggggca ggacagcaag ggggaggatt 3780
gggaagacaa tagcaggcat gctggggaga gatccacgat aacaaacagc tttttggggg 3840
tgaacatatt gactgaattc cctgcaggtt ggccactccc tctctgcgcg ctcgctcgct 3900
cactgaggcc gcccgggcaa agcccgggcg tcgggcgacc tttggtcgcc cggcctcagt 3960
gagcgagcga gcgcgcagag agggagtggc caactccatc actaggggtt cct 4013

<210> SEQ ID NO 38
<211> LENGTH: 4606
<212> TYPE: DNA
<213> ORGANISM: Artificial Sequence
<220> FEATURE:
<223> OTHER INFORMATION: Synthetic polynucleotide

<400> SEQUENCE: 38
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg agggcggagt 300
tagggcggag ccaatcagcg tgcgccgttc cgaaagttgc cttttatggc tgggcggaga 360
atgggcggtg aacgccgatg attatataag gacgcgccgg gtgtggcaca gctagttccg 420
tcgcagccgg gatttgggtc gcggttcttg tttgtggatc cctgtgatcg tcacttggta 480
agtcactgac tgtctatgcc tgggaaaggg tgggcaggag atggggcagt gcaggaaaag 540
tggcactatg aaccctcctg gtggcgaggg gagggggtg gtcctcgaac gccttgcaga 600
actggcctgg atacagagtg gaccggctgg ccccatctgg aagacttcga gatacactgt 660
tgtcttactg cgctcaacag tgtatctcga agtcttccaa atggtgccag ccatcgcagc 720
ggggtgcagg aaatgggggc agcccccctt tttggctatc cttccacgtg ttcttttttg 780
tatcttttgt gtttcctaga aaacatctca gtcaccaccg cagccctagg aatgcatcta 840
gacaattgta ctaaccttct tctctttcct ctcctgacag tccggaaagc caccatgtac 900
gccctgttcc tgctggccag cctgctgggc gccgccctgg ccggccccgt gctgggcctg 960
aaggagtgca cccgcggcag cgccgtgtgg tgccagaacg tgaagaccgc cagcgactgc 1020
ggcgccgtga agcactgcct gcagaccgtg tggaacaagc ccaccgtgaa gagcctgccc 1080
tgcgacatct gcaaggacgt ggtgaccgcc gccggcgaca tgctgaagga caacgccacc 1140
gaggaggaga tcctggtgta cctggagaag acctgcgact ggctgcccaa gcccaacatg 1200
agcgccagct gcaaggagat cgtggacagc tacctgcccg tgatcctgga catcatcaag 1260
ggcgagatga gccgccccgg cgaggtgtgc agcgccctga acctgtgcga gagcctgcag 1320
aagcacctgg ccgagctgaa ccaccagaag cagctggaga gcaacaagat ccccgagctg 1380
gacatgaccg aggtggtggc cccccttcatg gccaacatcc ccctgctgct gtaccccccag 1440
gacggccccc gcagcaagcc ccagcccaag gacaacggcg acgtgtgcca ggactgcatc 1500
cagatggtga ccgacatcca gaccgccgtg cgcaccaaca gcaccttcgt gcaggccctg 1560
gtggagcacg tgaaggagga gtgcgaccgc ctgggccccg gcatggccga catctgcaag 1620
aactacatca gccagtacag cgagatcgcc atccagatga tgatgcacat gcagcccaag 1680
gagatctgcg ccctggtggg cttctgcgac gaggtgaagg agatgcccat gcagaccctg 1740
gtgcccgcca aggtggccag caagaacgtg atccccgccc tggagctggt ggagcccatc 1800
aagaagcacg aggtgcccgc caagagcgac gtgtactgcg aggtgtgcga gttcctggtg 1860
aaggaggtga ccaagctgat cgacaacaac aagaccgaga aggagatcct ggacgccttc 1920
gacaagatgt gcagcaagct gcccaagagc ctgagcgagg agtgccagga ggtggtggac 1980
acctacggca gcagcatcct gagcatcctg ctggaggagg tgagccccga gctggtgtgc 2040
agcatgctgc acctgtgcag cggcacccgc ctgcccgccc tgaccgtgca cgtgacccag 2100
cccaaggacg gcggcttctg cgaggtgtgc aagaagctgg tgggctacct ggaccgcaac 2160
ctggagaaga acagcaccaa gcaggagatc ctggccgccc tggagaaggg ctgcagcttc 2220
ctgcccgacc cctaccagaa gcagtgcgac cagttcgtgg ccgagtacga gcccgtgctg 2280
atcgagatcc tggtggaggt gatggacccc agcttcgtgt gcctgaagat cggcgcctgc 2340
cccagcgccc acaagcccct gctgggcacc gagaagtgca tctggggccc cagctactgg 2400
tgccagaaca ccgagaccgc cgcccagtgc aacgccgtgg agcactgcaa gcgccacgtg 2460
tggaacagaa gaaagagagg aagtggagag ggcagaggaa gtcttctgac atgcggagac 2520
gtggaagaga atcccggccc tatggaattc agcagcccca gcagagagga atgccccaag 2580
cctctgagcc gggtgtcaat catggccgga tctctgacag gactgctgct gcttcaggcc 2640
gtgtcttggg cttctggcgc tagaccttgc atccccaaga gcttcggcta cagcagcgtc 2700
gtgtgcgtgt gcaatgccac ctactgcgac agcttcgacc ctcctacctt tcctgctctg 2760
ggcaccttca gcagatacga gagcaccaga tccggcagac ggatggaact gagcatggga 2820
cccatccagg ccaatcacac aggcactggc ctgctgctga cactgcagcc tgagcagaaa 2880
ttccagaaag tgaaaggctt cggcggagcc atgacagatg ccgccgctct gaatatcctg 2940
gctctgtctc caccagctca gaacctgctg ctcaagagct acttcagcga ggaaggcatc 3000

-continued ggctacaaca tcatcagagt gcccatggcc agctgcgact tcagcatcag gacctacacc 3060
tacgccgaca cacccgacga tttccagctg cacaacttca gcctgcctga agaggacacc 3120
aagctgaaga tccctctgat ccacagagcc ctgcagctgg cacaaagacc cgtgtcactg 3180
ctggcctctc catggacatc tcccacctgg ctgaaaacaa atggcgccgt gaatggcaag 3240
ggcagcctga aaggccaacc tggcgacatc taccaccaga cctgggccag atacttcgtg 3300
aagttcctgg acgcctatgc cgagcacaag ctgcagtttt gggccgtgac agccgagaac 3360
gaaccttctg ctggactgct gagcggctac ccctttcagt gcctgggctt tacacccgag 3420
caccagcggg actttatcgc ccgtgatctg ggacccacac tggccaatag cacccaccat 3480
aatgtgcggc tgctgatgct ggacgaccag agactgcttc tgccccactg ggctaaagtg 3540
gtgctgacag atcctgaggc cgccaaatac gtgcacggaa tcgccgtgca ctggtatctg 3600
gactttctgg cccctgccaa ggccacactg ggagagacac acagactgtt ccccaacacc 3660
atgctgttcg ccagcgaagc ctgtgtgggc agcaagtttt gggaacagag cgtgcggctc 3720
ggcagctggg atagaggcat gcagtacagc cacagcatca tcaccaacct gctgtaccac 3780
gtcgtcggct ggaccgactg gaatctggcc ctgaatcctg aaggcggccc taactgggtc 3840
cgaaacttcg tggacagccc catcatcgtg gacatcacca aggacacctt ctacaagcag 3900
cccatgttct accacctggg acacttcagc aagttcatcc ccgagggctc tcagcgcgtt 3960
ggactggtgg cttcccagaa gaacgatctg gacgccgtgg ctctgatgca ccctgatgga 4020
tctgctgtgg tggtggtcct gaaccgcagc agcaaagatg tgcccctgac catcaaggat 4080
cccgccgtgg gattcctgga aacaatcagc cctggctact ccatccacac ctacctgtgg 4140
cgtagacagt gacaattgtt aattaagttt aaaccctcga ggccgcaagc cgcatcgata 4200
ccgtcgacta gagctcgctg atcagcctcg actgtgcctt ctagttgcca gccatctgtt 4260
gtttgcccct cccccgtgcc ttccttgacc ctggaaggtg ccactcccac tgtcctttcc 4320
taataaaatg aggaaattgc atcgcattgt ctgagtaggt gtcattctat tctggggggt 4380
ggggtggggc aggacagcaa gggggaggat tgggaagaca atagcaggca tgctggggat 4440
gtacactgaa ttccctgcag gttggccact ccctctctgc gcgctcgctc gctcactgag 4500
gccgcccggg caaagcccgg gcgtcgggcg acctttggtc gcccggcctc agtgagcgag 4560
cgagcgcgca gagagggagt ggccaactcc atcactaggg gttcct 4606

<210> SEQ ID NO 39
<211> LENGTH: 10699
<212> TYPE: DNA
<213> ORGANISM: Artificial Sequence
<220> FEATURE:
<223> OTHER INFORMATION: PR001A vector first strand sequence

<400> SEQUENCE: 39
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480

```
aatgggtgga gtatttacgg taaactgccc acttggcagt acatcaagtg tatcatatgc    540
caagtacgcc ccctattgac gtcaatgacg gtaaatggcc cgcctggcat tatgcccagt    600
acatgacctt atgggacttt cctacttggc agtacatcta cgtattagtc atcgctatta    660
ccatggtcga ggtgagcccc acgttctgct tcactctccc catctccccc ccctccccac    720
ccccaatttt gtatttattt atttttaat tattttgtgc agcgatgggg gcgggggggg    780
ggggggggcg cgcgccaggc ggggcggggc ggggcgaggg gcggggcggg gcgaggcgga    840
gaggtgcggc ggcagccaat cagagcggcg cgctccgaaa gtttcctttt atggcgaggc    900
ggcggcggcg gcggccctat aaaaagcgaa gcgcgcggcg ggcgggagtc gctgcgcgct    960
gccttcgccc cgtgccccgc tccgccgccg cctcgcgccg cccgccccgg ctctgactga   1020
ccgcgttact cccacaggtg agcgggcggg acggcccttc tcctccgggc tgtaattagc   1080
gcttggttta atgacggctt gtttcttttc tgtggctgcg tgaaagcctt gaggggctcc   1140
gggagctaga gcctctgcta accatgttca tgccttcttc tttttcctac agctcctggg   1200
caacgtgctg gttattgtgc tgtctcatca ttttggcaaa gaattcctcg aagatccgaa   1260
gggaaagtct tccacgactg tgggatccgt tcgaagatat caccggttga gccaccatgg   1320
aattcagcag ccccagcaga gaggaatgcc ccaagcctct gagccgggtg tcaatcatgg   1380
ccggatctct gacaggactg ctgctgcttc aggccgtgtc ttgggcttct ggcgctagac   1440
cttgcatccc caagagcttc ggctacagca gcgtcgtgtg cgtgtgcaat gccacctact   1500
gcgacagctt cgaccctcct acctttcctg ctctgggcac cttcagcaga tacgagagca   1560
ccagatccgg cagacggatg gaactgagca tgggacccat ccaggccaat cacacaggca   1620
ctggcctgct gctgacactg cagcctgagc agaaattcca gaaagtgaaa ggcttcggcg   1680
gagccatgac agatgccgcc gctctgaata tcctggctct gtctccacca gctcagaacc   1740
tgctgctcaa gagctacttc agcgaggaag gcatcggcta caacatcatc agagtgccca   1800
tggccagctg cgacttcagc atcaggacct acacctacgc cgacacaccc gacgatttcc   1860
agctgcacaa cttcagcctg cctgaagagg acaccaagct gaagatccct ctgatccaca   1920
gagccctgca gctggcacaa agacccgtgt cactgctggc ctctccatgg acatctccca   1980
cctggctgaa aacaaatggc gccgtgaatg gcaagggcag cctgaaaggc caacctggcg   2040
acatctacca ccagacctgg gccagatact tcgtgaagtt cctggacgcc tatgccgagc   2100
acaagctgca gttttgggcc gtgacagccg agaacgaacc ttctgctgga ctgctgagcg   2160
gctacccctt tcagtgcctg ggctttacac ccgagcacca gcgggacttt atcgcccgtg   2220
atctgggacc cacactggcc aatagcaccc accataatgt gcggctgctg atgctggacg   2280
accagagact gcttctgccc cactgggcta aagtggtgct gacagatcct gaggccgcca   2340
aatacgtgca cggaatcgcc gtgcactggt atctggactt tctggcccct gccaaggcca   2400
cactgggaga gacacacaga ctgttcccca acaccatgct gttcgccagc gaagcctgtg   2460
tgggcagcaa gttttgggaa cagagcgtgc ggctcggcag ctgggataga ggcatgcagt   2520
acagccacag catcatcacc aacctgctgt accacgtcgt cggctggacc gactggaatc   2580
tggccctgaa tcctgaaggc ggccctaact gggtccgaaa cttcgtggac agccccatca   2640
tcgtggacat caccaaggac accttctaca agcagcccat gttctaccac ctgggacact   2700
tcagcaagtt catccccgag ggctctcagc gcgttggact ggtggcttcc cagaagaacg   2760
atctggacgc cgtggctctg atgcaccctg atggatctgc tgtggtggtg gtcctgaacc   2820
```

-continued

```
gcagcagcaa agatgtgccc ctgaccatca aggatcccgc cgtgggattc ctggaaacaa   2880
tcagccctgg ctactccatc cacacctacc tgtggcgtag acagtgacaa ttgttaatta   2940
agtttaaacc ctcgaggccg caagcttatc gataatcaac ctctggatta caaaatttgt   3000
gaaagattga ctggtattct taactatgtt gctcctttta cgctatgtgg atacgctgct   3060
ttaatgcctt tgtatcatgc tattgcttcc cgtatggctt tcattttctc ctccttgtat   3120
aaatcctggt tgctgtctct ttatgaggag ttgtggcccg ttgtcaggca acgtggcgtg   3180
gtgtgcactg tgtttgctga cgcaaccccc actggttggg gcattgccac cacctgtcag   3240
ctcctttccg ggactttcgc tttccccctc cctattgcca cggcggaact catcgccgcc   3300
tgccttgccc gctgctggac aggggctcgg ctgttgggca ctgacaattc cgtggtgttg   3360
tcggggaaat catcgtcctt tccttggctg ctcgcctgtg ttgccacctg gattctgcgc   3420
gggacgtcct tctgctacgt cccttcggcc ctcaatccag cggaccttcc ttcccgcggc   3480
ctgctgccgg ctctgcggcc tcttccgcgt cttcgccttc gccctcagac gagtcggatc   3540
tccctttggg ccgcctcccc gcatcgatac cgtcgactag agctcgctga tcagcctcga   3600
ctgtgccttc tagttgccag ccatctgttg tttgcccctc ccccgtgcct tccttgaccc   3660
tggaaggtgc cactcccact gtcctttcct aataaaatga ggaaattgca tcgcattgtc   3720
tgagtaggtg tcattctatt ctggggggtg gggtggggca ggacagcaag ggggaggatt   3780
gggaagacaa tagcaggcat gctggggaga gatccacgat aacaaacagc tttttttgggg   3840
tgaacatatt gactgaattc cctgcaggtt ggccactccc tctctgcgcg ctcgctcgct   3900
cactgaggcc gcccgggcaa agcccgggcg tcgggcgacc tttggtcgcc cggcctcagt   3960
gagcgagcga gcgcgcagag agggagtggc caactccatc actaggggtt cctgcggccg   4020
ctcgtacggt ctcgaggaat tcctgcagga taacttgcca acctcattct aaaatgtata   4080
tagaagccca aaagacaata acaaaaatat tcttgtagaa caaaatggga aagaatgttc   4140
cactaaatat caagatttag agcaaagcat gagatgtgtg gggatagaca gtgaggctga   4200
taaaatagag tagagctcag aaacagaccc attgatatat gtaagtgacc tatgaaaaaa   4260
atatggcatt ttacaatggg aaaatgatgg tctttttctt ttttagaaaa acagggaaat   4320
atatttatat gtaaaaaata aaagggaacc catatgtcat accatacaca caaaaaaatt   4380
ccagtgaatt ataagtctaa atggagaagg caaaacttta aatcttttag aaaataaatat   4440
agaagcatgc agaccagcct ggccaacatg atgaaaccct ctctactaat aataaaatca   4500
gtagaactac tcaggactac tttgagtggg aagtcctttt ctatgaagac ttctttggcc   4560
aaaattaggc tctaaatgca aggagatagt gcatcatgcc tggctgcact tactgataaa   4620
tgatgttatc accatcttta accaaatgca caggaacaag ttatggtact gatgtgctgg   4680
attgagaagg agctctactt ccttgacagg acacatttgt atcaacttaa aaaagcagat   4740
ttttgccagc agaactattc attcagaggt aggaaactta gaatagatga tgtcactgat   4800
tagcatggct tccccatctc cacagctgct tcccacccag gttgcccaca gttgagtttg   4860
tccagtgctc agggctgccc actctcagta agaagcccca caccagcccc tctccaaata   4920
tgttggctgt tccttccatt aaagtgaccc cactttagag cagcaagtgg atttctgttt   4980
cttacagttc aggaaggagg agtcagctgt gagaacctgg agcctgagat gcttctaagt   5040
cccactgcta ctggggtcag ggaagccaga ctccagcatc agcagtcagg agcactaagc   5100
ccttgccaac atcctgtttc tcagagaaac tgcttccatt ataatggttg tccttttttta   5160
agctatcaag ccaaacaacc agtgtctacc attattctca tcacctgaag ccaagggttc   5220
```

-continued

```
tagcaaaagt caagctgtct tgtaatggtt gatgtgcctc cagcttctgt cttcagtcac   5280
tccactctta gcctgctctg aatcaactct gaccacagtt ccctggagcc cctgccacct   5340
gctgcccctg ccaccttctc catctgcagt gctgtgcagc cttctgcact cttgcagagc   5400
taataggtgg agacttgaag gaagaggagg aaagtttctc ataatagcct tgctgcaagc   5460
tcaaatggga ggtgggcact gtgcccagga gccttggagc aaaggctgtg cccaacctct   5520
gactgcatcc aggtttggtc ttgacagaga taagaagccc tggcttttgg agccaaaatc   5580
taggtcagac ttaggcagga ttctcaaagt ttatcagcag aacatgaggc agaagaccct   5640
ttctgctcca gcttcttcag gctcaacctt catcagaata gatagaaaga gaggctgtga   5700
gggttcttaa aacagaagca aatctgactc agagaataaa caacctccta gtaaactaca   5760
gcttagacag agcatctggt ggtgagtgtg ctcagtgtcc tactcaactg tctggtatca   5820
gccctcatga ggacttctct tctttccctc atagacctcc atctctgttt tccttagcct   5880
gcagaaatct ggatggctat tcacagaatg cctgtgcttt cagagttgca tttttttctct   5940
ggtattctgg ttcaagcatt tgaaggtagg aaaggttctc caagtgcaag aaagccagcc   6000
ctgagcctca actgcctggc tagtgtggtc agtaggatgc aaaggctgtt gaatgccaca   6060
aggccaaact ttaacctgtg taccacaagc ctagcagcag aggcagctct gctcactgga   6120
actctctgtc ttctttctcc tgagcctttt cttttcctga gttttctagc tctcctcaac   6180
cttacctctg ccctacccag gacaaaccca agagccactg tttctgtgat gtcctctcca   6240
gccctaatta ggcatcatga cttcagcctg accttccatg ctcagaagca gtgctaatcc   6300
acttcagatg agctgctcta tgcaacacag gcagagccta caaacctttg caccagagcc   6360
ctccacatat cagtgtttgt tcatactcac ttcaacagca aatgtgactg ctgagattaa   6420
gattttacac aagatggtct gtaatttcac agttagtttt atcccattag gtatgaaaga   6480
attagcataa ttccccttaa acatgaatga atcttagatt ttttaataaa tagttttgga   6540
agtaaagaca gagacatcag gagcacaagg aatagcctga gaggacaaac agaacaagaa   6600
agagtctgga aatacacagg atgttcttgg cctcctcaaa gcaagtgcaa gcagatagta   6660
ccagcagccc caggctatca gagcccagtg aagagaagta ccatgaaagc cacagctcta   6720
accaccctgt tccagagtga cagacagtcc ccaagacaag ccagcctgag ccagagagag   6780
aactgcaaga gaaagtttct aatttaggtt ctgttagatt cagacaagtg caggtcatcc   6840
tctctccaca gctactcacc tctccagcct aacaaagcct gcagtccaca ctccaaccct   6900
ggtgtctcac ctcctagcct ctcccaacat cctgctctct gaccatcttc tgcatctctc   6960
atctcaccat ctcccactgt ctacagccta ctcttgcaac taccatctca ttttctgaca   7020
tcctgtctac atcttctgcc atactctgcc atctaccata ccacctctta ccatctacca   7080
caccatcttt tatctccatc cctctcagaa gcctccaagc tgaatcctgc tttatgtgtt   7140
catctcagcc cctgcatgga aagctgaccc cagaggcaga actattccca gagagcttgg   7200
ccaagaaaaa caaaactacc agcctggcca ggctcaggag tagtaagctg cagtgtctgt   7260
tgtgttctag cttcaacagc tgcaggagtt ccactctcaa atgctccaca tttctcacat   7320
cctcctgatt ctggtcacta cccatcttca aagaacagaa tatctcacat cagcatactg   7380
tgaaggacta gtcatgggtg cagctgctca gagctgcaaa gtcattctgg atggtggaga   7440
gcttacaaac atttcatgat gctccccccg ctctgatggc tggagcccaa tccctacaca   7500
gactcctgct gtatgtgttt tcctttcact ctgagccaca gccagagggc aggcattcag   7560
```

tctcctcttc aggctggggc tggggcactg agaactcacc caacaccttg ctctcactcc 7620
ttctgcaaaa caagaaagag ctttgtgctg cagtagccat gaagaatgaa aggaaggctt 7680
taactaaaaa atgtcagaga ttattttcaa ccccttactg tggatcacca gcaaggagga 7740
aacacaacac agagacattt tttcccctca aattatcaaa agaatcactg catttgttaa 7800
agagagcaac tgaatcagga agcagagttt tgaacatatc agaagttagg aatctgcatc 7860
agagacaaat gcagtcatgg ttgtttgctg cataccagcc ctaatcatta gaagcctcat 7920
ggacttcaaa catcattccc tctgacaaga tgctctagcc taactccatg agataaaata 7980
aatctgcctt tcagagccaa agaagagtcc accagcttct tctcagtgtg aacaagagct 8040
ccagtcaggt tagtcagtcc agtgcagtag aggagaccag tctgcatcct ctaattttca 8100
aaggcaagaa gatttgttta ccctggacac caggcacaag tgaggtcaca gagctcttag 8160
atatgcagtc ctcatgagtg aggagactaa agcgcatgcc atcaagactt cagtgtagag 8220
aaaacctcca aaaaagcctc ctcactactt ctggaatagc tcagaggccg aggcggcctc 8280
ggcctctgca taaataaaaa aaattagtca gccatggggc ggagaatggg cggaactggg 8340
cggagttagg ggcgggatgg gcggagttag gggcgggact atggttgctg actaattgag 8400
atgcatgctt tgcatacttc tgcctgctgg ggagcctggg gactttccac acctggttgc 8460
tgactaattg agatgcatgc tttgcatact tctgcctgct ggggagcctg gggactttcc 8520
acaccctaac tgacacacat tccacagctg cattaatgaa tcggccaacg cgcggggaga 8580
ggcggtttgc gtattgggcg ctcttccgct tcctcgctca ctgactcgct gcgctcggtc 8640
gttcggctgc ggcgagcggt atcagctcac tcaaaggcgg taatacggtt atccacagaa 8700
tcaggggata acgcaggaaa gaacatgtga gcaaaaggcc agcaaaaggc caggaaccgt 8760
aaaaaggccg cgttgctggc gtttttccat aggctccgcc cccctgacga gcatcacaaa 8820
aatcgacgct caagtcagag gtggcgaaac ccgacaggac tataaagata ccaggcgttt 8880
ccccctggaa gctccctcgt gcgctctcct gttccgaccc tgccgcttac cggatacctg 8940
tccgcctttc tcccttcggg aagcgtggcg ctttctcata gctcacgctg taggtatctc 9000
agttcggtgt aggtcgttcg ctccaagctg ggctgtgtgc acgaaccccc cgttcagccc 9060
gaccgctgcg ccttatccgg taactatcgt cttgagtcca acccggtaag acacgactta 9120
tcgccactgg cagcagccac tggtaacagg attagcagag cgaggtatgt aggcggtgct 9180
acagagttct tgaagtggtg gcctaactac ggctacacta gaagaacagt atttggtatc 9240
tgcgctctgc tgaagccagt taccttcgga aaaagagttg gtagctcttg atccggcaaa 9300
caaaccaccg ctggtagcgg tggttttttt gtttgcaagc agcagattac gcgcagaaaa 9360
aaaggatctc aagaagatcc tttgatcttt tctacggggt ctgacgctca gtggaacgaa 9420
aactcacgtt aagggatttt ggtcatgaga ttatcaaaaa ggatcttcac ctagatcctt 9480
ttaaattaaa aatgaagttt taaatcaatc taaagtatat atgagtaaac ttggtctgac 9540
agttaccaat gcttaatcag tgaggcacct atctcagcga tctgtctatt tcgttcatcc 9600
atagttgcct gactcctgca aaccacgttg tgtctcaaaa tctctgatgt tacattgcac 9660
aagataaaaa tatatcatca tgaacaataa aactgtctgc ttacataaac agtaatacaa 9720
ggggtgttat gagccatatt caacgggaaa cgtcttgctc gaggccgcga ttaaattcca 9780
acatggatgc tgatttatat gggtataaat gggctcgcga taatgtcggg caatcaggtg 9840
cgacaatcta tcgattgtat gggaagcccg atgcgccaga gttgtttctg aaacatggca 9900
aaggtagcgt tgccaatgat gttacagatg agatggtcag actaaactgg ctgacggaat 9960
ttatgcctct tccgaccatc aagcatttta tccgtactcc tgatgatgca tggttactca 10020
ccactgcgat ccccgggaaa acagcattcc aggtattaga agaatatcct gattcaggtg 10080
aaaatattgt tgatgcgctg gcagtgttcc tgcgccggtt gcattcgatt cctgtttgta 10140
attgtccttt taacagcgat cgcgtatttc gtctcgctca ggcgcaatca cgaatgaata 10200
acggtttggt tgatgcgagt gattttgatg acgagcgtaa tggctggcct gttgaacaag 10260
tctggaaaga aatgcataag cttttgccat tctcaccgga ttcagtcgtc actcatggtg 10320
atttctcact tgataacctt atttttgacg aggggaaatt aataggttgt attgatgttg 10380
gacgagtcgg aatcgcagac cgataccagg atcttgccat cctatggaac tgcctcggtg 10440
agttttctcc ttcattacag aaacggcttt ttcaaaaata tggtattgat aatcctgata 10500
tgaataaatt gcagtttcat ttgatgctcg atgagttttt ctaagggcgg cctgccacca 10560
tacccacgcc gaaacaagcg ctcatgagcc cgaagtggcg agcccgatct tccccatcgg 10620
tgatgtcggc gatataggcg ccagcaaccg cacctgtggc gccggtgatg agggcgcgcc 10680
aagtcgacgt ccggcagtc 10699

<210> SEQ ID NO 40
<211> LENGTH: 10699
<212> TYPE: DNA
<213> ORGANISM: Artificial Sequence
<220> FEATURE:
<223> OTHER INFORMATION: PR001A vector second strand sequence

<400> SEQUENCE: 40
gactgccgga cgtcgacttg gcgcgccctc atcaccggcg ccacaggtgc ggttgctggc 60
gcctatatcg ccgacatcac cgatggggaa gatcgggctc gccacttcgg gctcatgagc 120
gcttgtttcg gcgtgggtat ggtggcaggc cgcccttaga aaaactcatc gagcatcaaa 180
tgaaactgca atttattcat atcaggatta tcaataccat atttttgaaa aagccgtttc 240
tgtaatgaag gagaaaactc accgaggcag ttccatagga tggcaagatc ctggtatcgg 300
tctgcgattc cgactcgtcc aacatcaata caacctatta atttcccctc gtcaaaaata 360
aggttatcaa gtgagaaatc accatgagtg acgactgaat ccggtgagaa tggcaaaagc 420
ttatgcattt ctttccagac ttgttcaaca ggccagccat tacgctcgtc atcaaaatca 480
ctcgcatcaa ccaaaccgtt attcattcgt gattgcgcct gagcgagacg aaatacgcga 540
tcgctgttaa aaggacaatt acaaacagga atcgaatgca accggcgcag gaacactgcc 600
agcgcatcaa caatattttc acctgaatca ggatattctt ctaatacctg gaatgctgtt 660
ttcccgggga tcgcagtggt gagtaaccat gcatcatcag gagtacggat aaaatgcttg 720
atggtcggaa gaggcataaa ttccgtcagc cagtttagtc tgaccatctc atctgtaaca 780
tcattggcaa cgctaccttt gccatgtttc agaaacaact ctggcgcatc gggcttccca 840
tacaatcgat agattgtcgc acctgattgc ccgacattat cgcgagccca tttataccca 900
tataaatcag catccatgtt ggaatttaat cgcggcctcg agcaagacgt ttcccgttga 960
atatggctca taacacccct tgtattactg tttatgtaag cagacagttt tattgttcat 1020
gatgatatat ttttatcttg tgcaatgtaa catcagagat tttgagacac aacgtggttt 1080
gcaggagtca ggcaactatg gatgaacgaa atagacagat cgctgagata ggtgcctcac 1140
tgattaagca ttggtaactg tcagaccaag tttactcata tatactttag attgatttaa 1200
aacttcattt ttaatttaaa aggatctagg tgaagatcct ttttgataat ctcatgacca 1260

-continued

```
aaatccctta acgtgagttt tcgttccact gagcgtcaga ccccgtagaa aagatcaaag   1320
gatcttcttg agatcctttt tttctgcgcg taatctgctg cttgcaaaca aaaaaaccac   1380
cgctaccagc ggtggtttgt ttgccggatc aagagctacc aactcttttt ccgaaggtaa   1440
ctggcttcag cagagcgcag ataccaaata ctgttcttct agtgtagccg tagttaggcc   1500
accacttcaa gaactctgta gcaccgccta catacctcgc tctgctaatc ctgttaccag   1560
tggctgctgc cagtggcgat aagtcgtgtc ttaccgggtt ggactcaaga cgatagttac   1620
cggataaggc gcagcggtcg ggctgaacgg ggggttcgtg cacacagccc agcttggagc   1680
gaacgaccta caccgaactg agatacctac agcgtgagct atgagaaagc gccacgcttc   1740
ccgaagggag aaaggcggac aggtatccgg taagcggcag ggtcggaaca ggagagcgca   1800
cgagggagct tccaggggga aacgcctggt atctttatag tcctgtcggg tttcgccacc   1860
tctgacttga gcgtcgattt ttgtgatgct cgtcaggggg gcggagccta tggaaaaacg   1920
ccagcaacgc ggccttttta cggttcctgg ccttttgctg gccttttgct cacatgttct   1980
ttcctgcgtt atcccctgat tctgtggata accgtattac cgcctttgag tgagctgata   2040
ccgctcgccg cagccgaacg accgagcgca gcgagtcagt gagcgaggaa gcggaagagc   2100
gcccaatacg caaaccgcct ctccccgcgc gttggccgat tcattaatgc agctgtggaa   2160
tgtgtgtcag ttagggtgtg gaaagtcccc aggctcccca gcaggcagaa gtatgcaaag   2220
catgcatctc aattagtcag caaccaggtg tggaaagtcc ccaggctccc cagcaggcag   2280
aagtatgcaa agcatgcatc tcaattagtc agcaaccata gtcccgcccc taactccgcc   2340
catcccgccc ctaactccgc ccagttccgc ccattctccg ccccatggct gactaatttt   2400
ttttatttat gcagaggccg aggccgcctc ggcctctgag ctattccaga agtagtgagg   2460
aggctttttt ggaggttttc tctacactga agtcttgatg gcatgcgctt tagtctcctc   2520
actcatgagg actgcatatc taagagctct gtgacctcac ttgtgcctgg tgtccagggt   2580
aaacaaatct tcttgccttt gaaaattaga ggatgcagac tggtctcctc tactgcactg   2640
gactgactaa cctgactgga gctcttgttc acactgagaa gaagctggtg gactcttctt   2700
tggctctgaa aggcagattt attttatctc atggagttag gctagagcat cttgtcagag   2760
ggaatgatgt ttgaagtcca tgaggcttct aatgattagg gctggtatgc agcaaacaac   2820
catgactgca tttgtctctg atgcagattc ctaacttctg atatgttcaa aactctgctt   2880
cctgattcag ttgctctctt taacaaatgc agtgattctt ttgataattt gaggggaaaa   2940
aatgtctctg tgttgtgttt cctccttgct ggtgatccac agtaaggggt tgaaaataat   3000
ctctgacatt ttttagttaa agccttcctt tcattcttca tggctactgc agcacaaagc   3060
tctttcttgt tttgcagaag gagtgagagc aaggtgttgg gtgagttctc agtgccccag   3120
ccccagcctg aagaggagac tgaatgcctg ccctctggct gtggctcaga gtgaaaggaa   3180
aacacataca gcaggagtct gtgtagggat tgggctccag ccatcagagc gggggggagca   3240
tcatgaaatg tttgtaagct ctccaccatc cagaatgact ttgcagctct gagcagctgc   3300
acccatgact agtccttcac agtatgctga tgtgagatat tctgttcttt gaagatgggt   3360
agtgaccaga atcaggagga tgtgagaaat gtggagcatt tgagagtgga actcctgcag   3420
ctgttgaagc tagaacacaa cagacactgc agcttactac tcctgagcct ggccaggctg   3480
gtagttttgt ttttcttggc caagctctct gggaatagtt ctgcctctgg ggtcagcttt   3540
ccatgcaggg gctgagatga acacataaag caggattcag cttggaggct tctgagaggg   3600
atggagataa aagatggtgt ggtagatggt aagaggtggt atggtagatg gcagagtatg   3660
```

gcagaagatg tagacaggat gtcagaaaat gagatggtag ttgcaagagt aggctgtaga 3720
cagtgggaga tggtgagatg agagatgcag aagatggtca gagagcagga tgttgggaga 3780
ggctaggagg tgagacacca gggttggagt gtggactgca ggctttgtta ggctggagag 3840
gtgagtagct gtggagagag gatgacctgc acttgtctga atctaacaga acctaaatta 3900
gaaactttct cttgcagttc tctctctggc tcaggctggc ttgtcttggg gactgtctgt 3960
cactctggaa cagggtggtt agagctgtgg ctttcatggt acttctcttc actgggctct 4020
gatagcctgg ggctgctggt actatctgct tgcacttgct ttgaggaggc caagaacatc 4080
ctgtgtattt ccagactctt tcttgttctg tttgtcctct caggctattc cttgtgctcc 4140
tgatgtctct gtctttactt ccaaaactat ttattaaaaa atctaagatt cattcatgtt 4200
taaggggaat tatgctaatt ctttcatacc taatgggata aaactaactg tgaaattaca 4260
gaccatcttg tgtaaaatct taatctcagc agtcacattt gctgttgaag tgagtatgaa 4320
caaacactga tatgtggagg gctctggtgc aaaggtttgt aggctctgcc tgtgttgcat 4380
agagcagctc atctgaagtg gattagcact gcttctgagc atggaaggtc aggctgaagt 4440
catgatgcct aattagggct ggagaggaca tcacagaaac agtggctctt gggtttgtcc 4500
tgggtagggc agaggtaagg ttgaggagag ctagaaaact caggaaaaga aaaggctcag 4560
gagaaagaag acagagagtt ccagtgagca gagctgcctc tgctgctagg cttgtggtac 4620
acaggttaaa gtttggcctt gtggcattca acagcctttg catcctactg accacactag 4680
ccaggcagtt gaggctcagg gctggctttc ttgcacttgg agaacctttc ctaccttcaa 4740
atgcttgaac cagaatacca gagaaaaaat gcaactctga aagcacaggc attctgtgaa 4800
tagccatcca gatttctgca ggctaaggaa aacagagatg gaggtctatg agggaaagaa 4860
gagaagtcct catgagggct gataccagac agttgagtag gacactgagc acactcacca 4920
ccagatgctc tgtctaagct gtagtttact aggaggttgt ttattctctg agtcagattt 4980
gcttctgttt taagaaccct cacagcctct ctttctatct attctgatga aggttgagcc 5040
tgaagaagct ggagcagaaa gggtcttctg cctcatgttc tgctgataaa ctttgagaat 5100
cctgcctaag tctgacctag attttggctc caaaagccag ggcttcttat ctctgtcaag 5160
accaaacctg gatgcagtca gaggttgggc acagcctttg ctccaaggct cctgggcaca 5220
gtgcccacct cccatttgag cttgcagcaa ggctattatg agaaactttc ctcctcttcc 5280
ttcaagtctc cacctattag ctctgcaaga gtgcagaagg ctgcacagca ctgcagatgg 5340
agaaggtggc aggggcagca ggtggcaggg gctccaggga actgtggtca gagttgattc 5400
agagcaggct aagagtggag tgactgaaga cagaagctgg aggcacatca accattacaa 5460
gacagcttga cttttgctag aacccttggc ttcaggtgat gagaataatg gtagacactg 5520
gttgtttggc ttgatagctt aaaaaaggac aaccattata atggaagcag tttctctgag 5580
aaacaggatg ttggcaaggg cttagtgctc ctgactgctg atgctggagt ctggcttccc 5640
tgaccccagt agcagtggga cttagaagca tctcaggctc caggttctca cagctgactc 5700
ctccttcctg aactgtaaga aacagaaatc cacttgctgc tctaaagtgg ggtcacttta 5760
atggaaggaa cagccaacat atttggagag gggctggtgt ggggcttctt actgagagtg 5820
ggcagccctg agcactggac aaactcaact gtgggcaacc tgggtgggaa gcagctgtgg 5880
agatggggaa gccatgctaa tcagtgacat catctattct aagtttccta cctctgaatg 5940
aatagttctg ctggcaaaaa tctgcttttt taagttgata caaatgtgtc ctgtcaagga 6000

-continued agtagagctc cttctcaatc cagcacatca gtaccataac ttgttcctgt gcatttggtt 6060
aaagatggtg ataacatcat ttatcagtaa gtgcagccag gcatgatgca ctatctcctt 6120
gcatttagag cctaattttg gccaaagaag tcttcataga aaaggacttc ccactcaaag 6180
tagtcctgag tagttctact gattttatta ttagtagaga gggtttcatc atgttggcca 6240
ggctggtctg catgcttcta tattattttc taaaagattt aaagttttgc cttctccatt 6300
tagacttata attcactgga attttttgt gtgtatggta tgacatatgg gttccctttt 6360 atttttaca tataaatata tttccctgtt tttctaaaaa agaaaaagac catcattttc 6420
ccattgtaaa atgccatatt tttttcatag gtcacttaca tatatcaatg ggtctgtttc 6480
tgagctctac tctattttat cagcctcact gtctatcccc acacatctca tgctttgctc 6540
taaatcttga tatttagtgg aacattcttt cccattttgt tctacaagaa tatttttgtt 6600
attgtctttt gggcttctat atacatttta gaatgaggtt ggcaagttat cctgcaggaa 6660
ttcctcgaga ccgtacgagc ggccgcagga acccctagtg atggagttgg ccactccctc 6720
tctgcgcgct cgctcgctca ctgaggccgg gcgaccaaag gtcgcccgac gcccgggctt 6780
tgcccgggcg gcctcagtga gcgagcgagc gcgcagagag ggagtggcca acctgcaggg 6840
aattcagtca atatgttcac cccaaaaaag ctgtttgtta tcgtggatct ctccccagca 6900
tgcctgctat tgtcttccca atcctccccc ttgctgtcct gccccacccc accccccaga 6960
atagaatgac acctactcag acaatgcgat gcaatttcct cattttatta ggaaaggaca 7020
gtgggagtgg caccttccag ggtcaaggaa ggcacggggg aggggcaaac aacagatggc 7080
tggcaactag aaggcacagt cgaggctgat cagcgagctc tagtcgacgg tatcgatgcg 7140
gggaggcggc ccaaagggag atccgactcg tctgagggcg aaggcgaaga cgcggaagag 7200
gccgcagagc cggcagcagg ccgcgggaag gaaggtccgc tggattgagg gccgaaggga 7260
cgtagcagaa ggacgtcccg cgcagaatcc aggtggcaac acaggcgagc agccaaggaa 7320
aggacgatga tttccccgac aacaccacgg aattgtcagt gcccaacagc cgagcccctg 7380
tccagcagcg ggcaaggcag gcggcgatga gttccgccgt ggcaataggg agggggaaag 7440
cgaaagtccc ggaaaggagc tgacaggtgg tggcaatgcc ccaaccagtg ggggttgcgt 7500
cagcaaacac agtgcacacc acgccacgtt gcctgacaac gggccacaac tcctcataaa 7560
gagacagcaa ccaggattta tacaaggagg agaaaatgaa agccatacgg gaagcaatag 7620
catgatacaa aggcattaaa gcagcgtatc cacatagcgt aaaaggagca acatagttaa 7680
gaataccagt caatctttca caaattttgt aatccagagg ttgattatcg ataagcttgc 7740
ggcctcgagg gtttaaactt aattaacaat tgtcactgtc tacgccacag gtaggtgtgg 7800
atggagtagc cagggctgat tgtttccagg aatcccacgg cgggatcctt gatggtcagg 7860
ggcacatctt tgctgctgcg gttcaggacc accaccacag cagatccatc agggtgcatc 7920
agagccacgg cgtccagatc gttcttctgg gaagccacca gtccaacgcg ctgagagccc 7980
tcggggatga acttgctgaa gtgtcccagg tggtagaaca tgggctgctt gtagaaggtg 8040
tccttggtga tgtccacgat gatggggctg tccacgaagt ttcggaccca gttagggccg 8100
ccttcaggat tcagggccag attccagtcg gtccagccga cgacgtggta cagcaggttg 8160
gtgatgatgc tgtggctgta ctgcatgcct ctatcccagc tgccgagccg cacgctctgt 8220
tcccaaaact tgctgcccac acaggcttcg ctggcgaaca gcatggtgtt ggggaacagt 8280
ctgtgtgtct ctcccagtgt ggccttggca ggggccagaa agtccagata ccagtgcacg 8340
gcgattccgt gcacgtattt ggcggcctca ggatctgtca gcaccacttt agcccagtgg 8400

-continued

```
ggcagaagca gtctctggtc gtccagcatc agcagccgca cattatggtg ggtgctattg   8460
gccagtgtgg gtcccagatc acgggcgata aagtcccgct ggtgctcggg tgtaaagccc   8520
aggcactgaa aggggtagcc gctcagcagt ccagcagaag gttcgttctc ggctgtcacg   8580
gcccaaaact gcagcttgtg ctcggcatag gcgtccagga acttcacgaa gtatctggcc   8640
caggtctggt ggtagatgtc gccaggttgg cctttcaggc tgcccttgcc attcacggcg   8700
ccatttgttt tcagccaggt gggagatgtc catggagagg ccagcagtga cacgggtctt   8760
tgtgccagct gcagggctct gtggatcaga gggatcttca gcttggtgtc ctcttcaggc   8820
aggctgaagt tgtgcagctg gaaatcgtcg ggtgtgtcgg cgtaggtgta ggtcctgatg   8880
ctgaagtcgc agctggccat gggcactctg atgatgttgt agccgatgcc ttcctcgctg   8940
aagtagctct tgagcagcag gttctgagct ggtggagaca gagccaggat attcagagcg   9000
gcggcatctg tcatggctcc gccgaagcct ttcactttct ggaatttctg ctcaggctgc   9060
agtgtcagca gcaggccagt gcctgtgtga ttggcctgga tgggtcccat gctcagttcc   9120
atccgtctgc cggatctggt gctctcgtat ctgctgaagg tgcccagagc aggaaaggta   9180
ggagggtcga agctgtcgca gtaggtggca ttgcacacgc acacgacgct gctgtagccg   9240
aagctcttgg ggatgcaagg tctagcgcca gaagcccaag acacggcctg aagcagcagc   9300
agtcctgtca gagatccggc catgattgac acccggctca gaggcttggg gcattcctct   9360
ctgctggggc tgctgaattc catggtggct caaccggtga tatcttcgaa cggatcccac   9420
agtcgtggaa gactttccct tcggatcttc gaggaattct ttgccaaaat gatgagacag   9480
cacaataacc agcacgttgc ccaggagctg taggaaaaag aagaaggcat gaacatggtt   9540
agcagaggct ctagctcccg gagcccctca aggctttcac gcagccacag aaaagaaaca   9600
agccgtcatt aaaccaagcg ctaattacag cccggaggag aagggccgtc ccgcccgctc   9660
acctgtggga gtaacgcggt cagtcagagc cggggcgggc ggcgcgaggc ggcggcggag   9720
cggggcacgg ggcgaaggca gcgcgcagcg actcccgccc gccgcgcgct tcgcttttta   9780
tagggccgcc gccgccgccg cctcgccata aaaggaaact ttcggagcgc gccgctctga   9840
ttggctgccg ccgcacctct ccgcctcgcc ccgccccgcc cctcgccccg ccccgccccg   9900
cctggcgcgc gccccccccc cccccccgcc cccatcgctg cacaaaataa ttaaaaaata   9960
aataaataca aaattggggg tggggagggg ggggagatgg ggagagtgaa gcagaacgtg  10020
gggctcacct cgaccatggt aatagcgatg actaatacgt agatgtactg ccaagtagga  10080
aagtcccata aggtcatgta ctgggcataa tgccaggcgg gccatttacc gtcattgacg  10140
tcaatagggg gcgtacttgg catatgatac acttgatgta ctgccaagtg ggcagtttac  10200
cgtaaatact ccacccattg acgtcaatgg aaagtcccta ttggcgttac tatgggaaca  10260
tacgtcatta ttgacgtcaa tgggcggggg tcgttgggcg gtcagccagg cgggccattt  10320
accgtaagtt atgtaacgcg gaactccata tatgggctat gaactaatga ccccgtaatt  10380
gattactatt aataactagg taccgaattc agatccaagc ttcaccatgg gagacgtcac  10440
cggttctaga acctagggag ctctggtacc cactagtagt cgacgaacgc gtaacctccc  10500
gcttcaaaat ggagaccctg cgtgctcact cgggcttaaa tacccagagc tagcaggaac  10560
ccctagtgat ggagttggcc actccctctc tgcgcgctcg ctcgctcact gaggccgggc  10620
gaccaaaggt cgcccgacgc ccgggctttg cccgggcggc ctcagtgagc gagcgagcgc  10680
gcagagaggg agtggccaa                                               10699
```

<210> SEQ ID NO 41
<211> LENGTH: 10960
<212> TYPE: DNA
<213> ORGANISM: Artificial Sequence
<220> FEATURE:
<223> OTHER INFORMATION: PR004B vector first strand sequence

<400> SEQUENCE: 41

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg aattcggtac    300

cctagttatt aatagtaatc aattacgggg tcattagttc atagcccata tatggagttc    360

cgcgttacat aacttacggt aaatggcccg cctggctgac cgcccaacga cccccgccca    420

ttgacgtcaa taatgacgta tgttcccata gtaacgccaa tagggacttt ccattgacgt    480

caatgggtgg actatttacg gtaaactgcc cacttggcag tacatcaagt gtatcatatg    540

ccaagtacgc cccctattga cgtcaatgac ggtaaatggc ccgcctggca ttatgcccag    600

tacatgacct tatgggactt tcctacttgg cagtacatct acgtattagt catcgctatt    660

accatggtcg aggtgagccc cacgttctgc ttcactctcc ccatctcccc cccctcccca    720

cccccaattt tgtatttatt tattttttaa ttattttgtg cagcgatggg ggcggggggg    780

gggggggggc gcgcgccagg cggggcgggg cggggcgagg ggcggggcgg ggcgaggcgg    840

agaggtgcgg cggcagccaa tcagagcggc gcgctccgaa agtttccttt tatggcgagg    900

cggcggcggc ggcggcccta taaaaagcga agcgcgcggc gggcgggagt cgctgcgacg    960

ctgccttcgc cccgtgcccc gctccgccgc cgcctcgcgc cgcccgcccc ggctctgact   1020

gaccgcgtta ctcccacagg tgagcgggcg ggacggccct tctcctccgg gctgtaatta   1080

gcgcttggtt taatgacggc ttgtcctggt ggcgagggga gggggggtggt cctcgaacgc   1140

cttgcagaac tggcctggat acagagtgga ccggctggcc ccatctggaa gacttcgaga   1200

tacactgttg tcttactgcg ctcaacagtg tatctcgaag tcttccaaat ggtgccagcc   1260

atcgcagcgg ggtgcaggaa atgggggcag ccccccttt tggctatcct tccacgtgtt   1320

ctttttgta tcttttgtgt ttcctagaaa acatctcagt caccaccttt ctgtggctgc   1380

gtgaaagcct tgaggggctc cgggagctag agcctctgct aaccatgttc atgccttctt   1440

ctttttccta cagctcctgg gcaacgtgct ggttattgtg ctgtctcatc attttggcaa   1500

agaattcctc gaagatccga agggaaagtc ttccacgact gtgggatccg ttcgaagata   1560

tcaccggttg agccaccatg gaattcagca gccccagcag agaggaatgc cccaagcctc   1620

tgagccgggt gtcaatcatg gccggatctc tgacaggact gctgctgctt caggccgtgt   1680

cttgggcttc tggcgctaga ccttgcatcc ccaagagctt cggctacagc agcgtcgtgt   1740

gcgtgtgcaa tgccacctac tgcgacagct tcgaccctcc tacctttcct gctctgggca   1800

ccttcagcag atacgagagc accagatccg gcagacggat ggaactgagc atgggaccca   1860

tccaggccaa tcacacaggc actggcctgc tgctgacact gcagcctgag cagaaattcc   1920

agaaagtgaa aggcttcggc ggagccatga cagatgccgc cgctctgaat atcctggctc   1980

tgtctccacc agctcagaac ctgctgctca agagctactt cagcgaggaa ggcatcggct   2040

acaacatcat cagagtgccc atggccagct gcgacttcag catcaggacc tacacctacg   2100
```

ccgacacacc cgacgatttc cagctgcaca acttcagcct gcctgaagag gacaccaagc 2160
tgaagatccc tctgatccac agagccctgc agctggcaca aagacccgtg tcactgctgg 2220
cctctccatg gacatctccc acctggctga aaacaaatgg cgccgtgaat ggcaagggca 2280
gcctgaaagg ccaacctggc gacatctacc accagacctg ggccagatac ttcgtgaagt 2340
tcctggacgc ctatgccgag cacaagctgc agttttgggc cgtgacagcc gagaacgaac 2400
cttctgctgg actgctgagc ggctacccct ttcagtgcct gggctttaca cccgagcacc 2460
agcgggactt tatcgcccgt gatctgggac ccacactggc caatagcacc caccataatg 2520
tgcggctgct gatgctggac gaccagagac tgcttctgcc ccactgggct aaagtggtgc 2580
tgacagatcc tgaggccgcc aaatacgtgc acggaatcgc cgtgcactgg tatctggact 2640
ttctggcccc tgccaaggcc acactgggag agacacacag actgttcccc aacaccatgc 2700
tgttcgccag cgaagcctgt gtgggcagca agttttggga acagagcgtg cggctcggca 2760
gctgggatag aggcatgcag tacagccaca gcatcatcac caacctgctg taccacgtcg 2820
tcggctggac cgactggaat ctggccctga atcctgaagg cggccctaac tgggtccgaa 2880
acttcgtgga cagccccatc atcgtggaca tcaccaagga caccttctac aagcagccca 2940
tgttctacca cctgggacac ttcagcaagt tcatccccga gggctctcag cgcgttggac 3000
tggtggcttc ccagaagaac gatctggacg ccgtggctct gatgcaccct gatggatctg 3060
ctgtggtggt ggtcctgaac cgcagcagca aagatgtgcc cctgaccatc aaggatcccg 3120
ccgtgggatt cctggaaaca atcagccctg gctactccat ccacacctac ctgtggcgta 3180
gacagtgaca attgttaatt aagtttaaac cctcgaggcc gcaagcttat cgataatcaa 3240
cctctggatt acaaaatttg tgaaagattg actggtattc ttaactatgt tgctcctttt 3300
acgctatgtg gatacgctgc tttaatgcct ttgtatcatg ctattgcttc ccgtatggct 3360
ttcattttct cctccttgta taaatcctgg ttgctgtctc tttatgagga gttgtggccc 3420
gttgtcaggc aacgtggcgt ggtgtgcact gtgtttgctg acgcaacccc cactggttgg 3480
ggcattgcca ccacctgtca gctcctttcc gggactttcg ctttccccct ccctattgcc 3540
acggcggaac tcatcgccgc ctgccttgcc cgctgctgga caggggctcg gctgttgggc 3600
actgacaatt ccgtggtgtt gtcggggaaa tcatcgtcct ttccttggct gctcgcctgt 3660
gttgccacct ggattctgcg cgggacgtcc ttctgctacg tcccttcggc cctcaatcca 3720
gcggaccttc cttcccgcgg cctgctgccg gctctgcggc ctcttccgcg tcttcgcctt 3780
cgccctcaga cgagtcggat ctccctttgg gccgcctccc cgcatcgata ccgtcgacta 3840
gagctcgctg atcagcctcg actgtgcctt ctagttgcca gccatctgtt gtttgcccct 3900
cccccgtgcc ttccttgacc ctggaaggtg ccactcccac tgtcctttcc taataaaatg 3960
aggaaattgc atcgcattgt ctgagtaggt gtcattctat tctggggggt ggggtggggc 4020
aggacagcaa gggggaggat tgggaagaca atagcaggca tgctggggag agatccacga 4080
taacaaacag ctttttttggg gtgaacatat tgactgaatt ccctgcaggt tggccactcc 4140
ctctctgcgc gctcgctcgc tcactgaggc cgcccgggca aagcccgggc gtcgggcgac 4200
ctttggtcgc ccggcctcag tgagcgagcg agcgcgcaga gagggagtgg ccaactccat 4260
cactaggggt tcctgcggcc gctcgtacgg tctcgaggaa ttcctgcagg ataacttgcc 4320
aacctcattc taaaatgtat atagaagccc aaaagacaat aacaaaaata ttcttgtaga 4380
acaaaatggg aaagaatgtt ccactaaata tcaagattta gagcaaagca tgagatgtgt 4440

-continued

```
ggggatagac agtgaggctg ataaaataga gtagagctca gaaacagacc cattgatata   4500
tgtaagtgac ctatgaaaaa aatatggcat tttacaatgg gaaaatgatg gtctttttct   4560
tttttagaaa aacagggaaa tatatttata tgtaaaaaat aaaagggaac ccatatgtca   4620
taccatacac acaaaaaaat tccagtgaat tataagtcta aatggagaag gcaaaacttt   4680
aaatctttta gaaaataata tagaagcatg cagaccagcc tggccaacat gatgaaaccc   4740
tctctactaa taataaaatc agtagaacta ctcaggacta ctttgagtgg gaagtccttt   4800
tctatgaaga cttctttggc caaaattagg ctctaaatgc aaggagatag tgcatcatgc   4860
ctggctgcac ttactgataa atgatgttat caccatcttt aaccaaatgc acaggaacaa   4920
gttatggtac tgatgtgctg gattgagaag gagctctact tccttgacag gacacatttg   4980
tatcaactta aaaaagcaga tttttgccag cagaactatt cattcagagg taggaaactt   5040
agaatagatg atgtcactga ttagcatggc ttccccatct ccacagctgc ttcccaccca   5100
ggttgcccac agttgagttt gtccagtgct cagggctgcc cactctcagt aagaagcccc   5160
acaccagccc ctctccaaat atgttggctg ttccttccat taaagtgacc ccactttaga   5220
gcagcaagtg gatttctgtt tcttacagtt caggaaggag gagtcagctg tgagaacctg   5280
gagcctgaga tgcttctaag tcccactgct actggggtca gggaagccag actccagcat   5340
cagcagtcag gagcactaag cccttgccaa catcctgttt ctcagagaaa ctgcttccat   5400
tataatggtt gtcctttttt aagctatcaa gccaaacaac cagtgtctac cattattctc   5460
atcacctgaa gccaagggtt ctagcaaaag tcaagctgtc ttgtaatggt tgatgtgcct   5520
ccagcttctg tcttcagtca ctccactctt agcctgctct gaatcaactc tgaccacagt   5580
tccctggagc ccctgccacc tgctgcccct gccaccttct ccatctgcag tgctgtgcag   5640
ccttctgcac tcttgcagag ctaataggtg gagacttgaa ggaagaggag gaaagtttct   5700
cataatagcc ttgctgcaag ctcaaatggg aggtgggcac tgtgcccagg agccttggag   5760
caaaggctgt gcccaacctc tgactgcatc caggtttggt cttgacagag ataagaagcc   5820
ctggcttttg gagccaaaat ctaggtcaga cttaggcagg attctcaaag tttatcagca   5880
gaacatgagg cagaagaccc tttctgctcc agcttcttca ggctcaacct tcatcagaat   5940
agatagaaag agaggctgtg agggttctta aaacagaagc aaatctgact cagagaataa   6000
acaacctcct agtaaactac agcttagaca gagcatctgg tggtgagtgt gctcagtgtc   6060
ctactcaact gtctggtatc agccctcatg aggacttctc ttctttccct catagacctc   6120
catctctgtt ttccttagcc tgcagaaatc tggatggcta ttcacagaat gcctgtgctt   6180
tcagagttgc atttttctc tggtattctg gttcaagcat ttgaaggtag gaaaggttct   6240
ccaagtgcaa gaaagccagc cctgagcctc aactgcctgg ctagtgtggt cagtaggatg   6300
caaaggctgt tgaatgccac aaggccaaac tttaacctgt gtaccacaag cctagcagca   6360
gaggcagctc tgctcactgg aactctctgt cttctttctc ctgagccttt tcttttcctg   6420
agttttctag ctctcctcaa ccttacctct gccctaccca ggacaaaccc aagagccact   6480
gtttctgtga tgtcctctcc agccctaatt aggcatcatg acttcagcct gaccttccat   6540
gctcagaagc agtgctaatc cacttcagat gagctgctct atgcaacaca ggcagagcct   6600
acaaaccttt gcaccagagc cctccacata tcagtgtttg ttcatactca cttcaacagc   6660
aaatgtgact gctgagatta agattttaca caagatggtc tgtaatttca cagttagttt   6720
tatcccatta ggtatgaaag aattagcata attcccctta aacatgaatg aatcttagat   6780
tttttaataa atagttttgg aagtaaagac agagacatca ggagcacaag gaatagcctg   6840
```

```
agaggacaaa cagaacaaga aagagtctgg aaatacacag gatgttcttg gcctcctcaa   6900
agcaagtgca agcagatagt accagcagcc ccaggctatc agagcccagt gaagagaagt   6960
accatgaaag ccacagctct aaccaccctg ttccagagtg acagacagtc cccaagacaa   7020
gccagcctga gccagagaga gaactgcaag agaaagtttc taatttaggt tctgttagat   7080
tcagacaagt gcaggtcatc ctctctccac agctactcac ctctccagcc taacaaagcc   7140
tgcagtccac actccaaccc tggtgtctca cctcctagcc tctcccaaca tcctgctctc   7200
tgaccatctt ctgcatctct catctcacca tctcccactg tctacagcct actcttgcaa   7260
ctaccatctc attttctgac atcctgtcta catcttctgc catactctgc catctaccat   7320
accacctctt accatctacc acaccatctt ttatctccat ccctctcaga agcctccaag   7380
ctgaatcctg ctttatgtgt tcatctcagc ccctgcatgg aaagctgacc ccagaggcag   7440
aactattccc agagagcttg gccaagaaaa acaaaactac cagcctggcc aggctcagga   7500
gtagtaagct gcagtgtctg ttgtgttcta gcttcaacag ctgcaggagt tccactctca   7560
aatgctccac atttctcaca tcctcctgat tctggtcact acccatcttc aaagaacaga   7620
atatctcaca tcagcatact gtgaaggact agtcatgggt gcagctgctc agagctgcaa   7680
agtcattctg gatggtggag agcttacaaa catttcatga tgctcccccc gctctgatgg   7740
ctggagccca atccctacac agactcctgc tgtatgtgtt ttcctttcac tctgagccac   7800
agccagaggg caggcattca gtctcctctt caggctgggg ctggggcact gagaactcac   7860
ccaacacctt gctctcactc cttctgcaaa acaagaaaga gctttgtgct gcagtagcca   7920
tgaagaatga aaggaaggct ttaactaaaa aatgtcagag attattttca accccttact   7980
gtggatcacc agcaaggagg aaacacaaca cagagacatt ttttcccctc aaattatcaa   8040
aagaatcact gcatttgtta aagagagcaa ctgaatcagg aagcagagtt ttgaacatat   8100
cagaagttag gaatctgcat cagagacaaa tgcagtcatg gttgtttgct gcataccagc   8160
cctaatcatt agaagcctca tggacttcaa acatcattcc ctctgacaag atgctctagc   8220
ctaactccat gagataaaat aaatctgcct ttcagagcca aagaagagtc caccagcttc   8280
ttctcagtgt gaacaagagc tccagtcagg ttagtcagtc cagtgcagta gaggagacca   8340
gtctgcatcc tctaattttc aaaggcaaga agatttgttt accctggaca ccaggcacaa   8400
gtgaggtcac agagctctta gatatgcagt cctcatgagt gaggagacta aagcgcatgc   8460
catcaagact tcagtgtaga gaaaacctcc aaaaaagcct cctcactact tctggaatag   8520
ctcagaggcc gaggcggcct cggcctctgc ataaataaaa aaaattagtc agccatgggg   8580
cggagaatgg gcggaactgg gcggagttag gggcgggatg ggcggagtta ggggcgggac   8640
tatggttgct gactaattga gatgcatgct ttgcatactt ctgcctgctg gggagcctgg   8700
ggactttcca cacctggttg ctgactaatt gagatgcatg ctttgcatac ttctgcctgc   8760
tggggagcct ggggactttc cacaccctaa ctgacacaca ttccacagct gcattaatga   8820
atcggccaac gcgcggggag aggcggtttg cgtattgggc gctcttccgc ttcctcgctc   8880
actgactcgc tgcgctcggt cgttcggctg cggcgagcgg tatcagctca ctcaaaggcg   8940
gtaatacggt tatccacaga atcaggggat aacgcaggaa agaacatgtg agcaaaaggc   9000
cagcaaaagg ccaggaaccg taaaaaggcc gcgttgctgg cgtttttcca taggctccgc   9060
ccccctgacg agcatcacaa aaatcgacgc tcaagtcaga ggtggcgaaa cccgacagga   9120
ctataaagat accaggcgtt tccccctgga agctccctcg tgcgctctcc tgttccgacc   9180
```

ctgccgctta ccggatacct gtccgccttt ctcccttcgg gaagcgtggc gctttctcat 9240
agctcacgct gtaggtatct cagttcggtg taggtcgttc gctccaagct gggctgtgtg 9300
cacgaacccc ccgttcagcc cgaccgctgc gccttatccg gtaactatcg tcttgagtcc 9360
aacccggtaa gacacgactt atcgccactg gcagcagcca ctggtaacag gattagcaga 9420
gcgaggtatg taggcggtgc tacagagttc ttgaagtggt ggcctaacta cggctacact 9480
agaagaacag tatttggtat ctgcgctctg ctgaagccag ttaccttcgg aaaaagagtt 9540
ggtagctctt gatccggcaa acaaaccacc gctggtagcg gtggtttttt tgtttgcaag 9600
cagcagatta cgcgcagaaa aaaaggatct caagaagatc ctttgatctt ttctacgggg 9660
tctgacgctc agtggaacga aaactcacgt taagggattt tggtcatgag attatcaaaa 9720
aggatcttca cctagatcct tttaaattaa aaatgaagtt ttaaatcaat ctaaagtata 9780
tatgagtaaa cttggtctga cagttaccaa tgcttaatca gtgaggcacc tatctcagcg 9840
atctgtctat ttcgttcatc catagttgcc tgactcctgc aaaccacgtt gtgtctcaaa 9900
atctctgatg ttacattgca caagataaaa atatatcatc atgaacaata aaactgtctg 9960
cttacataaa cagtaataca aggggtgtta tgagccatat tcaacgggaa acgtcttgct 10020
cgaggccgcg attaaattcc aacatggatg ctgatttata tgggtataaa tgggctcgcg 10080
ataatgtcgg gcaatcaggt gcgacaatct atcgattgta tgggaagccc gatgcgccag 10140
agttgtttct gaaacatggc aaaggtagcg ttgccaatga tgttacagat gagatggtca 10200
gactaaactg gctgacggaa tttatgcctc ttccgaccat caagcatttt atccgtactc 10260
ctgatgatgc atggttactc accactgcga tccccgggaa aacagcattc caggtattag 10320
aagaatatcc tgattcaggt gaaaatattg ttgatgcgct ggcagtgttc ctgcgccggt 10380
tgcattcgat tcctgtttgt aattgtcctt ttaacagcga tcgcgtattt cgtctcgctc 10440
aggcgcaatc acgaatgaat aacggtttgg ttgatgcgag tgattttgat gacgagcgta 10500
atggctggcc tgttgaacaa gtctggaaag aaatgcataa gcttttgcca ttctcaccgg 10560
attcagtcgt cactcatggt gatttctcac ttgataacct tatttttgac gaggggaaat 10620
taataggttg tattgatgtt ggacgagtcg gaatcgcaga ccgataccag gatcttgcca 10680
tcctatggaa ctgcctcggt gagttttctc cttcattaca gaaacggctt tttcaaaaat 10740
atggtattga taatcctgat atgaataaat tgcagtttca tttgatgctc gatgagtttt 10800
tctaagggcg gcctgccacc atacccacgc cgaaacaagc gctcatgagc ccgaagtggc 10860
gagcccgatc ttccccatcg gtgatgtcgg cgatataggc gccagcaacc gcacctgtgg 10920
cgccggtgat gagggcgcgc caagtcgacg tccggcagtc 10960

<210> SEQ ID NO 42
<211> LENGTH: 10960
<212> TYPE: DNA
<213> ORGANISM: Artificial Sequence
<220> FEATURE:
<223> OTHER INFORMATION: PR004B vector second strand sequence

<400> SEQUENCE: 42
gactgccgga cgtcgacttg gcgcgccctc atcaccggcg ccacaggtgc ggttgctggc 60
gcctatatcg ccgacatcac cgatggggaa gatcgggctc gccacttcgg gctcatgagc 120
gcttgtttcg gcgtgggtat ggtggcaggc cgcccttaga aaaactcatc gagcatcaaa 180
tgaaactgca atttattcat atcaggatta tcaataccat atttttgaaa aagccgtttc 240
tgtaatgaag gagaaaactc accgaggcag ttccatagga tggcaagatc ctggtatcgg 300

-continued

```
tctgcgattc cgactcgtcc aacatcaata caacctatta atttcccctc gtcaaaaata    360
aggttatcaa gtgagaaatc accatgagtg acgactgaat ccggtgagaa tggcaaaagc    420
ttatgcattt ctttccagac ttgttcaaca ggccagccat tacgctcgtc atcaaaatca    480
ctcgcatcaa ccaaaccgtt attcattcgt gattgcgcct gagcgagacg aaatacgcga    540
tcgctgttaa aaggacaatt acaaacagga atcgaatgca accggcgcag gaacactgcc    600
agcgcatcaa caatattttc acctgaatca ggatattctt ctaatacctg gaatgctgtt    660
ttcccgggga tcgcagtggt gagtaaccat gcatcatcag gagtacggat aaaatgcttg    720
atggtcggaa gaggcataaa ttccgtcagc cagtttagtc tgaccatctc atctgtaaca    780
tcattggcaa cgctaccttt gccatgtttc agaaacaact ctggcgcatc gggcttccca    840
tacaatcgat agattgtcgc acctgattgc ccgacattat cgcgagccca tttataccca    900
tataaatcag catccatgtt ggaatttaat cgcggcctcg agcaagacgt ttcccgttga    960
atatggctca taacacccct tgtattactg tttatgtaag cagacagttt tattgttcat   1020
gatgatatat ttttatcttg tgcaatgtaa catcagagat tttgagacac aacgtggttt   1080
gcaggagtca ggcaactatg gatgaacgaa atagacagat cgctgagata ggtgcctcac   1140
tgattaagca ttggtaactg tcagaccaag tttactcata tatactttag attgatttaa   1200
aacttcattt ttaatttaaa aggatctagg tgaagatcct ttttgataat ctcatgacca   1260
aaatccctta acgtgagttt tcgttccact gagcgtcaga ccccgtagaa aagatcaaag   1320
gatcttcttg agatcctttt tttctgcgcg taatctgctg cttgcaaaca aaaaaaccac   1380
cgctaccagc ggtggtttgt ttgccggatc aagagctacc aactcttttt ccgaaggtaa   1440
ctggcttcag cagagcgcag ataccaaata ctgttcttct agtgtagccg tagttaggcc   1500
accacttcaa gaactctgta gcaccgccta catacctcgc tctgctaatc ctgttaccag   1560
tggctgctgc cagtggcgat aagtcgtgtc ttaccgggtt ggactcaaga cgatagttac   1620
cggataaggc gcagcggtcg ggctgaacgg ggggttcgtg cacacagccc agcttggagc   1680
gaacgaccta caccgaactg agatacctac agcgtgagct atgagaaagc gccacgcttc   1740
ccgaagggag aaaggcggac aggtatccgg taagcggcag ggtcggaaca ggagagcgca   1800
cgagggagct tccaggggga aacgcctggt atctttatag tcctgtcggg tttcgccacc   1860
tctgacttga gcgtcgattt ttgtgatgct cgtcaggggg gcggagccta tggaaaaacg   1920
ccagcaacgc ggccttttta cggttcctgg ccttttgctg gccttttgct cacatgttct   1980
ttcctgcgtt atcccctgat tctgtggata accgtattac cgcctttgag tgagctgata   2040
ccgctcgccg cagccgaacg accgagcgca gcgagtcagt gagcgaggaa gcggaagagc   2100
gcccaatacg caaaccgcct ctccccgcgc gttggccgat tcattaatgc agctgtggaa   2160
tgtgtgtcag ttagggtgtg gaaagtcccc aggctcccca gcaggcagaa gtatgcaaag   2220
catgcatctc aattagtcag caaccaggtg tggaaagtcc ccaggctccc cagcaggcag   2280
aagtatgcaa agcatgcatc tcaattagtc agcaaccata gtcccgcccc taactccgcc   2340
catcccgccc ctaactccgc ccagttccgc ccattctccg ccccatggct gactaatttt   2400
ttttatttat gcagaggccg aggccgcctc ggcctctgag ctattccaga agtagtgagg   2460
aggctttttt ggaggttttc tctacactga agtcttgatg gcatgcgctt tagtctcctc   2520
actcatgagg actgcatatc taagagctct gtgacctcac ttgtgcctgg tgtccagggt   2580
aaacaaatct tcttgccttt gaaaattaga ggatgcagac tggtctcctc tactgcactg   2640
```

gactgactaa cctgactgga gctcttgttc acactgagaa gaagctggtg gactcttctt 2700
tggctctgaa aggcagattt attttatctc atggagttag gctagagcat cttgtcagag 2760
ggaatgatgt ttgaagtcca tgaggcttct aatgattagg gctggtatgc agcaaacaac 2820
catgactgca tttgtctctg atgcagattc ctaacttctg atatgttcaa aactctgctt 2880
cctgattcag ttgctctctt taacaaatgc agtgattctt ttgataattt gaggggaaaa 2940
aatgtctctg tgttgtgttt cctccttgct ggtgatccac agtaaggggt tgaaaataat 3000
ctctgacatt ttttagttaa agccttcctt tcattcttca tggctactgc agcacaaagc 3060
tctttcttgt tttgcagaag gagtgagagc aaggtgttgg gtgagttctc agtgccccag 3120
ccccagcctg aagaggagac tgaatgcctg ccctctggct gtggctcaga gtgaaaggaa 3180
aacacataca gcaggagtct gtgtagggat tgggctccag ccatcagagc ggggggagca 3240
tcatgaaatg tttgtaagct ctccaccatc cagaatgact ttgcagctct gagcagctgc 3300
acccatgact agtccttcac agtatgctga tgtgagatat tctgttcttt gaagatgggt 3360
agtgaccaga atcaggagga tgtgagaaat gtggagcatt tgagagtgga actcctgcag 3420
ctgttgaagc tagaacacaa cagacactgc agcttactac tcctgagcct ggccaggctg 3480
gtagttttgt ttttcttggc caagctctct gggaatagtt ctgcctctgg ggtcagcttt 3540
ccatgcaggg gctgagatga acacataaag caggattcag cttggaggct tctgagaggg 3600
atggagataa aagatggtgt ggtagatggt aagaggtggt atggtagatg gcagagtatg 3660
gcagaagatg tagacaggat gtcagaaaat gagatggtag ttgcaagagt aggctgtaga 3720
cagtgggaga tggtgagatg agagatgcag aagatggtca gagagcagga tgttgggaga 3780
ggctaggagg tgagacacca gggttggagt gtggactgca ggctttgtta ggctggagag 3840
gtgagtagct gtggagagag gatgacctgc acttgtctga atctaacaga acctaaatta 3900
gaaactttct cttgcagttc tctctctggc tcaggctggc ttgtcttggg gactgtctgt 3960
cactctggaa cagggtggtt agagctgtgg ctttcatggt acttctcttc actgggctct 4020
gatagcctgg ggctgctggt actatctgct tgcacttgct ttgaggaggc caagaacatc 4080
ctgtgtattt ccagactctt tcttgttctg tttgtcctct caggctattc cttgtgctcc 4140
tgatgtctct gtctttactt ccaaaactat ttattaaaaa atctaagatt cattcatgtt 4200
taaggggaat tatgctaatt ctttcatacc taatgggata aaactaactg tgaaattaca 4260
gaccatcttg tgtaaaatct taatctcagc agtcacattt gctgttgaag tgagtatgaa 4320
caaacactga tatgtggagg gctctggtgc aaaggtttgt aggctctgcc tgtgttgcat 4380
agagcagctc atctgaagtg gattagcact gcttctgagc atggaaggtc aggctgaagt 4440
catgatgcct aattagggct ggagaggaca tcacagaaac agtggctctt gggtttgtcc 4500
tgggtagggc agaggtaagg ttgaggagag ctagaaaact caggaaaaga aaaggctcag 4560
gagaaagaag acagagagtt ccagtgagca gagctgcctc tgctgctagg cttgtggtac 4620
acaggttaaa gtttggcctt gtggcattca acagcctttg catcctactg accacactag 4680
ccaggcagtt gaggctcagg gctggctttc ttgcacttgg agaacctttc ctaccttcaa 4740
atgcttgaac cagaatacca gagaaaaaat gcaactctga aagcacaggc attctgtgaa 4800
tagccatcca gatttctgca ggctaaggaa aacagagatg gaggtctatg agggaaagaa 4860
gagaagtcct catgagggct gataccagac agttgagtag gacactgagc acactcacca 4920
ccagatgctc tgtctaagct gtagtttact aggaggttgt ttattctctg agtcagattt 4980
gcttctgttt taagaaccct cacagcctct ctttctatct attctgatga aggttgagcc 5040
tgaagaagct ggagcagaaa gggtcttctg cctcatgttc tgctgataaa ctttgagaat 5100
cctgcctaag tctgacctag attttggctc caaaagccag ggcttcttat ctctgtcaag 5160
accaaacctg gatgcagtca gaggttgggc acagcctttg ctccaaggct cctgggcaca 5220
gtgcccacct cccatttgag cttgcagcaa ggctattatg agaaactttc ctcctcttcc 5280
ttcaagtctc cacctattag ctctgcaaga gtgcagaagg ctgcacagca ctgcagatgg 5340
agaaggtggc aggggcagca ggtggcaggg gctccaggga actgtggtca gagttgattc 5400
agagcaggct aagagtggag tgactgaaga cagaagctgg aggcacatca accattacaa 5460
gacagcttga cttttgctag aacccttggc ttcaggtgat gagaataatg gtagacactg 5520
gttgtttggc ttgatagctt aaaaaaggac aaccattata atggaagcag tttctctgag 5580
aaacaggatg ttggcaaggg cttagtgctc ctgactgctg atgctggagt ctggcttccc 5640
tgaccccagt agcagtggga cttagaagca tctcaggctc caggttctca cagctgactc 5700
ctccttcctg aactgtaaga aacagaaatc cacttgctgc tctaaagtgg ggtcacttta 5760
atggaaggaa cagccaacat atttggagag gggctggtgt ggggcttctt actgagagtg 5820
ggcagccctg agcactggac aaactcaact gtgggcaacc tgggtgggaa gcagctgtgg 5880
agatggggaa gccatgctaa tcagtgacat catctattct aagtttccta cctctgaatg 5940
aatagttctg ctggcaaaaa tctgcttttt taagttgata caaatgtgtc ctgtcaagga 6000
agtagagctc cttctcaatc cagcacatca gtaccataac ttgttcctgt gcatttggtt 6060
aaagatggtg ataacatcat ttatcagtaa gtgcagccag gcatgatgca ctatctcctt 6120
gcatttagag cctaattttg gccaaagaag tcttcataga aaaggacttc ccactcaaag 6180
tagtcctgag tagttctact gattttatta ttagtagaga gggtttcatc atgttggcca 6240
ggctggtctg catgcttcta tattattttc taaaagattt aaagttttgc cttctccatt 6300
tagacttata attcactgga atttttttgt gtgtatggta tgacatatgg gttccctttt 6360
attttttaca tataaatata tttccctgtt tttctaaaaa agaaaaagac catcattttc 6420
ccattgtaaa atgccatatt tttttcatag gtcacttaca tatatcaatg ggtctgtttc 6480
tgagctctac tctattttat cagcctcact gtctatcccc acacatctca tgctttgctc 6540
taaatcttga tatttagtgg aacattcttt cccattttgt tctacaagaa tatttttgtt 6600
attgtctttt gggcttctat atacatttta gaatgaggtt ggcaagttat cctgcaggaa 6660
ttcctcgaga ccgtacgagc ggccgcagga acccctagtg atggagttgg ccactccctc 6720
tctgcgcgct cgctcgctca ctgaggccgg gcgaccaaag gtcgcccgac gcccgggctt 6780
tgcccgggcg gcctcagtga gcgagcgagc gcgcagagag ggagtggcca acctgcaggg 6840
aattcagtca atatgttcac ccccaaaaag ctgtttgtta tcgtggatct ctccccagca 6900
tgcctgctat tgtcttccca atcctccccc ttgctgtcct gccccacccc accccccaga 6960
atagaatgac acctactcag acaatgcgat gcaatttcct cattttatta ggaaaggaca 7020
gtgggagtgg caccttccag ggtcaaggaa ggcacggggg aggggcaaac aacagatggc 7080
tggcaactag aaggcacagt cgaggctgat cagcgagctc tagtcgacgg tatcgatgcg 7140
gggaggcggc ccaaagggag atccgactcg tctgagggcg aaggcgaaga cgcggaagag 7200
gccgcagagc cggcagcagg ccgcgggaag gaaggtccgc tggattgagg gccgaaggga 7260
cgtagcagaa ggacgtcccg cgcagaatcc aggtggcaac acaggcgagc agccaaggaa 7320
aggacgatga tttccccgac aacaccacgg aattgtcagt gcccaacagc cgagcccctg 7380

-continued

```
tccagcagcg ggcaaggcag gcggcgatga gttccgccgt ggcaataggg agggggaaag   7440
cgaaagtccc ggaaaggagc tgacaggtgg tggcaatgcc ccaaccagtg gggggttgcgt   7500
cagcaaacac agtgcacacc acgccacgtt gcctgacaac gggccacaac tcctcataaa   7560
gagacagcaa ccaggattta tacaaggagg agaaaatgaa agccatacgg gaagcaatag   7620
catgatacaa aggcattaaa gcagcgtatc cacatagcgt aaaaggagca acatagttaa   7680
gaataccagt caatctttca caaattttgt aatccagagg ttgattatcg ataagcttgc   7740
ggcctcgagg gtttaaactt aattaacaat tgtcactgtc tacgccacag gtaggtgtgg   7800
atggagtagc cagggctgat tgtttccagg aatcccacgg cgggatcctt gatggtcagg   7860
ggcacatctt tgctgctgcg gttcaggacc accaccacag cagatccatc agggtgcatc   7920
agagccacgg cgtccagatc gttcttctgg gaagccacca gtccaacgcg ctgagagccc   7980
tcggggatga acttgctgaa gtgtcccagg tggtagaaca tgggctgctt gtagaaggtg   8040
tccttggtga tgtccacgat gatggggctg tccacgaagt ttcggaccca gttagggccg   8100
ccttcaggat tcagggccag attccagtcg gtccagccga cgacgtggta cagcaggttg   8160
gtgatgatgc tgtggctgta ctgcatgcct ctatcccagc tgccgagccg cacgctctgt   8220
tcccaaaact tgctgcccac acaggcttcg ctggcgaaca gcatggtgtt ggggaacagt   8280
ctgtgtgtct ctcccagtgt ggccttggca ggggccagaa agtccagata ccagtgcacg   8340
gcgattccgt gcacgtattt ggcggcctca ggatctgtca gcaccacttt agcccagtgg   8400
ggcagaagca gtctctggtc gtccagcatc agcagccgca cattatggtg ggtgctattg   8460
gccagtgtgg gtcccagatc acgggcgata aagtcccgct ggtgctcggg tgtaaagccc   8520
aggcactgaa aggggtagcc gctcagcagt ccagcagaag gttcgttctc ggctgtcacg   8580
gcccaaaact gcagcttgtg ctcggcatag gcgtccagga acttcacgaa gtatctggcc   8640
caggtctggt ggtagatgtc gccaggttgg cctttcaggc tgcccttgcc attcacggcg   8700
ccatttgttt tcagccaggt gggagatgtc catggagagg ccagcagtga cacgggtctt   8760
tgtgccagct gcagggctct gtggatcaga gggatcttca gcttggtgtc ctcttcaggc   8820
aggctgaagt tgtgcagctg gaaatcgtcg ggtgtgtcgg cgtaggtgta ggtcctgatg   8880
ctgaagtcgc agctggccat gggcactctg atgatgttgt agccgatgcc ttcctcgctg   8940
aagtagctct tgagcagcag gttctgagct ggtggagaca gagccaggat attcagagcg   9000
gcggcatctg tcatggctcc gccgaagcct ttcactttct ggaatttctg ctcaggctgc   9060
agtgtcagca gcaggccagt gcctgtgtga ttggcctgga tgggtcccat gctcagttcc   9120
atccgtctgc cggatctggt gctctcgtat ctgctgaagg tgcccagagc aggaaaggta   9180
ggagggtcga agctgtcgca gtaggtggca ttgcacacgc acacgacgct gctgtagccg   9240
aagctcttgg ggatgcaagg tctagcgcca gaagcccaag acacggcctg aagcagcagc   9300
agtcctgtca gagatccggc catgattgac acccggctca gaggcttggg gcattcctct   9360
ctgctggggc tgctgaattc catggtggct caaccggtga tatcttcgaa cggatcccac   9420
agtcgtggaa gactttccct tcggatcttc gaggaattct ttgccaaaat gatgagacag   9480
cacaataacc agcacgttgc ccaggagctg taggaaaaag aagaaggcat gaacatggtt   9540
agcagaggct ctagctcccg gagcccctca aggctttcac gcagccacag aaaggtggtg   9600
actgagatgt tttctaggaa acacaaaaga tacaaaaaag aacacgtgga aggatagcca   9660
aaaagggggg ctgcccccat ttcctgcacc ccgctgcgat ggctggcacc atttggaaga   9720
cttcgagata cactgttgag cgcagtaaga caacagtgta tctcgaagtc ttccagatgg   9780
```

ggccagccgg tccactctgt atccaggcca gttctgcaag gcgttcgagg accaccccc 9840 tcccctcgcc accaggacaa gccgtcatta aaccaagcgc taattacagc ccggaggaga 9900
agggccgtcc cgcccgctca cctgtgggag taacgcggtc agtcagagcc ggggcgggcg 9960
gcgcgaggcg gcggcggagc ggggcacggg gcgaaggcag cgtcgcagcg actcccgccc 10020
gccgcgcgct tcgcttttta tagggccgcc gccgccgccg cctcgccata aaaggaaact 10080
ttcggagcgc gccgctctga ttggctgccg ccgcacctct ccgcctcgcc ccgccccgcc 10140
cctcgccccg ccccgccccg cctggcgcgc gccccccccc cccccccgcc cccatcgctg 10200
cacaaaataa ttaaaaaata aataaataca aaattggggg tggggagggg ggggagatgg 10260
ggagagtgaa gcagaacgtg gggctcacct cgaccatggt aatagcgatg actaatacgt 10320
agatgtactg ccaagtagga aagtcccata aggtcatgta ctgggcataa tgccaggcgg 10380
gccatttacc gtcattgacg tcaatagggg gcgtacttgg catatgatac acttgatgta 10440
ctgccaagtg ggcagtttac cgtaaatagt ccacccattg acgtcaatgg aaagtcccta 10500
ttggcgttac tatgggaaca tacgtcatta ttgacgtcaa tgggcggggg tcgttgggcg 10560
gtcagccagg cgggccattt accgtaagtt atgtaacgcg gaactccata tatgggctat 10620
gaactaatga ccccgtaatt gattactatt aataactagg gtaccgaatt cagatccaag 10680
cttcaccatg ggagacgtca ccggttctag aacctaggga gctctggtac ccactagtag 10740
tcgacgaacg cgtaacctcc cgcttcaaaa tggagaccct gcgtgctcac tcgggcttaa 10800
atacccagag ctagcaggaa cccctagtga tggagttggc cactccctct ctgcgcgctc 10860
gctcgctcac tgaggccgcc cgggcaaagc ccgggcgtcg ggcgaccttt ggtcgcccgg 10920
cctcagtgag cgagcgagcg cgcagagagg gagtggccaa 10960

<210> SEQ ID NO 43
<211> LENGTH: 10960
<212> TYPE: DNA
<213> ORGANISM: Artificial Sequence
<220> FEATURE:
<223> OTHER INFORMATION: PR004E vector first strand sequence

<400> SEQUENCE: 43
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
cctagttatt aatagtaatc aattacgggg tcattagttc atagcccata tatggagttc 360
cgcgttacat aacttacggt aaatggcccg cctggctgac cgcccaacga cccccgccca 420
ttgacgtcaa taatgacgta tgttcccata gtaacgccaa tagggacttt ccattgacgt 480
caatgggtgg actatttacg gtaaactgcc cacttggcag tacatcaagt gtatcatatg 540
ccaagtacgc cccctattga cgtcaatgac ggtaaatggc ccgcctggca ttatgcccag 600
tacatgacct tatgggactt tcctacttgg cagtacatct acgtattagt catcgctatt 660
accatggtcg aggtgagccc cacgttctgc ttcactctcc ccatctcccc cccctcccca 720
cccccaattt tgtatttatt tatttttaa ttattttgtg cagcgatggg ggcggggggg 780
gggggggggc gcgcgccagg cggggcgggg cggggcgagg ggcggggcgg ggcgaggcgg 840

-continued

```
agaggtgcgg cggcagccaa tcagagcggc gcgctccgaa agtttccttt tatggcgagg    900
cggcggcggc ggcggcccta taaaaagcga agcgcgcggc gggcgggagt cgctgcgacg    960
ctgccttcgc cccgtgcccc gctccgccgc cgcctcgcgc cgcccgcccc ggctctgact   1020
gaccgcgtta ctcccacagg tgagcgggcg ggacggccct tctcctccgg gctgtaatta   1080
gcgcttggtt taatgacggc ttgtcctggt ggcgagggga ggggggtggt cctcgaacgc   1140
cttgcagaac tggcctggat acagagtgga ccggctggcc ccatctggaa gacttcgaga   1200
tacactgttg tcttactgcg ctcaacagtg tatctcgaag tcttccaaat ggtgccagcc   1260
atcgcagcgg ggtgcaggaa atgggggcag cccccctttt tggctatcct tccacgtgtt   1320
ctttttgta tcttttgtgt ttcctagaaa acatctcagt caccaccttt ctgtggctgc   1380
gtgaaagcct tgaggggctc cgggagctag agcctctgct aaccatgttc atgccttctt   1440
ctttttccta cagctcctgg gcaacgtgct ggttattgtg ctgtctcatc attttggcaa   1500
agaattcctc gaagatccga agggaaagtc ttccacgact gtgggatccg ttcgaagata   1560
tcaccggttg agccaccatg gaattcagca gccccagcag agaggaatgc cccaagcctc   1620
tgagccgggt gtcaatcatg gccggatctc tgacaggact gctgctgctt caggccgtgt   1680
cttgggcttc tggcgctaga ccttgcatcc ccaagagctt cggctacagc agcgtcgtgt   1740
gcgtgtgcaa tgccacctac tgcgacagct tcgaccctcc tacctttcct gctctgggca   1800
ccttcagcag atacgagagc accagatccg gcagacggat ggaactgagc atgggaccca   1860
tccaggccaa tcacacaggc actggcctgc tgctgacact gcagcctgag cagaaattcc   1920
agaaagtgaa aggcttcggc ggagccatga cagatgccgc cgctctgaat atcctggctc   1980
tgtctccacc agctcagaac ctgctgctca agagctactt cagcgaggaa ggcatcggct   2040
acaacatcat cagagtgccc atggccagct gcgacttcag catcaggacc tacacctacg   2100
ccgacacacc cgacgatttc cagctgcaca acttcagcct gcctgaagag gacaccaagc   2160
tgaagatccc tctgatccac agagccctgc agctggcaca aagacccgtg tcactgctgg   2220
cctctccatg gacatctccc acctggctga aaacaaatgg cgccgtgaat ggcaagggca   2280
gcctgaaagg ccaacctggc gacatctacc accagacctg ggccagatac ttcgtgaagt   2340
tcctggacgc ctatgccgag cacaagctgc agttttgggc cgtgacagcc gagaacgaac   2400
cttctgctgg actgctgagc ggctacccct ttcagtgcct gggctttaca cccgagcacc   2460
agcgggactt tatcgcccgt gatctgggac ccacactggc caatagcacc caccataatg   2520
tgcggctgct gatgctggac gaccagagac tgcttctgcc ccactgggct aaagtggtgc   2580
tgacagatcc tgaggccgcc aaatacgtgc acggaatcgc cgtgcactgg tatctggact   2640
ttctggcccc tgccaaggcc acactgggag agacacacag actgttcccc aacaccatgc   2700
tgttcgccag cgaagcctgt gtgggcagca agttttggga acagagcgtg cggctcggca   2760
gctgggatag aggcatgcag tacagccaca gcatcatcac caacctgctg taccacgtcg   2820
tcggctggac cgactggaat ctggccctga atcctgaagg cggccctaac tgggtccgaa   2880
acttcgtgga cagccccatc atcgtggaca tcaccaagga caccttctac aagcagccca   2940
tgttctacca cctgggacac ttcagcaagt tcatccccga gggctctcag cgcgttggac   3000
tggtggcttc ccagaagaac gatctggacg ccgtggctct gatgcaccct gatggatctg   3060
ctgtggtggt ggtcctgaac cgcagcagca aagatgtgcc cctgaccatc aaggatcccg   3120
ccgtgggatt cctggaaaca atcagccctg gctactccat ccacacctac ctgtggcgta   3180
gacagtgaca attgttaatt aagtttaaac cctcgaggcc gcaagcttat cgataatcaa   3240
```

```
cctctggatt acaaaatttg tgaaagattg actggtattc ttaactatgt tgctcctttt   3300

acgctatgtg gatacgctgc tttaatgcct ttgtatcatg ctattgcttc ccgtatggct   3360

ttcattttct cctccttgta taaatcctgg ttgctgtctc tttatgagga gttgtggccc   3420

gttgtcaggc aacgtggcgt ggtgtgcact gtgtttgctg acgcaacccc cactggttgg   3480

ggcattgcca ccacctgtca gctcctttcc gggactttcg ctttccccct ccctattgcc   3540

acggcggaac tcatcgccgc ctgccttgcc cgctgctgga caggggctcg gctgttgggc   3600

actgacaatt ccgtggtgtt gtcggggaaa tcatcgtcct ttccttggct gctcgcctgt   3660

gttgccacct ggattctgcg cgggacgtcc ttctgctacg tcccttcggc cctcaatcca   3720

gcggaccttc cttcccgcgg cctgctgccg gctctgcggc ctcttccgcg tcttcgcctt   3780

cgccctcaga cgagtcggat ctccctttgg gccgcctccc cgcatcgata ccgtcgacta   3840

gagctcgctg atcagcctcg actgtgcctt ctagttgcca gccatctgtt gtttgcccct   3900

cccccgtgcc ttccttgacc ctggaaggtg ccactcccac tgtcctttcc taataaaatg   3960

aggaaattgc atcgcattgt ctgagtaggt gtcattctat tctggggggt ggggtggggc   4020

aggacagcaa gggggaggat tgggaagaca atagcaggca tgctggggag agatccacga   4080

taacaaacag ctttttttggg gtgaacatat tgactgaatt ccctgcagga ggaaccccta   4140

gtgatggagt tggccactcc ctctctgcgc gctcgctcgc tcactgaggc cgcccgggca   4200

aagcccgggc gtcgggcgac ctttggtcgc ccggcctcag tgagcgagcg agcgcgcaga   4260

gagggagtgg ccaagcggcc gctcgtacgg tctcgaggaa ttcctgcagg ataacttgcc   4320

aacctcattc taaaatgtat atagaagccc aaaagacaat aacaaaaata ttcttgtaga   4380

acaaaatggg aaagaatgtt ccactaaata tcaagattta gagcaaagca tgagatgtgt   4440

ggggatagac agtgaggctg ataaaataga gtagagctca gaaacagacc cattgatata   4500

tgtaagtgac ctatgaaaaa aatatggcat tttacaatgg gaaaatgatg gtctttttct   4560

tttttagaaa aacagggaaa tatatttata tgtaaaaaat aaaagggaac ccatatgtca   4620

taccatacac acaaaaaaat tccagtgaat tataagtcta aatggagaag gcaaaacttt   4680

aaatctttta gaaaataata tagaagcatg cagaccagcc tggccaacat gatgaaaccc   4740

tctctactaa taataaaatc agtagaacta ctcaggacta ctttgagtgg gaagtccttt   4800

tctatgaaga cttctttggc caaaattagg ctctaaatgc aaggagatag tgcatcatgc   4860

ctggctgcac ttactgataa atgatgttat caccatcttt aaccaaatgc acaggaacaa   4920

gttatggtac tgatgtgctg gattgagaag gagctctact tccttgacag gacacatttg   4980

tatcaactta aaaaagcaga tttttgccag cagaactatt cattcagagg taggaaactt   5040

agaatagatg atgtcactga ttagcatggc ttccccatct ccacagctgc ttcccaccca   5100

ggttgcccac agttgagttt gtccagtgct cagggctgcc cactctcagt aagaagcccc   5160

acaccagccc ctctccaaat atgttggctg ttccttccat taaagtgacc ccactttaga   5220

gcagcaagtg gatttctgtt tcttacagtt caggaaggag gagtcagctg tgagaacctg   5280

gagcctgaga tgcttctaag tcccactgct actggggtca gggaagccag actccagcat   5340

cagcagtcag gagcactaag cccttgccaa catcctgttt ctcagagaaa ctgcttccat   5400

tataatggtt gtcctttttt aagctatcaa gccaaacaac cagtgtctac cattattctc   5460

atcacctgaa gccaagggtt ctagcaaaag tcaagctgtc ttgtaatggt tgatgtgcct   5520

ccagcttctg tcttcagtca ctccactctt agcctgctct gaatcaactc tgaccacagt   5580
```

-continued

```
tccctggagc ccctgccacc tgctgcccct gccaccttct ccatctgcag tgctgtgcag   5640
ccttctgcac tcttgcagag ctaataggtg gagacttgaa ggaagaggag gaaagtttct   5700
cataatagcc ttgctgcaag ctcaaatggg aggtgggcac tgtgcccagg agccttggag   5760
caaaggctgt gcccaacctc tgactgcatc caggtttggt cttgacagag ataagaagcc   5820
ctggcttttg gagccaaaat ctaggtcaga cttaggcagg attctcaaag tttatcagca   5880
gaacatgagg cagaagaccc tttctgctcc agcttcttca ggctcaacct tcatcagaat   5940
agatagaaag agaggctgtg agggttctta aaacagaagc aaatctgact cagagaataa   6000
acaacctcct agtaaactac agcttagaca gagcatctgg tggtgagtgt gctcagtgtc   6060
ctactcaact gtctggtatc agccctcatg aggacttctc ttctttccct catagacctc   6120
catctctgtt ttccttagcc tgcagaaatc tggatggcta ttcacagaat gcctgtgctt   6180
tcagagttgc atttttctc tggtattctg gttcaagcat ttgaaggtag gaaaggttct   6240
ccaagtgcaa gaaagccagc cctgagcctc aactgcctgg ctagtgtggt cagtaggatg   6300
caaaggctgt tgaatgccac aaggccaaac tttaacctgt gtaccacaag cctagcagca   6360
gaggcagctc tgctcactgg aactctctgt cttctttctc ctgagccttt tcttttcctg   6420
agttttctag ctctcctcaa ccttacctct gccctaccca ggacaaaccc aagagccact   6480
gtttctgtga tgtcctctcc agccctaatt aggcatcatg acttcagcct gaccttccat   6540
gctcagaagc agtgctaatc cacttcagat gagctgctct atgcaacaca ggcagagcct   6600
acaaaccttt gcaccagagc cctccacata tcagtgtttg ttcatactca cttcaacagc   6660
aaatgtgact gctgagatta agattttaca caagatggtc tgtaatttca cagttagttt   6720
tatcccatta ggtatgaaag aattagcata attcccctta aacatgaatg aatcttagat   6780
tttttaataa atagttttgg aagtaaagac agagacatca ggagcacaag gaatagcctg   6840
agaggacaaa cagaacaaga aagagtctgg aaatacacag gatgttcttg gcctcctcaa   6900
agcaagtgca agcagatagt accagcagcc ccaggctatc agagcccagt gaagagaagt   6960
accatgaaag ccacagctct aaccaccctg ttccagagtg acagacagtc cccaagacaa   7020
gccagcctga gccagagaga gaactgcaag agaaagtttc taatttaggt tctgttagat   7080
tcagacaagt gcaggtcatc ctctctccac agctactcac ctctccagcc taacaaagcc   7140
tgcagtccac actccaaccc tggtgtctca cctcctagcc tctcccaaca tcctgctctc   7200
tgaccatctt ctgcatctct catctcacca tctcccactg tctacagcct actcttgcaa   7260
ctaccatctc attttctgac atcctgtcta catcttctgc catactctgc catctaccat   7320
accacctctt accatctacc acaccatctt ttatctccat ccctctcaga agcctccaag   7380
ctgaatcctg ctttatgtgt tcatctcagc ccctgcatgg aaagctgacc ccagaggcag   7440
aactattccc agagagcttg gccaagaaaa acaaaactac cagcctggcc aggctcagga   7500
gtagtaagct gcagtgtctg ttgtgttcta gcttcaacag ctgcaggagt tccactctca   7560
aatgctccac atttctcaca tcctcctgat tctggtcact acccatcttc aaagaacaga   7620
atatctcaca tcagcatact gtgaaggact agtcatgggt gcagctgctc agagctgcaa   7680
agtcattctg gatggtggag agcttacaaa catttcatga tgctcccccc gctctgatgg   7740
ctggagccca atccctacac agactcctgc tgtatgtgtt ttcctttcac tctgagccac   7800
agccagaggg caggcattca gtctcctctt caggctgggg ctggggcact gagaactcac   7860
ccaacacctt gctctcactc cttctgcaaa acaagaaaga gctttgtgct gcagtagcca   7920
tgaagaatga aaggaaggct ttaactaaaa aatgtcagag attattttca accccttact   7980
```

gtggatcacc agcaaggagg aaacacaaca cagagacatt ttttcccctc aaattatcaa 8040
aagaatcact gcatttgtta aagagagcaa ctgaatcagg aagcagagtt ttgaacatat 8100
cagaagttag gaatctgcat cagagacaaa tgcagtcatg gttgtttgct gcataccagc 8160
cctaatcatt agaagcctca tggacttcaa acatcattcc ctctgacaag atgctctagc 8220
ctaactccat gagataaaat aaatctgcct ttcagagcca aagaagagtc caccagcttc 8280
ttctcagtgt gaacaagagc tccagtcagg ttagtcagtc cagtgcagta gaggagacca 8340
gtctgcatcc tctaattttc aaaggcaaga agatttgttt accctggaca ccaggcacaa 8400
gtgaggtcac agagctctta gatatgcagt cctcatgagt gaggagacta aagcgcatgc 8460
catcaagact tcagtgtaga gaaaacctcc aaaaaagcct cctcactact tctggaatag 8520
ctcagaggcc gaggcggcct cggcctctgc ataaataaaa aaaattagtc agccatgggg 8580
cggagaatgg gcggaactgg gcggagttag gggcgggatg ggcggagtta ggggcgggac 8640
tatggttgct gactaattga gatgcatgct ttgcatactt ctgcctgctg gggagcctgg 8700
ggactttcca cacctggttg ctgactaatt gagatgcatg ctttgcatac ttctgcctgc 8760
tggggagcct ggggactttc cacaccctaa ctgacacaca ttccacagct gcattaatga 8820
atcggccaac gcgcggggag aggcggtttg cgtattgggc gctcttccgc ttcctcgctc 8880
actgactcgc tgcgctcggt cgttcggctg cggcgagcgg tatcagctca ctcaaaggcg 8940
gtaatacggt tatccacaga atcaggggat aacgcaggaa agaacatgtg agcaaaaggc 9000
cagcaaaagg ccaggaaccg taaaaaggcc gcgttgctgg cgtttttcca taggctccgc 9060
ccccctgacg agcatcacaa aaatcgacgc tcaagtcaga ggtggcgaaa cccgacagga 9120
ctataaagat accaggcgtt tccccctgga agctccctcg tgcgctctcc tgttccgacc 9180
ctgccgctta ccggatacct gtccgccttt ctcccttcgg gaagcgtggc gctttctcat 9240
agctcacgct gtaggtatct cagttcggtg taggtcgttc gctccaagct gggctgtgtg 9300
cacgaacccc ccgttcagcc cgaccgctgc gccttatccg gtaactatcg tcttgagtcc 9360
aacccggtaa gacacgactt atcgccactg gcagcagcca ctggtaacag gattagcaga 9420
gcgaggtatg taggcggtgc tacagagttc ttgaagtggt ggcctaacta cggctacact 9480
agaagaacag tatttggtat ctgcgctctg ctgaagccag ttaccttcgg aaaaagagtt 9540
ggtagctctt gatccggcaa acaaaccacc gctggtagcg gtggtttttt tgtttgcaag 9600
cagcagatta cgcgcagaaa aaaaggatct caagaagatc ctttgatctt ttctacgggg 9660
tctgacgctc agtggaacga aaactcacgt taagggattt tggtcatgag attatcaaaa 9720
aggatcttca cctagatcct tttaaattaa aaatgaagtt ttaaatcaat ctaaagtata 9780
tatgagtaaa cttggtctga cagttaccaa tgcttaatca gtgaggcacc tatctcagcg 9840
atctgtctat ttcgttcatc catagttgcc tgactcctgc aaaccacgtt gtgtctcaaa 9900
atctctgatg ttacattgca caagataaaa atatatcatc atgaacaata aaactgtctg 9960
cttacataaa cagtaataca aggggtgtta tgagccatat tcaacgggaa acgtcttgct 10020
cgaggccgcg attaaattcc aacatggatg ctgatttata tgggtataaa tgggctcgcg 10080
ataatgtcgg gcaatcaggt gcgacaatct atcgattgta tgggaagccc gatgcgccag 10140
agttgtttct gaaacatggc aaaggtagcg ttgccaatga tgttacagat gagatggtca 10200
gactaaactg gctgacggaa tttatgcctc ttccgaccat caagcatttt atccgtactc 10260
ctgatgatgc atggttactc accactgcga tccccgggaa aacagcattc caggtattag 10320
aagaatatcc tgattcaggt gaaaatattg ttgatgcgct ggcagtgttc ctgcgccggt 10380
tgcattcgat tcctgtttgt aattgtcctt ttaacagcga tcgcgtattt cgtctcgctc 10440
aggcgcaatc acgaatgaat aacggtttgg ttgatgcgag tgattttgat gacgagcgta 10500
atggctggcc tgttgaacaa gtctggaaag aaatgcataa gcttttgcca ttctcaccgg 10560
attcagtcgt cactcatggt gatttctcac ttgataacct tatttttgac gaggggaaat 10620
taataggttg tattgatgtt ggacgagtcg gaatcgcaga ccgataccag gatcttgcca 10680
tcctatggaa ctgcctcggt gagttttctc cttcattaca gaaacggctt tttcaaaaat 10740
atggtattga taatcctgat atgaataaat tgcagtttca tttgatgctc gatgagtttt 10800
tctaagggcg gcctgccacc atacccacgc cgaaacaagc gctcatgagc ccgaagtggc 10860
gagcccgatc ttccccatcg gtgatgtcgg cgatataggc gccagcaacc gcacctgtgg 10920
cgccggtgat gagggcgcgc caagtcgacg tccggcagtc 10960

<210> SEQ ID NO 44
<211> LENGTH: 10960
<212> TYPE: DNA
<213> ORGANISM: Artificial Sequence
<220> FEATURE:
<223> OTHER INFORMATION: PR004E vector second strand sequence

<400> SEQUENCE: 44
gactgccgga cgtcgacttg gcgcgccctc atcaccggcg ccacaggtgc ggttgctggc 60
gcctatatcg ccgacatcac cgatggggaa gatcgggctc gccacttcgg gctcatgagc 120
gcttgtttcg gcgtgggtat ggtggcaggc cgcccttaga aaaactcatc gagcatcaaa 180
tgaaactgca atttattcat atcaggatta tcaataccat atttttgaaa aagccgtttc 240
tgtaatgaag gagaaaactc accgaggcag ttccatagga tggcaagatc ctggtatcgg 300
tctgcgattc cgactcgtcc aacatcaata caacctatta atttcccctc gtcaaaaata 360
aggttatcaa gtgagaaatc accatgagtg acgactgaat ccggtgagaa tggcaaaagc 420
ttatgcattt ctttccagac ttgttcaaca ggccagccat tacgctcgtc atcaaaatca 480
ctcgcatcaa ccaaaccgtt attcattcgt gattgcgcct gagcgagacg aaatacgcga 540
tcgctgttaa aaggacaatt acaaacagga atcgaatgca accggcgcag gaacactgcc 600
agcgcatcaa caatattttc acctgaatca ggatattctt ctaatacctg gaatgctgtt 660
ttcccgggga tcgcagtggt gagtaaccat gcatcatcag gagtacggat aaaatgcttg 720
atggtcggaa gaggcataaa ttccgtcagc cagtttagtc tgaccatctc atctgtaaca 780
tcattggcaa cgctaccttt gccatgtttc agaaacaact ctggcgcatc gggcttccca 840
tacaatcgat agattgtcgc acctgattgc ccgacattat cgcgagccca tttataccca 900
tataaatcag catccatgtt ggaatttaat cgcggcctcg agcaagacgt ttcccgttga 960
atatggctca taacacccct tgtattactg tttatgtaag cagacagttt tattgttcat 1020
gatgatatat ttttatcttg tgcaatgtaa catcagagat tttgagacac aacgtggttt 1080
gcaggagtca ggcaactatg gatgaacgaa atagacagat cgctgagata ggtgcctcac 1140
tgattaagca ttggtaactg tcagaccaag tttactcata tatactttag attgatttaa 1200
aacttcattt ttaatttaaa aggatctagg tgaagatcct ttttgataat ctcatgacca 1260
aaatccctta acgtgagttt tcgttccact gagcgtcaga ccccgtagaa aagatcaaag 1320
gatcttcttg agatcctttt tttctgcgcg taatctgctg cttgcaaaca aaaaaaccac 1380
cgctaccagc ggtggtttgt ttgccggatc aagagctacc aactcttttt ccgaaggtaa 1440

```
ctggcttcag cagagcgcag ataccaaata ctgttcttct agtgtagccg tagttaggcc   1500
accacttcaa gaactctgta gcaccgccta catacctcgc tctgctaatc ctgttaccag   1560
tggctgctgc cagtggcgat aagtcgtgtc ttaccgggtt ggactcaaga cgatagttac   1620
cggataaggc gcagcggtcg ggctgaacgg ggggttcgtg cacacagccc agcttggagc   1680
gaacgaccta caccgaactg agatacctac agcgtgagct atgagaaagc gccacgcttc   1740
ccgaagggag aaaggcggac aggtatccgg taagcggcag ggtcggaaca ggagagcgca   1800
cgagggagct tccaggggga aacgcctggt atctttatag tcctgtcggg tttcgccacc   1860
tctgacttga gcgtcgattt ttgtgatgct cgtcaggggg gcggagccta tggaaaaacg   1920
ccagcaacgc ggccttttta cggttcctgg ccttttgctg gccttttgct cacatgttct   1980
ttcctgcgtt atcccctgat tctgtggata accgtattac cgcctttgag tgagctgata   2040
ccgctcgccg cagccgaacg accgagcgca gcgagtcagt gagcgaggaa gcggaagagc   2100
gcccaatacg caaaccgcct ctccccgcgc gttggccgat tcattaatgc agctgtggaa   2160
tgtgtgtcag ttagggtgtg gaaagtcccc aggctcccca gcaggcagaa gtatgcaaag   2220
catgcatctc aattagtcag caaccaggtg tggaaagtcc ccaggctccc cagcaggcag   2280
aagtatgcaa agcatgcatc tcaattagtc agcaaccata gtcccgcccc taactccgcc   2340
catcccgccc ctaactccgc ccagttccgc ccattctccg ccccatggct gactaatttt   2400
ttttatttat gcagaggccg aggccgcctc ggcctctgag ctattccaga agtagtgagg   2460
aggctttttt ggaggttttc tctacactga agtcttgatg gcatgcgctt tagtctcctc   2520
actcatgagg actgcatatc taagagctct gtgacctcac ttgtgcctgg tgtccagggt   2580
aaacaaatct tcttgccttt gaaaattaga ggatgcagac tggtctcctc tactgcactg   2640
gactgactaa cctgactgga gctcttgttc acactgagaa gaagctggtg gactcttctt   2700
tggctctgaa aggcagattt attttatctc atggagttag gctagagcat cttgtcagag   2760
ggaatgatgt ttgaagtcca tgaggcttct aatgattagg gctggtatgc agcaaacaac   2820
catgactgca tttgtctctg atgcagattc ctaacttctg atatgttcaa aactctgctt   2880
cctgattcag ttgctctctt taacaaatgc agtgattctt ttgataattt gaggggaaaa   2940
aatgtctctg tgttgtgttt cctccttgct ggtgatccac agtaaggggt tgaaaataat   3000
ctctgacatt ttttagttaa agccttcctt tcattcttca tggctactgc agcacaaagc   3060
tctttcttgt tttgcagaag gagtgagagc aaggtgttgg gtgagttctc agtgccccag   3120
ccccagcctg aagaggagac tgaatgcctg ccctctggct gtggctcaga gtgaaaggaa   3180
aacacataca gcaggagtct gtgtagggat tgggctccag ccatcagagc ggggggagca   3240
tcatgaaatg tttgtaagct ctccaccatc cagaatgact ttgcagctct gagcagctgc   3300
acccatgact agtccttcac agtatgctga tgtgagatat tctgttcttt gaagatgggt   3360
agtgaccaga atcaggagga tgtgagaaat gtggagcatt tgagagtgga actcctgcag   3420
ctgttgaagc tagaacacaa cagacactgc agcttactac tcctgagcct ggccaggctg   3480
gtagttttgt ttttcttggc caagctctct gggaatagtt ctgcctctgg ggtcagcttt   3540
ccatgcaggg gctgagatga acacataaag caggattcag cttggaggct tctgagaggg   3600
atggagataa aagatggtgt ggtagatggt aagaggtggt atggtagatg gcagagtatg   3660
gcagaagatg tagacaggat gtcagaaaat gagatggtag ttgcaagagt aggctgtaga   3720
cagtgggaga tggtgagatg agagatgcag aagatggtca gagagcagga tgttgggaga   3780
```

-continued ggctaggagg tgagacacca gggttggagt gtggactgca ggctttgtta ggctggagag 3840
gtgagtagct gtggagagag gatgacctgc acttgtctga atctaacaga acctaaatta 3900
gaaactttct cttgcagttc tctctctggc tcaggctggc ttgtcttggg gactgtctgt 3960
cactctggaa cagggtggtt agagctgtgg ctttcatggt acttctcttc actgggctct 4020
gatagcctgg ggctgctggt actatctgct tgcacttgct ttgaggaggc caagaacatc 4080
ctgtgtattt ccagactctt tcttgttctg tttgtcctct caggctattc cttgtgctcc 4140
tgatgtctct gtctttactt ccaaaactat ttattaaaaa atctaagatt cattcatgtt 4200
taaggggaat tatgctaatt ctttcatacc taatgggata aaactaactg tgaaattaca 4260
gaccatcttg tgtaaaatct taatctcagc agtcacattt gctgttgaag tgagtatgaa 4320
caaacactga tatgtggagg gctctggtgc aaaggtttgt aggctctgcc tgtgttgcat 4380
agagcagctc atctgaagtg gattagcact gcttctgagc atggaaggtc aggctgaagt 4440
catgatgcct aattagggct ggagaggaca tcacagaaac agtggctctt gggtttgtcc 4500
tgggtagggc agaggtaagg ttgaggagag ctagaaaact caggaaaaga aaaggctcag 4560
gagaaagaag acagagagtt ccagtgagca gagctgcctc tgctgctagg cttgtggtac 4620
acaggttaaa gtttggcctt gtggcattca acagcctttg catcctactg accacactag 4680
ccaggcagtt gaggctcagg gctggctttc ttgcacttgg agaacctttc ctaccttcaa 4740
atgcttgaac cagaatacca gagaaaaaat gcaactctga aagcacaggc attctgtgaa 4800
tagccatcca gatttctgca ggctaaggaa aacagagatg gaggtctatg agggaaagaa 4860
gagaagtcct catgagggct gataccagac agttgagtag gacactgagc acactcacca 4920
ccagatgctc tgtctaagct gtagtttact aggaggttgt ttattctctg agtcagattt 4980
gcttctgttt taagaaccct cacagcctct ctttctatct attctgatga aggttgagcc 5040
tgaagaagct ggagcagaaa gggtcttctg cctcatgttc tgctgataaa ctttgagaat 5100
cctgcctaag tctgacctag attttggctc caaaagccag ggcttcttat ctctgtcaag 5160
accaaacctg gatgcagtca gaggttgggc acagcctttg ctccaaggct cctgggcaca 5220
gtgcccacct cccatttgag cttgcagcaa ggctattatg agaaactttc ctcctcttcc 5280
ttcaagtctc cacctattag ctctgcaaga gtgcagaagg ctgcacagca ctgcagatgg 5340
agaaggtggc aggggcagca ggtggcaggg gctccaggga actgtggtca gagttgattc 5400
agagcaggct aagagtggag tgactgaaga cagaagctgg aggcacatca accattacaa 5460
gacagcttga cttttgctag aacccttggc ttcaggtgat gagaataatg gtagacactg 5520
gttgtttggc ttgatagctt aaaaaaggac aaccattata atggaagcag tttctctgag 5580
aaacaggatg ttggcaaggg cttagtgctc ctgactgctg atgctggagt ctggcttccc 5640
tgaccccagt agcagtggga cttagaagca tctcaggctc caggttctca cagctgactc 5700
ctccttcctg aactgtaaga aacagaaatc cacttgctgc tctaaagtgg ggtcacttta 5760
atggaaggaa cagccaacat atttggagag gggctggtgt ggggcttctt actgagagtg 5820
ggcagccctg agcactggac aaactcaact gtgggcaacc tgggtgggaa gcagctgtgg 5880
agatggggaa gccatgctaa tcagtgacat catctattct aagtttccta cctctgaatg 5940
aatagttctg ctggcaaaaa tctgcttttt taagttgata caaatgtgtc ctgtcaagga 6000
agtagagctc cttctcaatc cagcacatca gtaccataac ttgttcctgt gcatttggtt 6060
aaagatggtg ataacatcat ttatcagtaa gtgcagccag gcatgatgca ctatctcctt 6120
gcatttagag cctaattttg gccaaagaag tcttcataga aaaggacttc ccactcaaag 6180

-continued

```
tagtcctgag tagttctact gattttatta ttagtagaga gggtttcatc atgttggcca   6240
ggctggtctg catgcttcta tattattttc taaaagattt aaagttttgc cttctccatt   6300
tagacttata attcactgga attttttgt gtgtatggta tgacatatgg gttccctttt   6360
atttttaca tataaatata tttccctgtt tttctaaaaa agaaaaagac catcattttc   6420
ccattgtaaa atgccatatt tttttcatag gtcacttaca tatatcaatg ggtctgtttc   6480
tgagctctac tctattttat cagcctcact gtctatcccc acacatctca tgctttgctc   6540
taaatcttga tatttagtgg aacattcttt cccattttgt tctacaagaa tatttttgtt   6600
attgtctttt gggcttctat atacatttta gaatgaggtt ggcaagttat cctgcaggaa   6660
ttcctcgaga ccgtacgagc ggccgcttgg ccactccctc tctgcgcgct cgctcgctca   6720
ctgaggccgg gcgaccaaag gtcgcccgac gcccgggctt tgcccgggcg gcctcagtga   6780
gcgagcgagc gcgcagagag ggagtggcca actccatcac taggggttcc tcctgcaggg   6840
aattcagtca atatgttcac ccaaaaaaag ctgtttgtta tcgtggatct ctccccagca   6900
tgcctgctat tgtcttccca atcctccccc ttgctgtcct gccccacccc accccccaga   6960
atagaatgac acctactcag acaatgcgat gcaatttcct cattttatta ggaaaggaca   7020
gtgggagtgg caccttccag ggtcaaggaa ggcacggggg aggggcaaac aacagatggc   7080
tggcaactag aaggcacagt cgaggctgat cagcgagctc tagtcgacgg tatcgatgcg   7140
gggaggcggc ccaaagggag atccgactcg tctgagggcg aaggcgaaga cgcggaagag   7200
gccgcagagc cggcagcagg ccgcgggaag gaaggtccgc tggattgagg gccgaaggga   7260
cgtagcagaa ggacgtcccg cgcagaatcc aggtggcaac acaggcgagc agccaaggaa   7320
aggacgatga tttccccgac aacaccacgg aattgtcagt gcccaacagc cgagcccctg   7380
tccagcagcg ggcaaggcag gcggcgatga gttccgccgt ggcaataggg agggggaaag   7440
cgaaagtccc ggaaaggagc tgacaggtgg tggcaatgcc ccaaccagtg gggggttgcgt   7500
cagcaaacac agtgcacacc acgccacgtt gcctgacaac gggccacaac tcctcataaa   7560
gagacagcaa ccaggattta tacaaggagg agaaaatgaa agccatacgg gaagcaatag   7620
catgatacaa aggcattaaa gcagcgtatc cacatagcgt aaaaggagca acatagttaa   7680
gaataccagt caatctttca caaattttgt aatccagagg ttgattatcg ataagcttgc   7740
ggcctcgagg gtttaaactt aattaacaat tgtcactgtc tacgccacag gtaggtgtgg   7800
atggagtagc cagggctgat tgtttccagg aatcccacgg cgggatcctt gatggtcagg   7860
ggcacatctt tgctgctgcg gttcaggacc accaccacag cagatccatc agggtgcatc   7920
agagccacgg cgtccagatc gttcttctgg gaagccacca gtccaacgcg ctgagagccc   7980
tcggggatga acttgctgaa gtgtcccagg tggtagaaca tgggctgctt gtagaaggtg   8040
tccttggtga tgtccacgat gatggggctg tccacgaagt ttcggaccca gttagggccg   8100
ccttcaggat tcagggccag attccagtcg gtccagccga cgacgtggta cagcaggttg   8160
gtgatgatgc tgtggctgta ctgcatgcct ctatcccagc tgccgagccg cacgctctgt   8220
tcccaaaact tgctgcccac acaggcttcg ctggcgaaca gcatggtgtt ggggaacagt   8280
ctgtgtgtct ctcccagtgt ggccttggca ggggccagaa agtccagata ccagtgcacg   8340
gcgattccgt gcacgtattt ggcggcctca ggatctgtca gcaccacttt agcccagtgg   8400
ggcagaagca gtctctggtc gtccagcatc agcagccgca cattatggtg ggtgctattg   8460
gccagtgtgg gtcccagatc acgggcgata aagtcccgct ggtgctcggg tgtaaagccc   8520
```

aggcactgaa aggggtagcc gctcagcagt ccagcagaag gttcgttctc ggctgtcacg 8580
gcccaaaact gcagcttgtg ctcggcatag gcgtccagga acttcacgaa gtatctggcc 8640
caggtctggt ggtagatgtc gccaggttgg cctttcaggc tgcccttgcc attcacggcg 8700
ccatttgttt tcagccaggt gggagatgtc catggagagg ccagcagtga cacgggtctt 8760
tgtgccagct gcagggctct gtggatcaga gggatcttca gcttggtgtc ctcttcaggc 8820
aggctgaagt tgtgcagctg gaaatcgtcg ggtgtgtcgg cgtaggtgta ggtcctgatg 8880
ctgaagtcgc agctggccat gggcactctg atgatgttgt agccgatgcc ttcctcgctg 8940
aagtagctct tgagcagcag gttctgagct ggtggagaca gagccaggat attcagagcg 9000
gcggcatctg tcatggctcc gccgaagcct ttcactttct ggaatttctg ctcaggctgc 9060
agtgtcagca gcaggccagt gcctgtgtga ttggcctgga tgggtcccat gctcagttcc 9120
atccgtctgc cggatctggt gctctcgtat ctgctgaagg tgcccagagc aggaaaggta 9180
ggagggtcga agctgtcgca gtaggtggca ttgcacacgc acacgacgct gctgtagccg 9240
aagctcttgg ggatgcaagg tctagcgcca gaagcccaag acacggcctg aagcagcagc 9300
agtcctgtca gagatccggc catgattgac acccggctca gaggcttggg gcattcctct 9360
ctgctggggc tgctgaattc catggtggct caaccggtga tatcttcgaa cggatcccac 9420
agtcgtggaa gactttccct tcggatcttc gaggaattct ttgccaaaat gatgagacag 9480
cacaataacc agcacgttgc ccaggagctg taggaaaaag aagaaggcat gaacatggtt 9540
agcagaggct ctagctcccg gagcccctca aggctttcac gcagccacag aaaggtggtg 9600
actgagatgt tttctaggaa acacaaaaga tacaaaaaag aacacgtgga aggatagcca 9660
aaaagggggg ctgcccccat ttcctgcacc ccgctgcgat ggctggcacc atttggaaga 9720
cttcgagata cactgttgag cgcagtaaga caacagtgta tctcgaagtc ttccagatgg 9780
ggccagccgg tccactctgt atccaggcca gttctgcaag gcgttcgagg accacccccc 9840
tcccctcgcc accaggacaa gccgtcatta aaccaagcgc taattacagc ccggaggaga 9900
agggccgtcc cgcccgctca cctgtgggag taacgcggtc agtcagagcc ggggcgggcg 9960
gcgcgaggcg gcggcggagc ggggcacggg gcgaaggcag cgtcgcagcg actcccgccc 10020
gccgcgcgct tcgcttttta tagggccgcc gccgccgccg cctcgccata aaaggaaact 10080
ttcggagcgc gccgctctga ttggctgccg ccgcacctct ccgcctcgcc ccgccccgcc 10140
cctcgccccg ccccgccccg cctggcgcgc gccccccccc cccccccgcc cccatcgctg 10200
cacaaaataa ttaaaaaata aataaataca aaattggggg tggggagggg ggggagatgg 10260
ggagagtgaa gcagaacgtg gggctcacct cgaccatggt aatagcgatg actaatacgt 10320
agatgtactg ccaagtagga aagtcccata aggtcatgta ctgggcataa tgccaggcgg 10380
gccatttacc gtcattgacg tcaatagggg gcgtacttgg catatgatac acttgatgta 10440
ctgccaagtg ggcagtttac cgtaaatagt ccacccattg acgtcaatgg aaagtcccta 10500
ttggcgttac tatgggaaca tacgtcatta ttgacgtcaa tgggcggggg tcgttgggcg 10560
gtcagccagg cgggccattt accgtaagtt atgtaacgcg gaactccata tatgggctat 10620
gaactaatga ccccgtaatt gattactatt aataactagg gtaccgaatt cagatccaag 10680
cttcaccatg ggagacgtca ccggttctag aacctaggga gctctggtac ccactagtag 10740
tcgacgaacg cgtaacctcc cgcttcaaaa tggagaccct gcgtgctcac tcgggcttaa 10800
atacccagag ctagcaggaa cccctagtga tggagttggc cactccctct ctgcgcgctc 10860
gctcgctcac tgaggccgcc cgggcaaagc ccgggcgtcg ggcgaccttt ggtcgcccgg 10920
cctcagtgag cgagcgagcg cgcagagagg gagtggccaa 10960

<210> SEQ ID NO 45
<211> LENGTH: 9348
<212> TYPE: DNA
<213> ORGANISM: Artificial Sequence
<220> FEATURE:
<223> OTHER INFORMATION: PR014A vector first strand sequence

<400> SEQUENCE: 45
ttggccactc cctctctgcg cgctcgctcg ctcactgagg ccgcccgggc aaagcccggg 60
cgtcgggcga cctttggtcg cccggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
ctagttatta atagtaatca attacggggt cattagttca tagcccatat atggagttcc 360
gcgttacata acttacggta aatggcccgc ctggctgacc gcccaacgac ccccgcccat 420
tgacgtcaat aatgacgtat gttcccatag taacgccaat agggactttc cattgacgtc 480
aatgggtgga gtatttacgg taaactgccc acttggcagt acatcaagtg tatcatatgc 540
caagtacgcc ccctattgac gtcaatgacg gtaaatggcc cgcctggcat tatgcccagt 600
acatgacctt atgggacttt cctacttggc agtacatcta cgtattagtc atcgctatta 660
ccatggtcga ggtgagcccc acgttctgct tcactctccc catctccccc ccctccccac 720
ccccaatttt gtatttattt atttttttaat tattttgtgc agcgatgggg gcgggggggg 780 gggggggcg cgcgccaggc ggggcggggc ggggcgaggg gcggggcggg gcgaggcgga 840
gaggtgcggc ggcagccaat cagagcggcg cgctccgaaa gtttcctttt atggcgaggc 900
ggcggcggcg gcggccctat aaaaagcgaa gcgcgcggcg ggcgggagtc gctgcgacgc 960
tgccttcgcc ccgtgccccg ctccgccgcc gcctcgcgcc gcccgccccg gctctgactg 1020
accgcgttac tcccacaggt gagcgggcgg gacggccctt ctcctcagcg ctgtaattag 1080
cgcttggttt aatgacggct tgtcctggtg gcgaggggag gggggtggtc ctcgaacgcc 1140
ttgcagaact ggcctggata cagagtggac cggctggccc catctggaag acttcgagat 1200
acactgttgt cttactgcgc tcaacagtgt atctcgaagt cttccaaatg gtgccagcca 1260
tcgcagcggg gtgcaggaaa tgggggcagc ccccctttt ggctatcctt ccacgtgttc 1320
ttttttgtat cttttgtgtt tcctagaaaa catctcagtc accacctttc tgtggctgcg 1380
tgaaagcctt gaggggctcc gggagctaga gcctctgcta accatgttca tgccttcttc 1440
tttttcctac agctcctggg caacgtgctg gttattgtgc tgtctcatca ttttggcaaa 1500
gaattcctcg aagatccgaa gggaaagtct tccacgactg tgggatccgt tcgaagatat 1560
caccggttga gccacccaat tgttaattaa gtttaaaccc tcgaggccgc aagcttatcg 1620
ataatcaacc tctggattac aaaatttgtg aaagattgac tggtattctt aactatgttg 1680
ctccttttac gctatgtgga tacgctgctt taatgccttt gtatcatgct attgcttccc 1740
gtatggcttt cattttctcc tccttgtata aatcctggtt gctgtctctt tatgaggagt 1800
tgtggcccgt tgtcaggcaa cgtggcgtgg tgtgcactgt gtttgctgac gcaaccccca 1860
ctggttgggg cattgccacc acctgtcagc tcctttccgg gactttcgct ttccccctcc 1920
ctattgccac ggcggaactc atcgccgcct gccttgcccg ctgctggaca ggggctcggc 1980

-continued

```
tgttgggcac tgacaattcc gtggtgttgt cggggaaatc atcgtccttt ccttggctgc   2040
tcgcctgtgt tgccacctgg attctgcgcg ggacgtcctt ctgctacgtc ccttcggccc   2100
tcaatccagc ggaccttcct tcccgcggcc tgctgccggc tctgcggcct cttccgcgtc   2160
ttcgccttcg ccctcagacg agtcggatct ccctttgggc cgcctccccg catcgatacc   2220
gtcgactaga gctcgctgat cagcctcgac tgtgccttct agttgccagc catctgttgt   2280
ttgcccctcc cccgtgcctt ccttgaccct ggaaggtgcc actcccactg tcctttccta   2340
ataaaatgag gaaattgcat cgcattgtct gagtaggtgt cattctattc tggggggtgg   2400
ggtggggcag gacagcaagg gggaggattg ggaagacaat agcaggcatg ctggggagag   2460
atccacgata acaaacagct tttttggggt gaacatattg actgaattcc ctgcaggagg   2520
aacccctagt gatggagttg gccactccct ctctgcgcgc tcgctcgctc actgaggccg   2580
cccgggcaaa gcccgggcgt cgggcgacct ttggtcgccc ggcctcagtg agcgagcgag   2640
cgcgcagaga gggagtggcc aagcggccgc tcgtacggtc tcgaggaatt cctgcaggat   2700
aacttgccaa cctcattcta aaatgtatat agaagcccaa aagacaataa caaaaatatt   2760
cttgtagaac aaaatgggaa agaatgttcc actaaatatc aagatttaga gcaaagcatg   2820
agatgtgtgg ggatagacag tgaggctgat aaaatagagt agagctcaga aacagaccca   2880
ttgatatatg taagtgacct atgaaaaaaa tatggcattt tacaatggga aaatgatggt   2940
ctttttcttt tttagaaaaa cagggaaata tatttatatg taaaaaataa aagggaaccc   3000
atatgtcata ccatacacac aaaaaaattc cagtgaatta taagtctaaa tggagaaggc   3060
aaaactttaa atcttttaga aaataatata gaagcatgca gaccagcctg gccaacatga   3120
tgaaaccctc tctactaata ataaaatcag tagaactact caggactact ttgagtggga   3180
agtccttttc tatgaagact tctttggcca aaattaggct ctaaatgcaa ggagatagtg   3240
catcatgcct ggctgcactt actgataaat gatgttatca ccatctttaa ccaaatgcac   3300
aggaacaagt tatggtactg atgtgctgga ttgagaagga gctctacttc cttgacagga   3360
cacatttgta tcaacttaaa aaagcagatt tttgccagca gaactattca ttcagaggta   3420
ggaaacttag aatagatgat gtcactgatt agcatggctt ccccatctcc acagctgctt   3480
cccacccagg ttgcccacag ttgagtttgt ccagtgctca gggctgccca ctctcagtaa   3540
gaagccccac accagcccct ctccaaatat gttggctgtt ccttccatta aagtgacccc   3600
actttagagc agcaagtgga tttctgtttc ttacagttca ggaaggagga gtcagctgtg   3660
agaacctgga gcctgagatg cttctaagtc ccactgctac tggggtcagg gaagccagac   3720
tccagcatca gcagtcagga gcactaagcc cttgccaaca tcctgtttct cagagaaact   3780
gcttccatta taatggttgt cctttttttaa gctatcaagc caaacaacca gtgtctacca   3840
ttattctcat cacctgaagc caagggttct agcaaaagtc aagctgtctt gtaatggttg   3900
atgtgcctcc agcttctgtc ttcagtcact ccactcttag cctgctctga atcaactctg   3960
accacagttc cctggagccc ctgccacctg ctgcccctgc caccttctcc atctgcagtg   4020
ctgtgcagcc ttctgcactc ttgcagagct aataggtgga gacttgaagg aagaggagga   4080
aagtttctca taatagcctt gctgcaagct caaatgggag gtgggcactg tgcccaggag   4140
ccttggagca aaggctgtgc ccaacctctg actgcatcca ggtttggtct tgacagagat   4200
aagaagccct ggcttttgga gccaaaatct aggtcagact taggcaggat tctcaaagtt   4260
tatcagcaga acatgaggca gaagaccctt tctgctccag cttcttcagg ctcaaccttc   4320
atcagaatag atagaaagag aggctgtgag ggttcttaaa acagaagcaa atctgactca   4380
```

```
gagaataaac aacctcctag taaactacag cttagacaga gcatctggtg gtgagtgtgc   4440
tcagtgtcct actcaactgt ctggtatcag ccctcatgag gacttctctt ctttccctca   4500
tagacctcca tctctgtttt ccttagcctg cagaaatctg gatggctatt cacagaatgc   4560
ctgtgctttc agagttgcat tttttctctg gtattctggt tcaagcattt gaaggtagga   4620
aaggttctcc aagtgcaaga aagccagccc tgagcctcaa ctgcctggct agtgtggtca   4680
gtaggatgca aaggctgttg aatgccacaa ggccaaactt taacctgtgt accacaagcc   4740
tagcagcaga ggcagctctg ctcactggaa ctctctgtct tctttctcct gagccttttc   4800
ttttcctgag ttttctagct ctcctcaacc ttacctctgc cctacccagg acaaacccaa   4860
gagccactgt ttctgtgatg tcctctccag ccctaattag gcatcatgac ttcagcctga   4920
ccttccatgc tcagaagcag tgctaatcca cttcagatga gctgctctat gcaacacagg   4980
cagagcctac aaacctttgc accagagccc tccacatatc agtgtttgtt catactcact   5040
tcaacagcaa atgtgactgc tgagattaag attttacaca agatggtctg taatttcaca   5100
gttagtttta tcccattagg tatgaaagaa ttagcataat tccccttaaa catgaatgaa   5160
tcttagattt tttaataaat agttttggaa gtaaagacag agacatcagg agcacaagga   5220
atagcctgag aggacaaaca gaacaagaaa gagtctggaa atacacagga tgttcttggc   5280
ctcctcaaag caagtgcaag cagatagtac cagcagcccc aggctatcag agcccagtga   5340
agagaagtac catgaaagcc acagctctaa ccaccctgtt ccagagtgac agacagtccc   5400
caagacaagc cagcctgagc cagagagaga actgcaagag aaagtttcta atttaggttc   5460
tgttagattc agacaagtgc aggtcatcct ctctccacag ctactcacct ctccagccta   5520
acaaagcctg cagtccacac tccaaccctg gtgtctcacc tcctagcctc tcccaacatc   5580
ctgctctctg accatcttct gcatctctca tctcaccatc tcccactgtc tacagcctac   5640
tcttgcaact accatctcat tttctgacat cctgtctaca tcttctgcca tactctgcca   5700
tctaccatac cacctcttac catctaccac accatctttt atctccatcc ctctcagaag   5760
cctccaagct gaatcctgct ttatgtgttc atctcagccc ctgcatggaa agctgacccc   5820
agaggcagaa ctattcccag agagcttggc caagaaaaac aaaactacca gcctggccag   5880
gctcaggagt agtaagctgc agtgtctgtt gtgttctagc ttcaacagct gcaggagttc   5940
cactctcaaa tgctccacat ttctcacatc ctcctgattc tggtcactac ccatcttcaa   6000
agaacagaat atctcacatc agcatactgt gaaggactag tcatgggtgc agctgctcag   6060
agctgcaaag tcattctgga tggtggagag cttacaaaca tttcatgatg ctccccccgc   6120
tctgatggct ggagcccaat ccctacacag actcctgctg tatgtgtttt cctttcactc   6180
tgagccacag ccagagggca ggcattcagt ctcctcttca ggctggggct ggggcactga   6240
gaactcaccc aacaccttgc tctcactcct tctgcaaaac aagaaagagc tttgtgctgc   6300
agtagccatg aagaatgaaa ggaaggcttt aactaaaaaa tgtcagagat tattttcaac   6360
cccttactgt ggatcaccag caaggaggaa acacaacaca gagacatttt ttcccctcaa   6420
attatcaaaa gaatcactgc atttgttaaa gagagcaact gaatcaggaa gcagagtttt   6480
gaacatatca gaagttagga atctgcatca gagacaaatg cagtcatggt tgtttgctgc   6540
ataccagccc taatcattag aagcctcatg gacttcaaac atcattccct ctgacaagat   6600
gctctagcct aactccatga gataaaataa atctgccttt cagagccaaa gaagagtcca   6660
ccagcttctt ctcagtgtga acaagagctc cagtcaggtt agtcagtcca gtgcagtaga   6720
```

-continued

```
ggagaccagt ctgcatcctc taattttcaa aggcaagaag atttgtttac cctggacacc   6780
aggcacaagt gaggtcacag agctcttaga tatgcagtcc tcatgagtga ggagactaaa   6840
gcgcatgcca tcaagacttc agtgtagaga aaacctccaa aaaagcctcc tcactacttc   6900
tggaatagct cagaggccga ggcggcctcg gcctctgcat aaataaaaaa aattagtcag   6960
ccatggggcg gagaatgggc ggaactgggc ggagttaggg gcgggatggg cggagttagg   7020
ggcgggacta tggttgctga ctaattgaga tgcatgcttt gcatacttct gcctgctggg   7080
gagcctgggg actttccaca cctggttgct gactaattga gatgcatgct ttgcatactt   7140
ctgcctgctg gggagcctgg ggactttcca caccctaact gacacacatt ccacagctgc   7200
attaatgaat cggccaacgc gcggggagag gcggtttgcg tattgggcgc tcttccgctt   7260
cctcgctcac tgactcgctg cgctcggtcg ttcggctgcg gcgagcggta tcagctcact   7320
caaaggcggt aatacggtta tccacagaat caggggataa cgcaggaaag aacatgtgag   7380
caaaaggcca gcaaaaggcc aggaaccgta aaaaggccgc gttgctggcg tttttccata   7440
ggctccgccc ccctgacgag catcacaaaa atcgacgctc aagtcagagg tggcgaaacc   7500
cgacaggact ataaagatac caggcgtttc cccctggaag ctccctcgtg cgctctcctg   7560
ttccgaccct gccgcttacc ggatacctgt ccgcctttct cccttcggga agcgtggcgc   7620
tttctcatag ctcacgctgt aggtatctca gttcggtgta ggtcgttcgc tccaagctgg   7680
gctgtgtgca cgaacccccc gttcagcccg accgctgcgc cttatccggt aactatcgtc   7740
ttgagtccaa cccggtaaga cacgacttat cgccactggc agcagccact ggtaacagga   7800
ttagcagagc gaggtatgta ggcggtgcta cagagttctt gaagtggtgg cctaactacg   7860
gctacactag aagaacagta tttggtatct gcgctctgct gaagccagtt accttcggaa   7920
aaagagttgg tagctcttga tccggcaaac aaaccaccgc tggtagcggt ggtttttttg   7980
tttgcaagca gcagattacg cgcagaaaaa aaggatctca agaagatcct ttgatctttt   8040
ctacggggtc tgacgctcag tggaacgaaa actcacgtta agggattttg gtcatgagat   8100
tatcaaaaag gatcttcacc tagatccttt taaattaaaa atgaagtttt aaatcaatct   8160
aaagtatata tgagtaaact tggtctgaca gttaccaatg cttaatcagt gaggcaccta   8220
tctcagcgat ctgtctattt cgttcatcca tagttgcctg actcctgcaa accacgttgt   8280
gtctcaaaat ctctgatgtt acattgcaca agataaaaat atatcatcat gaacaataaa   8340
actgtctgct tacataaaca gtaatacaag gggtgttatg agccatattc aacgggaaac   8400
gtcttgctcg aggccgcgat taaattccaa catggatgct gatttatatg ggtataaatg   8460
ggctcgcgat aatgtcgggc aatcaggtgc gacaatctat cgattgtatg ggaagcccga   8520
tgcgccagag ttgtttctga aacatggcaa aggtagcgtt gccaatgatg ttacagatga   8580
gatggtcaga ctaaactggc tgacggaatt tatgcctctt ccgaccatca agcattttat   8640
ccgtactcct gatgatgcat ggttactcac cactgcgatc cccgggaaaa cagcattcca   8700
ggtattagaa gaatatcctg attcaggtga aaatattgtt gatgcgctgg cagtgttcct   8760
gcgccggttg cattcgattc ctgtttgtaa ttgtcctttt aacagcgatc gcgtatttcg   8820
tctcgctcag gcgcaatcac gaatgaataa cggtttggtt gatgcgagtg attttgatga   8880
cgagcgtaat ggctggcctg ttgaacaagt ctggaaagaa atgcataagc ttttgccatt   8940
ctcaccggat tcagtcgtca ctcatggtga tttctcactt gataacctta tttttgacga   9000
ggggaaatta ataggttgta ttgatgttgg acgagtcgga atcgcagacc gataccagga   9060
tcttgccatc ctatggaact gcctcggtga gttttctcct tcattacaga aacggctttt   9120
```

tcaaaaatat ggtattgata atcctgatat gaataaattg cagtttcatt tgatgctcga 9180
tgagtttttc taagggcggc ctgccaccat acccacgccg aaacaagcgc tcatgagccc 9240
gaagtggcga gcccgatctt ccccatcggt gatgtcggcg atataggcgc cagcaaccgc 9300
acctgtggcg ccggtgatga gggcgcgcca agtcgacgtc cggcagtc 9348

<210> SEQ ID NO 46
<211> LENGTH: 9348
<212> TYPE: DNA
<213> ORGANISM: Artificial Sequence
<220> FEATURE:
<223> OTHER INFORMATION: PR014A vector second strand sequence

<400> SEQUENCE: 46
gactgccgga cgtcgacttg gcgcgccctc atcaccggcg ccacaggtgc ggttgctggc 60
gcctatatcg ccgacatcac cgatggggaa gatcgggctc gccacttcgg gctcatgagc 120
gcttgtttcg gcgtgggtat ggtggcaggc cgcccttaga aaaactcatc gagcatcaaa 180
tgaaactgca atttattcat atcaggatta tcaataccat atttttgaaa aagccgtttc 240
tgtaatgaag gagaaaactc accgaggcag ttccatagga tggcaagatc ctggtatcgg 300
tctgcgattc cgactcgtcc aacatcaata caacctatta atttcccctc gtcaaaaata 360
aggttatcaa gtgagaaatc accatgagtg acgactgaat ccggtgagaa tggcaaaagc 420
ttatgcattt ctttccagac ttgttcaaca ggccagccat tacgctcgtc atcaaaatca 480
ctcgcatcaa ccaaaccgtt attcattcgt gattgcgcct gagcgagacg aaatacgcga 540
tcgctgttaa aaggacaatt acaaacagga atcgaatgca accggcgcag gaacactgcc 600
agcgcatcaa caatattttc acctgaatca ggatattctt ctaatacctg gaatgctgtt 660
ttcccgggga tcgcagtggt gagtaaccat gcatcatcag gagtacggat aaaatgcttg 720
atggtcggaa gaggcataaa ttccgtcagc cagtttagtc tgaccatctc atctgtaaca 780
tcattggcaa cgctaccttt gccatgtttc agaaacaact ctggcgcatc gggcttccca 840
tacaatcgat agattgtcgc acctgattgc ccgacattat cgcgagccca tttataccca 900
tataaatcag catccatgtt ggaatttaat cgcggcctcg agcaagacgt ttcccgttga 960
atatggctca taacacccct tgtattactg tttatgtaag cagacagttt tattgttcat 1020
gatgatatat ttttatcttg tgcaatgtaa catcagagat tttgagacac aacgtggttt 1080
gcaggagtca ggcaactatg gatgaacgaa atagacagat cgctgagata ggtgcctcac 1140
tgattaagca ttggtaactg tcagaccaag tttactcata tatactttag attgatttaa 1200
aacttcattt ttaatttaaa aggatctagg tgaagatcct ttttgataat ctcatgacca 1260
aaatccctta acgtgagttt tcgttccact gagcgtcaga ccccgtagaa aagatcaaag 1320
gatcttcttg agatcctttt tttctgcgcg taatctgctg cttgcaaaca aaaaaaccac 1380
cgctaccagc ggtggtttgt ttgccggatc aagagctacc aactcttttt ccgaaggtaa 1440
ctggcttcag cagagcgcag ataccaaata ctgttcttct agtgtagccg tagttaggcc 1500
accacttcaa gaactctgta gcaccgccta catacctcgc tctgctaatc ctgttaccag 1560
tggctgctgc cagtggcgat aagtcgtgtc ttaccgggtt ggactcaaga cgatagttac 1620
cggataaggc gcagcggtcg ggctgaacgg ggggttcgtg cacacagccc agcttggagc 1680
gaacgaccta caccgaactg agatacctac agcgtgagct atgagaaagc gccacgcttc 1740
ccgaagggag aaaggcggac aggtatccgg taagcggcag ggtcggaaca ggagagcgca 1800

-continued

```
cgagggagct tccaggggga aacgcctggt atctttatag tcctgtcggg tttcgccacc   1860
tctgacttga gcgtcgattt ttgtgatgct cgtcaggggg gcggagccta tggaaaaacg   1920
ccagcaacgc ggccttttta cggttcctgg ccttttgctg gccttttgct cacatgttct   1980
ttcctgcgtt atcccctgat tctgtggata accgtattac cgcctttgag tgagctgata   2040
ccgctcgccg cagccgaacg accgagcgca gcgagtcagt gagcgaggaa gcggaagagc   2100
gcccaatacg caaaccgcct ctccccgcgc gttggccgat tcattaatgc agctgtggaa   2160
tgtgtgtcag ttagggtgtg gaaagtcccc aggctcccca gcaggcagaa gtatgcaaag   2220
catgcatctc aattagtcag caaccaggtg tggaaagtcc ccaggctccc cagcaggcag   2280
aagtatgcaa agcatgcatc tcaattagtc agcaaccata gtcccgcccc taactccgcc   2340
catcccgccc ctaactccgc ccagttccgc ccattctccg ccccatggct gactaatttt   2400
ttttatttat gcagaggccg aggccgcctc ggcctctgag ctattccaga agtagtgagg   2460
aggctttttt ggaggtttc tctacactga agtcttgatg gcatgcgctt tagtctcctc   2520
actcatgagg actgcatatc taagagctct gtgacctcac ttgtgcctgg tgtccagggt   2580
aaacaaatct tcttgccttt gaaaattaga ggatgcagac tggtctcctc tactgcactg   2640
gactgactaa cctgactgga gctcttgttc acactgagaa gaagctggtg gactcttctt   2700
tggctctgaa aggcagattt attttatctc atggagttag gctagagcat cttgtcagag   2760
ggaatgatgt ttgaagtcca tgaggcttct aatgattagg gctggtatgc agcaaacaac   2820
catgactgca tttgtctctg atgcagattc ctaacttctg atatgttcaa aactctgctt   2880
cctgattcag ttgctctctt taacaaatgc agtgattctt ttgataattt gaggggaaaa   2940
aatgtctctg tgttgtgttt cctccttgct ggtgatccac agtaaggggt tgaaaataat   3000
ctctgacatt ttttagttaa agccttcctt tcattcttca tggctactgc agcacaaagc   3060
tctttcttgt tttgcagaag gagtgagagc aaggtgttgg gtgagttctc agtgccccag   3120
ccccagcctg aagaggagac tgaatgcctg ccctctggct gtggctcaga gtgaaaggaa   3180
aacacataca gcaggagtct gtgtagggat tgggctccag ccatcagagc ggggggagca   3240
tcatgaaatg tttgtaagct ctccaccatc cagaatgact ttgcagctct gagcagctgc   3300
acccatgact agtccttcac agtatgctga tgtgagatat tctgttcttt gaagatgggt   3360
agtgaccaga atcaggagga tgtgagaaat gtggagcatt tgagagtgga actcctgcag   3420
ctgttgaagc tagaacacaa cagacactgc agcttactac tcctgagcct ggccaggctg   3480
gtagttttgt ttttcttggc caagctctct gggaatagtt ctgcctctgg ggtcagcttt   3540
ccatgcaggg gctgagatga acacataaag caggattcag cttggaggct tctgagaggg   3600
atggagataa aagatggtgt ggtagatggt aagaggtggt atggtagatg gcagagtatg   3660
gcagaagatg tagacaggat gtcagaaaat gagatggtag ttgcaagagt aggctgtaga   3720
cagtgggaga tggtgagatg agagatgcag aagatggtca gagagcagga tgttgggaga   3780
ggctaggagg tgagacacca gggttggagt gtggactgca ggctttgtta ggctggagag   3840
gtgagtagct gtggagagag gatgacctgc acttgtctga atctaacaga acctaaatta   3900
gaaactttct cttgcagttc tctctctggc tcaggctggc ttgtcttggg gactgtctgt   3960
cactctggaa cagggtggtt agagctgtgg ctttcatggt acttctcttc actgggctct   4020
gatagcctgg ggctgctggt actatctgct tgcacttgct ttgaggaggc caagaacatc   4080
ctgtgtattt ccagactctt tcttgttctg tttgtcctct caggctattc cttgtgctcc   4140
tgatgtctct gtctttactt ccaaaactat ttattaaaaa atctaagatt cattcatgtt   4200
```

-continued

```
taaggggaat tatgctaatt ctttcatacc taatgggata aaactaactg tgaaattaca   4260
gaccatcttg tgtaaaatct taatctcagc agtcacattt gctgttgaag tgagtatgaa   4320
caaacactga tatgtggagg gctctggtgc aaaggtttgt aggctctgcc tgtgttgcat   4380
agagcagctc atctgaagtg gattagcact gcttctgagc atggaaggtc aggctgaagt   4440
catgatgcct aattagggct ggagaggaca tcacagaaac agtggctctt gggtttgtcc   4500
tgggtagggc agaggtaagg ttgaggagag ctagaaaact caggaaaaga aaaggctcag   4560
gagaaagaag acagagagtt ccagtgagca gagctgcctc tgctgctagg cttgtggtac   4620
acaggttaaa gtttggcctt gtggcattca acagcctttg catcctactg accacactag   4680
ccaggcagtt gaggctcagg gctggctttc ttgcacttgg agaacctttc ctaccttcaa   4740
atgcttgaac cagaatacca gagaaaaaat gcaactctga aagcacaggc attctgtgaa   4800
tagccatcca gatttctgca ggctaaggaa aacagagatg gaggtctatg agggaaagaa   4860
gagaagtcct catgagggct gataccagac agttgagtag gacactgagc acactcacca   4920
ccagatgctc tgtctaagct gtagtttact aggaggttgt ttattctctg agtcagattt   4980
gcttctgttt taagaaccct cacagcctct ctttctatct attctgatga aggttgagcc   5040
tgaagaagct ggagcagaaa gggtcttctg cctcatgttc tgctgataaa ctttgagaat   5100
cctgcctaag tctgacctag attttggctc caaaagccag ggcttcttat ctctgtcaag   5160
accaaacctg gatgcagtca gaggttgggc acagcctttg ctccaaggct cctgggcaca   5220
gtgcccacct cccatttgag cttgcagcaa ggctattatg agaaactttc ctcctcttcc   5280
ttcaagtctc cacctattag ctctgcaaga gtgcagaagg ctgcacagca ctgcagatgg   5340
agaaggtggc aggggcagca ggtggcaggg gctccaggga actgtggtca gagttgattc   5400
agagcaggct aagagtggag tgactgaaga cagaagctgg aggcacatca accattacaa   5460
gacagcttga cttttgctag aacccttggc ttcaggtgat gagaataatg gtagacactg   5520
gttgtttggc ttgatagctt aaaaaaggac aaccattata atggaagcag tttctctgag   5580
aaacaggatg ttggcaaggg cttagtgctc ctgactgctg atgctggagt ctggcttccc   5640
tgaccccagt agcagtggga cttagaagca tctcaggctc caggttctca cagctgactc   5700
ctccttcctg aactgtaaga aacagaaatc cacttgctgc tctaaagtgg ggtcacttta   5760
atggaaggaa cagccaacat atttggagag gggctggtgt ggggcttctt actgagagtg   5820
ggcagccctg agcactggac aaactcaact gtgggcaacc tgggtgggaa gcagctgtgg   5880
agatggggaa gccatgctaa tcagtgacat catctattct aagtttccta cctctgaatg   5940
aatagttctg ctggcaaaaa tctgcttttt taagttgata caaatgtgtc ctgtcaagga   6000
agtagagctc cttctcaatc cagcacatca gtaccataac ttgttcctgt gcatttggtt   6060
aaagatggtg ataacatcat ttatcagtaa gtgcagccag gcatgatgca ctatctcctt   6120
gcatttagag cctaattttg gccaaagaag tcttcataga aaaggacttc ccactcaaag   6180
tagtcctgag tagttctact gattttatta ttagtagaga gggtttcatc atgttggcca   6240
ggctggtctg catgcttcta tattattttc taaaagattt aaagttttgc cttctccatt   6300
tagacttata attcactgga attttttgt gtgtatggta tgacatatgg gttccctttt   6360
attttttaca tataaatata tttccctgtt tttctaaaaa agaaaaagac catcattttc   6420
ccattgtaaa atgccatatt tttttcatag gtcacttaca tatatcaatg ggtctgtttc   6480
tgagctctac tctattttat cagcctcact gtctatcccc acacatctca tgctttgctc   6540
```

-continued

```
taaatcttga tatttagtgg aacattcttt cccattttgt tctacaagaa tatttttgtt   6600
attgtctttt gggcttctat atacatttta gaatgaggtt ggcaagttat cctgcaggaa   6660
ttcctcgaga ccgtacgagc ggccgcttgg ccactccctc tctgcgcgct cgctcgctca   6720
ctgaggccgg gcgaccaaag gtcgcccgac gcccgggctt tgcccgggcg gcctcagtga   6780
gcgagcgagc gcgcagagag ggagtggcca actccatcac taggggttcc tcctgcaggg   6840
aattcagtca atatgttcac cccaaaaaag ctgtttgtta tcgtggatct ctccccagca   6900
tgcctgctat tgtcttccca atcctccccc ttgctgtcct gccccacccc accccccaga   6960
atagaatgac acctactcag acaatgcgat gcaatttcct cattttatta ggaaaggaca   7020
gtgggagtgg caccttccag ggtcaaggaa ggcacggggg aggggcaaac aacagatggc   7080
tggcaactag aaggcacagt cgaggctgat cagcgagctc tagtcgacgg tatcgatgcg   7140
gggaggcggc ccaaagggag atccgactcg tctgagggcg aaggcgaaga cgcggaagag   7200
gccgcagagc cggcagcagg ccgcgggaag gaaggtccgc tggattgagg gccgaaggga   7260
cgtagcagaa ggacgtcccg cgcagaatcc aggtggcaac acaggcgagc agccaaggaa   7320
aggacgatga tttccccgac aacaccacgg aattgtcagt gcccaacagc cgagcccctg   7380
tccagcagcg ggcaaggcag gcggcgatga gttccgccgt ggcaataggg agggggaaag   7440
cgaaagtccc ggaaaggagc tgacaggtgg tggcaatgcc ccaaccagtg gggttgcgt    7500
cagcaaacac agtgcacacc acgccacgtt gcctgacaac gggccacaac tcctcataaa   7560
gagacagcaa ccaggattta tacaaggagg agaaaatgaa agccatacgg gaagcaatag   7620
catgatacaa aggcattaaa gcagcgtatc cacatagcgt aaaaggagca acatagttaa   7680
gaataccagt caatctttca caaattttgt aatccagagg ttgattatcg ataagcttgc   7740
ggcctcgagg gtttaaactt aattaacaat tgggtggctc aaccggtgat atcttcgaac   7800
ggatcccaca gtcgtggaag actttccctt cggatcttcg aggaattctt tgccaaaatg   7860
atgagacagc acaataacca gcacgttgcc caggagctgt aggaaaaaga agaaggcatg   7920
aacatggtta gcagaggctc tagctcccgg agcccctcaa ggctttcacg cagccacaga   7980
aaggtggtga ctgagatgtt ttctaggaaa cacaaaagat acaaaaaaga acacgtggaa   8040
ggatagccaa aaagggggc tgccccatt tcctgcaccc cgctgcgatg gctggcacca     8100
tttggaagac ttcgagatac actgttgagc gcagtaagac aacagtgtat ctcgaagtct   8160
tccagatggg gccagccggt ccactctgta tccaggccag ttctgcaagg cgttcgagga   8220
ccacccccct cccctcgcca ccaggacaag ccgtcattaa accaagcgct aattacagcg   8280
ctgaggagaa gggccgtccc gcccgctcac ctgtgggagt aacgcggtca gtcagagccg   8340
gggcgggcgg cgcgaggcgg cggcggagcg gggcacgggg cgaaggcagc gtcgcagcga   8400
ctcccgcccg ccgcgcgctt cgctttttat agggccgccg ccgccgccgc ctcgccataa   8460
aaggaaactt tcggagcgcg ccgctctgat tggctgccgc cgcacctctc cgcctcgccc   8520
cgccccgccc ctcgccccgc cccgccccgc ctggcgcgcg cccccccccc ccccccgccc   8580
ccatcgctgc acaaaataat taaaaaataa ataaatacaa aattgggggt ggggaggggg   8640
gggagatggg gagagtgaag cagaacgtgg ggctcacctc gaccatggta atagcgatga   8700
ctaatacgta gatgtactgc caagtaggaa agtcccataa ggtcatgtac tgggcataat   8760
gccaggcggg ccatttaccg tcattgacgt caatagggg cgtacttggc atatgataca    8820
cttgatgtac tgccaagtgg gcagtttacc gtaaatactc cacccattga cgtcaatgga   8880
aagtccctat tggcgttact atgggaacat acgtcattat tgacgtcaat gggcgggggt   8940
```

-continued

```
cgttgggcgg tcagccaggc gggccattta ccgtaagtta tgtaacgcgg aactccatat   9000

atgggctatg aactaatgac cccgtaattg attactatta ataactaggt accgaattca   9060

gatccaagct tcaccatggg agacgtcacc ggttctagaa cctagggagc tctggtaccc   9120

actagtagtc gacgaacgcg taacctcccg cttcaaaatg gagaccctgc gtgctcactc   9180

gggcttaaat acccagagct agcaggaacc cctagtgatg gagttggcca ctccctctct   9240

gcgcgctcgc tcgctcactg aggccgggcg accaaaggtc gcccgacgcc cgggctttgc   9300

ccgggcggcc tcagtgagcg agcgagcgcg cagagaggga gtggccaa               9348


<210> SEQ ID NO 47
<211> LENGTH: 263
<212> TYPE: DNA
<213> ORGANISM: Artificial Sequence
<220> FEATURE:
<223> OTHER INFORMATION: First strand sequence encoding aSyn shRNA

<400> SEQUENCE: 47

cctggtggcg aggggagggg ggtggtcctc gaacgccttg cagaactggc ctggatacag     60

agtggaccgg ctggccccat ctggaagact tcgagataca ctgttgtctt actgcgctca    120

acagtgtatc tcgaagtctt ccaaatggtg ccagccatcg cagcggggtg caggaaatgg    180

gggcagcccc cctttttggc tatccttcca cgtgttcttt tttgtatctt ttgtgtttcc    240

tagaaaacat ctcagtcacc acc                                            263


<210> SEQ ID NO 48
<211> LENGTH: 263
<212> TYPE: DNA
<213> ORGANISM: Artificial Sequence
<220> FEATURE:
<223> OTHER INFORMATION: Second strand sequence encoding aSyn shRNA

<400> SEQUENCE: 48

ggtggtgact gagatgtttt ctaggaaaca caaaagatac aaaaaagaac acgtggaagg     60

atagccaaaa agggggggctg cccccatttc ctgcaccccg ctgcgatggc tggcaccatt    120

tggaagactt cgagatacac tgttgagcgc agtaagacaa cagtgtatct cgaagtcttc    180

cagatggggc cagccggtcc actctgtatc caggccagtt ctgcaaggcg ttcgaggacc    240

acccccctcc cctcgccacc agg                                            263
```